United States Patent
Yamada et al.

(10) Patent No.: US 11,465,965 B2
(45) Date of Patent: Oct. 11, 2022

(54) DOUBLE-HEADED PROTEASE INHIBITOR

(71) Applicant: UBE INDUSTRIES, LTD., Ube (JP)

(72) Inventors: Haruka Yamada, Ube (JP); Ken-ichi Komori, Ube (JP); Yusuke Shiraishi, Ube (JP); Satoshi Umezaki, Ube (JP); Naoya Kinoshita, Ube (JP); Koji Ito, Ube (JP); Tomoko Kanda, Ube (JP); Kenji Yoneda, Ube (JP); Yasunori Tokunaga, Ube (JP); Tomio Kimura, Shinagawa-ku (JP)

(73) Assignee: UBE INDUSTRIES, LTD., Ube (JP)

( * ) Notice: Subject to any disclaimer, the term of this patent is extended or adjusted under 35 U.S.C. 154(b) by 0 days.

(21) Appl. No.: 16/760,755

(22) PCT Filed: Nov. 2, 2018

(86) PCT No.: PCT/JP2018/040915
§ 371 (c)(1),
(2) Date: Apr. 30, 2020

(87) PCT Pub. No.: WO2019/088270
PCT Pub. Date: May 9, 2019

(65) Prior Publication Data
US 2020/0347011 A1    Nov. 5, 2020

(30) Foreign Application Priority Data
Nov. 2, 2017    (JP) .............................. JP2017-213163

(51) Int. Cl.
*C07C 307/06* (2006.01)
*C07C 279/18* (2006.01)
*A61P 3/04* (2006.01)
*C07D 407/12* (2006.01)

(52) U.S. Cl.
CPC .............. *C07C 307/06* (2013.01); *A61P 3/04* (2018.01); *C07C 279/18* (2013.01); *C07D 407/12* (2013.01)

(58) Field of Classification Search
CPC ....... C07C 307/06; C07C 279/18; A61P 3/04; C07D 407/12
See application file for complete search history.

(56) References Cited

U.S. PATENT DOCUMENTS

| | | |
|---|---|---|
| 2009/0036431 A1 | 2/2009 | Gauzy et al. |
| 2009/0192140 A1 | 7/2009 | Laurent et al. |
| 2009/0253799 A1 | 10/2009 | Verkman et al. |
| 2009/0312363 A1 | 12/2009 | Bradner et al. |
| 2012/0263670 A1 | 10/2012 | Charmot et al. |
| 2012/0283222 A1 | 11/2012 | Konishi et al. |
| 2013/0338132 A1 | 12/2013 | Koshiba et al. |
| 2014/0094489 A1 | 4/2014 | Suzuki et al. |
| 2014/0378459 A1 | 12/2014 | Fujiyasu et al. |
| 2015/0099733 A1 | 4/2015 | Koshiba et al. |
| 2015/0225361 A1 | 8/2015 | Ikeda et al. |
| 2016/0031847 A1 | 2/2016 | Fujiyasu et al. |
| 2016/0159754 A1* | 6/2016 | Schultz .................. A61P 11/00 514/252.11 |
| 2017/0349605 A1 | 12/2017 | Sasaki et al. |
| 2018/0072694 A1 | 3/2018 | Kakegawa et al. |

FOREIGN PATENT DOCUMENTS

| | | |
|---|---|---|
| EP | 0 184 363 A2 | 6/1986 |
| EP | 3 650 440 A1 | 5/2020 |
| JP | 52-89640 A | 7/1977 |
| JP | 61-143325 A | 7/1986 |
| JP | 2009-524636 A | 7/2009 |
| JP | 2009-526864 A | 7/2009 |
| JP | 2009-537461 A | 10/2009 |
| JP | 2011-516499 A | 5/2011 |
| JP | 2012-514009 A | 6/2012 |

(Continued)

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784. (Year: 1995).*

(Continued)

*Primary Examiner* — Jared Barsky

(74) *Attorney, Agent, or Firm* — Oblon, McClelland, Maier & Neustadt, L.L.P.

(57) ABSTRACT

The present invention provides a compound that is highly safe and useful in the prevention, alleviation, and/or treatment of various diseases involving enteropeptidase inhibition and/or trypsin inhibition, a pharmaceutical composition containing the compound, a method for producing the compound, and the like. Specifically, the present invention provides a compound represented by the following general formula (I):

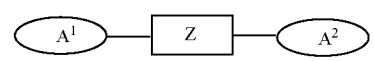

(I)

[wherein: $A^1$ and $A^2$ each independently represent an inhibitor residue having at least one activity selected from an enteropeptidase inhibitory activity and a trypsin inhibitory activity; and Z represents a spacer that links $A^1$ to $A^2$] or a pharmaceutically acceptable salt thereof.

40 Claims, No Drawings

(56) References Cited

FOREIGN PATENT DOCUMENTS

| JP | 2016-525508 A | 8/2016 |
| JP | 2017-506627 A | 3/2017 |
| WO | WO 2006/050999 A2 | 5/2006 |
| WO | WO 2009/071601 A1 | 6/2009 |
| WO | WO 2011/071048 A1 | 6/2011 |
| WO | WO 2012/169579 A1 | 12/2012 |
| WO | WO 2013/039187 A1 | 3/2013 |
| WO | WO 2013/187533 A1 | 12/2013 |
| WO | WO 2014/142219 A1 | 9/2014 |
| WO | WO 2015/003083 A1 | 1/2015 |
| WO | WO 2015/122187 A1 | 8/2015 |
| WO | WO 2015/122188 A1 | 8/2015 |
| WO | WO 2016/104630 A1 | 6/2016 |
| WO | WO 2016/158788 A1 | 10/2016 |
| WO | WO 2020/045326 A1 | 3/2020 |

OTHER PUBLICATIONS

Extended European Search Report dated Jul. 12, 2021 in European Patent Application No. 18872421.5, 7 pages.
International Search Report dated Jan. 22, 2019 in PCT/JP2018/040915, 2 pages.
International Preliminary Report on Patentability dated May 5, 2020 in PCT/JP2018/040915 filed Nov. 2, 2018, 1 page.
English translation of Written Opinion of the International Searching Authority dated Jan. 22, 2019 in PCT/JP2018/040915 filed Nov. 2, 2018, 5 pages.

* cited by examiner

DOUBLE-HEADED PROTEASE INHIBITOR

TECHNICAL FIELD

The present invention relates to double-headed novel compounds having protease inhibitory activities that are useful as medicines and pharmaceutical compositions comprising them, especially novel compounds and pharmaceutical compositions comprising them for the prevention, alleviation, and/or treatment of diseases of which symptoms are improved by enteropeptidase inhibition and/or trypsin inhibition, and methods for producing the compounds.

BACKGROUND ART

Proteins derived from diets are degraded by digestive enzymes, and finally converted into amino acids or peptides to be absorbed by the body. The major protease is trypsin. Enteropeptidase is a serine protease which is secreted from duodenal mucosal cells, and converts trypsinogen secreted from a pancreas by diets into trypsin. It is also known that trypsin acts on protease precursors such as chymotrypsinogen, procarboxypeptidase, proelastase, and procolipase to activate various enzymes. Accordingly, it is believed that a compound which inhibits enteropeptidase and/or trypsin is expected to have effects to suppress the degradation and absorption of proteins, effects to suppress the absorption of lipids, and effects to lowering the ability to digest sugars, and thus is useful as a therapeutic drug for obesity and an antidiabetic drug.

Patent Document 1 discloses that compounds which inhibit both enteropeptidase and trypsin have anti-obesity effects. Patent Document 2 discloses that compounds having inhibitory activities on enteropeptidase, trypsin, plasmin, kallikrein, and the like have anti-obesity effects. Patent Document 3 discloses that administration of enteropeptidase inhibitors has anti-obesity effects and effects to improve type 2 diabetes. As a compound which has a trypsin inhibitory activity and is useful in the prevention, alleviation, and/or treatment of pancreatitis and reflux esophagitis, Patent Document 4 discloses camostat mesilate of the following formula which is clinically used in the treatment of chronic pancreatitis and reflux esophagitis.

As compounds having trypsin inhibitory activities and are useful in the prevention, alleviation, and/or treatment of renal diseases and diseases involving trypsin, Patent Documents 5 and 6 disclose guanidinobenzoic acid compounds, but do not disclose the double-headed compounds of the present invention. As compounds which have enteropeptidase inhibitory activities and are useful in the prevention, alleviation, and/or treatment of obesity and diseases associated with abnormal lipid metabolism, Patent Document 2 discloses boron peptides, but does not disclose the double-headed compounds of the present invention. As compounds which have serine protease inhibitory activities, especially enteropeptidase and trypsin inhibitory activities, and are useful in the prevention, alleviation, and/or treatment of obesity, diabetes, and the like, Patent Documents 7 to 9 disclose heteroaryl carboxylic acid ester derivatives, but do not disclose the double-headed compounds of the present invention. As compounds which have enteropeptidase inhibitory activities and are useful in the prevention, alleviation, and/or treatment of obesity, diabetes, and the like, Patent Documents 3 and 10 to 12 disclose heterocyclic compounds, but do not disclose the double-headed compounds of the present invention.

CITATION LIST

Patent Document

Patent Document 1: WO 2006/050999 pamphlet
Patent Document 2: WO 2009/071601 pamphlet
Patent Document 3: WO 2015/122187 pamphlet
Patent Document 4: JP S52-089640 A
Patent Document 5: WO 2013/039187 pamphlet
Patent Document 6: WO 2014/142219 pamphlet
Patent Document 7: WO 2011/071048 pamphlet
Patent Document 8: WO 2012/169579 pamphlet
Patent Document 9: WO 2013/187533 pamphlet
Patent Document 10: WO 2015/122188 pamphlet
Patent Document 11: WO 2016/104630 pamphlet
Patent Document 12: WO 2016/158788 pamphlet

SUMMARY OF THE INVENTION

Problems to be Solved by Invention

The present invention provides double-headed novel compounds which are useful in the prevention, alleviation, and/or treatment of diseases of which symptoms are improved by enteropeptidase inhibition and/or trypsin inhibition, pharmaceutical compositions comprising them, and methods for producing them.

Means to Solve Problems

The present inventors have earnestly studied compounds which have enteropeptidase inhibitory activities and/or

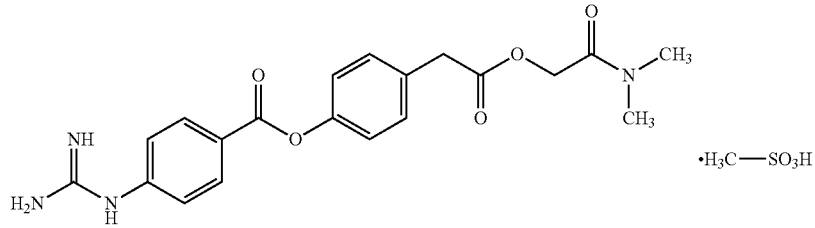

trypsin inhibitory activities, and show very low exposure amount to blood after orally administered. As a result, they have found that double-headed compounds or pharmaceutically acceptable salts thereof in which two inhibitor molecules having at least one activity selected from an enteropeptidase inhibitory activity and a trypsin inhibitory activity are linked by a single bond or an appropriate spacer have excellent enteropeptidase inhibitory activities and/or trypsin inhibitory activities, potently inhibit enteropeptidase and/or trypsin in the intestine after orally administered, show very low exposure amount to blood, and are useful in the prevention, alleviation, and/or treatment of diseases of which symptoms are improved by enteropeptidase inhibition and/or trypsin inhibition, especially in the prevention, alleviation, and/or treatment of obesity, and completed the present invention.

The present invention provides the following [1] to [29].

[1] A compound represented by the following general formula (I):

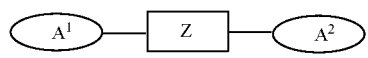

[wherein:

A¹ and A² each independently represent an inhibitor residue having at least one activity selected from an enteropeptidase inhibitory activity and a trypsin inhibitory activity; and Z represents a spacer that links A¹ to A²]

or a pharmaceutically acceptable salt thereof. [2] The compound according to [1] or a pharmaceutically acceptable salt thereof, wherein A¹ and A² each independently represent an inhibitor residue formed by removing any one hydrogen atom or any one hydroxy group from an inhibitor molecule selected from the following inhibitor molecule group:

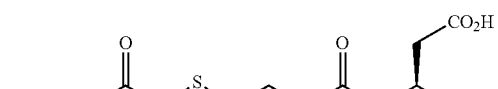

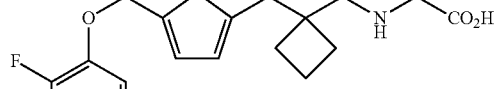

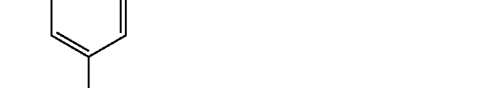

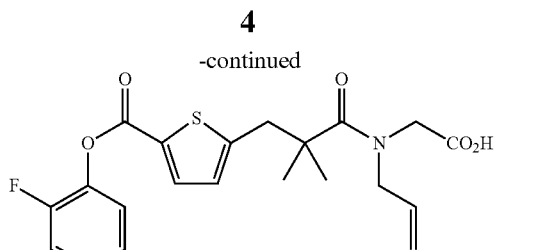

-continued

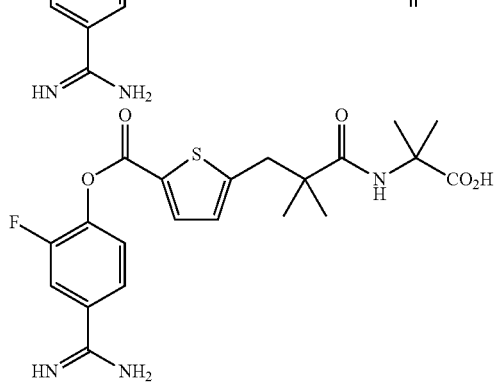

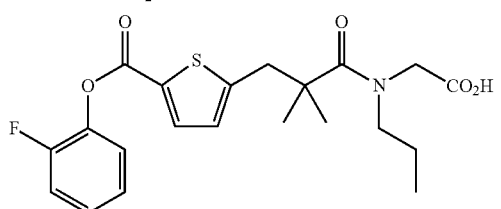

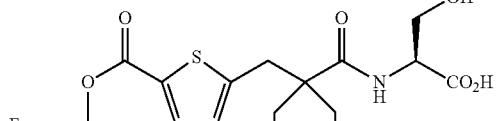

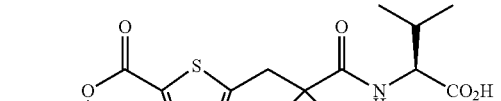

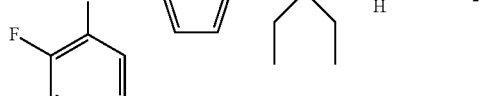

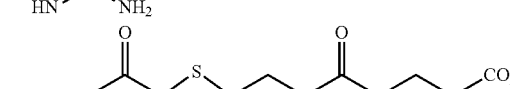

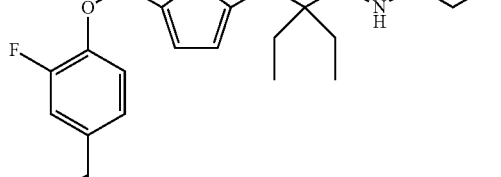

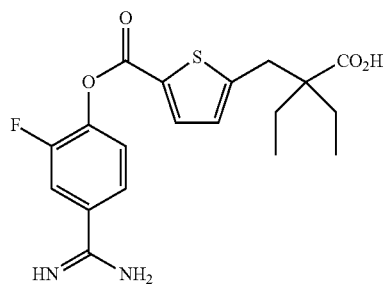
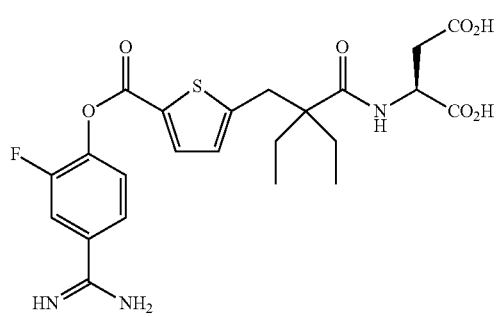
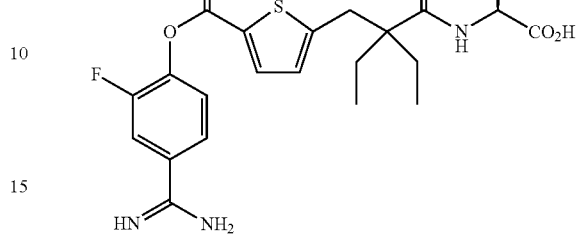
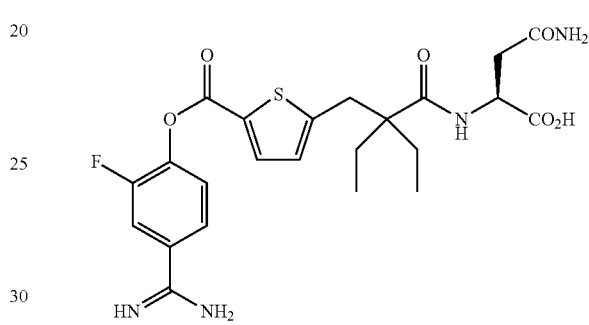
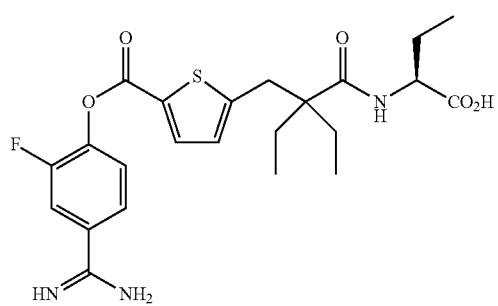
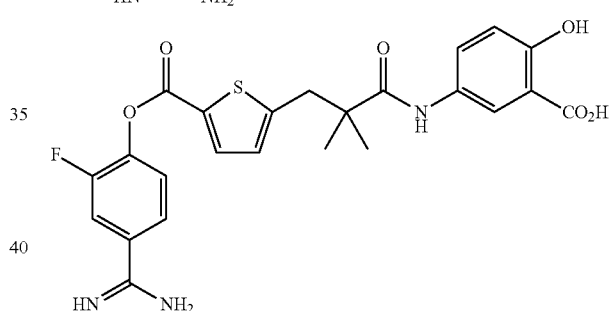
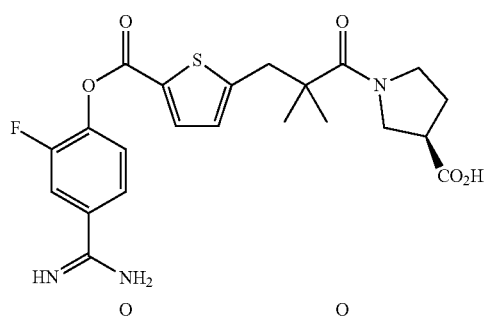
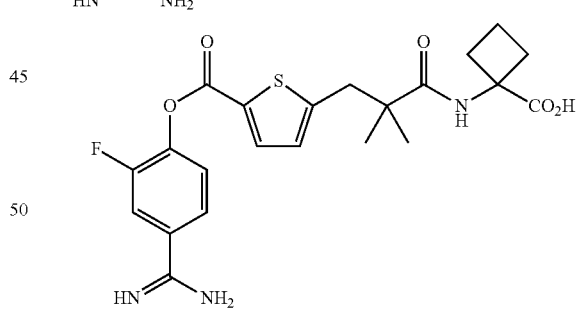
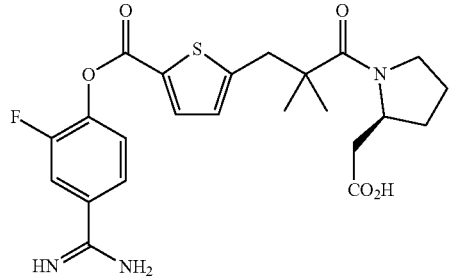
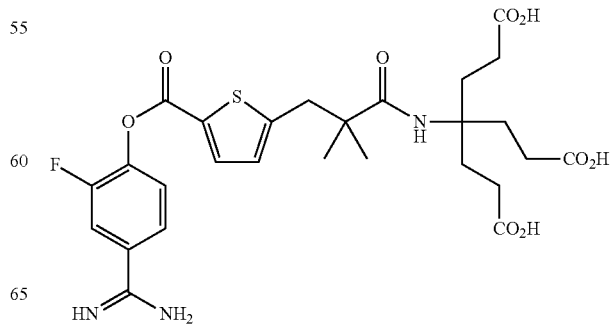

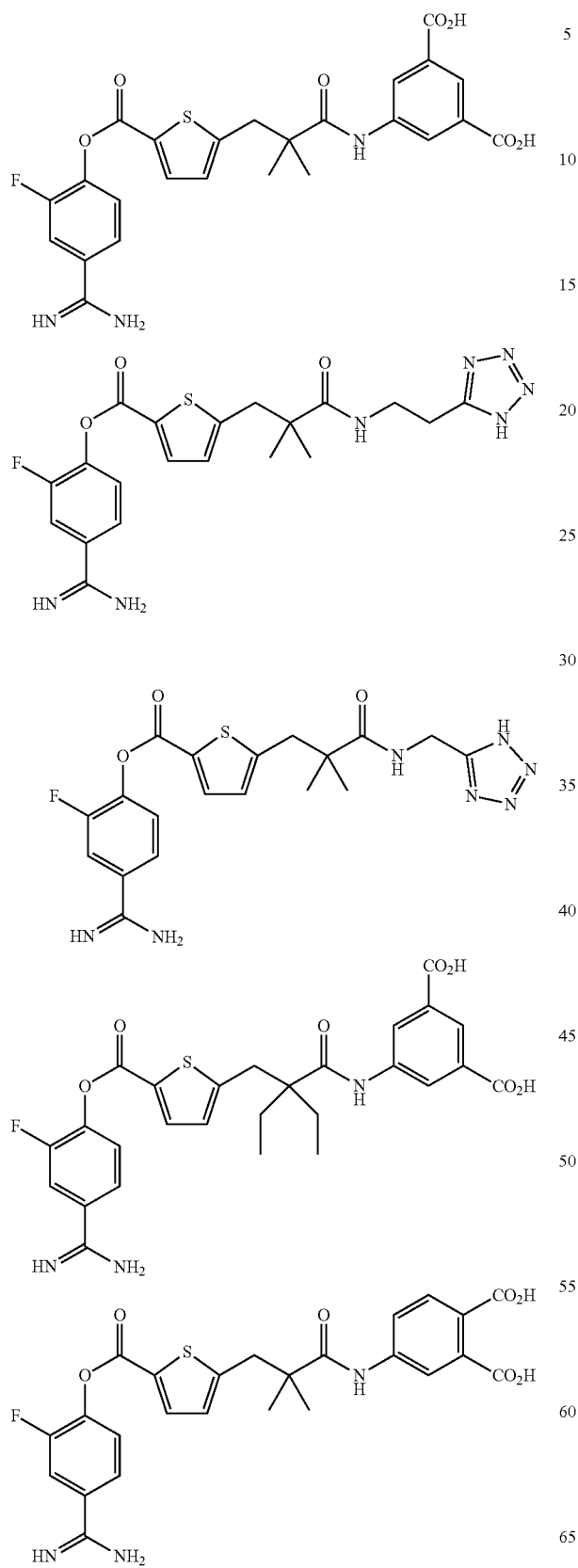
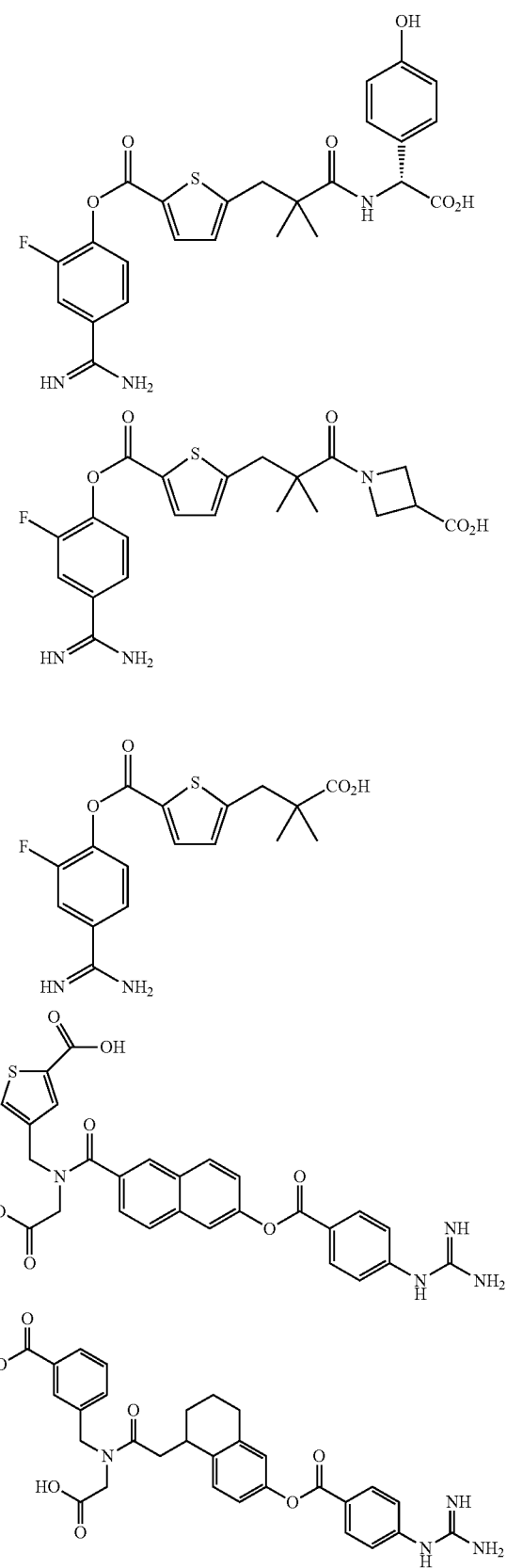

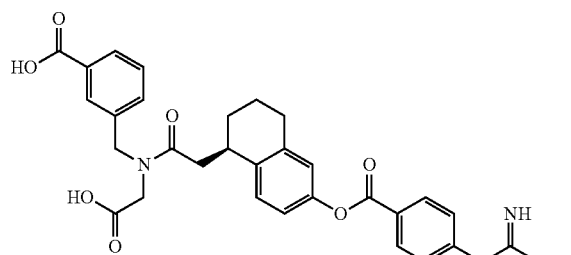
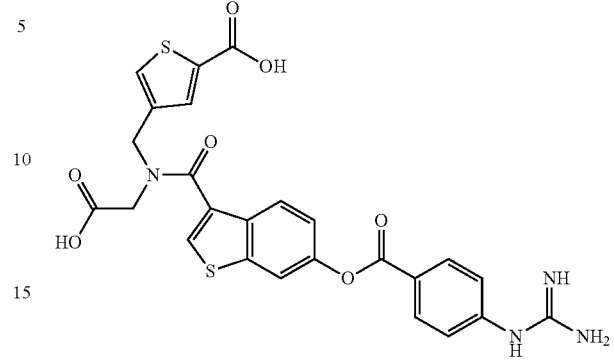
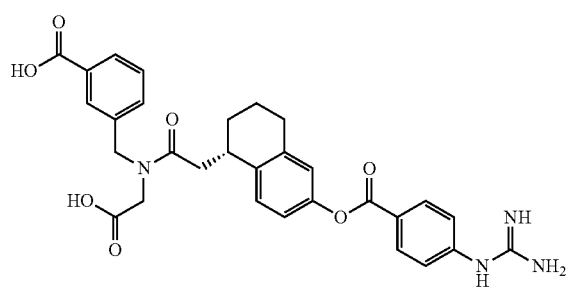
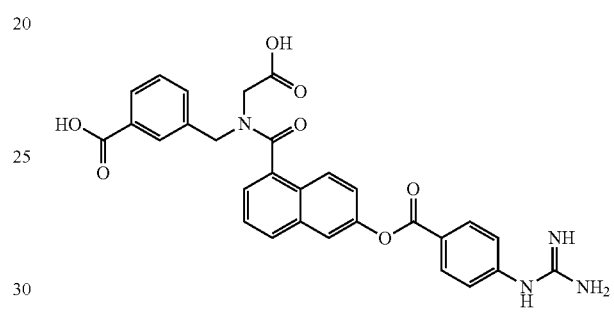
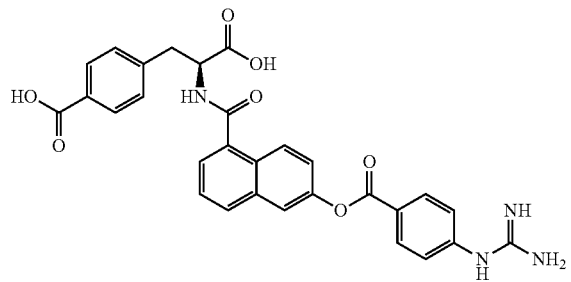
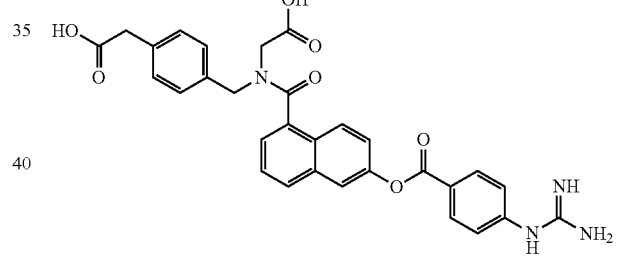
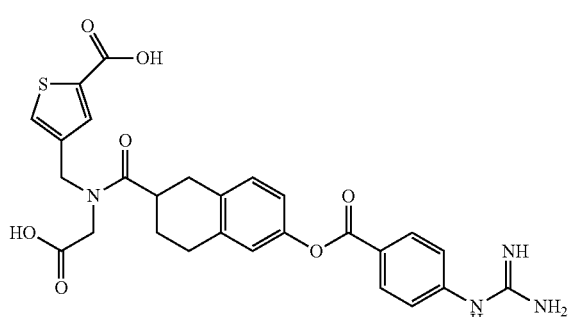
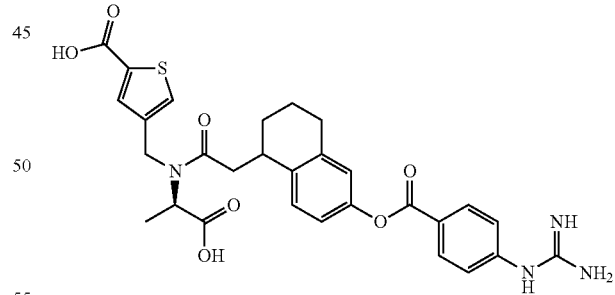
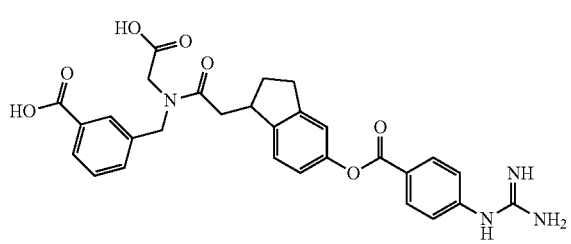
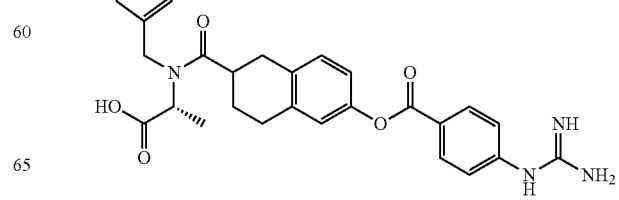

-continued

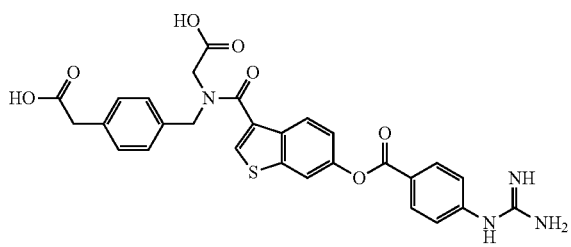
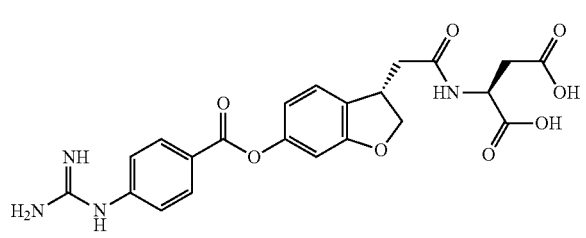
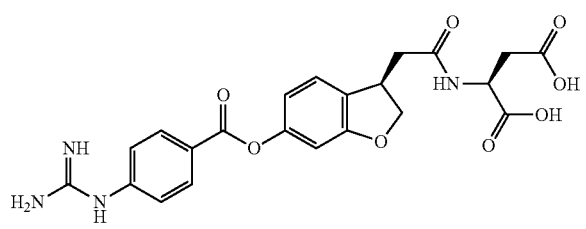
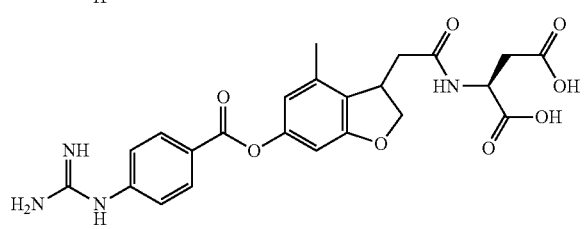
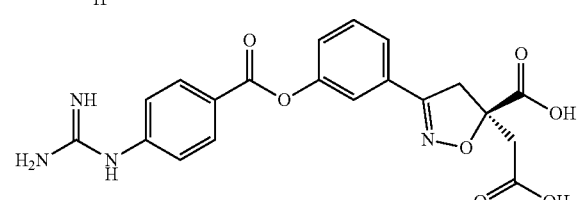
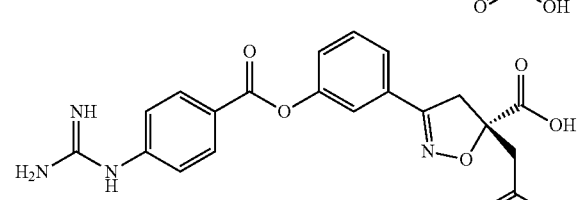
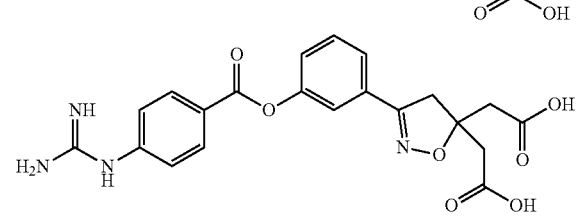

or an inhibitor molecule represented by the following general formula (II)

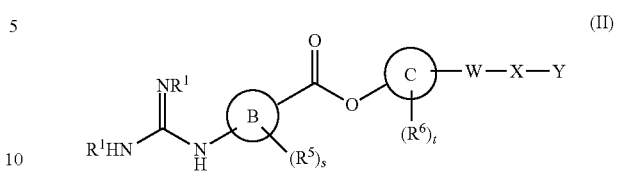

[wherein:
ring B and ring C each independently represent an aryl group or a heteroaryl group;
$R^1$ each independently represents a hydrogen atom or a —COO—($C_1$-$C_4$ alkyl group);
W represents a single bond or a $C_1$-$C_4$ alkylene group;
X represents —C(=O)—, —O—C(=O)—, or —NG-$SO_2$—;
G represents a hydrogen atom, a $C_1$-$C_4$ alkyl group, or —$COOR^2$;
$R^2$ represents a $C_1$-$C_4$ alkyl group optionally substituted with 1 to 5 aryl group(s);
Y represents —$NG^2G^4$, —$NG^2$-L-COOH, —$NG^2$-$L^1$-C(=O)—$NH_2$, —$NG^2$-$L^1$-C(=O)—$NG^3$-$L^2$-COOH, —$NG^2$-$L^1$-C(=O)—$NG^3$-$L^2$-C(=O)—$NG^3$-$L^2$-COOH, —$NG^2$-$L^1$-C(=O)—$NG^3$-$L^2$-C(=O)—$NH_2$, —$NG^2$-$L^3$-OH, or —$NG^2$-($CH_2$—$CH_2$—O)$_q$—$CH_2$—$CH_2$—COOH;
q represents an integer of 1 to 6;
$G^2$ and $G^3$ each independently represent a hydrogen atom, or a $C_1$-$C_6$ alkyl group optionally substituted with 1 to 5 substituent(s) independently selected from the group consisting of a phenyl group optionally substituted with 1 to 5 —$COOR^3$ group(s) and a —$COOR^2$ group;
$G^4$ represents a hydrogen atom, a $C_1$-$C_4$ alkyl group, or a $C_1$-$C_4$ alkoxy-$C_1$-$C_4$ alkyl group;
$R^3$ each independently represents a hydrogen atom or a $C_1$-$C_4$ alkyl group optionally substituted with 1 to 5 aryl group(s);
$L^1$ and $L^2$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_6$ alkylene group substituted with a $C_7$-$C_{12}$ aralkyl group optionally substituted with 1 to 5 substituent(s) independently selected from the group consisting of a hydroxy group and a carboxy group, a $C_1$-$C_4$ alkylene-phenylene group, or a phenylene-$C_1$-$C_4$ alkylene group;
$L^3$ represents a $C_1$-$C_4$ alkylene-phenylene group wherein the phenylene moiety is optionally substituted with 1 to 3 —$COOR^4$ group(s);
$R^4$ each independently represents a hydrogen atom or a $C_1$-$C_4$ alkyl group optionally substituted with 1 to 5 substituent(s) independently selected from the group consisting of an aryl group and a trimethylsilyl group;
$R^5$ and $R^6$ each independently represent a hydrogen atom, a halogen atom, a $C_1$-$C_4$ alkyl group, a $C_1$-$C_4$ alkoxy group, a carboxy group, or —C(=O)—$NG^2G^4$;
s and t each independently represent an integer of 1 to 4;
two or more $R^5$ and/or two or more $R^6$ may be the same or different with each other;
or any one of $R^5$ and any one of $R^6$ may be combined with each other to form a $C_1$-$C_4$ alkyleneoxy group]; and
Z represents a single bond, an arylene group, a heteroarylene group, or a $C_2$-$C_{30}$ alkylene group (provided that one or more methylene group(s) in the chain of said alkylene group may be replaced with group(s) independently selected from the group consisting of —C(=O)—, —$NR^7$—, —O—, —$SiR^8R^9$—, —$SO_2$—, an arylene group, and a heteroarylene group, $R^7$ represents a hydrogen atom or a $C_1$-$C_4$ alkyl group, $R^8$ and $R^9$ each independently represent a $C_1$-$C_4$ alkyl group, and r represents an integer of 0 to 2).

[3] The compound according to [2] or a pharmaceutically acceptable salt thereof, wherein $A^1$ and $A^2$ each independently represent an inhibitor residue formed by removing any one hydrogen atom or any one hydroxy group from the inhibitor molecule represented by general formula (II).

[4] The compound according to any one of [2] to [3] or a pharmaceutically acceptable salt thereof, wherein $A^1$ has a structure represented by

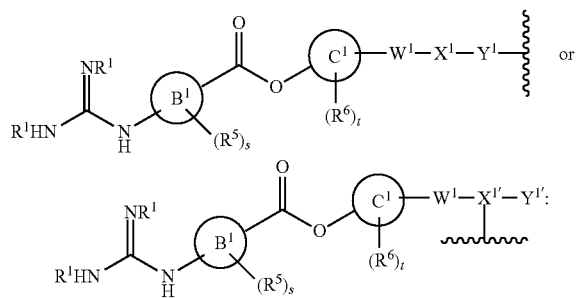

$A^2$ has a structure represented by

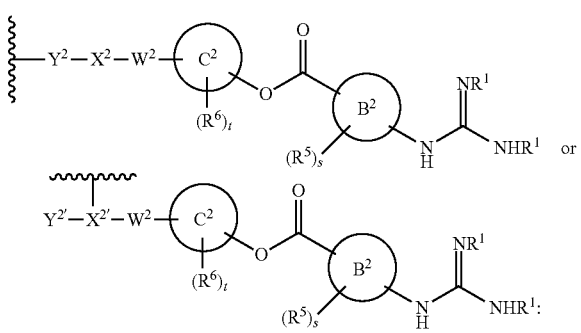

[wherein:

ring $B^1$, ring $B^2$, ring $C^1$, and ring $C^2$ each independently represent an aryl group;

$R^1$ each independently represents a hydrogen atom or a —COO—($C_1$-$C_4$ alkyl group);

$W^1$ and $W^2$ each independently represent a single bond or a $C_1$-$C_4$ alkylene group;

$X^1$ represents —C(=O)—, —O—C(=O)—, or —NG$^{11}$-SO$_2$—;

$X^{1'}$ represents —NG$^Z$-SO$_2$—;

$X^2$ represents —C(=O)—, —C(=O)—O—, or —SO$_2$—NG$^{12}$-;

$X^{2'}$ represents —SO$_2$—NG$^Z$-;

$G^{11}$ and $G^{12}$ each independently represent a hydrogen atom, a $C_1$-$C_4$ alkyl group, or —COOR$^2$;

$G^Z$ represents a single bond that links $X^{1'}$ or $X^{2'}$ to Z;

$R^2$ represents a $C_1$-$C_4$ alkyl group optionally substituted with 1 to 5 aryl group(s);

$Y^1$ represents —NG$^{21}$-, —NG$^{21}$-L$^{11}$-C(=O)—, —NG$^{21}$-L$^{11}$-C(=O)—NH—, —NG$^{21}$-L$^{11}$-C(=O)—NG$^{31}$-L$^{21}$-C(=O)—, —NG$^{21}$-L$^{11}$-C(=O)—NG$^{31}$-L$^{21}$-C(=O)—NH—, —NG$^{21}$-L$^3$-O—, or —NG$^{21}$-G$^{4'}$-;

$Y^{1'}$ represents —NG$^{21}$H, —NG$^{21}$-L$^{11}$-COOH, or —NG$^{21}$-L$^{11}$-C(=O)—NG$^{31}$-L$^{21}$-COOH;

$Y^2$ represents —NG$^{22}$-, —C(=O)-L$^{12}$-NG$^{22}$-, —NH—C(=O)-L$^{12}$-NG$^{22}$-, —C(=O)-L$^{22}$-NG$^{32}$-C(=O)-L$^{12}$-NG$^{22}$-, —NH—C(=O)-L$^{22}$-NG$^{32}$-C(=O)-L$^{12}$-NG$^{22}$-, —O-L$^3$-NG$^{22}$-, or -G$^{4'}$-NG$^{22}$-;

$Y^{2'}$ represents HNG$^{22}$-, HOOC-L$^{12}$-NG$^{22}$-, or HOOC-L$^{22}$-NG$^{32}$-C(=O)-L$^{12}$-NG$^{22}$-;

$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —COOR$^3$ group(s) and a —COOR$^3$ group;

$G^{4'}$ represents a $C_1$-$C_4$ alkylene group or a $C_1$-$C_4$ alkyleneoxy-$C_1$-$C_4$ alkylene group;

$R^3$ each independently represents a hydrogen atom or a $C_1$-$C_4$ alkyl group optionally substituted with 1 to 5 aryl group(s);

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —COOR$^4$ group(s), a $C_1$-$C_4$ alkylene-phenylene group, or a phenylene-$C_1$-$C_4$ alkylene group;

$L^3$ represents a $C_1$-$C_4$ alkylene-phenylene group wherein the phenylene moiety is optionally substituted with 1 to 3 —COOR$^4$ group(s);

$R^4$ each independently represents a hydrogen atom or a $C_1$-$C_4$ alkyl group optionally substituted with 1 to 5 substituent(s) independently selected from the group consisting of an aryl group and a trimethylsilyl group;

$R^5$ and $R^6$ each independently represent a hydrogen atom, a halogen atom, a $C_1$-$C_4$ alkyl group, or a $C_1$-$C_4$ alkoxy group;

s and t each independently represent an integer of 1 to 4;

two or more $R^5$ and/or two or more $R^6$ may be the same or different with each other;

or any one of $R^5$ and any one of $R^6$ may be combined with each other to form a $C_1$-$C_4$ alkyleneoxy group; and the symbol

∿∿∿∿ represents the point of attachment to Z]; and

Z represents a single bond, an arylene group, a heteroarylene group, or a $C_2$-$C_{30}$ alkylene group (provided that one or more methylene group(s) in the chain of said alkylene group may be replaced with group(s) independently selected from the group consisting of —C(=O)—, —NR$^7$—, —O—, an arylene group, and a heteroarylene group, and $R^7$ represents a hydrogen atom or a $C_1$-$C_4$ alkyl group).

[5] The compound according to [4] or a pharmaceutically acceptable salt thereof, wherein $A^1$ has a structure represented by

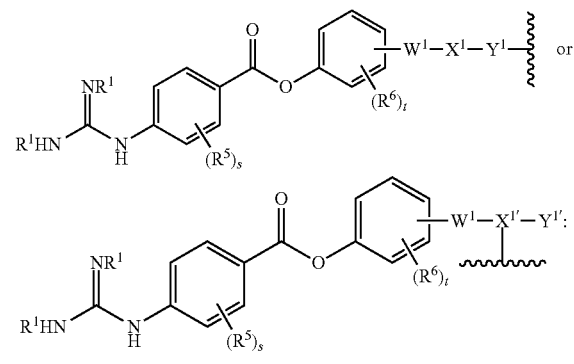

$A^2$ has a structure represented by

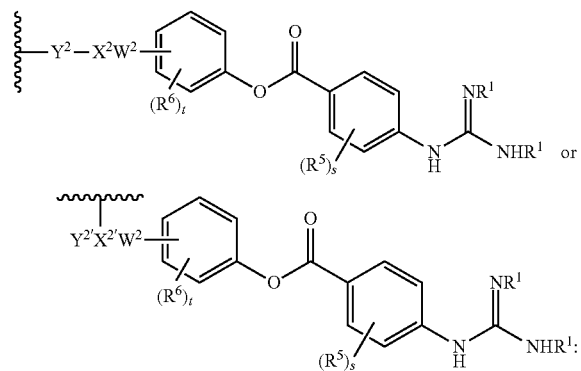

Z represents a single bond, a $C_6$-$C_{12}$ arylene group, $-(CH_2-CH_2-O)_m-CH_2-CH_2-$, $-(CH_2-O-CH_2)_m-$, $-(CH_2)_m-(C_6$-$C_{12}$ arylene)-$(CH_2)_m-$, or $-(CH_2)_n-$;

m represents an integer of 1 to 6; and n represents an integer of 2 to 12.

[6] The compound according to any one of [4] to [5] or a pharmaceutically acceptable salt thereof, wherein $A^1$ has a structure represented by

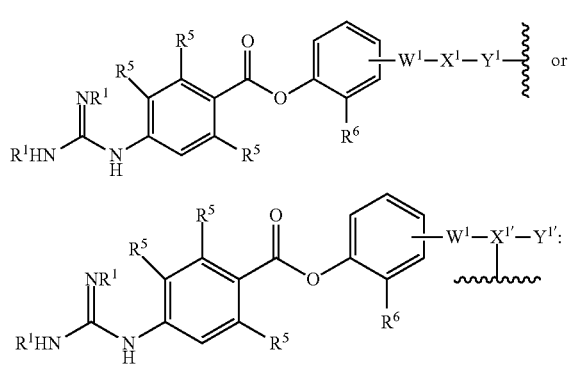

$A^2$ as a structure represented by

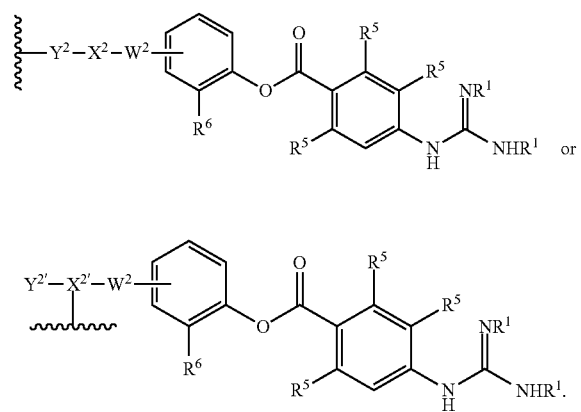

[7] The compound according to any one of [4] to [6] or a pharmaceutically acceptable salt thereof, wherein $A^1$ has a structure represented by

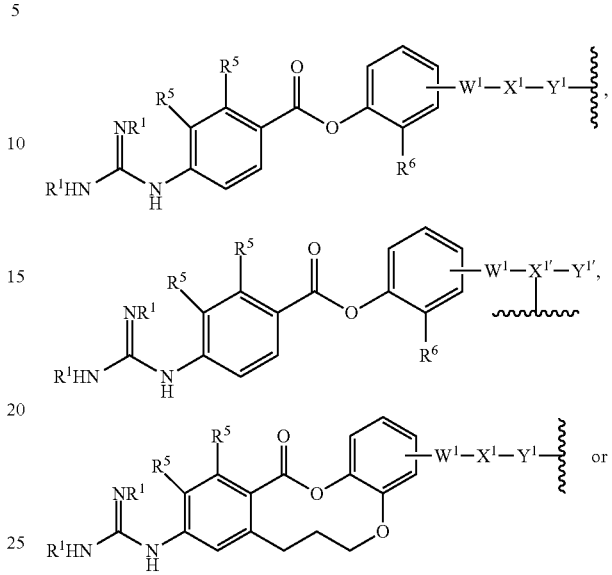

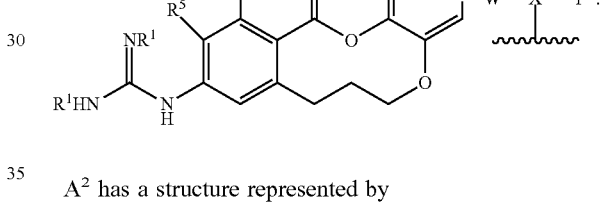

$A^2$ has a structure represented by

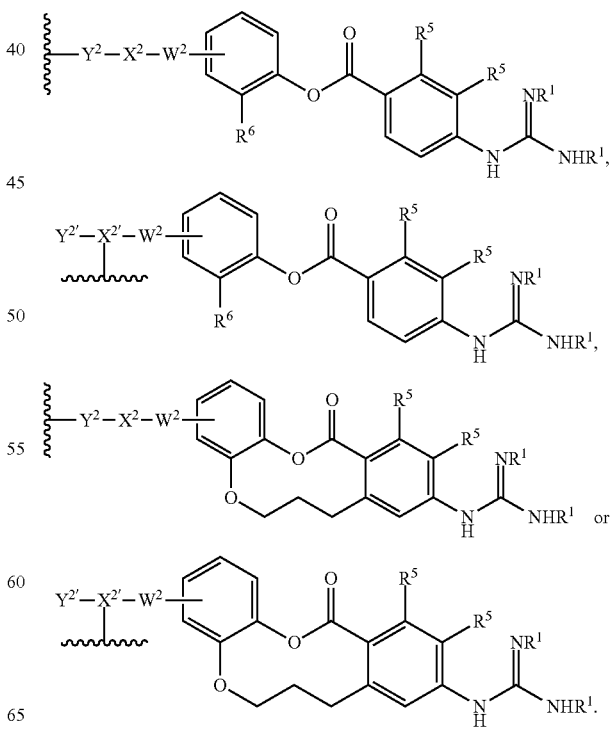

[8] The compound according to any one of [4] to [7] represented by the following general formula (III):

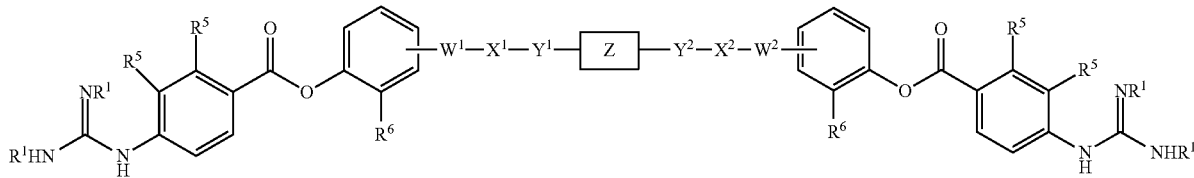

(III)

or the following general formula (IV):

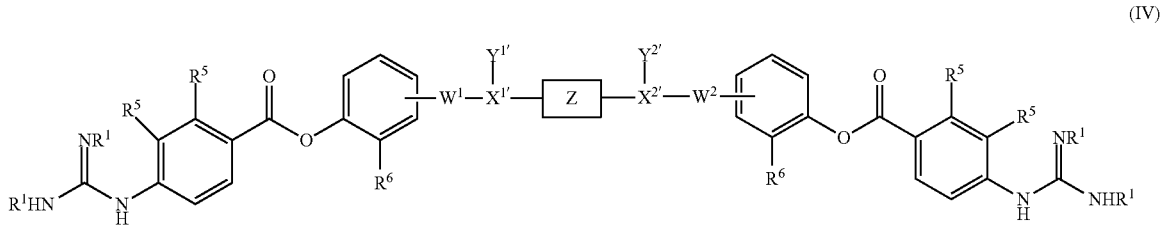

(IV)

or a pharmaceutically acceptable salt thereof.

[9] The compound according to [8] or a pharmaceutically acceptable salt thereof, wherein $R^1$ each independently represents a hydrogen atom or a tert-butoxycarbonyl group;

$W^1$ and $W^2$ each independently represent a single bond or $C_1$-$C_4$ alkylene group;

$X^1$ represents —C(=O)—, —O—C(=O)—, or —$NG^{11}$—$SO_2$—;

$X^{1'}$ represents —$NG^Z$-$SO_2$—;

$X^2$ represents —C(=O)—, —C(=O)—O—, or —$SO_2$—$NG^{12}$—;

$X^{2'}$ represents —$SO_2$—$NG^2$—;

$G^{11}$ and $G^{12}$ each independently represent a hydrogen atom, a $C_1$-$C_4$ alkyl group, or —$COOR^2$;

$G^Z$ represents a single bond that links $X^{1'}$ or $X^{2'}$ to Z;

$R^2$ represents a $C_1$-$C_4$ alkyl group optionally substituted with 1 to 5 aryl group(s);

$Y^1$ represents —$NG^{21}$—, —$NG^{21}$-$L^{11}$-C(=O)—, —$NG^{21}$-$L^{11}$-C(=O)—NH—, —$NG^{21}$-$L^{11}$-C(=O)—$NG^{31}$-$L^{21}$-C(=O)—, —$NG^{21}$-$L^{11}$-C(=O)—$NG^{31}$-$L^{21}$-C(=O)—NH—, —$NG^{21}$-$L^3$-O—, or —$NG^{21}$-$G^{4'}$—;

$Y^{1'}$ represents —$NG^{21}$H, —$NG^{21}$-$L^{11}$-COOH, or —$NG^{21}$-$L^{11}$-C(=O)—$NG^{31}$-$L^{21}$-COOH;

$Y^2$ represents —$NG^{22}$—, —C(=O)-$L^{12}$-$NG^{22}$—, —NH—C(=O)-$L^{12}$-$NG^{22}$—, —C(=O)-$L^{22}$-$NG^{32}$-C(=O)-$L^{12}$-$NG^{22}$—, —NH—C(=O)-$L^{22}$-$NG^{32}$. C(=O)-$L^{12}$-$NG^{22}$—, —O-$L^3$-$NG^{22}$—, or -$G^{4'}$-$NG^{22}$—;

$Y^{2'}$ represents $HNG^{22}$—, HOOC-$L^{12}$-$NG^{22}$—, or HOOC-$L^{22}$-$NG^{32}$-C(=O)-$L^{12}$-$NG^{22}$—;

$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —$COOR^3$ group(s) and a —$COOR^3$ group;

$G^{4'}$ represents a $C_1$-$C_4$ alkylene group or a $C_1$-$C_4$ alkyleneoxy-$C_1$-$C_4$ alkylene group;

$R^3$ each independently represents a hydrogen atom, a benzyl group, or a tert-butyl group;

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group;

$L^3$ represents a $C_1$-$C_4$ alkylene-phenylene group wherein the phenylene moiety is optionally substituted with 1 to 3 —$COOR^4$ group(s);

$R^4$ each independently represents a hydrogen atom, a benzyl group, a 2-(trimethylsilyl)ethyl group, or a tert-butyl group;

$R^5$ and $R^6$ each independently represent a hydrogen atom, a halogen atom, a $C_1$-$C_4$ alkyl group, or a $C_1$-$C_4$ alkoxy group;

each $R^5$ may be the same or different with each other;

Z represents a single bond, a $C_5$-$C_{12}$ arylene group, —(CH$_2$—CH$_2$—O)$_m$—CH$_2$—CH$_2$—, —(CH$_2$O—CH$_2$)$_m$—, —(CH$_2$)$_m$—($C_6$-$C_{12}$ arylene)-(CH$_2$)$_m$—, or —(CH$_2$)$_n$—;

m represents an integer of 1 to 6; and n represents an integer of 2 to 12.

[10] The compound according to [9] or a pharmaceutically acceptable salt thereof, wherein $R^1$ each independently represents a hydrogen atom or a tert-butoxycarbonyl group;

$W^1$ and $W^2$ each independently represent a single bond or a $C_1$-$C_4$ alkylene group;

$X^1$ represents —C(=O)—, —O—C(=O)—, or —$NG^{12}$—$SO_2$—;

$X^{1'}$ represents —$NG^Z$-$SO_2$—;

$X^2$ represents —C(=O)—, —C(=O)—O—, or —$SO_2$—$NG^{12}$—;

$X^{2'}$ represents —$SO_2$—$NG^Z$.

$G^{11}$ and $G^{22}$ each independently represent a hydrogen atom, a $C_1$-$C_4$ alkyl group, or —$COOR^2$;

$G^Z$ represents a single bond that links $X^{1'}$ or $X^{2'}$ to Z;

$R^2$ represents a $C_1$-$C_4$ alkyl group optionally substituted with 1 to 3 aryl group(s);

$Y^1$ represents —$NG^{21}$—, —$NG^{21}$-$L^{11}$-C(=O)—, —$NG^{21}$-$L^{11}$-C(=O)—NH—, —$NG^{21}$-$L^{11}$-C(=O)—$NG^{31}$-$L^{21}$-C(=O)—, —$NG^{21}$-$L^{11}$-C(=O)—$NG^{31}$-$L^{21}$-C(=O)—NH—, or —$NG^{21}$-$L^3$-O—;

Y$^{1'}$ represents —NG$^{21}$H, —NG$^{21}$-L-COOH, or —NG$^{21}$-L$^{11}$-C(=O)—NG$^{31}$-L$^{21}$-COOH;

Y$^2$ represents —NG$^{22}$-, —C(=O)-L$^{12}$-NG$^{22}$-, —NH—C(=O)-L$^{12}$-NG$^{22}$-, —C(=O)-L$^{22}$-NG$^{32}$-C(=O)-L$^{12}$-NG$^{22}$-, —NH—C(=O)-L$^{22}$-NG$^{32}$-C(=O)-L$^{12}$-NG$^{22}$-, or —O-L$^3$-NG$^{22}$-;

Y$^{2'}$ represents HNG$^{22}$-, HOOC-L$^{12}$-NG$^{22}$-, or HOOC-L$^{22}$-NG$^{32}$-C(=O)-L$^{12}$-NG$^{22}$-;

G$^{21}$, G$^{31}$, G$^{22}$, and G$^{32}$ each independently represent a hydrogen atom, or a C$_1$-C$_6$ alkyl group optionally substituted with 1 to 3 substituent(s) independently selected from the group consisting of a phenyl group optionally substituted with 1 to 3 —COOR$^3$ group(s) and a —COOR$^3$ group;

R$^3$ each independently represents a hydrogen atom, a benzyl group, or a tert-butyl group;

G$^{21}$ and G$^{22}$ each independently represent a hydrogen atom, or a C$_1$-C$_3$ alkyl group substituted with 1 to 3 carboxy group(s);

R$^5$ and R$^6$ each independently represent a hydrogen atom, a fluorine atom, a methyl group, or a methoxy group;

each R$^5$ may be the same or different with each other;

Z represents a single bond, [1,1'-biphenyl]-3,3'-diyl, —(CH$_2$—CH$_2$—O)$_m$—CH$_2$—CH$_2$—, —(CH$_2$—O—CH$_2$)$_m$—, —(CH$_2$)$_m$([1,1'-biphenyl]-3,3'-diyl)-(CH$_2$)$_m$—, or —(CH$_2$)$_n$—;

m represents an integer of 1 to 6; and n represents an integer of 2 to 12.

[12] The compound according to any one of [4] to [7] represented by the following general formula (V):

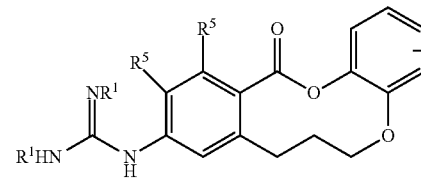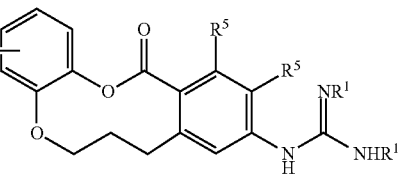

(V)

L$^{11}$, L$^{21}$, L$^{12}$, and L$^{22}$ each independently represent a C$_1$-C$_6$ alkylene group optionally substituted with 1 to 5 C$_1$-C$_6$ alkyl group(s) optionally substituted with 1 to 5 —COOR$^4$ group(s), a C$_1$-C$_4$ alkylene-phenylene group, or a phenylene-C$_1$-C$_4$ alkylene group;

L$^3$ represents a C$_1$-C$_2$ alkylene-phenylene group wherein the phenylene moiety is optionally substituted with 1 to 2 —COOR$^4$ group(s);

R$^4$ each independently represents a hydrogen atom, a benzyl group, a 2-(trimethylsilyl)ethyl group, or a tert-butyl group;

R$^5$ and R$^6$ each independently represent a hydrogen atom, a halogen atom, a C$_1$-C$_4$ alkyl group, or a C$_1$-C$_4$ alkoxy group;

each R$^5$ may be the same or different with each other;

Z represents a single bond, a biphenylene group, —(CH$_2$—CH$_2$—O)$_m$—CH$_2$—CH$_2$—, —(CH$_2$—O—CH$_2$)$_m$—, —(CH$_2$)$_m$-biphenylene-(CH$_2$)$_m$—, or —(CH$_2$)$_n$—;

m represents an integer of 1 to 6; and n represents an integer of 2 to 12.

[11] The compound according to [10] or a pharmaceutically acceptable salt thereof, wherein R$^1$ each represents a hydrogen atom;

W$^1$ and W$^2$ each independently represent a single bond or a C$_1$-C$_4$ alkylene group;

X$^1$ represents —C(=O)— or —NG$^{11}$-SO$_2$—;

X$^{1'}$ represents —NG$^Z$-SO$_2$—;

X$^2$ represents —C(=O)— or —SO$_2$—NG$^1$-;

X$^{2'}$ represents —SO$_2$—NG$^Z$-;

G$^{11}$ and G$^{12}$ each independently represent a hydrogen atom or —COOR$^2$;

G$^Z$ represents a single bond that links X$^{1'}$ or X$^{2'}$ to Z;

R$^2$ represents a C$_1$-C$_4$ alkyl group optionally substituted with one phenyl group;

Y$^1$ represents —NG$^{21}$-;

Y$^{1'}$ represents —NG$^{21}$H;

Y$^2$ represents —NG$^{22}$-;

Y$^{2'}$ represents HNG$^{22}$-;

[wherein:

R$^1$ each independently represents a hydrogen atom or a —COO—(C$_1$-C$_4$ alkyl group);

W$^1$ and W$^2$ each independently represent a single bond or a C$_1$-C$_4$ alkylene group;

X$^1$ represents —C(=O)— or —NG$^1$-SO$_2$—;

X$^2$ represents —C(=O)— or —SO$_2$—NG$^{12}$-;

G$^{11}$ and G$^{12}$ each independently represent a hydrogen atom, a C$_1$-C$_4$ alkyl group, or —COOR$^2$;

R$^Z$ represents a C$_1$-C$_4$ alkyl group optionally substituted with 1 to 5 aryl group(s);

Y$^1$ represents —NG$^{21}$-, —NG$^{21}$-L$^{11}$-C(=O)—, —NG$^2$-L$^{11}$-C(=O)—NH—, —NG$^{21}$-L$^{11}$-C(=O)—NG$^{31}$-L$^{21}$-C(=O)—, —NG$^{21}$-L$^{11}$-C(=O)—NG$^{31}$-L$^{21}$-C(=O)—NH—, —NG$^{21}$-L$^3$-O—, or —NG$^{21}$-G$^{4'}$-;

Y$^2$ represents —NG$^{22}$-, —C(=O)-L$^{12}$-NG$^{22}$-, —NH—C(=O)-L$^{12}$-NG$^{22}$-, —C(=O)-L$^{22}$-NG$^{32}$-C(=O)-L$^{12}$-NG$^{22}$-, —NH—C(=O)-L$^{22}$-NG$^{32}$-C(=O)-L$^{12}$-NG$^{22}$-, —O-L$^3$-NG$^{22}$-, or -G$^{4'}$-NG$^{22}$-;

G$^{21}$, G$^{31}$, G$^{22}$, and G$^{32}$ each independently represent a hydrogen atom, or a C$_1$-C$_6$ alkyl group optionally substituted with 1 to 5 substituent(s) independently selected from the group consisting of a phenyl group optionally substituted with 1 to 5-COOR$^3$ group(s) and a —COOR$^3$ group;

G$^{4'}$ represents a C$_1$-C$_4$ alkylene group or a C$_1$-C$_4$ alkyleneoxy-C$_1$-C$_4$ alkylene group;

R$^3$ each independently represents a hydrogen atom or a C$_1$-C$_4$ alkyl group optionally substituted with 1 to 5 aryl group(s);

L$^1$, L$^{21}$, L$^{12}$, and L$^{22}$ each independently represent a C$_1$-C$_6$ alkylene group optionally substituted with 1 to 5 C$_1$-C$_6$ alkyl group(s) optionally substituted with 1 to 5 —COOR$^4$ group(s), a C$_1$-C$_4$ alkylene-phenylene group, or a phenylene-C$_1$-C$_4$ alkylene group;

L$^3$ represents a C$_1$-C$_4$ alkylene-phenylene group wherein the phenylene moiety is optionally substituted with 1 to 3 —COOR$^4$ group(s);

R$^4$ each independently represents a hydrogen atom or a C$_1$-C$_4$ alkyl group optionally substituted with 1 to 5 substituent(s) independently selected from the group consisting of an aryl group and a trimethylsilyl group;

$R^5$ each independently represents a hydrogen atom, a halogen atom, a $C_1$-$C_4$ alkyl group, or a $C_1$—C alkoxy group;

Z represents a single bond, a $C_6$-$C_2$ arylene group, —(CH$_2$—CH$_2$—O)$_m$—CH$_2$—CH$_2$—, —(CH$_2$—O—CH$_2$)$_m$—, —(CH$_2$)$_m$—($C_6$-$C_{12}$ arylene)-(CH$_2$)$_m$—, or —(CH$_2$)$_n$—;

m represents an integer of 1 to 6; and n represents an integer of 2 to 12]

or a pharmaceutically acceptable salt thereof.

[13] The compound according to [12] represented by the following general formula (VI):

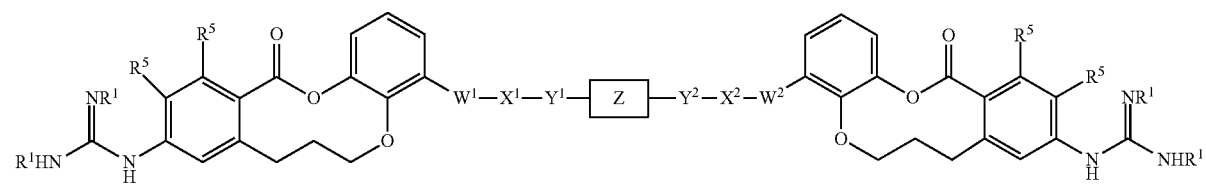

(VI)

or a pharmaceutically acceptable salt thereof.

[14] The compound according to [13] or a pharmaceutically acceptable salt thereof, wherein $R^1$ each independently represents a hydrogen atom or a tert-butoxycarbonyl group;

$W^1$ and $W^2$ each independently represent a single bond or a $C_1$-$C_2$ alkylene group;

$X^1$ represents —C(=O)— or —NG$^{11}$-SO$_2$—;

$X^2$ represents —C(=O)— or —SO$_2$—NG$^2$-;

$G^{11}$ and $G^{12}$ each represent a hydrogen atom;

$Y^1$ represents —NG$^{21}$-, —NG$^{21}$-L$^{11}$-C(=O)—, —NG$^{21}$-L$^{11}$-C(=O)—NH—, —NG$^{21}$-L$^{11}$-C(=O)—NG$^{31}$-L$^{21}$-C(=O)—, —NG$^{21}$-L$^{11}$-C(=O)—NG$^{32}$-L$^{21}$-C(=O)—NH—, —NG$^{21}$-L$^3$-O—, or —NG$^{21}$-G$^{4'}$-;

$Y^2$ represents —NG$^{22}$-, —C(=O)-L$^{12}$-NG$^{22}$-, —NH—C(=O)-L$^{12}$-NG$^{22}$-, —C(=O)-L$^2$-NG$^{32}$-C(=O)-L$^{12}$-NG$^{22}$-, —NH—C(=O)-L$^{22}$-NG$^{32}$-C(=O)-L$^{12}$-NG$^{22}$-, —O-L$^3$-NG$^{22}$-, or -G$^{4'}$-NG$^2$-;

$G^{21}$, $G^{31}$, $G^{22}$, and $G^{32}$ each independently represent a hydrogen atom, or a $C_1$-$C_3$ alkyl group optionally substituted with 1 to 3 —COOR$^3$ group(s);

$G^{4'}$ represents a $C_1$-$C_2$ alkylene group or a $C_1$-$C_2$ alkyleneoxy-$C_1$-$C_2$ alkylene group;

$R^3$ each independently represents a hydrogen atom or a tert-butyl group;

$L^{11}$, $L^{21}$, $L^{12}$, and $L^{22}$ each independently represent a $C_1$-$C_2$ alkylene group;

$L^3$ represents a $C_1$-$C_4$ alkylene-phenylene group wherein the phenylene moiety is optionally substituted with 1 to 3 —COOR$^4$ group(s);

$R^4$ each independently represents a hydrogen atom or a $C_1$-$C_4$ alkyl group optionally substituted with 1 to 5 substituent(s) independently selected from the group consisting of an aryl group and a trimethylsilyl group;

$R^5$ each independently represents a hydrogen atom, a halogen atom, a $C_1$-$C_4$ alkyl group, or a $C_1$-$C_4$ alkoxy group;

Z represents a single bond, a biphenylene group, —(CH$_2$—CH$_2$—O)$_m$—CH$_2$—CH$_2$—, —(CH$_2$—O—CH$_2$)$_m$—, —(CH$_2$)$_m$-biphenylene-(CH$_2$)$_m$—, or —(CH$_2$)$_n$—;

m represents an integer of 1 to 6; and n represents an integer of 2 to 12.

[15] The compound according to [14] or a pharmaceutically acceptable salt thereof, wherein $R^1$ each represents a hydrogen atom;

$W^1$ and $W^2$ each represent a single bond;

$X^1$ represents —C(O)—;

$X^2$ represents —C(=O)—;

$Y^1$ represents —NG$^2$-, —NG$^{21}$-L$^3$-O—, or —NG$^{21}$-G$^{4'}$-;

$Y^2$ represents —NG$^{22}$-, —O-L$^3$-NG$^{22}$-, or -G$^{4'}$-NG$^{22}$-;

$G^{21}$ and $G^{22}$ each independently represent a $C_1$-$C_3$ alkyl group substituted with 1 to 3 carboxy group(s);

$G^{4'}$ represents a $C_1$-$C_2$ alkylene group or a $C_1$-$C_2$ alkyleneoxy-$C_1$-$C_2$ alkylene group;

$L^3$ represents a $C_1$-$C_2$ alkylene-phenylene group wherein the phenylene moiety is optionally substituted with 1 to 2 —COOR$^4$ group(s);

$R^4$ each independently represents a hydrogen atom or a $C_1$-$C_4$ alkyl group optionally substituted with 1 to 5 substituent(s) independently selected from the group consisting of an aryl group and a trimethylsilyl group;

$R^5$ each independently represents a hydrogen atom, a fluorine atom, a methyl group, or a methoxy group;

Z represents a single bond, [1,1'-biphenyl]-3,3'-diyl, —(CH$_2$—CH$_2$—O)$_m$—CH$_2$—CH$_2$—, —(CH$_2$—O—CH$_2$)$_m$—, —(CH$_2$)$_m$—([1,1'-biphenyl]-3,3'-diyl)-(CH$_2$)$_m$—, or —(CH$_2$)$_n$—;

m represents an integer of 1 to 6; and n represents an integer of 2 to 12.

[16] The compound according to any one of [1] to [6] or a pharmaceutically acceptable salt thereof, wherein $A^1$ has a structure represented by

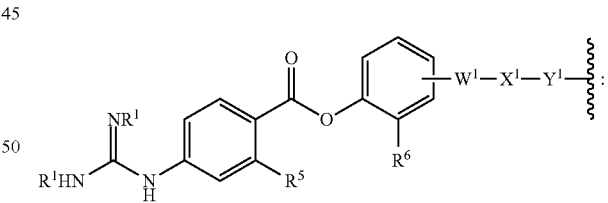

$A^2$ has a structure represented by

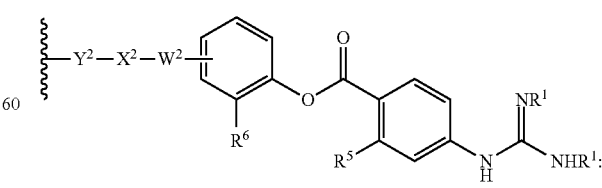

[wherein:

$R^1$ each independently represents a hydrogen atom or a —COO—($C_1$-$C_4$ alkyl group);

W$^1$ and W$^2$ each independently represent a single bond or a C$_1$-C$_4$ alkylene group;

X$^1$ represents —C(=O)—, —O—C(=O)—, or —NG$^{11}$-SO$_2$—;

X$^2$ represents —C(=O)—, —C(=O)—O—, or —SO$_2$—NG$^{12}$-;

G$^{11}$ and G$^{12}$ each independently represent a hydrogen atom or —COOR$^2$;

R$^2$ represents a C$_1$-C$_4$ alkyl group optionally substituted with 1 to 5 aryl group(s);

Y$^1$ represents —NG$^{21}$-, —NG$^{21}$-L$^{11}$-C(=O)—NH—, or —NG$^{21}$-L$^{11}$-C(=O)—NG$^{31}$-L$^{21}$-C(=O)—NH—;

Y$^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$;

G$^{21}$, G$^{31}$, G$^{22}$, and G$^{32}$ each independently represent a hydrogen atom, or a C$_1$-C$_6$ alkyl group optionally substituted with 1 to 5 substituent(s) independently selected from the group consisting of a phenyl group optionally substituted with 1 to 5 —COOR$^3$ group(s) and a —COOR$^3$ group;

R$^3$ each independently represents a hydrogen atom or a C$_1$-C$_4$ alkyl group optionally substituted with 1 to 5 aryl group(s);

L$^{11}$, L$^{21}$, L$^{12}$, and L$^{22}$ each independently represent a C$_1$-C$_6$ alkylene group optionally substituted with 1 to 5 C$_1$-C$_6$ alkyl group(s) optionally substituted with 1 to 5 —COOR$^4$ group(s), a C$_1$-C$_4$ alkylene-phenylene group, or a phenylene-C$_1$-C$_4$ alkylene group;

R$^4$ each independently represents a hydrogen atom or a C$_1$-C$_4$ alkyl group optionally substituted with 1 to 5 aryl group(s);

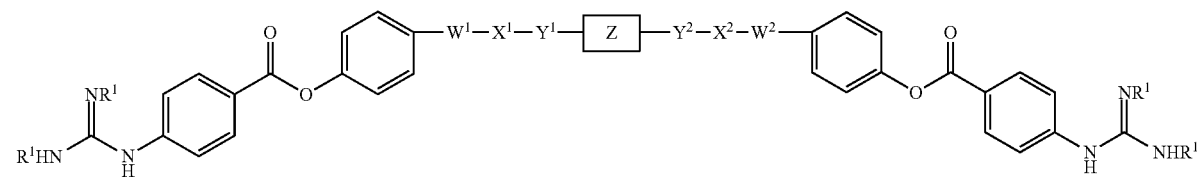

R$^5$ and R$^6$ each independently represent a hydrogen atom, a C$_1$-C$_4$ alkyl group, or a C$_1$-C$_4$ alkoxy group, or R$^5$ and R$^6$ may be combined with each other to form a C$_1$-C$_4$ alkyleneoxy group; and the symbol

∽∽∽∽∽ represents the point of attachment to Z]; and

Z represents —(CH$_2$—CH$_2$—O)$_m$—CH$_2$—CH$_2$— or —(CH$_2$)$_n$—;

m represents an integer of 1 to 6; and n represents an integer of 2 to 12.

[17] The compound according to [16] or a pharmaceutically acceptable salt thereof, wherein A$^1$ has a structure represented by

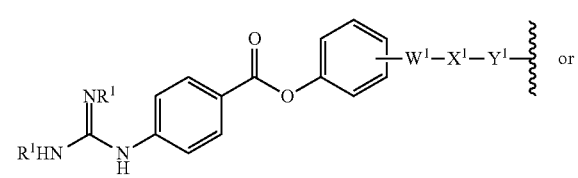

or

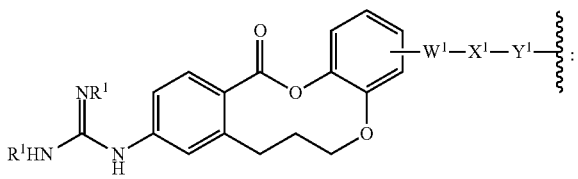

and

A$^2$ has a structure represented by

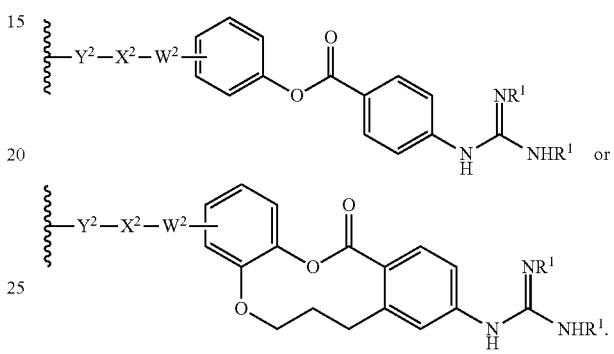

[18] The compound according to any one of [1] and [16] to [17] represented by the following general formula (VII):

(VII)

[wherein:

R$^1$ each independently represents a hydrogen atom or a —COO—(C$_1$-C$_4$ alkyl group);

W$^1$ and W$^2$ each independently represent a single bond or a C$_1$-C$_4$ alkylene group;

X$^1$ represents —O—C(=O)— or —NG$^1$-SO$_2$—;

X$^2$ represents —C(=O)—O— or —SO$_2$—NG$^{12}$-;

G$^{11}$ and G$^{12}$ each independently represent a hydrogen atom or —COOR$^2$;

R$^2$ represents a C$_1$-C$_4$ alkyl group optionally substituted with 1 to 5 aryl group(s);

Y$^1$ represents —NG$^{21}$-, —NG$^{21}$-L$^{11}$-C(=O)—NH—, or —NG$^{21}$-L$^{11}$-C(=O)—NG$^{31}$-L$^{21}$-C(=O)—NH—;

Y$^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;

G$^{21}$, G$^{31}$, G$^{22}$, and G$^{32}$ each independently represent a hydrogen atom, or a C$_1$-C$_6$ alkyl group optionally substituted with 1 to 5 substituent(s) independently selected from the group consisting of a phenyl group optionally substituted with 1 to 5 —COOR$^3$ group(s) and a —COOR$^3$ group;

R$^3$ each independently represents a hydrogen atom or a C$_1$-C$_4$ alkyl group optionally substituted with 1 to 5 aryl group(s);

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —COOR$^4$ group(s), a $C_1$-$C_4$ alkylene-phenylene group, or a phenylene-$C_1$-$C_4$ alkylene group;

R$^4$ each independently represents a hydrogen atom or a $C_1$-$C_4$ alkyl group optionally substituted with 1 to 5 aryl group(s);

Z represents —(CH$_2$—CH$_2$—O)$_m$—CH$_2$—CH$_2$— or —(CH$_2$)$_n$—;

m represents an integer of 1 to 6; and n represents an integer of 2 to 12]

or a pharmaceutically acceptable salt thereof.

[19] The compound according to [18] or a pharmaceutically acceptable salt thereof, wherein R$^1$ each independently represents a hydrogen atom or a tert-butoxycarbonyl group;

W$^1$ and W$^2$ each represent a $C_1$-$C_4$ alkylene group;

X$^1$ represents —O—C(=C)— or —NG$^{11}$-SO$_2$—;

X$^2$ represents —C(=O)—O— or —SO$_2$—NG$^{12}$—;

G$^{11}$ and G$^{12}$ each independently represent a hydrogen atom or —COOR$^2$;

R$^1$ represents a $C_1$-$C_4$ alkyl group optionally substituted with 1 to 3 phenyl group(s);

Y$^1$ represents —NG$^{21}$-, —NG$^{21}$-L$^{11}$-C(=O)—NH—, or —NG$^{21}$-L$^{11}$-C(=O)—NG$^{31}$-L$^{21}$-C(=O)—NH—;

Y$^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;

G$^{21}$, G$^{31}$, G$^{22}$, and G$^{32}$ each independently represent a hydrogen atom, or a $C_1$-$C_4$ alkyl group optionally substituted with 1 to 3 substituent(s) independently selected from the group consisting of a phenyl group optionally substituted with 1 to 3 —COOR$^3$ group(s) and a —COOR$^3$ group;

R$^3$ each independently represents a hydrogen atom, a benzyl group, or a tert-butyl group;

L$^{11}$, L$^{21}$, L$^{12}$, and L$^{22}$ each independently represent a $C_1$-$C_6$ alkylene group optionally substituted with 1 to 5 $C_3$-$C_6$ alkyl group(s) optionally substituted with 1 to 5 —COOR$^4$ group(s), a $C_1$-$C_4$ alkylene-phenylene group, or a phenylene-$C_1$-$C_4$ alkylene group;

R$^4$ each independently represents a hydrogen atom, a benzyl group, or a tert-butyl group;

Z represents —(CH$_2$—CH$_2$—O)$_m$—CH$_2$—CH$_2$— or —(CH$_2$)$_n$—;

m represents an integer of 1 to 6; and n represents an integer of 2 to 12.

[20] The compound according to [19] or a pharmaceutically acceptable salt thereof, wherein R$^1$ each independently represents a hydrogen atom or a tert-butoxycarbonyl group;

W$^1$ and W$^2$ each represent a $C_1$-$C_2$ alkylene group;

X$^1$ represents —O—C(=O)— or —NG$^{11}$-SO$_2$—;

X$^2$ represents —C(=O)—O— or —SO$_2$—NG$^{12}$—;

G$^{11}$ and G$^{12}$ each independently represent a hydrogen atom or —COOR$^2$;

R$^2$ represents a $C_1$-$C_4$ alkyl group optionally substituted with one phenyl group;

Y$^1$ represents —NG$^{21}$-, —NG$^{21}$-L$^{11}$-C(=O)—NH—, or —NG$^{21}$-L$^{11}$-C(=O)—NG$^{31}$-L$^{21}$-C(=O)—NH—;

Y$^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;

G$^{21}$, G$^{31}$, G$^{22}$, and G$^{32}$ each independently represent a hydrogen atom, or a $C_1$-$C_2$ alkyl group optionally substituted with 1 to 3 substituent(s) independently selected from the group consisting of a phenyl group optionally substituted with one —COOR$^3$ group and a —COOR$^3$ group;

R$^3$ each independently represents a hydrogen atom or a tert-butyl group;

L$^{11}$, L$^{21}$, L$^{12}$, and L$^{22}$ each independently represent a $C_1$-$C_2$ alkylene group optionally substituted with 1 to 2 $C_1$-$C_2$ alkyl group(s) optionally substituted with 1 to 2 —COOR$^4$ group(s), a $C_1$-$C_2$ alkylene-phenylene group, or a phenylene-$C_1$-$C_2$ alkylene group;

R$^4$ each independently represents a hydrogen atom or a term-butyl group;

Z represents —(CH$_2$—CH$_2$—O)$_m$—CH$_2$—CH$_2$— or —(CH$_2$)$_n$—;

m represents an integer of 1 to 6; and n represents an integer of 2 to 12.

[21] The compound according to [20] or a pharmaceutically acceptable salt thereof, wherein R$^1$ each represents a hydrogen atom;

W$^1$ and W$^2$ each represent a $C_1$-$C_2$ alkylene group;

X$^1$ represents —NG$^{11}$-SO$_2$—;

X$^2$ represents —SO$_2$—NG$^{12}$-;

G$^{11}$ and G$^{12}$ each independently represent a hydrogen atom or —COOR$^2$;

R$^2$ represents a $C_1$-$C_4$ alkyl group optionally substituted with one phenyl group;

Y$^1$ represents —NG$^{21}$-;

Y$^2$ represents —NG$^{22}$-;

G$^{21}$ and G$^{22}$ each independently represent a $C_1$-$C_3$ alkyl group substituted with 1 to 3 substituent(s) independently selected from the group consisting of a phenyl group substituted with one carboxy group and a carboxy group;

Z represents —(CH$_2$—CH$_2$—O)$_m$—CH$_2$—CH$_2$— or —(CH$_2$)$_n$—;

m represents an integer of 1 to 6; and n represents an integer of 2 to 12.

[22] The compound according to any one of [1] and [16] to [17] represented by the following general formula (VIII):

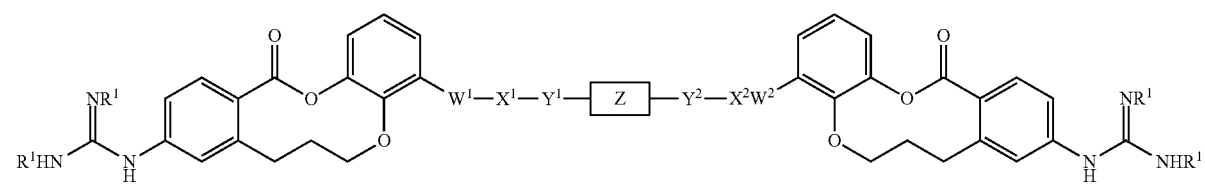

(VIII)

[wherein:

R$^1$ each independently represents a hydrogen atom or a —COO—(C$_1$-$C_4$ alkyl group);

W$^1$ and W$^2$ each independently represent a single bond or a $C_1$-$C_4$ alkylene group;

X$^1$ represents —C(=O)— or —NG$^{11}$-SO$_2$—;

X$^2$ represents —C(=O)— or —SO$_2$—NG$^{12}$-;

$G^{11}$ and $G^{12}$ each independently represent a hydrogen atom or —COOR$^2$;

R$^2$ represents a $C_1$-$C_4$ alkyl group optionally substituted with 1 to 5 aryl group(s);

Y$^1$ represents —NG$^{21}$-, —NG$^{21}$-L$^{11}$-C(=O)—NH—, or —NG$^{21}$-L$^{11}$-C(=O)—NG$^{31}$-L$^{21}$-C(=O)—NH—;

Y$^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;

$G^{21}$, $C^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —COOR$^3$ group(s) and a —COOR$^3$ group;

R$^3$ each independently represents a hydrogen atom or a $C_1$-$C_4$ alkyl group optionally substituted with 1 to 5 aryl group(s);

L$^{11}$, L$^{21}$, L$^{12}$, and L$^{22}$ each independently represent a $C_1$-$C_6$ alkylene group optionally substituted with 1 to 5 $C_1$-$C_6$ alkyl group(s) optionally substituted with 1 to 5 —COOR$^4$ group(s), a $C_1$-$C_4$ alkylene-phenylene group, or a phenylene-$C_1$-$C_4$ alkylene group;

R$^4$ each independently represents a hydrogen atom or a $C_1$-$C_4$ alkyl group optionally substituted with 1 to 5 aryl group(s);

Z represents —(CH$_2$—CH$_2$—O)$_n$—CH$_2$—CH$_2$— or —(CH$_2$)$_n$—;

m represents an integer of 1 to 6; and n represents an integer of 2 to 12]

or a pharmaceutically acceptable salt thereof.

[23] The compound according to [22] or a pharmaceutically acceptable salt thereof, wherein R$^1$ each independently represents a hydrogen atom or a tert-butoxycarbonyl group;

W$^1$ and W$^2$ each independently represent a single bond or a $C_1$-$C_2$ alkylene group;

X$^1$ represents —C(O)— or —NG$^{11}$-SO$_2$—;

X$^2$ represents —C(=O)— or —SO$_2$—NG$^{12}$-;

$G^{11}$ and $G^{12}$ each represent a hydrogen atom;

Y$^1$ represents —NG$^{21}$-, —NG$^{21}$-L$^{11}$-C(=O)—NH—, or —NG$^{21}$-L$^{11}$-C(=O)—NG$^{31}$-L$^{21}$-C(=O)—NH—;

Y$^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;

$G^{21}$, $G^{31}$, $G^{22}$, and $G^{32}$ each independently represent a hydrogen atom, or a $C_1$-$C_3$ alkyl group optionally substituted with 1 to 3 —COOR$^3$ group(s);

R$^3$ each independently represents a hydrogen atom or a tert-butyl group;

L$^{11}$, L$^{21}$, L$^{12}$, and L$^{22}$ each independently represent a $C_1$-$C_2$ alkylene group;

Z represents —(CH$_2$—CH$_2$—O)$_m$—CH$_2$—CH$_2$— or —(CH$_2$)$_n$—;

m represents an integer of 1 to 6; and n represents an integer of 2 to 12.

[24] The compound according to [23] or a pharmaceutically acceptable salt thereof, wherein R$^1$ each represents a hydrogen atom;

W$^1$ and W$^2$ each represent a single bond;

X$^1$ represents —C(=O)—;

X$^2$ represents —C(=O)—;

Y$^1$ represents —NG$^{21}$-;

Y$^2$ represents —NG$^{22}$-;

$G^{21}$ and $G^{22}$ each independently represent a $C_1$-$C_3$ alkyl group substituted with 1 to 3 carboxy group(s);

Z represents —(CH$_2$—CH$_2$—O)$_m$—CH$_n$—CH$_2$—; and m represents an integer of 1 to 6.

[25] The compound according to any one of [1] to [7] selected from the group consisting of (2S,2'S)-2,2'-((oxybis(ethane-2,1-diyl))bis((N-(4-((4-guanidinobenzoyl)oxy)benzyl)sulfamoyl)azanediyl))disuccinic acid;

(2S,13S)-3,12-bis(N-(4-((4-guanidinobenzoyl)oxy)benzyl)sulfamoyl)-6,9-dioxa-3,12-diazatetradecane-1,2,13,14-tetracarboxylic acid;

(2S,16S)-3,15-bis(N-(4-((4-guanidinobenzoyl)oxy)benzyl)sulfamoyl)-6,9,12-trioxa-3,15-diazaheptadecane-1,2,16,17-tetracarboxylic acid;

(2S,19S)-3,18-bis(N-(4-((4-guanidinobenzoyl)oxy)benzyl)sulfamoyl)-6,9,12,15-tetraoxa-3,18-diazaicosane-1,2,19,20-tetracarboxylic acid;

(2S,22S)-3,21-bis(N-(4-((4-guanidinobenzoyl)oxy)benzyl)sulfamoyl)-6,9,12,15,18-pentaoxa-3,21-diazatricosane-1,2,22,23-tetracarboxylic acid;

(2S,25S)-3,24-bis(N-(4-((4-guanidinobenzoyl)oxy)benzyl)sulfamoyl)-6,9,12,15,18,21-hexaoxa-3,24-diazahexacosane-1,2,25,26-tetracarboxylic acid;

(2S,2'S)-2,2'-(propane-1,3-diylbis((N-(4-((4-guanidinobenzoyl)oxy)benzyl)sulfamoyl)azanediyl))disuccinic acid;

(2S,2'S)-2,2'-(butane-1,4-diylbis((N-(4-((4-guanidinobenzoyl)oxy)benzyl)sulfamoyl)azanediyl))disuccinic acid;

(2S,2'S)-2,2'-(pentane-1,5-diylbis((N-(4-((4-guanidinobenzoyl)oxy)benzyl)sulfamoyl)azanediyl))disuccinic acid:

3,18-bis(((4-((4-guanidinobenzoyl)oxy)benzyl)oxy)carbonyl)-6,9,12,15-tetraoxa-3,18-diazaicosane-1,2,19,20-tetracarboxylic acid;

2,2'-(1,20-bis(4-((4-guanidinobenzoyl)oxy)phenyl)-3,18-dioxo-2,19-dioxa-4,17-diazaicosane-4,17-diyl)disuccinic acid;

(3S,6S,25S,28S)-6,25-bis(carboxymethyl)-3,28-bis((((4-((4-guanidinobenzoyl)oxy)benzyl)oxy)carbonyl)amino)-4,7,24,27-tetraoxo-11,14,17,20-tetraoxa-5,8,23,26-tetraazatriacontane-1,30-dioic acid;

(3S,6S,23S,26S)-6,23-bis(carboxymethyl)-3,26-bis((((4-((4-guanidinobenzoyl)oxy)benzyl)oxy)carbonyl)amino)-4,7,22,25-tetraoxo-5,8,21,24-tetraazaoctacosane-1,28-dioic acid;

(3S,22S)-3,22-bis(2-((3-carboxybenzyl)(((4-((4-guanidinobenzoyl)oxy)benzyl)oxy)carbonyl)amino)acetamido)-4,21-dioxo-8,11,14,17-tetraoxa-5,20-diazatetracosane-1,24-dioic acid;

(4S,7S,26S,29S)-4,7,26,29-tetrakis(carboxymethyl)-3,30-bis(((4-(4-guanidinobenzoyl)oxy)benzyl)oxy)carbonyl)-5,8,25,28-tetraoxo-12,15,18,21-tetraoxa-3,6,9,24,27,30-hexaazadotriacontane-1,32-dioic acid;

(3S,22S)-3,22-bis((3-carboxybenzyl) (((4-((4-guanidinobenzoyl)oxy)benzyl)oxy)carbonyl)amino)-4,21-dioxo-8,11,14,17-tetraoxa-5,20-diazatetracosane-1,24-dioic acid;

(2S,2'S)-2,2'-(((5,8,11,14-tetraoxa-2,17-diazaoctadecane-1,18-dioyl)bis(3,1-phenylene))bis(methylene))bis((((4-((4-guanidinobenzoyl)oxy)benzyl)oxy)carbonyl)azanediyl))disuccinic acid;

(2S,2'S)-2,2'-((((5,8,11,14-tetraoxa-2,17-diazaoctadecane-1,18-dioyl)bis(3,1-phenylene))bis(methylene))bis(N-(4-((4-guanidinobenzoyl)oxy)benzyl)sulfamoyl)azanediyl))disuccinic acid;

3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid;

(2S,13S)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid;

(2R,13R)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid;

(2S,13S)-3,12-bis(N-(4-((4-guanidinobenzoyl)oxy)benzyl)-
N-methylsulfamoyl)-6,9-dioxa-3,12-diazatetradecane-1,
2,13,14-tetracarboxylic acid;
3,3'-(((ethane-1,2-diylbis(oxy))bis(ethane-2,1-diyl))bis((N-
(4-((4-guanidinobenzoyl)oxy)benzyl)sulfamoyl)
azanediyl))dipentanedioic acid;
(2S,2'S)-2,2'-((1,12-bis(4-((4-guanidinobenzoyl)oxy)phe-
nyl)-5,8-dioxa-2,11-diazadodecanedisulfonyl)bis
(azanediyl))disuccinic acid;
(2S,13S)-3,12-bis(N-(3-((4-guanidinobenzoyl)oxy)benzyl)
sulfamoyl)-6,9-dioxa-3,12-diazatetradecane-1,2,13,14-
tetracarboxylic acid;
(2S,2'S)-2,2'-((oxybis(ethane-2,1-diyl))bis((10-guanidino-
13-oxo-6,7,8,13-tetrahydrodibenzo[b,f][1,4]dioxecin-4-
carbonyl)azanediyl))disuccinic acid;
(2S,16S)-3,15-bis(10-guanidino-13-oxo-6,7,8,13-tetrahy-
drodibenzo[b,f][1,4]dioxecin-4-carbonyl)-6,9,12-trioxa-
3,15-diazaheptadecane-1,2,16,17-tetracarboxylic acid;
(2S,2'S)-2,2'-(([1,1'-biphenyl]-3,3'-diylbis(methylene))bis
((10-guanidino-13-oxo-6,7,8,13-tetrahydrodibenzo[b,f]
[1,4]dioxecin-4-carbonyl)azanediyl))disuccinic acid;
(2S,2'S)-2,2'-(((((oxybis(ethane-2,1-diyl))bis(oxy))bis(3-
carboxy-5,1-phenylene))bis(methylene))bis((10-guani-
dino-13-oxo-6,7,8,13-tetrahydrodibenzo[b,f][1,4]diox-
ecin-4-carbonyl)azanediyl))disuccinic acid; and
(2S,2'S)-2,2'-((oxybis(ethane-2,1-diyl))bis((3-((4-guanidi-
nobenzoyl)oxy)benzoyl)azanediyl))disuccinic acid or a
pharmaceutically acceptable salt thereof.
[26] The compound according to any one of [1] to 17]
selected from the group consisting of
(2S,2'S)-2,2'-((oxybis(ethane-2,1-diyl))bis((N-(4-((4-guani-
dinobenzoyl)oxy)benzyl)sulfamoyl)azanediyl))disuccinic
acid;
(2S,13S)-3,12-bis(N-(4-((4-guanidinobenzoyl)oxy)benzyl)
sulfamoyl)-6,9-dioxa-3,12-diazatetradecane-1,2,13,14-
tetracarboxylic acid;
(2S,2'S)-2,2'-(butane-1,4-diylbis((N-(4-((4-guanidinoben-
zoyl)oxy)benzyl)sulfamoyl)azanediyl))disuccinic acid;
(2S,13S)-3,12-bis(10-guanidino-13-oxo-6,7,8,13-tetrahy-
drodibenzo[b,f][1,4]dioxecin-4-carbonyl)-6,9-dioxa-3,
12-diazatetradecane-1,2,13,14-tetracarboxylic acid;
(2S,2'S)-2,2'-((oxybis(ethane-2,1-diyl))bis((10-guanidino-
13-oxo-6,7,8,13-tetrahydrodibenzo[b,f][1,4]dioxecin-4-
carbonyl)azanediyl))disuccinic acid;
(2S,16S)-3,15-bis(10-guanidino-13-oxo-6,7,8,13-tetrahy-
drodibenzo[b,f][1,4]dioxecin-4-carbonyl)-6,9,12-trioxa-
3,15-diazaheptadecane-1,2,16,17-tetracarboxylic acid;
(2S,2'S)-2,2'-(([1,1'-biphenyl]-3,3'-diylbis(methylene))bis
((10-guanidino-13-oxo-6,7,8,13-tetrahydrodibenzo[b,f]
[1,4]dioxecin-4-carbonyl)azanediyl))disuccinic acid; and
(2S,2'S)-2,2'-(((((oxybis(ethane-2,1-diyl))bis(oxy))bis(3-
carboxy-5,1-phenylene))bis(methylene))bis((10-guani-
dino-13-oxo-6,7,8,13-tetrahydrodibenzo[b,f][1,4]diox-
ecin-4-carbonyl)azanediyl))disuccinic acid or a
pharmaceutically acceptable salt thereof.
[27, The compound according to any one of [1] to [26] or a pharmaceutically acceptable salt thereof having a molecular weight of 1000 or more.
[28] A pharmaceutical composition comprising the compound according to any one of [1] to [27] or a pharmaceutically acceptable salt thereof.
[29] The pharmaceutical composition according to [28] for the prevention, alleviation, and/or treatment of obesity.

Effect of Invention

The compounds represented by general formula (I) or pharmaceutically acceptable salts thereof of the present invention have excellent enteropeptidase inhibitory activities and/or excellent trypsin inhibitory activities, and have pharmacokinetic properties that they potently inhibit enteropeptidase and/or trypsin in the intestine after orally administered and show very low exposure amount to blood. Accordingly, the compounds represented by general formula (I) or pharmaceutically acceptable salts thereof are useful as agents for the prevention, alleviation, and/or treatment of various diseases of which symptoms are improved by enteropeptidase inhibition and/or trypsin inhibition such as obesity. The compounds of the present invention are also useful as medicaments having high safety with reduced side effects caused by exposure to blood.

MODE FOR CARRYING OUT THE INVENTION

Embodiments of the present invention are described below. In the present description, "compound represented by general formula (I)" and the like are also conveniently referred to as "Compound (I)" and the like, respectively. Various substituents defined or illustrated below may be optionally selected and combined with ea h other. Also, embodiments created by optionally select ng or combining each embodiment defined below are also encompassed by the present invention.

The definition of each term used in the present description is as follows.

The term "inhibitor" in "inhibitor", "inhibitor molecule", and "inhibitor residue" as described herein refers to a compound having at least one activity selected from an enteropeptidase inhibitory activity and a trypsin inhibitory activity.

The term "halogen atom" as described herein refers to a fluorine atom, a chlorine atom, a bromine atom, or an iodine atom. Preferable examples of the halogen atom include a fluorine atom and a chlorine atom.

The term "$C_1$-$C_4$ alkyl group" as described herein refers to a straight or branched saturated hydrocarbon group having 1 to 4 carbon atom(s). Examples of the $C_1$-$C_4$ alkyl group include a methyl group, an ethyl group, a n-propyl group, an isopropyl group, a n-butyl group, an isobutyl group, a sec-butyl group, and a tert-butyl group. Preferable examples thereof include a methyl group, an ethyl group, a n-propyl group, an isopropyl group, a n-butyl group, and a tert-butyl group.

Also, the term "$C_1$-$C_6$ alkyl group" as described herein refers to a straight or branched saturated hydrocarbon group having 1 to 6 carbon atom(s). Examples of the $C_1$-$C_6$ alkyl group include groups encompassed by the above "$C_1$-$C_4$ alkyl group", as well as a n-pentyl group, an isopentyl group, a n-hexyl group, and an isohexyl group. Preferable examples thereof include a methyl group, an ethyl group, a n-propyl group, an isopropyl group, a n-butyl group, a tert-butyl group, a n-pentyl group, and a n-hexyl group.

Examples of further preferable embodiments of the "$C_1$-$C_4$ alkyl group" and "$C_1$-$C_6$ alkyl group" include a $C_1$-$C_3$ alkyl group (namely a methyl group, an ethyl group, a n-propyl group, and an isopropyl group, preferably a methyl group, an ethyl group, and a n-propyl group), and a $C_1$-$C_2$ alkyl group (namely a methyl group and an ethyl group, preferably a methyl group).

The term "$C_1$-$C_4$ alkylene group" as described herein refers to a divalent group formed by removing any one hydrogen atom from the above "$C_1$-$C_4$ alkyl group". Examples of the $C_1$-$C_4$ alkylene group include a methylene group, an ethylene group, a methylmethylene group, a trimethylene group, an ethylmethylene group, a dimethyl-methylene group, and a tetramethylene group. Preferable examples thereof include a methylene group, an ethylene group, a methylmethylene group, a trimethylene group, and a tetramethylene group.

The term "$C_1$-$C_6$ alkylene group" as described herein refers to a divalent group formed by removing any one hydrogen atom from the above "$C_1$-$C_6$ alkyl group". Examples of the $C_1$-$C_6$ alkylene group include groups encompassed by the above "$C_1$-$C_4$ alkylene group", as well as a pentamethylene group and a hexamethylene group. Preferable examples thereof include a methylene group, an ethylene group, a methylmethylene group, a trimethylene group, a tetramethylene group, a pentamethylene group, and a hexamethylene group.

Examples of further preferable embodiments of the "$C_1$-$C_4$ alkylene group" and "$C_1$-$C_6$ alkylene group" include a $C_1$-$C_2$ alkylene group (namely a methylene group and an ethylene group, preferably a methylene group).

The term "$C_2$-$C_{30}$ alkylene group (provided that one or more methylene group(s) in the chain of said alkylene group may be replaced with group(s) independently selected from the group consisting of —C(=O)—, —NR$^7$—, —O—, —SiR$^8$R$^9$—, —SO—, an arylene group, and a heteroarylene group, R$^7$ represents a hydrogen atom or a $C_1$-$C_4$ alkyl group, R$^8$ and R$^9$ each independently represent a $C_1$-$C_4$ alkyl group, and r represents an integer of 0 to 2)" as described herein refers to a divalent group formed by removing any one hydrogen atom from a straight or branched saturated hydrocarbon group having 2 to 30 carbon atom(s), wherein one or more methylene group(s) in the chain may be replaced with group(s) independently selected from the group consisting of —C(=O)—, —NR$^2$—, —O—, —SiR$^8$R$^9$—, —SO$_2$—, an arylene group, and a heteroarylene group, and examples thereof include —(CH$_2$—CH$_2$—C(=O))$_M$—CH$_2$—CH$_2$— (wherein M represents an integer of 1 to 9), —(CH$_2$—CH$_2$—NR$^7$)$_M$—CH$_2$—CH$_2$— (wherein M represents an integer of 1 to 9), —(CH$_2$—CH$_2$—O)$_M$—CH$_2$—CH$_2$— (wherein M represents an integer of 1 to 9), —(CH$_2$—CH$_2$—SiR$^8$R$^9$)$_M$—CH$_2$—CH$_2$— (wherein M represents an integer of 1 to 9), —(CH$_2$—CH$_2$—SO$_r$)$_M$—CH$_2$—CH$_2$— (wherein M represents an integer of 1 to 9), —(CH$_2$—CH$_2$-arylene)$_M$-CH$_2$—CH$_2$— (wherein M represents an integer of 1 to 9), —(CH$_2$—CH$_2$-heteroarylene)$_M$-CH$_2$—CH$_2$— (wherein M represents an integer of 1 to 9), and —(CH$_2$)$_N$— (wherein N represents an integer of 2 to 30). Preferable examples thereof include —(CH$_2$—CH$_2$—O)$_m$—CH$_2$—CH$_2$— (wherein m represents an integer of 1 to 6), —(CH$_2$—O—CH$_2$)$_m$— (wherein m represents an integer of 1 to 6), —(CH$_2$)$_m$—($C_6$-$C_{12}$ arylene)-(CH$_2$)$_m$— (wherein m represents an integer of 1 to 6), and —(CH$_2$)$_n$— (wherein n represents an integer of 2 to 12). Preferable examples of —(CH$_2$)—($C_6$-$C_{12}$ arylene)-(CH$_2$)$_m$— (wherein m represents an integer of 1 to 6) include —(CH$_2$)$_m$-biphenylene-(CH$_2$)$_m$— (wherein m represents an integer of 1 to 6), and more preferable examples thereof include —(CH$_2$)$_m$—([1,1'-biphenyl]-3,3'-diyl)-(CH$_2$)$_m$— (wherein m represents an integer of 1 to 6).

The term "phenylene group" as described herein refers to a divalent group formed by removing any one hydrogen atom from a phenyl group. Examples of the phenylene group include a o-phenylene group, a m-phenylene group, and a p-phenylene group. The term "biphenylene group" as described herein refers to a divalent group formed by linking two phenylene groups by a single bond. Examples of the biphenylene group include a [1,1'-biphenyl]-2,2'-diyl group, a [1,1'-biphenyl]-3,3'-diyl group, and a [1,1'-biphenyl]-4,4'-diyl group, and preferable examples thereof include a [1,1'-biphenyl]-3,3'-diyl group.

The term "aryl group" as described herein refers to a monocyclic or bicyclic aromatic hydrocarbon group having 6 to 12 ring carbon atoms ($C_6$ to $C_{12}$) such as $C_9$ to $C_{11}$. Examples thereof include monocyclic aryl groups such as a phenyl group; and optionally partially saturated bicyclic aryl groups having 9 to 12 ring carbon atoms ($C_9$ to $C_{12}$) such as $C_9$ to $C_{11}$ such as a naphthyl group, a tetrahydronaphthyl group, an indenyl group, and an indanyl group. Preferable examples of the aryl group include a phenyl group and a naphthyl group, and more preferable examples thereof include a phenyl group.

The term "arylene group" or "$C_6$-$C_{12}$ arylene group" as described herein refers to a divalent group formed by removing any one hydrogen atom from the above "aryl group".

The term "heteroaryl group" as described herein refers to a 5 to 11 membered monocyclic or bicyclic aromatic heterocyclic group comprising 1 to 4 hetero atom(s) selected from an oxygen atom, a sulfur atom, and a nitrogen atom other than carbon atom(s), and examples thereof include 5 to 6 membered monocyclic heteroaryl groups comprising 1 to 4 hetero atom(s) selected from an oxygen atom, a sulfur atom, and a nitrogen atom other than carbon atom(s) such as a pyrrolyl group, a furyl group, a thienyl group, a pyrazolyl group, an imidazolyl group, an oxazolyl group, an isoxazolyl group, a thiazolyl group, an isothiazolyl group, a thiadiazolyl group, a pyridyl group, a pyrazinyl group, a pyrimidinyl group, a pyridazinyl group, and a triazinyl group; 8 to 11 membered bicyclic heteroaryl groups comprising 1 to 4 hetero atom(s) selected from an oxygen atom, a sulfur atom, and a nitrogen atom other than carbon atoms) such as an indolyl group, an indolinyl group, an isoindolinyl group, an indazolyl group, a tetrahydroindazolyl group, a benzofuranyl group, a dihydrobenzofuranyl group, a dihydroisobenzofuranyl group, a benzothiophenyl group, a dihydrobenzothiophenyl group, a dihydroisobenzothiophenyl group, a benzoxazolyl group, a dihydrobenzoxazolyl group, a benzothiazolyl group, a dihydrobenzothiazolyl group, a quinolyl group, a tetrahydroquinolyl group, an isoquinolyl group, a tetrahydroisoquinolyl group, a naphthyridinyl group, a tetrahydronaphthyridinyl group, a quinoxalinyl group, a tetrahydroquinoxalinyl group, and a quinazolinyl group. Preferable examples thereof include a pyrrolyl group, a furyl group, a thienyl group, a pyrazolyl group, an imidazolyl croup, an oxazolyl group, an isoxazolyl group, a thiazolyl group, an isothiazolyl group, a thiadiazolyl group, a pyridyl group, a pyrazinyl group, a pyrimidinyl group, a pyridazinyl group, and a triazinyl group, and more preferable examples thereof include a pyrrolyl group, a furyl group, and a thienyl group.

The term "heteroarylene group" as described herein refers to a divalent group formed by removing any one hydrogen atom from the above "heteroaryl group".

The term "$C_1$-$C_4$ alkoxy group" as described herein refers to a monovalent group wherein the above $C_1$-$C_4$ alkyl group binds to an oxy group. Examples of the $C_1$-$C_4$ alkoxy group include a methoxy group, an ethoxy group, a n-propoxy group, an isopropoxy group, a n-butoxy group, an isobutoxy group, a sec-butoxy group, and a tert-butoxy group. Preferable examples thereof include a methoxy group, an ethoxy group, and a n-propoxy group.

The term "$C_1$-$C_4$ alkoxy-$C_1$-$C_4$ alkyl group" as described herein refers to a group wherein the above $C_1$-$C_4$ alkyl group is substituted with a $C_1$-$C_4$ alkoxy group. Examples of the $C_1$-$C_4$ alkoxy-$C_1$-$C_4$ alkyl group include a methoxymethyl group, a methoxyethyl group, an ethoxymethyl group, an ethoxyethyl group, a n-propoxymethyl group, an iso-propoxymethyl group, a n-butoxymethyl group, an isobutoxymethyl group, a sec-butoxymethyl group, and a tert-butoxymethyl group. Preferable examples thereof include a methoxymethyl group, a methoxyethyl group, an ethoxymethyl group, and an ethoxyethyl group.

The term "$C_1$-$C_4$ alkyleneoxy group" as described herein refers to a divalent group wherein the above $C_1$-$C_4$ alkylene group binds to an oxy group. Examples of the $C_1$-$C_4$ alkyleneoxy group include a methyleneoxy group, an ethyleneoxy group, a methylmethyleneoxy group, a trimethyleneoxy group, an ethylmethyleneoxy group, a dimethylmethyleneoxy group, and a tetramethyleneoxy group. Preferable examples thereof include an ethyleneoxy group, a trimethyleneoxy group, and a tetramethyleneoxy group.

The term "$C_7$-$C_{12}$ aralkyl group" as described herein refers to a group wherein the above $C_1$-$C_6$ alkyl group is substituted with the above aryl group. Examples of the $C_7$-$C_{12}$ aralkyl group include a benzyl group and a phenethyl group. Preferable examples thereof include a benzyl group.

The term "any one hydrogen atom" in "group formed by removing any one hydrogen atom or any one hydroxy group" as described herein refers to any one hydrogen atom bound to a carbon atom, a nitrogen atom, or an oxygen atom.

The term "any one hydroxy group" in "group formed by removing any one hydrogen atom or any one hydroxy group" as described herein may be a hydroxy group, or a hydroxy group present in a carboxy group.

The term "at room temperature" as described herein refers to a temperature within a range of 1 to 30° C., preferably 10 to 30° C.

Compound (I)

One embodiment of the present invention is a compound represented by the following general formula (I) or a pharmaceutically acceptable salt thereof.

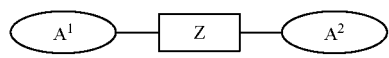

(I)

In the general formula (I), $A^1$ and $A^2$ each independently represent an inhibitor residue having at least one activity selected from an enteropeptidase inhibitory activity and a trypsin inhibitory activity; and Z represents a spacer that links $A^1$ to $A^2$, and also includes a single bond.

In the above definition, the term "inhibitor residue" refers to an inhibitor residue wherein a hydrogen atom or a hydroxy group is removed from an inhibitor molecule having at least one activity selected from an enteropeptidase inhibitory activity and a trypsin inhibitory activity. Examples of such inhibitor include, but are not limited to, the compounds disclosed in the Patent Documents 1 to 12, and compounds synthesized in the present description.

Also, the term "spacer" refers to a structure that links two residues, and examples thereof include linkers.

In the Compound (I), $A^1$ and $A^2$ may have the same structure, or different structures with each other.

In one embodiment of the present invention, $A^1$ and $A^2$ each independently represent an inhibitor residue formed by removing any one hydrogen atom or any one hydroxy group from an inhibitor molecule selected from the following inhibitor molecule group:

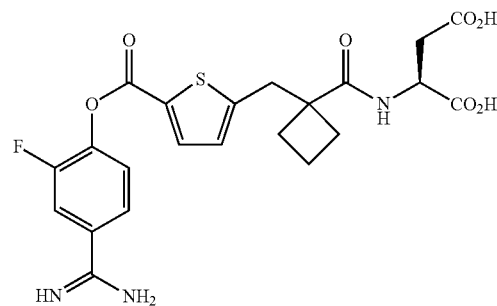

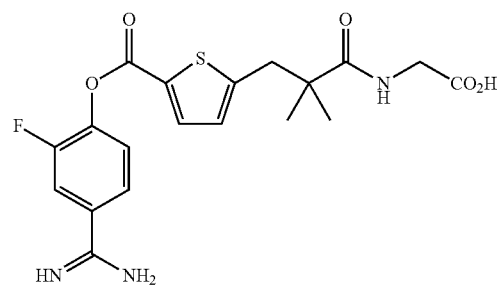

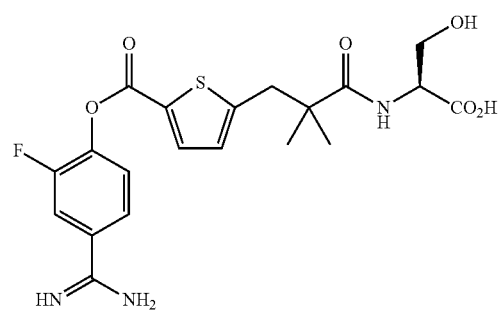

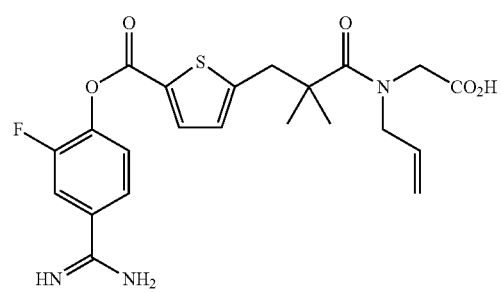

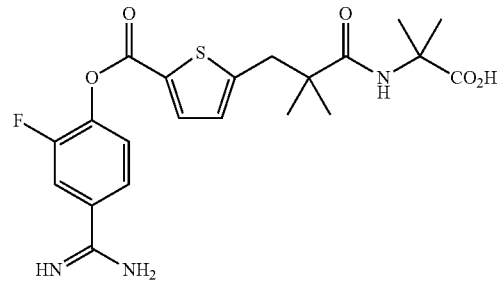

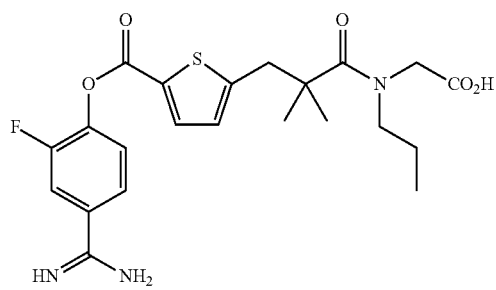
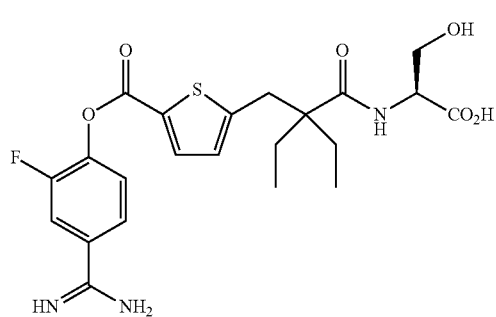
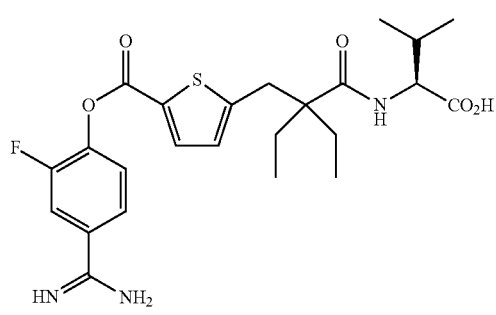
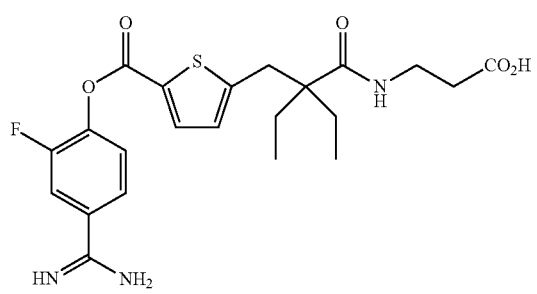
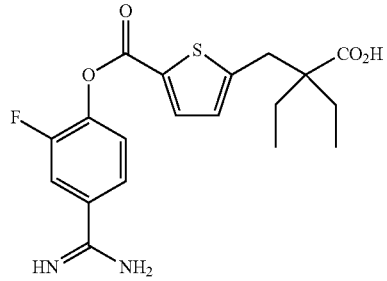
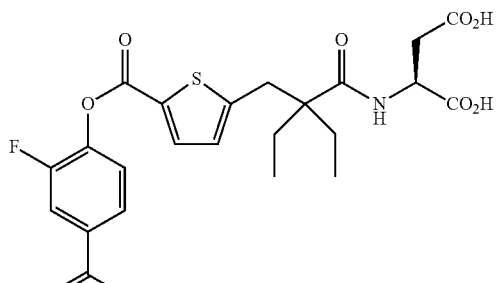
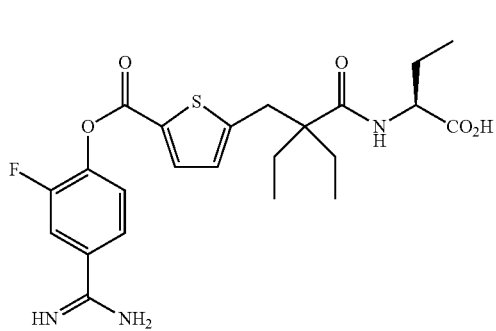
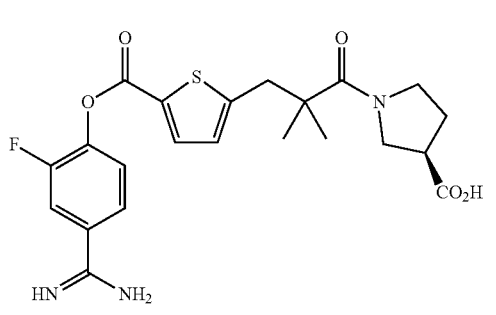
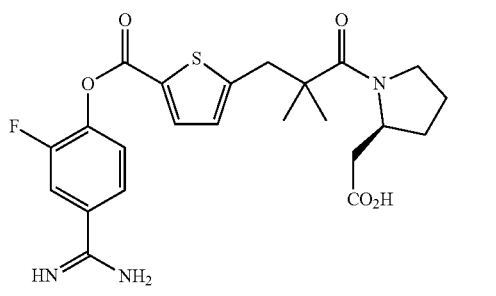
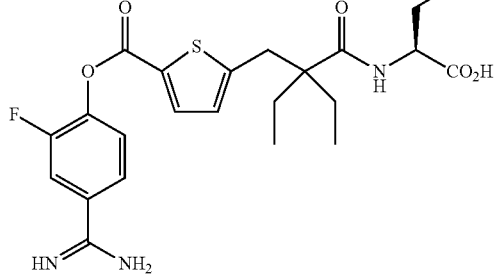

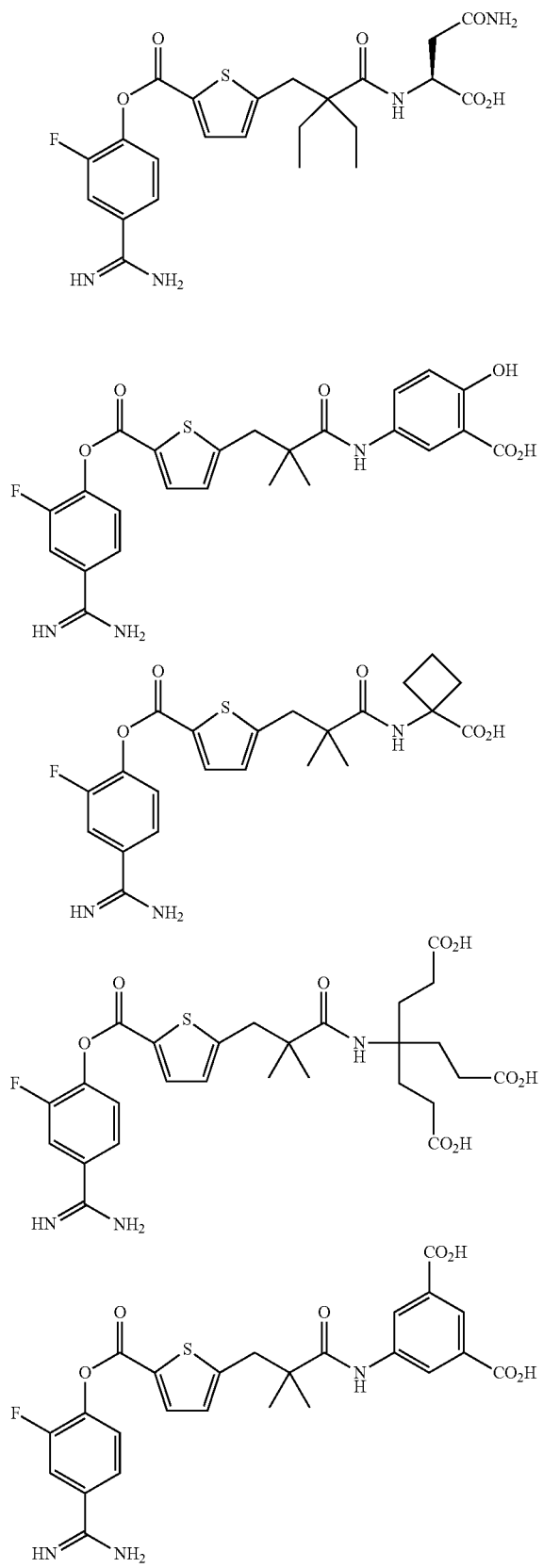
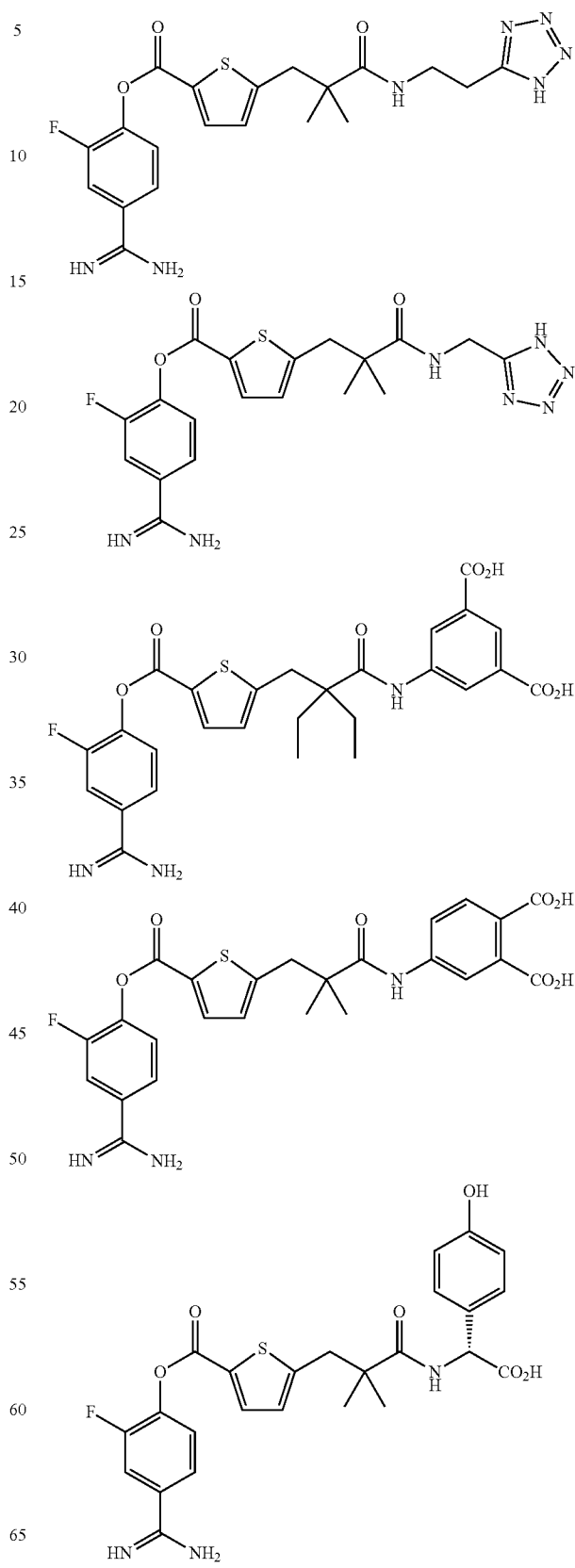

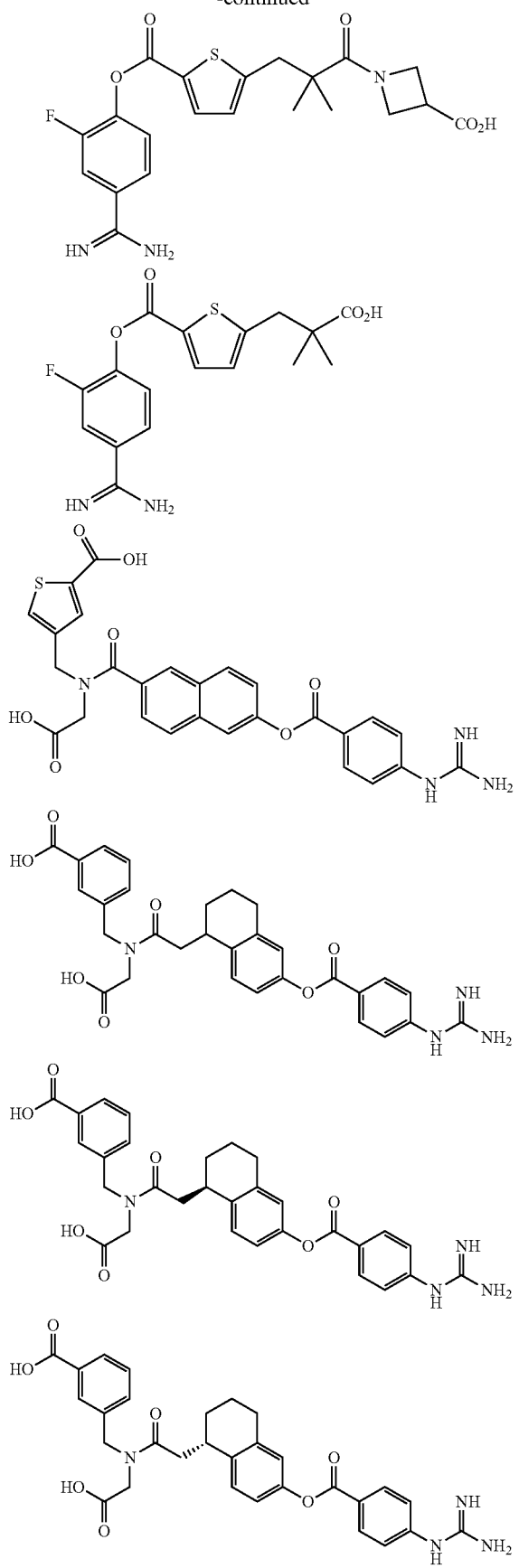

-continued

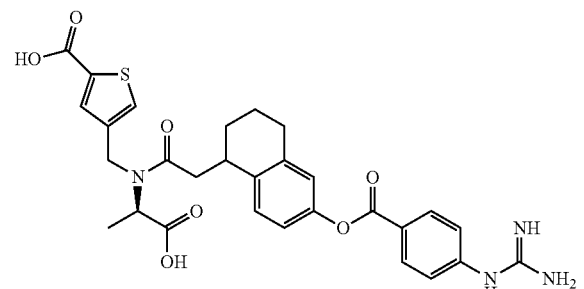
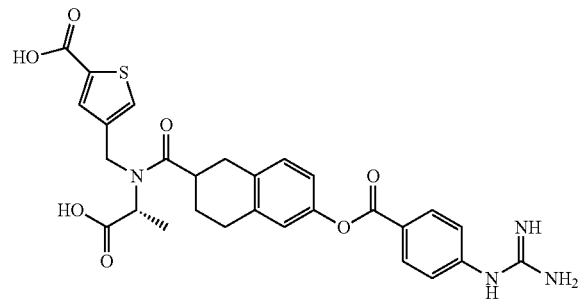
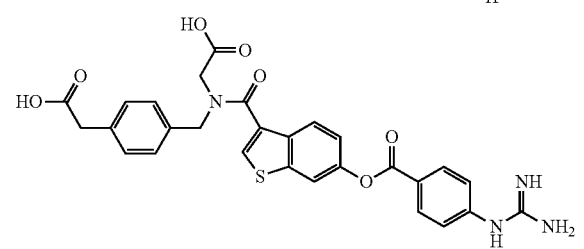
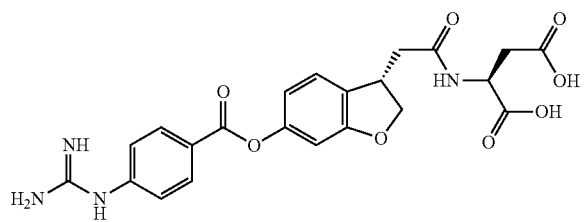
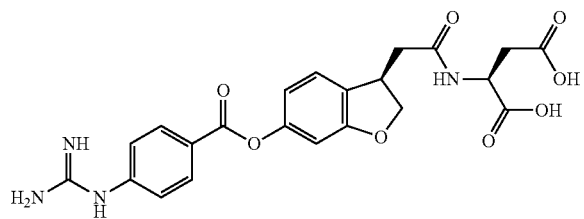
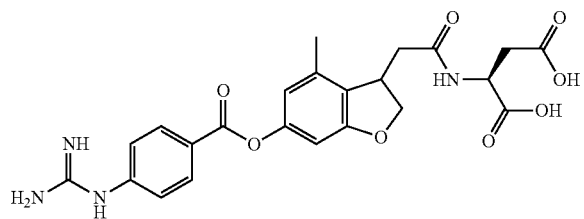
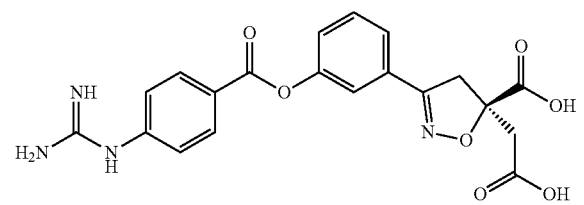

-continued

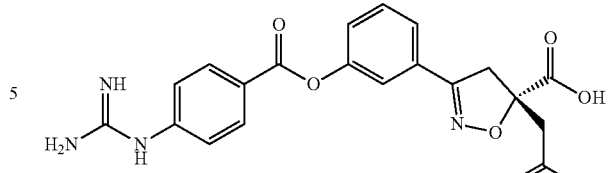
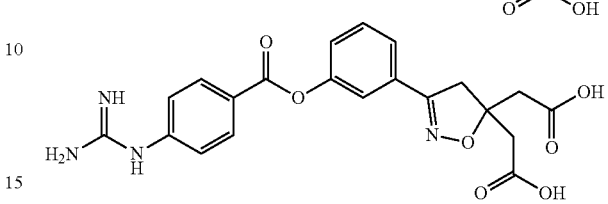

or an inhibitor molecule represented by the following general formula (II)

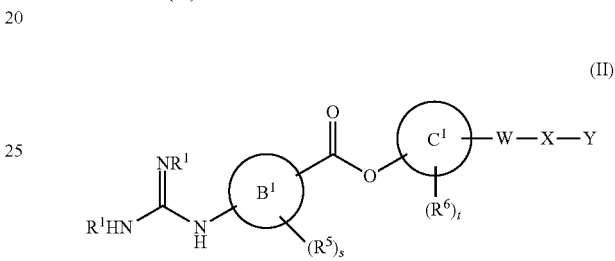

[wherein:

ring B and ring C each independently represent an aryl group or a heteroaryl group;

$R^1$ each independently represents a hydrogen atom or a —COO—($C_1$-$C_4$ alkyl group);

W represents a single bond or a $C_1$-$C_4$ alkylene group;

X represents —C(=O)—, —O—C(=O)—, or —NG-$SO_2$—;

G represents a hydrogen atom, a $C_1$-$C_4$ alkyl group, or —$COOR^2$;

$R^2$ represents a $C_1$-$C_4$ alkyl group optionally substituted with 1 to 5 aryl group(s);

Y represents —$NG^2G^4$, —$NG^2$-$L^1$-COOH, —$NG^2$-$L^1$-C(=O)—$NH_2$, —$NG^2$-$L^1$-C(=O)—$NG^3$-$L^2$-COOH, —$NG^2$-$L^1$-C(=O)—$NG^3$-$L^2$-C(=O)—$NG^3$-$L^2$-COOH, —$NG^2$-$L^1$-C(=O)—$NG^3$-$L^2$-C(=O)—$NH_2$, —$NG^2$-$L^3$-OH, or —$NG^2$-($CH_2$—$CH_2$—O)$_q$—$CH_2$—$CH_2$—COOH;

q represents an integer of 1 to 6;

$G^2$ and $G^3$ each independently represent a hydrogen atom, or a $C_1$-$C_6$ alkyl group optionally substituted with 1 to 5 substituent(s) independently selected from the group consisting of a phenyl group optionally substituted with 1 to 5 —$COOR^3$ group(s) and a —$COOR^3$ group;

$G^4$ represents a hydrogen atom, a $C_1$-$C_4$ alkyl group, or a $C_1$-$C_4$ alkoxy-$C_1$-$C_4$ alkyl group;

$R^3$ each independently represents a hydrogen atom or a $C_1$-$C_4$ alkyl group optionally substituted with 1 to 5 aryl group(s);

$L^1$ and $L^2$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene group substituted with a $C_1$-$C_4$ aralkyl group optionally substituted with 1 to 5 substituent(s) independently selected from the group consisting of a hydroxy group and a carboxy group, a $C_1$-$C_4$ alkylene-phenylene group, or a phenylene-$C_1$-$C_4$ alkylene group;

$L^3$ represents a $C_1$-$C_4$ alkylene-phenylene group wherein the phenylene moiety is optionally substituted with 1 to 3 —COOR$^4$ group(s);

$R^4$ each independently represents a hydrogen atom or a $C_1$-$C_4$ alkyl group optionally substituted with 1 to 5 substituent(s) independently selected from the group consisting of an aryl group and a trimethylsilyl group;

$R^5$ and $R^6$ each independently represent a hydrogen atom, a halogen atom, a $C_1$-$C_4$ alkyl group, a $C_1$-$C_4$ alkoxy group, a carboxy group, or —C(=O)—NG$^2$G$^4$;

s and t each independently represent an integer of 1 to 4;

two or more $R^5$ and/or two or more $R^6$ may be the same or different with each other;

or any one of $R^5$ and any one of $R^6$ may be combined with each other to form a $C_1$-$C_4$ alkyleneoxy group]; and Z represents a single bond, an arylene group, a heteroarylene group, or a $C_2$-$C_{30}$ alkylene group (provided that one or more methylene group(s) in the chain of said alkylene group may be replaced with group(s) independently selected from the group consisting of —C(=O)—, —NR$^7$—, —O—, —SiR$^8$R$^9$—, —SO$_r$—, an arylene group, and a heteroarylene group, R$^7$ represents a hydrogen atom or a $C_1$-$C_4$ alkyl group, RB and R$^9$ each independently represent a $C_1$-$C_4$ alkyl group, and r represents an integer of 0 to 2).

In one embodiment of the present invention, $A^1$ and $A^2$ each independently represent an inhibitor residue formed by removing any one hydrogen atom or any one hydroxy group from the inhibitor molecule represented by general formula (II).

In one embodiment of the present invention, $A^1$ has a structure represented by

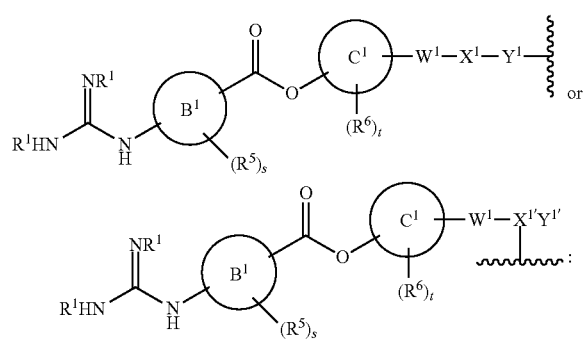

$A^2$ has a structure represented by

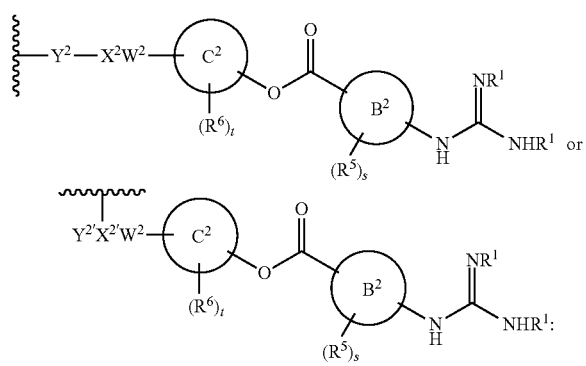

[wherein ring $B^1$, ring $B^2$, ring $C^1$, and ring $C^2$ each independently represent an aryl group;

$R^1$ each independently represents a hydrogen atom or a —COO—($C_1$-$C_4$ alkyl group);

$W^1$ and $W^2$ each independently represent a single bond or a $C_1$-$C_4$ alkylene group;

$X^1$ represents —C(=O)—, —O—C(=O)—, or —NG$^{11}$-SO$_2$—;

$X^{1'}$ represents —NG$^7$-SO$_2$—;

$X^2$ represents —C(=O)—, —C(=O)—O—, or —SO$_2$—NG$^{12}$-;

$X^{2'}$ represents —SO$_2$—NG$^Z$-;

$G^{11}$ and $G^{12}$ each independently represent a hydrogen atom, a $C_1$-$C_4$ alkyl group, or —COOR$^2$;

$G^Z$ represents a single bond that links $X^1$ or $X^{2'}$ to Z;

$R^2$ represents a $C_1$-$C_4$ alkyl group optionally substituted with 1 to 5 aryl group(s);

$Y^1$ represents —NG$^{21}$-, —NG$^{21}$-L$^{11}$-C(=O)—, —NG$^{21}$-L$^{11}$-C(=O)—NH—, —NG$^{21}$-L$^{11}$-C(=O)—NG$^{31}$-L$^{21}$-C(=O)—, —NG$^{21}$-L$^{11}$-C(=O)—NG$^{31}$-L$^{21}$-C(=O)—NH—, —NG$^{21}$-L$^3$-O—, or —NG$^{21}$-G$^{4'}$-;

$Y^{1'}$ represents —NG$^{21}$H, —NG$^1$-L$^{11}$-COOH, or —NG$^{21}$-L$^{11}$-C(=O)—NG$^{31}$-L$^{21}$-COOH;

$Y^2$ represents —NG$^{22}$-, —C(=O)-L$^{12}$-NG$^{22}$-, —NH—C(=O)-L$^{12}$-NG$^{22}$-, —C(=O)-L$^{22}$-NG$^{32}$-C(=O)-L$^{12}$-NG$^{22}$-, —NH—C(=O)-L$^{22}$-NG$^{32}$-C(=O)-L$^{12}$-NG$^2$-, —O-L$^3$-NG$^{22}$-, or -G$^{4'}$-NG$^{22}$-;

$Y^{2'}$ represents HNG$^{22}$-, HOOC-L$^{12}$-NG$^{22}$-, or HOOC-L$^{22}$-NG$^{32}$-C(=O)-L$^{12}$-NG$^{22}$-;

$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —COOR$^3$ group(s) and a —COOR$^3$ group;

$G^{4'}$ represents a $C_1$-$C_4$ alkylene group or a $C_1$-$C_4$ alkyleneoxy-$C_1$-$C_4$ alkylene group;

$R^3$ each independently represents a hydrogen atom or a $C_1$-$C_4$ alkyl group optionally substituted with 1 to 5 aryl group(s);

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —COOR$^4$ group(s), a $C_1$-$C_4$ alkylene-phenylene group, or a phenylene-$C_1$-$C_4$ alkylene group;

$L^3$ represents a $C_1$-$C_4$ alkylene-phenylene group wherein the phenylene moiety is optionally substituted with 1 to 3 —COOR$^4$ group(s);

$R^4$ each independently represents a hydrogen atom or a $C_1$-$C_4$ alkyl group optionally substituted with 1 to 5 substituent(s) independently selected from the group consisting of an aryl group and a trimethylsilyl group;

$R^5$ and $R^6$ each independently represent a hydrogen atom, a halogen atom, a $C_1$-$C_4$ alkyl group, or a $C_1$-$C_4$ alkoxy group;

s and t each independently represent an integer of 1 to 4;

two or more $R^5$ and/or two or more $R^6$ may be the same or different with each other;

or any one of $R^5$ and any one of $R^6$ may be combined with each other to form a $C_1$-$C_4$ alkyleneoxy group; and the symbol

∼∼∼∼ represents the point of attachment to Z]; and

Z represents a single bond, an arylene group, a heteroarylene group, or a $C_2$-$C_{30}$ alkylene group (provided that one or more methylene group(s) in the chain of said alkylene group may be replaced with group(s) independently selected from the group consisting of —C(=O)—, —NR$^7$—, —O—, an arylene group, and a heteroarylene group, and R, represents a hydrogen atom or a $C_1$-$C_4$ alkyl group).

Embodiments of each substituent of the Compound (I) are as follows.

In one embodiment, the aryl group in ring B and ring C each independently represent a $C_6$ to $C_{12}$ aryl group, preferably a phenyl group or a naphthyl group, more preferably a phenyl group.

In one embodiment, the heteroaryl group in ring B and ring C each independently represent a 5 to 11 membered monocyclic or bicyclic aromatic heterocyclic group comprising 1 to 4 hetero atom(s) selected from an oxygen atom, a sulfur atom, and a nitrogen atom other than carbon atom(s), preferably a pyrrolyl group, a furyl group, and a thienyl group, more preferably a thienyl group.

In one embodiment, ring B and ring C each independently represent an aryl group, preferably each represent a phenyl group.

In one embodiment, ring B and ring C each independently represent a phenyl group, a naphthyl group, or a thienyl group, preferably ring B and ring C each represent a phenyl group.

In one embodiment, ring $B^1$, ring $B^2$, ring $C^1$, and ring $C^2$ each independently represent a phenyl group or a naphthyl group, preferably ring B, ring $B^2$, ring $C^1$, and ring $C^2$ each represent a phenyl group.

In one embodiment, the $C_1$-$C_4$ alkyl group of "—COO—($C_1$-$C_4$ alkyl group)" in R; represents a methyl group, an ethyl group, a n-propyl group, an isopropyl group, a n-butyl group, or a tert-butyl group.

In one embodiment, $R^1$ represents a hydrogen atom or a tert-butoxycarbonyl group, preferably a hydrogen atom.

In one embodiment, W represents a $C_1$-$C_4$ alkylene group, for example a methylene group, an ethylene group, a trimethylene group, or a tetramethylene group, preferably a $C_1$-$C_2$ alkylene group, for example a methylene group. In another embodiment, W represents a single bond or a $C_1$-$C_2$ alkylene group, preferably a single bond or a methylene group.

In one embodiment, $W^1$ represents a $C_1$-$C_4$ alkylene group, for example a methylene group, an ethylene group, a trimethylene group, or a tetramethylene group, preferably a $C_1$-$C_2$ alkylene group, for example a methylene group. In another embodiment, $W^1$ represents a single bond or a $C_1$-$C_4$ alkylene group, preferably a single bond or a $C_1$-$C_2$ alkylene group, more preferably a single bond or a methylene group, still more preferably a single bond.

In one embodiment, $W^2$ represents a $C_1$-$C_4$ alkylene group, for example a methylene group, an ethylene group, a trimethylene group, or a tetramethylene group, preferably a $C_1$-$C_2$ alkylene group, for example a methylene group. In another embodiment, $W^2$ represents a single bond or a $C_1$-$C_4$ alkylene group, preferably a single bond or a $C_1$-$C_2$ alkylene group, more preferably a single bond or a methylene group, still more preferably a single bond.

In one embodiment, X represents —O—C(=O)— or —NG-$SO_2$—, preferably —NG-$SO_2$—. In another embodiment, X represents —C(=O)— or —NG-$SO_2$—, preferably —C(=O)—.

In one embodiment, $X^1$ represents —O—C(=O)— or —NG-$SO_2$—, preferably —NG-$SO_2$—. In another embodiment, X represents —C(=O)— or —$NG^{11}$-$SO_2$—, preferably —C(=O)—.

In one embodiment, $X^2$ represents —C(=O)—O— or —$SO_2$—$NG^{12}$-, preferably —$SO_2$—$NG^{12}$-. In another embodiment, $X^2$ represents —C(=O)— or —$SO_2$—$NG^{12}$-, preferably —C(=O)—.

In one embodiment, the "$C_1$-$C_4$ alkyl group" in G represents a methyl group, an ethyl group, a n-propyl group, an isopropyl group, a n-butyl group, or a tert-butyl group, preferably a methyl group or an ethyl group.

In one embodiment, $R^2$ of "—$COOR^2$ group" in G represents a $C_3$-$C_4$ alkyl group optionally substituted with 1 to 3 phenyl group(s), for example a methyl group, an ethyl group, a n-propyl group, an isopropyl group, a n-butyl group, a tert-butyl group, or a benzyl group, preferably a $C_1$-$C_4$ alkyl group optionally substituted with one phenyl group, more preferably a tert-butyl group or a benzyl group.

In one embodiment, G represents a hydrogen atom, a methyl group, a tert-butoxycarbonyl group, or a benzyloxycarbonyl group, preferably a hydrogen atom, a methyl group, or a benzyloxycarbonyl group, more preferably a hydrogen atom or a methyl group.

In one embodiment, the "$C_1$-$C_4$ alkyl group" in $G^{11}$ and $G^{12}$ represents a methyl group, an ethyl group, a n-propyl group, an isopropyl group, a n-butyl group, or a tert-butyl group, preferably a methyl group or an ethyl group.

In one embodiment, $R^2$ of "—$COOR^2$ group" in $G^{11}$ and $G^{12}$ represents a $C_1$-$C_4$ alkyl group, for example a methyl group, an ethyl group, a n-propyl group, an isopropyl group, a n-butyl group, a tert-butyl group, or a benzyl group, optionally substituted with 1 to 3 aryl group(s), for example phenyl group(s), preferably a $C_1$-$C_4$ alkyl group optionally substituted with one phenyl group, more preferably a tert-butyl group or a benzyl group.

In one embodiment, $G^{11}$ represents a hydrogen atom, a methyl group, a tert-butoxycarbonyl group, or a benzyloxycarbonyl group, preferably a hydrogen atom, a methyl group, or a benzyloxycarbonyl group, more preferably a hydrogen atom or a methyl group. In another embodiment, $G^{11}$ represents a hydrogen atom or —$COOR^2$, preferably a hydrogen atom, a tert-butoxycarbonyl group, or a benzyloxycarbonyl group, more preferably a hydrogen atom or a benzyloxycarbonyl group, still more preferably a hydrogen atom.

In one embodiment, $G^{12}$ represents a hydrogen atom, a methyl group, a tert-butoxycarbonyl group, or a benzyloxycarbonyl group, preferably a hydrogen atom, a methyl group, or a benzyloxycarbonyl group, more preferably a hydrogen atom or a methyl group. In another embodiment, $G^{12}$ represents a hydrogen atom or —$COOR^2$, preferably a hydrogen atom, a tert-butoxycarbonyl group, or a benzyloxycarbonyl group, more preferably a hydrogen atom or a benzyloxycarbonyl group, still more preferably a hydrogen atom.

In one embodiment, Y represents —$NG^2G^4$, —$NG^2$-$L^1$-COOH, —$NG^2$-$L^1$-C(=O)—$NH_2$, —$NG^2$-$L^1$-C(=O)—$NG^3$-$L^2$-COOH, —$NG^2$-$L^1$-C(=O)—$NG^3$-$L^2$-C(=O)—$NH_2$, —$NG^2$-$L^3$-OH, or —$NG^2$-($CH_2$—$CH_2$—O)$_q$—$CH_2$—$CH_2$—COOH, preferably —$NG^2G^4$, —NG-$L^1$-COOH, —$NG^2$-$L^1$-C(=O)—$NH_2$, —$NG^2$-$L^1$-C(=O)—$NG^3$-$L^2$-COOH, —$NG^2$-$L^1$-C(=O)—$NG^3$-$L^2$-C(=O)—$NH_2$, or —$NG^2$-$L^3$-OH, more preferably —$NG^2G^4$.

In one embodiment, $Y^1$ represents —$NG^{21}$-, —$NG^{21}$-$L^{11}$-C(=O)—, —$NG^{21}$-$L^{11}$-C(=O)—NH—, —$NG^{22}$-$L^{11}$-C(=O)—$NG^{31}$-$L^{21}$-C(=O)—, —$NG^{21}$-$L^{11}$-C(=O)—$NG^{31}$-$L^{21}$-C(=O)—NH—, or —$NG^1$-$L^3$-O—. In another embodiment, $Y^1$ represents —$NG^{21}$-, —$NG^{21}$-$L^3$-O—, or -$NG^{21}$-$G^{4'}$-. Preferably, $Y^1$ represents —$NG^{21}$-.

In one embodiment, $Y^{1'}$ represents —$NG^{21}$H.

In one embodiment, $Y^2$ represents —$NG^{22}$-, —C(=O)-$L^2$-$NG^2$-, —NH—C(=O)-$L^{12}$-$NG^{22}$-, —C(=O)-$L^{22}$-$NG^{32}$-C(=O)-$L^{12}$-$NG^{22}$-, —NH—C(=O)-$L^{22}$-$NG^{32}$-C(=O)-$L^{12}$-$NG^{22}$-, or —O-L-$NG^{22}$-. In another embodiment, $Y^2$ represents —$NG^{22}$-, —O-$L^3$-$NG^{22}$-, or -$G^{4'}$-$NG^{22}$-. Preferably, $Y^2$ represents —$NG^{22}$-.

In one embodiment, $Y^{2'}$ represents $HNG^{22}$-.

In one embodiment, q represents an integer of 1 to 4, preferably an integer of 1 to 3, more preferably an integer of 1 to 2.

In one embodiment, the "phenyl group optionally substituted with 1 to 5 —$COOR^3$ group(s)" in $G^2$ and $G^3$ represents preferably a phenyl group optionally substituted with 1 to 3 —$COOR^3$ group(s), more preferably a phenyl group optionally substituted with one —$COOR^3$ group, for example a 2-($COOR^3$)-phenyl group, a 3-($COOR^3$)-phenyl group, a 4-($COOR^3$)-phenyl group, or the like.

In one embodiment, $R^3$ of "—$COOR^3$ group" in $G^2$ and $G^3$ each independently represents a hydrogen atom, a methyl group, an ethyl group, a n-propyl group, an isopropyl group, a n-butyl group, a tert-butyl group, or a benzyl group, preferably a hydrogen atom, a benzyl group, or a tert-butyl group, more preferably a hydrogen atom or a tert-butyl group, still more preferably a hydrogen atom.

In one embodiment, $G^2$ represents a hydrogen atom, or a $C_1$-$C_6$ alkyl group optionally substituted with 1 to 3 substituent(s) independently selected from the group consisting of a phenyl group optionally substituted with 1 to 3 —$COOR^3$ group(s) and a —$COOR^3$ group, preferably a hydrogen atom, or a $C_1$-$C_3$ alkyl group optionally substituted with 1 to 3 substituent(s) independently selected from the group consisting of a phenyl group optionally substituted with one —$COOR^3$ group and a —$COOR^3$ group, more preferably a $C_1$-$C_3$ alkyl group substituted with 1 to 3 substituent(s) independently selected from the group consisting of a phenyl group substituted with one carboxy group and a carboxy group.

In another embodiment, $G^2$ represents a hydrogen atom, or a $C_1$-$C_3$ alkyl group optionally substituted with 1 to 3 —$COOR^3$ group(s), preferably a $C_1$-$C_3$ alkyl group substituted with 1 to 3 carboxy group(s).

In one embodiment, $G^3$ represents a hydrogen atom, or a $C_1$-$C_3$ alkyl group optionally substituted with 1 to 3 substituent(s) independently selected from the group consisting of a phenyl group optionally substituted with 1 to 3 —$COOR^3$ group(s) and a —$COOR^3$ group, preferably a hydrogen atom, or a $C_1$-$C_3$ alkyl group optionally substituted with 1 to 3 substituent (s) independently selected from the group consisting of a phenyl group optionally substituted with one —$COOR^3$ group and a —$COOR^3$ group, more preferably a hydrogen atom.

In another embodiment, $G^3$ represents a hydrogen atom, or a $C_1$-$C_3$ alkyl group optionally substituted with 1 to 3 —$COOR^3$ groups), preferably a hydrogen atom.

In one embodiment, the "phenyl group optionally substituted with 1 to 5 —$COOR^3$ group(s)" in $G^{21}$, $G^{31}$, $G^{22}$, and $G^{32}$ represents preferably a phenyl group optionally substituted with 1 to 3 —$COOR^3$ group(s), more preferably a phenyl group optionally substituted with one —$COOR^3$ group, for example a 2-($COOR^3$-phenyl group, a 3-($COOR^3$)-phenyl group, a 4-($COOR^3$)-phenyl group, or the like.

In one embodiment, $R^3$ of "—$COOR^3$ group" in $G^{21}$, $G^{31}$, $G^{22}$ and $G^{32}$ each independently represents a hydrogen atom, a methyl group, an ethyl group, a n-propyl group, an isopropyl group, a n-butyl group, a tert-butyl group, or a benzyl group, preferably a hydrogen atom, a benzyl group, or a tert-butyl group, more preferably a hydrogen atom or a tert-butyl group, still more preferably a hydrogen atom.

In one embodiment, $G^{21}$ represents a hydrogen atom, or a $C_1$-$C_6$ alkyl group optionally substituted with 1 to 3 substituent(s) independently selected from the group consisting of a phenyl group optionally substituted with 1 to 3 —$COOR^3$ group(s) and a —$COOR^3$ group, preferably a hydrogen atom, or a $C_1$-$C_3$ alkyl group optionally substituted with 1 to 3 substituent(s) independently selected from the group consisting of a phenyl group optionally substituted with one —$COOR^3$ group and a —$COOR^3$ group, more preferably a $C_1$-$C_3$ alkyl group substituted with 1 to 3 substituent(s) independently selected from the group consisting of a phenyl group substituted with one carboxy group and a carboxy group.

In another embodiment, $G^{31}$ represents a hydrogen atom, or a $C_1$-$C_3$ alkyl group optionally substituted with 1 to 3 —$COOR^3$ group(s), preferably a hydrogen atom, or a $C_1$-$C_3$ alkyl group substituted with 1 to 3 carboxy group(s), more preferably a $C_1$-$C_3$ alkyl group substituted with 1 to 3 carboxy group(s).

In one embodiment, $G^{31}$ represents a hydrogen atom, or a $C_1$-$C_6$ alkyl group optionally substituted with 1 to 3 substituent(s) independently selected from the group consisting of a phenyl group optionally substituted with 1 to 3 —$COOR^3$ group(s) and a —$COOR^3$ group, preferably a hydrogen atom, or a $C_1$-$C_3$ alkyl group optionally substituted with 1 to 3 substituent(s) independently selected from the group consisting of a phenyl group optionally substituted with one —$COOR^3$ group and a —$COOR^3$ group, more preferably a hydrogen atom.

In another embodiment, $G^{31}$ represents a hydrogen atom, or a $C_1$-$C_3$ alkyl group optionally substituted with 1 to 3 —$COOR^3$ group(s), preferably a hydrogen atom.

In one embodiment, $G^{22}$ represents a hydrogen atom, or a $C_1$-$C_6$ alkyl group optionally substituted with 1 to 3 substituent(s) independently selected from the group consisting of a phenyl group optionally substituted with 1 to 3 —$COOR^3$ group(s) and a —$COOR^3$ group, preferably a hydrogen atom, or a $C_1$-$C_3$ alkyl group optionally substituted with 1 to 3 substituent (s) independently selected from the group consisting of a phenyl group optionally substituted with one —$COOR^3$ group and a —$COOR^3$ group, more preferably a $C_1$-$C_3$ alkyl group substituted with 1 to 3 substituent(s) independently selected from the group consisting of a phenyl group substituted with one carboxy group and a carboxy group.

In another embodiment, $G^{22}$ represents a hydrogen atom, or a $C_1$-$C_3$ alkyl group optionally substituted with 1 to 3 —$COOR^3$ group(s), preferably a hydrogen atom, or a $C_1$-$C_3$ alkyl group substituted with 1 to 3 carboxy group (s), more preferably a $C_1$-$C_3$ alkyl group substituted with 1 to 3 carboxy group(s).

In one embodiment, $G^{32}$ represents a hydrogen atom, or a $C_1$-$C_6$ alkyl group optionally substituted with 1 to 3 substituent (s) independently selected from the group consisting of a phenyl group optionally substituted with 1 to 3 —$COOR^3$ group(s) and a —$COOR^3$ group, preferably a hydrogen atom, or a $C_1$-$C_3$ alkyl group optionally substituted with 1 to 3 substituent (s) independently selected from the group consist or a phenyl group optionally substituted with one —$COOR^3$ group and a —$COOR^3$ group, more preferably a hydrogen atom.

In another embodiment, $G^{32}$ represents a hydrogen atom, or a $C_1$-$C_3$ alkyl group optionally substituted with 1 to 3 —$COOR^3$ group(s), preferably a hydrogen atom.

In one embodiment, $G^4$ represents a hydrogen atom, a $C_1$-$C_2$ alkyl group, or a $C_1$-$C_2$ alkoxy-$C_1$-$C_2$ alkyl group, preferably a methyl group, an ethyl croup, or a methoxyethyl group, more preferably a methyl group or a methoxyethyl group.

In one embodiment, $G^{4'}$ represents a $C_1$-$C_2$ alkylene group or a $C_1$-$C_2$ alkyleneoxy-$C_1$-$C_2$ alkylene group, preferably a methylene group, an ethylene group, or a methyleneoxymethylene group, more preferably a methylene group, or a methyleneoxymethylene group.

In one embodiment, $R^4$ of "—COOR$^4$ group" in $L^1$ and $L^1$ each independently represents a hydrogen atom, a methyl group, an ethyl group, a n-propyl group, an isopropyl group, a n-butyl group, a tert-butyl group, or a benzyl group, preferably a hydrogen atom, a tert-butyl group, or a benzyl group, more preferably a hydrogen atom or a tert-butyl group, still more preferably a hydrogen atom.

In one embodiment, $L^1$ represents a $C_1$-$C_6$ alkylene group optionally substituted with 1 to 2 $C_1$-$C_6$ alkyl group(s) optionally substituted with 1 to 2 —COOR$^4$ group(s), a $C_1$-$C_4$ alkylene group substituted with a benzyl group wherein the phenyl group moiety is optionally substituted with 1 to 2 substituent(s) independently selected from the group consisting of a hydroxy group and a carboxy group, a $C_1$-$C_4$ alkylene-phenylene group, or a phenylene-$C_1$-$C_4$ alkylene group, preferably a methylene group optionally substituted with a $C_1$-$C_6$ alkyl group optionally substituted with a —COOR$^4$ group, a methylenephenylene group, or a phenylenemethylene group.

In another embodiment, $L^1$ represents a $C_1$-$C_2$ alkylene group, preferably a methylene group.

In another embodiment, $L^1$ represents a $C_1$-$C_2$ alkylene group optionally substituted with 1 to 2 $C_1$-$C_2$ alkyl group(s) optionally substituted with 1 to 2 —COOR$^4$ group(s), a $C_1$-$C_2$ alkylene-phenylene group, or a phenylene-$C_1$-$C_2$ alkylene group.

In one embodiment, $L^2$ represents a $C_1$-$C_6$ alkylene group optionally substituted with 1 to 2 $C_1$-$C_6$ alkyl group(s) optionally substituted with 1 to 2 —COOR$^4$ group(s), a $C_1$-$C_4$ alkylene group substituted with a benzyl group wherein the phenyl group moiety is optionally substituted with 1 to 2 substituent(s) independently selected from the group consisting of a hydroxy group and a carboxy group, a $C_1$-$C_4$ alkylene-phenylene group, or a phenylene-$C_1$-$C_4$ alkylene group, preferably a methylene group optionally substituted with a $C_1$-$C_6$ alkyl group optionally substituted with a —COOR$^4$ group.

In another embodiment, $L^2$ represents a $C_1$-$C_2$ alkylene group, preferably a methylene group.

In another embodiment, $L^2$ represents a $C_1$-$C_2$ alkylene group optionally substituted with 1 to 2 $C_1$-$C_2$ alkyl group(s) optionally substituted with 1 to 2 —COOR$^4$ group(s), a $C_1$-$C_2$ alkylene-phenylene group, or a phenylene-$C_1$-$C_2$ alkylene group.

In one embodiment, $R^4$ of "—COOR$^4$ group" in $L^{11}$, $L^{21}$, $L^{12}$, and $L^{22}$ each independently represents a hydrogen atom, a methyl group, an ethyl group, a n-propyl group, an isopropyl group, a n-butyl group, a tert-butyl group, or a benzyl group, preferably a hydrogen atom, a tert-butyl group, or a benzyl group, more preferably a hydrogen atom or a tert-butyl group, still more preferably a hydrogen atom.

In one embodiment, $L^{11}$ represents a $C_1$-$C_6$ alkylene group optionally substituted with 1 to 2 $C_1$-$C_6$ alkyl group(s) optionally substituted with 1 to 2 —COOR$^4$ group(s), a $C_1$-$C_4$ alkylene group substituted with a benzyl group wherein the phenyl group moiety is optionally substituted with 1 to 2 substituent(s) independently selected from the group consisting of a hydroxy group and a carboxy group, a $C_1$-$C_4$ alkylene-phenylene group, or a phenylene-$C_1$-$C_4$ alkylene group, preferably a $C_1$-$C_6$ alkylene group optionally substituted with 1 to 2 $C_1$-$C_6$ alkyl group(s) optionally substituted with 1 to 2 —COOR$^4$ group(s), a $C_1$-$C_4$ alkylene-phenylene group, or a phenylene-$C_1$-$C_4$ alkylene group, more preferably a $C_1$-$C_6$ alkylene group optionally substituted with 1 to 2 $C_1$-$C_6$ alkyl group(s) optionally substituted with 1 to 2 —COOR$^4$ group(s), or a $C_1$-$C_4$ alkylene-phenylene group, still more preferably a methylene group optionally substituted with a $C_1$-$C_6$ alkyl group optionally substituted with a —COOR$^4$ group, or a methylenephenylene group.

In another embodiment, $L^{11}$ represents a $C_1$-$C_2$ alkylene group, preferably a methylene group.

In another embodiment, $L^{11}$ represents a $C_1$-$C_2$ alkylene group optionally substituted with 1 to 2 $C_1$-$C_2$ alkyl group(s) optionally substituted with 1 to 2 —COOR$^1$ group(s), or a $C_1$-$C_2$ alkylene-phenylene group.

In one embodiment, $L^{21}$ represents a $C_1$-$C_6$ alkylene group optionally substituted with 1 to 2 $C_1$-$C_6$ alkyl group(s) optionally substituted with 1 to 2 —COOR$^4$ group(s), a $C_1$-$C_4$ alkylene group substituted with a benzyl group wherein the phenyl group moiety is optionally substituted with 1 to 2 substituent(s) independently selected from the group consisting of a hydroxy group and a carboxy group, a $C_1$-$C_4$ alkylene-phenylene group, or a phenylene-$C_1$-$C_4$ alkylene group, preferably a $C_1$-$C_6$ alkylene group optionally substituted with 1 to 2 $C_1$-$C_6$ alkyl group(s) optionally substituted with 1 to 2 —COOR$^4$ group(s), a $C_1$-$C_4$ alkylene-phenylene group, or a phenylene-$C_1$-$C_4$ alkylene group, more preferably a $C_1$-$C_6$ alkylene group optionally substituted with 1 to 2 $C_1$-$C_6$ alkyl group(s) optionally substituted with 1 to 2 —COOR$^4$ group(s), or a $C_1$-$C_4$ alkylene-phenylene group, still more preferably a methylene group optionally substituted with a $C_1$-$C_6$ alkyl group optionally substituted with a —COOR$^4$ group.

In another embodiment, $L^{21}$ represents a $C_1$-$C_2$ alkylene group, preferably a methylene group.

In another embodiment, $L^{21}$ represents a $C_1$-$C_2$ alkylene group optionally substituted with 1 to 2 $C_1$-$C_2$ alkyl group(s) optionally substituted with 1 to 2 —COOR$^4$ group(s), or a $C_1$-$C_2$ alkylene-phenylene group.

In one embodiment, $L^{12}$ represents a $C_1$-$C_6$ alkylene group optionally substituted with 1 to 2 $C_1$-$C_4$ alkyl group(s) optionally substituted with 1 to 2 —COOR$^4$ group(s), a $C_1$-$C_4$ alkylene group substituted with a benzyl group wherein the phenyl group moiety is optionally substituted with 1 to 2 substituent(s) independently selected from the group consisting of a hydroxy group and a carboxy group, a $C_1$-$C_4$ alkylene-phenylene group, or a phenylene-$C_1$-$C_4$ alkylene group, preferably a $C_1$-$C_6$ alkylene group optionally substituted with 1 to 2 $C_1$-$C_6$ alkyl group(s) optionally substituted with 1 to 2 —COOR$^4$ group(s), a $C_1$-$C_4$ alkylene-phenylene group, or a phenylene-$C_1$-$C_4$ alkylene group, more preferably a $C_1$-$C_6$ alkylene group optionally substituted with 1 to 2 $C_1$-$C_6$ alkyl group(s) optionally substituted with 1 to 2 —COOR$^4$ group(s), or a phenylene-$C_1$-$C_4$ alkylene group, still more preferably a methylene group optionally substituted with a $C_1$-$C_6$ alkyl group optionally substituted with a —COOR$^4$ group, or a phenylenemethylene group.

In another embodiment, $L^{12}$ represents a $C_1$-$C_2$ alkylene group, preferably a methylene group.

In another embodiment, $L^{12}$ represents a $C_1$-$C_2$ alkylene group optionally substituted with 1 to 2 $C_1$-$C_2$ alkyl group(s) optionally substituted with 1 to 2 —COOR$^4$ group(s), or a phenylene-$C_1$-$C_2$ alkylene group.

In one embodiment, $L^{22}$ represents a $C_1$-$C_6$ alkylene group optionally substituted with 1 to 2 $C_1$-$C_6$ alkyl group(s) optionally substituted with 1 to 2 —COOR$^4$ group(s), a $C_1$-$C_4$ alkylene group substituted with a benzyl group wherein the phenyl group moiety is optionally substituted with 1 to 2 substituent(s) independently selected from the group consisting of a hydroxy group and a carboxy group, a $C_1$-$C_4$ alkylene-phenylene group, or a phenylene-$C_1$-$C_4$ alkylene group, preferably a $C_1$-$C_6$ alkylene group optionally substituted with 1 to 2 $C_1$-$C_6$ alkyl group(s) optionally substituted with 1 to 2 —$COOR^4$ group(s), a $C_1$-$C_4$ alkylene-phenylene group, or a phenylene-$C_1$-$C_4$ alkylene group, more preferably a $C_1$-$C_6$ alkylene group optionally substituted with 1 to 2 $C_1$-$C_6$ alkyl group(s) optionally substituted with 1 to 2 —$COOR^4$ group(s), or a phenylene-$C_1$-$C_4$ alkylene group, still more preferably a methylene group optionally substituted with a $C_1$-$C_6$ alkyl group optionally substituted with a —$COOR^4$ group.

In another embodiment, $L^{22}$ represents a $C_1$-$C_2$ alkylene group, preferably a methylene group.

In another embodiment, $L^{22}$ represents a $C_1$-$C_2$ alkylene group optionally substituted with 1 to 2 $C_1$-$C_2$ alkyl group(s) optionally substituted with 1 to 2 —$COOR^4$ group(s), or a phenylene-$C_1$-$C_2$ alkylene group.

In one embodiment, $R^4$ of "—$COOR^4$ group" in $L^3$ each independently represents a hydrogen atom, or a $C_1$-$C_4$ alkyl group optionally substituted with one trimethylsilyl group, preferably a hydrogen atom or a 2-(trimethylsilyl)ethyl group, more preferably a hydrogen atom.

In one embodiment, $L^3$ represents a $C_1$-$C_2$ alkylene-phenylene group wherein the phenylene moiety is optionally substituted with 1 to 2 —$COOR^4$ group(s), preferably a methylenephenylene group wherein the phenylene moiety is optionally substituted with one —$COOR^4$ group.

In one embodiment, $R^5$ and $R^6$ each independently represent a hydrogen atom, a halogen atom, a $C_1$-$C_4$ alkyl group, or a $C_1$-$C_4$ alkoxy group, preferably a hydrogen atom, a fluorine atom, a methyl group, or a methoxy group; more preferably $R^5$ and $R^6$ each represent a hydrogen atom.

In another embodiment, any one of $R^5$ and any one of $R^6$ may be combined with each other to form a $C_1$-$C_4$ alkyleneoxy group, preferably a trimethyleneoxy group.

In one embodiment, s and t each independently represent an integer of 1 to 3, preferably an integer of 1 to 2, more preferably each represent.

In one embodiment, at least one of $R^1$, $R^3$, $R^4$, and G represents a hydrogen atom. In another embodiment, at least one of $R^1$ and $R^4$ represents a hydrogen atom. In another embodiment, $R^1$, $R^3$, $R^4$, and G each represent a hydrogen atom.

In one embodiment, at least one of $R^1$, $R^3$, $R^4$, $G^{11}$, and $G^{12}$ represents a hydrogen atom. In another embodiment, at least one of $R^1$ and $R^4$ represents a hydrogen atom. In another embodiment, $R^1$, $R^3$, $R^4$, $G^{11}$, and $G^{12}$ each represent a hydrogen atom.

In one embodiment, Z represents an arylene group, a heteroarylene group, a single bond, or a $C_2$-$C_{30}$ alkylene group (provided that one or more methylene group(s) in the chain of said alkylene group may be replaced with group(s) independently selected from the group consisting of —C(=O)—, —$NR^2$—, —O—, an arylene group, and a heteroarylene group, and $R^7$ represents a hydrogen atom or a $C_1$-$C_4$ alkyl group).

In another embodiment, Z represents a single bond, a $C_6$-$C_{12}$ arylene group, —($CH_2$—$CH_2$—O)$_m$—$CH_2$—$CH_2$—, —($CH_2$—O—$CH_2$)$_m$—, —($CH_2$)$_n$—($C_6$-$C_{12}$ arylene)-($CH_2$)$_m$—, or —($CH_2$)$_n$—, preferably a single bond, a biphenylene group, —($CH_2$—$CH_2$—O)$_m$—$CH_2$—$CH_2$—, —($CH_2$—O—$CH_2$)$_m$—, —($CH_2$)$_m$-biphenylene-($CH_2$)$_m$—, or —($CH_2$)$_m$—, more preferably a single bond, [1,1'-biphenyl]-3,3'-diyl, —($CH_2$—$CH_2$—O)$_m$—$CH_2$—$CH_2$—, —($CH_2$—O—$CH_2$)$_m$—, —($CH_2$)$_m$—([1,1'-biphenyl]-3,3'-diyl)-($CH_2$)$_m$—, or —($CH_2$)$_n$—, still more preferably —($CH_2$—$CH_2$—O)$_m$—$CH_2$—$CH_2$—, or —($CH_2$)$_n$—, especially preferably —($CH_2$—$CH_2$—O)$_m$—$CH_2$—$CH_2$—.

In one embodiment, m represents an integer of 1 to 6, and n represents an integer of 2 to 12, preferably m represents an integer of 1 to 4, and n represents an integer of 2 to 6.

In another embodiment, m represents an integer of 1 to 6, and n represents an integer of 2 to 12, preferably m represents an integer of 1 to 4.

In one embodiment, the "group formed by removing any one hydrogen atom or any one hydroxy group from a compound represented by general formula (II)" represents a group formed by removing any one hydrogen atom or any one hydroxy group present in X or Y of a compound represented by general formula (II). The "any one hydrogen atom" represents preferably a hydrogen atom that binds to any one nitrogen atom or any one oxygen atom, more preferably a hydrogen atom that binds to any one nitrogen atom. The "any one hydroxy group" refers to a hydroxy group present in any one hydroxy group or any one carboxy group, more preferably a hydroxy group present in any one carboxy group.

In one embodiment of the Compound (I),
$A^1$ has a structure represented by

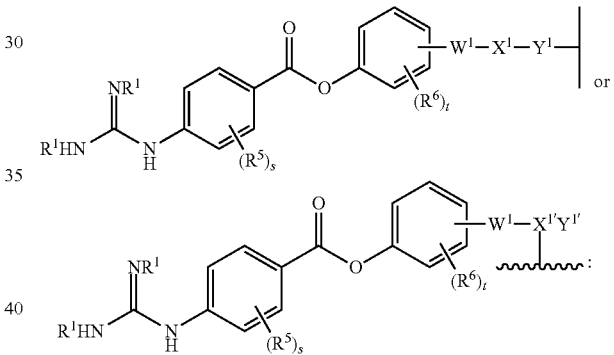

$A^2$ has a structure represented by

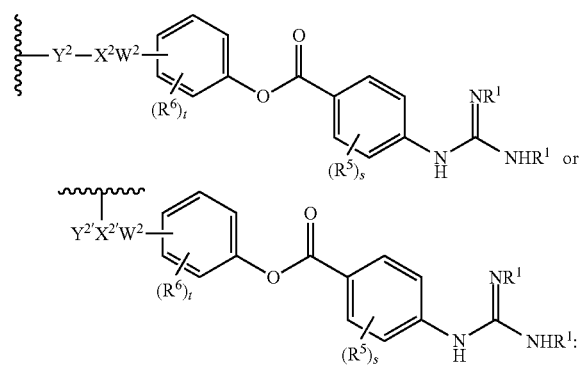

Z represents a single bond, a $C_6$-$C_{12}$ arylene group, —($CH_2$—$CH_2$—O)$_m$—$CH_2$—$CH_2$—, —($CH_2$—O—$CH_2$)$_m$—, ($CH_2$)$_n$—$C_6$-$C_{12}$ arylene)-($CH_2$)$_m$—, or —($CH_2$)$_n$—;
m represents an integer of 1 to 6; and
n represents an integer of 2 to 12.

In one embodiment of the Compound (I),
A¹ has a structure represented by

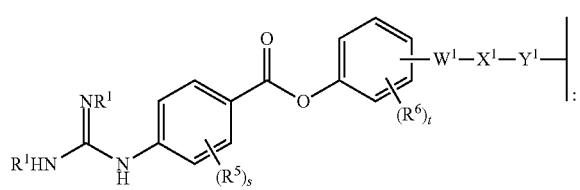

and
A² has a structure represented by

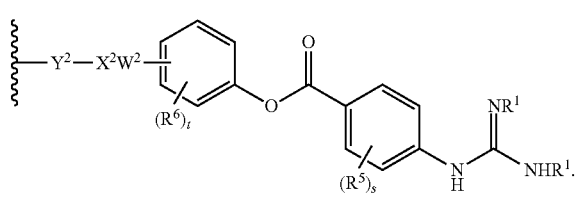

In one embodiment of the Compound (I),
A¹ has a structure represented by

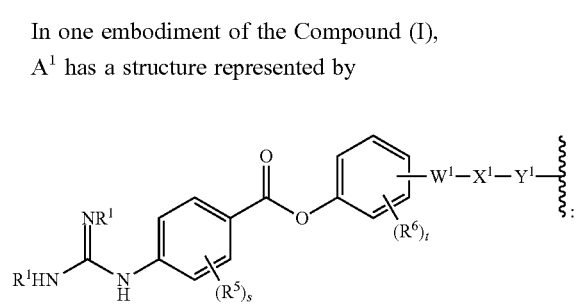

and
A² has a structure represented by

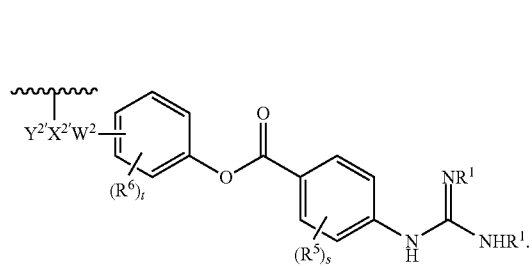

In one embodiment of the Compound (I),
A¹ has a structure represented by

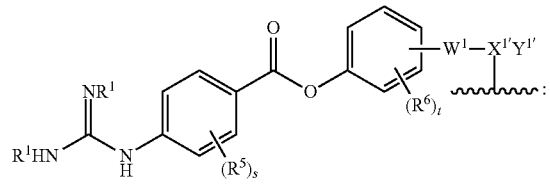

and
A² has a structure represented by

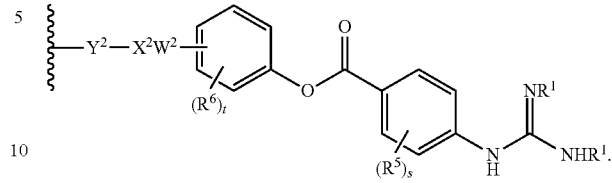

In one embodiment of the Compound (I),
A¹ has a structure represented by

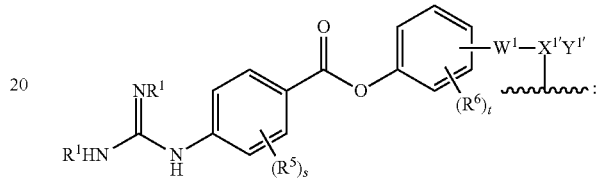

and
A² has a structure represented by

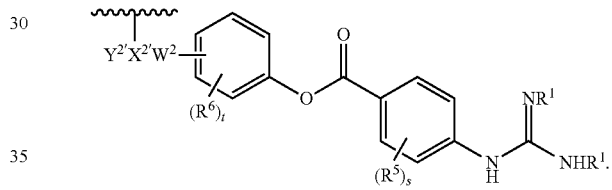

In one embodiment of the Compound (I),
A¹ has a structure represented by

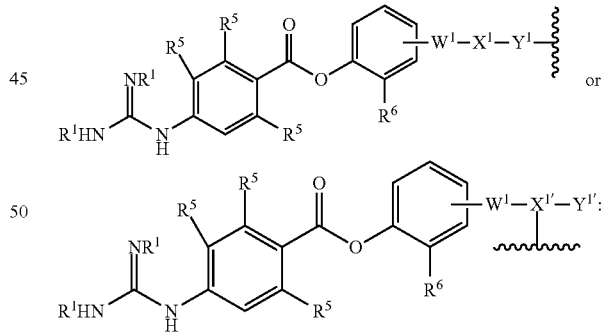 or and
A² has a structure represented by

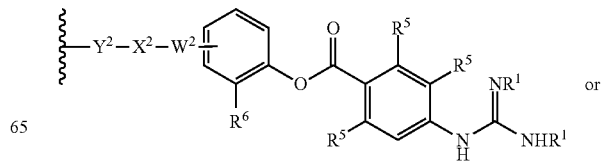 or

-continued
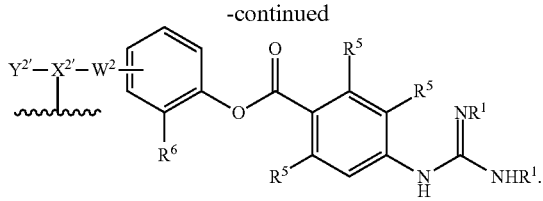
In one embodiment of the Compound (I), A¹ has a structure represented by
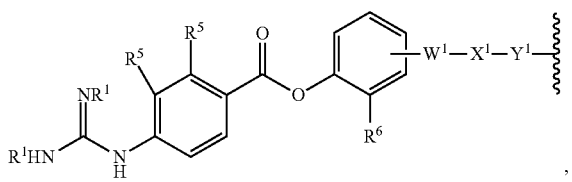
,
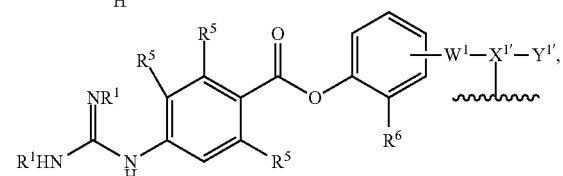
,
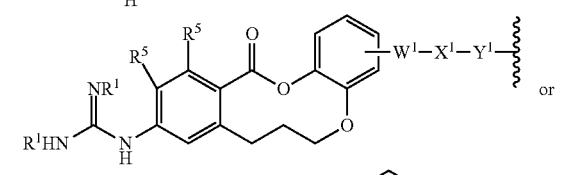
or
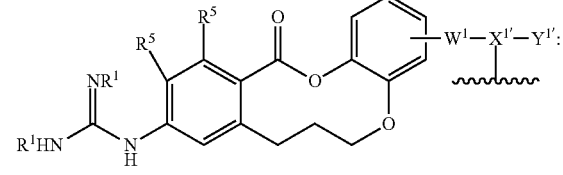
:
and
A² has a structure represented by
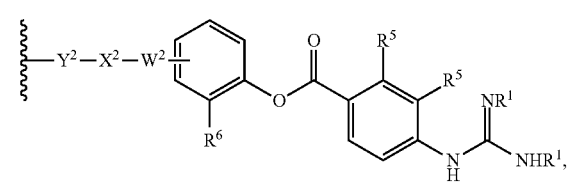
,
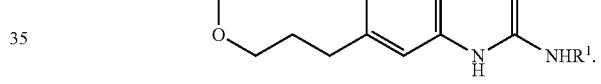
,
or
Compound (III) and Compound (IV)
In one embodiment, the Compound (I) has a structure represented by the following general formula (III):
(III)
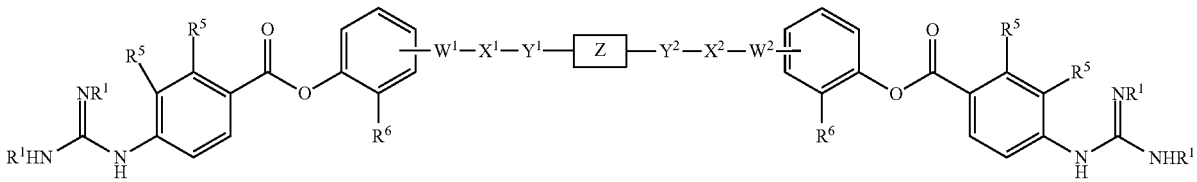
or the following general formula (IV):
(IV)
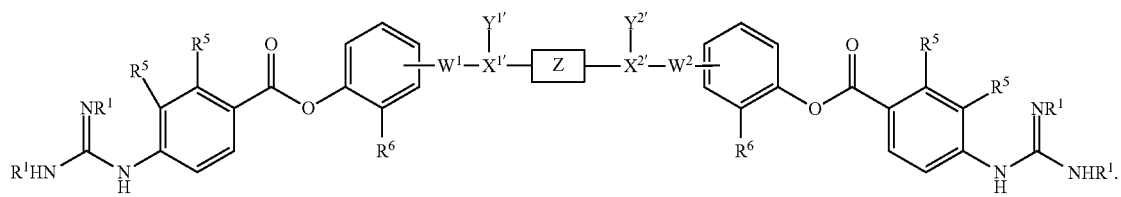

In one embodiment of the Compound (III) and the Compound (IV), a compound or a pharmaceutically acceptable salt thereof, wherein $R^1$ each independently represents a hydrogen atom or a tert-butoxycarbonyl group;

$W^1$ and $W^2$ each independently represent a single bond or a $C_1$-$C_4$ alkylene group;

$X^1$ represents —C(=O)—, —O—C(=O)—, or —$NG^{11}$-$SO_2$—;

$X^{1'}$ represents —$NG^Z$-$SO_2$—;

$X^2$ represents —C(=O)—, —C(=O)—O—, or —$SO_2$—$NG^{12}$-;

$X^{2'}$ represents —$SO_2$—$NG^Z$-;

$G^{11}$ and $G^{12}$ each independently represent a hydrogen atom, a $C_1$-$C_4$ alkyl group, or —$COOR^2$;

$G^Z$ represents a single bond that links $X^{1'}$ or $X^{2'}$ to Z;

$R^2$ represents a $C_1$-$C_4$ alkyl group optionally substituted with 1 to 5 aryl group(s);

$Y^1$ represents —$NG^{21}$-, —$NG^{21}$-$L^{11}$-C(=O)—, —$NG^{21}$-$L^{11}$-C(=O)—NH—, —$NG^{21}$-$L^{11}$-C(=O)—$NG^{31}$-$L^{21}$-C(=O)—, —$NG^{21}$-$L^{11}$-C(=O)—$NG^{31}$-$L^{21}$-C(=O)—NH—, —$NG^{21}$-$L^3$-O—, or —$NG^{21}$-$G^{4'}$-;

$Y^{1'}$ represents —$NG^{21}$H, —$NG^{21}$-$L^{11}$-COOH, or —$NG^{21}$-$L^{11}$-C(=O)—$NG^{31}$-$L^{21}$-COOH;

$Y^2$ represents —$NG^{22}$-, —C(=O)-$L^{12}$-$NG^{22}$-, —NH—C(=O)-$L^{12}$-$NG^{22}$-, —C(=O)-$L^{22}NG^{32}$-C(=O)-$L^{12}$-$NG^{22}$-, —NH—C(=O)-$L^{22}$-$NG^{32}$-C(=O)-$L^{12}$-$NG^{22}$-, —O-$L^3$-$NG^{22}$-, or -$G^{4'}$-$NG^{22}$-;

$Y^{2'}$ represents $HNG^{22}$-, $HOOC$-$L^{12}$-$NG^{22}$-, or $HOOC$-$L^{22}$-$NG^{32}$-C(=O)-$L^{12}$-$NG^{22}$-;

$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —$COOR^2$ group(s) and a —$COOR^3$ group;

$G^{4'}$ represents a $C_1$-$C_4$ alkylene group or a $C_1$-$C_4$ alkyleneoxy-$C_1$-$C_4$ alkylene group;

$R^3$ each independently represents a hydrogen atom, a benzyl group, or a tert-butyl group;

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group;

$L^3$ represents a $C_1$-$C_4$ alkylene-phenylene group wherein the phenylene moiety is optionally substituted with 1 to 3 —$COOR^4$ group(s);

$R^4$ each independently represents a hydrogen atom, a benzyl group, a 2-(trimethylsilyl)ethyl group, or a tert-butyl group;

$R^5$ and $R^6$ each independently represent a hydrogen atom, a halogen atom, a $C_1$-$C_4$ alkyl group, or a $C_1$-$C_4$ alkoxy group;

each $R^5$ may be the same or different with each other;

Z represents a single bond, a $C_1$-$C_{12}$ arylene group, —($CH_2$—$CH_2$—O$)_m$—$CH_2$—$CH_2$—, —($CH_2$O—$CH_2$$)_m$—, —($CH_2$$)_m$—($C_6$-$C_{12}$ arylene)-($CH_2$$)_m$—, or —($CH_2$$)_n$—;

m represents an integer of 1 to 6; and n represents an integer of 2 to 12 is provided.

In one embodiment of the Compound (III) and the Compound (IV), a compound or a pharmaceutically acceptable salt thereof, wherein $R^1$ each represents a hydrogen atom;

$W^1$ and $W^2$ each independently represent a single bond or a $C_1$-$C_4$ alkylene group;

$X^1$ represents —C(=O)—, —O—C(=O)—, or —$NG^{11}$-$SO_2$—;

$X^{1'}$ represents —$NG^Z$-$SO_2$—;

$X^2$ represents —C(=O)—, —C(=O)—O—, or —$SO_2$—$NG^{12}$-;

$X^{2'}$ represents —$SO_2$—$NG^Z$-;

$G^{11}$ and $G^{12}$ each independently represent a hydrogen atom, a $C_1$-$C_4$ alkyl group, or —$COOR^2$;

$G^Z$ represents a single bond that links $X^{1'}$ or $X^{2'}$ to Z;

$R^2$ represents a $C_1$-$C_4$ alkyl group optionally substituted with 1 to 5 aryl group(s);

$Y^1$ represents —$NG^{21}$-, —$NG^{21}$-$L^{11}$-C(=O)—, —$NG^{21}$-$L^{11}$-C(=O)—NH—, —$NG^{21}$-$L^{11}$-C(=O)—$NG^{31}$-$L^{21}$-C(=O)—, —$NG^{21}$-$L^{11}$-C(=O)—$NG^{31}$-$L^{21}$-C(=O)—NH—, —$NG^{21}$-$L^3$-O—, or —$NG^{21}$-$G^{4'}$-;

$Y^{1'}$ represents —$NG^{21}$H, —$NG^{21}$-$L^{11}$-COOH, or —$NG^{21}$-$L^{11}$-C(=O)—$NG^1$-$L^{21}$-COOH;

$Y^2$ represents —$NG^{22}$-, —C(=O)-$L^{12}$-$NG^{22}$-, —NH—C(=O)-$L^{12}$-$NG^{22}$-, —C(=O)-$L^{22}$-$NG^{32}$-C(=O)-$L^{12}$-$NG^{22}$-, —NH—C(=O)-$L^{22}$-$NG^{32}$-C(=O)-$L^{12}$-$NG^{12}$-, —O-$L^3$-$NG^{22}$-, or -$G^{4'}$-$NG^{12}$-;

$Y^{2'}$ represents $HNG^2$-, $HOOC$-$L^{12}$-$NG^{22}$-, or $HOOC$-$L^{12}$-$NG^{12}$-C(=O)-$L^{12}$-$NG^2$-;

$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —$COOR^3$ group(s) and a —$COOR^3$ group;

$G^{4'}$ represents a $C_1$-$C_4$ alkylene group or a $C_1$-$C_4$ alkyleneoxy-$C_1$-$C_4$ alkylene group;

$R^3$ each independently represents a hydrogen atom, a benzyl group, or a tert-butyl group;

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group;

$L^3$ represents a $C_1$-$C_4$ alkylene-phenylene group wherein the phenylene moiety is optionally substituted with 1 to 3 —$COOR^4$ group(s);

$R^4$ each represents a hydrogen atom;

$R^5$ and $R^6$ each independently represent a hydrogen atom, a halogen atom, a $C_1$-$C_4$ alkyl group, or a $C_1$-$C_4$ alkoxy group;

each $R^5$ may be the same or different with each other;

Z represents a single bond, a $C_6$-$C_{12}$ arylene group, —($CH_2$—$CH_2$—O$)_m$—$CH_2$—$CH_2$—, —($CH_2$—O—$CH_2$$)_m$—, —($CH_2$$)_m$—($C_6$-$C_{12}$ arylene)-($CH_2$$)_m$—, or —($CH_2$$)_n$—;

m represents an integer of 1 to 6; and n represents an integer of 2 to 12 is provided.

In one embodiment of the Compound (III) and the Compound (IV), a compound or a pharmaceutically acceptable salt thereof, wherein $R^1$ each represents a hydrogen atom;

$W^1$ and $W^2$ each independently represent a single bond or a $C_1$-$C_4$ alkylene group;

$X^1$ represents —C(=O)—, —C(=O)— or —$NG^{11}$-$SO_2$—;

$X^{1'}$ represents —$NG^2$-$SO_2$—;

$X^2$ represents —C(=O)—, —C(=O)—O—, or —$SO_2$—$NG^{12}$-;

$X^{2'}$ represents —$SO_2$—$NG^2$-;

$G^{11}$ and $G^{12}$ each represent a hydrogen atom;

$G^Z$ represents a single bond that links $X^{1'}$ or $X^{2'}$ to Z;

$Y^1$ represents —$NG^{21}$—, —$NG^{21}$-$L^{11}$-C(=O)—, —$NG^{21}$-$L^{11}$-C(=O)—NH—, —$NG^{21}$-$L^{11}$-C(=O)—$NG^{31}$-$L^{21}$-C(=O)—, —$NG^{21}$-$L^{11}$-C(=O)—$NG^{32}$-$L^{21}$-C(=O)—NH—, —$NG^{21}$-$L^3$-O—, or —$NG^{21}$-$G^{4'}$-;

$Y^{1'}$ represents —$NG^{21}$H, —$NG^{21}$-$L^{11}$-COOH, or —$NG^{21}$-$L^{11}$-C(=O)—$NG^{31}$-$L^{21}$-COOH;

$Y^2$ represents —$NG^{22}$—, —C(=O)-$L^{12}$-$NG^{22}$-, —NH—C(=O)-$L^{12}$-$NG^{22}$-, —C(=O)-$L^{22}$-$NG^{32}$-C(=O)-$L^{12}$-$NG^{22}$-, —NH—C(=O)-$L^{22}$-$NG^{32}$-C(=O)-$L^{12}$-$NG^{22}$-, —O-$L^3$-$NG^{22}$-, or -$G^{4'}$-$NG^{22}$-;

$Y^{2'}$ represents HN$G^{22}$-, HOOC-$L^{12}$-$NG^{22}$-, or HOOC-$L^{22}$-$NG^{32}$-C(=O)-$L^{12}$-$NG^{22}$-;

$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —COO$R^3$ group(s) and a —COO$R^3$ group;

$G^{4'}$ represents a $C_1$-$C_4$ alkylene group or a $C_1$-$C_4$ alkyleneoxy-$C_1$-$C_4$ alkylene group;

$R^3$ each represents a hydrogen atom;

$L^1$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —COO$R^4$ group(s), a $C_1$-$C_4$ alkylene-phenylene group, or a phenylene-$C_1$-$C_4$ alkylene group;

$L^3$ represents a $C_1$-$C_4$ alkylene-phenylene group wherein the phenylene moiety is optionally substituted with 1 to 3 —COO$R^4$ group(s);

$R^4$ each represents a hydrogen atom;

$R^5$ and $R^6$ each independently represent a hydrogen atom, a halogen atom, a $C_1$-$C_4$ alkyl group, or a $C_1$-$C_4$ alkoxy group;

each $R^5$ may be the same or different with each other;

Z represents a single bond, a $C_6$-$C_{12}$ arylene group, —(CH$_2$—CH$_2$—O)—CH$_2$—CH$_2$—, —(CH$_2$—O—CH$_2$)$_m$—, —(CH$_2$)$_m$—(C$_6$-C$_{12}$ arylene)-(C$_2$)$_m$—, or —(CH$_2$)$_n$—;

m represents an integer of 1 to 6; and n represents an integer of 2 to 12 is provided.

In another embodiment of the Compound (III) and the Compound (IV), a compound or a pharmaceutically acceptable salt thereof, wherein $R^1$ each independently represents a hydrogen atom or a tert-butoxycarbonyl group;

$W^1$ and $W^2$ each independently represent a single bond or a $C_1$-$C_4$ alkylene group;

$X^1$ represents —C(=O)—, —O—C(=O)—, or —$NG^{11}$-SO$_2$—;

$X^{1'}$ represents —$NG^Z$-SO$_2$—;

$X^2$ represents —C(=O)—, —C(=O)—O—, or —SO$_2$—$NG^{12}$-;

$X^{2'}$ represents —SO$_2$—$NG^Z$-;

$G^{11}$ and $G^{12}$ each independently represent a hydrogen atom, a $C_1$-$C_4$ alkyl group, or —COO$R^2$;

$G^Z$ represents a single bond that links $X^{1'}$ or $X^{2'}$ to Z;

$R^2$ represents a $C_1$-$C_4$ alkyl group optionally substituted with 1 to 3 aryl group(s);

$Y^1$ represents —$NG^{21}$-, —$NG^{21}$-$L^{11}$-C(=O)—, —$NG^{21}$-$L^{11}$-C(=O)—NH—, —$NG^{21}$-$L^{11}$-C(=O)—$NG^{31}$-$L^{21}$-C(=O)—, —$NG^{21}$-$L^{11}$-C(=O)—$NG^{31}$-$L^{21}$-C(=O)—NH—, or —$NG^{21}$-$L^3$-O—;

$Y^{1'}$ represents —$NG^{21}$H, —$NG^{21}$-$L^{11}$-COOH, or —$NG^{21}$-$L^{11}$-C(=O)—$NG^{31}$-$L^{21}$-COOH;

$Y^2$ represents —$NG^{22}$-, —C(=O)-$L^{12}$-$NG^{22}$-, —NH—C(=O)-$L^{12}$-$NG^{22}$-, —C(=O)-$L^{22}$-$NG^{32}$-C(=O)-$L^{12}$-$NG^{22}$-, —NH—C(=O)-$L^{22}$-$NG^{32}$-C(=O)-$L^{12}$-$NG^{22}$-, or —O-$L^3$-$NG^{22}$-;

$Y^{2'}$ represents HN$G^{22}$-, HOOC-$L^{12}$-$NG^{22}$-, or HOOC-$L^{22}$-$NG^{32}$-C(=O)-$L^{12}$-$NG^{22}$-;

$G^{21}$, $G^{31}$, $G^{22}$, and $G^{32}$ each independently represent a hydrogen atom, or a $C_1$-$C_6$ alkyl group optionally substituted with 1 to 3 substituent(s) independently selected from the group consisting of a phenyl group optionally substituted with 1 to 3 —COO$R^3$ group(s) and a —COO$R^3$ group;

$R^3$ each independently represents a hydrogen atom, a benzyl group, or a tert-butyl group;

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —COO$R^4$ group(s), a $C_1$-$C_4$ alkylene-phenylene group, or a phenylene-$C_1$-$C_4$ alkylene group;

$L^3$ represents a $C_1$-$C_2$ alkylene-phenylene group wherein the phenylene moiety is optionally substituted with 1 to 2 —COO$R^4$ group(s);

$R^4$ each independently represents a hydrogen atom, a benzyl group, a 2-(trimethylsilyl)ethyl group, or a tert-butyl group;

$R^5$ and $R^6$ each independently represent a hydrogen atom, a halogen atom, a $C_1$-$C_4$ alkyl group, or a $C_1$-$C_4$ alkoxy group;

each R may be the same or different with each other;

Z represents a single bond, a biphenylene group, —(CH$_2$—CH$_2$—O)$_m$—CH$_2$—CH$_2$—, —CH$_2$—O—CH$_2$)$_m$—, —(CH$_2$)$_m$-biphenylene-(CH$_2$)$_m$, or —(CH$_2$)$_n$—;

m represents an integer of 1 to 6; and n represents an integer of 2 to 12 is provided.

In another embodiment of the Compound (III) and the Compound (IV), a compound or a pharmaceutically acceptable salt thereof, wherein $R^1$ each represents a hydrogen atom;

$W^1$ and $W^2$ each independently represent a single bond or a $C_1$-$C_4$ alkylene group;

$X^1$ represents —C(=O)—, —O—C(O)—, or —$NG^{11}$-SO$_2$—;

$X^{1'}$ represents —$NG^Z$-SO$_2$—;

$X^2$ represents —C(=O)—, —C(=O)—O—, or —SO$_2$—$NG^{12}$-;

$X^{2'}$ represents —SO$_2$$NG^Z$-;

$G^{11}$ and $G^{12}$ each independently represent a hydrogen atom, a $C_1$-$C_4$ alkyl group, or —COO$R^2$;

$G^Z$ represents a single bond that links $X^{1'}$ or $X^{2'}$ to Z;

$R^2$ represents a $C_1$-$C_4$ alkyl group optionally substituted with 1 to 3 phenyl group(s);

$Y^1$ represents —$NG^{21}$-, —$NG^{21}$-$L^{11}$-C(=O)—, —$NG^{21}$-$L^{11}$-C(=O)—NH—, —$NG^{21}$-$L^{21}$-C(=O) $NG^{31}$-$L^{23}$-C(=O)—, —$NG^{21}$-$L^{11}$-C(=O)—$NG^{31}$-$L^{21}$-C(=O)—NH—, or —$NG^{21}$-$L^3$-O—;

$Y^{1'}$ represents —$NG^2$-, —$NG^{21}$-$L^{11}$-COOH, or —$NG^{21}$-$L^{11}$-C(=O)—$NG^{31}$-$L^{21}$-COOH;

$Y^2$ represents —$NG^{22}$-, —C(=O)-$L^{11}$-$NG^{22}$-NH—C(=O)-$L^{12}$-$NG^{22}$-, —C(=O)-$L^{22}$-$NG^{32}$-C(=O)-$L^{12}$-$NG^{22}$-, —NH—C(=O)-$L^{22}$-$NG^{32}$-C(=O)-$L^{12}$-$NG^{22}$-, or —O-$L^3$-$NG^{22}$-;

$Y^{2'}$ represents HN$G^{22}$-, HOOC-$L^{12}$-$NG^{22}$-, or HOOC-$L^{22}$-$NG^{32}$-C(=O)-$L^{12}$-$NG^{22}$-;

$G^{21}$, $G^3$, $G^{22}$, and $G^{32}$ each independently represent a hydrogen atom, or a $C_1$-$C_6$ alkyl group optionally substituted with 1 to 3 substituent(s) independently selected from the group consisting of a phenyl group optionally substituted with 1 to 3 —COO$R^3$ group(s) and a —COO$R^3$ group;

$R^3$ each represents a hydrogen atom;

$L^{11}$, $L^{21}$, $L^{12}$, and $L^{22}$ each independently represent a $C_1$-$C_4$ alkylene group optionally substituted with 1 to 2

$C_1$-$C_6$ alkyl group(s) optionally substituted with 1 to 2 —COOR$^4$ group(s), a $C_1$-$C_4$ alkylene-phenylene group, or a phenylene-$C_1$-$C_4$ alkylene group;

L$^3$ represents a $C_1$-$C_2$ alkylene-phenylene group wherein the phenylene moiety is optionally substituted with 1 to 2 —COOR$^4$ group(s);

R$^4$ each represents a hydrogen atom;

R$^5$ and R$^6$ each independently represent a hydrogen atom, a fluorine atom, a methyl group, or a methoxy group;

each R may be the same or different with each other;

Z represents a single bond, a biphenylene group, —($CH_2$—$CH_2$—O)$_m$—$CH_2$—$CH_2$—, —($CH_2$—O—$CH_2$)$_m$—, —($CH_2$)$_m$-biphenylene-($CH_2$)$_m$— or —($CH_2$)$_n$—;

m represents an integer of 1 to 6; and n represents an integer of 2 to 12 is provided.

In another embodiment of the Compound (III) and the Compound (IV), a compound or a pharmaceutically acceptable salt thereof, wherein R$^1$ each represents a hydrogen atom;

W$^1$ and W$^2$ each independently represent a single bond or a $C_1$-$C_4$ alkylene group;

X$^1$ represents —C(=O)—, —O—C(=O)—, or —NG$^{11}$-SO$_2$—;

X$^{1'}$ represents —NG$^Z$-SO$_2$—;

X$^2$ represents —C(=O)—, —C(=O)—O—, or —SO$_2$—NG$^{12}$-;

X$^{2'}$ represents —SO$_2$—NG$^Z$-;

G$^{11}$ and G$^{12}$ each represent a hydrogen atom;

G$^Z$ represents a single bond that links X$^{1'}$ or X$^{2'}$ to Z;

Y$^1$ represents —NG$^{21}$-, —NG$^{21}$-L$^{11}$-C(=O)—, —NG$^{21}$-L$^{11}$-C(=O)—NH—, —NG$^{21}$-L$^{11}$-C(=O)—NG$^{31}$-L$^2$-C(=O)—, —NG$^{21}$-L$^{11}$-C(=O)—NG$^{31}$-L$^{21}$-C(=O)—NH—, or —NG$^{21}$-L$^3$-O—;

Y$^{1'}$ represents —NG$^{21}$H, —NG$^{21}$-L$^{11}$-COOH, or —NG$^{21}$-L$^{11}$-C(=O)—NG$^{31}$-L$^{21}$-COOH;

Y$^2$ represents —NG$^{22}$-, —C(=O)-L$^{12}$-NG$^{22}$-, —NH—C(=O)-L$^{12}$-NG$^{22}$-, —C(=O)-L$^{22}$-NG$^{32}$-C(=O)-L$^{12}$-NG$^{22}$-, —NH—C(=O)-L$^{22}$-NG$^{32}$-C(=O)-L$^{12}$-NG$^{22}$-, or —O-L$^3$-NG$^{22}$-;

Y$^{2'}$ represents HNG$^{22}$-, HOOC-L$^{12}$-NG$^{22}$-, or HOOC-L$^{22}$-NG$^{32}$-C(=O)-L$^{12}$-NG$^{22}$-;

G$^{21}$, G$^{31}$, G$^{22}$, and G$^{32}$ each independently represent a hydrogen atom, or a $C_1$-$C_6$ alkyl group optionally substituted with 1 to 3 substituent(s) independently selected from the group consisting of a phenyl group optionally substituted with 1 to 3 —COOR$^3$ group(s) and a —COOR$^3$ group;

R each represents a hydrogen atom;

L$^{11}$, L$^{21}$, L$^{12}$, and L$^{22}$ each independently represent a $C_1$-$C_6$ alkylene group optionally substituted with 1 to 2 $C_1$-$C_6$ alkyl group (s) optionally substituted with 1 to 2 —COOR$^4$ group(s), a $C_1$-$C_4$ alkylene-phenylene group, or a phenylene-$C_1$-$C_4$ alkylene group;

L$^3$ represents a $C_1$-$C_2$ alkylene-phenylene group wherein the phenyl ene moiety is optionally substituted with 1 to 2 COOR$^4$ group(s);

R$^4$ each represents a hydrogen atom;

R$^5$ and R$^6$ each independently represent a hydrogen atom, a fluorine atom, a methyl group, or a methoxy group;

each R$^5$ may be the same or different with each other;

Z represents a single bond, a biphenylene group, —($CH_2$—$CH_2$—O)$_m$—$CH_2$—$CH_2$—, —($CH$—O—$CH_2$)$_m$—, —($CH_2$)$_m$-biphenylene-($CH_2$)$_m$—, or —($CH_2$)$_n$—;

m represents an integer of 1 to 6; and n represents an integer of 2 to 12 is provided.

In another embodiment of the Compound (II) and the Compound (IV), a compound or a pharmaceutically acceptable salt thereof, wherein R$^1$ each represents a hydrogen atom;

W$^1$ and W$^2$ each independently represent a single bond or a $C_1$-$C_4$ alkylene group;

X$^1$ represents —C(=O)—, —O—C(=O)—, or —NG$^{11}$-SO$_2$—;

X$^{1'}$ represents —NG$^Z$-SO$_2$—;

X$^2$ represents —C(=O)—, —C(=O)—O—, or —SO$_2$—NG$^{12}$-;

X$^{2'}$ represents —SO$_2$—NG$^Z$-;

G$^{11}$ and G$^{12}$ each independently represent a hydrogen atom, a $C_1$-$C_4$ alkyl group, or —COOR$^2$;

G$^Z$ represents a single bond that links X$^{1'}$ or X$^{2'}$ to Z;

R$^2$ represents a $C_1$-$C_4$ alkyl group optionally substituted with one phenyl group;

Y$^1$ represents —NG$^{21}$-, —NG$^{21}$-L$^{11}$-C(=O)—, —NG$^{21}$-L$^{11}$-C(=O)—NH—, —NG$^{21}$-L$^{11}$-C(=O)—NG$^{13}$-L$^{21}$-C(=O)—, —NG$^{21}$-L$^{11}$-C(=O)—NG$^{31}$-L$^{21}$-C(=O)—NH—, or —NG$^{21}$-L$^3$-O—;

Y$^{1'}$ represents —NG$^{21}$H, —NG$^{21}$-L$^{11}$-COOH, or —NG$^{21}$-L$^{11}$-C(=O)—NG$^{31}$-L$^{21}$-COOH;

Y$^2$ represents —NG$^{22}$-, —C(=O)-L$^{12}$-NG$^{22}$-, —NH—C(=O)-L$^{12}$-NG$^{22}$-, —C(=O)-L$^{22}$-NG$^{32}$-C(=O)-L$^{12}$-NG$^{22}$-, —NH—C(=O)-L$^{22}$-NG$^{32}$-C(=O)-L$^{12}$-NG$^{22}$-, or —O-L$^3$-NG$^{22}$-;

Y$^{2'}$ represents HNG$^{22}$-, HOOC-L$^{12}$-NG$^{22}$-, or HOOC-L$^{22}$-NG$^{32}$-C(=O)-L$^{12}$-NG$^{22}$-;

G$^{21}$ and G$^{22}$ each independently represent a hydrogen atom, or a $C_1$-$C_3$ alkyl group substituted with 1 to 3 carboxy group(s);

G$^{31}$ and G$^{32}$ each represents a hydrogen atom;

L$^{11}$ and L$^{21}$ each independently represent a $C_1$-$C_6$ alkylene group optionally substituted with 1 to 2 $C_1$-$C_6$ alkyl group(s) optionally substituted with 1 to 2 —COOR$^9$ group(s), or a $C_1$-$C_4$ alkylene-phenylene group;

L$^{12}$ and L$^{22}$ each independently represent a $C_1$-$C_6$ alkylene group optionally substituted with 1 to 2 $C_1$-$C_6$ alkyl group(s) optionally substituted with 1 to 2 —COOR$^4$ group(s), or a phenylene-$C_1$-$C_4$ alkylene group;

L$^3$ represents a methylenephenylene group wherein the phenylene moiety is optionally substituted with one —COOR$^4$ group;

R$^4$ represents a hydrogen atom;

R$^5$ and R$^6$ each independently represent a hydrogen atom, a fluorine atom, a methyl group, or a methoxy group;

each R$^5$ may be the same or different with each other;

Z represents a single bond, [1,1'-biphenyl]-3,3'-diyl, —($CH_2$—$CH_2$—O)$_m$—$CH_2$—$CH_2$, —($CH_2$—O—$CH_2$)$_m$—, —($CH_2$)$_m$—([1,1'-biphenyl]-3,3'-diyl)-($CH_2$)$_m$—, or —($CH_2$)$_n$—;

m represents an integer of 1 to 6; and n represents an integer of 2 to 12 is provided.

In another embodiment of the Compound (III) and the Compound (IV), a compound or a pharmaceutically acceptable salt thereof, wherein R$^1$ each represents a hydrogen atom;

W$^1$ and W$^2$ each independently represent a single bond or a $C_1$-$C_4$ alkylene group;

X$^1$ represents —C(=O)—, —O—C(=O)—, or —NG$^{11}$-SO$_2$—;

X$^{1'}$ represents —NG$^Z$-SO$_2$—;

X$^2$ represents —C(=O)—, —C(=O)—O—, or —SO$_2$—NG$^{12}$-;

X$^{2'}$ represents —SO$_2$—NG$^Z$-;

$G^{11}$ and $G^{12}$ each represent a hydrogen atom;

$G^Z$ represents a single bond that links $X^{1'}$ or $X^{2'}$ to Z;

$Y^1$ represents $-NG^{23}-$, $-NG^{21}-L^{11}-C(=O)-$, $-NG^{21}-L^{11}-C(=O)-NH-$, $-NG^{21}-L^{11}-C(=O)-NG^{31}-L^{21}-C(=O)-$, $-NG^{21}-L^{11}-C(=O)-NG^{31}-L^{21}-C(=O)-NH-$, or $-NG^{21}-L^3-O-$;

$Y^{1'}$ represents $-NG^{21}H$, $-NG^{21}-L^{11}-COOH$, or $-NG^{21}-L^{11}-C(=O)-NG^{31}-L^{21}-COOH$;

$Y^2$ represents $-NG^{22}-$, $-C(=O)-L^{12}-NG^{22}-$, $-NH-C(=O)-L^{12}-NG^{22}-$, $-C(=O)-L^{22}-NG^{32}-C(=O)-L^{12}-NG^{22}-$, $-NH-C(=O)-L^{22}-NG^{32}-C(=O)-L^{12}-NG^{22}-$, or $-O-L^3-NG^{22}-$;

$Y^{2'}$ represents $HNG^{22}-$, $HOOC-L^{12}-NG^{22}-$, or $HOOC-L^{22}-NG^{32}-C(=O)-L^{12}-NG^{22}-$;

$G^{21}$ and $G^{22}$ each independently represent a hydrogen atom, or a $C_1$-$C_3$ alkyl group substituted with 1 to 3 carboxy group(s);

$G^{31}$ and $G^{32}$ each represents a hydrogen atom;

$L^{11}$ and $L^{21}$ each independently represent a $C_1$-$C_6$ alkylene group optionally substituted with 1 to 2 $C_1$-$C_6$ alkyl group(s) optionally substituted with 1 to 2-$COOR^4$ group(s), or a $C_1$-$C_4$ alkylene-phenylene group;

$L^{12}$ and $L^{22}$ each independently represent a $C_1$-$C_6$ alkylene group optionally substituted with 1 to 2 $C_1$-$C_6$ alkyl group(s) optionally substituted with 1 to 2-$COOR^4$ group(s), or a phenylene-$C_1$-$C_4$ alkylene group;

$L^3$ represents a methylenephenylene group wherein the phenylene moiety is optionally substituted with one $-COOR^4$ group;

$R^4$ represents a hydrogen atom;

$R^5$ and $R^6$ each independently represent a hydrogen atom, a fluorine atom, a methyl group, or a methoxy group;

each $R^1$ may be the same or different with each other;

Z represents a single bond, [1,1'-biphenyl]-3,3'-diyl, $-(CH_2-CH_2-O)_m-CH_2-CH_2-$, $-(CH_2-O-CH_2)_m-$, $-(CH_2)_m-([1,1'-biphenyl]-3,3'-diyl)-(CH_2)_m-$, or $-(CH_2)_n-$;

m represents an integer of 1 to 6; and n represents an integer of 2 to 12 is provided.

In another embodiment of the Compound (III) and the Compound (IV), a compound or a pharmaceutically acceptable salt thereof, wherein $R^1$ each represents a hydrogen atom;

$W^1$ and $W^2$ each independently represent a single bond or a $C_1$-$C_4$ alkylene group;

$X^1$ represents $-C(=O)-$ or $-NG^{11}-SO_2-$;

$X^{1'}$ represents $-NG^Z-SO_2-$;

$X^2$ represents $-C(=O)-$ or $-SO_2-NG^{12}-$;

$X^{2'}$ represents $-SO_2-NG^Z-$;

$G^{11}$ and $G^{12}$ each independently represent a hydrogen atom or $-COOR^2$;

$G^Z$ represents a single bond that links $X^{1'}$ or $X^{2'}$ to Z;

$R^2$ represents a $C_1$-$C_4$ alkyl group optionally substituted with one phenyl group;

$Y^1$ represents $-NG^{21}-$;

$Y^{1'}$ represents $-NG^{21}H$;

$Y^2$ represents $-NG^{22}-$;

$Y^{2'}$ represents $HNG^{22}-$;

$G^{21}$ and $G^{22}$ each independently represent a hydrogen atom, or a $C_1$-$C_3$ alkyl group substituted with 1 to 3 carboxy group(s);

$R^5$ and $R^6$ each independently represent a hydrogen atom, a fluorine atom, a methyl group, or a methoxy group;

each $R^5$ may be the same or different with each other;

Z represents a single bond, [1,1'-biphenyl]-3,3'-diyl, $-(CH_2-CH_2-O)_m-CH_2-CH_2-$, $-(CH_2-O-CH_2)_m-$, $-(CH_2)_m-([1,1'-biphenyl]-3,3'-diyl)-(CH_2)_m-$, or $-(CH_2)_n-$;

m represents an integer of 1 to 6; and n represents an integer of 2 to 12 is provided.

In another embodiment of the Compound (III) and the Compound (IV), a compound or a pharmaceutically acceptable salt thereof, wherein $R^1$ each represents a hydrogen atom;

$W^1$ and $W^2$ each independently represent a single bond or a $C_1$-$C_2$ alkylene group;

$X^1$ represents $-C(=O)-$ or $-NG^{11}-SO_2-$;

$X^{1'}$ represents $-NG^Z-SO_2-$;

$X^2$ represents $-C(=O)-$ or $-SO_2-NG^{12}-$;

$X^{2'}$ represents $-SO_2-NG^Z-$;

$G^{11}$ and $G^{12}$ each represent a hydrogen atom;

$G^Z$ represents a single bond that links $X^{1'}$ or $X^{2'}$ to Z;

$Y^1$ represents $-NG^{21}-$;

$Y^{1'}$ represents $-NG^{21}H$;

$Y^2$ represents $-NG^{22}-$;

$Y^{2'}$ represents $HNG^{22}-$;

$G^{21}$ and $G^{22}$ each independently represent a $C_1$-$C_3$ alkyl group substituted with 1 to 3 carboxy group(s);

$R^5$ and $R^6$ each represents a hydrogen atom;

Z represents a single bond, [1,1'-biphenyl]-3,3'-diyl, $-(CH_2-CH_2-O)_m-CH_2-CH_2-$, $-(CH_2-O-CH_2)_m-$, $-(CH_2)_m-([1,1'-biphenyl]-3,3'-diyl)-(CH_2)_m-$, or $-(CH_2)_n-$;

m represents an integer of 1 to 6; and n represents an integer of 2 to 12 is provided.

Compound (V) and Compound (VI)

In one embodiment, the Compound (I) has a structure represented by the following general formula (V):

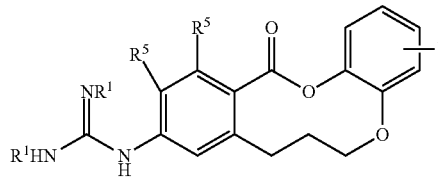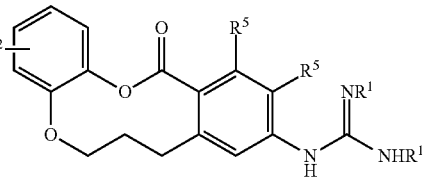

(V)

[wherein:

$R^1$ each independently represents a hydrogen atom or a —COO—($C_1$-$C_4$ alkyl group);

$W^1$ and $W^2$ each independently represent a single bond or a $C_1$-$C_4$ alkylene group;

$X^1$ represents —C(=O)— or —$NG^{11}$-$SO_2$—;

$X^2$ represents —C(=O)— or —$SO_2$—$NG^{12}$-;

$G^{11}$ and $G^{12}$ each independently represent a hydrogen atom, a $C_1$-$C_4$ alkyl group, or —$COOR^2$;

$R^2$ represents a $C_1$-$C_4$ alkyl group optionally substituted with 1 to 5 aryl group(s);

$Y^1$ represents —$NG^{21}$-, —$NG^{21}$-$L^{11}$-C(=O)—, —$NG^{21}$-$L^{11}$-C(=O)—NH—, —$NG^{21}$-$L^{11}$-C(=O)—$NG^{31}$-$L^{21}$-C(=O)—, —$NG^{23}$-$L^{11}$-C(=O)—$NG^{31}$-$L^{21}$-C(=O)—NH—, —$NG^{21}$-$L^3$-O—, or —$NG^{21}$-$G^{4'}$-;

$Y^2$ represents —$NG^{22}$-, —C(=O)-$L^{12}$-$NG^{22}$-, —NH—C(=O)-$L^{12}$-$NG^{22}$-, —C(=O)-$L^{22}$-$NG^{32}$-C(=O)-$L^{12}$-$NG^{22}$-, —NH—C(=O)-$L^{22}$-$NG^{32}$-C(=O)-$L^{12}$-$NG^{22}$-, —O-$L^3$-$NG^{22}$-, or -$G^{4'}$-$NG^{22}$-;

$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —$COOR^3$ group(s) and a —$COOR^3$ group;

$G^{4'}$ represents a $C_1$-$C_4$ alkylene group or a $C_1$-$C_4$ alkyleneoxy-$C_1$-$C_4$ alkylene group;

$R^3$ each independently represents a hydrogen atom, or a $C_1$-$C_4$ alkyl group optionally substituted with 1 to 5 aryl group(s);

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group;

$L^3$ represents a $C_1$-$C_4$ alkylene-phenylene group wherein the phenylene moiety is optionally substituted with 1 to 3 —$COOR^4$ group (s);

$R^1$ each independently represents a hydrogen atom, or a $C_1$-$C_4$ alkyl group optionally substituted with 1 to 5 substituent(s) independently selected from the group consisting of an aryl group and a trimethylsilyl group;

$R^5$ each independently represents a hydrogen atom, a halogen atom, a $C_1$-$C_4$ alkyl group, or a $C_1$-$C_4$ alkoxy group;

Z represents a single bond, a $C_6$-$C_{12}$ arylene group, —($CH_2$—$CH_2$—O)$_m$—$CH_2$—$CH_2$—, —($CH_2$—O—$CH_2$)$_m$—, —($CH_2$)$_m$—($C_6$-$C_{12}$ arylene)-($CH_2$)$_m$—, or —($CH_2$)$_n$—;

m represents an integer of 1 to 6; and n represents an integer of 2 to 12].

In one embodiment of the Compound (V), a compound or a pharmaceutically acceptable salt thereof, wherein $R^1$ each represents a hydrogen atom;

$W^1$ and $W^2$ each independently represent a single bond or a $C_1$-$C_4$ alkylene group;

$X^1$ represents —C(=O)— or —$NG^{11}$-$SO_2$—;

$X^2$ represents —C(=O)— or —$SO_2$—$NG^{12}$-;

$G^{11}$ and $G^{12}$ each independently represent a hydrogen atom, a $C_1$-$C_4$ alkyl group, or —$COOR^2$;

$R^2$ represents a $C_1$-$C_4$ alkyl group optionally substituted with 1 to 5 aryl group(s);

$Y^1$ represent —$NG^{22}$-, —$NG^1$-$L^{11}$-C(=O)—, —$NG^{21}$-$L^{11}$-C(=O)—NH—, —$NG^{21}$-$L^{11}$-C(=O)—$NG^3$-$L^{11}$-C(=O)—, —$NG^{21}$-$L^{11}$-C(=O)—$NG^{31}$-$L^{21}$-C(=O)—NH—, —$NG^{21}$-$L^3$-O—, or —$NG^{21}$-$G^{4'}$-;

$Y^2$ represents —$NG^{22}$, —C(=O)-$L^{12}$-$NG^{22}$-, —NH—C(=O)-$L^{12}$-$NG^{22}$-, —C(=O)-$L^{22}$-$NG^{32}$-C(=O)-$L^{12}$-$NG^{22}$-, —NH—C(=O)-$L^{22}$-$NG^{32}$-C(=O)-$L^{12}$-$NG^{22}$-, —O-$L^3$-$NG^{22}$-, or -$G^{4'}$-$NG^{22}$-;

$G^{21}$, $G^{31}$, $G^{22}$, and $C^{32}$ each independently represent a hydrogen atom, or a $C_1$-$C_6$ alkyl group optionally substituted with 1 to 5 substituent (s) independently selected from the group consisting of a phenyl group optionally substituted with 1 to 5 —$COOR^3$ group(s) and a —$COOR^3$ group;

$G^{4'}$ represents a $C_1$-$C_4$ alkylene group or a $C_1$-$C_4$ alkyleneoxy-$C_1$-$C_4$ alkylene group;

$R^3$ each independently represents a hydrogen atom, or a $C_1$-$C_4$ alkyl group optionally substituted with 1 to 3 aryl group(s);

$L^{11}$, $L^{21}$, $L^{12}$, and $L^{22}$ each independently represent a $C_1$-$C_4$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group;

$L^3$ represents a $C_1$-$C_4$ alkylene-phenylene group wherein the phenylene moiety is optionally substituted with 1 to 3 —$COOR^4$ group(s);

$R^4$ each represents a hydrogen atom;

$R^5$ each independently represents a hydrogen atom, a halogen atom, a $C_1$-$C_4$ alkyl group, or a $C_1$-$C_4$ alkoxy group;

Z represents a single bond, a $C_6$-$C_{12}$ arylene group, —($CH_2$—$CH_2$—O)$_m$—$CH_2$—$CH_2$—, —($CH_2$—O—$CH_2$)$_m$—, —($CH_2$)$_m$—($C_6$-$C_{12}$ arylene)-($CH_2$)$_m$—, or —($CH_2$)$_n$—;

m represents an integer of 1 to 6; and n represents an integer of 2 to 12 is provided.

In another embodiment of the Compound (V), a compound or a pharmaceutically acceptable salt thereof, wherein $R^1$ each represents a hydrogen atom;

$W^1$ and $W^2$ each independently represent a single bond or a $C_1$-$C_4$ alkylene group;

$X^1$ represents —C(=O)— or —$NG^{11}$-$SO_2$—;

$X^2$ represents —C(=O)— or —$SO_2$—$NG^{12}$-;

$G^{11}$ and $G^{12}$ each represent a hydrogen atom;

$Y^1$ represents —$NG^{21}$-, —$NG^{21}$-$L^{11}$-C(=O)—, —$NG^{21}$-$L^{11}$-C(=O)—NH—, —$NG^{21}$-$L^{11}$-C(=O)—$NG^{31}$-$L^{21}$-C(=O)—, —$NG^{21}$-$L^{11}$-C(=O)—$NG^{31}$-$L^{21}$-C(=O)—NH—, —$NG^{21}$-$L^3$-O—, or —$NG^{21}$-$G^{4'}$-;

$Y^2$ represents —$NG^{22}$-, —C(=O)-$L^{12}$-$NG^{22}$-, —NH—C(=O)-$L^{12}$-$NG^{22}$-, —C(=O)-$L^{22}$-$NG^{32}$-C(=O)-$L^{12}$-$NG^{22}$-, —NH—C(=O)-$L^{22}$-$NG^{32}$-C(=O)-$L^{12}$-$NG^{22}$-, —O-$L^3$-$NG^{22}$-, or -$G^{4'}$-$NG^{22}$-;

$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —$COOR^3$ group(s) and a —$COOR^3$ group;

$G^{4'}$ represents a $C_1$-$C_4$ alkylene group or a $C_1$-$C_4$ alkyleneoxy-$C_1$-$C_4$ alkylene group;

$R^3$ each represents a hydrogen atom;

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group;

$L^3$ represents a $C_1$-$C_4$ alkylene-phenylene group wherein the phenylene moiety is optionally substituted with 1 to 3 —$COOR^4$ group(s);

$R^4$ each represents a hydrogen atom;

$R^5$ each independently represents a hydrogen atom, a halogen atom, a $C_1$-$C_6$ alkyl group, or a $C_1$-$C_4$ alkoxy group;

Z represents a single bond, a $C_6$-$C_{12}$ arylene group, —$(CH_2-CH_2-O)_m-CH_2-CH_2$—, —$(CH_2-O-CH_2)_m$—, —$(CH_2)_m-(C_6-C_{12}$ arylene$)-(CH_2)_m$—, or —$(CH_2)_n$—;

m represents an integer of 1 to 6; and n represents an integer of 2 to 12 is provided.

In one embodiment, the Compound (V) has a structure represented by the following general formula (VI):

$G^{21}$, $G^{31}$, $G^{22}$, and $G^{32}$ each independently represent a hydrogen atom, or a $C_1$-$C_3$ alkyl group optionally substituted with 1 to 3 —$COOR^3$ group(s);

$G^{4'}$ represents a $C_1$-$C_2$ alkylene group or a $C_1$-$C_2$ alkyleneoxy-$C_1$-$C_2$ alkylene group;

$R^3$ each independently represents a hydrogen atom or a tert-butyl group;

$L^{11}$, $L^{21}$, $L^{12}$, and $L^{22}$ each independently represent a $C_1$-$C_2$ alkylene group;

$L^3$ represents a $C_1$-$C_4$ alkylene-phenylene group wherein the phenylene moiety is optionally substituted with 1 to 3 —$COOR^4$ group(s);

$R^4$ each independently represents a hydrogen atom, or a $C_1$-$C_4$ alkyl group optionally substituted with 1 to 5 substituent (s) independently selected from the group consisting of an aryl group and a trimethylsilyl group;

$R^5$ each independently represents a hydrogen atom, a halogen atom, a $C_1$-$C_4$ alkyl group, or a $C_1$-$C_4$ alkoxy group;

Z represents a single bond, a biphenylene group, —$(CH_2-CH_2-O)_m-CH_2-CH_2$—, —$(CH_2-O-CH_2)_m$—, —$(CH_2)_m$-biphenylene-$(CH_2)_m$—, or —$(CH_2)_n$—;

m represents an integer of 1 to 6; and n represents an integer of 2 to 12 is provided.

In another embodiment of the Compound (VI), a compound or a pharmaceutically acceptable salt thereof, wherein $R^1$ each represents a hydrogen atom;

$W^1$ and $W^2$ each independently represent a single bond or a $C_1$-$C_2$ alkylene group;

$X^1$ represents —C(=O)— or —$NG^{11}$-$SO_2$—;

$X^2$ represents —C(=O)— or —$SO_2$—$NG^{12}$-;

$G^{11}$ and $C^{12}$ each represent a hydrogen atom;

$Y^1$ represents —$NG^{21}$-, —$NG^{21}$-$L^{11}$-C(=O)—, —$NG^{21}$-$L^{11}$-C(=O)—NH—, —$NG^{21}$-$L^{11}$-C(=O)—$NG^{31}$-$L^{21}$-C(=O)—, —$NG^{21}$-$L^{11}$-C(=O)—$NG^{31}$-$L^{21}$-C(=O)—NH—, —$NG^{21}$-$L^3$-O—, or —$NG^{21}$-$G^{4'}$-;

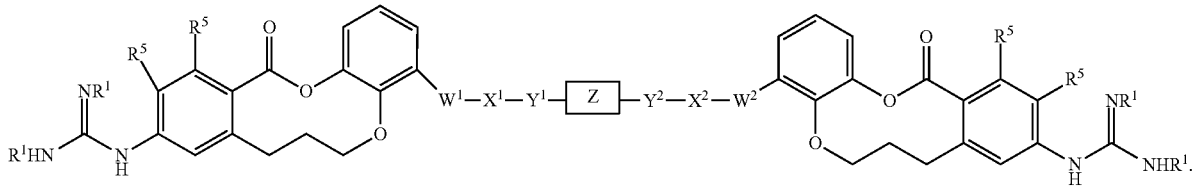

(VI)

In one embodiment of the Compound (VI), a compound or a pharmaceutically acceptable salt thereof, wherein $R^1$ each independently represents a hydrogen atom or a tert-butoxycarbonyl group;

$W^1$ and $W^2$ each independently represent a single bond or a $C_1$-$C_2$ alkylene group;

$X^1$ represents —C(=O)— or —$NG^{11}$-$SO_2$—;

$X^2$ represents —C(=O)— or —$SO_2$—$NG^{12}$-;

$G^1C$ and $G^{12}$ each represent a hydrogen atom;

$Y^1$ represents —$NG^{21}$, —$NG^{21}$-$L^{11}$-C(=O)—, —$NG^{21}$-$L^{11}$-C(=O)—NH—, —$NG^{21}$-$L^{11}$-C(=O)—$NG^{31}$-$L^{21}$-C(=O)—, —$NG^{21}$-$L^{11}$-C(=O)—$NG^{31}$-$L^{21}$-C(=O)—NH—, —$NG^{22}$-$L^3$-O—, or —$NG^{22}$-$G^{4'}$-;

$Y^2$ represents —$NG^{22}$-, —C(O)-$L^{12}$-$NG^{22}$-, —NH—C(=O)-$L^{12}$-$NG^{22}$-, —C(=O)-$L^{22}$-$NG^{32}$-C(=O)-$L^{12}$-$NG^{22}$-, —NH—C(=O)-$L^{22}$-$NG^{32}$-C(=O)-$L^{12}$-$NG^{22}$-, —O-$L^3$-$NG^{22}$-, or -$G^{4'}$-$NG^{22}$-;

$Y^2$ represents —$NG^{22}$-, —C(=O)-$L^{12}$-$NG^{22}$-, —NH—C(=O)-$L^{12}$-$NG^{22}$-, —C(O)-$L^{22}$-$NG^{32}$-C(=O)-$L^{12}$-$NG^{22}$-, —NH—C(=O)-$L^{22}$-$NG^{12}$-C(=O)-$L^{12}$-$NG^{22}$-, —O-$L^3$-$NG^{22}$-, or -$G^{4'}$-$NG^{22}$-;

$G^{21}$, $G^{31}$, $G^{22}$, and $G^{32}$ each independently represent a hydrogen atom, or a $C_1$-$C_3$ alkyl group optionally substituted with 1 to 3 —$COOR^3$ group(s);

$G^{4'}$ represents a $C_1$-$C_2$ alkylene group or a $C_1$-$C_2$ alkyleneoxy-$C_1$-$C_2$ alkylene group;

$R^3$ each represents a hydrogen atom;

$L^{11}$, $L^{21}$, $L^{12}$, and $L^{22}$ each independently represent a $C_1$-$C_2$ alkylene group;

$L^3$ represents a $C_1$-$C_2$ alkylene-phenylene group wherein the phenylene moiety is optionally substituted with 1 to 2 —$COOR^4$ group(s);

$R^4$ each independently represents a hydrogen atom, or a $C_1$-$C_4$ alkyl group optionally substituted with 1 to 5 substituent(s) independently selected from the group consisting of an aryl group and a trimethylsilyl group;

$R^5$ each independently represents a hydrogen atom, a fluorine atom, a methyl group, or a methoxy group;

Z represents a single bond, [1,1'-biphenyl]-3,3'-diyl, —($CH_2$—$CH_2$—O)$_m$—$CH_2$—$CH_2$—, —($CH_2$—O—$CH_{12}$)$_m$—, —($CH_2$)$_m$—([1,1'-biphenyl]-3,3'-diyl)-($CH_2$)$_m$—, or —($CH_2$)$_n$—;

m represents an integer of 1 to 6; and
n represents an integer of 2 to 12
is provided.

In another embodiment of the Compound (VI), a compound or a pharmaceutically acceptable salt thereof, wherein
$R^1$ each represents a hydrogen atom;
$W^1$ and $W^2$ each independently represent a single bond or a $C_1$-$C_2$ alkylene group;
$X^1$ represents —C(=O)— or —$NG^{11}$-$SO_2$—;
$X^2$ represents —C(=O)— or —$SO_2$—$NG^{12}$-;
$G^{11}$ and $G^{12}$ each represent a hydrogen atom;
$Y^1$ represents —$NG^{21}$-, —$NG^{21}$-$L^{11}$-C(=O)—, —$NG^{21}$-$L^{11}$-C(=O)—NH—, —$NG^{21}$-$L^{11}$-C(=O)—$NG^{31}$-$L^{21}$-C(=O)—, —$NG^{22}$-$L^{11}$-C(=O)—$NG^{31}$-$L^{21}$-C(=O)—NH—, —$NG^{21}$-$L^3$-O—, or —$NG^{21}$-$G^{4'}$-;
$Y^2$ represents —$NG^{22}$-, —C(=O)-$L^{12}$-$NG^{22}$-, —NH—C(=O)-$L^{12}$-$NG^{22}$-, —C(=O)-$L^{22}$-$NG^{32}$-C(=O)-$L^{12}$-$NG^{22}$-, —NH—C(=O)-$L^{22}$-$NG^{32}$-C(=O)-$L^{12}$-$NG^{22}$-, —O-$L^3$-$NG^{22}$-, or -$G^{4'}$-$NG^{22}$-;
$G^{21}$, $G^{31}$, $G^{22}$, and $G^{32}$ each independently represent a hydrogen atom, or a $C_1$-$C_3$ alkyl group optionally substituted with 1 to 3 —$COOR^3$ group(s);
$G^{4'}$ represents a $C_1$-$C_2$ alkylene group or a $C_1$-$C_2$ alkyleneoxy-$C_1$-$C_2$ alkylene group;
$R^3$ each represents a hydrogen atom;
$L^{11}$, $L^{21}$, $L^{12}$, and $L^{22}$ each independently represent a $C_1$-$C_2$ alkylene group;
$L^3$ represents a $C_1$-$C_2$ alkylene-phenylene group wherein the phenylene moiety is optionally substituted with 1 to 2 —$COOR^4$ group(s);
$R^4$ each represents a hydrogen atom;
$R^5$ each independently represents a hydrogen atom, a fluorine atom, a methyl group, or a methoxy group;

Z represents a single bond, [1,1'-biphenyl]-3,3'-diyl, —($CH_2$—$CH_2$—O)$_m$—$CH_2$—$CH_2$—, —($CH_2$—O—$CH_2$)$_m$—, —($CH_2$)$_m$-([1,1'-biphenyl]-3,3'-diyl)-($CH_2$)$_m$—, or —($CH_2$)$_n$—;

m represents an integer of 1 to 6; and
n represents an integer of 2 to 12
is provided.

In another embodiment of the Compound (VI), a compound or a pharmaceutically acceptable salt thereof, wherein
$R^1$ each represents a hydrogen atom;
$W^1$ and $W^2$ each independently represent a single bond or a $C_1$-$C_2$ alkylene group;
$X^1$ represents —C(=O)— or —$NG^{11}$-$SO_2$—;
$X^2$ represents —C(=O)— or —$SO_2$—$NG^{12}$-;
$G^{11}$ and $G^{12}$ each represent a hydrogen atom;
$Y^1$ represents —$NG^{21}$-, —$NG^{21}$-$L^{11}$-C(=O)—, —$NG^{21}$-$L^{11}$-C(=O)—NH—, —$NG^{21}$-$L^{11}$-C(=O)—$NG^{31}$-$L^{21}$-C(=O)—, —$NG^{21}$-$L^{11}$-C(=O)—$NG^{31}$-$L^{21}$-C(=O)—NH—, —$NG^{21}$-$L^3$-O—, or —$NG^2$-$G^{4'}$-;
$Y^2$ represents —$NG^{22}$-, —C(=O)-$L^{12}$-$NG^2$-, —NH—C(=O)-$L^1$-$NG^{22}$-, —C(=O)-$L^2$-$NG^2$-C(=O)-$L^2$-$NG^2$-, —NH—C(=O)-$L^{22}$-$NG^{32}$-C(=O)-$L^{12}$-$NG^{22}$-, —O-$L^3$-$NG^{22}$-, or -$G^{4'}$-$NG^{22}$-;
$G^{21}$ and $G^{22}$ each independently represent a hydrogen atom, or a $C_1$-$C_3$ alkyl group optionally substituted with 1 to 3 —$COOR^3$ group(s);
$G^{31}$ and $G^{32}$ each represents a hydrogen atom;
$G^{4'}$ represents a $C_1$-$C_2$ alkylene group or a $C_1$-$C_2$ alkyleneoxy-$C_1$-$C_2$ alkylene group;
$R^3$ each represents a hydrogen atom;
$L^{11}$, $L^{21}$, $L^{12}$, and $L^{22}$ each independently represent a $C_1$-$C_2$ alkylene group;
$L^3$ represents a $C_1$-$C_4$ alkylene-phenylene group wherein the phenylene moiety is optionally substituted with 1 to 2 —$COOR^4$ group(s);
$R^4$ each represents a hydrogen atom;
$R^5$ each independently represents a hydrogen atom, a fluorine atom, a methyl group, or a methoxy group;

Z represents a single bond, [1,1'-biphenyl]-3,3'-diyl, —($CH_2$—$CH_2$—O)$_m$—$CH_2$—$CH_2$—, —($CH_2$—O—$CH_2$)$_m$—, —($CH_2$)$_m$—, —($CH_2$)$_m$-([1,1'-biphenyl]-3,3'-diyl)-($CH_2$)$_m$—, or —($CH_2$)$_n$—;

m represents an integer of 1 to 6; and
n represents an integer of 2 to 12
is provided.

In another embodiment of the Compound (VI), a compound or a pharmaceutically acceptable salt thereof, wherein
$R^1$ each represents a hydrogen atom;
$W^1$ and $W^2$ each independently represent a single bond or a $C_1$-$C_2$ alkylene group;
$X^1$ represents —C(=O)— or —$NG^{11}$-$SO_2$—;
$X^2$ represents —C(=O)— or —$SO_2$—$NG^{12}$-;
$G^{11}$ and $G^{12}$ each represent a hydrogen atom;
$Y^1$ represents —$NG^{21}$-, —$NG^{21}$-$L^{11}$-C(=O)—, —$NG^1$-$L^{11}$-C(=O)—NH—, —$NG^{21}$-$L^{11}$-C(=O)—$NG^{31}$-$L^{21}$-C(=O)—, —$NG^{21}$-$L^{11}$-C(=O)—$NG^{31}$-$L^{21}$-C(=O)—NH—, —$NG^{21}$-$L^3$-O—, or —$NG^{21}$-$G^{4'}$-;
$Y^2$ represents —$NG^{22}$-, —C(=O)-$L^{12}$-$NG^{22}$-, —NH—C(=O)-$L^{12}$-$NG^{22}$-, —C(=O)-$L^{22}$-$NG^{32}$-C(=O)-$L^{12}$-$NG^{22}$-, —NH—C(=O)-$L^{22}$-$NG^{32}$-C(=O)-$L^{12}$-$NG^{22}$-, —O-$L^3$-$NG^{22}$-, or -$G^{4'}$-$NG^{22}$-;
$G^{21}$ and $G^{22}$ each independently represent a hydrogen atom, or a $C_1$-$C_3$ alkyl group optionally substituted with 1 to 3 —$COOR^3$ group(s);
$G^{31}$ and $G^{32}$ each represents a hydrogen atom;

In one embodiment of the Compound (VI), a compound or a pharmaceutically acceptable salt thereof, wherein
$R^1$ each represents a hydrogen atom;
$W^1$ and $W^2$ each represent a single bond;
$X^1$ represents —C(=O)—;
$X^2$ represents —C(=O)—;
$Y^1$ represents —$NG^{21}$-, —$NG^{21}$-$L^3$-O—, or —$NG^{21}$-$G^{4'}$-;
$Y^2$ represents —$NG^{22}$-, —O-$L^3$-$NG^{22}$-, or -$G^{4'}$-$NG^{22}$;

$G^{21}$ and $G^{22}$ each independently represent a $C_1$-$C_3$ alkyl group substituted with 1 to 3 carboxy group(s);

$G^{4'}$ represents a $C_1$-$C_2$ alkylene group or a $C_1$-$C_2$ alkyleneoxy-$C_1$-$C_2$ alkylene group;

$L^3$ represents a $C_1$-$C_2$ alkylene-phenylene group wherein the phenylene moiety is optionally substituted with 1 to 2 —$COOR^4$ group(s);

$R^4$ each independently represents a hydrogen atom, or a $C_1$-$C_4$ alkyl group optionally substituted with 1 to 5 substituent(s) independently selected from the group consisting of an aryl group and a trimethylsilyl group;

$R^5$ each independently represents a hydrogen atom, a fluorine atom, a methyl group, or a methoxy group;

Z represents a single bond, [1,1'-biphenyl]-3,3'-diyl, —($CH_2$—$CH_2$—O)$_m$—$CH_2$—$CH_2$—, —($CH_2$—O—$CH_2$)$_m$—, —($CH_2$)$_m$—([1,1'-biphenyl]-3,3'-diyl)-($CH_2$)$_m$—, or —($CH_2$)$_n$—;

m represents an integer of 1 to 6; and
n represents an integer of 2 to 12
is provided.

In one embodiment of the Compound (VI), a compound or a pharmaceutically acceptable salt thereof, wherein
$R^1$ each represents a hydrogen atom;
$W^1$ and $W^2$ each represent a single bond;
$X^1$ represents —C(=O)—;
$X$, represents —C(=O)—;
$Y^1$ represents —$NG^{21}$-, —$NG^{21}$-$L^3$-O—, or —$NG^{21}$-$G^{4'}$-;
$Y^2$ represents —$NG^{22}$-, —O-$L^3$-$NG^{22}$-, or -$G^{4'}$-$NG^{22}$-;
$G^{21}$ and $G^{22}$ each independently represent a $C_1$-$C_3$ alkyl group substituted with 1 to 3 carboxy group(s);
$G^{4'}$ represents a $C_1$-$C_2$ alkylene group or a $C_1$-$C_2$ alkyleneoxy-$C_1$-$C_2$ alkylene group;
$L^3$ represents a $C_1$-$C_2$ alkylene-phenylene group wherein the phenylene moiety is optionally substituted with 1 to 2 —$COOR^4$ group (s);
$R^4$ each represents a hydrogen atom;
$R^5$ each represents a hydrogen atom;
Z represents a single bond, [1,1'-biphenyl]-3,3'-diyl, —($CH_2$—$CH_2$—O)$_m$—$CH_2$—$CH_2$—, —($CH_2$—O—$CH_2$)$_m$—, —($CH_2$)$_m$—([1,1'-biphenyl]-3,3'-diyl)-($CH_2$)$_m$—, or —($CH_2$)$_n$—;

m represents an integer of 1 to 6; and
n represents an integer of 2 to 12
is provided.

In one embodiment of the present invention,
$A^1$ has a structure represented by

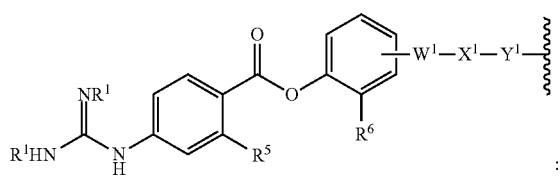

:

$A^2$ has a structure represented by

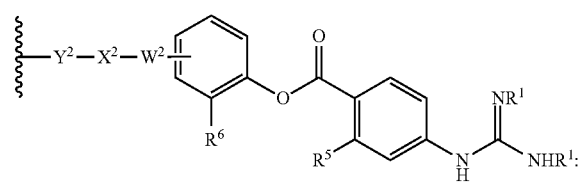

[wherein:
$R^1$ each independently represents a hydrogen atom or a —COO—($C_1$-$C_4$ alkyl group);
$W^1$ and $W^2$ each independently represent a single bond or a $C_1$-$C_4$ alkylene group;
$X^1$ represents —C(=O)—, —O—C(=O)—, or —$NG^{11}$-$SO_2$—;
$X^2$ represents —C(=O)—, —C(=O)—O—, or —$SO_2$—$NG^{12}$-;
$G^{11}$ and $G^{12}$ each independently represent a hydrogen atom or —$COOR^2$;
$R^2$ represents a $C_1$-$C_4$ alkyl group optionally substituted with 1 to 5 aryl group(s);
$Y^1$ represents —$NG^{21}$-, —$NG^{21}$-$L^{11}$-C(=O)—NH—, or —$NG^{21}$-$L^{11}$-C(=O)—$NG^{31}$-$L^1$-C(=O)—NH—;
$Y^2$ represents —$NG^{22}$-, —NH—C(=O)-$L^{12}$-$NG^{22}$-, or —NH—C(=O)-$L^{22}$-$NG^{32}$-C(=O)-$L^{12}$-$NG^{22}$-;
$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —$COOR^3$ group(s) and a —$COOR^3$ group;
$R^3$ each independently represents a hydrogen atom, or a $C_1$-$C_4$ alkyl group optionally substituted with 1 to 5 aryl group(s);
$L^{11}$, $L^{21}$, $L^{12}$, and $L^{12}$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group;
$R^4$ each independently represents a hydrogen atom, or a $C_1$-$C_4$ alkyl group optionally substituted with 1 to 5 aryl group(s);
$R^5$ and $R^6$ each independently represent a hydrogen atom, a $C_1$-$C_4$ alkyl group, or a $C_1$-$C_4$ alkoxy group, or $R^5$ and $R^6$ may be combined with each other to form a $C_1$-$C_4$ alkyleneoxy group; and
the symbol

〰〰〰 represents the point of attachment to Z];
Z represents —($CH_2$—$CH_2$—O)$_m$—$CH_2$—$CH_2$— or —($CH_2$)$_n$—;
m represents an integer of 1 to 6; and
n represents an integer of 2 to 12.

In another embodiment of the present invention, a compound or a pharmaceutically acceptable salt thereof, wherein
$A^1$ has a structure represented by

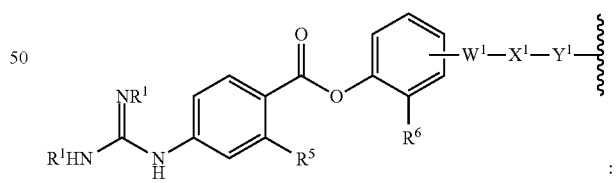

:

$A^2$ has a structure represented by

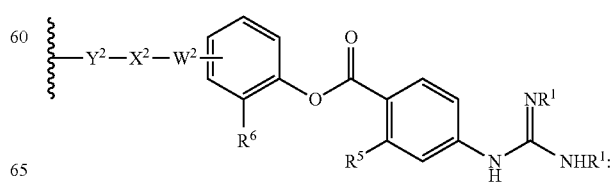

[wherein:

R$^1$ each represents a hydrogen atom;

W$^1$ and W$^2$ each independently represent a single bon or a C$_1$-C$_4$ alkylene group;

X$^1$ represents —C(=O)—, —C(=O)—, or —NG$^{11}$-SO$_2$—;

X$^2$ represents —C(=O)—, —C(=O)—O—, or —SO$_2$—NG$^{12}$-;

G$^{11}$ and G$^{12}$ each independently represent a hydrogen atom or —COOR$^2$;

R$^2$ represents a C$_1$-C$_4$ alkyl group optionally substituted with 1 to 5 aryl group(s);

Y$^1$ represents —NG$^{21}$-, —NG$^{21}$-L$^{12}$-C(=O)—NH—, or —NG$^{21}$-L$^{11}$-C(=O)—NG$^{31}$-L$^{21}$-C(=O)—NH—;

Y$^2$ represents —NG$^{22}$-, —NH—C(=O)-L$^{12}$-NG$^{22}$-, or —NH—C(=O)-L$^{22}$-NG$^{32}$-C(=O)— L$^{12}$-NG$^{22}$-;

G$^{21}$, G$^{31}$, G$^{22}$, and G$^{32}$ each independently represent a hydrogen atom, or a C$_1$-C$_6$ alkyl group optionally substituted with 1 to 5 substituent (s) independently selected from the group consisting of a phenyl group optionally substituted with 1 to 5 —COOR$^3$ group(s) and a —COOR$^3$ group;

R$^3$ each independently represents a hydrogen atom, or a C$_1$-C$_4$ alkyl group optionally substituted with 1 to 5 aryl group(s);

L$^{11}$, L$^{21}$, L$^{12}$, and L$^{22}$ each independently represent a C$_1$-C$_6$ alkylene group optionally substituted with 1 to 5 C$_1$-C$_6$ alkyl group(s) optionally substituted with 1 to 5 —COOR$^4$ group(s), a C$_1$-C$_4$ alkylene-phenylene group, or a phenylene C$_1$-C$_4$ alkylene group;

R$^4$ each represents a hydrogen atom;

R$^5$ and R$^6$ each independently represent a hydrogen atom, a C$_1$-C$_4$ alkyl group, or a C$_1$-C$_4$ alkoxy group, or R and RV may be combined with each other to form a C$_1$-C$_4$ alkyleneoxy group; and the symbol

∿∿∿∿∿ represents the point of attachment to Z];

Z represents —(CH$_2$—CH$_2$—O)$_m$—CH$_2$—CH$_2$— or —(CH$_2$)$_n$—;

m represents an integer of 1 to 6; and n represents an integer of 2 to 12 is provided.

In another embodiment of the present invention, a compound or a pharmaceutically acceptable salt thereof, wherein A$^1$ has a structure represented by

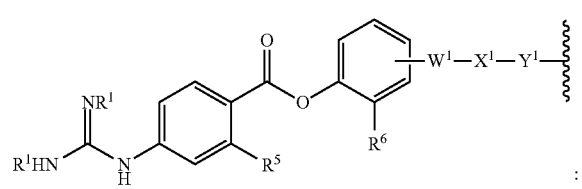

A$^2$ has a structure represented by

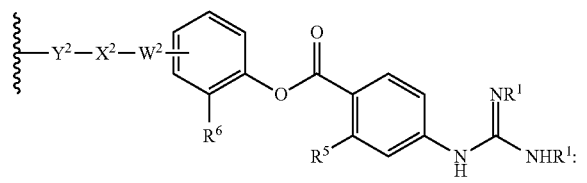

[wherein:

R$^1$ each represents a hydrogen atom;

W$^1$ and W$^2$ each independently represent a single bond or a C$_1$-C$_4$ alkylene group;

X$^1$ represents —C(=O)—, —O—C(=O), or —NG$^{11}$-SO$_2$—;

X$^2$ represents —C(=O)—, —C(=O)—O—, or —SO$_2$—NG$^{12}$-;

G$^{11}$ and G$^{12}$ each represents a hydrogen atom;

Y$^1$ represents —NG$^2$-, —NG$^{21}$-L$^{11}$-C(=O)—NH— or —NG$^{22}$-L$^{11}$-C(=O)—NG$^{31}$-L$^{21}$-C(=O)—NH—;

Y$^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;

G$^{21}$, G$^{31}$, G$^{22}$, and G$^{22}$ each independently represent a hydrogen atom, or a C$_1$-C$_6$ alkyl group optionally substituted with 1 to 5 substituent (s) independently selected from the group consisting of a phenyl group optionally substituted with 1 to 5 —COOR$^3$ group(s) and a —COOR$^3$ group;

R$^3$ each represents a hydrogen atom;

L$^{11}$, L$^{21}$, L$^{12}$ and L$^{22}$ each independently represent a C$_1$-C$_6$ alkylene group optionally substituted with 1 to 5 C$_1$-C$_6$ alkyl group(s) optionally substituted with 1 to 5 —COOR$^4$ group(s), a C$_1$-C$_4$ alkylene-phenylene group, or a phenyl ene-C$_1$-C$_4$ alkylene group;

R$^4$ each represents a hydrogen atom;

R$^5$ and R$^6$ each independently represent a hydrogen atom, a C$_1$-C$_4$ alkyl group, or a C$_1$-C$_4$ alkoxy group, or R$^5$ and R$^6$ may be combined with each other to form a C$_1$-C$_4$ alkyleneoxy group; and the symbol

∿∿∿∿∿ represents the point of attachment to Z];

Z represents —(CH$_2$—CH$_2$—O)$_m$—CH$_2$—CH$_2$— or (CH$_2$)$_n$—;

m represents an integer of 1 to 6; and n represents an integer of 2 to 12 is provided.

In one embodiment of the Compound (I),

A$^1$ has a structure represented by

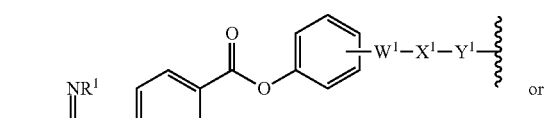

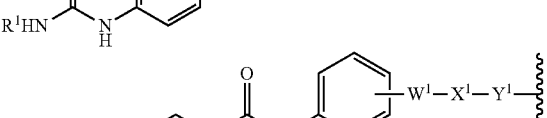

and

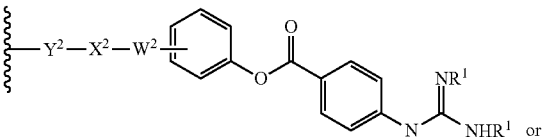

-continued

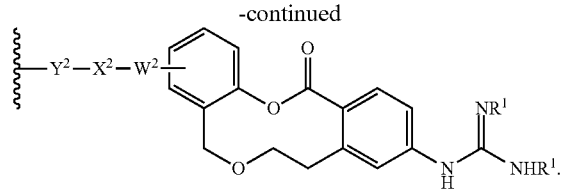

In one embodiment of the Compound (I),
A² has a structure represented by

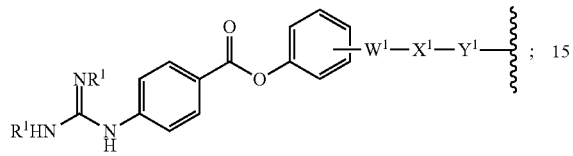

and
A² has a structure represented by

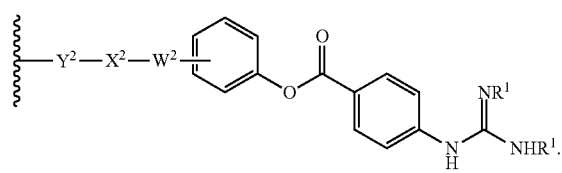

In another embodiment of the Compound (I),
A¹ has a structure represented by

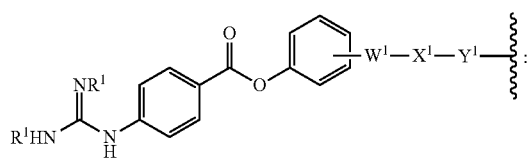

A² has a structure represented by

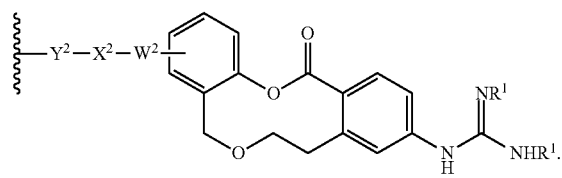
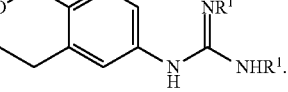

In another embodiment of the Compound (I),
A¹ has a structure represented by

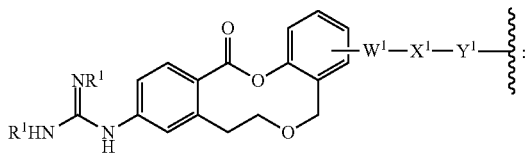

and
A² has a structure represented by

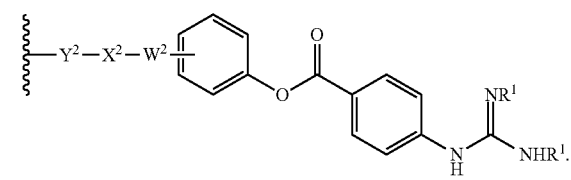

In another embodiment of the Compound (I),
A¹ has a structure represented by

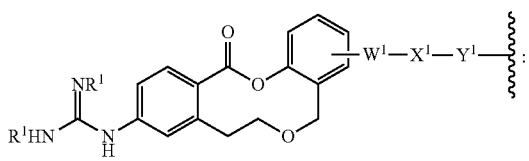

and
A² has a structure represented by

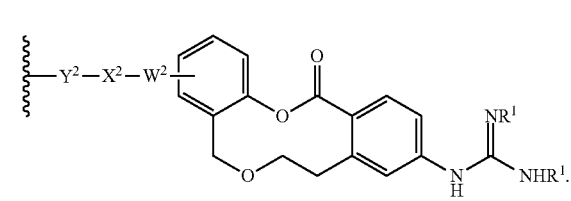

Compound (VII)

In one embodiment of the present invention, the Compound (I) or a pharmaceutically acceptable salt thereof represents a compound represented by the following general formula (VII):

(VII)

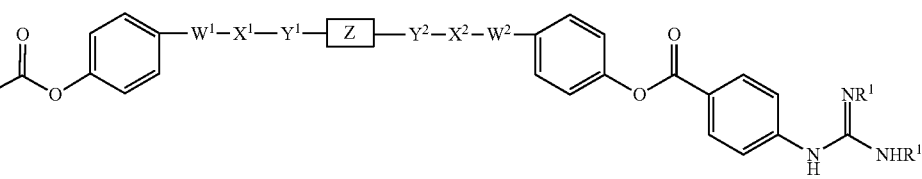

[wherein:

$R^1$ each independently represents a hydrogen atom or a COO—($C_1$-$C_4$ alkyl group);

$W^1$ and $W^2$ each independently represent a single bond or a $C_1$-$C_4$ alkylene group;

$X^1$ represents —O—C(=O)— or —$NG^{11}$-$SO_2$—;

$X^2$ represents —C(=O)—O— or —$SO_2$—$NG^{12}$-;

$G^{11}$ and $G^{12}$ each independently represent a hydrogen atom or —$COOR^2$;

$R^2$ represents a $C_1$-$C_4$ alkyl group optionally substituted with 1 to 5 aryl group(s);

$Y^1$ represents —$NG^{21}$-, —$NG^2$-$L^{21}$-C(=O)—NH—, or —$NG^{21}$-$L^{11}$-C(=O)—$NG^{31}$-$L^{21}$-C(=O)—NH—;

$Y^2$ represents —$NG^{22}$-, —NH—C(=O)-$L^{12}$-$NG^{22}$-, or —NH—C(=O)-$L^{22}$-$NG^{32}$-C(=O)-$L^{12}$-$NG^{22}$-;

$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —$COOR^3$ group(s) and a —$COOR^3$ group;

$R^3$ each independently represents a hydrogen atom, or a $C_1$-$C_4$ alkyl group optionally substituted with 1 to 5 aryl group(s);

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group;

$R^4$ each independently represents a hydrogen atom, or a $C_1$-$C_4$ alkyl group optionally substituted with 1 to 5 aryl group(s);

Z represents —($CH_2$—$CH_2$—O)$_m$—$CH_2$—$CH_2$— or —($CH_2$)$_n$—;

m represents an integer of 1 to 6; and n represents an integer of 2 to 12]

or a pharmaceutically acceptable salt thereof.

Examples of embodiments of each substituent of the Compound (VII) include the followings in addition to the above embodiments of each substituent of the Compound (I).

In one embodiment, the $C_1$-$C_4$ alkyl group of "—COO—($C_1$-$C_4$ alkyl group)" in $R^1$ represents a methyl group, an ethyl group, a n-propyl group, an isopropyl group, a n-butyl group, or a tert-butyl group.

In one embodiment, $R^1$ represents a hydrogen atom or a tert-butoxycarbonyl group, preferably a hydrogen atom.

In one embodiment, $W^1$ represents a $C_1$-$C_4$ alkylene group, for example a methylene group, an ethylene group, a trimethylene group, or a tetramethylene group, preferably a $C_1$-$C_2$ alkylene group, for example a methylene group.

In one embodiment, $W^2$ represents a $C_1$-$C_4$ alkylene group, for example a methylene group, an ethylene group, a trimethylene group, or a tetramethylene group, preferably a $C_1$-$C_2$ alkylene group, for example a methylene group.

In one embodiment, $X^1$ represents —$NG^{11}$-$SO_2$—.

In one embodiment, $X^2$ represents —$SO_2$—$NG^{12}$-.

In one embodiment, $R^2$ of "—$COOR^2$ group" in $G^{11}$ and $G^{12}$ represents a $C_1$-$C_4$ alkyl group optionally substituted with 1 to 3 phenyl group(s), for example a methyl group, an ethyl group, a n-propyl group, an isopropyl group, a n-butyl group, a tert-butyl group, or a benzyl group, preferably a $C_1$-$C_4$ alkyl group optionally substituted with one phenyl group, more preferably a tert-butyl group or a benzyl group.

In one embodiment, $G^{11}$ represents a hydrogen atom, a tert-butoxycarbonyl group, or a benzyloxycarbonyl group, preferably a hydrogen atom or a benzyloxycarbonyl group, more preferably a hydrogen atom.

In one embodiment, $G^{12}$ represents a hydrogen atom, a tert-butoxycarbonyl group, or a benzyloxycarbonyl group, preferably a hydrogen atom or a benzyloxycarbonyl group, more preferably a hydrogen atom.

In one embodiment, $Y^1$ represents —$NG^{21}$-.

In one embodiment, $Y^2$ represents —$NG^{22}$-.

In one embodiment, the "phenyl group optionally substituted with 1 to 5 —$COOR^3$ group(s)" in $G^{21}$, $G^{31}$, $G^{22}$, and $G^{32}$ represents a 2-($COOR^3$)-phenyl group, a 3-($COOR^3$)-phenyl group, a 4-($COOR^3$)-phenyl group, or the like.

In one embodiment, $R^3$ of "—$COOR^3$ group" in $G^{21}$, $G^{31}$, $G^{22}$, and $G^{32}$ each independently represents a hydrogen atom, a methyl group, an ethyl group, a n-propyl group, an isopropyl group, a n-butyl group, a tert-butyl group, or a benzyl group, preferably a hydrogen atom, a benzyl group, or a tert-butyl group, more preferably a hydrogen atom or a tert-butyl group, still more preferably a hydrogen atom.

In one embodiment, $G^{21}$ represents a hydrogen atom, or a $C_1$-$C_6$ alkyl group optionally substituted with 1 to 3 substituent(s) independently selected from the group consisting of a phenyl group optionally substituted with 1 to 3 —$COOR^3$ group(s) and a —$COOR^3$ group, preferably a hydrogen atom, or a $C_1$-$C_3$ alkyl group optionally substituted with 1 to 3 substituent(s) independently selected from the group consisting of a phenyl group optionally substituted with one —$COOR^3$ group and a —$COOR^3$ group, more preferably a $C_1$-$C_3$ alkyl group substituted with 1 to 3 substituent(s) independently selected from the group consisting of a phenyl group substituted with one carboxy group and a carboxy group.

In one embodiment, $G^{22}$ represents a hydrogen atom, or a $C_1$-$C_6$ alkyl group optionally substituted with 1 to 3 substituent(s) independently selected from the group consisting of a phenyl group optionally substituted with 1 to 3 —$COOR^3$ group(s) and a —$COOR^3$ group, preferably a hydrogen atom, or a $C_1$-$C_3$ alkyl group optionally substituted with 1 to 3 substituent(s) independently selected from the group consisting of a phenyl group optionally substituted with one —$COOR^3$ group and a —$COOR^3$ group, more preferably a hydrogen atom.

In one embodiment, $G^{22}$ represents a hydrogen atom, or a $C_1$-$C_6$ alkyl group optionally substituted with 1 to 3 substituent(s) independently selected from the group consisting of a phenyl group optionally substituted with 1 to 3 —$COOR^3$ group(s) and a —$COOR^3$ group, preferably a hydrogen atom, or a $C_1$-$C_3$ alkyl group optionally substituted with 1 to 3 substituent(s) independently selected from the group consisting of a phenyl group optionally substituted with one —$COOR^3$ group and a —$COOR^3$ group, more preferably a $C_1$-$C_3$ alkyl group substituted with 1 to 3 substituent(s) independently selected from the group consisting of a phenyl group substituted with one carboxy group and a carboxy group.

In one embodiment, $G^{32}$ represents a hydrogen atom, or a $C_1$-$C_6$ alkyl group optionally substituted with 1 to 3 substituent(s) independently selected from the group consisting of a phenyl group optionally substituted with 1 to 3 —$COOR^3$ group(s) and a —$COOR^3$ group, preferably a hydrogen atom, or a $C_1$-$C_3$ alkyl group optionally substituted with 1 to 3 substituent(s) independently selected from the group consisting of a phenyl group optionally substituted with one —$COOR^3$ group and a —$COOR^3$ group, more preferably a hydrogen atom.

In one embodiment, $R^4$ of "—$COOR^4$ group" in $L^{11}$, $L^{21}$, $L^{12}$, and $L^{22}$ each independently represents a hydrogen atom, a methyl group, an ethyl group, a n-propyl group, an isopropyl group, a n-butyl group, a tert-butyl group, or a benzyl group, preferably a hydrogen atom, a tert-butyl group, or a benzyl group, more preferably a hydrogen atom or a tert-butyl group, still more preferably a hydrogen atom.

In one embodiment, $L^{11}$ represents a $C_1$-$C_6$ alkylene group optionally substituted with 1 to 2 $C_1$-$C_6$ alkyl group(s) optionally substituted with 1 to 2 —COOR$^4$ group(s), or a $C_1$-$C_4$ alkylene-phenylene group, preferably a methylene group optionally substituted with a $C_1$-$C_6$ alkyl group optionally substituted with a —COOR$^4$, or a methylenephenylene group.

In another embodiment, $L^{11}$ represents a $C_1$-$C_2$ alkylene group optionally substituted with 1 to 2 $C_1$-$C_2$ alkyl group(s) optionally substituted with 1 to 2 —COOR$^4$ group(s), or a $C_1$-$C_2$ alkylene-phenylene group.

In one embodiment, $L^{21}$ represents a $C_1$-$C_6$ alkylene group optionally substituted with 1 to 2 $C_1$-$C_6$ alkyl group(s) optionally substituted with 1 to 2 —COOR$^4$ group(s), or a $C_1$-$C_4$ alkylene-phenylene group, preferably a methylene group optionally substituted with a $C_1$-$C_6$ alkyl group optionally substituted with a —COOR$^4$ group.

In another embodiment, $L^{21}$ represents a $C_1$-$C_2$ alkylene group optionally substituted with 1 to 2 $C_1$-$C_2$ alkyl group(s) optionally substituted with 1 to 2 —COOR$^4$ group(s), or a $C_1$-$C_2$ alkylene-phenylene group.

In one embodiment, $L^{12}$ represents a $C_1$-$C_6$ alkylene group optionally substituted with 1 to 2 $C_1$-$C_6$ alkyl group(s) optionally substituted with 1 to 2 —COOR$^4$ group(s), or a phenylene-$C_1$-$C_4$ alkylene group, preferably a methylene group optionally substituted with a $C_1$-$C_6$ alkyl group optionally substituted with a —COOR$^4$ group, or a phenylenemethylene group.

In another embodiment, $L^{12}$ represents a $C_1$-$C_2$ alkylene group optionally substituted with 1 to 2 $C_1$-$C_2$ alkyl group(s) optionally substituted with 1 to 2 —COOR$^4$ group(s), or a phenylene-$C_1$-$C_2$ alkylene group.

In one embodiment, $L^{22}$ represents a $C_1$-$C_6$ alkylene group optionally substituted with 1 to 2 $C_1$-$C_6$ alkyl group(s) optionally substituted with 1 to 2 —COOR$^4$ group(s), or a phenylene-$C_1$-$C_4$ alkylene group, preferably a methylene group optionally substituted with a $C_1$-$C_6$ alkyl group optionally substituted with a —COOR$^4$ group.

In another embodiment, $L^{22}$ represents a $C_1$-$C_2$ alkylene group optionally substituted with 1 to 2 $C_1$-$C_2$ alkyl group(s) optionally substituted with 1 to 2 —COOR$^4$ group(s), or a phenylene-$C_1$-$C_2$ alkylene group.

In one embodiment, at least one of $R^1$, $R^3$, $R^4$, $G^{11}$, and $G^{12}$ represents a hydrogen atom. In another embodiment, at least one of $R^1$ and $R^4$ represents a hydrogen atom. In another embodiment, $R^1$, $R^3$, $R^4$, $G^{11}$, and $G^{12}$ each represent a hydrogen atom.

In one embodiment, Z represents —(CH$_2$—CH$_2$—O)$_m$—CH$_2$—CH$_2$— or —(CH$_2$)$_n$—, preferably —(CH$_2$—CH$_2$—O)$_m$—CH$_2$—CH$_2$—.

In one embodiment, m represents an integer of 1 to 6, and n represents an integer of 2 to 12, preferably m represents an integer of 1 to 4, and n represents an integer of 2 to 6.

In one embodiment of the Compound (VII), a compound or a pharmaceutically acceptable salt thereof, wherein $R^1$ each represents a hydrogen atom;
$W^1$ and $W^2$ each independently represent a single bond or a $C_1$-$C_4$ alkylene group;
$X^1$ represents —O—C(=O)— or —NG$^{11}$-SO$_2$—;
$X^2$ represents —C(=O)—O— or —SO$_2$—NG$^{12}$-;
$G^{11}$ and $G^{12}$ each independently represent a hydrogen atom or —COOR$^2$;
$R^2$ represents a $C_1$-$C_4$ alkyl group optionally substituted with 1 to 5 aryl group(s);
$Y^1$ represents —NG$^{21}$-, —NG$^{21}$-L$^{11}$-C(=O)—NH—, or —NG$^{21}$-L$^{11}$—C(=O)—NG$^{31}$-L$^{21}$-C(=O)—NH—;
$Y^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;
$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —COOR$^3$ group(s) and a —COOR$^3$ group;
$R^3$ each independently represents a hydrogen atom, or a $C_1$-$C_4$ alkyl group optionally substituted with 1 to 5 aryl group(s);
$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —COOR$^4$ group(s), a $C_1$-$C_4$ alkylene-phenylene group, or a phenylene-$C_1$-$C_4$ alkylene group;
$R^4$ each represents a hydrogen atom;
Z represents —(CH$_2$—CH$_2$—O)$_m$—CH$_2$—CH$_2$— or —(CH$_2$)$_n$—;
m represents an integer of 1 to 6; and
n represents an integer of 2 to 12
is provided.

In one embodiment of the Compound (VII), a compound or a pharmaceutically acceptable salt thereof, wherein $R^1$ each represents a hydrogen atom;
$W^1$ and $W^2$ each independently represent a single bond or a $C_1$-$C_4$ alkylene group;
$X^1$ represents —O—C(=O)— or —NG$^{11}$-O—SO$_2$—;
$X^2$ represents —C(=O)—O— or —SO$_2$—NG$^{12}$-;
$G^{11}$ and $G^{12}$ each represent a hydrogen atom;
$Y^1$ represents —NG$^3$-, —NG$^{21}$-L$^{11}$-C(=O)—NH—, or —NG$^{21}$-L$^{11}$-C(=O)—NG$^{31}$-L$^{21}$-C(=O)—NH—;
$Y^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;
$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —COOR$^3$ group(s) and a —COOR$^3$ group;
$R^3$ each represents a hydrogen atom;
$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —COOR$^4$ group(s), a $C_1$-$C_4$ alkylene-phenylene group, or a phenylene-$C_1$-$C_4$ alkylene group;
$R^4$ each represents a hydrogen atom;
Z represents —(CH$_2$—CH$_2$—O)$_m$—CH$_2$—CH$_2$— or —(CH$_2$)$_n$—;
m represents an integer of 1 to 6; and
n represents an integer of 2 to 12
is provided.

In another embodiment of the Compound (VII), a compound or a pharmaceutically acceptable salt thereof, wherein $R^1$ each independently represents a hydrogen atom or a tert-butoxycarbonyl group;
$W^1$ and $W^2$ each represent a $C_1$-$C_4$ alkylene group;
$X^1$ represents —O—C(=O)— or —NG$^{11}$-SO$_2$—;
$X^2$ represents —C(=O)—O— or —SO$_2$—NG$^{12}$-;
$G^{11}$ and $G^{12}$ each independently represent a hydrogen atom or —COOR$^2$;
$R^2$ represents a $C_1$-$C_4$ alkyl group optionally substituted with 1 to 3 phenyl group(s);
$Y^1$ represents —NG$^{21}$-, —NG$^{21}$-L$^{11}$-C(=O)—NH—, or —NG$^{21}$-L$^{11}$-C(=O)—NG$^{31}$-L$^{21}$-C(=C)—NH—;
$Y^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;

$G^{21}$, $G^{31}$, $G^{22}$, and $G^{32}$ each independently represent a hydrogen atom, or a $C_1$-$C_6$ alkyl group optionally substituted with 1 to 3 substituent(s) independently selected from the group consisting of a phenyl group optionally substituted with 1 to 3 —COOR$^3$ group(s) and a —COOR$^3$ group;

$R^3$ each independently represents a hydrogen atom, a benzyl group, or a tert-butyl group;

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —COOR$^4$ group(s), a $C_1$-$C_4$ alkylene-phenylene group, or a phenylene-$C_1$-$C_4$ alkylene group;

$R^4$ each independently represents a hydrogen atom, a benzyl group, or a tert-butyl group;

Z represents —(CH$_2$—CH$_2$—O)$_m$—CH$_2$—CH$_2$— or —(CH$_2$)$_n$—;

m represents an integer of 1 to 6; and n represents an integer of 2 to 12 is provided.

In another embodiment of the Compound (VII), a compound or a pharmaceutically acceptable salt thereof, wherein $R^1$ each represents a hydrogen atom;

$W^1$ and $W^2$ each represent a $C_1$-$C_4$ alkylene group;

$X^1$ represents —O—C(=O)— or —NG$^{11}$-SO$_2$—;

$X^2$ represents —C(=O)—O— or —SO$_2$—NG$^{12}$-;

$G^{11}$ and $G^{12}$ each independently represent a hydrogen atom or —COOR$^2$;

$R^2$ represents a $C_1$-$C_4$ alkyl group optionally substituted with 1 to 3 phenyl group(s);

$Y^1$ represents —NG$^{21}$-, —NG$^{21}$-L$^{11}$-C(=O)—NH—, or —NG$^{21}$-L$^{11}$-C(=C)—NG$^{31}$-L$^{21}$-C(=O)—NH—;

$Y^2$ represents —NG$^{22}$-, —NH—C(=O)-L$^{12}$-NG$^{22}$-, or —NH—C(=O)-L$^{22}$-NG$^3$-C(=O)-L$^{12}$-NG$^{22}$-;

$G^{21}$, $G^{31}$, $G^{22}$, and $G^{32}$ each independently represent a hydrogen atom, or a $C_1$-$C_6$ alkyl group optionally substituted with 1 to 3 substituent(s) independently selected from the group consisting of a phenyl group optionally substituted with 1 to 3 —COOR$^3$ group(s) and a —COOR$^3$ group;

$R^3$ each independently represents a hydrogen atom, a benzyl group, or a tert-butyl group;

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —COOR$^4$ group(s), a $C_1$-$C_6$ alkylene-phenylene group, or a phenylene-$C_1$-$C_4$ alkylene group;

$R^4$ each represents a hydrogen atom;

Z represents —(CH$_2$—CH$_2$—O)—CH$_2$—CH$_2$— or —(CH$_2$)$_n$—;

m represents an integer of 1 to 6; and n represents an integer of 2 to 12 is provided.

In another embodiment of the Compound (VII), a compound or a pharmaceutically acceptable salt thereof, wherein $R^1$ each represents hydrogen atom;

$W^1$ and $W^2$ each represent a $C_1$-$C_4$ alkylene group;

$X^1$ represents —O—C(=O)— or —NG$^{11}$-SO$_2$—;

$X^2$ represents —C(=O)—O— or —SO$_2$—NG$^{12}$-;

$G^{11}$ and $G^{12}$ each represent a hydrogen atom;

$Y^1$ represents —NG$^{21}$-, —NG$^{21}$-L$^{11}$-C(=O)—NH—, or —NG$^{21}$-L$^{11}$-C(=O)—NG$^{31}$-L$^{21}$-C(=O)—NH—;

$Y^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;

$G^{21}$, $G^{31}$, $G^{22}$, and $G^{12}$ each independently represent a hydrogen atom, or a $C_1$-$C_6$ alkyl group optionally substituted with 1 to 3 substituent(s) independently selected from the group consisting of a phenyl group optionally substituted with 1 to 3 —COOR$^3$ group(s) and a —COOR$^3$ group;

$R^3$ each represents a hydrogen atom;

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —COOR$^4$ group(s), a $C_1$-$C_4$ alkylene-phenylene group, or a phenylene-$C_1$-$C_4$ alkylene group;

$R^4$ each represents a hydrogen atom;

Z represents —(CH$_2$—CH$_2$—O)$_m$—CH$_2$—CH$_2$— or —(CH$_2$)$_n$—;

m represents an integer of 1 to 6; and n represents an integer of 2 to 12 is provided.

In one embodiment of the Compound (VII), a compound or a pharmaceutically acceptable salt thereof, wherein $R^1$ each independently represents a hydrogen atom or a tert-butoxycarbonyl group;

$W^1$ and $W^2$ each represent a $C_1$-$C_2$ alkylene group;

$X^1$ represents —O—C(=O)— or —NG$^{11}$-SO$_2$—;

$X^2$ represents —C(=O)—O— or —SO$_2$—NG$^{12}$-;

$G^{11}$ and $G^{12}$ each independently represent a hydrogen atom or —COOR$^2$;

$R^2$ represents a $C_1$-$C_4$ alkyl group optionally substituted with one phenyl group;

$Y^1$ represents —NG$^{21}$-, —NG$^{21}$-L$^{11}$-C(=O)—NH—, or —NG$^{21}$-L$^{11}$-C(=O)—NG$^{31}$-L$^{21}$-C(=O)—NH—;

$Y^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;

$G^{21}$, $G^{31}$, $G^{22}$, and $G^{32}$ each independently represent a hydrogen atom, or a $C_1$-$C_3$ alkyl group optionally substituted with 1 to 3 substituent(s) independently selected from the group consisting of a phenyl group optionally substituted with one —COOR$^3$ group and a —COOR$^3$ group;

$R^3$ each independently represents a hydrogen atom or a tert-butyl group;

$L^{11}$, $L^{21}$, $L^{12}$, and $L^{22}$ each independently represent a $C_1$-$C_2$ alkylene group optionally substituted with 1 to 2 $C_1$-$C_2$ alkyl group(s) optionally substituted with 1 to 2 —COOR$^4$ group(s), a $C_1$-$C_2$ alkylene-phenylene group, or a phenylene-$C_1$-$C_2$ alkylene group;

$R^4$ each independently represents a hydrogen atom or a tert-butyl group;

Z represents —(CH$_2$—CH$_2$—O)$_m$—CH$_2$—CH$_2$— or —(CH$_2$)$_n$—;

m represents an integer of 1 to 6; and n represents an integer of 2 to 12 is provided.

In one embodiment of the Compound (VII), a compound or a pharmaceutically acceptable salt thereof, wherein $R^1$ each represents a hydrogen atom;

$W^1$ and $W^2$ each represent a $C_1$-$C_2$ alkylene group;

$X^1$ represents —O—C(=O)— or —NG$^{11}$-SO$_2$—;

$X^2$ represents —C(=O)—O— or —SO$_2$—NG$^{12}$-;

$G^{11}$ and $G^{12}$ each independently represent a hydrogen atom or —COOR$^2$;

$R^2$ represents a $C_1$-$C_4$ alkyl group optionally substituted with one phenyl group;

$Y^1$ represents —NG$^{21}$-, —NG$^{21}$-L$^{11}$-O—NH—, or —NG$^{21}$-L$^{11}$-C(=O)—NG$^{31}$-L$^{21}$-C(=O)—NH—;

$Y^2$ represents —NG$^{22}$, —NH—C(=O)-L$^{12}$-NG$^{22}$-, or —NH—C(=O)-L$^{22}$-NG$^{31}$-L$^{21}$-C(=O)—NH—;

$G^{21}$ and $G^{22}$ each independently represent a hydrogen atom, or a $C_1$-$C_3$ alkyl group optionally substituted with 1 to 3 substituent (s) independently selected from the group consisting of a phenyl group optionally substituted with one —COOR$^3$ group and a —COOR$^3$ group;

$G^{31}$ and $G^{32}$ each represents a hydrogen atom;

$R^3$ each represents a hydrogen atom;

$L^{11}$, $L^{21}$, $L^{12}$, and $L^{22}$ each independently represent a $C_1$-$C_3$ alkylene group optionally substituted with 1 to 2 $C_1$-$C_2$ alkyl group(s) optionally substituted with 1 to 2 —COOR$^4$ group(s), a $C_1$-$C_2$ alkylene-phenylene group, or a phenylene-$C_1$-$C_2$ alkylene group;

R$^4$ each represents a hydrogen atom;

Z represents —(CH$_2$—CH$_2$—O)$_m$—CH$_2$—CH$_2$— or —(CH$_2$)$_n$—;

m represents an integer of 1 to 6; and n represents an integer of 2 to 12 is provided.

In one embodiment of the Compound (VII), a compound or a pharmaceutically acceptable salt thereof, wherein R$^1$ each represents a hydrogen anon;

W$^1$ and W$^2$ each represent a $C_1$-$C_2$ alkylene group;

X$^1$ represents —O—C(=O)— or —NG$^{11}$-SO$_2$—;

X$^2$ represents —C(=O)—O— or —SO$_2$—NG$^{12}$-;

G$^{11}$ and G$^{12}$ each independently represent a hydrogen atom or —COOR$^2$;

R$^2$ represents a $C_1$-$C_4$ alkyl group optionally substituted with one phenyl group;

Y$^1$ represents —NG$^{21}$-, —NG$^{21}$-L$^{11}$-C(=O)—NH—, or —NG$^{21}$-L$^{11}$-C(=O)—NG$^{33}$-L$^{21}$-C(=O)—NH—;

Y$^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;

G$^{21}$ and G$^{22}$ each independently represent a hydrogen atom, or a $C_1$-$C_3$ alkyl group optionally substituted with 1 to 3 substituent(s) independently selected from the group consisting of a phenyl group optionally substituted with one —COOR$^3$ group and a —COOR$^3$ group;

G$^{31}$ and G$^{32}$ each represents a hydrogen atom;

R$^3$ each represents a hydrogen atom;

L$^{11}$ and L$^{21}$ each independently represent a $C_1$-$C_2$ alkylene group optionally substituted with 1 to 2 $C_1$-$C_2$ alkyl group(s) optionally substituted with 1 to 2 —COOR$^4$ group(s), or a $C_1$-$C_2$ alkylene-phenylene group;

L$^{12}$ and L$^{22}$ each independently represent a $C_1$-$C_2$ alkylene group optionally substituted with 1 to 2 $C_1$-$C_2$ alkyl group(s) optionally substituted with 1 to 2 —COOR$^4$ group(s), or a phenylene-$C_1$-$C_2$ alkylene group;

R$^4$ each represents a hydrogen atom;

Z represents —(CH$_2$—CH$_2$—O)$_m$—CH$_2$—CH$_2$— or —(CH$_2$)$_n$—;

m represents an integer of 1 to 6; and n represents an integer of 2 to 12 is provided.

In one embodiment of the Compound (VII), a compound or a pharmaceutically acceptable salt thereof, wherein R$^1$ each represents a hydrogen atom;

W$^1$ and W$^2$ each represent a $C_1$-$C_2$ alkylene group;

X$^1$ represents —O—C(=O)— or —NG$^{11}$-SO$_2$—;

X$^2$ represents —C(=O)—O— or —SO$_2$—NG$^{12}$-;

G$^{11}$ and G$^{12}$ each represent a hydrogen atom;

Y$^1$ represents —NG$^{21}$-, —NG$^{21}$-L$^{11}$-C(=O)—NH—, or —NG$^{21}$-L$^{11}$-C(=O)—NG$^{31}$-L$^{21}$-C(=O)—NH—;

Y$^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;

G$^{21}$ and G$^{22}$ each independently represent a hydrogen atom, or a $C_1$-$C_3$ alkyl group optionally substituted with 1 to 3 substituent(s) independently selected from the group consisting of a phenyl group optionally substituted with one —COOR$^3$ group and a —COOR$^3$ group;

G$^{31}$ and G$^{32}$ each represents a hydrogen atom;

R$^3$ each represents a hydrogen atom;

L$^{11}$ and L$^{21}$ each independently represent a $C_1$-$C_2$ alkylene group optionally substituted with 1 to 2 $C_1$-$C_2$ alkyl group(s) optionally substituted with 1 to 2 —COOR$^4$ group(s), or a $C_1$-$C_2$ alkylene-phenylene group;

L$^{12}$ and L$^{22}$ each independently represent a $C_1$-$C_2$ alkylene group optionally substituted with 1 to 2 $C_1$-$C_2$ alkyl group(s) optionally substituted with 1 to 2 —COOR$^4$ group(s), or a phenylene-$C_1$-$C_2$ alkylene group;

R$^4$ each represents a hydrogen atom;

Z represents —(CH$_2$—CH$_2$—O)$_m$—CH$_2$—CH$_2$— or —(CH$_2$)$_n$—;

m represents an integer of 1 to 6; and n represents an integer of 2 to 12 is provided.

In one embodiment of the Compound (VII), a compound or a pharmaceutically acceptable salt thereof, wherein R$^1$ each represents a hydrogen atom;

W$^1$ and W$^2$ each represent a $C_1$-$C_2$ alkylene group;

X$^1$ represents —NG$^{11}$-SO$_2$—;

X$^2$ represents —SO$_2$—NG$^{12}$-;

G$^{11}$ and G$^{12}$ each independently represent a hydrogen atom or —COOR$^2$;

R$^2$ represents a $C_1$-$C_4$ alkyl group optionally substituted with one phenyl group;

Y$^1$ represents —NG$^{21}$-;

Y$^2$ represents —NG$^{22}$-;

G$^{21}$ and G$^{22}$ each independently represent a $C_1$-$C_3$ alkyl group substituted with 1 to 3 substituent(s) independently selected from the group consisting of a phenyl group substituted with one carboxy group and a carboxy group;

Z represents —(CH$_2$—CH$_2$—O)$_m$—CH$_2$—CH$_2$— or —(CH$_2$)$_n$—;

m represents an integer of 1 to 6; and n represents an integer of 2 to 12 is provided.

In one embodiment of the Compound (VII), a compound or a pharmaceutically acceptable salt thereof, wherein R$^1$ each represents a hydrogen atom;

W$^1$ and W$^2$ each represent a $C_1$-$C_2$ alkylene group;

X$^1$ represents —NG$^{11}$-SO$_2$—;

X$^2$ represents —SO$_2$—NG$^{12}$-;

G$^{11}$ and G$^{12}$ each represent a hydrogen atom;

Y$^1$ represents —NG$^{21}$-;

Y$^2$ represents —NG$^{22}$-;

G$^{21}$ and G$^{22}$ each independently represent a $C_1$-$C_3$ alkyl group substituted with 1 to 3 substituent(s) independently selected from the group consisting of a phenyl group substituted with one carboxy group and a carboxy group;

Z represents —(CH$_2$—CH$_2$—O)$_m$—CH$_2$—CH$_2$— or —(CH$_2$)$_n$—;

m represents an integer of 1 to 6; and n represents an integer of 2 to 12 is provided.

Compound (VIII)

In one embodiment of the present invention, the Compound (I) or a pharmaceutically acceptable salt thereof represents a compound represented by the following general formula (VIII):

(VIII)

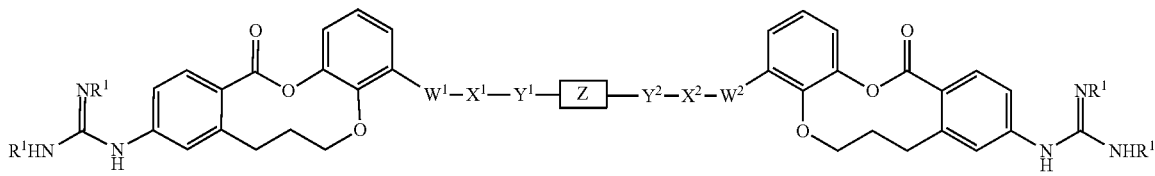

[wherein:

$R^1$ each independently represents a hydrogen atom or a —COO—($C_1$-$C_4$ alkyl group);

$W^1$ and $W^2$ each independently represent a single bond or a $C_1$-$C_4$ alkylene group;

$X^1$ represents —C(=O)— or —$NG^{11}$-$SO_2$—;

$X^2$ represents —C(=O)— or —$SO_2$—$NG^{12}$-;

$G^{11}$ and $G^{12}$ each independently represent a hydrogen atom or —$COOR^2$;

$R^2$ represents a $C_1$-$C_4$ alkyl group optionally substituted with 1 to 5 aryl group(s);

$Y^1$ represents —$NG^{21}$-, —$NG^{21}$-$L^{11}$-C(=O)—NH—, or —$NG^{21}$-$L^{11}$-C(=O)—$NG^{31}$-$L^{21}$-C(=O)—NH—;

$Y^2$ represents —$NG^{22}$-, —NH—C(=O)-$L^{12}$-$NG^{22}$-, or —NH—C(=C)-$L^{22}$-$NG^{32}$-C(=O)-$L^{12}$-$NG^{22}$-;

$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —$COOR^3$ group(s) and a —$COOR^3$ group;

$R^3$ each independently represents a hydrogen atom, or a $C_1$-$C_4$ alkyl group optionally substituted with 1 to 5 aryl group(s);

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group;

$R^4$ each independently represents a hydrogen atom, or a $C_1$-$C_4$ alkyl group optionally substituted with 1 to 5 aryl group(s);

Z represents —($CH_2$—$CH_2$—O)$_m$—$CH_2$—$CH_2$— or —($CH_2$)$_n$—;

m represents an integer of 1 to 6; and n represents an integer of 2 to 12]

or a pharmaceutically acceptable salt thereof.

Examples of embodiments of each substituent of the Compound (VIII) include the followings in addition to the above embodiments of each substituent of the Compound (I)

In one embodiment, the $C_1$-$C_4$ alkyl group of "—COO—($C_1$-$C_4$ alkyl group)" in $R^1$ represents a methyl group, an ethyl group, a n-propyl group, an isopropyl group, a n-butyl group, or a tert-butyl group.

In one embodiment, $R^1$ represents a hydrogen atom or a tert-butoxycarbonyl group, preferably a hydrogen atom.

In one embodiment, $W^1$ represents a single bond or a $C_1$-$C_2$ alkylene group, preferably a single band.

In one embodiment, $W^2$ represents a single bond or a $C_1$-$C_2$ alkylene group, preferably a single bond.

In one embodiment, $X^1$ represents —C(=O)— or —$NG^{11}$-$SO_2$—, preferably —C(=O)—.

In one embodiment, $X^2$ represents —C(=O)— or —$SO_2$—$NG^{12}$-, preferably —C(=O)—.

In one embodiment, $R^2$ of "—$COOR^2$ group" in $G^{11}$ and $G^{12}$ represents a $C_1$-$C_6$ alkyl group optionally substituted with 1 to 3 phenyl group(s), preferably a $C_1$-$C_4$ alkyl group optionally substituted with one phenyl group, more preferably a methyl group, an ethyl group, a n-propyl group, an isopropyl group, a n-butyl group, a tert-butyl group, or a benzyl group.

In one embodiment, $G^{11}$ represents a hydrogen atom, a tert-butoxycarbonyl group, or a benzyloxycarbonyl group, preferably a hydrogen atom or a benzyloxycarbonyl group, more preferably a hydrogen atom.

In one embodiment, $C^{12}$ represents a hydrogen atom, a tert-butoxycarbonyl group, or a benzyloxycarbonyl group, preferably a hydrogen atom or a benzyloxycarbonyl group, more preferably a hydrogen atom.

In one embodiment, $Y^1$ represents —$NG^{21}$-.

In one embodiment, $Y^2$ represents —$NG^{22}$-.

In one embodiment, the "phenyl group optionally substituted with 1 to 5 —$COOR^3$ group(s)" in $G^{21}$, $G^{31}$, $G^{22}$, and $G^{32}$ represents a 2-($COOR^3$)-phenyl group, a 3-($COOR^3$)-phenyl group, a 4-($COOR^3$)-phenyl group, or the like.

In one embodiment, $R^3$ of "—$COOR^3$ group" in $G^{21}$, $G^{31}$, $G^{22}$, and $G^{32}$ each independently represents a hydrogen atom, a methyl group, an ethyl group, a n-propyl group, an isopropyl group, a n-butyl group, a tert-butyl group, or a benzyl group, preferably a hydrogen atom, a benzyl group, or a tert-butyl group, more preferably a hydrogen atom or a tert-butyl group, still more preferably a hydrogen atom.

In one embodiment, $G^{21}$ represents a hydrogen atom, or a $C_1$-$C_3$ alkyl group optionally substituted with 1 to 3 —$COOR^3$ group(s), preferably a $C_1$-$C_3$ alkyl group substituted with 1 to 3 carboxy group(s).

In one embodiment, $G^{31}$ represents a hydrogen atom, or a $C_1$-$C_3$ alkyl group optionally substituted with 1 to 3 —$COOR^3$ group(s), preferably a hydrogen atom.

In one embodiment, $G^{22}$ represents a hydrogen atom, or a $C_1$-$C_3$ alkyl group optionally substituted with 1 to 3 —$COOR^3$ group(s), preferably a $C_1$-$C_3$ alkyl group substituted with 1 to 3 carboxy group(s).

In one embodiment, $G^{32}$ represents a hydrogen atom, or a $C_1$-$C_3$ alkyl group optionally substituted with 1 to 3 —$COOR^3$ group(s), preferably a hydrogen atom.

In one embodiment, $R^4$ of "—$COOR^4$ group" in $L^{11}$, $L^{12}$, $L^{21}$, and $L^{22}$ each independently represents a hydrogen atom, a methyl group, an ethyl group, a n-propyl group, an isopropyl group, a n-butyl group, a tert-butyl group, or a benzyl group, preferably a hydrogen atom, a tert-butyl group, or a benzyl group, more preferably a hydrogen atom or a tert-butyl group, still more preferably a hydrogen atom.

In one embodiment, $L^{11}$ represents a $C_1$-$C_2$ alkylene group, preferably a methylene group.

In one embodiment, $L^{12}$ represents a $C_1$-$C_2$ alkylene group, preferably a methylene group.

In one embodiment, $L^{21}$ represents a $C_1$-$C_2$ alkylene group, preferably a methylene group.

In one embodiment, $L^{22}$ represents a $C_1$-$C_2$ alkylene group, preferably a methylene group.

In one embodiment, at least one of $R^1$, $R^3$, $R^4$, $G^{11}$, and $G^{12}$ represents a hydrogen atom. In another embodiment, at least one of $R^1$ and $R^4$ represents a hydrogen atom. In another embodiment, $R^1$, $R^3$, $R^4$, $G^{11}$, and $G^{12}$ each represent a hydrogen atom.

In one embodiment, Z represents —$(CH_2—CH_2—O)_m$—$CH_2—CH_2$— or —$(CH_2)_n$—, preferably —$(CH_2—CH_2—O)_m$—$CH_2—CH_2$—.

In one embodiment, m represents an integer of 1 to 6, and n represents an integer of 2 to 12, preferably m represents an integer of 1 to 4, and n represents an integer of 2 to 6.

In one embodiment of the Compound (VIII), a compound or a pharmaceutically acceptable salt thereof, wherein
$R^1$ each represents a hydrogen atom;
$W^1$ and $W^2$ each independently represent a single bond or a $C_1$-$C_4$ alkylene group;
$X^1$ represents —C(=O)— or —$NG^{11}$-$SO_2$—;
$X^2$ represents —C(=O)— or —$SO_2$—$NG^{12}$-;
$G^{11}$ and $G^{12}$ each independently represent a hydrogen atom or —$COOR^2$;
$R^2$ represents a $C_2$-$C_4$ alkyl group optionally substituted with 1 to 5 aryl group(s);
$R^2$ represents —$NG^{21}$-, —$NG^{21}$-$L^{11}$-C(=O)—NH—, or —$NG^{21}$-$L^{11}$-C(=O)—$NG^{31}$-$L^2$-C(=O)—NH—;
$Y^2$ represents —$NG^{22}$-, —NH—C(=O)-$L^{12}$-$NG^{22}$-, or —NH—C(=O)-$L^{22}$-$NG^{32}$-C(=O)-$L^{12}$-$NG^{22}$-;
$G^{21}$, $G^{31}$, $G^{22}$, and $G^{22}$ each independently represent a hydrogen atom, or a $C_1$-$C_6$ alkyl group optionally substituted with 1 to 5 substituent (s) independently selected from the group consisting of a phenyl group optionally substituted with 1 to 5 —$COOR^3$ group(s) and a —$COOR^3$ group;
$R^3$ each independently represents a hydrogen atom, or a $C_1$-$C_4$ alkyl group optionally substituted with 1 to 5 aryl group(s);
$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group;
$R^4$ each represents a hydrogen atom;
Z represents —$(CH_2—CH_2—O)_m$—$CH_2—CH_2$— or —$(CH_2)_n$—;
m represents an integer of 1 to 6; and
n represents an integer of 2 to 12
is provided.

In another embodiment of the Compound (VIII), a compound or a pharmaceutically acceptable salt thereof, wherein
$R^1$ each represents a hydrogen atom;
$W^1$ and $W^2$ each independently represent a single bond or a $C_1$-$C_4$ alkylene group;
$X^1$ represents —C(=O)— or —$NG^{11}$-$SO_2$—;
$X^2$ represents —C(=O)— or —$SO_2$—$NG^{12}$-;
$G^{11}$ and $G^{12}$ each represent a hydrogen atom;
$Y^1$ represents —$NG^{21}$-, —$NG^{21}$-$L^{11}$-C(=O)—NH—, or —$NG^{21}$-$L^{11}$-C(=O)—$NG^{31}$-$L^{21}$-C(=O)—NH—;
$Y^2$ represents —$NG^{22}$-, —NH—C(=O)-$L^{12}$-$NG^{22}$-, or —NH—C(=O)-$L^{22}$-$NG^{32}$-C(=O)-$L^{12}$-$NG^{22}$-;
$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —$COOR^3$ group(s) and a —$COOR^3$ group;
$R^3$ each represents a hydrogen atom;
$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group;
$R^4$ each represents a hydrogen atom;
Z represents —$(CH_2—CH_2—O)_m$—$CH_2—CH_2$— or —$(CH_2)_n$—;
m represents an integer of 1 to 6; and
n represents an integer of 2 to 12
is provided.

In another embodiment of the Compound (VIII), a compound or a pharmaceutically acceptable salt thereof, wherein
$R^1$ each independently represents a hydrogen atom or a tert-butoxycarbonyl group;
$W^1$ and $W^2$ each independently represent a single bond or a $C_1$-$C_2$ alkylene group;
$X^1$ represents —C(=O)— or —$NG^{11}$-$SO_2$—;
$X^2$ represents —C(=O)— or —$SO_2$—$NG^{12}$-;
$G^{11}$ and $G^{12}$ each represent a hydrogen atom;
$Y^1$ represents —$NG^{21}$-, —$NG^{21}$-L l-C(=O)—NH—, or —$NG^{21}$-$L^{11}$-C(=O)—$NG^{31}$-$L^{21}$-C(=O)—NH—;
$Y^2$ represents —$NG^{22}$-, —NH—C(=O)-$L^{12}$-$NG^{22}$-, or —NH—C(=O)-$L^{22}$-$NG^{32}$-C(=O)-$L^{12}$-$NG^{22}$-;
$G^{21}$, $G^{31}$, $G^{22}$, and $G^{32}$ each independently represent a hydrogen atom, or a $C_1$-$C_2$ alkyl group optionally substituted with 1 to 3 —$COOR^3$ group(s);
$R^3$ each independently represents a hydrogen atom or a tert-butyl group;
$L^{11}$, $L^{21}$, $L^{12}$, and $L^{22}$ each independently represent a $C_1$-$C_2$ alkylene group;
Z represents —$(CH_2—CH_2—O)_m$—$CH_2—CH_2$— or —$(CH_2)_n$—;
m represents an integer of 1 to 6; and
n represents an integer of 2 to 12
is provided.

In another embodiment of the Compound (VIII), a compound or a pharmaceutically acceptable salt thereof, wherein
$R^1$ each represents a hydrogen atom;
$W^1$ and $W^2$ each independently represent a single bond or a $C_1$-$C_2$ alkylene group;
$X^1$ represents —C(=O)— or —$NG^{11}$-$SO_2$—;
$X^2$ represents —C(=O)— or —$SO_2$—$NG^{12}$-;
$G^{11}$ and $G^{12}$ each represent a hydrogen atom;
$Y^1$ represents —$NG^{21}$-, —$NG^2$-$L^{11}$-C(=O)—NH—, or —$NG^{21}$-$L^{11}$-C(=O)—$NG^{31}$-$L^{21}$-C(=O)—NH—;
$Y^2$ represents —$NG^{12}$-, —NH—C(=O)-$L^{12}$-$NG^{22}$-, or —NH—C(=O)-$L^{22}$-$NG^{32}$-C(=O)-$L^{12}$-$NG^{22}$-;
$G^{21}$, $G^{31}$, $G^{22}$, and $G^{22}$ each independently represent a hydrogen atom, or a $C_1$-$C_3$ alkyl group optionally substituted with 1 to 3 —$COOR^3$ group(s);
$R^3$ each independently represents a hydrogen atom or a tert-butyl group;
$L^{11}$, $L^{21}$, $L^{12}$, and $L^{22}$ each independently represent a $C_1$-$C_2$ alkylene group;
Z represents —$(CH_2—CH_2—O)_m$—$CH_2—CH_2$— or —$(CH_2)_n$—;
m represents an integer of 1 to 6; and
n represents an integer of 2 to 12
is provided.

In another embodiment of the Compound (VIII), a compound or a pharmaceutically acceptable salt thereof, wherein
$R^1$ each represents a hydrogen atom;
$W^1$ and $W^2$ each independently represent a single bond or a $C_1$-$C_2$ alkylene group;
$X^1$ represents —C(=O)— or —$NG^{11}$-$SO_2$—;
$X^2$ represents —C(=O)— or —$SO_2$—$NG^{21}$-;
$G^{11}$ and $G^{12}$ each represent a hydrogen atom;
$Y^2$ represents —$NG^{21}$-, —$NG^{21}$-$L^{11}$-C(=O)—NH—, or —$NG^{21}$-$L^{21}$-C(=O)—$NG^{31}$-$L^{21}$-C(=O)—NH—;

$Y^2$ represents —$NG^{22}$—, —NH—C(═O)-$L^{12}$-$NG^{22}$—, or —NH—C(═O)-$L^{22}$-$NG^{32}$-C(═O)-$L^{12}$-$NG^{22}$—;

$G^{21}$ and $G^{22}$ each independently represent a hydrogen atom, or a $C_1$-$C_3$ alkyl group optionally substituted with 1 to 3 —$COOR^3$ group(s);

$G^{31}$ and $G^{32}$ each represents a hydrogen atom;

$R^3$ each represents a hydrogen atom;

$L^{11}$, $L^{21}$, $L^{12}$, and $L^{22}$ each independently represent a $C_1$-$C_2$ alkylene group;

Z represents —($CH_2$—$CH_2$—O)$_n$—$CH_2$—$CH_2$— or —($CH_2$)$_n$—;

m represents an integer of 1 to 6; and n represents an integer of 2 to 12 is provided.

In another embodiment of the Compound (VIII), a compound or a pharmaceutically acceptable salt thereof, wherein $R^1$ each represents a hydrogen atom;

$W^1$ and $W^2$ each represent a single bond;

$X^1$ represents —C(═O)—;

$X^2$ represents —C(═O)—;

$Y^1$ represents —$NG^{21}$—;

$Y^2$ represents —$NG^{22}$—;

$G^{21}$ and $G^{22}$ each independently represent a $C_1$-$C_3$ alkyl group substituted with 1 to 3 carboxy group(s);

Z represents —($CH_2$—$CH_2$—O)$_m$—$CH_2$—$CH_2$—; and m represents an integer of 1 to 6.

In one embodiment of the present invention, $A^1$ and $A^2$ each independently represent an inhibitor residue formed by removing any one hydrogen atom or any one hydroxy group from an inhibitor molecule selected from the following inhibitor molecule group.

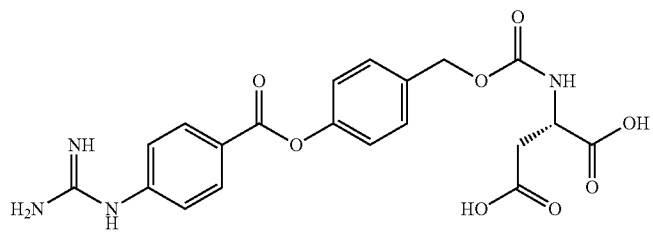

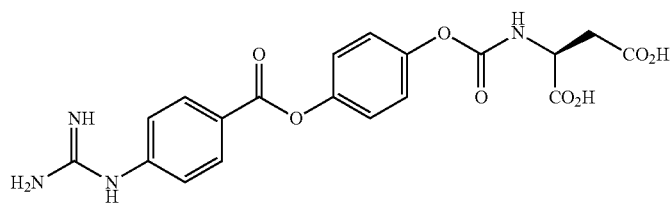

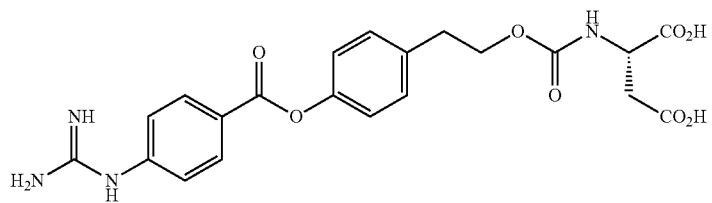

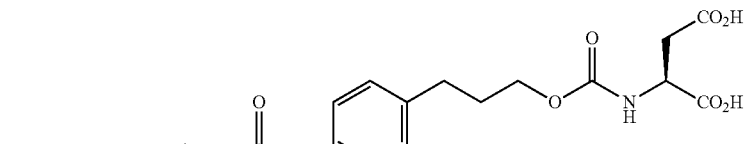

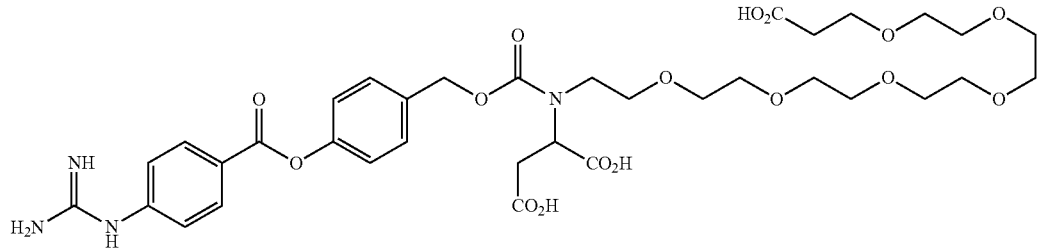

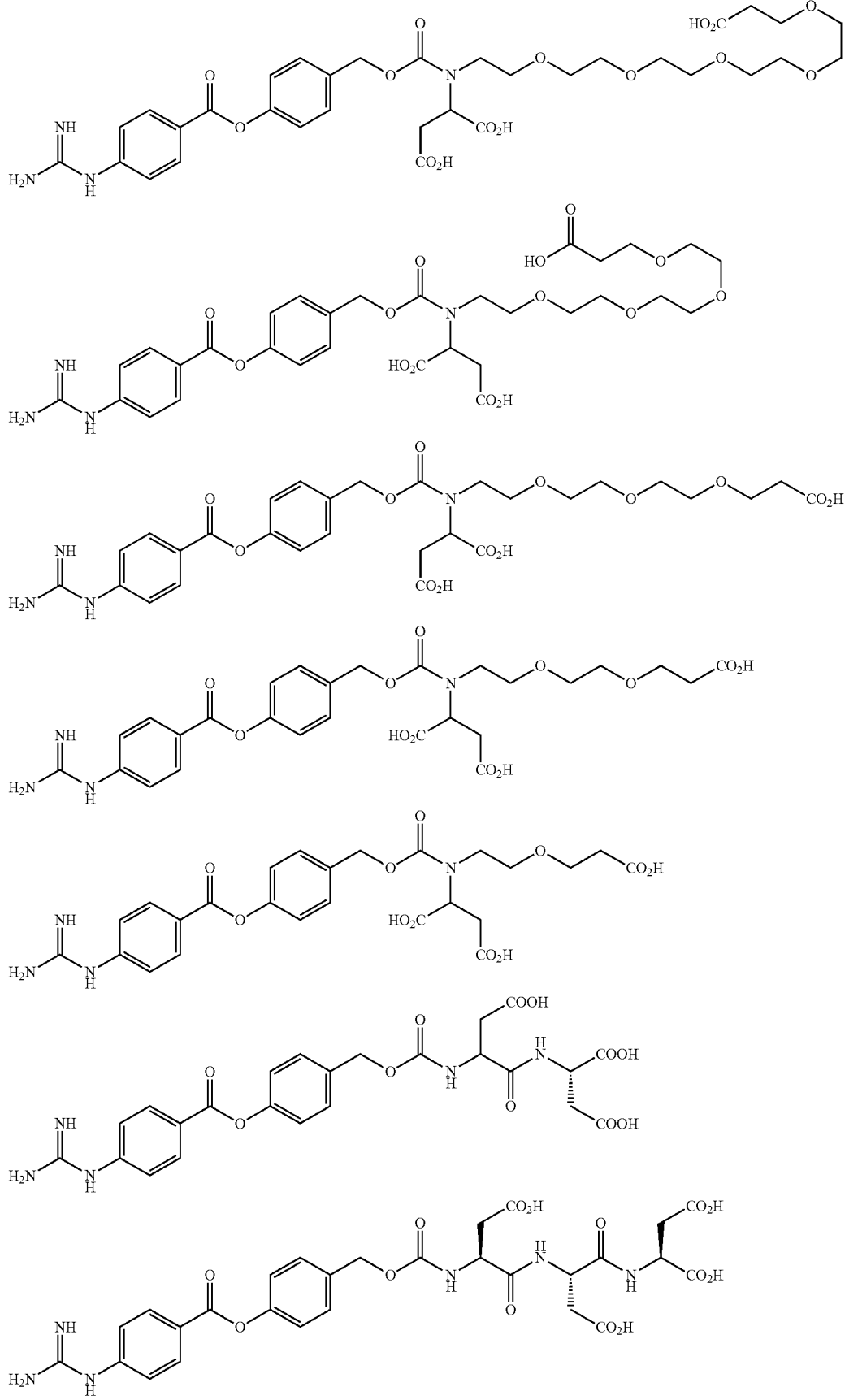

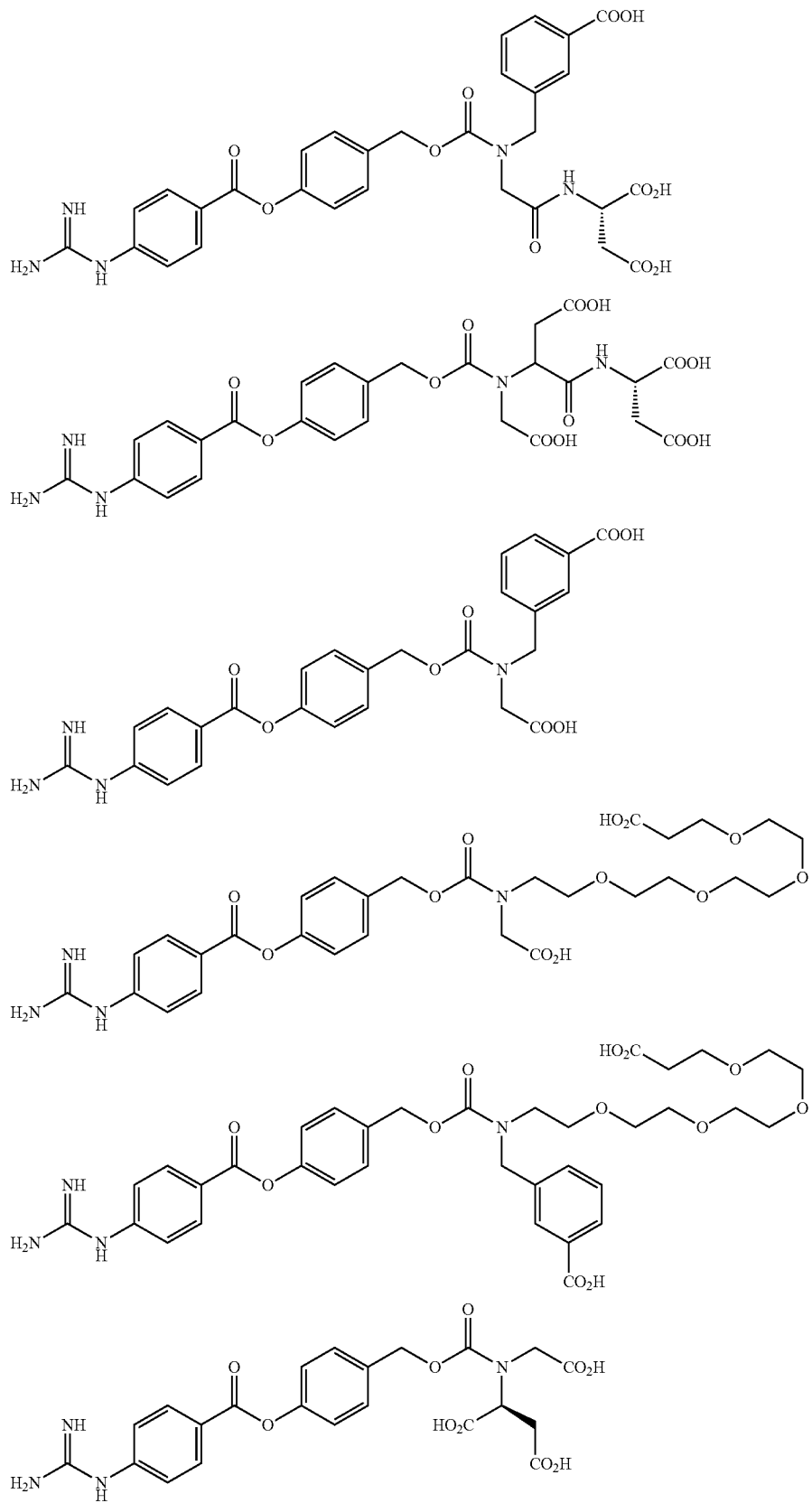

-continued
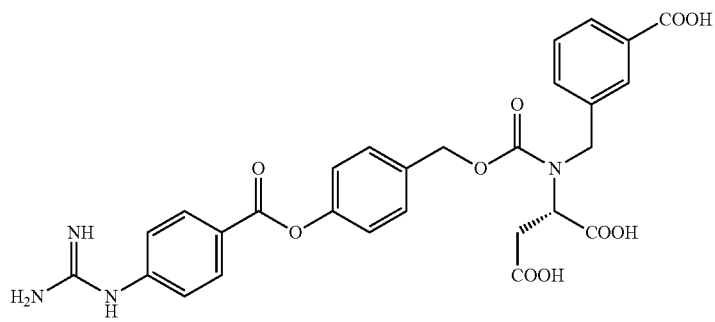
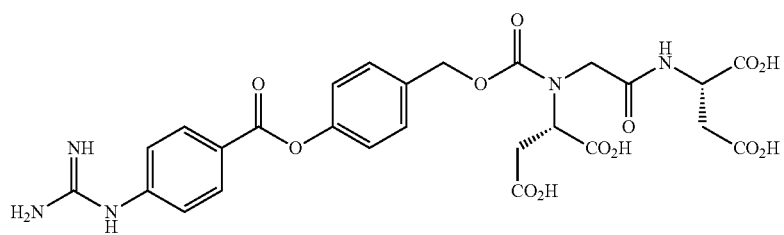
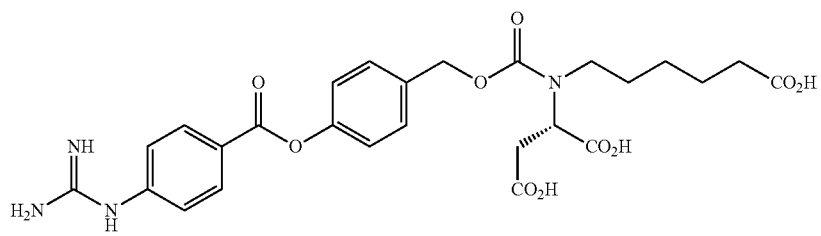
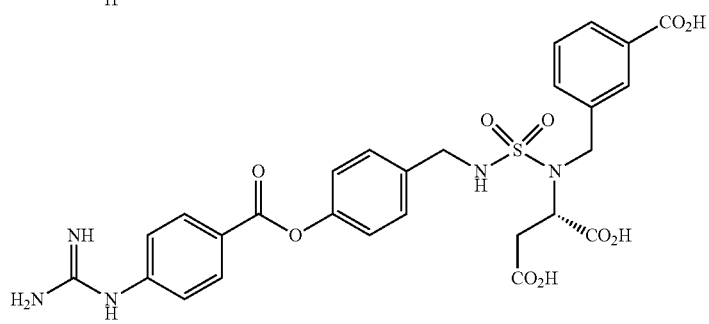
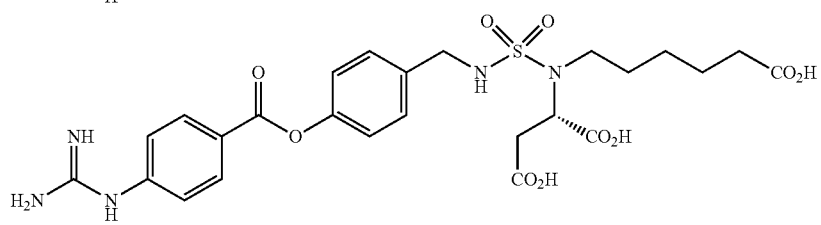
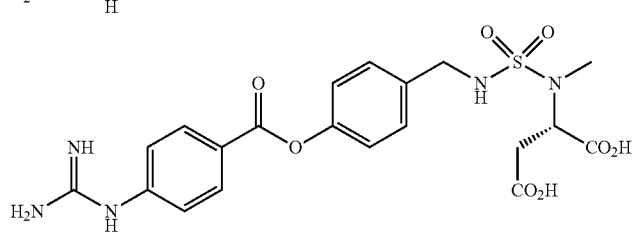

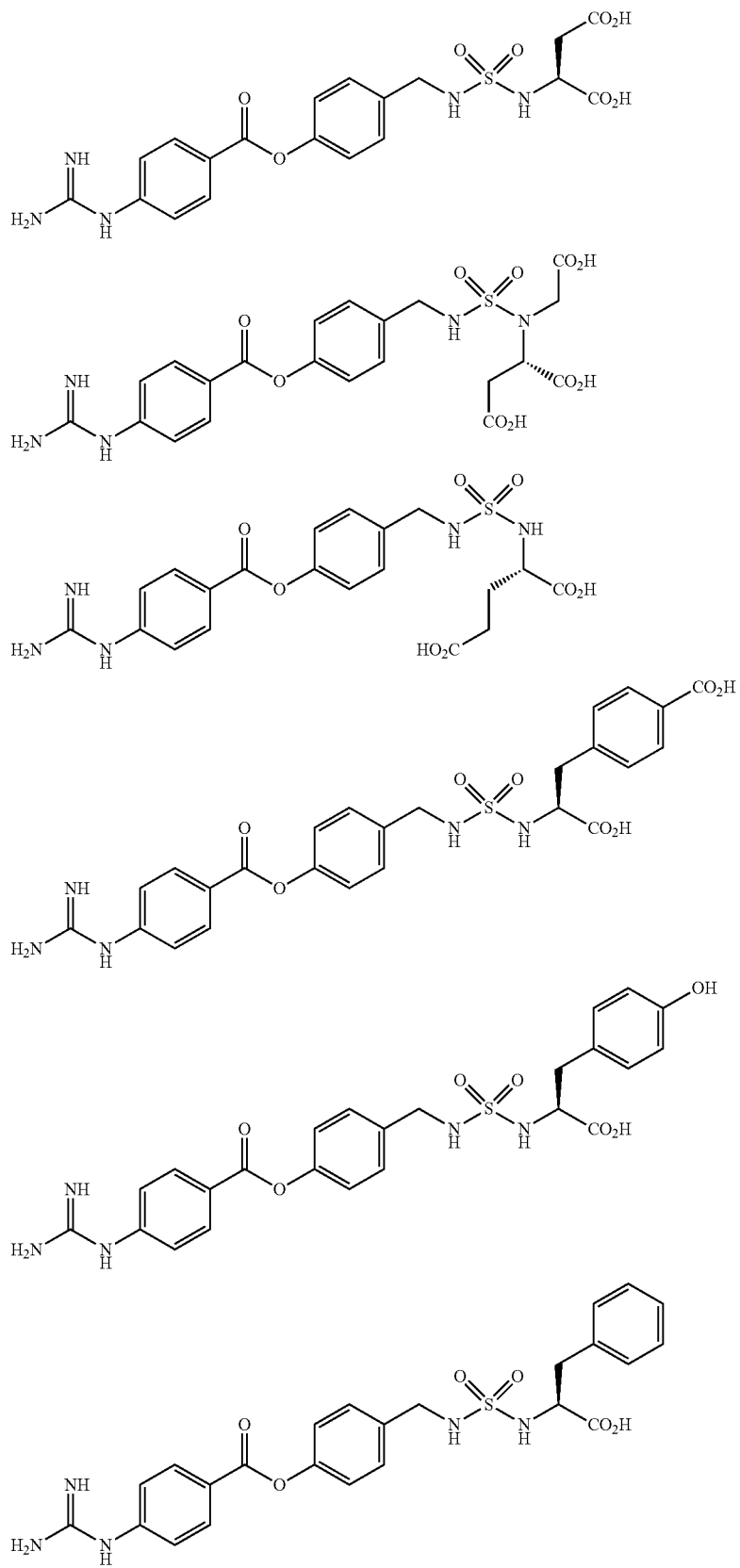

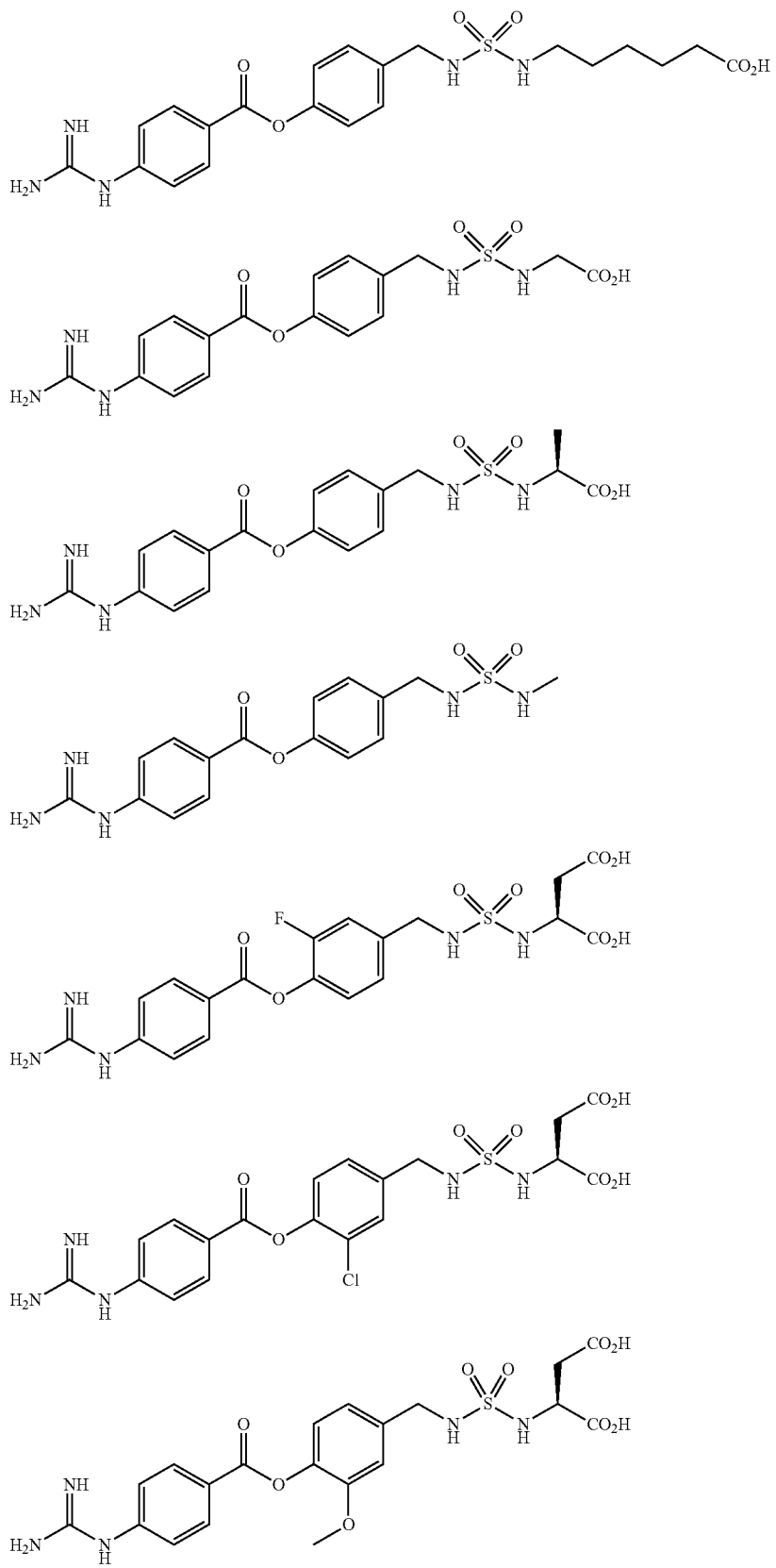

-continued
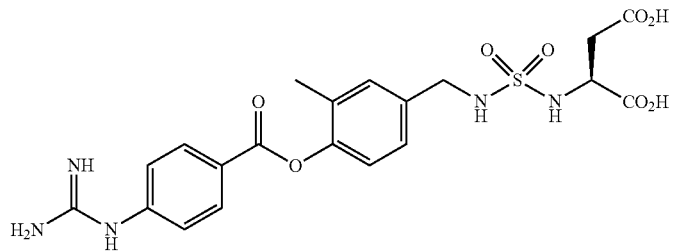
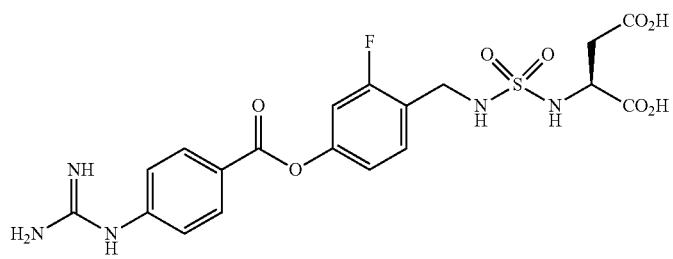
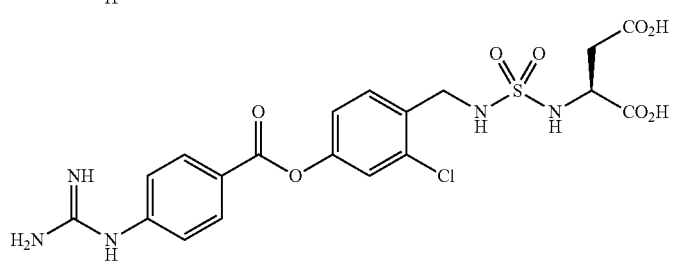
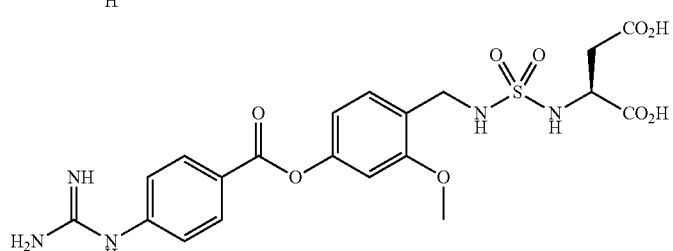
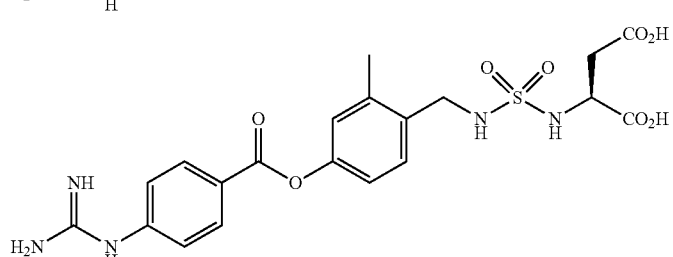
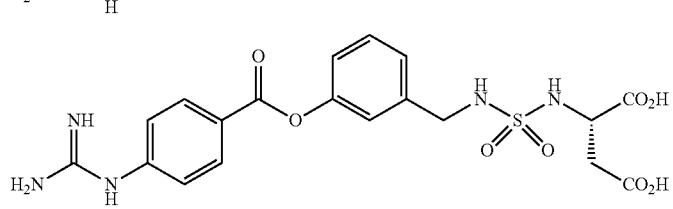
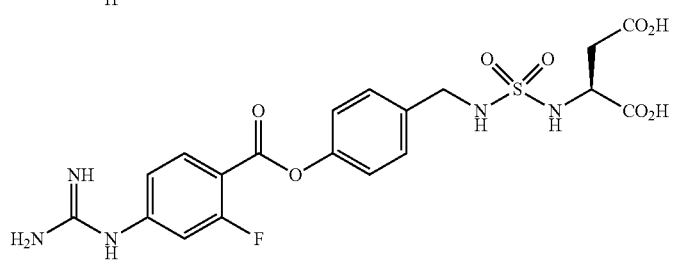

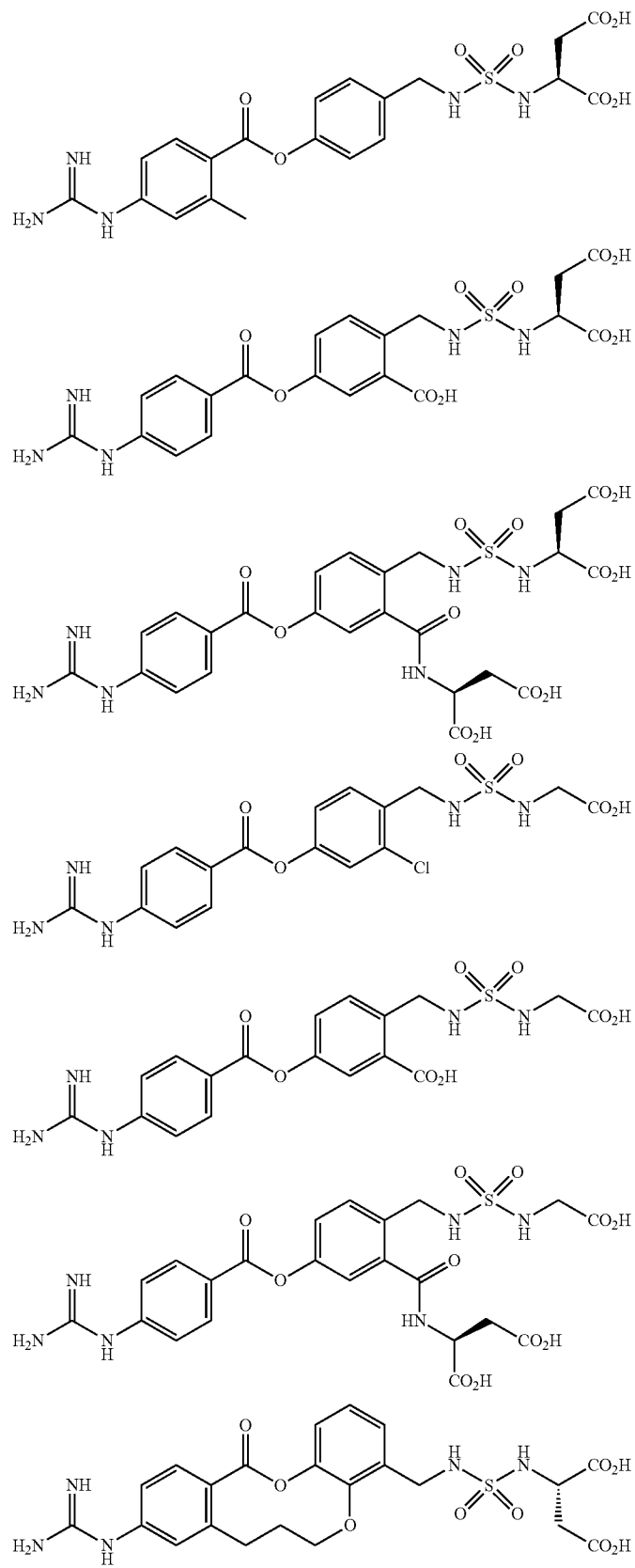

-continued
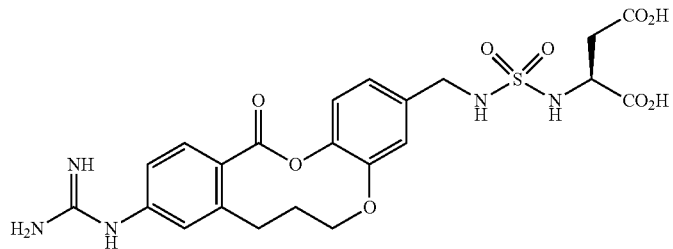
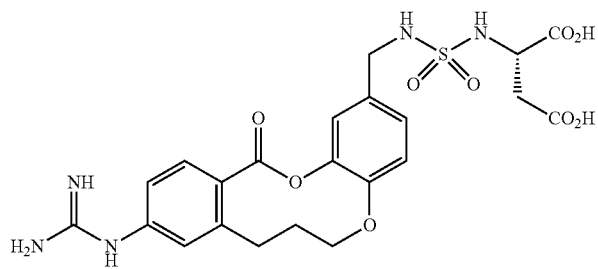
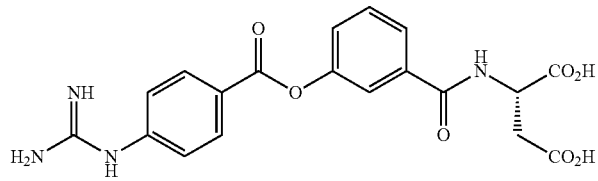
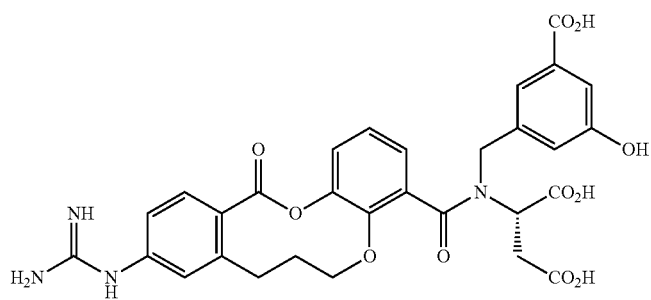
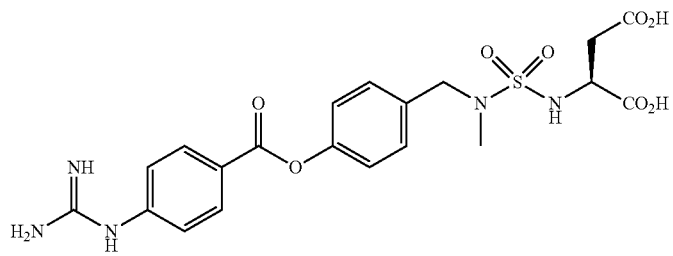
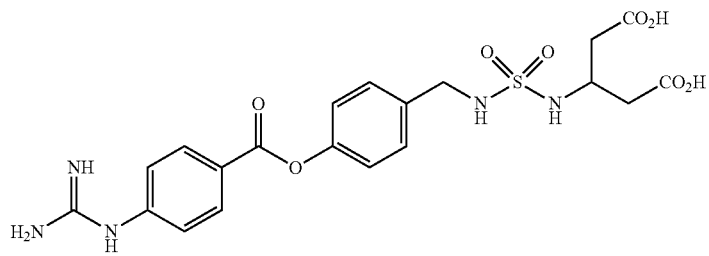
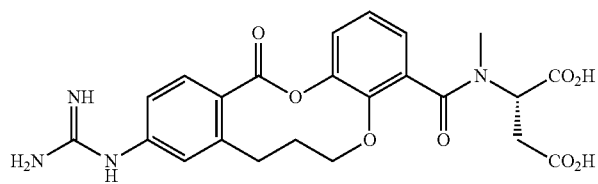

-continued
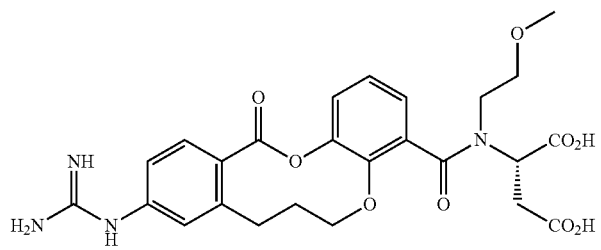
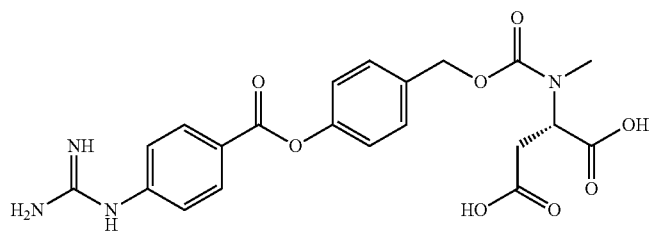
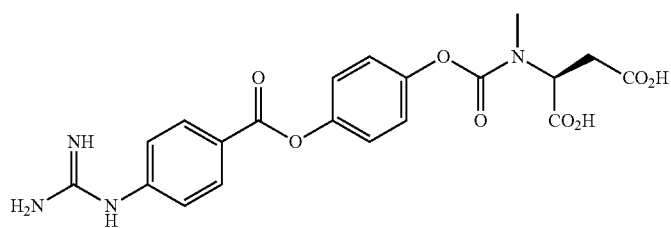
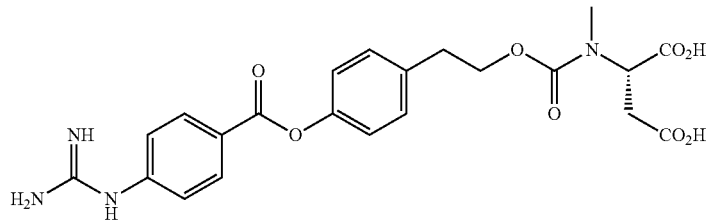
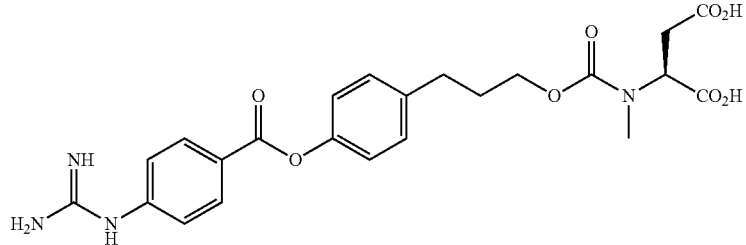
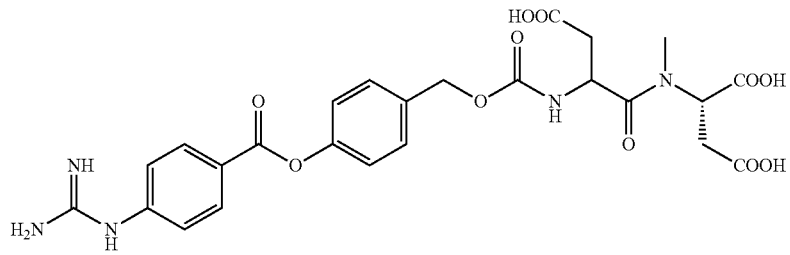
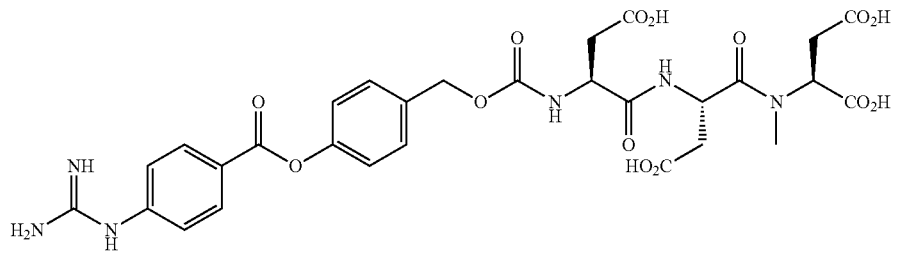

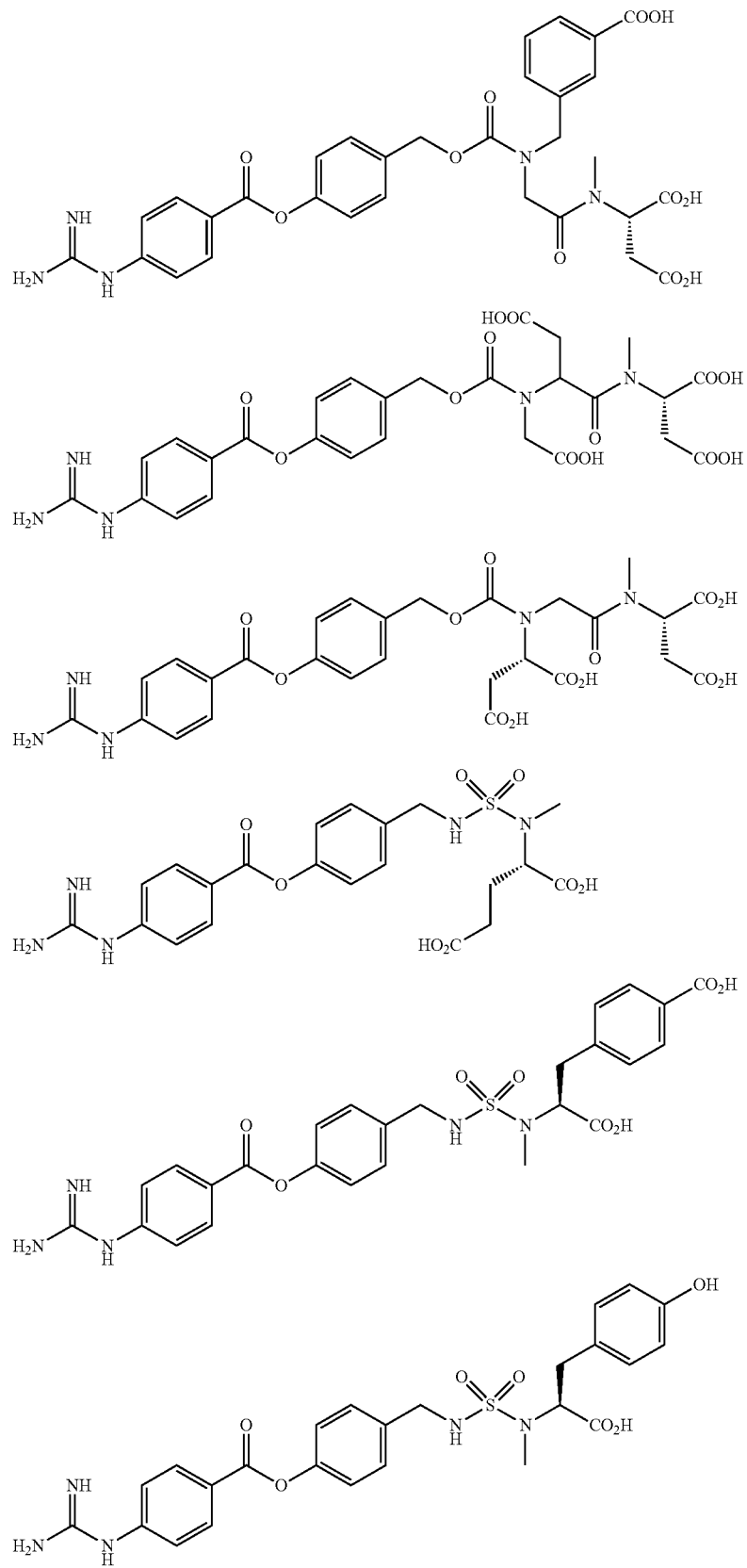

-continued
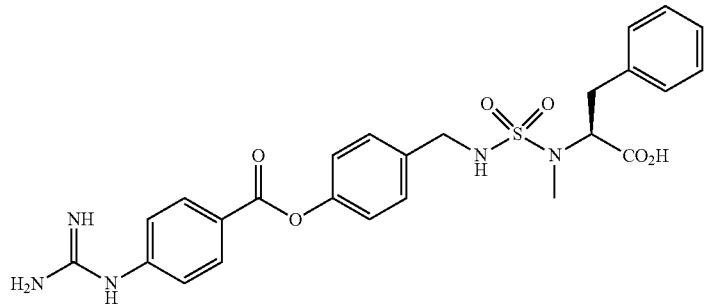
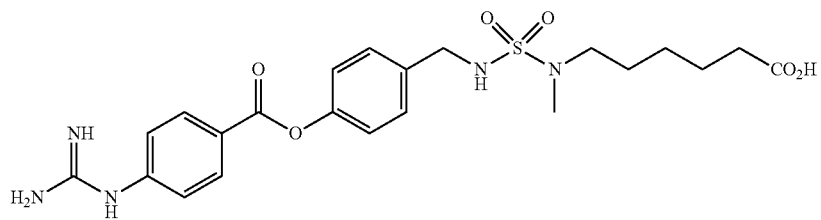
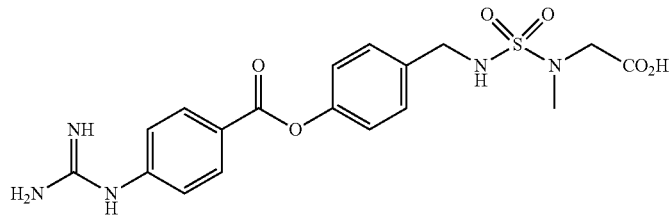
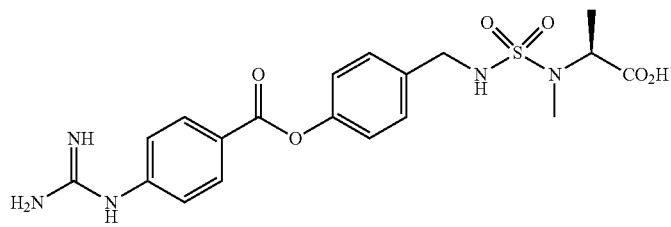
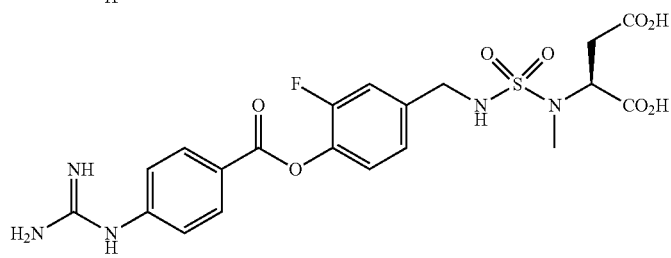
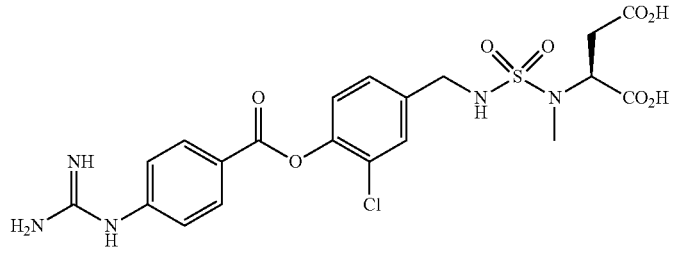
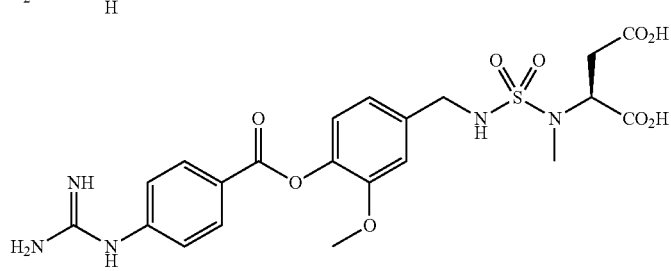

-continued
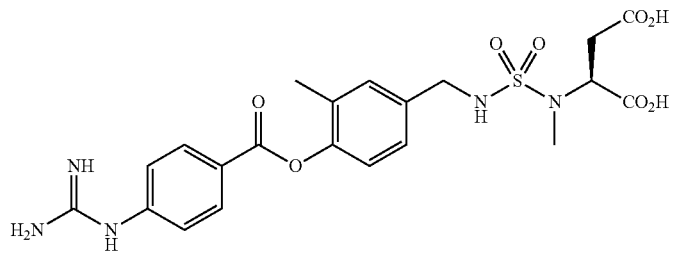
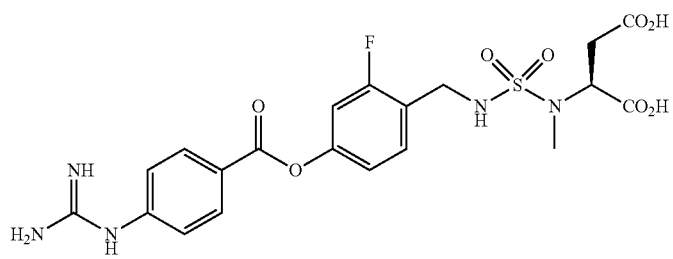
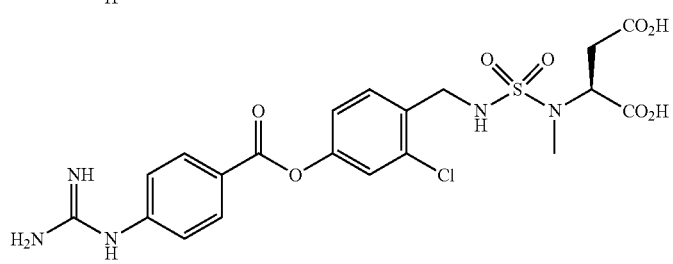
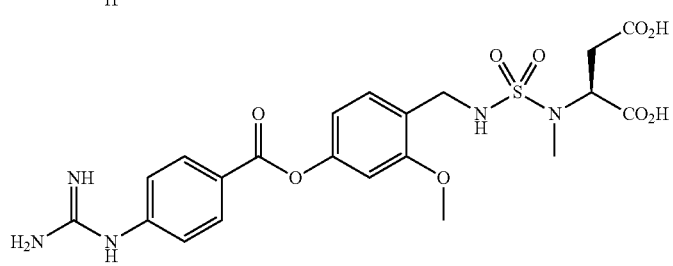
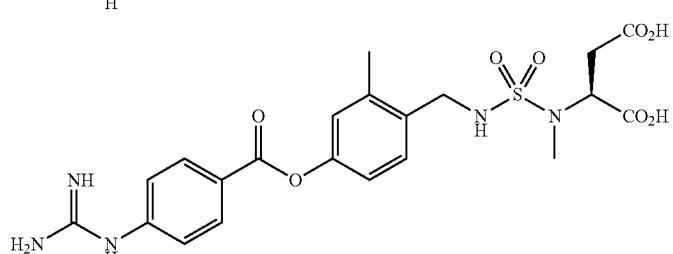
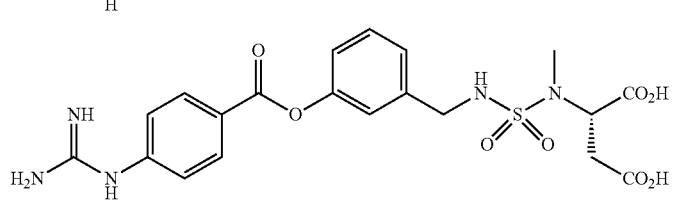
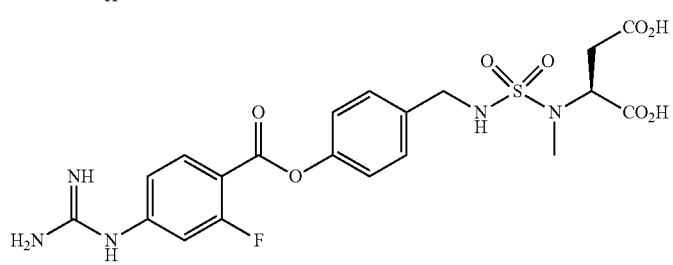

-continued
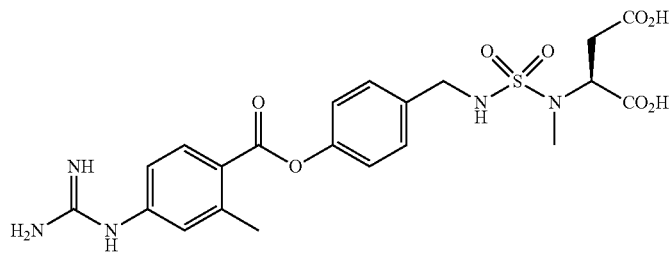
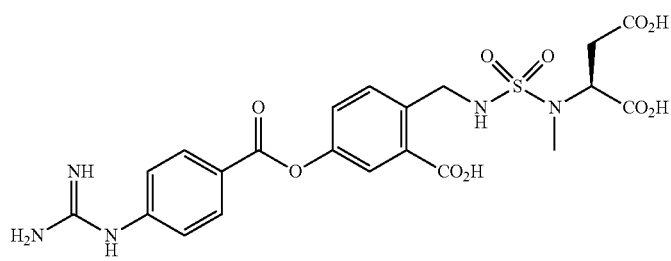
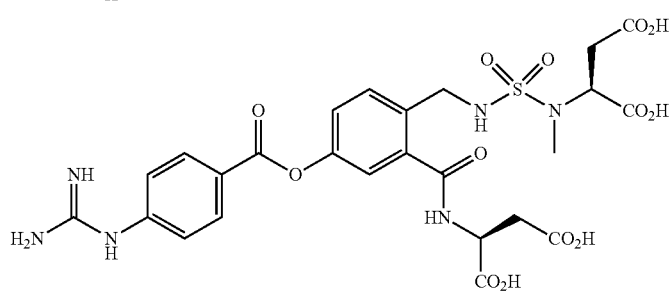
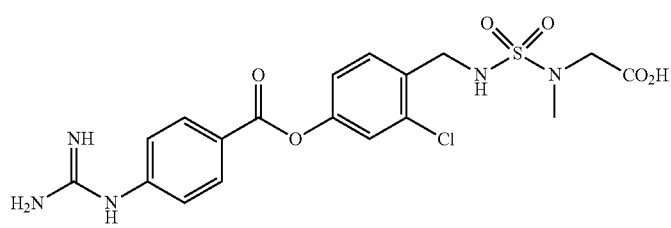
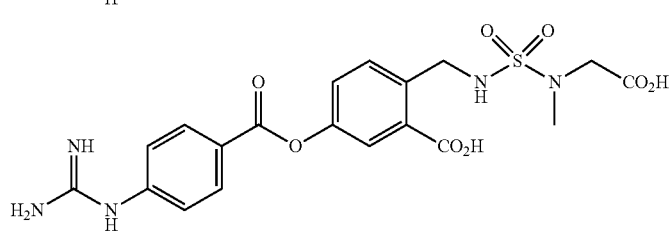
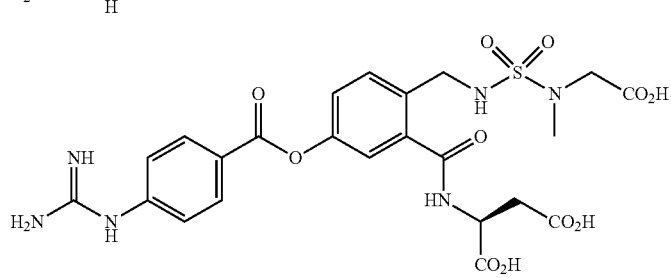
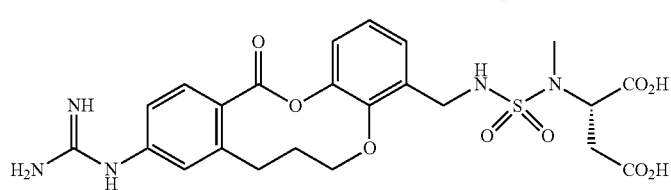

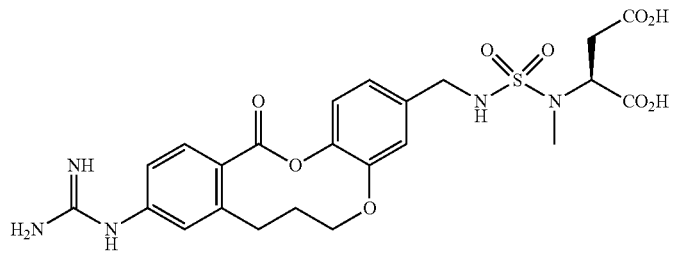
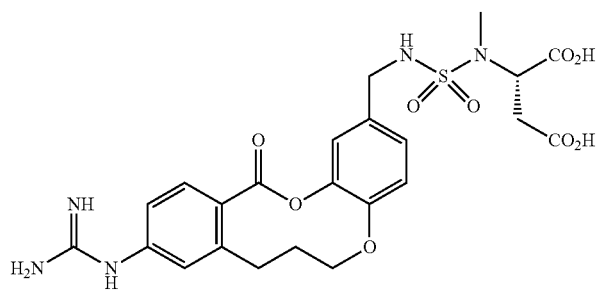
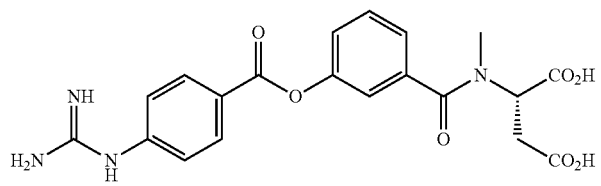
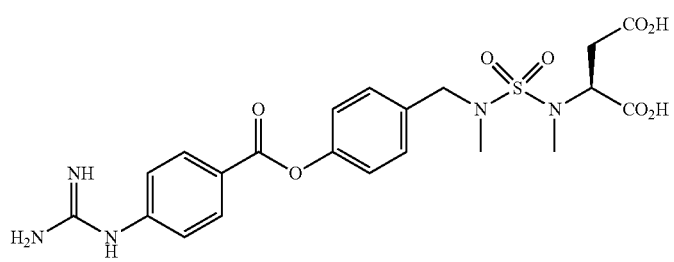
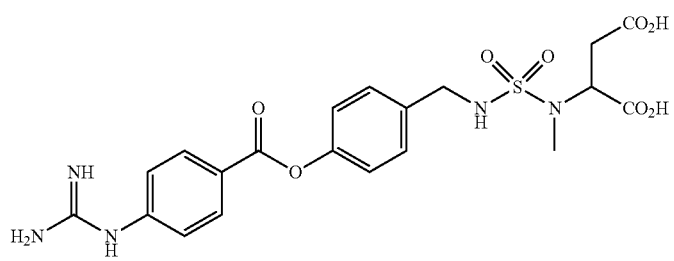
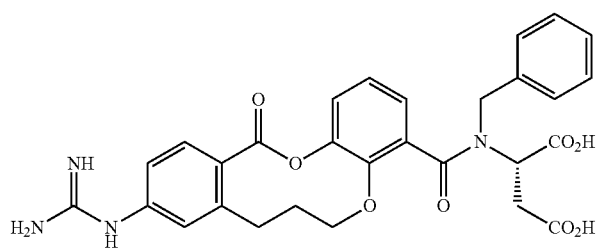

In one embodiment of the present invention, $A^1$ and $A^2$ each independently represent an inhibitor residue selected from the following group.
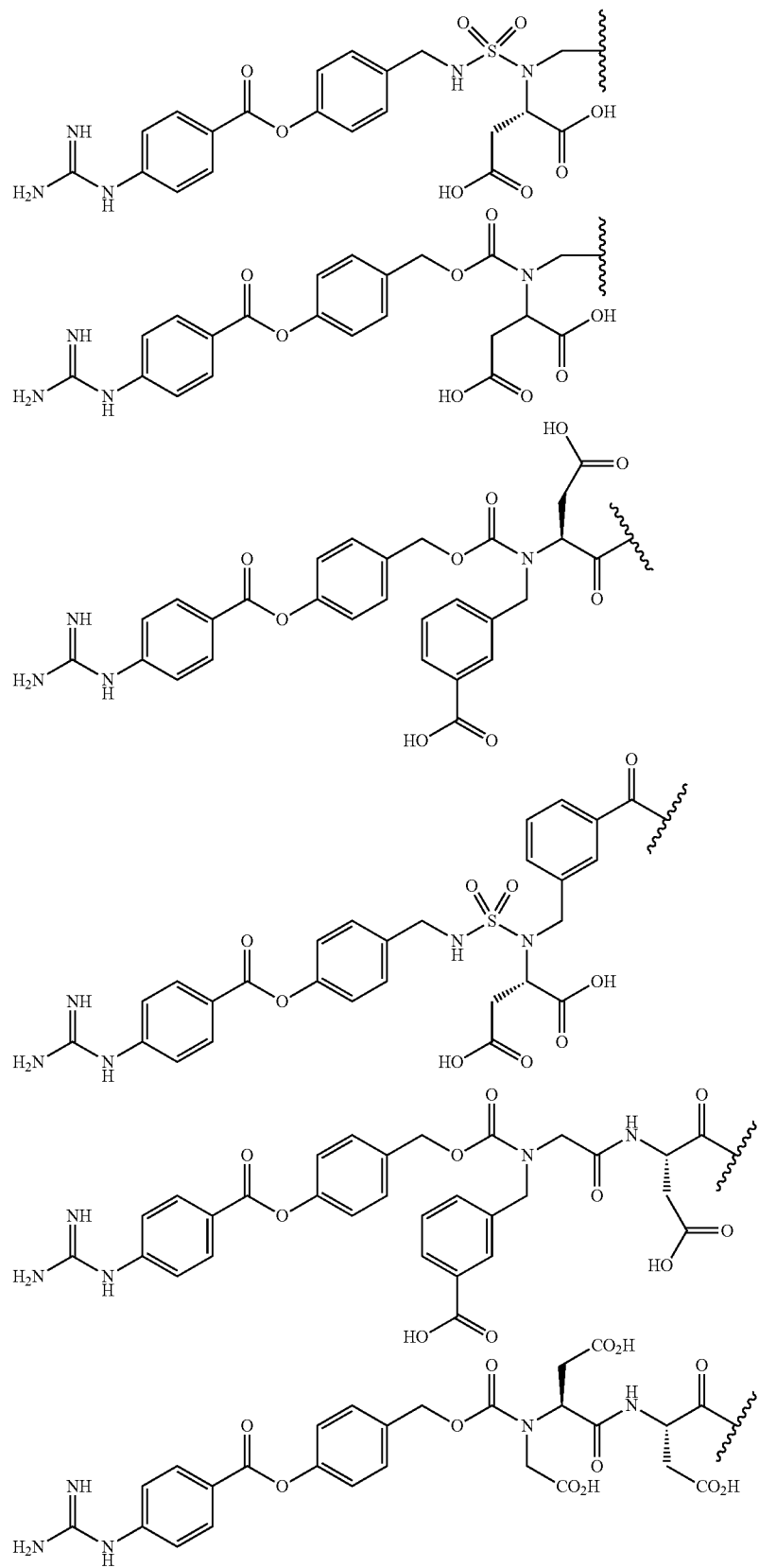

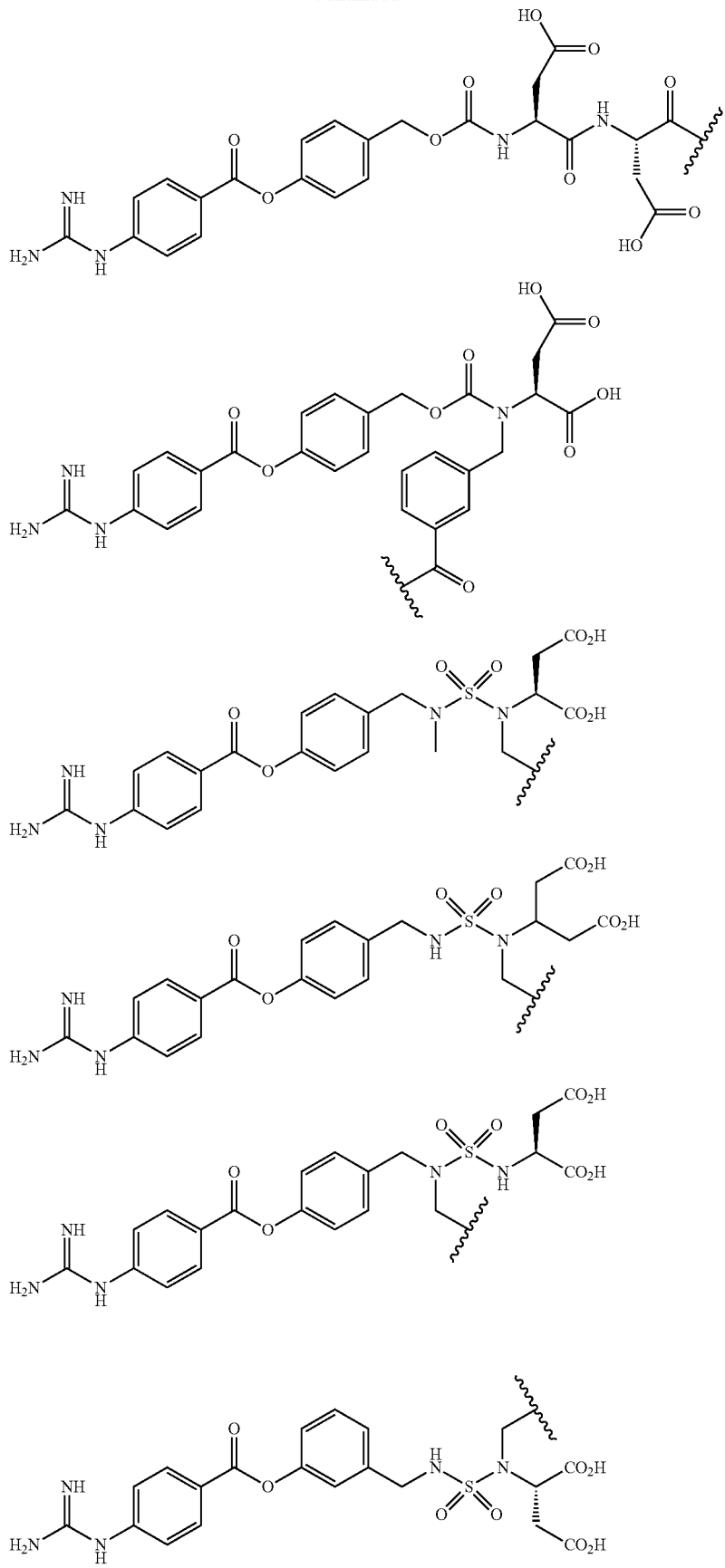

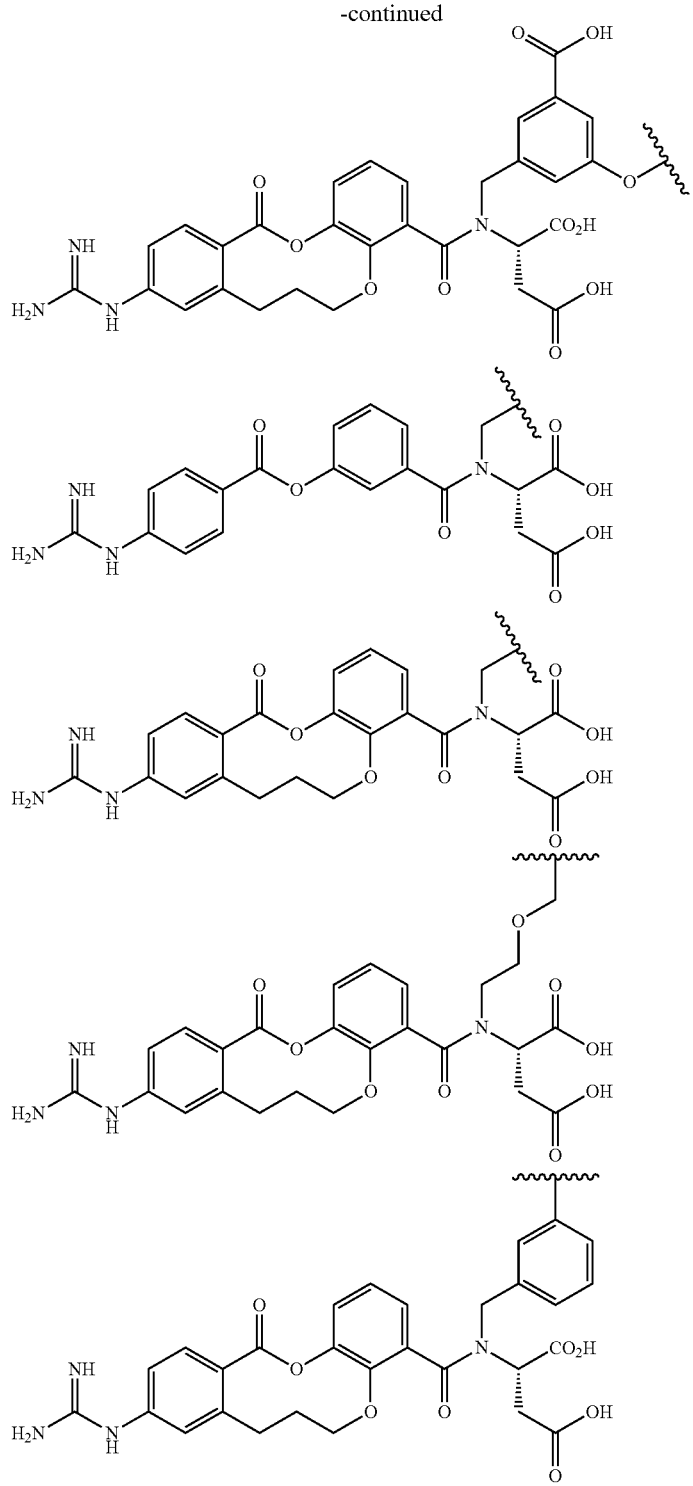

[wherein the symbol 〜〜〜 represents the point of attachment to Z.]

Example Compounds

In one embodiment of the present invention, the Compound (I) or a pharmaceutically acceptable salt thereof represents a compound selected from the group consisting of (2S,2'S)-tetra-tert-butyl 2,2'-((oxybis(ethane-2,1-diyl))bis((N-((benzyloxy)carbonyl)-N-(4-((4-(2,3-bis(tert-butoxycarbonyl)guanidino)benzoyl)oxy)benzyl)sulfamoyl)azanediyl))disuccinate;

(2S,2'S)-2,2'-((oxybis(ethane-2,1-diyl))bis((N-(4-((4-guanidinobenzoyl)oxy)benzyl)sulfamoyl)azanediyl))disuccinic acid;

(2S,13S)-tetra-tert-butyl 3,12-bis(N-((benzyloxy)carbonyl)-N-(4-((4-(2,3-bis(tert-butoxycarbonyl)guanidino)benzoyl)oxy)benzyl)sulfamoyl)-6,9-dioxa-3,12-diazatetradecane-1,2,13,14-tetracarboxylate;

(2S,13S)-3,12-bis(N-(4-((4-guanidinobenzoyl)oxy)benzyl)sulfamoyl)-6,9-dioxa-3,12-diazatetradecane-1,2,13,14-tetracarboxylic acid;

(2S,16S)-tetra-tert-butyl 3,15-bis(N-((benzyloxy)carbonyl)-N-(4-((4-(2,3-bis(tert-butoxycarbonyl)guanidino)benzoyl)oxy)benzyl)sulfamoyl)-6,9,12-trioxa-3,15-diazaheptadecane-1,2,16,17-tetracarboxylate;

(2S,16S)-3,15-bis(N-(4-((4-guanidinobenzoyl)oxy)benzyl)sulfamoyl)-6,9,12-trioxa-3,15-diazaheptadecane-1,2,16,17-tetracarboxylic acid;

(2S,19S)-tetra-tert-butyl 3,18-bis(N-((benzyloxy)carbonyl)-N-(4-((4-(2,3-bis(tert-butoxycarbonyl)guanidino)benzoyl)oxy)benzyl)sulfamoyl)-6,9,12,15-tetraoxa-3,18-diazaicosane-1,2,19,20-tetracarboxylate;

(2S,19S)-3,18-bis(N-(4-((4-guanidinobenzoyl)oxy)benzyl)sulfamoyl)-6,9,12,15-tetraoxa-3,18-diazaicosane-1,2,19,20-tetracarboxylic acid;

(2S,22S)-tetra-tert-butyl 3,21-bis(N-((benzyloxy)carbonyl)-N-(4-((4-(2,3-bis(tert-butoxycarbonyl)guanidino)benzoyl)oxy)benzyl)sulfamoyl)-6,9,12,15,18-pentaoxa-3,21-diazatricosane-1,2,22,23-tetracarboxylate;

(2S,22S)-3,21-bis(N-(4-((4-guanidinobenzoyl)oxy)benzyl)sulfamoyl)-6,9,12,15,18-pentaoxa-3,21-diazatricosane-1,2,22,23-tetracarboxylic acid;

(2S,25S)-tetra-tert-butyl 3,24-bis(N-((benzyloxy)carbonyl)-N-(4-((4-(2,3-bis(tert-butoxycarbonyl)guanidino)benzoyl)oxy)benzyl)sulfamoyl)-6,9,12,15,18,21-hexaoxa-3,24-diazahexacosane-1,2,25,26-tetracarboxylate;

(2S,25S)-3,24-bis(N-(4-((4-guanidinobenzoyl)oxy)benzyl)sulfamoyl)-6,9,12,15,18,21-hexaoxa-3,24-diazahexacosane-1,2,25,26-tetracarboxylic acid;

(2S,2'S)-tetra-tert-butyl 2,2'-(propane-1,3-diylbis((N-((benzyloxy)carbonyl)-N-(4-((4-(2,3-bis(tert-butoxycarbonyl)guanidino)benzoyl)oxy)benzyl)sulfamoyl)azanediyl))disuccinate;

(2S,2'S)-2,2'-(propane-1,3-diylbis((N-(4-((4-guanidinobenzoyl)oxy)benzyl)sulfamoyl)azanediyl))disuccinic acid;

(2S,2'S)-tetra-tert-butyl 2,2'-(butane-1,4-diylbis((N-(benzyloxy)carbonyl)-N-(4-((4-(2,3-bis(tert-butoxycarbonyl)guanidino)benzoyl)oxy)benzyl)sulfamoyl)azanediyl))disuccinate;

(2S,2'S)-2,2'-(butane-1,4-diyl bis((N-(4-((4-guanidinobenzoyl)oxy)benzyl)sulfamoyl)azanediyl))disuccinic acid;

(2S,2'S)-tetra-tert-butyl 2,2'-(pentane-1,5-diylbis((N-((benzyloxy)carbonyl)-N-(4-((4-(2,3-bis(tert-butoxycarbonyl)guanidino)benzoyl)oxy)benzyl)sulfamoyl)azanediyl))disuccinate; guanidinobenzoyl)oxy)benzyl)sulfamoyl)azanediyl))disuccinic acid;

tera-tert-butyl 3,18-bis(((4-((4-(2,3-his (tert-butoxycarbonyl)guanidinobenzoyl)oxy)benzyl)oxy)carbonyl)-6,9,12,15-tetraoxa-3,13-diazaicosane-1,2,19,20-tetracarboxylate;

3,18-bis(((4-((4-guanidinobenzoyl)oxy)benzyl)oxy)carbonyl)-6,9,12,15-tetraoxa-3,18-diazaicosane-1,2,19,20-tetracarboxylic acid;

tetra-tert-butyl 2,2'-(1,20-bis(4-((4-(2,3-bis(tert-butoxycarbonyl)guanidino)benzoyl)oxy)phenyl)-3,13-dioxo-2,19-dioxa-4,17-diazaicosane-4,17-diyl)disuccinate;

2,2'-(1,20-bis(4-((4-guanidinobenzoyl)oxyphenyl)-3,18-dioxo-2,19-dioxa-4,17-diazaicosane-4,17-diyl)disuccinic acid;

(3S,6S,25S,28S)-di-tert-butyl 3,28-bis(((4-((4-(2,3-bis(tert-butoxycarbonyl)guanidino)benzoyl)oxy)benzyl)oxycarbonyl)amino)-6,25-bis(2-(tert-butoxy)-2-oxoethyl)-4,7,24,27-tetraoxo-11,14,17,20-tetraoxa-5,8,23,26-tetraazatriacontane-1,30-dioate;

(3S,6S,25S,28S)-6,25-bis(carboxymethyl)-3,28-bis((((4-((4-guanidinobenzoyl)oxy)benzyl)oxy)carbonyl)amino)-4,7,24,27-tetraoxo-11,14,17,20-tetraoxa-5,8,23,26-tetraazatriacontane-1,30-dioic acid;

(3S,6S,23S,26S)-di-tert-butyl 3,26-bis((((4-((4-(2,3-bis(tert-butoxycarbonyl)guanidino)benzoyl)oxy)benzyl)oxy)carbonyl)amino)-6,23-bis(2-(tert-butoxy)-2-oxoethyl)-4,7,22,25-tetraoxo-5,8,21,24-tetraazaoctacosane-1,28-dioate;

(3S,6S,23S,26S)-6,23-bis(carboxymethyl)-3,26-bis((((4-((4-guanidinobenzoyl)oxy)benzyl)oxy)carbonyl)amino)-4,7,22,25-tetraoxo-5,8,21,24-tetraazaoctacosane-1,28-dioic acid;

(3S,22S)-di-tert-butyl 3,22-bis(2-(((((4-((4-(2,3-bis(tert-butoxycarbonyl)guanidino)benzoyl)oxy)benzyl)oxy)carbonyl)(3-(tert-butoxycarbonyl)benzyl)amino)acetamido)-4,21-dioxo-8,11,14,17-tetraoxa-5,20-diazatetracosane-1,24-dioate;

(3S,22S)-3,22-bis(2-((3-carboxybenzyl)(((4-((4-guanidinobenzoyl)oxy)benzyl)oxy)carbonyl)amino)acetamido)-4,21-dioxo-8,11,14,17-tetraoxa-5,20-diazatetracosane-1,24-dioic acid;

(4S,7S,26S,29S)-di-tert-butyl 3,30-bis(((4-((4-(2,3-bis(tert-butoxycarbonyl)guanidino)benzoyl)oxy)benzyl)oxy)carbonyl)-4,7,26,29-tetrakis(2-(tert-butoxy)-2-oxoethyl)-5,8,25,28-tetraoxo-12,15,18,21-tetraoxa-3,6,9,24,27,30-hexaazadotriacontane-1,32-dioate;

(4S,7S,26S,29S)-4,7,26,29-tetrakis(carboxymethyl)-3,30-bis(((4-((4-guanidinobenzoyl)oxy)benzyl)oxy)carbonyl)-5,8,25,28-tetraoxo-12,15,18,21-tetraoxa-3,6,9,24,27,30-hexaazadotriacontane-1,32-dioic acid;

(3S,22S)-di-tert-butyl 3,22-bis((((4-((4-(2,3-bis(tert-butoxycarbonyl)guanidino)benzoyl)oxy)benzyl)oxy)carbonyl)(3-(tert-butoxycarbonyl)benzyl)amino)-4,21-dioxo-8,11,14,17-tetraoxa-5,20-diazatetracosane-1,24-dioate;

(3S,22S)-3,22-bis((3-carboxybenzyl)(((4-((4-guanidinobenzoyl)oxy)benzyl)oxy)carbonyl)amino)-4,21-dioxo-8,11,14,17-tetraoxa-5,20-diazatetracosane-1,24-dioic acid;

(2S,2'S)-tetra-tert-butyl 2,2'-((((5,8,11,14-tetraoxa-2,17-diazaoctadecane-1,18-dioyl)bis(3,1-phenylene))bis(methylene))bis(((4-((4-(2,3-bis(tert-butoxycarbonyl)guanidino)benzoyloxy)benzyl)oxy)carbonyl)azanediyl))disuccinate;

(2S,2'S)-2,2'-((((5,8,11,14-tetraoxa-2,17-diazaoctadecane-1,18-dioyl)bis(3,1-phenylene))bis(methylene))bis((((4-((4-guanidinobenzoyl)oxy)benzyl)oxy)carbonyl)azanediyl))disuccinic acid;

(2S,2'S)-tetra-tert-butyl 2,2'-((((5,8,11,14-tetraoxa-2,17-diazaoctadecane-1,18-diyl)bis(3,1-phenylene))bis(methylene))bis((N-((benzyloxy)carbonyl)-N-(4-((4-(2,3-bis(tert-butoxycarbonyl)guanidino)benzoyl)oxy)benzyl)sulfamoyl)azanediyl))disuccinate;

(2S,2'S)-2,2'-((((5,8,11,14-tetraoxa-2,17-diazaoctadecane-1,18-dioyl)bis(3,1-phenylene))bis(methylene))bis((N-(4-((4-guanidinobenzoyl)oxy)benzyl)sulfamoyl-azanediyl))disuccinic acid;

tetra-tert-butyl 3,12-bis(10-(2,3-bis(tert-butoxycarbonyl)guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylate;

3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid;

(2S,13S)-tetra-tert-butyl 3,12-bis(_0-(2,3-bis(tert-butoxycarbonyl)guanidino)-13-oxo-6,7,8,13-tetrahydrodibenzo

[b,f]1,4]dioxecin-4-carbonyl-6,9-dioxa-3,12-diazatetradecane-1,2,13,14-tetracarboxylate;
(2S,13S)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid;
(2R,13R)-tetra-tert-butyl 3,12-bis(10-(2,3-bis(tert-butoxycarbonyl; guanidino)-13-oxo-6,7,8,13-tetrahydrodibenzo[b,f][1,4]dioxecin-4-carbonyl)-6,9-dioxa-3,12-diazatetradecane-1,2,13,14-tetracarboxylate;
(2R,13R)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid;
(2S,13S)-3,12-bis(N-(4-((4-guanidinobenzoyl)oxy)benzyl)-N-methylsulfamoyl)-6,9-dioxa-3,12-diazatetradecane-1,2,13,14-tetracarboxylic acid;
tetrabenzyl 3,3' ((ethane-1,2-diylbis(oxy))bis(ethane-2,1-diyl))bis((N-((benzyloxy)carbonyl)-N-(4-((4-(2,3-bis(tert-butoxycarbonyl)guanidino)benzoyl)oxy)benzyl)sulfamoyl)azanediyl))dipentanedioate;
3,3'-(((ethane-1,2-diylbis(oxy))bis(ethane-2,1-diyl))bis((N-(4-((4-(2,3-bis(tert-butoxycarbonyl)guanidino)benzoyl)oxy)benzyl)sulfamoyl)azanediyl))dipentanedioic acid;
3,3'-(((ethane-1,2-diylbis(oxy))bis(ethane-2,1-diyl))bis((N-(4-((4-guanidinobenzoyl)oxy)benzyl)sulfamoyl)azanediyl))dipentanedioic acid;
(2S,2'S)-2,2'-((1,12-bis(4-((4-guanidinobenzoyl)oxy)phenyl)-5,8-dioxa-2,11-diazadodecanedisulfonyl)bis(azanediyl))disuccinic acid;
(2S,13S)-tetra-tert-butyl 3,12-bis(N-((benzyloxy)carbonyl)-N-(3-(((4-(2,3-bis(tert-butoxycarbonyl)guanidino)benzoyl)oxy))benzyl)sulfamoyl)-6,9-dioxa-3,12-diazatetradecane-1,2,13,14-tetracarboxylate;
(2S,13S)-3,12-bis(N-(3-((4-guanidinobenzoyl)oxy)benzyl)sulfamoyl)-6,9-dioxa-3,12-diazatetradecane-1,2,13,14-tetracarboxylic acid;
(2S,2'S)-tetra-tert-butyl 2,2'-((oxybis(ethane-2,1-diyl))bis((10-(2,3-bis(tert-butoxycarbonyl)guanidino)-13-oxo-6,7,8,13-tetrahydrodibenzo[b,f][1,4]dioxecin-4-carbonyl)azanediyl))disuccinate;
(2S,2'S)-2,2'-((oxybis(ethane-2,1-diyl))bis((10-guanidino-13-oxo-6,7,8,13-tetrahydrodibenzo[b,f][1,4]dioxecin-4-carbonyl)azanediyl))disuccinic acid;
(2S,16S)-tetra-tert-butyl 3,15-bis(10-(2,3-bis(tert-butoxycarbonyl)guanidino)-13-oxo-6,7,8,13-tetrahydrodibenzo[b,f][1,4]dioxecin-4-carbonyl)-6,9,12-trioxa-3,15-diazaheptadecane-1,2,16,17-tetracarboxylate;
(2S,16S)-3,15-bis(10-guanidino-13-oxo-6,7,8,13-tetrahydrodibenzo[b,f][1,4]dioxecin-4-carbonyl)-6,9,12-trioxa-3,15-diazaheptadecane-1,2,16,17-tetracarboxylic acid;
(2S,2'S)-tetrabenzyl 2,2'-(([1,1'-biphenyl]-3,3'-diylbis(methylene))bis((10-(2,3-bis(tert-butoxycarbonyl)guanidino)-13-oxo-6,7,8,13-tetrahydrodibenzo[b,f][1,4]dioxecin-4-carbonyl)azanediyl))disuccinate;
(2S,2'S)-tetrabenzyl 2,2'-(([1,1'-biphenyl]-3,3'-diylbis(methylene))bis((10-guanidino-13-oxo-6,7,8,13-tetrahydrodibenzo[b,f][1,4]dioxecin-4-carbonyl)azanediyl))disuccinate;
(2S,2'S)-2,2'-(([1,1'-biphenyl]-3,3'-diylbis(methylene))bis((10-guanidino-13-oxo-6,7,8,13-tetrahydrodibenzo[b,f][1,4]dioxecin-4-carbonyl)azanediyl))disuccinic acid;
(2S,2'S)-tetra-tert-butyl 2,2'-(((((oxybis(ethane-2,1-diyl))bis(oxy))bis(3-((2-(trimethylsilyl)ethoxy)carbonyl)-5,1-phenylene))bis(methylene))bis((10-(2,3-bis(tert-butoxycarbonyl)guanidino)-13-oxo-6,7,8,13-tetrahydrodibenzo[b,f][1,4]dioxecin-4-carbonyl)azanediyl))disuccinate;
(S)-5,5'-((oxybis(ethane-2,1-diyl))bis(oxy))bis(3-((10-(2,3-bis(tert-butoxycarbonyl)guanidino)-N—((S)-1,4-di-tert-butoxy-1,4-dioxobutan-2-yl)-13-oxo-6,7,8,13-tetrahydrodibenzo[b,f][1,4]dioxecin-4-carboxamido)methyl)benzoic acid);
(2S,2'S)-2,2'-(((((oxybis(ethane-2,1-diyl))bis(oxy))bis(3-carboxy-5,1-phenylene))bis(methylene))bis((10-guanidino-13-oxo-6,7,8,13-tetrahydrodibenzo[b,f][1,4]dioxecin-4-carbonyl)azanediyl))disuccinic acid; and
(2S,2'S)-2,2'-((oxybis(ethane-2,1-diyl))bis((3-((4-guanidinobenzoyl)oxy)benzoyl)azanediyl))disuccinic acid or a pharmaceutically acceptable salt thereof.

In one embodiment of the present invention, the Compound (I) or a pharmaceutically acceptable salt thereof represents a compound selected from the group consisting of
(2S,2'S)-2,2'-((oxybis(ethane-2,1-diyl))bis((N-(4-((4-guanidinobenzoyl)oxy)benzyl)sulfamoyl)azanediyl))disuccinic acid;
(2S,13S)-3,12-bis(N-(4-((4-guanidinobenzoyl)oxy)benzyl)sulfamoyl)-6,9-dioxa-3,12-diazatetradecane-1,2,13,14-tetracarboxylic acid;
(2S,16S)-3,15-bis(N-(4-((4-guanidinobenzoyl)oxy)benzyl)sulfamoyl)-6,9,12-trioxa-3,15-diazaheptadecane-1,2,16,17-tetracarboxylic acid;
(2S,19S)-3,18-bis(N-(4-((4-guanidinobenzoyl)oxy)benzyl)sulfamoyl)-6,9,12,15-tetraoxa-3,18-diazaicosane-1,2,19,20-tetracarboxylic acid;
(2S,22S)-3,21-bis(N-(4-((4-guanidinobenzoyl)oxy)benzyl)sulfamoyl)-6,9,12,15,19-pentaoxa-3,21-diazatricosane-1,2,22,23-tetracarboxylic acid;
(2S,25S)-3,24-bis(N-(4-((4-guanidinobenzoyl)oxy)benzyl)sulfamoyl)-6,9,12,15,18,21-hexaoxa-3,24-diazahexacosane-1,2,25,26-tetracarboxylic acid;
(2S,2'S)-2,2'-(propane-1,3-diylbis((N-(4-((4-guanidinobenzoyl)oxy)benzyl)sulfamoyl)azanediyl))disuccinic acid;
(2S,2'S)-2,2'-(butane-1,4-diylbis((N-(4-((4-guanidinobenzoyl)oxy)benzyl)sulfamoyl)azanediyl))disuccinic acid;
(2S,2'S)-2,2'-(pentane-1,5-diylbis((N-(4-((4-guanidinobenzoyl)oxy)benzyl)sulfamoyl)azanediyl))disuccinic acid:
3,18-bis(((4-((4-guanidinobenzoyl)oxy)benzyl)oxy)carbonyl)-6,9,12,15-tetraoxa-3,18-diazaicosane-1,2,19,20-tetracarboxylic acid;
2,2'-(1,20-bis(4-((4-guanidinobenzoyl)oxy)phenyl)-3,18-dioxo-2,19-dioxa-4,17-diazaicosane-4,17-diyl)disuccinic acid;
(3S,6S,25S,28S)-6,25-bis(carboxymethyl)-3,28-bis((((4-((4-guanidinobenzoyl)oxy)benzyl)oxy)carbonyl)amino)-4,7,24,27-tetraoxo-11,14,17,20-tetraoxa-5,8,23,26-tetraazatriacontane-1,30-dioic acid;
(3S,6S,23S,26S)-6,23-bis(carboxymethyl)-3,26-bis((((4-((4-guanidinobenzoyl)oxy)benzyl)oxy)carbonyl)amino)-4,7,22,25-tetraoxo-5,8,21,24-tetraazaoctacosane-1,28-dioic acid;
(3S,22S)-3,22-bis(2-((3-carboxybenzyl)(((4-((4-guanidinobenzoyl)oxy)benzyl)oxy)carbonyl)amino)acetamido)-4,21-dioxo-8,11,14,17-tetraoxa-5,20-diazatetracosane-1,24-dioic acid;
(4S,7S,26S,29S)-4,7,26,29-tetrakis(carboxymethyl)-3,30-bis(((4-((4-guanidinobenzoyl)oxy)benzyl)oxy)carbonyl)-5,8,25,28-tetraoxo-12,15,18,21-tetraoxa-3,6,9,24,27,30-hexaazadotriacontane-1,32-dioic acid;
(3S,22S)-3,22-bis((3-carboxybenzyl) (((4-((4-guanidinobenzoyl)oxy)benzyl)oxy)carbonyl)amino)-4,21-dioxo-8,11,14,17-tetraoxa-5,20-diazatetracosane-1,24-dioic acid;
(2,2'S)-2,2'-(((((5,8,11,14-tetraoxa-2,17-diazaoctadecane-1,18-dioyl)bis(3,1-phenylene))bis(methylene))bis((((4-((4-guanidinobenzoyl)oxy)benzyl)oxy)carbonyl)azanediyl))disuccinic acid;

(2S,2'S)-2,2'-(((((5,8,11,14-tetraoxa-2,17-diazaoctadecane-1,18-dioyl)bis(3,1-phenylene))bis(methylene))bis((N-(4-((4-guanidinobenzoyl)oxy)benzyl)sulfamoyl)azanediyl) disuccinic acid;

3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid;

(2S,13S)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid;

(2R,13R)-3,12-bis 10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid;

(2S,13S)-3,12-bis(N-(4-((4-guanidinobenzoyl)oxy)benzyl)-N-methylsulfamoyl)-6,9-dioxa-3,12-diazatetradecane-1,2,13,14-tetracarboxylic acid;

3,3' ((((ethane-1,2-diylbis(oxy))bis((ethane-2,1-diyl))bis((N-(4-((4-guanidinobenzoyl)oxy)benzyl)sulfamoyl) azanediyl))dipentanedioic acid;

(2S,2'S)-2,2'-((1,12-bis(4-((4-guanidinobenzoyl)oxy)phenyl)-5,8-dioxa-2,11-diazadodecanedisulfonyl)bis (azanediyl))disuccinic acid;

(2S,13S)-3,12-bis(N-(3-((4-guanidinobenzoyl oxy)benzyl) sulfamoyl)-6,9-dioxa-3,12-diazatetradecane-1,2,13,14-tetracarboxylic acid;

(2S,2'S)-2,2'-((oxybis(ethane-2,1-diyl)bis(10-guanidino-13-oxo-6,7,8,13-tetrahydrodibenzo[b,f][1,4]dioxecin-4-carbonyl)azanediyl))succinic acid;

(2S,16S)-3,15-bis(10-guanidino-13-oxo-6,7,8,13-tetrahydrodibenzo[b,f][1,4]dioxecin-4-carbonyl)-6,9,12-trioxa-3,15-diazaheptadecane-1,2,16,17-tetracarboxylic acid;

(2S,2'S)-2,2'-(i[1,1'-biphenyl]-3,3'-diylbis(methylene))bis ((10-guanidino-13-oxo-6,7,8,13-tetrahydrodibenzo[b,f][1,4]dioxecin-4-carbonyl)azanediyl))disuccinic acid;

(2S,2'S)-2,2'-(((((oxybis(ethane-2,1-diyl))bis(oxy))bis(3-carboxy-5,1-phenylene))bis(methylene))bis((10-guanidino-13-oxo-6,7,8,13-tetrahydrodibenzo[b,f][1,4]dioxecin-4-carbonyl)azanediyl))disuccinic acid; and (2S,2'S)-2,2'-((oxybis(ethane-2,1-diyl))bis((3-((4-guanidinobenzoyl)oxy)benzoyl)azanediyl)disuccinic acid or a pharmaceutically acceptable salt thereof.

In one embodiment of the present invention, the Compound (I) or a pharmaceutically acceptable salt thereof represents a compound selected from the group consisting of (2S,2'S)-2,2'-((oxybis(ethane-2,1-diyl))bis((N-(4-((4-guanidinobenzoyl)oxy)benzyl)sulfamoyl)azanediyl))disuccinic acid;

(2S,13S)-3,12-bis(N-(4-((4-guanidinobenzoyl)oxy)benzyl) sulfamoyl)-6,9-dioxa-3,12-diazatetradecane-1,2,13,14-tetracarboxylic acid;

(2S,2'S)-2,2'-(butane-1,4-diylbis((N-(4-((4-guanidinobenzoyl)oxy)benzyl)sulfamoyl)azanediyl))disuccinic acid;

(2S,13S)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid;

(2S,2'S)-2,2'-((oxybis(ethane-2,1-diyl))bis((10-guanidino-13-oxo-6,7,8,13-tetrahydrodibenzo[b,f][1,4]dioxecin-4-carbonyl)azanediyl))disuccinic acid;

(2S,16S)-3,15-bis(10-guanidino-13-oxo-6,7,8,13-tetrahydrodibenzo[b,f][1,4]dioxecin-4-carbonyl)-6,9,12-trioxa-3,15-diazaheptadecane-1,2,16,17-tetracarboxylic acid;

(2S,2'S)-2,2'-(([1,1'-biphenyl]-3,3'-diylbis(methylene))bis ((10-guanidino-13-oxo-6,7,8,13-tetrahydrodibenzo[b,f][1,4]dioxecin-4-carbonyl)azanediyl))disuccinic acid; and (2S,2'S)-2,2'-(((((oxybis(ethane-2,1-diyl))bis(oxy))bis(3-carboxy-5,1-phenylene))bis(methylene))bis((10-guanidino-13-oxo-6,7,8,13-tetrahydrodibenzo[b,f][1,4]dioxecin-4-carbonyl)azanediyl))disuccinic acid or a pharmaceutically acceptable salt thereof.

Compound (II)

The present invention provides a compound represented by the following general formula (II)

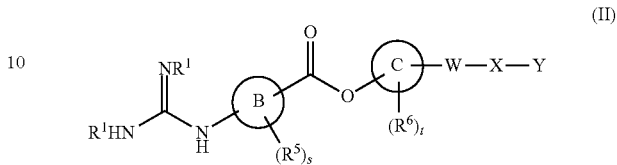

(II)

[wherein:

ring B and ring C each independently represent an aryl group or a heteroaryl group;

$R^1$ each independently represents a hydrogen atom or a —COO—($C_1$-$C_4$ alkyl group);

W represents a single bond or a $C_1$-$C_4$ alkylene group;

X represents —C(=O)—, —O—C(=O)—, or —NG$^Z$-SO$_2$—;

G represents a hydrogen atom, a $C_1$-$C_4$ alkyl group, or —COOR$^2$;

$R^2$ represents a $C_1$-$C_4$ alkyl, group optionally substituted with 1 to 5 aryl group(s);

Y represents —NG$^2$G$^4$, —NG$^2$-L$^1$-COOH, —NG$^2$-L$^1$-C(=O)—NH$_2$, —NG$^2$-L$^1$-C(=O)—NG$^3$-L$^2$-COOH, —NG$^2$-L$^1$-C(=O)—NG$^3$-L$^2$-C(=O)—NG$^3$-L$^2$-COOH, —NG$^2$-L$^{11}$-C(=O)—NG$^3$-L$^2$-C(=O)—NH$_2$, —NG$^2$-L$^3$-OH, or —NG$^2$-(CH$_2$—CH$_2$—O)$_q$—CH$_2$—CH$_2$—COOH;

q represents an integer of 1 to 6;

$G^2$ and $G^3$ each independently represent a hydrogen atom, or a $C_1$-$C_6$ alkyl group optionally substituted with 1 to 5 substituent(s) independently selected from the group consisting of a phenyl group optionally substituted with 1 to 5 —COOR$^3$ group(s) and a —COOR$^3$ group;

$G^4$ represents a hydrogen atom, a $C_1$-$C_4$ alkyl group, or a $C_1$-$C_4$ alkoxy-$C_1$-$C_4$ alkyl group;

$R^3$ each independently represents a hydrogen atom, or a $C_1$—C alkyl group optionally substituted with 1 to 5 aryl group(s);

$L^1$ and $L^2$ each independently represent a $C_1$-$C_6$ alkylene group optionally substituted with 1 to 5 $C_1$-$C_6$ alkyl group(s) optionally substituted with 1 no 5 —COOR$^4$ group(s), a $C_1$-$C_6$ alkylene croup substituted with a $C_7$-$C_{12}$ aralkyl group optionally substituted with 1 to 5 substituent (s) independently selected from the group consisting of a hydroxy group and a carboxy group, a $C_1$-$C_4$ alkylene-phenylene group, or a phenylene-$C_1$-$C_4$ alkylene group;

$L^3$ represents a $C_1$-$C_4$ alkylene-phenylene group wherein the phenylene moiety is optionally substituted with 1 to 3 —COOR$^4$ group(s);

$R^4$ each independently represents a hydrogen atom, or a $C_1$-$C_4$ alkyl group optionally substituted with 1 to 5 substituent(s) independently selected from the group consisting of an aryl group and a trimethylsilyl group;

$R^5$ and $R^6$ each independently represent a hydrogen atom, a halogen atom, a $C_1$-$C_4$ alkyl group, a $C_1$-$C_4$ alkoxy group, a carboxy group, or —C(=O)—NG$^2$G$^4$;

s and t each independently represent an integer of 1 to 4;

two or more RE and/or two or more $R^6$ may be the same or different with each other]

or a pharmaceutically acceptable salt thereof.

In one embodiment, the aryl group in ring B and ring C each independently represent a $C_6$ to $C_{12}$ aryl group, preferably a phenyl group or a naphthyl group, more preferably a phenyl group.

In one embodiment, the heteroaryl group in ring B and ring C each independently represent a 5 to 11 membered monocyclic or bicyclic aromatic heterocyclic group comprising 1 to 4 hetero atom(s) selected from an oxygen atom, a sulfur atom, and a nitrogen atom other than carbon atom(s), preferably a pyrrolyl group, a furyl group, and a thienyl group, more preferably a thienyl group.

In one embodiment, ring B and ring C each independently represent an aryl group, preferably each represent a phenyl group.

In one embodiment, ring B and ring C each independently represent a phenyl group, a naphthyl group, or a thienyl group, preferably ring B and ring C each represent a phenyl group.

In one embodiment, the $C_1$-$C_4$ alkyl group of "—COO—($C_1$-$C_4$ alkyl group)" in $R^1$ represents a methyl group, an ethyl group, a n-propyl group, an isopropyl group, a n-butyl group, or a tert-butyl group.

In one embodiment, $R^1$ represents a hydrogen atom or a tert-butoxycarbonyl group, preferably a hydrogen atom.

In one embodiment, W represents a $C_1$-$C_4$ alkylene group, for example a methylene group, an ethylene group, a trimethylene group, or a tetramethylene group, preferably a $C_1$-$C_2$ alkylene group, for example a methylene group. In another embodiment, W represents a single bond or a $C_5$-$C_2$ alkylene group, preferably a single bond or a methylene group.

In one embodiment, X represents —O—C(=O)— or —NG$^Z$-SO$_2$—, preferably —NG$^Z$-SO$_2$—. In another embodiment, X represents —C(=O)— or —NG$^Z$-SO$_2$—, preferably —C(=O)—.

In one embodiment, the "$C_1$-$C_4$ alkyl group" in G represents a methyl group, an ethyl group, a n-propyl group, an isopropyl group, a n-butyl group, or a tert-butyl group, preferably a methyl group or an ethyl group.

In one embodiment, $R^2$ of "—COOR$^2$ group" in G represents a $C_1$-$C_4$ alkyl group optionally substituted with 1 to 3 phenyl group(s), for example a methyl group, an ethyl group, a n-propyl group, an isopropyl group, a n-butyl group, a tert-butyl group, or a benzyl group, preferably a $C_1$-$C_4$ alkyl group optionally substituted with one phenyl group, more preferably a tert-butyl group or a benzyl group.

In one embodiment, G represents a hydrogen atom, a methyl group, a tert-butoxycarbonyl group, or a benzyloxycarbonyl group, preferably a hydrogen atom, a methyl group, or a benzyloxycarbonyl group, more preferably a hydrogen atom or a methyl group.

In one embodiment, Y represents —NG$^2$G$^4$, —NG$^2$-L$^1$-COOH, —NG$^2$-L$^1$-C(=O)—NH$_2$, —NG$^2$-L-C(=O)—NG$^3$-L$^2$, —NG$^2$-L$^1$-C(=O)—NG$^3$-L$^2$-C(=O)—NH$_2$, —NG$^2$-L$^3$-OH, or —NG$^2$-(CH$_2$—CH$_2$—O)$_q$—CH$_2$—CH$_2$—COOH, preferably —NG$^2$G$^4$, —NG$^2$-L-COOH, —NG$^2$-L$^1$-C(=C)—NH$_2$, —NG$^2$-L$^1$-C(=O)—NG$^3$-L$^2$-G$^4$, —NG$^2$-L$^1$-C(=O)—NG$^3$-L$^1$-C(=O)—NH$_2$, or —NG$^2$-L$^3$-OH, more preferably —NG$^2$G$^4$.

In another embodiment, Y represents —NG$^2$G$^4$, —NG$^2$-L$^3$-OH, or —NG$^2$-(CH$_2$—CH$_2$—O)$_q$—CH$_2$—CH$_2$—COOH.

In another embodiment, Y represents —NG$^2$G$^4$, —NG$^2$-L$^1$-C(=O)—NH$_2$, —NG$^2$-L$^1$-C(=O)—NG$^3$-L$^2$-C(=O)—NH$_2$, or —NG$^2$-(CH$_2$—CH$_2$—O)$_q$—CH$_2$—CH$_2$—COOH.

In another embodiment, Y represents —NG$^2$G$^4$, —NG$^2$-L$^1$-C(=O)—NH$_2$, or —NG$^2$-L$^1$-C(=O)—NG$^3$-L$^2$-C(O)—NH$_2$.

In one embodiment, q represents an integer of 1 to 4, preferably an integer of 1 to 3, more preferably an integer of 1 to 2.

In one embodiment, the "phenyl group optionally substituted with 1 to 5 —COOR$^3$ group(s)" in G$^2$ and G$^2$ represents preferably a phenyl group optionally substituted with 1 to 3 —COOR$^3$ group(s), more preferably a phenyl group optionally substituted with one —COOR$^3$ group, for example a 2-(COOR$^3$)-phenyl group, a 3-(COOR$^3$)-phenyl group, a 4-(COOR$^3$)-phenyl group, or the like.

In one embodiment, $R^3$ of "—COOR$^3$ group" in G$^2$ and G$^3$ each independently represents a hydrogen atom, a methyl group, an ethyl group, a n-propyl group, an isopropyl group, a n-butyl group, a tert-butyl group, or a benzyl group, preferably a hydrogen atom, a benzyl group, or a tert-butyl group, more preferably a hydrogen atom or a tert-butyl group, still more preferably a hydrogen atom.

In one embodiment, G$^2$ represents a hydrogen atom, or a $C_1$-$C_6$ alkyl group optionally substituted with 1 to 3 substituent(s) independently selected from the group consisting of a phenyl group optionally substituted with 1 to 3 —COOR$^3$ group(s) and a —COOR$^3$ group, preferably a hydrogen atom, or a $C_1$-$C_3$ alkyl group optionally substituted with 1 to 3 substituent(s) independently selected from the group consisting of a phenyl group optionally substituted with one —COOR$^3$ group and a —COOR$^3$ group, more preferably a $C_1$-$C_3$ alkyl group substituted with 1 to 3 substituent(s) independently selected from the group consisting of a phenyl group substituted with one carboxy group and a carboxy group.

In another embodiment, G$^2$ represents a hydrogen atom, or a $C_1$-$C_3$ alkyl group optionally substituted with 1 to 3 —COOR$^3$ group(s), preferably a $C_1$-$C_3$ alkyl group substituted with 1 to 3 carboxy group(s).

In one embodiment, G$^3$ represents a hydrogen atom, or a $C_1$-$C_6$ alkyl group optionally substituted with 1 to 3 substituent(s) independently selected from the group consisting of a phenyl group optionally substituted with 1 to 3 —COOR$^3$ group(s) and a —COOR$^3$ group, preferably a hydrogen atom, or a $C_1$-$C_3$ alkyl group optionally substituted with 1 to 3 substituent(s) independently selected from the group consisting of a phenyl group optionally substituted with one —COOR$^3$ group and a —COOR$^3$ group, more preferably a hydrogen atom.

In another embodiment, G$^3$ represents a hydrogen atom, or a $C_1$-$C_3$ alkyl group optionally substituted with 1 to 3 —COOR$^3$ group(s), preferably a hydrogen atom.

In one embodiment, G$^4$ represents a hydrogen atom, a $C_1$-$C_2$ alkyl group, or a $C_1$-$C_2$ alkoxy-$C_1$-$C_2$ alkyl group, preferably an ethyl group or a methoxyethyl group, more preferably methoxyethyl group.

In one embodiment, $R^4$ of "—COOR$^4$ group" in L$^1$ and L$^2$ each independently represents a hydrogen atom, a methyl group, an ethyl group, a n-propyl group, an isopropyl group, a n-butyl group, a tert-butyl group, or a benzyl group, preferably a hydrogen atom, a tert-butyl group, or a benzyl group, more preferably a hydrogen atom or a tert-butyl group, still more preferably a hydrogen atom.

In one embodiment, L$^1$ represents a $C_1$-$C_6$ alkylene group optionally substituted with 1 to 2 $C_1$-$C_6$ alkyl group(s) optionally substituted with 1 to 2 —COOR$^4$ group(s), a $C_1$-$C_4$ alkylene group substituted with a benzyl group wherein the phenyl group moiety is optionally substituted with 1 to 2 substituent(s) independently selected from the group consisting of a hydroxy group and a carboxy group, a $C_1$-$C_4$ alkylene-phenylene group, or a phenylene-$C_1$-$C_4$ alkylene group, preferably a methylene group optionally substituted with a $C_1$-$C_6$ alkyl group optionally substituted with a —COOR$^4$ group, a methylenephenylene group, or a phenylenemethylene group.

In another embodiment, L$^1$ represents a $C_1$-$C_2$ alkylene group, preferably a methylene group.

In another embodiment, L$^1$ represents a $C_1$-$C_2$ alkylene group optionally substituted with 1 to 2 $C_1$-$C_2$ alkyl group(s) optionally substituted with 1 to 2 —COOR$^4$ group(s), a $C_1$-$C_2$ alkylene-phenylene group, or a phenylene-$C_1$-$C_2$ alkylene group.

In one embodiment, L$^2$ represents a $C_1$-$C_6$ alkylene group optionally substituted with 1 to 2 $C_1$-$C_6$ alkyl group(s) optionally substituted with 1 to 2 —COOR$^4$ group(s), a $C_1$-$C_4$ alkylene group substituted with a benzyl group wherein the phenyl group moiety is optionally substituted with 1 to 2 substituent(s) independently selected from the group consisting of a hydroxy group and a carboxy group, a $C_1$-$C_4$ alkylene-phenylene group, or a phenylene-$C_1$-$C_4$ alkylene group, preferably a methylene group optionally substituted with a $C_1$-$C_6$ alkyl group optionally substituted with a —COOR$^4$ group.

In another embodiment, L$^2$ represents a $C_1$-$C_2$ alkylene group, preferably a methylene group.

In another embodiment, L$^2$ represents a $C_1$-$C_2$ alkylene group optionally substituted with 1 to 2 $C_1$-$C_2$ alkyl group(s) optionally substituted with 1 to 2 —COOR$^4$ group(s), a $C_1$-$C_2$ alkylene-phenylene group, or a phenylene-$C_1$-$C_2$ alkylene group.

In one embodiment, R$^4$ of "—COOR$^4$ group" in L$^3$ each independently represents a hydrogen atom, or a $C_1$-$C_4$ alkyl group optionally substituted with one trimethylsilyl group, preferably a hydrogen atom or a 2-(trimethylsilyl)ethyl group, more preferably a hydrogen atom.

In one embodiment, L$^3$ represents a $C_1$-$C_2$ alkylene-phenylene group wherein the phenylene moiety is optionally substituted with 1 to 2 —COOR$^4$ group(s), preferably a methylenephenylene group wherein the phenylene moiety is optionally substituted with one —COOR$^4$ group.

In one embodiment, R$^5$ and R$^6$ each independently represent a hydrogen atom, a halogen atom, a $C_1$-$C_4$ alkyl group, or a $C_1$-$C_4$ alkoxy group, preferably a hydrogen atom, a fluorine atom, a methyl group, or a methoxy group, more preferably RE and R$^6$ each represent a hydrogen atom.

In one embodiment, s and t each independently represent an integer of 1 to 3, preferably an integer of 1 to 2, more preferably each represent 1.

In one embodiment, at least one of R$^1$, R$^3$, R$^4$, and G represents a hydrogen atom. In another embodiment, at least one of R$^1$ and R$^4$ represents a hydrogen atom. In another embodiment, R$^1$, R$^3$, R$^4$, and G each represent a hydrogen atom.

In one embodiment, the Compound (II) has a structure represented by

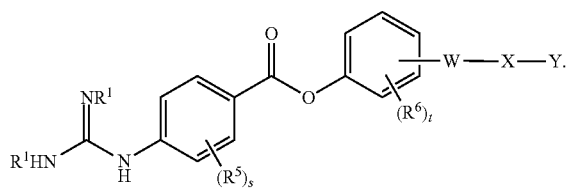

In one embodiment, the Compound (II) has a structure represented by

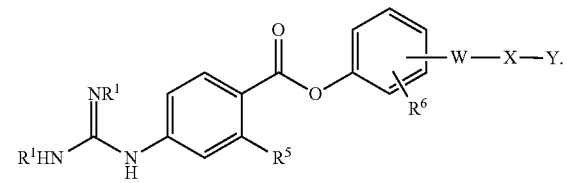

In one embodiment, the Compound (II) has a structure represented by

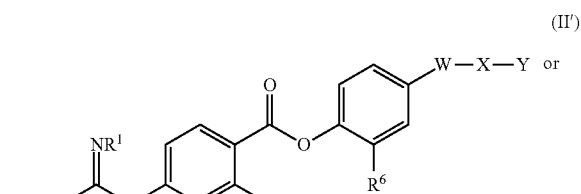

(II')

(II")

In one embodiment, the Compound (II) has a structure represented by the following general formula (II'):

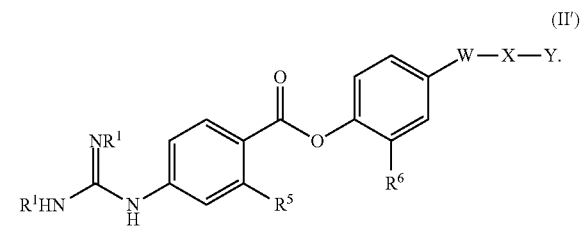

(II')

In one embodiment of the Compound (II'), a compound or a pharmaceutically acceptable salt thereof, wherein R$^1$ each independently represents a hydrogen atom or a tert-butoxycarbonyl group;

W represents a single bond or a $C_1$-$C_4$ alkylene group;

X represents —C(=O)—, —O—C(=O)—, or —NG-SO$_2$—;

G represents a hydrogen atom, a $C_1$-$C_4$ alkyl group, or —COOR$^2$;

R$^2$ represents a $C_1$-$C_4$ alkyl group optionally substituted with 1 to 5 aryl group(s);

Y represents —NG$^2$G$^4$, —NG$^2$-L$^1$-COOH, —NG$^{21}$-L$^{11}$-C(=O)—NG$^3$-L$^2$-COOH, —NG$^2$-L$^3$-OH, or —NG$^2$-(CH$_2$—CH$_2$—O)$_q$—CH$_2$—CH$_2$—COOH;

q represents an integer of 1 to 6;

G$^2$ and G$^3$ each independently represent a hydrogen atom, or a $C_1$-$C_6$ alkyl group optionally substituted with 1 to 5 substituent (s) independently selected from the group consisting of a phenyl group optionally substituted with 1 to 5 —COOR$^3$ group(s) and a —COOR$^3$ group;

G$^4$ represents a hydrogen atom, a C$_1$-C$_4$ alkyl group, or a C$_1$-C$_4$ alkoxy-C$_1$-C$_4$ alkyl group;

R$^3$ each independently represents a hydrogen atom, a benzyl group, or a tert-butyl group;

L$^1$ and L$^2$ each independently represent a C$_1$-C$_6$ alkylene group optionally substituted with 1 to 5 C$_1$-C$_6$ alkyl group(s) optionally substituted with 1 to 5 —COOR$^4$ group(s), a C$_1$-C$_6$ alkylene group substituted with a C$_7$-C$_{12}$ aralkyl group optionally substituted with 1 to 5 substituent(s) independently selected from the group consisting of a hydroxy group and a carboxy group, a C$_1$-C$_4$ alkylene-phenylene group, or a phenylene-C$_1$-C$_4$ alkylene group;

L$^3$ represents a C$_1$-C$_4$ alkylene-phenylene group wherein the phenylene moiety is optionally substituted with 1 to 3 —COOR$^4$ group(s);

R$^4$ each independently represents a hydrogen atom, a benzyl group, or a tert-butyl group; and R$^5$ and R$^6$ each independently represent a hydrogen atom, a halogen atom, a C$_1$-C$_4$ alkyl group, or a C$_1$-C$_4$ alkoxy group is provided.

In another embodiment of the Compound (II'), a compound or a pharmaceutically acceptable salt thereof, wherein R$^1$ each independently represents a hydrogen atom or a tert-butoxycarbonyl group;

W represents a single bond or a C$_1$-C$_4$ alkylene group;

X represents —O—C(=O)— or —NG-SO$_2$—;

G represents a hydrogen atom, a C$_1$-C$_4$ alkyl group, or —COOR$^2$;

R$^2$ represents a C$_1$-C$_4$ alkyl group optionally substituted with 1 to 3 aryl group(s);

Y represents —NG$^2$G$^4$, —NG$^2$-L$^{11}$-COOH, —NG$^2$-L$^{11}$-C(=O)—NG$^3$-L$^2$-COOH, or —NG$^2$-(CH$_2$—CH$_2$—O)$_q$—CH$_2$—CH$_2$—COOH;

q represents an integer of 1 to 6;

G$^2$ and G$^3$ each independently represent a hydrogen atom, or a C$_1$-C$_6$ alkyl group optionally substituted with 1 to 3 substituent(s) independently selected from the group consisting of a phenyl group optionally substituted with 1 to 3 —COOR$^3$ group(s) and a —COOR$^3$ group;

G$^4$ represents a hydrogen atom, a C$_1$-C$_4$ alkyl group, or a C$_1$-C$_4$ alkoxy-C$_1$-C$_4$ alkyl group;

R$^3$ each independently represents a hydrogen atom, a benzyl group, or a tert-butyl group;

L$^1$ and L$^2$ each independently represent a C$_1$-C$_6$ alkylene group optionally substituted with 1 to 5 C$_1$-C$_6$ alkyl group(s) optionally substituted with 1 to 5 —COOR$^4$ group(s), a C$_1$-C$_4$ alkylene-phenylene group, or a phenylene-C$_1$-C$_4$ alkylene group;

L$^3$ represents a C$_1$-C$_2$ alkylene-phenylene group wherein the phenylene moiety is optionally substituted with 1 to 2 —COOR$^4$ group(s);

R$^4$ each independently represents a hydrogen atom, a benzyl group, or a tert-butyl group; and R$^5$ and R$^6$ each independently represent a hydrogen atom, a halogen atom, a C$_1$-C$_4$ alkyl group, or a C$_1$-C$_4$ alkoxy group is provided.

In another embodiment of the Compound (II'), a compound or a pharmaceutically acceptable salt thereof, wherein R$^1$ each represents a hydrogen atom;

W represents a C$_1$-C$_4$ alkylene group;

X represents —O—C(=O)— or —NG-SO$_2$—;

G represents a hydrogen atom;

Y represents —NG$^2$G$^4$, —NG$^2$-L$^1$-COOH, —NG$^2$-L$^1$-C(=O)—NG$^3$-L$^2$-COOH, or —NG$^2$-(CH$_2$—CH$_2$—O)$_q$—CH$_2$—CH$_2$—COOH;

q represents an integer of 1 to 6;

G$^2$ represents a hydrogen atom, or a C$_1$-C; alkyl group substituted with 1 to 3 carboxy group(s);

G$^3$ represents a hydrogen atom;

G$^4$ represents a hydrogen atom, a C$_1$-C$_2$ alkyl group, or a C$_1$-C$_2$ alkoxy-C$_1$-C$_2$ alkyl group;

L$^1$ and L$^2$ each independently represent a C$_1$-C$_6$ alkylene group optionally substituted with 1 to 2 C$_2$-C$_6$ alkyl group(s) optionally substituted with 1 to 2 —COOR$^4$ group(s), or a C$_1$-C$_4$ alkylene-phenylene group;

L$^3$ represents a methylenephenylene group wherein the phenylene moiety is optionally substituted with one —COOR$^3$ group;

R$^4$ represents a hydrogen atom; and

R$^5$ and R$^6$ each independently represent a hydrogen atom, a fluorine atom, a chlorine atom, a methyl group, or a methoxy group is provided.

In one embodiment, the Compound (II) has a structure represented by the following general formula (II"):

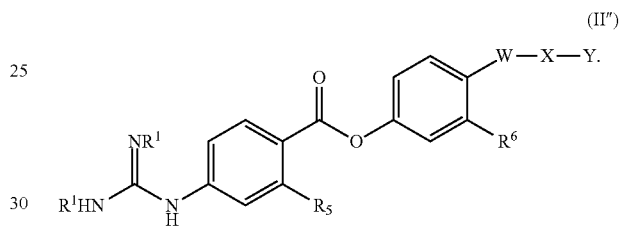

In one embodiment of the Compound (II"), a compound or a pharmaceutically acceptable salt thereof, wherein R$^1$ each independently represents a hydrogen atom or a tert-butoxycarbonyl group;

W represents a single bond or a C$_1$-C$_4$ alkylene group;

X represents —C(=O)—, —O—C(=O)—, or —NG-SO$_2$—;

G represents a hydrogen atom, a C$_1$-C$_4$ alkyl group, or COOR$^2$;

R$^2$ represents a C$_1$-C$_4$ alkyl group optionally substituted with 1 to 5 aryl group(s);

Y represents —NG$^2$G$^4$, —NG$^2$-L$^1$-COOH, —NG$^2$-L$^1$-C(=O)—NG$^3$-L$^2$-COOH, —NG$^2$-L$^3$-OH, or —NG$^2$-(CH$_2$—O)$_q$—CH$_2$—CH$_2$—COOH;

q represents an integer of 1 to 6;

G$^2$ and G$^3$ each independently represent a hydrogen atom, or a C$_1$-C$_6$ alkyl group optionally substituted with 1 to 5 substituent(s) independently selected from the group consisting of a phenyl group optionally substituted with 1 to 5 —COOR$^3$ group(s) and a —COOR$^3$ group;

G$^4$ represents a hydrogen atom, a C$_1$-C$_4$ alkyl group, or a C$_1$-C$_4$ alkoxy-C$_1$-C$_4$ alkyl group;

R$^3$ each independently represents a hydrogen atom, a benzyl group, or a tert-butyl group;

L$^1$ and L$^2$ each independently represent a C$_1$-C$_6$ alkylene group optionally substituted with 1 to 5 C$_1$-C$_6$ alkyl group(s) optionally substituted with 1 to 5 —COOR$^4$ group(s), a C$_1$-C$_6$ alkylene group substituted with a C$_7$-C$_{12}$ aralkyl group optionally substituted with 1 to 5 substituent(s) independently selected from the group consisting of a hydroxy group and a carboxy group, a C$_1$-C$_4$ alkylene-phenylene group, or a phenylene-C$_1$-C$_4$ alkylene group;

L$^3$ represents a C$_1$-C$_4$ alkylene-phenylene group wherein the phenylene moiety is optionally substituted with 1 to 3 —COOR$^4$ group(s);

$R^4$ each independently represents a hydrogen atom, a benzyl group, or a tert-butyl group; and $R^5$ and $R^6$ each independently represent a hydrogen atom, a halogen atom, a $C_1$-$C_6$ alkyl group, a $C_1$-$C_4$ alkoxy group, a carboxy group, or —C(=O)—$NG^2G^4$
is provided.

In another embodiment of the Compound (II″), a compound or a pharmaceutically acceptable salt thereof, wherein $R^1$ each independently represents a hydrogen atom or a tert-butoxycarbonyl group;

W represents a single bond or a $C_2$-$C_4$ alkylene group;

X represents —O—C(=O)— or —NG-$SO_2$—;

G represents a hydrogen atom, a $C_1$-$C_4$ alkyl group, or —$COOR^2$;

$R^2$ represents a $C_1$-$C_4$ alkyl group optionally substituted with 1 to 3 aryl group(s);

Y represents —$NG^2G^4$, —$NG^2$-$L^1$-COOH, —$NG^2$-$L^1$-C(=O)—$NG^3$-$L^2$-COOH, or —$NG^2$-($CH_2$—$CH_2$—O)$_q$—$CH_2$—$CH_2$—COOH;

q represents an integer of 1 to 6;

$G^2$ and $G^3$ each independently represent a hydrogen atom, or a $C_1$-$C_6$ alkyl group optionally substituted with 1 to 3 substituent(s) independently selected from the group consisting of a phenyl group optionally substituted with 1 to 3 —$COOR^3$ group(s) and a —$COOR^3$ group;

$G^1$ represents a hydrogen atom, a $C_1$-$C_4$ alkyl group, or a $C_1$-$C_4$ alkoxy-$C_1$-$C_4$ alkyl group;

$R^3$ each independently represents a hydrogen atom, a benzyl group, or a tert-butyl group;

$L^1$ and $L^2$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group;

$L^3$ represents a $C_1$-$C_2$ alkylene-phenylene group wherein the phenylene moiety is optionally substituted with 1 to 2 —$COOR^4$ group(s);

$R^4$ each independently represents a hydrogen atom, a benzyl group, or a tert-butyl group; and $R^5$ and $R^6$ each independently represent a hydrogen atom, a halogen atom, a $C_1$-$C_4$ alkyl group, a $C_1$-$C_4$ alkoxy group, a carboxy group, or —C(=O)—$NG^2G^4$
is provided.

In another embodiment of the Compound (II″), a compound or a pharmaceutically acceptable salt thereof, wherein $R^1$ each represents a hydrogen atom;

W represents a $C_1$-$C_4$ alkylene group;

X represents —O—C(=O)— or —NG-$SO_2$—;

G represents a hydrogen atom;

Y represents —$NG^2G^4$, —$NG^2$-$L^1$-COOH, —$NG^2$-$L^1$-C(=O)—$NG^3$-$L^2$-COOH, or —$NG^2$-($CH_2$—$CH_2$—O)$_q$—$CH_2$—$CH_2$—COOH;

q represents an integer of 1 to 6;

$G^2$ represents a hydrogen atom, or a $C_1$-$C_3$ alkyl group substituted with 1 to 3 carboxy group(s);

$G^3$ represents a hydrogen atom;

$G^4$ represents a hydrogen atom, a $C_1$-$C_2$ alkyl group, or a $C_1$-$C_2$ alkoxy-$C_1$-$C_2$ alkyl group;

$L^1$ and $L^2$ each independently represent a $C_1$-$C_6$ alkylene group optionally substituted with 1 to 2 $C_1$-$C_6$ alkyl group(s) optionally substituted with 1 to 2 —$COOR^1$ group(s), or a $C_1$-$C_4$ alkylene-phenylene group;

$L^3$ represents a methylenephenylene group wherein the phenylene moiety is optionally substituted with one —$COOR^4$ group;

$R^4$ represents a hydrogen atom; and $R^5$ and $R^6$ each independently represent a hydrogen atom, a fluorine atom, a chlorine atom, a methyl group, a methoxy group, a carboxy group, or —C(=O)—$NG^2G^4$
is provided.

In one embodiment, the Compound (II) has a structure represented by:

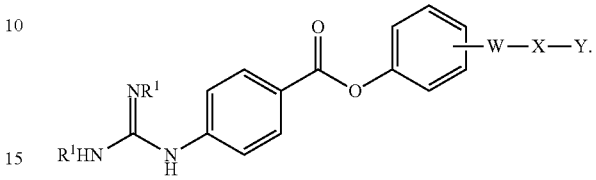

In one embodiment, the Compound (II) represents a compound represented by the following general formula (II‴)

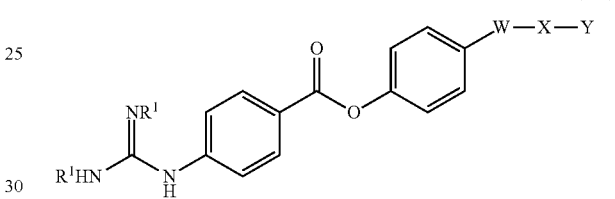

(II‴)

[wherein:

$R^1$ each independently represents a hydrogen atom or a —COO—($C_1$-$C_4$ alkyl group);

W represents a single bond or a $C_1$-$C_4$ alkylene group;

X represents —O—C(=O)— or —$NG^Z$-$SO_2$—;

G represents a hydrogen atom or —$COOR^2$;

$R^2$ represents a $C_1$-$C_4$ alkyl group optionally substituted with 1 to 5 aryl group(s);

Y represents —$NG^2G^4$, —$NG^2$-$L^1$-C(=O)—$NH_2$, —$NG^2$-$L^1$-C(=O)-$NG^3$-$L^2$-C(=O)—$NH_2$, or —$NG^2$-($CH_2$—$CH_2$—O)$_q$—$CH_2$—$CH_2$—COOH;

q represents an integer of 1 to 6;

$G^2$ and $G^3$ each independently represent a hydrogen atom, or a $C_1$-$C_6$ alkyl group optionally substituted with 1 to 5 substituent(s) independently selected from the group consisting of a phenyl group optionally substituted with 1 to 5 —$COOR^3$ group(s) and a —$COOR^3$ group;

$G^4$ represents a hydrogen atom, a $C_1$-$C_4$ alkyl group, or a $C_1$-$C_4$ alkoxy-$C_1$-$C_4$ alkyl group;

$R^3$ each independently represents a hydrogen atom, or a $C_1$-$C_4$ alkyl group optionally substituted with 1 to 5 aryl group(s);

$L^1$ and $L^2$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group; and $R^4$ each independently represents a hydrogen atom, or a $C_1$-$C_4$ alkyl group optionally substituted with 1 to 5 aryl group(s)]
or a pharmaceutically acceptable salt thereof.

In another embodiment of the Compound (II‴), a compound or a pharmaceutically acceptable salt thereof, wherein $R^1$ each independently represents a hydrogen atom or a tert-butoxycarbonyl group;

W represents a $C_1$-$C_4$ alkylene group;

X represents —O—C(=O)— or —N$G^Z$-$SO_2$—;

G represents a hydrogen atom, or —$COOR^2$;

$R^2$ represents a $C_1$-$C_4$ alkyl group optionally substituted with 1 to 3 phenyl groups);

Y represents —$NG^2G^4$, —$NG^2$-$L^1$-C(=O)—$NH_2$, —$NG^2$-$L^1$-C(=O)-$NG^3$-$L^2$-C(=O)—$NH_2$, or —$NG^2$-($CH_2$—$CH_2$—O)$_q$—$CH_2$—$CH_2$—COOH;

q represents an integer of 1 to 6;

and $G^3$ each independently represent a hydrogen atom, or a $C_1$-$C_6$ alkyl group optionally substituted with 1 to 3 substituent(s) independently selected from the group consisting of a phenyl group optionally substituted with 1 to 3 —$COOR^3$ group(s) and a —$COOR^3$ group;

$G^4$ represents a hydrogen atom, a $C_1$-$C_2$ alkyl group, or a $C_1$-$C_2$ alkoxy-$C_1$-$C_2$ alkyl group;

$R^3$ each independently represents a hydrogen atom, a benzyl group, or a tert-butyl group;

$L^1$ and $L^2$ each independently represent a $C_1$-$C_6$ alkylene group optionally substituted with 1 to 5 $C_1$-$C_6$ alkyl group(s), optionally substituted with 1 to 5 —$COOR^4$ group(s), a $C_1$-$C_4$ alkylene-phenylene group, or a phenylene-$C_1$-$C_4$ alkylene group; and $R^4$ each independently represents a hydrogen atom, a benzyl group, or a tert-butyl group is provided.

In another embodiment of the Compound (II'''), a compound or a pharmaceutically acceptable salt thereof, wherein $R^1$ each represents a hydrogen atom;

W represents a $C_1$-$C_2$ alkylene group;

X represents —NG-$SO_2$—;

G represents a hydrogen atom;

Y represents —$NG^2G^4$;

$G^2$ represents a $C_1$-$C_3$ alkyl group substituted with 1 to 3 substituent(s) independently selected from the group consisting of a phenyl group substituted with one carboxy group and a carboxy group; and $G^4$ represents a hydrogen atom, a $C_1$-$C_2$ alkyl group, or a $C_1$-$C_2$ alkoxy-$C_1$-$C_2$ alkyl group is provided.

Method for Producing Compound (I)

One embodiment of the present invention provides a method for producing the Compound (I). In one embodiment, the method for producing the Compound (I) comprises reacting a compound represented by the following general formula (I-A-1)

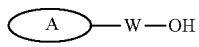
(I-A-1)

[wherein A represents a structure formed by removing —W—X—Y— from $A^1$ or $A^2$.]

or a salt thereof with a compound represented by the following general formula (I-A-2')

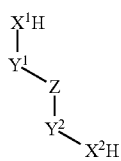
(I-A-2')

[wherein the symbols have the same meanings as those described above.]

or a salt thereof under a condition suitable for producing the Compound (I).

In one embodiment, the Compound (I-A-2') may be reacted with the Compound (I-A-1) in a solvent (for example, ethers such as tetrahydrofuran and 1,4-dioxane; aromatic hydrocarbons such as toluene; nitriles such as acetonitrile; and mixtures thereof), and in the presence of an azodicarboxylic acid derivative (for example, azodicarboxylic acid dialkyl esters such as diethyl azodicarboxylate and diisopropyl azodicarboxylate; and azodicarboxamides such as 1,1'-azobis(N,N-dimethylformamide)) and a phosphine derivative (for example, triarylphosphines such as triphenylphosphine; and trialkylphosphines such as tributylphosphine) to produce the Compound (T).

The Compound (I), the Compound (II), the Compound (III), the Compound (IV), the Compound (V), the Compound (VI), the Compound (VII), or Compound (VIII) of the present invention may exist in the form of a tautomer or a mixture thereof. The Compound (I), the Compound (II), the Compound (III), the Compound (IV), the Compound (V), the Compound (VI), the Compound (VII), or Compound (VIII) of the present invention may exist in the form of a stereoisomer such as an enantiomer and a diastereomer or a mixture thereof. The Compound (I), the Compound (II), the Compound (III), the Compound (IV), the Compound (V), the Compound (VI), the Compound (VII), or Compound (VIII) of the present invention encompasses a mixture of tautomers or stereoisomers or each pure or substantially pure isomer.

When the Compound (I), the Compound (II), the Compound (III), the Compound (IV), the Compound (V), the Compound (VI), the Compound (VII), or Compound (VIII) of the present invention is obtained in the form of a diastereomer or an enantiomer, it may be isolated by a known conventional method in this technical field such as chromatography and fractional crystallization method.

The Compound (I), the Compound (II), the Compound (III), the Compound (IV), the Compound (V), the Compound (VI), the Compound (VII), or Compound (VIII) of the present invention encompasses compounds labeled with an isotope (for example, $^2$H, $^3$H, $^{13}$, $^{14}$C, $^{15}$N, $^{18}$F, $^{32}$P, $^{35}$S, and $^{125}$I) and the like, and deuterated products.

Examples of the pharmaceutically acceptable salt of the Compound (I), the Compound (II), the Compound (III), the Compound (IV), the Compound (V), the Compound (VI), the Compound (VII), or Compound (VIII), include alkali metal salts such as lithium, sodium, and potassium salts; alkaline earth metal salts such as magnesium and calcium salts; salts with aluminum or zinc; salts with an amine such as ammonia, choline, diethanolamine, lysine, ethylenediamine, tert-butylamine, tert-octylamine, tris(hydroxymethyl)aminomethane, N-methyl-glucosamine, triethanolamine, and dehydroabietylamine; salts with an inorganic acid such as hydrogen chloride, hydrogen bromide, hydrogen iodide, sulfuric acid, nitric acid, and phosphoric acid; salts with an organic acid such as formic acid, acetic acid, trifluoroacetic acid, propionic acid, oxalic acid, malonic acid, succinic acid, fumaric acid, maleic acid, lactic acid, malic acid, tartaric acid, citric acid, methanesulfonic acid, ethanesulfonic acid, and benzenesulfonic acid; and salts with an acidic amino acid such as aspartic acid and glutamic acid.

Further, the pharmaceutically acceptable salt of the Compound (I), the Compound (II), the Compound (III), the Compound (IV), the Compound (V), the Compound (VI), the Compound (VII), or Compound (VIII) encompasses inner salts, hydrates, and solvates thereof.

The "pharmaceutically acceptable" ingredients in the present description generally mean that they are not harmful to a subject of administration and are compatible with each other in the preparation of a pharmaceutical composition, and include useful ingredients for use as human medicaments as well as useful ingredients for veterinary use.

The Compound (I), the Compound (II), the Compound (III), the Compound (IV), the Compound (V), the Compound (VI), the Compound (VII), or the Compound (VIII), or a pharmaceutically acceptable salt thereof of the present invention defined by the above each embodiment and a combination thereof is all useful as an active ingredient of a pharmaceutical composition, and all the compounds defined by the above embodiments and combinations thereof may be administered to a subject (preferably human). In one embodiment, the Compound (I), the Compound (II), the Compound (III), the Compound (IV), the Compound (V), the Compound (VI), the Compound (VII), or the Compound (VIII), or a pharmaceutically acceptable salt thereof wherein protecting group(s) such as a tert-butoxycarbonyl group and a benzyloxycarbonyl group is/are partially or completely deprotected is administered to a subject.

In one embodiment, the Compound (I) or the Compound (II), or a pharmaceutically acceptable salt thereof, wherein at least one of $R^1$, $R^3$, $R^4$, and G represents a hydrogen atom in any one of embodiments of the above each embodiment and a combination thereof is administered to a subject. In another embodiment, the Compound (I) or the Compound (II), or a pharmaceutically acceptable salt thereof, wherein at least one of $R^1$ and $R^4$ represents a hydrogen atom in any one of embodiments of the above each embodiment and a combination thereof is administered to a subject. In another embodiment, the Compound (I) or the Compound (II), or a pharmaceutically acceptable salt thereof, wherein $R^1$, $R^2$, $R^4$, and G each represent a hydrogen atom in any one of embodiments of the above each embodiment and a combination thereof is administered to a subject.

In one embodiment, the Compound (I), the Compound (III), the Compound (IV), the Compound (V), the Compound (VI), the Compound (VII), or the Compound (VIII), or a pharmaceutically acceptable salt thereof, wherein at least one of $R^1$, $R^3$, $R^4$, $G^{11}$, and $G^{12}$ represents a hydrogen atom in any one of embodiments of the above each embodiment and a combination thereof is administered to a subject. In another embodiment, the Compound (I), the Compound (III), the Compound (IV), the Compound (V), the Compound (VI), the Compound (VII), or the Compound (VIII), or a pharmaceutically acceptable salt thereof, wherein at least one of $R^1$ and $R^4$ represents a hydrogen atom in any one of embodiments of the above each embodiment and a combination thereof is administered to a subject. In another embodiment, the Compound (I), the Compound (II), the Compound (IV), the Compound (V), the Compound (V), the Compound (VII), or the Compound (VIII), or a pharmaceutically acceptable salt thereof, wherein $R^1$, $R^3$, $R^4$, $G^{11}$, and $G^{12}$ each represent a hydrogen atom in any one of embodiments of the above each embodiment and a combination thereof is administered to a subject.

The Compound (I), the Compound (II), the Compound (III), the Compound (IV), the Compound (V), the Compound (VI), the Compound (VII), or the Compound (VIII), or a pharmaceutically acceptable salt thereof of the present invention may be orally or parenterally administered alone or as a pharmaceutical composition comprising it and a pharmaceutically acceptable carrier. Preferably, the pharmaceutical composition of the present invention comprises the Compound (I), the Compound (II), the Compound (III), the Compound (IV), the Compound (V), the Compound (VI), the Compound (VII), or the Compound (VIII), or a pharmaceutically acceptable salt thereof of the present invention, and a pharmaceutically acceptable carrier. The pharmaceutically acceptable carrier may be any conventional carrier in this technical field, and examples thereof include diluents, binders (for example, syrup, gum arabic, gelatin, sorbitol, tragacanth, and polyvinylpyrrolidone), excipients (for example, lactose, sucrose, cornstarch, potassium phosphate, sorbitol, and glycine), lubricants (for example, magnesium stearate, talc, polyethylene glycol, and silica), disintegrants (for example, potato starch), and humectants (for example, sodium lauryl sulfate). Also, the dosage form of the pharmaceutical composition is not limited to a specific one, and the pharmaceutical composition may be used as a conventional pharmaceutical formulation such as a tablet, a granule, a capsule, a powder, an injection, an inhalant, and a suppository.

The dose (i.e., effective amount) of the Compound (I), the Compound (II), the Compound (III), the Compound (IV), the Compound (V), the Compound (VI), the Compound (VII), or the Compound (VIII), or a pharmaceutically acceptable salt thereof of the present invention varies depending on administration method, age, body weight, and condition of patient, and the like, and normally 0.001 to 500 mg/kg/day, in particular 0.01 to 10 mg/kg/day is preferable and administered at one time or two to four divided doses.

The Compound (I), the Compound (II), the Compound (III), the Compound (IV), the Compound (V), the Compound (VI), the Compound (VII), or the Compound (VIII), or a pharmaceutically acceptable salt thereof of the present invention has at least one activity selected from an enteropeptidase inhibitory activity and a trypsin inhibitory activity, and is useful in the prevention, alleviation, and/or treatment of diseases of which symptoms are improved by enteropeptidase inhibition and/or trypsin inhibition. Examples of such disease include obesity, pathological conditions or diseases associated with obesity, diabetes, diabetic complication, renal diseases, coronary artery diseases, bone and joint diseases, metabolic syndrome, hypertension, hyperuricemia, fatty liver (including nonalcoholic steatohepatitis), insulin resistance syndrome, glucose intolerance, cerebral infarction, Parkinson's disease, muscular dystrophy, Alzheimer's disease, eating disorder, hyperinsulinemia, acute or chronic diarrhea, inflammatory diseases, osteoporosis, and various cancers. The Compound (I), the Compound (II), the Compound (III), the Compound (IV), the Compound (V), the Compound (VI), the Compound (VII), or the Compound (VIII), or a pharmaceutically acceptable salt thereof of the present invention is especially useful in the prevention, alleviation, and/or treatment of obesity.

One embodiment of the present invention relates to a pharmaceutical composition comprising the Compound (I), the Compound (II), the Compound (III), the Compound (TV), the Compound (V), the Compound (VI), the Compound (VI), or the Compound (VIII), or a pharmaceutically acceptable salt thereof of the present invention, and pharmaceutically acceptable carrier(s), In a preferable embodiment, the above pharmaceutical composition is used for the prevention, alleviation, and/or treatment of diseases of which symptoms are improved by enteropeptidase inhibition and/or trypsin inhibition. In a further preferable embodiment, the above pharmaceutical composition is used for the prevention, alleviation, and/or treatment of obesity.

One embodiment of the present invention relates to use of the Compound (I), the Compound (II), the Compound (III), the Compound (IV), the Compound (V), the Compound (VI), the Compound (VII), or the Compound (VIII), or a pharmaceutically acceptable salt thereof of the present invention in the manufacture of a medicament. In a preferable embodiment, the above predicament is used for the prevention, alleviation, and/or treatment of the diseases of which symptoms are improved by enteropeptidase inhibition and/or trypsin inhibition. In a further preferable embodiment, the above medicament is used for the prevention, alleviation, and/or treatment of obesity.

One embodiment of the present invention relates to use of the Compound (I), the Compound (II), the Compound (III), the Compound (TV), the Compound (V), the Compound (VI), the Compound (VII), or the Compound (VIII), or a pharmaceutically acceptable salt thereof of the present invention for the prevention, alleviation, and/or treatment. A preferable embodiment of the present invention relates to the Compound (I), the Compound (II), the Compound (III), the Compound (IV), the Compound (V), the Compound (VI), the Compound (VII), or the Compound (VIII), or a pharmaceutically acceptable salt thereof of the present invention for the prevention, alleviation, and/or treatment of diseases of which symptoms are improved by enteropeptidase inhibition and/or trypsin inhibition. A further preferable embodiment relates to the Compound (I), the Compound (II), the Compound (III), the Compound (IV), the Compound (V), the Compound (VI), the Compound (VII), or the Compound (VIII), or a pharmaceutically acceptable salt thereof of the present invention for the prevention, alleviation, and/or treatment of obesity.

One embodiment of the present invention relates to a method for preventing, alleviating, and/or treating diseases of which symptoms are improved by enteropeptidase inhibition and/or trypsin inhibition, the method comprising administering the Compound (I), the Compound (II), the Compound (III), the Compound (IV), the Compound (V), the Compound (VI), the Compound (VII), or the Compound (VIII), or a pharmaceutically acceptable salt thereof of the present invention. A further preferable embodiment relates to a method for preventing, alleviating, and/or treating obesity, the method comprising administering the Compound (I), the Compound (II), the Compound (III), the Compound (IV), the Compound (V), the Compound (VI), the Compound (VII), or the Compound (VIII), or a pharmaceutically acceptable salt thereof of the present invention.

The Compound (I), the Compound (II), the Compound (III), the Compound (IV), the Compound (V), the Compound (VI), the Compound (VII), or the Compound (VIII), or a pharmaceutically acceptable salt thereof may be prepared according to, but is not limited to, the following methods. Also, each step in the following production methods may be carried out by appropriately combining with each other.

When a functional group in a compound needs to be protected in each production step of the Compound (I), the Compound (II), the Compound (III), the Compound (IV), the Compound (V), the Compound (VI), the Compound (VII), or Compound (VIII) described below, the protection nay be appropriately carried out by the specific methods described below or conventional methods. General descriptions of protecting groups and use thereof are described in T. W. Greene et al., "Protective Groups in Organic Synthesis", John Wiley & Sons, New York, Fifth Edition. A protecting group may be removed in a subsequent step by using the specific Methods described below or conventional methods.

Also, each interconversion of a carboxylic acid compound and a salt thereof co each other, or an amine compound and a salt thereof to each other may be carried cut by the specific methods described below or conventional salt formation and conventional desalination.

Production Method A

Among the compounds represented by formula (I), the Compound (I-A) wherein $X^1$ represents —$NG^{11}$-$SO_2$—, $X^2$ represents —$SO_2$—$NG^{12}$-, $Y^1$ represents —$NG^{21}$-, $Y^2$ represents —$NG^{22}$- and $G^{11}$ and $G^{12}$ each independently represent a hydrogen atom or a benzyloxycarbonyl group may ho prepared according to, for example, the following scheme.

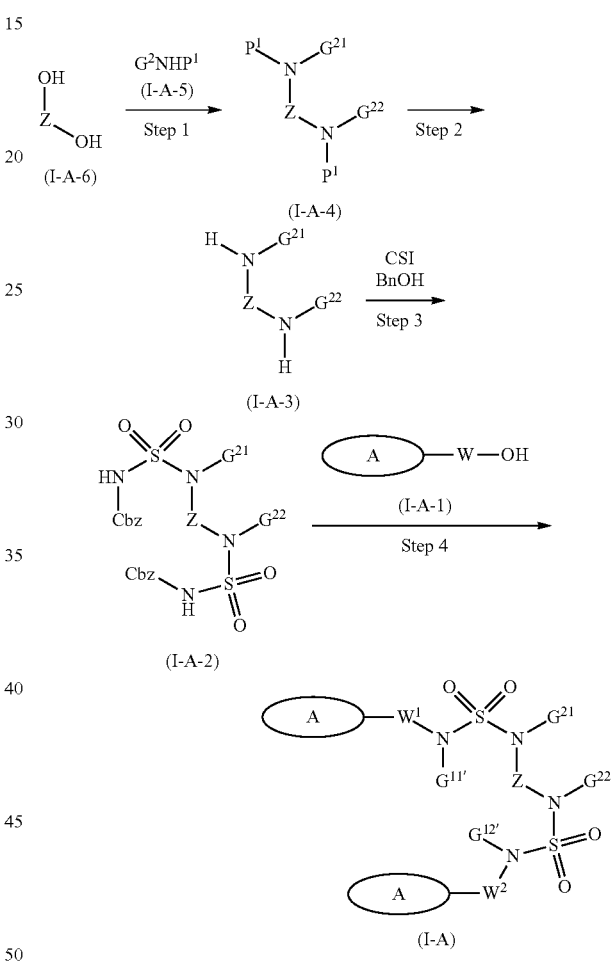

[wherein $P^1$ represents a protecting group such as a 2 nitrobenzenesulfonyl group; Cbz represents a benzyloxycarbonyl group; $G^{11'}$ and $G^{12'}$ each independently represent a hydrogen atom or a benzyloxycarbonyl group; and the other symbols have the sane meanings as those described above.]

Step 1

The Compound (I-A-6) may be a commercially available material, or may be prepared according to known method(s) from commercially available material(s).

The Compound (I-A-6) may be reacted with the Compound (I-A-5) in a solvent and in the presence of an azodicarboxylic acid derivative and a phosphine derivative to prepare the Compound (I-A-4).

The solvent may be any one which does not affect the reaction, and examples thereof include ethers such as tetrahydrofuran and dioxane; halogenated aliphatic hydrocarbons such as chloroform and dichloromethane; aromatic hydrocarbons such as toluene; nitriles such as acetonitrile; and mixtures thereof.

Examples of the azodicarboxylic acid derivative include azodicarboxylic acid dialkyl esters such as diethyl azodicarboxylate and diisopropyl azodicarboxylate; and azodicarboxamides such as 1,1'-azobis(N,N-dimethylformamide).

Examples of the phosphine derivative include triarylphosphines such as triphenylphosphine; and trialkylphosphines such as tributylphosphine.

The amount of the Compound (I-A-5) to be used may be 1.8 to 5.0 molar equivalents, preferably 1.8 to 3.0 molar equivalents, relative to the Compound (I-A-6).

The amount of the azodicarboxylic acid derivative to be used may be 2.0 to 6.0 molar equivalents, preferably 2.0 to 5.0 molar equivalents, relative to the Compound (I-A-6).

The amount of the phosphine derivative to be used may be 2.0 to 6.0 molar equivalents, preferably 2.0 to 5.0 molar equivalents, relative to the Compound (I-A-6).

The reaction may be carried out at room temperature to under heating, for example at room temperature to 100° C., preferably at room temperature.

Step 2

The Compound (I-A-4) may be reacted in a solvent and in the presence of a thiol and a base to prepare the Compound (I-A-3).

The solvent may be any one which does not affect the reaction, and examples thereof include amides such as N-methylpyrrolidone and N,N-dimethylformamide (hereinafter also referred to as dimethylformamide); ethers such as tetrahydrofuran and dioxane; nitriles such as acetonitrile; dimethyl sulfoxide; and mixtures thereof.

Examples of the thiol include thiophenols such as 4-tert-butylthiophenol; alkylthiols such as 1-dodecanethiol; and thiosalicylic acid.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; alkylamines such as triethylamine and N,N-diisopropylethylamine; organic bases such as pyridines such as pyridine and 4-dimethylaminopyridine, and 1,8-diazabicyclo[5.4.0]-7-undecene; and alkali metal fluorides such as cesium fluoride and potassium fluoride.

The amount of the thiol to be used may be 2.0 to 7.0 molar equivalents, preferably 2.0 to 5.0 molar equivalents, relative to the Compound (I-A-4).

The amount of the base to be used may be 2.0 to 10.0 molar equivalents, preferably 2.5 to 7.0 molar equivalents, relative to the Compound (I-A-4).

The reaction may be carried out at room temperature to under heating, or example at room temperature to 10° C., preferably at room temperature.

Step 3

The Compound (I-A-3) may be reacted in a solvent, in the presence of a base, and in the presence of benzyl chlorosulfonylcarbamate, which is a compound prepared by reacting chlorosulfonyl isocyanate (CSI) with benzyl alcohol (BnOH), to prepare the Compound (I-A-2).

The solvent nay be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; and mixtures thereof.

Examples of the base include alkylamines such as triethylamine and N,N-diisopropylethylamine; at organic bases such as pyridines such as pyridine and 4-dimethylaminopyridine, and 1,8-diazabicyclo[5.4.0]-7-undecene.

The amount of the base to be used may be 2.0 to 10.0 molar equivalents, preferably 2.0 to 7.0 molar equivalents, relative to the Compound (I-A-3).

The amount of the chlorosulfonyl isocyanate to be used may be 2.0 to 5.0 molar equivalents, preferably 2.0 to 3.0 molar equivalents, relative to the Compound (I-A-3).

The amount of the benzyl alcohol to be used may be 2.0 to 5.0 molar equivalents, preferably 2.0 to 3.0 molar equivalents, relative to the Compound (I-A-3).

When benzyl chlorosulfonylcarbamate is directly used, the amount thereof to be used may be 2.0 to 5.0 molar equivalents, preferably 2.0 to 3.0 molar equivalents, relative to the Compound (I-A-3).

The reaction may be carried out under ice-cooling to under heating, for example under ice-cooling to 100° C., preferably at 0° C. to room temperature.

Step 4

The Compound (I-A-2) may be reacted with the Compound (I-A-1) in a solvent and in the presence of an azodicarboxylic acid derivative and a phosphine derivative to prepare the Compound (I-A).

The solvent may be any one which does not affect the reaction, and examples thereof include ethers such as tetrahydrofuran and dioxane; aromatic hydrocarbons such as toluene; nitriles such as acetonitrile; and mixtures thereof.

Examples of the azodicarboxylic acid derivative include azodicarboxylic acid dialkyl esters such as diethyl azodicarboxylate and diisopropyl azodicarboxylate; and azodicarboxamides such as 1,1'-azobis(N,N-dimethylformamide).

Examples of the phosphine derivative include triarylphosphines such as triphenylphosphine; and trialkylphosphines such as tributylphosphine.

The amount of the Compound (I-A-1) to be used may be 2.0 to 5.0 molar equivalents, preferably 2.0 to 3.0 molar equivalents, relative to the Compound (I-A-2).

The amount of the azodicarboxylic acid derivative to be used may be 2.0 to 5.0 molar equivalents, preferably 2.0 to 3.5 molar equivalents, relative to the Compound (I-A-2).

The amount of the phosphine derivative to be used may be 2.0 to 5.0 molar equivalents, preferably 2.0 to 3.5 molar equivalents, relative to the Compound (I-A-2).

The reaction may be carried out at room temperature to under heating, for example at room temperature to 100° C., preferably at room temperature.

Step 5

Protecting group(s) present in the Compound (I-A) may be deprotected.

Step 5-1

For example, the Compound (I-A) may be reacted with an acid in a solvent, and in the presence or absence of a reducing agent to remove a protecting group such as a tert-butyl group and a tert-butoxycarbonyl group.

The solvent may be any one which does not affect the reaction, and examples thereof include esters such as ethyl acetate; ethers such as tetrahydrofuran and dioxane; amides such as N,N-dimethylformamide; halogenated aliphatic hydrocarbons such as chloroform and dichloromethane; aromatic hydrocarbons such as toluene; nitriles such as acetonitrile; carboxylic acids such as acetic acid; water; and mixtures thereof.

Examples of the acid include formic acid, hydrochloric acid, and trifluoroacetic acid.

Examples of the reducing agent include trialkylsilane such as triethylsilane.

The amount of the acid to be used may be 10.0 to 603 molar equivalents, preferably 15.0 to 500 molar equivalents, relative to the Compound (I-A).

The amount of the reducing agent to be used may be 3.0 to 20 molar equivalents, preferably 5.0 to 15 molar equivalents, relative to the Compound (I-A).

The reaction may be carried out at room temperature to under heating, far example at room temperature to 100° C., preferably at room temperature.

Step 5-2

For example, the Compound (I-A) may be treated with a catalyst in a solvent and under hydrogen atmosphere to remove a protecting group such as a benzyloxycarbonyl group and a benzyl group.

The solvent may be any one which does not affect the reaction, and examples thereof include ethers such as tetrahydrofuran and dioxane; alcohols such as methanol, ethanol, and isopropanol; aromatic hydrocarbons such as toluene; nitriles such as acetonitrile; carboxylic acids such as acetic acid; water; and mixtures thereof.

Examples of the catalyst include palladium carbon.

The amount of the catalyst to be used may be 0.01 to 20.0 molar equivalent(s), preferably 0.01 to 10.0 molar equivalent(s), relative to the Compound (I-A).

The reaction may be carried out at room temperature to under heating, for example at room temperature to 100° C., preferably at room temperature.

The Step 5-1 may be carried out simultaneously with the Step 5-2.

The compound prepared in the Step 4 or Step 5 may be reacted with an acid such as hydrochloric acid and trifluoroacetic acid according to known method(s) to prepare an acid addition salt such as hydrochloride and trifluoroacetate.

The amount of the acid to be used may be 2.0 to 20.0 molar equivalents, preferably 2.0 to 15.0 molar equivalents, relative to the compound prepared in the Step 4 or Step 5.

Production Method A-1 (Production of Intermediate Compound)

The Compound (I-A-5) may be prepared according to, for example, the following scheme.

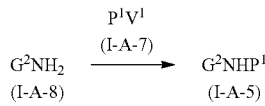

[wherein $V^1$ represents a halogen atom such as a chlorine atom; and the other symbols have the same meanings as those described above.]

The Compound (I-A-7) and the Compound (I-A-8) may be commercially available materials, or may be prepared according to known methods from commercially available materials. Also, the Compound (I-A-8) may be in a salt form such as hydrochloride.

The Compound (I-A-8) may be reacted with the Compound (I-A-7) in a solvent and in the presence of a base to prepare the Compound (I-A-5).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; and mixtures thereof.

Examples of the base include alkylamines such as triethylamine and N,N-diisopropylethylamine; and organic bases such as pyridines such as pyridine and 4-dimethylaminopyridine, and 1,8-diazabicyclo[5.4.0]-7-undecene.

The amount of the Compound (I-A-7) to be used may be 1.0 to 5.0 molar equivalent(s), preferably 1.0 to 2.0 molar equivalent(s), relative to the Compound (I-A-8).

The amount of the base to be used may be 1.0 to 5.0 molar equivalent (s, preferably 2.0 to 3.0 molar equivalents, relative to the Compound (I-A-4).

The reaction may be carried out at room temperature to under heating, for example at room temperature to 100° C., preferably at room temperature.

Production Method A-2 (Production of Intermediate Compound)

Among the Compound (I-A-1), the Compound (I-A-1')

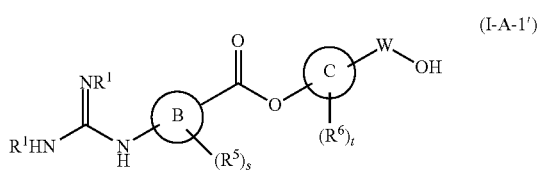

[wherein the symbols have the same meanings as those described above.]

may be prepared according to, for example, the following scheme.

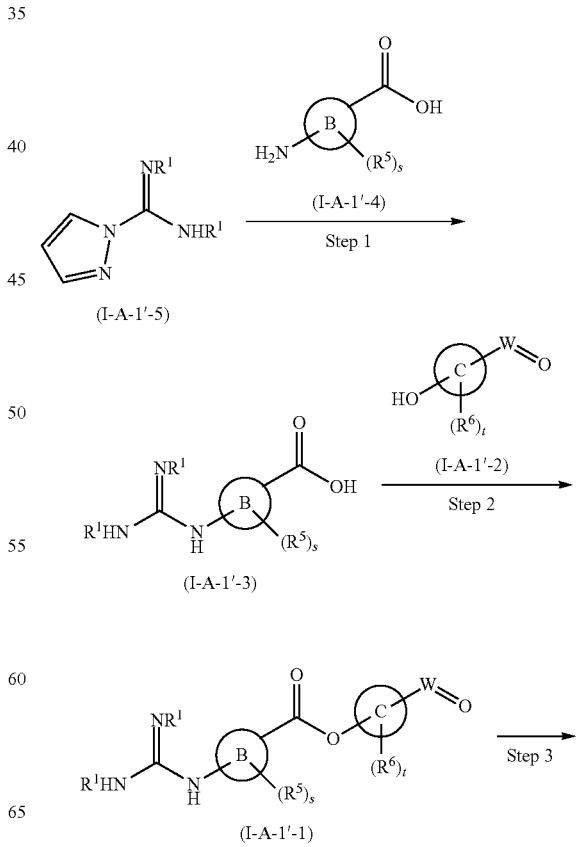

-continued

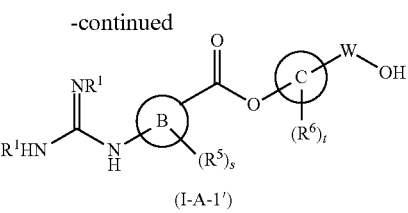

(I-A-1')

[wherein the symbols have the same meanings as those described above.]

Step 1

The Compound (I-A-1'-5) may be a commercially available material, or may be prepared according to known method(s) from commercially available material(s).

The Compound (I-A-1'-5) may be reacted with the Compound (I-A-1'-4) in a solvent and in the presence of a base to prepare the Compound (I-A-1'-3).

The solvent may be any one which does not affect the reaction, and examples thereof include ethers such as tetrahydrofuran and dioxane; alcohols such as methanol, ethanol, and isopropanol; aromatic hydrocarbons such as toluene; nitriles such as acetonitrile; water; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; amines such as triethylamine and N,N-diisopropylethylamine; and alkali metal fluorides such as cesium fluoride and potassium fluoride.

The amount of the Compound (I-A-1'-4) to be used may be 1.0 to 5.0 molar equivalent(s), preferably 1.0 to 2.0 molar equivalent(s), relative to the Compound (I-A-1'-5).

The amount of the base to be used may be 1.0 to 5.0 molar equivalent(s), preferably 2.0 to 3.0 molar equivalents, relative to the Compound (I-A-1'-5).

The reaction may be carried out at room temperature to under heating, for example at room temperature to 100° C., preferably at room temperature.

Step 2

The Compound (I-A-1'-3) may be reacted with the Compound (I-A-1'-2) in a solvent, in the presence or absence of a base, and in the presence of a condensing agent to prepare the Compound (I-A-1'-1).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; and mixtures thereof.

Examples of the base include alkali metal hydrogen carbonates such as sodium hydrogen carbonate; alkali metal carbonates such as potassium carbonate; inorganic bases such as alkali metal hydroxides such as sodium hydroxide; alkylamines such as triethylamine and N,N-diisopropylethylamine; and organic bases such as pyridines such as pyridine and 4-dimethylaminopyridine, and 1,8-diazabicyclo[5.4.0]-7-undecene.

Examples of the condensing agent include O-(7-azabenzotriazol-1-yl)-N,N,N',N'-tetramethyluronium hexafluorophosphate and 1-(3-dimethylaminopropyl)-3-ethylcarbodiimide hydrochloride.

The amount of the Compound (I-A-1'-2) to be used may be 1.0 to 5.0 molar equivalent(s), preferably 1.0 to 2.0 molar equivalent(s), relative to the Compound (I-A-1'-3).

The amount of the base to be used may be 0.1 to 3.0 molar equivalent(s), preferably 0.1 to 1.0 molar equivalent, relative to the Compound (I-A-1'-3).

The amount of the condensing agent to be used may be 1.0 to 5.0 molar equivalent(s), preferably 1.0 to 2.0 molar equivalent(s), relative to the Compound (I-A-1'-3).

The reaction may be carried out at room temperature to under heating, for example at room temperature to 100° C., preferably at room temperature.

Step 3

The Compound (I-A-1'-1) may be treated with a reducing agent in a solvent and in the presence or absence of an acid to prepare the Compound (I-A-1').

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; carboxylic acids such as acetic acid; and mixtures thereof.

Examples of the acid include acetic acid.

Examples of the reducing agent include sodium triacetoxyborohydride and sodium borohydride.

The amount of the acid to be used may be 1.0 to 5.0 molar equivalent(s), preferably 1.0 to 4.0 molar equivalent(s), relative to the Compound (I-A-1'-1).

The amount of the reducing agent to be used may be 1.0 to 5.0 molar equivalent(s), preferably 1.0 to 4.0 molar equivalent(s), relative to the Compound (I-A-1'-1).

The reaction may be carried out at room temperature to under heating, for example at room temperature to 100° C., preferably at room temperature.

Production Method A-3 (Production of Intermediate Compound)

The Compound (I-A-4') may also be used instead of the Compound (I-A-4).

[wherein $P^{1'}$ represents a protecting group such as a tert-butoxycarbonyl group, and the other symbols have the same meanings as those described above.]

The Compound (I-A-4') may be prepared according to the following scheme.

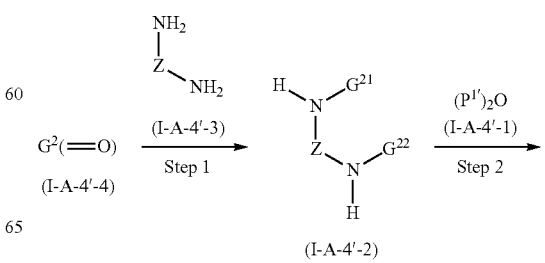

-continued

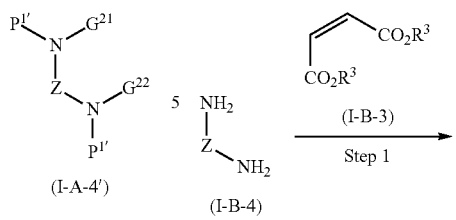

(I-A-4')

[wherein the symbols have the same meanings as those described above.]

Step 1

The Compound (I-A-4'-4) may be a commercially available material, or may be prepared according to known method(s) from commercially available material(s).

The Compound (I-A-4'-4) may be reacted with the Compound (I-A-4'-3) in a solvent and in the presence of an acid and a reducing agent to prepare the Compound (I-A-4'-2).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; carboxylic acids such as acetic acid; and mixtures thereof.

Examples of the acid include acetic acid.

Examples of the reducing agent include sodium triacetoxyborohydride and sodium borohydride.

The amount of the Compound (I-A-4'-3) to be used may be 0.4 to 1.0 molar equivalent, preferably 0.5 to 0.8 molar equivalent, relative to the Compound (I-A-4'-4).

The amount of the acid to be used may be 2.0 to 5.0 molar equivalents, preferably 2.0 to 3.0 molar equivalents, relative to the Compound (I-A-4'-4).

The amount of the reducing agent to be used may be 2.0 to 5.0 molar equivalents, preferably 2.0 to 3.0 molar equivalents, relative to the Compound (I-A-4'-4).

The reaction may be carried out at room temperature to under heating, for example at room temperature to 100° C., preferably at room temperature.

Step 2

The Compound (I-A-4'-2) may be reacted with the Compound (I-A-4'-1) in a solvent to prepare the Compound (I-A'-4).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; carboxylic acids such as acetic acid; and mixtures thereof.

The amount of the Compound (I-A-4'-1) to be used may be 2.0 to 5.0 molar equivalents, preferably 2.0 to 3.0 molar equivalents, relative to the Compound (I-A-4'-2).

The reaction may be carried out at room temperature to under heating, for example at room temperature to 100° C., preferably at room temperature.

Production Method B

Among the compound represented by formula (I), the Compound (I-B) wherein $X^1$ represents —O—C(=O)—, $X^2$ represents —C(=O)—O—, $Y^1$ represents —$NG^{21}$-, $Y^2$ represents —$NG^{22}$-, $G^{21}$ represents —CH($COOR^3$)—$CH_2$—$COOR^3$, and $G^{22}$ represents —CH($COOR^3$)—$CH_2$—$COOR^3$ may be prepared according to, for example, the following scheme.

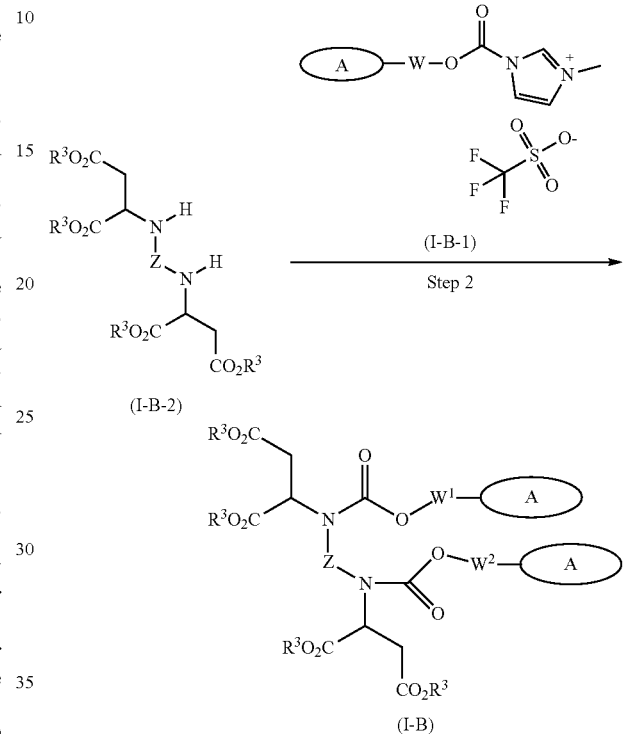

[wherein the symbols have the same meanings as those described above.]

Step 1

The Compound (I-B-3) and the Compound (I-B-4) may be commercially available materials, or may be prepared according to known methods from commercially available materials.

The Compound (I-B-4) may be reacted with the Compound (1-B-3) in a solvent and in the presence or absence of a base to prepare the Compound (I-B-2).

The solvent may be any one which does not affect the reaction, and examples thereof include ethers such as tetrahydrofuran and dioxane; aromatic hydrocarbons such as toluene; nitriles such as acetonitrile; and mixtures thereof.

Examples of the base include alkylamines such as triethylamine and N,N-diisopropylethylamine; organic bases such as pyridines such as pyridine and 4-dimethylaminopyridine, and 1,8-diazabicyclo[5.4.0]-7-undecene; and inorganic bases such as sodium carbonate, potassium carbonate, sodium hydrogen carbonate, and sodium hydride.

The amount of the Compound (I-B-3) to be used may be 2.0 to 5.0 molar equivalents, preferably 2.0 to 3.0 molar equivalents, relative to the Compound (I-B-4).

The amount of the base to be used may be 0.5 to 5.0 molar equivalent(s), preferably 0.5 to 2.0 molar equivalent(s), relative to the Compound (I-B-4).

The reaction may be carried out at room temperature to under heating, for example at room temperature to 100° C., preferably at room temperature.

Step 2

The Compound (I-B-2) may be reacted with the Compound (I-B-1) in a solvent and in the presence or absence of a base to prepare the Compound (I-B).

The solvent may be any one which does not affect the reaction, and examples thereof include amides such as N,N-dimethylformamide; halogenated aliphatic hydrocarbons such as chloroform and dichloromethane; aromatic hydrocarbons such as toluene; nitriles such as acetonitrile; carboxylic acids such as acetic acid; water; and mixtures thereof.

Examples of the base include alkylamines such as triethylamine and N,N-diisopropylethylamine; and organic bases such as pyridines such as pyridine and 4-dimethylaminopyridine, and 1,8-diazabicyclo[5.4.0]-7-undecene.

The amount of the Compound (I-B-1) to be used may be 2.0 to 5.0 molar equivalents, preferably 2.0 to 3.0 molar equivalents, relative to the Compound (I-B-2).

The amount of the base to be used may be 2.0 to 10.0 molar equivalents, preferably 2.0 to 4.0 molar equivalents, relative to the Compound (I-B-2).

The reaction may be carried out at room temperature to under heating, for example at room temperature to 100° C., preferably at room temperature.

Step 3

When protecting group(s) is/are present in the Compound (I-B), the protecting group(s) may be deprotected according to similar method(s) to the method(s) described in the Step 5-1 and/or Step 5-2 in the Production method A.

The compound prepared in the Step 2 or Step 3 may be reacted with an acid such as hydrochloric acid and trifluoroacetic acid according to known method(s) to prepare an acid addition salt such as hydrochloride and trifluoroacetate.

The amount of the acid to be used may be 2.0 to 20.0 molar equivalents, preferably 2.0 to 15.0 molar equivalents, relative to the compound prepared in the Step 2 or Step 3.

Production Method B-1 (Production of Intermediate Compound)

The Compound (I-B-1) may be prepared according to, for example, the following scheme.

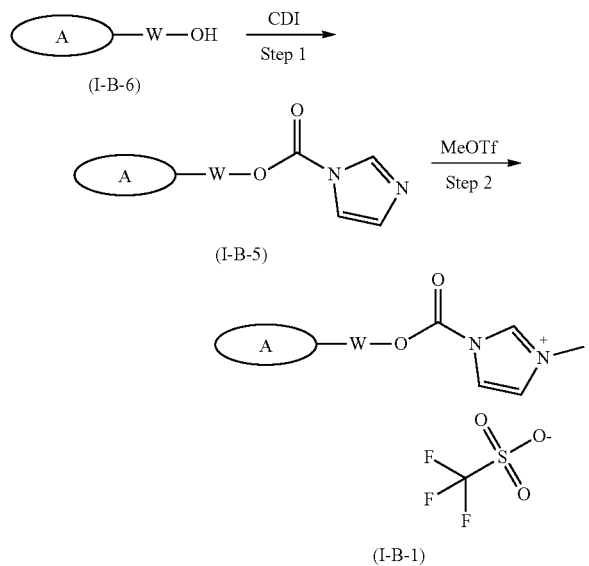

[wherein the symbols have the sane meanings as those described above.]

Step 1

The Compound (I-B-6) may be prepared according to the same manner as the Compound (I-A-1).

The Compound (I-B-6) may be reacted with 1,1'-carbonyldiimidazole (CDI) in a solvent and in the presence or absence of a base to prepare the Compound (I-B-5).

The solvent may be any one which does not affect the reaction, and examples thereof include amides such as N,N-dimethylformamide; halogenated aliphatic hydrocarbons such as chloroform and dichloromethane; aromatic hydrocarbons such as toluene; nitriles such as acetonitrile; carboxylic acids such as acetic acid; water; and mixtures thereof.

Examples of the base include alkylamines such as triethylamine and N,N-diisopropylethylamine; organic bases such as pyridines such as pyridine and 4-dimethylaminopyridine, and 1,8-diazabicyclo[5.4.0]-7-undecene; and metal hydrides such as sodium hydride.

The amount of the 1,1'-carbonyldiimidazole to be used may be 1.0 to 5.0 molar equivalent(s), preferably 1.0 to 2.0 molar equivalent(s), relative to the Compound (I-B-6).

The amount of the base to be used may be 0.1 to 3.0 molar equivalent(s), preferably 0.1 to 1.0 molar equivalent, relative to the Compound (I-B-6).

The reaction may be carried out at room temperature to under heating, for example at room temperature to 100° C., preferably at room temperature.

Step 2

The Compound (I-B-5) may be reacted with methyl trifluoromethanesulfonate (MeOTf) in a solvent to prepare the Compound (I-B-1).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; carboxylic acids such as acetic acid; and mixtures thereof.

The amount of the methyl trifluoromethanesulfonate to be used may be 1.0 to 5.0 molar equivalent(s), preferably 1.0 to 2.0 molar equivalent(s), relative to the Compound (I-B-5).

The reaction may be carried out at room temperature to under heating, for example at room temperature to 100° C., preferably at room temperature.

Production Method C

Among the compound represented by formula (I), the Compound (I-C) wherein $X^1$ represents —O—C(=O)—, $X^2$ represents —C(=O)—O—, $Y^1$ represents —NG$^{21}$-L$^{11}$-C(=O)—NG$^{31}$-L$^{21}$-C(=O)—, and $Y^2$ represents —C(=O)-L$^{22}$-NG$^{32}$-C(=O)-L$^{12}$-NG$^{22}$- may be prepared according to, for example, the following scheme.

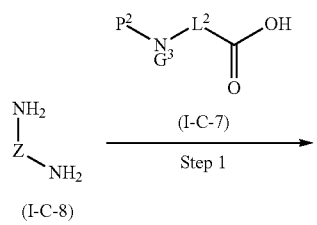
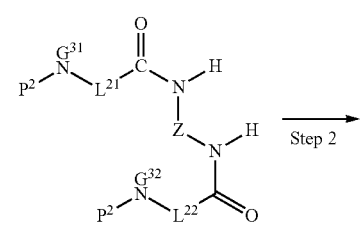
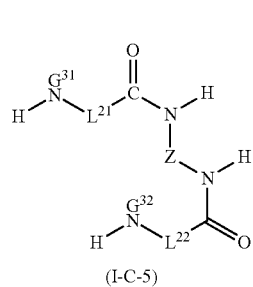
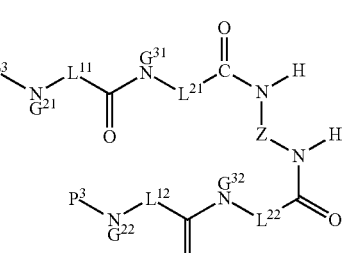
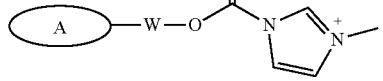
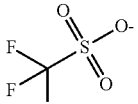
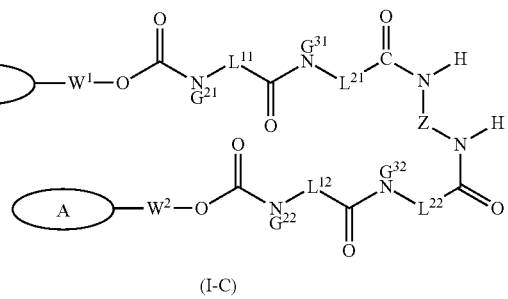

[wherein $P^2$ and $P^3$ each independently represent a protecting group such as a benzyloxycarbonyl group; and the other symbols have the same meaning as those describe above.]

Step 1

The Compound (I-C-7) and the Compound (I-C-8) may be commercially available materials, or may be prepared according to known methods from commercially available materials.

The Compound (I-C-8) may be reacted with the Compound (I-C-7) in a solvent, in the presence or absence of a base, and in the presence of a condensing agent to prepare the Compound (I-C-6).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; carboxylic acids such as acetic acid; water; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; amines such as triethylamine and N,N-diisopropylethylamine; and alkali metal fluorides such as cesium fluoride and potassium fluoride.

Examples of the condensing agent include O-(2-azabenzotriazol-1-yl)-N,N,N',N'-tetramethyluronium hexafluorophosphate, 1-(3-dimethylaminopropyl)-3-ethylcarbodiimide hydrochloride, and (1-cyano-2-ethoxy-2-oxoethylideneaminooxy)dimethylamino(morpholino)carbenium hexafluorophosphate (COMU).

The amount of the Compound (I-C-7) to be used may be 2.0 to 5.0 molar equivalents, preferably 2.0 to 3.5 molar equivalents, relative to the Compound (I-C-8).

The amount of the base to be used may be 2.0 to 5.0 molar equivalents, preferably 2.0 to 4.0 molar equivalents, relative to the Compound (I-C-8).

The amount of the condensing agent to be used may be 2.0 to 5.0 molar equivalents, preferably 2.0 to 4.0 molar equivalents, relative to the Compound (I-C-8).

The reaction may be carried out at room temperature to under heating, for example at room temperature to 100° C., preferably at room temperature.

Step 2

The Compound (I-C-6) may be reacted according to a similar method to the Step 5-2 of the Production method A to prepare the Compound (I-C-5).

Step 3

The Compound (I-C-5) and the Compound (I-C-4) may be reacted according to a similar method to the Step 1 to prepare the Compound (I-C-3).

Step 4

The Compound (I-C-3) may be reacted according to a similar method to the Step 5-2 of the Production method A to prepare the Compound (I-C-2).

Step 5

The Compound (I-C-2) and the Compound (I-C-1) may be reacted according to a similar method to the Step 2 of the Production method B to prepare the Compound (I-C). The Compound (I-C-1) may be prepared according to the same manner as the Compound (I-B-1)

Step 6

When protecting group(s) is/are present in the Compound (I-C), the protecting group(s) may be deprotected according to similar method(s) to the method(s) described in the Step 5-1 and/or Step 5-2 of the Production method A.

The compound prepared in the Step 5 or Step 6 may be reacted with an acid such as hydrochloric acid and trifluoroacetic acid according to known method(s) to prepare an acid addition salt such as hydrochloride and trifluoroacetate.

The amount of the acid to be used may be 2.0 to 20.0 molar equivalents, preferably 2.0 to 15.0 molar equivalents, relative to the compound prepared in the Step 5 or Step 6.

Production Method D

Among the compound represented by formula (I), the Compound (I-D) wherein $X^1$ represents —O—C(=O)—, $X^2$ represents —C(=O)—O—, $Y^1$ represents —NG$^{21}$-L$^{11}$-C(=O)—NG$^{31}$-L$^{21}$-C(=O)—, and $Y^2$ represents —C(=O)-L$^{22}$-NG$^{32}$-C(=O)-L$^{12}$-NG$^{22}$- may also be prepared according to, for example, the following scheme.

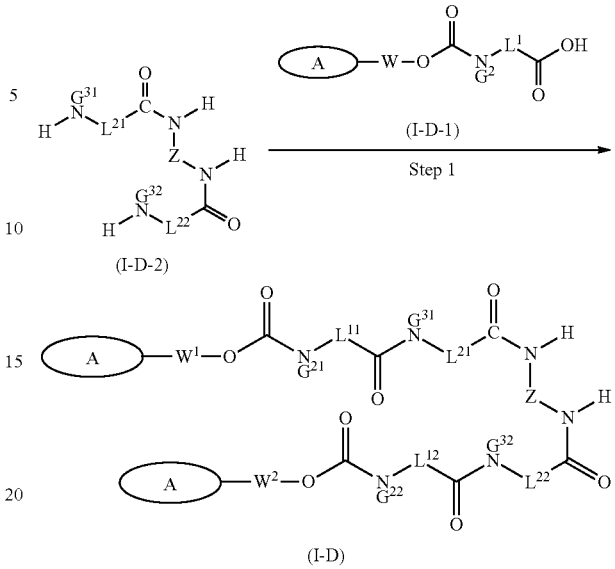

[wherein the symbols have the same meanings as those described above.]

Step 1

The Compound (I-D-2) may be prepared according to the same manner as the Compound (I-C-5).

The Compound (I-D-2) may be reacted with the Compound (I-D-1) in a solvent, in the presence or absence of a base, in the presence of a condensing agent, and in the presence or absence of an activating agent to prepare the Compound (I-D).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; carboxylic acids such as acetic acid; water; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; amines such as triethylamine and N,N-diisopropylethylamine; and alkali metal fluorides such as cesium fluoride and potassium fluoride.

Examples of the condensing agent include O-(7-azabenzotriazol-1-yl)-N,N,N',N'-tetramethyluronium hexafluorophosphate, 1-(3-dimethylaminopropyl)-3-ethylcarbodiimide hydrochloride, (1-cyano-2-ethoxy-2-oxoethylideneaminooxy)dimethylamino(morpholino)carbenium hexafluorophosphate (COM), and mixtures thereof.

Examples of the activating agent include tert-butyl peroxide, 1-hydroxy-7-azabenzotriazol (HOAt), 1-hydroxybenzotriazol (HDBt), and 4-dimethylaminopyridine.

The amount of the Compound (I-D-1) to be used may be 2.0 to 5.0 molar equivalents, preferably 2.0 to 3.0 molar equivalents, relative to the Compound (I-D-2).

The amount of the base to be used may be 2.0 to 6.0 molar equivalents, preferably 2.0 to 5.0 molar equivalents, relative to the Compound (I-D-2).

The amount of the condensing agent to be used may be 2.0 to 5.0 molar equivalents, preferably 2.0 to 3.3 molar equivalents, relative to the Compound (I-D-2).

The amount of the activating agent to be used way be 2.0 to 5.0 molar equivalents, preferably 2.3 to 3.0 molar equivalents, relative to the Compound (I-D-2).

The reaction may be carried out at room temperature to under heating, for example at room temperature to 100° C., preferably at room temperature.

Step 2

When protecting group(s) is/are present in the Compound (I-D), the protecting group(s) may be deprotected according to similar method(s) to the method(s) described in the Step 5-1 and/or Step 5-2 of the Production method A.

The compound prepared in the Step 1 or Step 2 may be reacted with an acid such as hydrochloric acid and trifluoroacetic acid according no known method(s) to prepare an acid addition salt such as hydrochloride and trifluoroacetate.

The amount of the acid to be used may be 2.0 to 20.0 molar equivalents, preferably 2.0 to 15.0 molar equivalents, relative to the compound prepared in the Step 1 or Step 2.

Production Method D-1 (Production of Intermediate Compound)

The Compound (I-D-1) may be prepared according to, for example, the following scheme.

[wherein $P^4$ represents a protecting group such as a 2-trimethylsilylethyl group; and the other symbols have the same meanings as those described above.]

Step 1

The Compound (I-D-5) may be prepared according to the same manner as the Compound (I-B-1).

The Compound (I-D-5) may be reacted with the Compound (I-D-4) in a solvent and in the presence or absence of a base to prepare the Compound (I-D-3).

The solvent may be any one which does not affect the reaction, and examples thereof include amides such as N,N-dimethylformamide; halogenated aliphatic hydrocarbons such as chloroform and dichloromethane; aromatic hydrocarbons such as toluene; nitriles such as acetonitrile; carboxylic acids such as acetic acid; water; and mixtures thereof.

Examples of the base include alkylamines such as triethylamine and N,N-diisopropylethylamine; and organic bases such as pyridines such as pyridine and 4-dimethylaminopyridine, and 1,8-diazabicyclo[5.4.0]-7-undecene.

The amount of the Compound (I-D-4) to be used may be 1.0 to 5.0 molar equivalent(s), preferably 1.0 to 3.0 molar equivalent(s), relative to the Compound (I-D-5).

The amount of the base to be used may be 1.0 to 5.0 molar equivalent(s), preferably 1.0 to 2.0 molar equivalent(s), relative to the Compound (I-D-5).

The reaction ray be carried out at room temperature to under heating, for example at room temperature to 100° C., preferably at room temperature.

Step 2

The Compound (I-D-3) may be treated with tetrabutylammonium fluoride in a solvent to prepare the Compound (I-D-1).

The solvent may be any one which does not affect the reaction, and examples thereof include ethers such as tetrahydrofuran and dioxane; aromatic hydrocarbons such as toluene; nitriles such as acetonitrile; and mixtures thereof.

The amount of the tetrabutylammonium fluoride to be used may be 1.0 to 20.0 molar equivalent(s), preferably 1.0 to 15.0 molar equivalent(s), relative to the Compound (I-D-3).

The reaction may be carried out at room temperature to under heating, for example at room temperature to 100° C., preferably at room temperature.

Production Method D-2 (Production of Intermediate Compound;

The Compound (I-D-4) may be prepared according to, for example, the following scheme.

[wherein $V^2$ represents a halogen atom such as a chlorine atom; and the other symbols have the same meanings as those described above.]

The Compound (I-D-6) may be a commercially available material, or may be prepared according to known method(s) from commercially available material(s).

The Compound (I-D-7) may be reacted with the Compound (I-D-6) in a solvent and in the presence of a base to prepare the Compound (I-D-4).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitrites such as acetonitrile; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; amines such as triethylamine and N,N-diisopropylethylamine; and alkali metal fluorides such as cesium fluoride and potassium fluoride.

The amount of the Compound (I-D-6) to be used may be 1.0 to 5.0 molar equivalent(s), preferably 1.0 to 2.0 molar equivalent(s), relative to the Compound (I-D-7).

The amount of the base to be used may be 1.0 to 5.0 molar equivalent(s), preferably 2.0 to 4.0 molar equivalents, relative to the Compound (I-D-7).

The reaction may be carried out at room temperature to under heating, for example at room temperature to 150° C., preferably at 50 to 100° C.

Production Method D-3 (Production of Intermediate Compound)

Among the Compound (I-D-4), a compound wherein $G^2$ represents a $C_1$-$C_6$ alkyl group substituted with one phenyl group optionally substituted with 1 to 5 —COOR$^3$ group(s) may also be prepared according to, for example, the following scheme.

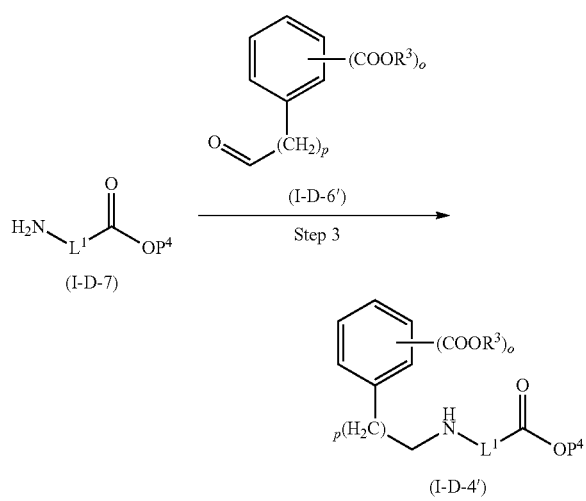

[wherein o represents an integer of 1 to 5; p represents an integer of 0 to 5; and the other symbols have the same meanings as those described above.]

The Compound (I-D-6') may be a commercially available material, or may be prepared according to known method(s) from commercially available material(s).

The Compound (I-D-7) may be reacted with the Compound (1-D-6') in a solvent, in the presence or absence of a dehydrating agent, and in the presence or absence of sodium acetate, and then may be treated with a reducing agent in the presence or absence of an acid to prepare the Compound (I-D-4').

The solvent may be any one which does not affect the react-on, and examples thereof include amides such as N,N-dimethylformamide; halogenated aliphatic hydrocarbons such as chloroform and dichloromethane; aromatic hydrocarbons such as toluene; nitriles such as acetonitrile; and mixtures thereof.

Examples of the dehydrating agent include magnesium sulfate and a molecular sieve.

Examples of the acid include acetic acid.

Examples of the reducing agent include sodium triacetoxyborohydride and sodium borohydride.

The amount of the Compound (I-D-6') to be used may be 0.5 to 5.0 molar equivalent(s), preferably 1.0 to 2.0 molar equivalent (s), relative to the Compound (I-D-7).

The amount of the dehydrating agent to be used may be 1.0 to 5.0 molar equivalent(s), preferably 1.0 to 2.0 molar equivalent(s), relative to the compound (I-D-7).

The amount of the sodium acetate to be used may be 1.0 to 5.0 molar equivalent(s), preferably 1.0 to 2.0 molar equivalent (s), relative to the Compound (I-D-7).

The amount of the acid to be used may be 1.0 to 5.0 molar equivalent (s), preferably 1.0 to 2.0 molar equivalent s), relative to the Compound (I-D-7).

The amount of the reducing agent to be used may be 1.0 to 5.0 molar equivalent(s), preferably 1.0 to 2.0 molar equivalent(s), relative to the Compound (I-D-7).

The reaction may be carried out at room temperature to under heating, for example at room temperature to 150° C., preferably at room temperature.

Production Method D-4 (Production of Intermediate Compound)

The Compound (I-2-7) may be prepared according to, for example, the following scheme.

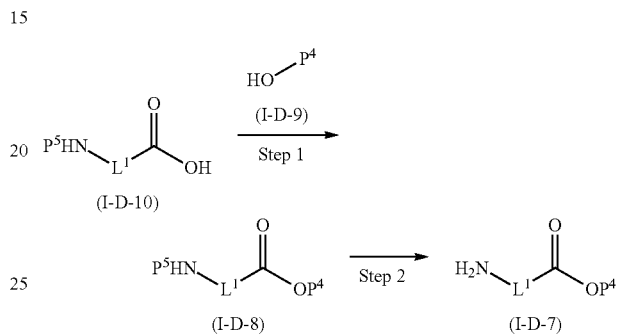

[wherein $P^5$ represents a protecting group such as a benzyloxycarbonyl group; and the other symbols have the same meanings as those described above.]

Step 1

The Compound (I-D-9) and the Compound (I-D-10) may be commercially available materials, or may be prepared according to known methods from commercially available materials.

The Compound (I-D-10) may be reacted with the Compound (I-D-9) in a solvent, in the presence or absence of a base, and in the presence of a condensing agent to prepare the Compound (I-D-8).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; carboxylic acids such as acetic acid; water; and mixtures thereof.

Examples of the base include alkali metal hydrogen carbonates such as sodium hydrogen carbonate; alkali metal carbonates such as potassium carbonate; inorganic bases such as alkali metal hydroxides such as sodium hydroxide; alkylamines such as triethylamine and N,N-diisopropylethylamine; and organic bases such as pyridines such as pyridine and 4-dimethylaminopyridine.

Examples of the condensing agent include O-(7-azabenzotriazol-1-yl)-N,N,N',N'-tetramethyluronium hexafluorophosphate, 1-(3-dimethylaminopropyl)-3-ethylcarbodiimide hydrochloride, (1-cyano-2-ethoxy-2-oxoethylideneaminooxy)dimethylamino(morpholino)carbenium hexafluorophosphate (COMU), and mixtures thereof.

The amount of the Compound (I-D-9) to be used may be 1.0 to 5.0 molar equivalent(s), preferably 1.0 to 2.0 molar equivalent(s), relative to the Compound (I-D-10).

The amount of the base to be used may be 0.1 to 5.0 molar equivalent(s), preferably 0.1 to 2.0 molar equivalent(s), relative to the Compound (I-D-10).

The amount of the condensing agent to be used may be 1.0 to 5.0 molar equivalent(s), preferably 1.0 to 2.0 molar equivalent(s), relative to the Compound (I-D-10).

The reaction may be carried out at room temperature to under heating, for example at room temperature to 100° C., preferably at room temperature.

Step 2

The Compound (I-D-8) may be reacted according to a similar method to the Step 5-2 of the Production method A to prepare the Compound (I-D-7).

Production Method E

Among the compound represented by formula (I), the Compound (I-E) wherein $X^1$ represents —O—C(=O)—, $X^2$ represents —C(=O)—O—, $Y^1$ represents —N$G^{21}$-$L^{11}$-C(=O)—, and $Y^2$ represents —C(=O)-$L^{12}$-N$G^{22}$- may also be prepared according to, for example, the following scheme.

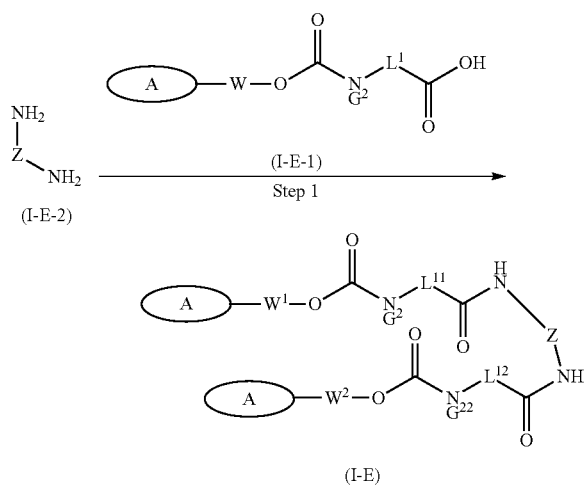

[wherein the symbols have the same meanings as those described above.]

Step 1

The Compound (I-E-2) and the Compound (I-E-1) may be reacted according to a similar method to the Step 1 of the Production method D to prepare the Compound (I-E). The Compound (I-E-2) may be a commercially available material, or may be prepared according to known method(s) from commercially available material(s).

Step 2

When protecting group(s) is/are present in the Compound (I-E), the protecting group(s) may be deprotected according to similar method(s) to the method(s) described in the Step 5-1 and/or Step 5-2 of the Production method A.

The resulting compound may be reacted with an acid such as hydrochloric acid and trifluoroacetic acid according to known method(s) to prepare an acid addition salt such as hydrochloride and trifluoroacetate.

The amount of the acid to be used may be 2.0 to 20.0 molar equivalents, preferably 2.0 to 15.0 molar equivalents, relative to the compound prepared in the Step 1 or Step 2.

Production Method E-1 (Production of Intermediate Compound)

The Compound (I-E-1) may be similarly prepared to the Compound (I-D-1) according to a similar method to the Production method D-1. Among the Compound (I-D-4), the Compound (I-E-3) wherein $L^1$ represents a $C_1$-$C_4$ alkylene-phenylene group may be prepared according to, for example, the following scheme.

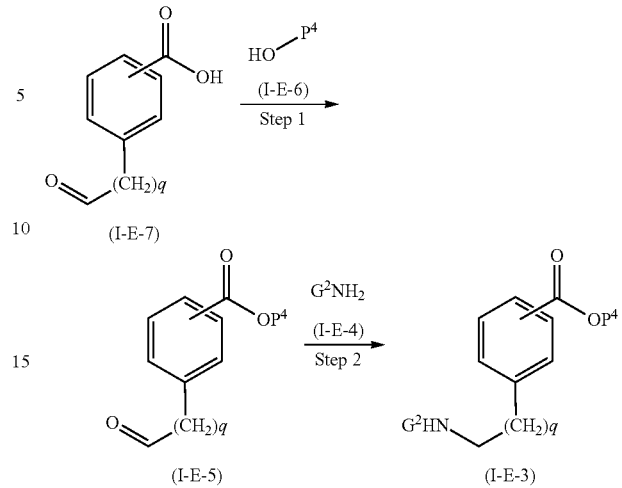

[wherein q represents an integer of 0 to 3; and the other symbols have the same meanings as those described above.]

Step 1

The Compound (I-E-7) and the Compound (I-E-6) may be commercially available materials, or may be prepared according to known methods from commercially available materials.

The Compound (I-E-7) may be reacted with a chlorinating agent in a solvent and in the presence or absence of a catalyst, and then may be reacted with the Compound (I-E-6) in the presence or absence of a base to prepare the Compound (I-E-5).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; and mixtures thereof.

Examples of the catalyst include dimethylformamide.

Examples of the chlorinating agent include oxalyl chloride.

Examples of the base include alkylamines such as triethylamine and N,N-diisopropylethylamine; and organic bases such as pyridines such as pyridine and 4-diethylaminopyridine, and 1,8-diazabicyclo[5.4.0]-7-undecene.

The amount of the Compound (I-E-6) to be used may be 1.0 to 5.0 molar equivalent(s), preferably 1.0 to 2.0 molar equivalent(s), relative to the Compound (I-E-7).

The amount of the catalyst to be used may be 0.01 to 0.1 molar equivalent, preferably 0.03 to 0.06 molar equivalent, relative to the Compound (I-E-7).

The amount of the chlorinating agent to be used may be 1.0 to 5.0 molar equivalent(s), preferably 1.0 to 2.0 molar equivalent(s), relative to the Compound (I-E-7).

The amount of the base to be used may be 1.0 to 5.0 molar equivalent(s), preferably 1.0 to 2.0 molar equivalent(s), relative to the Compound (I-E-7).

The reaction may be carried out at room temperature to under heating, for example at room temperature to 100° C., preferably at room temperature.

Step 2

The Compound (I-E-4) may be a commercially available material, or may be prepared from commercially available material(s) according to known method(s), or may also be in a salt form such as hydrochloride.

The Compound (I-E-5) may be reacted with the Compound (I-E-4) in a solvent, in the presence or absence of a dehydrating agent, and in the presence or absence of sodium acetate, and then may be treated with a reducing agent in the presence or absence of an acid to prepare the Compound (I-E-3).

The solvent may be any one which does not affect the reaction, and examples thereof include amides such as N,N-dimethylformamide; halogenated aliphatic hydrocarbons such as chloroform and dichloromethane; aromatic hydrocarbons such as toluene; nitriles such as acetonitrile; and mixtures thereof.

Examples of the dehydrating agent include magnesium sulfate and a molecular sieve.

Examples of the acid include acetic acid.

Examples of the reducing agent include sodium triacetoxyborohydride and sodium borohydride.

The amount of the Compound (I-E-4) to be used may be 1.0 to 5.0 molar equivalent(s), preferably 1.0 to 2.0 molar equivalent(s), relative to the Compound (I-E-5).

The amount of the dehydrating agent to be used may be 1.0 to 5.0 molar equivalent(s), preferably 1.0 to 2.0 molar equivalent(s), relative to the Compound (I-E-5).

The amount of the sodium acetate to be used may be 1.0 to 5.0 molar equivalent(s), preferably 1.0 to 2.0 molar equivalent(s), relative to the Compound (I-E-5).

The amount of the acid to be used may be 1.0 to 5.0 molar equivalent(s), preferably 1.0 to 2.0 molar equivalent(s), relative to the Compound (I-E-5).

The amount of the reducing agent to be used may be 1.0 to 5.0 molar equivalent(s), preferably 1.0 to 2.0 molar equivalent(s), relative to the Compound (I-E-5).

The reaction may be carried out at room temperature to under heating, for example at room temperature to 150° C., preferably at room temperature.

Production Method F

Among the compound represented by formula (I), the Compound (I-F) wherein $X^1$ represents —$NG^{11}$-$SO_2$—, $X^2$ represents —$SO_2$—$NG^{12}$-, $Y^1$ represents —$NG^{21}$-$L^{11}$-C(=O)—, and $Y^2$ represents —C(=O)-$L^{12}$-$NG^{22}$- may also be prepared according to, for example, the following scheme.

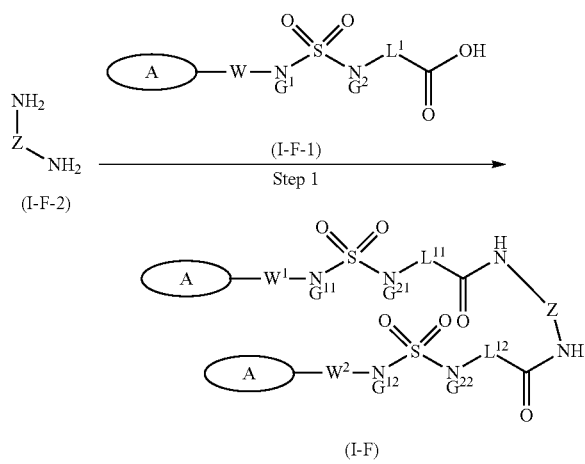

[wherein the symbols have the same meanings as those described above.]

Step 1

The Compound (I-F-2) may be a commercially available material, or may be prepared according to known method(s) from commercially available material(s).

The Compound (I-F-2) may be reacted with the Compound (i-F-1) in a solvent, in the presence or absence of a base, in the presence of a condensing agent, and in the presence or absence of an activating agent to prepare the Compound (I-F).

The solvent may be any one which does not affect the reaction, and examples thereof include amides such as N,N-dimethylformamide; halogenated aliphatic hydrocarbons such as chloroform and dichloromethane; aromatic hydrocarbons such as toluene; nitriles such as acetonitrile; carboxylic acids such as acetic acid; water; and mixtures thereof.

Examples of the base include alkali metal carbonates such a cesium carbonate, potassium carbonate, sodium carbonate, and sodium hydrogen carbonate; alkali metal phosphates such as tribasic potassium phosphate, sodium phosphate, and sodium hydrogen phosphate; amines such as triethylamine and N,N-disopropylethylamine; and alkali metal fluorides such as cesium fluoride and potassium fluoride.

Examples of the condensing agent include O-(7-azabenzotriazol-1-yl)-N,N, N',N'-tetramethyluronium hexafluorophosphate, 1-(3-dimethylaminopropyl)-3-ethylcarbodiimide hydrochloride, (1-cyano-2-ethoxy-2-oxoethylideneaminooxy)dimethylamino(morpholino)carbenium hexafluorophosphate (COMU), and mixtures thereof.

Examples of the activating agent include tert-butyl peroxide, 1-hydroxy-7-azabenzotriazol (HOAt), 1-hydroxybenzotriazole (HOBt), and 4-dimethylaminopyridine.

The amount of the Compound (I-F-1) to be used may be 2.0 to 5.0 molar equivalents, preferably 2.0 to 3.0 molar equivalents, relative to the Compound (I-F-2).

The amount of the base to be used may be 2.0 to 6-0 molar equivalents, preferably 2.0 to 4.0 molar equivalents, relative to the Compound (I-F-2).

The amount of the condensing agent to be used may be 2.0 to 5.0 molar equivalents, preferably 2.0 to 3.0 molar equivalents, relative to the Compound (I-F-2).

The amount of the activating agent to be used may be 2.0 to 5.0 molar equivalents, preferably 2.0 to 3.0 molar equivalents, relative to the Compound (I-F-2).

The reaction may be carried out at room temperature to under heating, for example at room temperature to 100° C., preferably at room temperature.

Step 2

When protecting group(s) is/are present in the Compound (I-F), the protecting group(s) may be deprotected according to similar method(s) to the method(s) described in the Step 5-1 and/or Step 5-2 of the Production method A.

The compound prepared in the Step 1 or Step 2 may be reacted with an acid such as hydrochloric acid and trifluoroacetic acid according to known method(s) to prepare an acid addition salt such as hydrochloride and trifluoroacetate.

The amount of the acid to be used may be 2.0 to 20.0 molar equivalents, preferably 2.0 to 15.0 molar equivalents, relative to the compound prepared in the Step 1 or Step 2.

Production Method F-1 (Production of Intermediate Compound)

Among the Compound (I-F-1), the Compound (I-F-1')

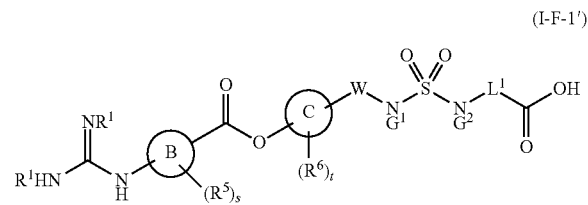

[wherein the symbols have the same meanings as those described above.]
may be prepared according to, for example, the following scheme.

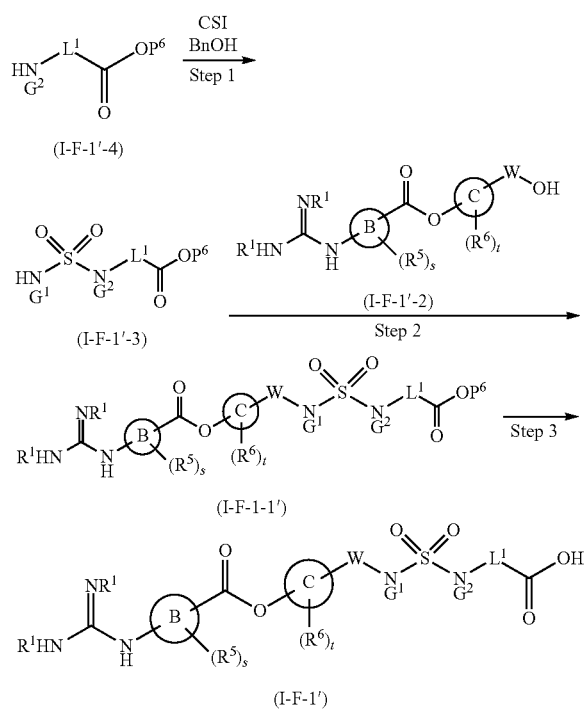

[wherein P⁶ represents a protecting group such as a 2-trimethylsilylethyl group; and the other symbols have the same meanings as those described above.]

Step 1

The Compound (I-F-1'-4) may be prepared according to the same manner as the Compound (I-D-4).

The Compound (I-F-1'-4) may be reacted in a solvent and in the presence of a base and benzyl N-chlorosulfonylcarbamate which is a compound prepared by reacting chlorosulfonyl isocyanate (CSI) with benzyl alcohol (BnOH) to prepare the Compound (I-F-1'-3).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; and mixtures thereof.

Examples of the base include alkylamines such as triethylamine and N,N-diisopropylethylamine; and organic bases such as pyridines such as pyridine and 4-dimethylaminopyridine, and 1,8-diazabicyclo[5.4.0]-7-undecene.

The amount of the base to be used may be 1.0 to 5.0 molar equivalent(s), preferably 1.0 to 3.5 molar equivalent(s), relative to the Compound (I-F-1'-4).

The amount of the chlorosulfonyl isocyanate to be used may be 1.0 to 5.0 molar equivalent(s), preferably 1.0 to 2.0 molar equivalent(s), relative to the Compound (I-F-1'-4).

The amount of the benzyl alcohol to be used may be 1.0 to 5.0 molar equivalent(s), preferably 1.0 to 2.0 molar equivalent(s), relative to the Compound (I-F-1'-4).

The reaction may be carried out at room temperature to under heating, for example at room temperature to 100° C., preferably at room temperature.

Step 2

The Compound (I-F-1'-2) may be prepared according to the same manner as the Compound (I-A-1').

The Compound (I-F-1'-3) may be reacted with the Compound (1-F-1'-2) in a solvent and in the presence of an azodicarboxylic acid derivative and a phosphine derivative to prepare the Compound (I-F-1'-1).

The solvent may be any one which does not affect the reaction, and examples thereof include ethers such as tetrahydrofuran and dioxane; aromatic hydrocarbons such as toluene; nitriles such as acetonitrile; and mixtures thereof.

Examples of the azodicarboxylic acid derivative include azodicarboxylic acid dialkyl esters such as diethyl azodicarboxylate and diisopropyl azodicarboxylate; and azodicarboxamides such as 1,1'-azobis(N,N-dimethylformamide) Examples of the phosphine derivative include triarylphosphines such as triphenylphosphine; and trialkylphosphines such as tributylphosphine.

The amount of the Compound (I-F-1'-2) to be used may be 1.0 to 5.0 molar equivalent(s), preferably 1.0 to 2.0 molar equivalent(s), relative to the Compound (I-F-1'-3).

The amount of the azodicarboxylic acid derivative to be used may be 1.0 to 5.0 molar equivalent(s), preferably 1.0 to 2.0 molar equivalent(s), relative to the Compound (I-F-1'-3).

The amount of the phosphine derivative to be used may be 1.0 to 5.0 molar equivalent(s), preferably 1.0 to 2.0 molar equivalent(s), relative to the Compound (I-F-1'-3).

The reaction may be carried out at room temperature to under heating, for example at room temperature to 100° C., preferably at room temperature.

Step 3

The Compound (I-F-1'-1) may be reacted according to a similar method to the Step 2 of the Production method D-1 to prepare the Compound (I-F-1').

Production Method G

Among the compound represented by formula (I), the Compound (I-G) wherein $X^1$ represents —C(=O)—, $X^2$ represents —C(=O)—, $Y^1$ represents —NG²¹-, and $Y^2$ represents —NG²²- may be prepared according to, for example, the following scheme.

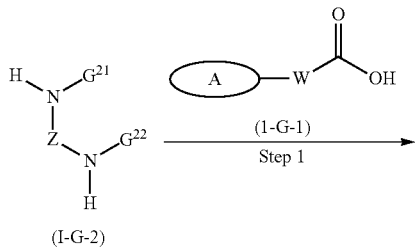

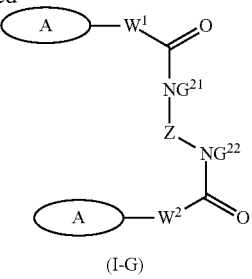

(I-G)

[wherein the symbols have the same meanings as those described above.]

Step 1

The Compound (I-G-2) may be prepared according to the same manner as the Compound (I-A-3).

The Compound (I-G-2) may be reacted with the Compound (1-G-1) in a solvent, in the presence or absence of a base, in the presence of a condensing agent, and in the presence or absence of an activating agent to prepare the Compound (I-G).

The solvent may be any one which does not affect the reaction, and examples thereof include aides such as N,N-dimethylformamide; ethers such as tetrahydrofuran and dioxane; halogenated aliphatic hydrocarbons such as chloroform and dichloromethane; aromatic hydrocarbons such as toluene; nitriles such as aceronitrile; carboxylic acids such as acetic acid; water; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; amines such as triethylamine and N,N-diisopropylethylamine; and alkali metal fluorides such as cesium fluoride and potassium fluoride.

Examples of the condensing agent include O-(7-azabenzotriazol-1-yl)-N,N,N',N'-tetramethyluronium hexafluorophosphate, 1-(3-dimethylaminopropyl)-3-ethylcarbodiimide hydrochloride, (1-cyano-2-ethoxy-2-oxoethylideneaminooxy)dimethylamino(morpholino)carbenium hexafluorophosphate (COMU), and 4-(4,6-dimethoxy-1,3,5-triazin-2-yl)-4-methylmorpholinium chloride.

Examples of the activating agent include tert-butyl peroxide, 1-hydroxy-7-azabenzotriazol (HOAt), 1-hydroxybenzotriazol (HOBt), and 4-dimethylaminopyridine.

The amount of the Compound (I-G-1) to be used may be 2.0 to 5.0 molar equivalents, preferably 2.0 to 3.5 molar equivalents, relative to the Compound (I-G-2).

The amount of the base to be used may be 2.0 to 10.0 molar equivalents, preferably 2.0 to 7.0 molar equivalents, relative to the Compound (I-G-2).

The amount of the condensing agent to be used may be 2.0 to 10.0 molar equivalents, preferably 2.0 to 7.0 molar equivalents, relative to the Compound (I-G-2).

The amount of the activating agent to be used may be 2.0 to 5.0 molar equivalents, preferably 2.0 to 3.0 molar equivalents, relative to the Compound (I-G-2).

The reaction may be carried out at room temperature to under heating, for example at room temperature to 100° C., preferably at room temperature.

Step 2

When protecting group(s) is/are present in the Compound (I-G), the protecting group(s) may be deprotected according to similar method(s) to the method(s) described in the Step 5-1 and/or Step 5-2 of the Production method A.

The compound prepared in the Step 1 or Step 2 may be reacted with an acid such as hydrochloric acid, formic acid, and trifluoroacetic acid according to known method(s) to prepare an acid addition salt such as hydrochloride, formate, and trifluoroacetate.

The amount of the acid to be used may be 2.0 to 20.0 molar equivalents, preferably 2.0 to 15.0 molar equivalents, relative to the compound prepared in the Step 1 or Step 2.

Production Method G (Alternative Method)

The Compound (I-G) may also be prepared by reacting the Compound (I-G-2) with the Compound (I-G'-1) according to a similar method to the Step 1 to prepare the Compound (I-G'), and then the Compound (I-G') may be reacted according to similar methods to the Steps 4 and 5 of the following Production method H.

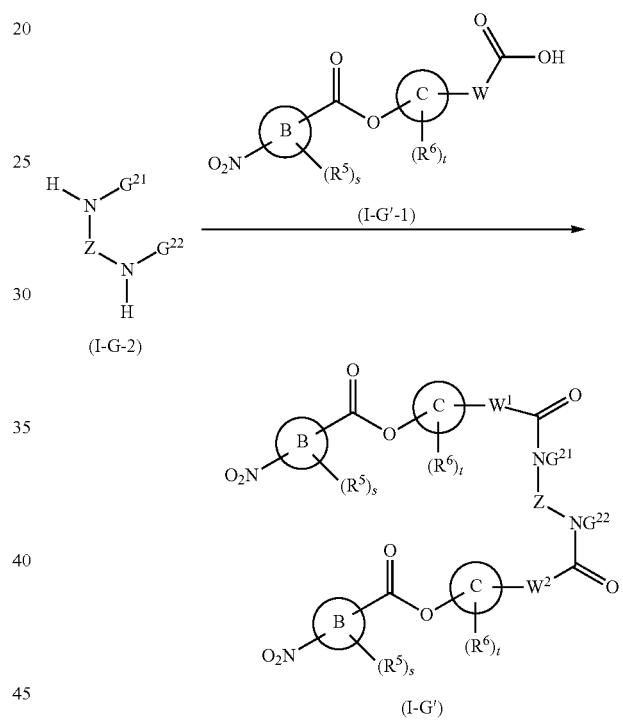

[wherein the symbols have the same meanings as those described above.]

The Compound (I-G-1') may be a commercially available material, or may be prepared according to known method(s) from commercially available material(s).

Production Method G-1 (Production of Intermediate Compound)

Among the Compound (I-G-1), the Compound (I-G-1')

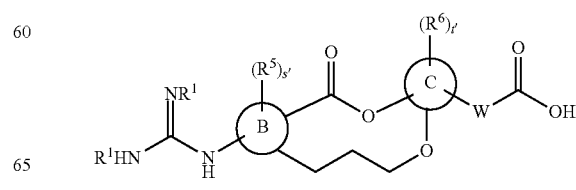

[wherein s' and t' each independently represent an integer of 0 to 3; and the other symbols have the same meanings as those described above.]

may be prepared according to, for example, the following scheme.

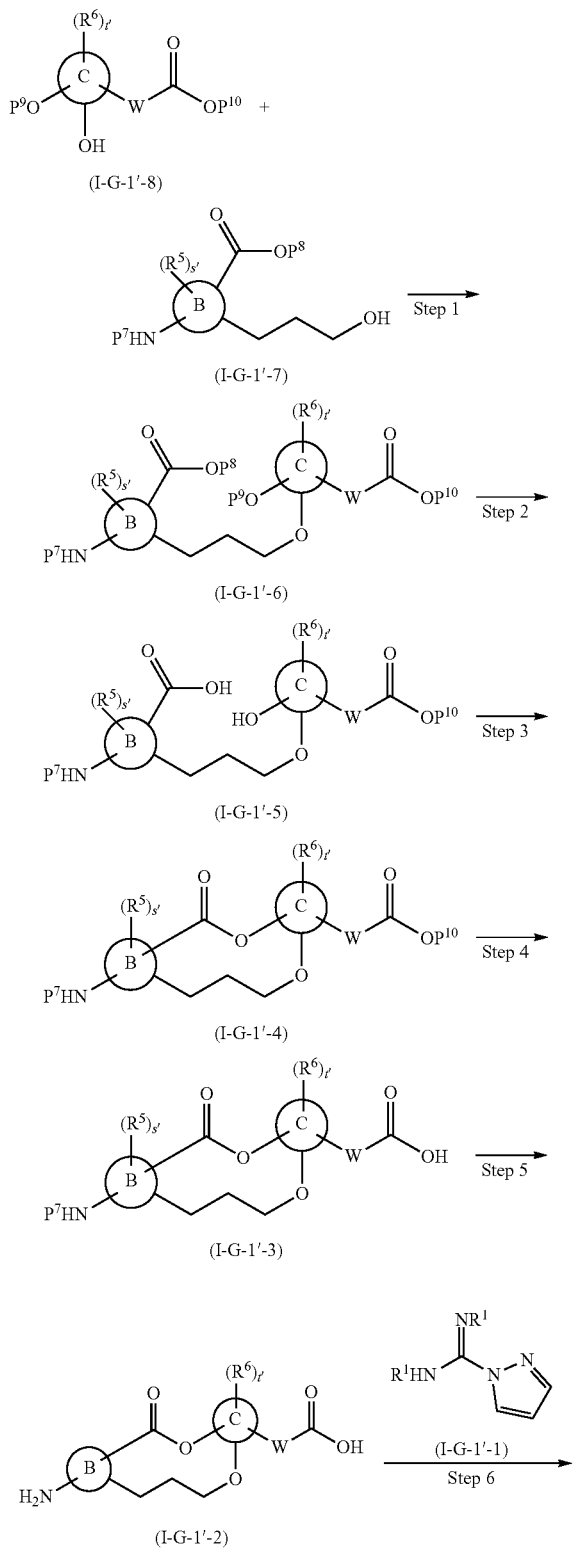

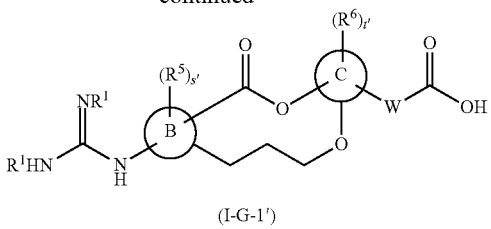

[wherein $P^7$ represents a protecting group such as a tert-butoxycarbonyl group; $P^8$ represents a protecting group such as a benzyl group; $P^9$ represents a protecting group such as a benzyl group; $P^{10}$ represents a protecting group such as a 2-trimethylsilylethyl group; and the other symbols have the same meanings as those described above.]

Step 1

The Compound (I-G-1'-8) may be reacted with the Compound (I-G-1'-7) in a solvent and in the presence of an azodicarboxylic acid derivative and a phosphine derivative to prepare the Compound (I-G-1'-6).

The solvent may be any one which does not affect the reaction, and examples thereof include ethers such as tetrahydrofuran and dioxane; aromatic hydrocarbons such as toluene; nitriles such as acetonitrile; and mixtures thereof.

Examples of the azodicarboxylic acid derivative include azodicarboxylic acid dialkyl esters such as diethyl azodicarboxylate and diisopropyl azodicarboxylate; and azodicarboxamides such as 1,1'-azobis(N,N-dimethylformamide).

Examples of the phosphine derivative include triarylphosphines such as triphenylphosphine; and trialkylphosphines such as tributylphosphine.

The amount of the Compound (I-G-1'-7) to be used may be 0.9 to 5.0 molar equivalent (s), preferably 0.9 to 2.0 molar equivalent (s), relative to the Compound (I-G-1'-8).

The amount of the azodicarboxylic acid derivative to be used may be 1.0 to 5.0 molar equivalent(s), preferably 1.0 to 3.0 molar equivalent(s), relative to the Compound (I-G-1'-8).

The amount of the phosphine derivative to be used may be 1.0 to 5.0 molar equivalent(s), preferably 1.0 to 3.0 molar equivalent(s), relative to the Compound (I-G-1'-8).

The reaction may be carried out at room temperature to under heating, for example at room temperature to 100° C., preferably at room temperature.

Step 2

The Compound (I-G-1'-6) may be reacted according to a similar method to the Step 5-2 of the Production method A to prepare the Compound (I-G-1'-5)

Step 3

The Compound (I-G-1'-5) may be treated with a condensing agent in a solvent and in the presence or absence of a base to prepare the Compound (I-G-1'-4).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; heterocyclic aromatic compounds such as pyridine; nitriles such as acetonitrile; carboxylic acids such as acetic acid; water; and mixtures thereof.

Examples of the case include alkali metal hydrogen carbonates such as sodium hydrogen carbonate; alkali metal carbonates such as potassium carbonate; inorganic bases such as alkali metal hydroxides such as sodium hydroxide; alkylamines such as triethylamine and N,N-diisopropylethylamine; and organic bases such as pyridines such as pyridine and 4-dimethylaminopyridine, and 1,8-diazabicyclo [5.4.0]-7-undecene.

Examples of the condensing agent include O-(7-azabenzotriazol-1-yl)-N,N,N',N'-tetramethyluronium hexafluorophosphate and 1-(3-dimethylaminopropyl)-3-ethylcarbodiimide hydrochloride.

The amount of the base to be used may be 1.0 to 5.0 molar equivalent(s), preferably 1.0 to 2.0 molar equivalent(s), relative to the Compound (I-G-1'-5).

The amount of the condensing agent to be used may be 1.0 to 5.0 molar equivalent(s), preferably 1.0 to 2.0 molar equivalent(s), relative to the Compound (I-G-1'-5).

The reaction may be carried out at room temperature to under heating, for example at room temperature to 100° C., preferably at room temperature.
Step 4

The Compound (I-G-1'-4) may be reacted according to a similar method to the Step 2 of the Production method D-1 to prepare the Compound (I-G-1'-3).
Step 5

The Compound (I-G-1'-3) may be reacted with an acid in a solvent to prepare the Compound (I-G-1'-2). The Compound (I-G-1'-2) may also be in a salt form such as hydrochloride.

The solvent may be any one which does not affect the reaction, and examples thereof include ethers such as tetrahydrofuran and dioxane; aromatic hydrocarbons such as toluene; nitriles such as acetonitrile; and mixtures thereof.

Examples of the acid include a solution of hydrogen chloride in cyclopentyl methyl ether.

The amount of the acid to be used may be 1 to 20 molar equivalent(s), preferably 5 to 15 molar equivalents, relative to the Compound (I-G-1'-3).
Step 6

The Compound (I-G-1'-1) may be a commercially available material, or may be prepared according to known method(s) from commercially available material(s).

The Compound (I-G-1'-2) may be reacted with the Compound (I-G-1'-1) in a solvent and in the presence of a base to prepare the Compound (I-G-1').

The solvent may be any one which does not affect the reaction, and examples thereof include ethers such as tetrahydrofuran, dioxane, and cyclopentyl methyl ether; alcohols such as methanol, ethanol, isopropanol, and tert-butyl alcohol; aromatic hydrocarbons such as toluene; nitriles such as acetonitrile; water; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; amines such as triethylamine and N,N-diisopropylethylamine; and alkali metal fluorides such as cesium fluoride and potassium fluoride.

The amount of the Compound (I-G-1'-1) to be used may be 1.0 to 10.0 molar equivalent(s), preferably 2.0 to 5.0 molar equivalents, relative to the Compound (I-G-1'-2).

The amount of the base to be used may be 1.0 to 10.0 molar equivalent(s), preferably 3.0 to 7.0 molar equivalents, relative to the Compound (I-G-1'-2).

The reaction may be carried out at room temperature to under heating, for example at room temperature to 100° C., preferably at room temperature.

Production Method G-2 (Production of Intermediate Compound)

The Compound (I-G-1'-8) may be prepared according to, for example, the following scheme.

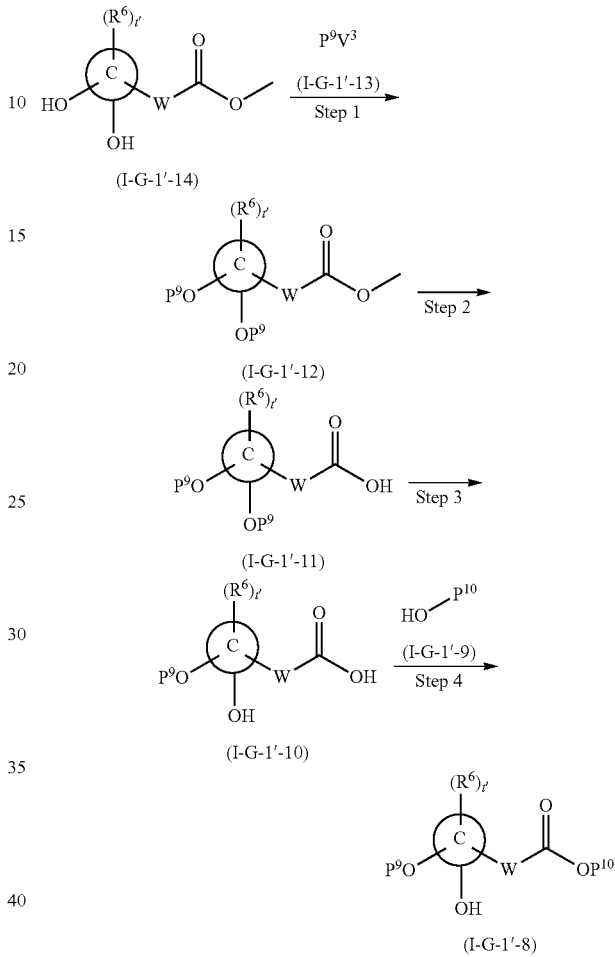

[wherein $V^3$ represents a halogen atom such as a bromine atom; and the other symbols have the same meanings as those described above.]
Step 1

The Compound (I-G-1'-13) and the Compound (I-G-1'-14) may be commercially available materials, or may be prepared according to known methods from commercially available materials.

The Compound (I-G-1'-14) may be reacted with the Compound (I-G-1'-13) in a solvent, in the presence of a base, and in the presence or absence of a catalyst to prepare the Compound (I-G-1'-12).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; alcohols such as methanol, ethanol, and isopropanol; ketones such as acetone, methyl ethyl ketone, and cyclohexanone; aromatic hydrocarbons such as toluene; nitriles such as acetonitrile; dimethyl sulfoxide; dimethylacetamide; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; amines such as triethylamine and N,N-diisopropylethylamine; and alkali metal fluorides such as cesium fluoride and potassium fluoride.

Examples of the catalyst include tetrabutylammonium bromide.

The amount of the Compound (I-G-1'-13) to be used may be 2.0 to 5.0 molar equivalents, preferably 2.0 to 3.0 molar equivalents, relative to the Compound (I-G-1'-14).

The amount of the base to be used may be 2.0 to 5.0 molar equivalents, preferably 3.0 to 4.0 molar equivalents, relative to the Compound (I-G-1'-14).

The amount of the catalyst to be used may be 0.01 to 1.0 molar equivalent, preferably 0.01 to 0.1 molar equivalent, relative to the Compound (I-G-1'-14).

The reaction may be carried out at room temperature to under heating, for example at room temperature to 100° C., preferably at room temperature.

Step 2

The Compound (I-G-1'-12) may be treated with a base in a solvent to prepare the Compound (I-G-1'-11).

The solvent may be any one which does not affect the reaction, and examples thereof include ethers such as tetrahydrofuran and dioxane; alcohols such as methanol, ethanol, and isopropanol; aromatic hydrocarbons such as toluene; nitriles such as acetonitrile; water; and mixtures thereof.

Examples of the base include alkali metal hydrogen carbonates such as sodium hydrogen carbonate; alkali metal carbonates such as potassium carbonate; inorganic bases such as alkali metal hydroxides such as sodium hydroxide; alkylamines such as triethylamine and N,N-diisopropylethylamine; and organic bases such as pyridines such as pyridine and 4-dimethylaminopyridine.

The amount of the base to be used may be 1.0 to 5.0 molar equivalent(s), preferably 2.0 to 3.0 molar equivalents, relative to the Compound (I-G-1'-12).

The reaction may be carried out at room temperature to under heating, for example at room temperature to 100° C., preferably at 40° C. to 100° C.

Step 3

The Compound (I-G-1'-11) may be treated with an amine in a solvent to prepare the Compound (I-G-1-10).

The solvent may be any one which does not affect the reaction, and examples thereof include amides such as N-methylpyrolidone and N,N-dimethylformamide (hereinafter also referred to as dimethylformamide); ethers such as tetrahydrofuran; nitriles such as acetonitrile; dimethyl sulfoxide; dimethylacetamide; and mixtures thereof.

Examples of the amine include pyrrolidine, piperidine, and morpholine.

The amount of the amine to be used may be 1.0 to 10.0 molar equivalent(s), preferably 3.0 to 6.0 molar equivalents, relative to the Compound (H-G-1'-11).

The reaction may be carried out at room temperature to under heating, for example at room temperature to 200° C., preferably an 100° C. so 200° C.

Step 4

The Compound (I-G-1'-10) may be reacted with the Compound (I-G-1'-9) in a solvent and in the presence of an azodicarboxylic acid derivative and a phosphine derivative to prepare the Compound (I-G-1'-8).

The solvent may be any one which does not affect the reaction, and examples thereof include ethers such as tetrahydrofuran and dioxane; aromatic hydrocarbons such as toluene; nitriles such as acetonitrile; and mixtures thereof.

Examples of the azodicarboxylic acid derivative include azodicarboxylic acid dialkyl esters such as diethyl azodicarboxylate and diisopropyl azodicarboxylate; and azodicarboxamides such as 1,1'-azobis(N,N-dimethylformamide).

Examples of the phosphine derivative include triarylphosphines such as triphenylphosphine; and trialkylphosphines such as tributylphosphine.

The amount of the Compound (I-G-1'-9) to be used may be 1.0 to 5.0 molar equivalent(s), preferably 2.0 to 3.0 molar equivalents, relative to the Compound (I-G-1'-10) The amount of the azodicarboxylic acid derivative to be used may be 1.0 to 5.0 molar equivalent(s), preferably 2.0 to 3.0 molar equivalents, relative to the Compound (I-G-1'-10).

The amount of the phosphine derivative to be used may be 1.0 to 5.0 molar equivalent(s), preferably 2.0 to 3.0 molar equivalents, relative to the Compound (I-G-1'-10).

The reaction may be carried out at room temperature to under heating, for example at room temperature to 100° C., preferably at room temperature.

Production Method G-3 (Production of Intermediate Compound)

The Compound (I-G-1'-7) may be prepared according to, for example, the following scheme.

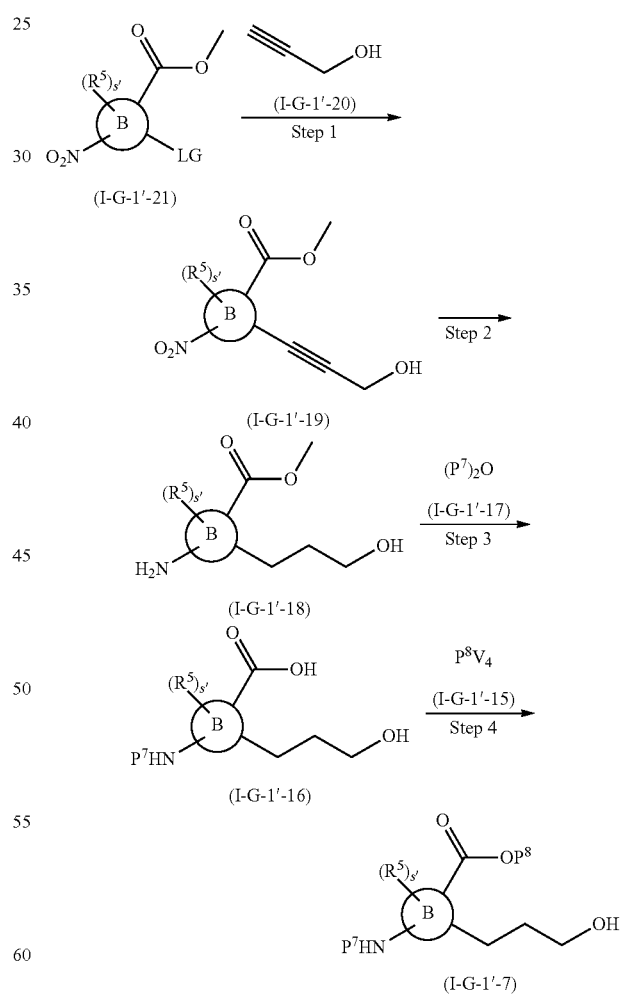

[wherein LG represents a leaving group such as a halogen atom such as a bromine atom; $V^4$ represents a halogen atom such as a bromine atom; and the other symbols have the same meanings as those described above.]

Step 1

The Compound (I-G-1'-20) and the Compound (I-G-1'-21) may be commercially available materials, or may be prepared according to known methods from commercially available materials.

The Compound (I-G-1'-21) may be reacted with the Compound (I-G-1'-20) in a solvent, in the presence of a base, in the presence of a Catalyst 1, in the presence or absence of an organic phosphine compound, and in the presence of a Catalyst 2 to prepare the Compound (I-G-1'-19).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; amines such as triethylamine and N,N-diisopropylethylamine; and alkali metal fluorides such as cesium fluoride and potassium fluoride.

Examples of the Catalyst 1 include palladium catalysts such as palladium(II) acetate, dichloro[1,1'-bis(diphenylphosphino)ferrocene]palladium, dichloro[1,1'-bis(diphenylphosphino)ferrocene]palladium dichloromethane adduct, tris(dibenzylideneacetone)dipalladium(0), tetrakistriphenylphosphinepalladium, and bis(triphenylphosphine)palladium dichloride.

Examples of the organic phosphine compound include triarylphosphines such as triphenylphosphine and tri(o-tolyl)phosphine; trialkylphosphines such as tri-tert-butylphosphine and tricyclohexylphosphine; and bidentate phosphines such as 1,1'-bis(diphenylphosphino)ferrocene and 4,5'-bis(diphenylphosphino)-9,9'-dimethylxanthine.

Examples of the Catalyst 2 include copper(I) iodide and iron(III) acetylacetonate.

The amount of the Compound (I-G-1'-20) to be used may be 1.0 to 5.0 molar equivalent(s), preferably 2.0 to 3.0 molar equivalents, relative to the Compound (I-G-1'-21).

The amount of the base to be used may be 1.0 to 5.0 molar equivalent(s), preferably 1.0 to 2.0 molar equivalent(s), relative to the Compound (I-G-1'-21).

The amount of the Catalyst 1 to be used may be 0.01 to 1.0 molar equivalent, preferably 0.01 to 0.1 molar equivalent, relative to the Compound (I-G-1'-21).

The amount of the organic phosphine compound to be used may be 0.01 to 1.0 molar equivalent, preferably 0.01 to 0.1 molar equivalent, relative to the Compound (I-G-1'-21).

The amount of the Catalyst 2 to be used may be 0.01 to 1.0 molar equivalent, preferably 0.01 to 0.1 molar equivalent, relative to the Compound (I-G-1'-21).

The reaction may be carried out at room temperature to under heating, for example at room temperature to 200° C., preferably at room temperature to 100° C.

Step 2

The Compound (I-G-1'-19) may be treated with a catalyst in a solvent and under hydrogen atmosphere to prepare the Compound (I-G-1'-18).

The solvent may be any one which does not affect the reaction, and examples thereof include ethers such as tetrahydrofuran and dioxane; alcohols such as methanol, ethanol, and isopropanol; aromatic hydrocarbons such as toluene; nitriles such as acetonitrile; carboxylic acids such as acetic acid; water; and mixtures thereof.

Examples of the catalyst include palladium carbon.

The amount of the catalyst to be used may be 0.01 to 20.0 molar equivalent(s), preferably 0.01 to 10.0 molar equivalent (s), relative to the Compound (I-G-1'-19).

The reaction may be carried out at room temperature to under heat ng, for example at room temperature to 100° C., preferably at room temperature.

Step 3

The Compound (I-G-1'-18) may be treated with a base and reacted with the Compound (I-G-1'-17) in a solvent to prepare the Compound (I-G-1'-6).

The solvent may be any one which does nor affect the reaction, and examples thereof include ethers such as tetrahydrofuran and dioxane; alcohols such as methanol, ethanol, and isopropanol; aromatic hydrocarbons such as toluene; nitriles such as acetonitrile; water; and mixtures thereof.

Examples of the base include alkali metal hydrogen carbonates such as sodium hydrogen carbonate; alkali metal carbonates such as potassium carbonate; inorganic bases such as alkali metal hydroxides such as sodium hydroxide.

The amount of the Compound (I-C-1'-17) to be used may be 1.0 to 5.0 molar equivalent(s), preferably 2.0 to 3.0 molar equivalents, relative to the Compound (I-G-1'-18).

The amount of the base to be used may be 1.0 to 5.0 molar equivalent(s), preferably 2.0 to 3.0 molar equivalents, relative to the Compound (I-G-1'-18).

The reaction may be carried out at room temperature to under heating, for example at room temperature to 100° C., preferably at room temperature to 60° C.

Step 4

The Compound (I-G-1'-16) may be reacted with the Compound (I-G-1'-15) in a solvent and in the presence of a base to prepare the Compound (I-G-1'-7).

The solvent may be any one which does not affect the reaction, and example thereof include amides such as N,N-dimethylformamide; ethers such as tetrahydrofuran an dioxane; halogenated aliphatic hydrocarbons such as chloroform and dichlorometnane; aromatic hydrocarbons such as toluene; nitriles such as acetonitrile; carboxylic acids such as acetic acid; water; and mixtures thereof.

Examples of the base include alkali metal hydrogen carbonates such as sodium hydrogen carbonate; alkali metal carbonates such as potassium carbonate; inorganic bases such as alkali metal hydroxides such as sodium hydroxide; alkylamines such as triethylamine and N,N-diisopropylethylamine; and organic bases such as pyridines such as pyridine and 4-dimethylaminopyridine.

The amount of the Compound (I-G-1'-15) to be used may be 1.0 to 5.0 molar equivalent(s), preferably 1.0 to 2.0 molar equivalent(s), relative to the Compound (I-G-1'-16).

The amount of the base to be used may be 1.0 to 5.0 molar equivalent(s), preferably 2.0 to 3.0 molar equivalents, relative to the Compound (I-G-1'-16).

The reaction may be carried out at room temperature to under heating, for example at room temperature to 100° C., preferably at room temperature.

Production Method H

Among the compound represented by formula (I), the Compound (I-H) wherein $R^1$ each represents a hydrogen atom, $X^1$ represents —$NG^{11}$-$SO_2$—, $X^2$ represents —$SO_2$—$NG^2$-, $Y^1$ represents —$NG^{21}$-, and $Y^2$ represents —$NG^{22}$- may be prepared according to, for example, the following scheme.

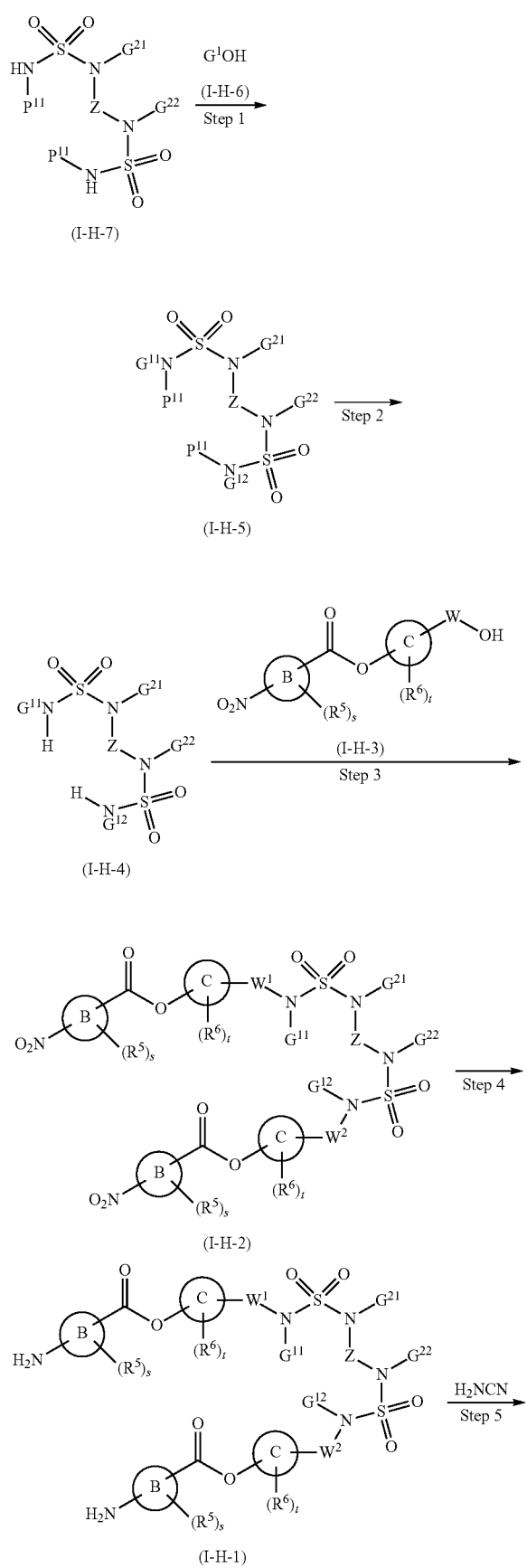
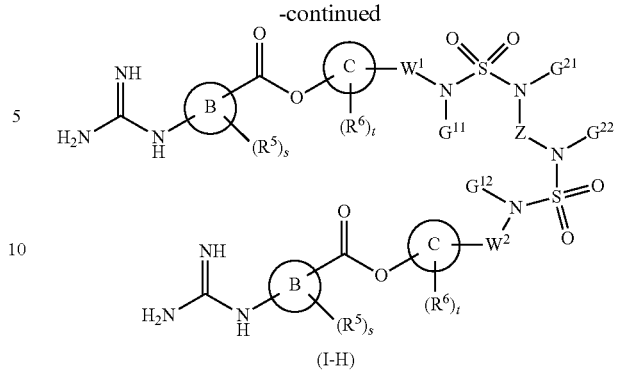

(I-H)

[wherein $P^{11}$ represents a protecting group such as a benzyloxycarbonyl group; and the other symbols have the same meanings as those described above.]

Step 1

The Compound (I-H-7) may be prepared according to the same manner as the Compound (I-A-2).

The Compound (I-H-6) may be a commercially available material, or may be prepared according to known method(s) from commercially available material(s).

The Compound (I-H-7) may be reacted with the Compound (I-H-6) in a solvent and in the presence of an azodicarboxylic acid derivative and a phosphine derivative to prepare the Compound (I-H-5).

The solvent may be any one which does not affect the reaction, and examples thereof include ethers such as tetrahydrofuran and dioxane; aromatic hydrocarbons such as toluene; nitriles such as acetonitrile; and mixtures thereof.

Examples of the azodicarboxylic acid derivative include azodicarboxylic acid dialkyl esters such as diethyl azodicarboxylate and diisopropyl azodicarboxylate; and azodicarboxamides such as 1,1'-azobis(N,N-dimethylformamide).

Examples of the phosphine derivative include triarylphosphines such as triphenylphosphine; and trialkylphosphines such as tributylphosphine.

The amount of the Compound (I-H-6) to be used may be 2.0 to 5.0 molar equivalents, preferably 2.0 to 3.0 molar equivalents, relative to the Compound (I-H-7).

The amount of the azodicarboxylic acid derivative to be used may be 2.0 to 6.0 molar equivalents, preferably 2.0 to 5.0 molar equivalents, relative to the Compound (I-H-7).

The amount of the phosphine derivative to be used may be 2.0 to 6.0 molar equivalents, preferably 2.0 to 5.0 molar equivalents, relative to the Compound (I-H-7).

The reaction may be carried out at room temperature to under heating, for example at room temperature to 100° C., preferably at room temperature.

Step 2

The Compound (I-H-5) may be reacted according to a similar method to the Step 5-2 of the Production method A to prepare the Compound (I-H-4).

Step 3

The Compound (I-H-3) may be a commercially available material, or may be prepared according to known method(s) from commercially available material(s).

The Compound (I-H-4) may be reacted with the Compound (I-H-3) in a solvent and in the presence of an azodicarboxylic acid derivative and a phosphine derivative to prepare the Compound (I-H-2).

The solvent may be any one which does not affect the reaction, and examples thereof include ethers such as tetrahydrofuran and dioxane; aromatic hydrocarbons such as toluene; nitriles such as acetonitrile; and mixtures thereof.

Examples of the azodicarboxylic acid derivative include azodicarboxylic acid dialkyl esters such as diethyl azodicarboxylate and diisopropyl azodicarboxylate; and azodicarboxamides such as 1,1'-azobis(N,N-dimethylformamide).

Examples of the phosphine derivative include triarylphosphines such as triphenylphosphine; and trialkylphosphines such as tributylphosphine.

The amount of the Compound (I-H-3) to be used may be 2.0 to 5.0 molar equivalents, preferably 2.0 to 3.0 molar equivalents, relative to the Compound (I-H-4).

The amount of the azodicarboxylic acid derivative to be used may be 2.0 to 6.0 molar equivalents, preferably 2.0 to 5.0 molar equivalents, relative to the Compound (I-H-4).

The amount of the phosphine derivative to be used may be 2.0 to 6.0 molar equivalents, preferably 2.0 to 5.0 molar equivalents, relative to the Compound (I-H-4).

The reaction may be carried out at room temperature to under heating, for example at room temperature to 100° C., preferably at room temperature.

Step 4-1

The Compound (I-H-2) may be reacted according to a similar method to the Step 2 of the Production method G-3 to prepare the Compound (I-H-1)

Step 4-21

The Compound (I-1) may be converted into hydrochloride, if necessary.

For example, the Compound (I-H-1) may be reacted with a solution of hydrogen chloride in cyclopentyl methyl ether or a solution of hydrogen chloride in dioxane to be converted into hydrochloride.

When the reaction is accompanied by the deprotection of tert-butoxycarbonyl group(s) in $G^{21}$ and $G^{22}$ of the Compound (I-H-1), the amount of the hydrogen chloride to be used may be 10 to 150 molar equivalents, preferably 20 to 100 molar equivalents, relative to the Compound (I-H-1).

The reaction may be carried out at room temperature to under heating, for example at room temperature to 100° C., preferably at room temperature.

Step 5

The Compound (I-H-1) may be reacted with cyanamide in a solvent and in the presence of an acid to prepare the Compound (I-H).

The solvent may be any one which does not affect the reaction, and examples thereof include ethers soon as tetrahydrofuran and dioxane; alcohols such as methanol, ethanol, isopropanol, and tert-butanol; aromatic hydrocarbons such as toluene; nitriles such as acetonitrile; carboxylic acids such as acetic acid; water; and mixtures thereof.

Examples of the acid include a solution of hydrogen chloride in dioxane and a solution of hydrogen chloride in cyclopentyl methyl ether.

The amount of the compound cyanamide to be used may be 3.0 to 15.0 molar equivalents, preferably 3.0 to 10.0 molar equivalents, relative to the Compound (I-H-1).

The amount of the acid to be used may be 2.0 to 15.0 molar equivalents, preferably 2.0 to 10.0 molar equivalents, relative to the Compound (I-H-1).

The reaction may be carried out at room temperature to under heating, for example at room temperature to 100° C., preferably at 50 to 100° C.

Production Method I

Among the compound represented by formula (I), the Compound (I-I) wherein $R^1$ each represents a hydrogen atom, $X^{1'}$ represents —$NG^Z$-$SO_2$—, $X^{2'}$ represents —$SO_2$— $NG^Z$-, $Y^{1'}$ represents —$NG^{21}H$, and $Y^{2'}$ represents $HNG^{22}$- may be prepared according to, for example, the following scheme.

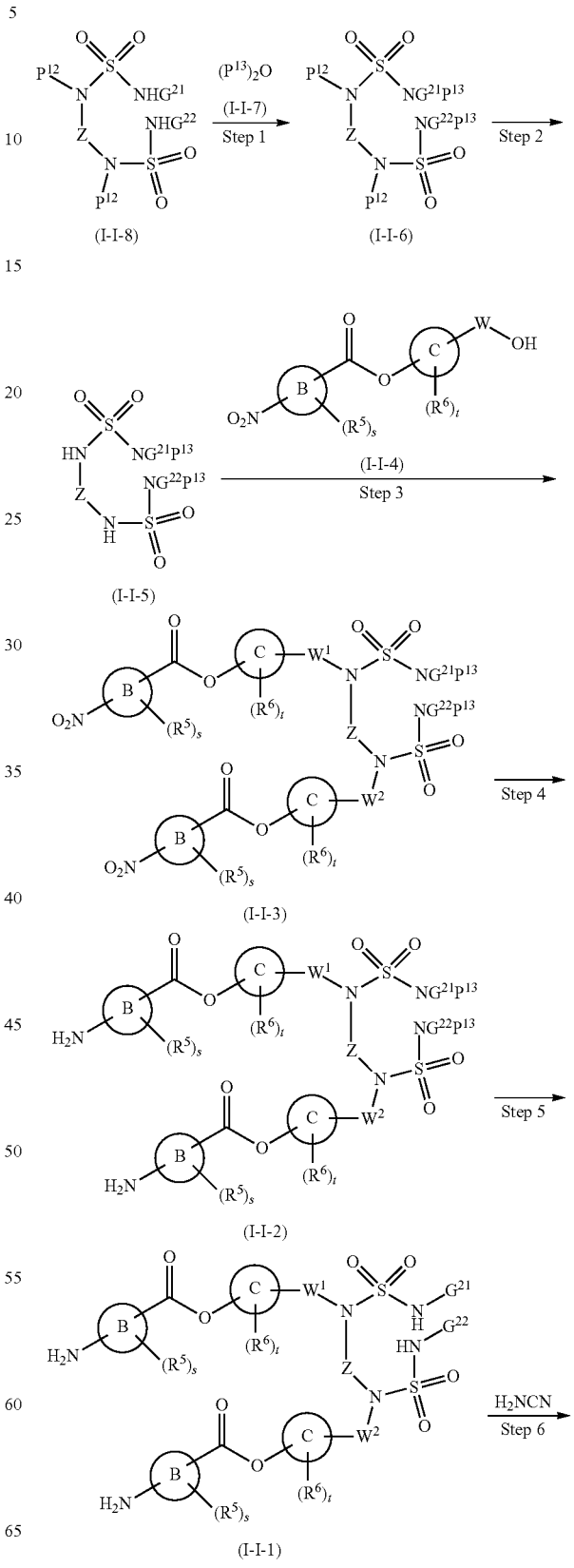

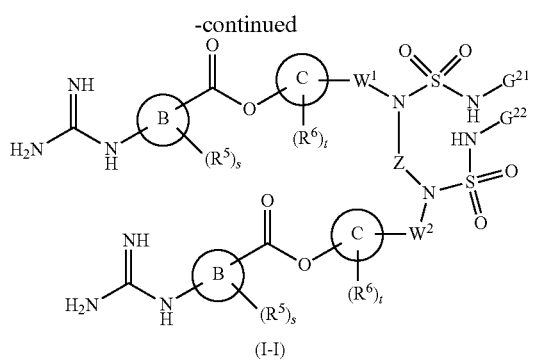

(I-I)

[wherein $P^{12}$ represents a protecting group such as a benzyloxycarbonyl group; $P^{13}$ represents a protecting group such as a tert-butoxycarbonyl group; and the other symbols have the same meanings as those described above.]

Step 1

The Compound (I-I-8) may be reacted with the Compound (I-I-7) in a solvent and in the presence of a base to prepare the Compound (I-I-6).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; and mixtures thereof.

Examples of the base include alkylamines such as triethylamine and N,N-diisopropylethylamine; and organic bases such as pyridines such as pyridine and 4-dimethylaminopyridine, and 1,8-diazabicyclo[5.4.0]-7-undecene.

The amount of the Compound (I-I-7) to be used may be 1.0 to 5.0 molar equivalent(s), preferably 1.0 to 3.0 molar equivalent(s), relative to the Compound (I-I-8).

The amount of the base to be used may be 2.0 to 5.0 molar equivalents, preferably 2.5 to 3.5 molar equivalents, relative to the Compound (I-I-8).

The reaction may be carried out at room temperature to under heating, for example at room temperature to 100° C., preferably at room temperature.

Step 2

The Compound (I-I-6) may be reacted according to a similar method to the Step 5-2 of the Production method A to prepare the Compound (I-I-5).

Step 3

The Compound (I-I-5) and the Compound (I-I-4) may be reacted according to a similar method to the Step 3 of the Production method H to prepare the Compound (I-I-3).

Step 4

The Compound (I-I-3) may be reacted according to a similar method to the Step 2 of the Production method G-3 to prepare the Compound (I-I-2).

Step 5

The Compound (I-I-2) may be reacted according to a similar method to the Step 4-2 of the Production method H to prepare the Compound (I-I-1).

Step 6

The Compound (I-I-1) may be reacted according to a similar method to the Step 5 of the Production method H to prepare the Compound (I-I).

Production Method I-1 (Production of Intermediate Compound)

The Compound (I-I-8) may be prepared according to, for example, the following scheme.

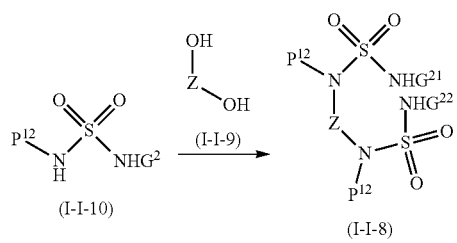

[wherein the symbols have the same meanings as those described above.]

The Compound (I-I-9) may be the same compound as the Compound (I-A-6).

The Compound (I-I-10) may be reacted with the Compound (I-I-9) in a solvent and in the presence of an azodicarboxylic acid derivative and a phosphine derivative to prepare the Compound (I-I-8).

The solvent may be any one which does not affect the reaction, and examples thereof include ethers such as tetrahydrofuran and dioxane; aromatic hydrocarbons such as toluene; nitriles such as acetonitrile; and mixtures thereof.

Examples of the azodicarboxylic acid derivative include azodicarboxylic acid dialkyl esters such as diethyl azodicarboxylate and diisopropyl azodicarboxylate; and azodicarboxamides such as 1,1'-azobis(N,N-dimethylformamide) Examples of the phosphine derivative include triarylphosphines such as triphenylphosphine; and trialkylphosphines such as tributylphosphine.

The amount of the Compound (I-I-9) to be used may be 0.3 to 0.5 molar equivalent, preferably 0.4 to 0.5 molar equivalent, relative to the Compound (I-I-10).

The amount of the azodicarboxylic acid derivative to be used may be 1.0 to 3.0 molar equivalent(s), preferably 1.0 to 2.0 molar equivalent(s), relative to the Compound (I-I-10).

The amount of the phosphine derivative to be used may be 1.0 to 3.0 molar equivalent(s), preferably 1.0 to 2.0 molar equivalent(s), relative to the Compound (I-I-10).

The reaction may be carried out at room temperature to under heating, for example at room temperature to 100° C., preferably at room temperature.

Production Method I-2 (Production of Intermediate Compound)

Among the Compound (I-I-10), the Compound (I-I-10') wherein $P^{12}$ represents a benzyloxycarbonyl group may be prepared according to, for example, the following scheme.

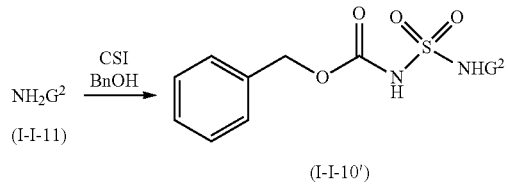

[wherein the symbols have the same meanings as those described above.]

The Compound (I-I-11) may be a commercially available material, or may be prepared according to known method(s)

from commercially available material(s). Also, the Compound (I-I-11) may be in a salt form such as hydrochloride.

The Compound (I-I-11) may be reacted with chlorosulfonyl isocyanate (CSI) and benzyl alcohol (BnOH) in a solvent and in the presence of a base to prepare the Compound (I-I-10').

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; and mixtures thereof.

Examples of the base include alkylamines such as triethylamine and N,N-diisopropylethylamine; and organic bases such as pyridines such as pyridine and 4-dimethylaminopyridine, and 1,8-diazabicyclo[5.4.0]-7-undecene.

The amount of the base to be used may be 1.0 to 5.0 molar equivalent(s), preferably 2.0 to 3.0 molar equivalents, relative to the Compound (I-I-11).

The amount of the chlorosulfonyl isocyanate to be used may be 1.0 to 3.0 molar equivalent(s), preferably 1.0 to 1.5 molar equivalent(s), relative to the Compound (I-I-11).

The amount of the benzyl alcohol to be used may be 1.0 to 3.0 molar equivalent(s), preferably 1.0 to 1.5 molar equivalent (s), relative to the Compound (I-I-11).

The reaction may be carried out at room temperature to under heating, for example at room temperature to 100° C., preferably at room temperature.

Production Method J

Among the compound represented by formula (I), the Compound (I-J) wherein $X^1$ represents —C(=O)—, $X^2$ represents —C(=O)—, $Y^1$ presents —$NG^{21}$-O—, and $Y^2$ represents —O-$L^3$-$NG^{22}$- may be prepared according so, for example, the following scheme.

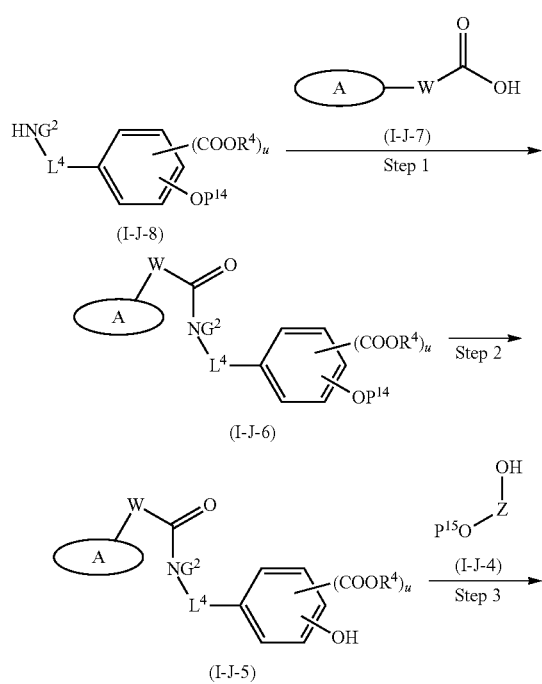

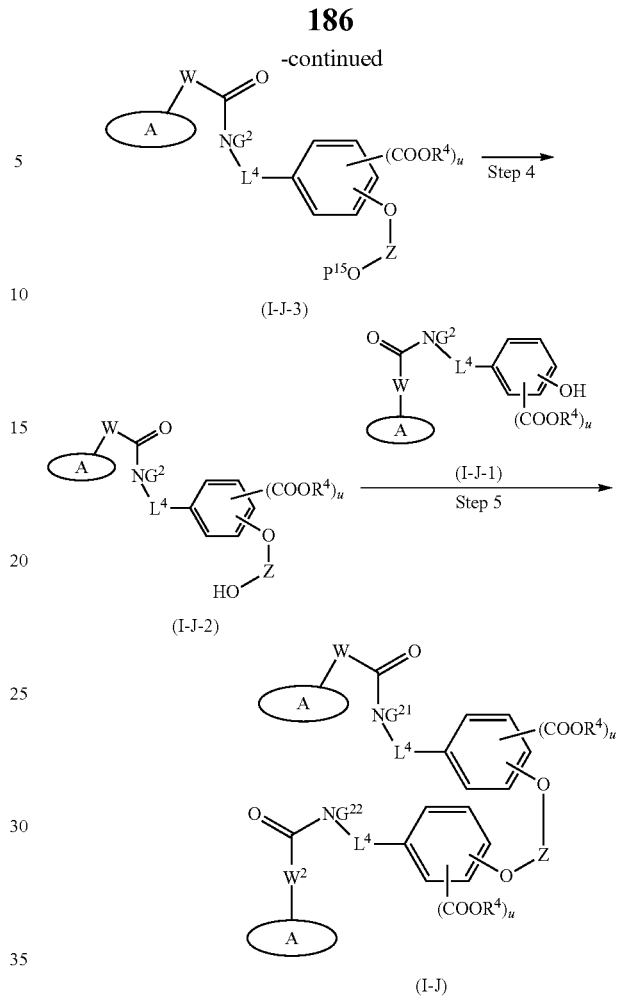

[wherein $L^4$ represents a $C_1$-$C_4$ alkylene group; $P^{14}$ and $P^{15}$ each independently represent a protecting group Such as a benzyl group; u represents an integer of 0 to 3; and the other symbols have the same meanings as those described above.

Step 1

The Compound (I-J-7) may be the same compound as the Compound (I-G-1).

The Compound (I-J-8) may be reacted with the Compound (I-J-7) in a solvent, in the presence or absence of a base, and in the presence of a condensing agent to prepare the Compound (I-J-6).

The solvent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; carboxylic acids such as acetic acid; water; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; amines such as triethylamine and N,N-diisopropylethylamine; and alkali metal fluorides such as cesium fluoride and potassium fluoride.

Examples of the condensing agent include O-(7-azabenzotriazol-1-yl)-N,N,N',N'-tetramethyluronium hexafluorophosphate, 1-(3-dimethylaminopropyl)-3-ethylcarbodiimide hydrochloride, (1-cyano-2-ethoxy-2-oxoethylideneaminooxy)dimethylamino(morpholino)carbenium hexafluorophosphate (COMU), and 4-(4,6-dimethoxy-1,3,5-triazin-2-yl)-4-methyl morpholinium chloride.

The amount of the Compound (I-J-7) to be used may be 1.0 to 3.0 molar equivalent(s), preferably 1.0 to 2.0 molar equivalent(s), relative to the Compound (I-J-8).

The amount of the base to be used may be 1.0 to 5.0 molar equivalent(s), preferably 2.0 to 4.0 molar equivalents, relative to the Compound (I-J-8).

The amount of the condensing agent to be used may be 1.0 to 5.0 molar equivalent(s), preferably 1.0 to 3.0 molar equivalent(s), relative to the Compound (I-J-8).

The reaction may be carried out at room temperature to under heating, for example at room temperature to 100° C., preferably at room temperature.

Step 2

The Compound (I-J-6) may be reacted according to a similar method to the Step 5-2 of the Production method A to prepare the Compound (I-J-5).

Step 2

The Compound (I-J-4) may be a commercially available a material, or may be prepared according to known method(s) from commercially available material(s).

The Compound (I-J-5) may be reacted with the Compound (I-J-4) in a solvent and in the presence of an azodicarboxylic acid derivative and a phosphine derivative to prepare the Compound (I-J-3).

The solvent may be any one which does not affect the reaction, and examples thereof include ethers such as tetrahydrofur n and dioxane; halogenated aliphatic hydrocarbons such as chloroform and dichloromethane; aromatic hydrocarbons such as toluene; nitriles such as acetonitrile; and mixtures thereof.

Examples of the azodicarboxylic acid derivative include azodicarboxylic acid dialkyl esters such as diethyl azodicarboxylate and diisopropyl azodicarboxylate; and azodicarboxamides such as 1,1'-azobis(N,N-dimethylformamide).

Examples of the phosphine derivative include triarylphosphines such as triphenylphosphine; and trialkylphosphines such as tributylphosphine.

The amount of the Compound (I-J-4) to be used may be 1.0 to 5.0 molar equivalent(s), preferably 1.0 to 2.0 molar equivalent(s), relative to the Compound (I-J-5).

The amount of the azodicarboxylic acid derivative to be used may be 1.0 to 50 molar equivalent (s), preferably 1.0 to 3.0 molar equivalent(s), relative to the Compound (I-J-5).

The amount of the phosphine derivative to be used may be 1.0 to 5.0 molar equivalent(s), preferably 1.0 to 3.0 molar equivalent(s), relative to the Compound (I-J-5).

The reaction may be carried out at room temperature to under heating, for example at room temperature to 100° C., preferably at room temperature.

Step 4

The Compound (I-J-3) may be reacted according to a similar method to the Step 5-2 of the Production method A to prepare the Compound (I-J-2).

Step 5

The Compound (I-J-1) may be the same compound as the Compound (I-J-5).

The Compound (I-J-2) may be reacted with the Compound (I-J-1) in a solvent and in the presence of an azodicarboxylic acid derivative and a phosphine derivative to prepare the Compound (I-J). The Compound (I-J) may also be in a salt form such as hydrochloride.

The solvent may be any one which does not affect the reaction, and examples thereof include ethers such as tetrahydrofuran and dioxane; halogenated aliphatic hydrocarbons such as chloroform and dichloromethane; aromatic hydrocarbons such as toluene; nitriles such as acetonitrile; and mixtures thereof.

Examples of the azodicarboxylic acid derivative include azodicarboxylic acid dialkyl esters such as diethyl azodicarboxylate and diisopropyl azodicarboxylate; and azodicarboxamides such as 1,1'-azobis(N,N-dimethylformamide).

Examples of the phosphine derivative include triarylphosphines such as triphenylphosphine; and trialkylphosphines such as tributylphosphine.

The amount of the Compound (I-J-1) to be used may be 1.0 to 5.0 molar equivalent(s), preferably 1.0 to 2.0 molar equivalent(s), relative to the Compound (I-J-2).

The amount of the azodicarboxylic acid derivative to be used may be 1.0 to 5.0 molar equivalent(s), preferably 1.0 to 3.0 molar equivalent(s), relative to the Compound (I-J-2).

The amount of the phosphine derivative to be used may be 1.0 to 5.0 molar equivalent(s), preferably 1.0 to 3.0 molar equivalent(s), relative to the Compound (I-J-2).

The reaction may be carried out at room temperature to under heating, for example at room temperature to 100° C., preferably at room temperature.

Step 6

Protecting group(s) present in the Compound (I-J) may be deprotected. For example, the Compound (I-J) may be reacted according to a similar method to the Step 5-1 of the Production method A or the Step 2 of the Production method D-1 to remove a protecting group such as a tert-butoxycarbonyl group and a 2-trimethylsilylethyl group.

Production Method J-1 (Production of Intermediate Compound)

Among the Compound (I-J-8), the Compound (I-J-8') having a COOR$^4$ group wherein R$^4$ represents a 2-trimethylsilylethyl group may be prepared according to, for example, the following scheme.

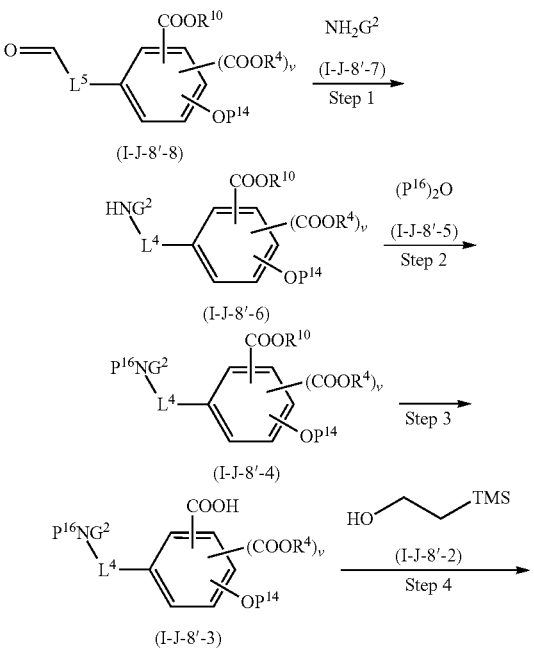

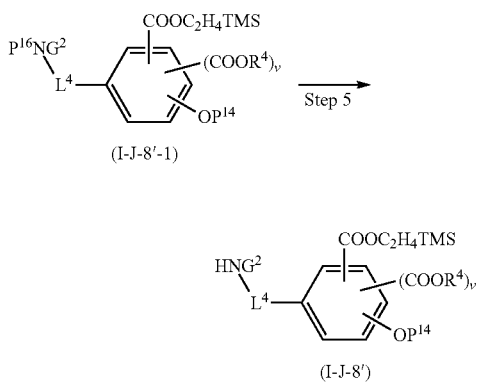

[wherein $L^5$ represents a single bond or a $C_1$-$C_3$ alkylene group; R represents a methyl group or an ethyl group; v represents an integer of 0 to 2; $P^{16}$ represents a protecting group such as a tert-butoxycarbonyl group; and the other symbols have the same meanings as those described above.]

Step 1

The Compound (I-J-8'-7) and the Compound (I-J-8'-8) may be commercially available materials, or may be prepared from commercially available materials according to known methods, or may also be in a salt form such as hydrochloride.

The Compound (I-J-8'-8) may be reacted with the Compound (I-J-8'-7) in a solvent, in the presence of a base, in the presence of an acid, and in the presence of a reducing agent to prepare the Compound (I-J-8'-6).

The solvent may be any one which does not affect the reaction, and examples thereof include amides such as N,N-dimethylformamide; halogenated aliphatic hydrocarbons such as chloroform and dichloromethane; aromatic hydrocarbons such as toluene; nitriles such as acetonitrile; and mixtures thereof.

Examples of the base include alkali metal carbonates such as cesium carbonate, potassium carbonate, sodium carbonate, and sodium hydrogen carbonate; alkali metal phosphates such as tribasic potassium phosphate, sodium phosphate, and sodium hydrogen phosphate; alkylamines such as triethylamine and N,N-diisopropylethylamine; organic bases such as pyridines such as pyridine and 4-dimethylaminopyridine, and 1,8-diazabicyclo[5.4.0]-7-undecene; and alkali metal fluorides such as cesium fluoride and potassium fluoride.

Examples of the acid include acetic acid.

Examples of the reducing agent include sodium triacetoxyborohydride and sodium borohydride.

The amount of the Compound (I-J-8'-7) to be used may be 1.0 to 5.0 molar equivalent(s), preferably 1.0 to 3.0 molar equivalent(s), relative to the Compound (I-J-8'-8).

The amount of the base to be used may be 1.0 to 5.0 molar equivalent(s), preferably 2.0 to 4.0 molar equivalents, relative to the Compound (I-J-8'-8).

The amount of the acid to be used may be 1.0 to 5.0 molar equivalent(s), preferably 2.0 to 4.0 molar equivalents, relative to the Compound (I-J-8'-8).

The amount of the reducing agent to be used may be 1.0 to 5.0 molar equivalent(s), preferably 2.0 to 4.0 molar equivalents, relative to the Compound (I-J-8'-8).

The reaction may be carried out at room temperature to under heating, for example at room temperature to 150° C., preferably at room temperature.

Step 2

The Compound (I-J-8'-5) and the Compound (I-J-8'-6) may be reacted according to a similar method to the Step 1 of the Production method I to prepare the Compound (I-J-8'-4).

Step 3

The Compound (I-J-8'-4) may be reacted with a base and an acid in a solvent to prepare the Compound (I-J-8'-3).

The solvent may be any one which does not affect the reaction, and examples thereof include ethers such as tetrahydrofuran and dioxane; alcohols such as methanol, ethanol, and isopropanol; water; and mixtures thereof.

Examples of the base include sodium hydroxide.

Examples of the acid include hydrochloric acid.

The amount of the base to be used may be 1.0 to 10.0 molar equivalent(s), preferably 2.0 to 5.0 molar equivalents, relative to the Compound (I-J-8'-4).

The amount of the acid to be used may be 1.0 to 10.0 molar equivalent(s), preferably 2.0 to 5.0 molar equivalents, relative to the Compound (I-J-8'-4).

The reaction may be carried out at room temperature to under heating, for example at room temperature to 150° C., preferably at room temperature.

Step 4

The Compound (I-J-8'-3) may be reacted with the Compound (I-J-8'-2) in a solvent, in the presence or absence of a base, and in the presence of a condensing agent to prepare the Compound (I-J-8-1).

The so-vent may be any one which does not affect the reaction, and examples thereof include amides such as N,N-dimethylformamide; ethers such as tetrahydrofuran and dioxane; halogenated aliphatic hydrocarbons such as chloroform and dichloromethane; aromatic hydrocarbons such as toluene; nitriles such as acetonitrile; and Mixtures thereof.

Examples of the base include alkali metal hydrogen carbonates such as sodium hydrogen carbonate; alkali metal carbonates such as potassium carbonate; inorganic bases such as alkali metal hydroxides such as sodium hydroxide; alkylamines such as triethylamine and N,N-diisopropylethylamine; and organic bases such as pyridines such as pyridine and 4-dimethylaminopyridine, and 1,8-diazabicyclo[5.4.0]-7-undecene.

Examples of the condensing agent include O-(7-azabenzotriazol-yl)-N,N,N',N'-tetramethyluronium hexafluorophosphate and 1-(3-dimethylaminopropyl)-3-ethylcarbodiimide hydrochloride.

The amount of the Compound (I-J-8'-2) to be used may be 1.0 to 3.0 molar equivalent(s), preferably 1.0 to 2.0 molar equivalent (s), relative to the Compound (I-J-8'-3).

The amount of the base to be used may be 0.1 to 3.0 molar equivalent(s), preferably 0.1 to 1.0 molar equivalent, relative to the Compound (I-J-8'-3).

The amount of the condensing agent to be used nay be 1.0 to 5.0 molar equivalent(s), preferably 1.0 to 2.0 molar equivalent(s), relative to the Compound (I-J-8'-3).

The reaction may be carried out at room temperature to under heating, for example at room temperature to 100° C., preferably at room temperature.

Step 5

The Compound (I-J-8'-1) may be reacted according to a similar method to the Step 5-1 of the Production method A to prepare the Compound (I-J-8').

The resulting target compound may be separated or purified if necessary, by appropriately combining conventional method(s) such as recrystallization, reprecipitation, filtration, concentration, and drying, or methods usually used in the separation or purification of organic compounds (for example, column chromatography).

The compounds of the present invention and the intermediate compounds may be produced according to the above Production methods, as well as the methods described in the following Examples and Reference Examples. Further, the compounds of the present invention and the intermediate compounds may be converted into other target compounds and intermediate compounds by the above Production methods, methods described in the following Examples and Reference Examples, and/or known methods, or combined methods thereof. Examples of such methods include the methods described in the following (1) to (5).

(1) Conversion of Alkoxycarbonyl Group into Benzyloxycarbonyl Group

A compound having an alkoxycarbonyl group may be reacted with benzyl alcohol under heating to be converted into a benzyloxycarbonyl group.

(2) Conversion of Alkoxycarbonyl Group into Carboxy Group

A compound having an alkoxycarbonyl group may be treated with a base (for example, sodium hydroxide) or an acid (for example, sulfuric acid) in a solvent (for example, tetrahydrofuran and methanol) to prepare a compound having a corresponding carboxy group.

(3) Conversion of Carboxy Group into Alkoxycarbonyl Group

A compound having a carboxy group may be reacted with an alcohol (for example, methanol and ethanol) in the presence of an acid (for example, sulfuric acid) or a base (for example, sodium hydroxide) to prepare a compound having an alkoxycarbonyl group.

(4) Conversion of Carboxy Group into Benzyloxycarbonyl Group

A compound having a carboxy group may be reacted with benzyl alcohol in a solvent (for example, chloroform), in the presence of an activating agent (for example, 4-dimethylaminopyridine), and in the presence of a condensing agent (for example, 1-(3-dimethylaminopropyl)-3-ethylcarbodiimidehydrochloride; to prepare a compound having a corresponding benzyloxycarbonyl group. Alternatively, a compound having a carboxy group may be reacted with a halogenated benzyl (for example, benzyl bromide) in a solvent (for example, dimethylformamide) and in the presence of a base (for example, cesium carbonate) to prepare a compound having a corresponding benzyloxycarbonyl group.

(5) Transesterification Reaction of Alkoxycarbonyl Group

A compound having an alkoxycarbonyl group may be reacted with an alcohol (for example, methanol and ethanol) in the presence of an acid (for example, sulfuric acid) or a base (for example, sodium hydroxide) to prepare a compound having a different alkoxycarbonyl group.

Further, other compounds of the present invention or the intermediate compounds may be prepared by using different starting materials from the starting materials described in the above Production methods, and the following Examples and Reference Examples, and by using the above Production methods, methods described in the following Examples and Reference Examples, and/or known methods, or combined methods thereof.

EXAMPLES

Hereinafter, the present invention is illustrated more in detail by way of Examples, Reference Examples, and Pharmacological Test Examples of the compounds or pharmaceutically acceptable salts thereof of the embodiments of the present invention. These Examples are provided for a better understanding of the present invention, and do not limit the scone of the present invention.

"DIOL silica gel" in silica gel column chromatography refers to CHROMATOREX (trade name) DIOL manufactured by Fuji Silysia Chemical Ltd.

"DNH silica gel" in silica gel column chromatography refers to CHROMATOREX (trade name) DNH manufactured by Fuji Silysia Chemical Ltd.

"DUIS" in the ionization mode of mass spectrum refers to a mixed mode of ESI and APCI.

Unless otherwise specified, a $^1$H-NMR is expressed as a chemical shift (δ) using tetramethylsilane as an internal standard (0 ppm), and a coupling constant (J value) is expressed by Hz. Also, abbreviations of splitting pattern of each peak are as follows. s: singlet, d: doublet, br: broad, m: multiplet.

When a configuration is described in a name and structure of a compound in a following Example or Reference Example, said compound is a compound having the configuration described in the Example or the Reference Example, an enantiomer or a diastereomer thereof, or a mixture of the enantiomers.

Abbreviations described in Examples, Reference Examples, and chemical structures have meanings usually used in the field of organic chemistry or pharmacy. Specifically, each abbreviation is understood by a skilled person as follows.

Poc: tert-butoxycarbonyl group
Cbz: benzyloxycarbonyl group
t-Bu: tert-butyl group
En: benzyl group
Ns: 2-nitrobenzenesulfonyl group
TMS: trimethylsilyl group
TFA: trifluoroacetic acid
tert-: tertiary
N: normality
M: molar concentration
COMU: (1-cyano-2-ethoxy-2-oxoethylideneaminooxy) dimethylamino(morpholino)carbenium hexafluorophosphate
EST: electrospray ionization
APCI: atmospheric pressure chemical ionization

EXAMPLES

Example 1

Example 1-(a)

Preparation of (2S,2'S)-tetra-tert-butyl 2,2'-((oxybis(ethane-2,1-diyl))bis((N-((benzyloxy)carbonyl)-N-(4-((4-(2,3-bis(tert-butoxycarbonyl)guanidino)benzoyl)oxy)benzyl)sulfamoyl)azanediyl))disuccinate

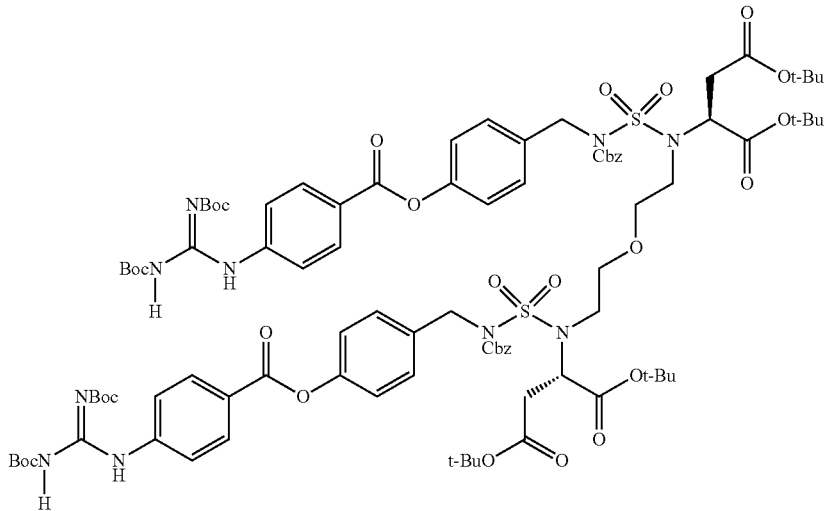

To a solution of (2S,2'S)-tetra-tert-butyl 2,2'-((oxybis(ethane-2,1-diyl))bis((N-((benzyloxy)carbonyl)sulfamoyl)azanediyl))disuccinate (10.74 g) prepared according to the same manner as the Reference Example 1-(d) in tetrahydrofuran (100 mL in a 300 mL round-bottom flask were added 4-(hydroxymethyl)phenyl 4-(2,3-bis(tert-butoxycarbonyl)guanidino)benzoate (11.52 g) prepared according to the same manner as the Reference Example 1-(g), diisopropyl azodicarboxylate (a 1.9 M solution in toluene) (12.60 mL), and triphenylphosphine (6.42 g) at room temperature under argon atmosphere with stirring, and the resulting mixture was stirred at room temperature for hour. After the reaction was completed, the reaction solution was concentrated under reduced pressure. The resulting residues were purified by medium pressure preparative chromatography (silica gel, elution solvent; hexane:ethyl acetate) to give the title compound (14.47 g as a white foam.

Mass spectrum (DUIS, m/z): 962 [M+2H]$^{2+}$.

$^1$H-NMR spectrum (400 MHz, CDCl$_3$) δ: 11.62 (s, 2H), 10.63 (s, 2H), 8.19-8.12 (m, 4H), 7.84-7.77 (m, 4H), 7.42-7.23 (m, 14H), 7.15-7.09 (m, 4H), 5.22-5.12 (m, 4H), 5.00-4.90 (m, 4H), 4.68 (dd, J=6.3, 7.9 Hz, 2H), 3.75-3.60 (m, 2H), 3.58-3.44 (m, 4H), 3.39-3.26 (m, 2H), 2.87 (dd, J=7.9, 16.6 Hz, 2H), 2.64 (dd, J=6.3, 16.6 Hz, 2H), 1.55 (s, 18H), 1.53 (s, 18H), 1.46 (s, 18H), 1.45 (s, 18H).

Example 1-(b)

Preparation of (2S,2'S)-2,2'-((oxybis(ethane-2,1-diyl))bis((N-(4-((4-guanidinobenzoyl)oxy)benzyl)sulfamoyl)azanediyl))disuccinic acid

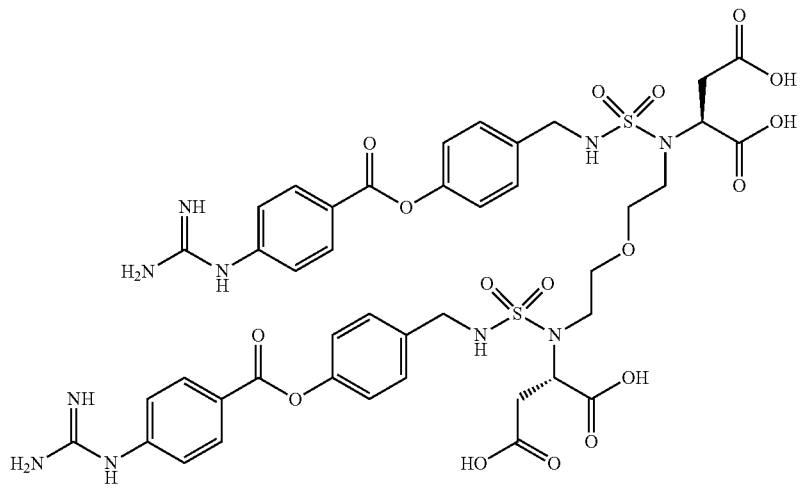 [SMILES: N=C(N)Nc1ccc(C(=O)Oc2ccc(CNS(=O)(=O)N(CCOCCN([C@@H](CC(=O)O)C(=O)O)S(=O)(=O)NCc3ccc(OC(=O)c4ccc(NC(=N)N)cc4)cc3)[C@@H](CC(=O)O)C(=O)O)cc2)cc1]

To a solution of (2S,2'S)-tetra-tert-butyl 2,2'-((oxybis(ethane-2,1-diyl))bis((N-((benzyloxy)carbonyl)-N-(4-((4-(2,3-bis(tert-butoxycarbonyl)guanidino)benzoyl)oxy)benzyl)sulfamoyl)azanediyl))disuccinate (14.47 g) prepared in the Example 1-(a) in dichloromethane (80 mL) in a 500 mL round-bottom flask was added trifluoroacetic acid (20 mL) at room temperature under argon atmosphere with stirring, and the resulting mixture was stirred at room temperature for 24 hours. The reaction solution was concentrated under reduced pressure. To the concentrated residues were added dichloromethane (40 ml) and trifluoroacetic acid (10 mL), and the resulting mixture was stirred at room temperature for 2 hours. The reaction solution was concentrated under reduced pressure to reduce the volume to approximately 20 mL, diisopropylether (10 mL) was added thereto, the precipitated solids were collected by filtration, and dried under reduced pressure. To a solution of the resulting solids in tetrahydrofuran (80 mL)/water (40 mL) in a 200 mL round-bottom flask was added 5% palladium carbon (wetted with 54.28% water, STD-type manufactured by NE CHEMCAT Corporation) (3.5 g) at room temperature under argon atmosphere with stirring, and the resulting mixture was stirred at room temperature under hydrogen atmosphere for 8 hours. After the reaction was completed, the resulting solids were separated by filtration, and washed with tetrahydrofuran/water. Tetrahydrofuran was distilled away under reduced pressure, to the resulting mixture was added acetonitrile to obtain a homogeneous solution, and then the solution was freeze-dried. The resulting residues were subjected to medium pressure preparative chromatography (ODS silica gel, elution solvent; aqueous solution with 0.1% trifluoroacetic acid:acetonitrile solution with 0.1% trifluoroacetic acid), to the fractions comprising the target compound was added dropwise a 10% aqueous ammonium acetate solution at room temperature with stirring to adjust the pH to 4. The precipitated solids were collected by filtration, washed with water, and dried under reduced pressure to give the title compound (5.86 g) as white solids.

Mass spectrum (ESI, m/z): 515 $[M+2H]^+$.

$^1$H-NMR spectrum (400 MHz, DMSO-$d_6$+$D_2O$) δ: 7.87-7.77 (m, 4), 7.28-7.18 (m, 8H), 7.07-6.99 (m, 4H), 1.51 (dd, J=5.0, 9.1 Hz, 2H), 4.22 (br d, J=14.5 Hz, 2H), 4.14 (br d, J=14.5 Hz, 2H), 3.89-3.20 (m, 8H), 2.96 (br dd, J=9.1, 15.7 Hz, 2H), 2.64-2.31 (m, 24).

Example 2

Example 2-(a)

Preparation of (2S,13S-tetra-tert-butyl 3,12-bis(N-((benzyloxy)carbonyl)-N-(4-((4-(2,3-bis(tert-butoxycarbonyl)guanidino)benzoyl)oxy)benzyl)sulfamoyl)-6,9-dioxa-3,12-diazatetradecane-1,2,13,14-tetracarboxylate

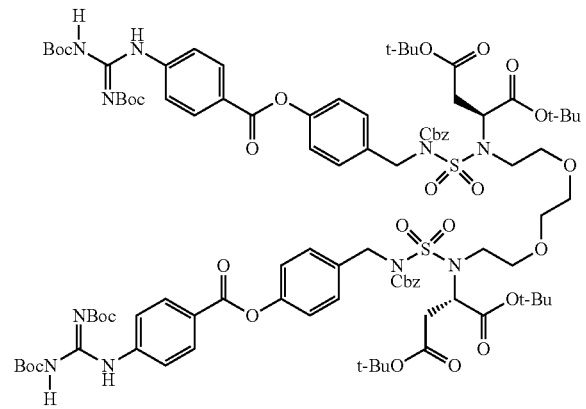

To a solution of 4-(hydroxymethyl)phenyl 4-(2,3-bis(tert-butoxycarbonyl)guanidino)benzoate (2.67 g) prepared according to the same manner as the Reference Example 1-(g), (2S,13S)-tetra-tert-butyl 3,12-bis(N-((benzyloxy)carbonyl)sulfamoyl)-6,9-dioxa-3,12-diazatetradecane-1,2,13,14-tetracarboxylate (2.70 q) prepared according to the same manner as the Reference Example 2-(c), and triphenylphosphine (2.05 g) in dehydrated tetrahydrofuran (20 mL) in a 200 mL round-bottom flask was added diisopropyl azodicarboxylate (a 1.9 M solution in toluene) (4.15 mL) at room temperature under argon atmosphere with stirring, and the resulting mixture was stirred at room temperature for 16 hours. After the reaction was completed, the reaction solution was concentrated under reduced pressure. The resulting residues were purified by medium pressure preparative chromatography (silica gel, elution solvent; hexane:ethyl acetate) to give the title compound (4.68 g) as a white foam.

Mass spectrum (ESI, m/z): 984 $[M+2H]^{2+}$.

$^1$H-NMR spectrum (400 MHz, CDCl$_3$) δ: 11.63 (s, 2H), 10.64 (s, 2H), 8.19-8.12 (m, 4H), 7.84-7.75 (m, 4H), 7.43-7.23 (m, 14H), 7.15-7.09 (m, 4H), 5.20 (d, J=11.9 Hz, 2H), 5.15 (d, J=11.9 Hz, 2H), 5.10-4.87 (m, 4H), 4.68 (dd, J=6.2, 8.0 Hz, 2H), 3.79-3.63 (m, 2H), 3.61-3.43 (m, 8H), 3.42-3.27 (m, 2H), 2.90 (dd, J=8.0, 16.7 Hz, 2H), 2.66 (dd, J=6.2, 16.7 Hz, 2H), 1.55 (s, 18H), 1.53 (s, 18H), 1.45 (s, 36H).

Example 2-(b)

Preparation of (2S,13S)-3,12-bis(N-(4-((4-guanidinobenzoyl)oxy)benzyl)sulfamoyl)-6,9-dioxa-3,12-diazatetradecane-1,2,13,14-tetracarboxylic acid trifluoroacetate

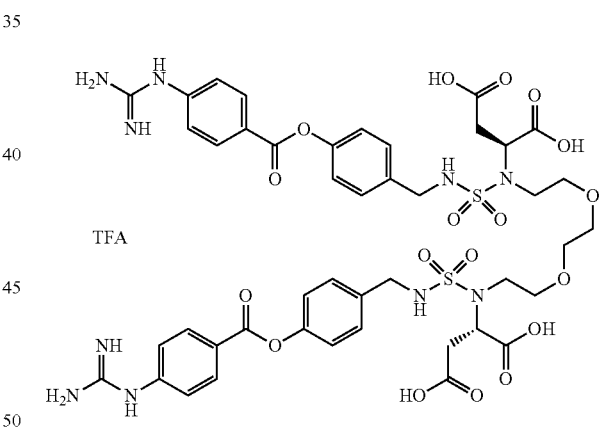

To a solution of (2S,13S)-tetra-tert-butyl 3,12-bis(N-((benzyloxy)carbonyl)-N-(4-((4-(2,3-bis(tert-butoxycarbonyl)guanidino)benzoyl)oxy)benzyl)sulfamoyl)-6,9-dioxa-3,12-diazatetradecane-1,2,13,14-tetracarboxylate (4.68 g) prepared in the Example 2-(a) in dehydrated dichloromethane (15 mL) in a 200 mL round-bottom flask was added trifluoroacetic acid (5.00 mL) under ice-cooling under argon atmosphere with stirring, and the resulting mixture was stirred at room temperature for 16 hours. The reaction solution was concentrated under reduced pressure. To a solution of the concentrated residues in dehydrated dichloromethane (6 mL) was added trifluoroacetic acid (5.03 mL) at room temperature under argon atmosphere with stirring, the resulting mixture was stirred at room temperature for 2 hours, and then the reaction solution was concentrated under reduced pressure. To a solution of the concentrated residues in methanol (6 mL) was added 10% palladium carbon (wetted with ca. 55% water, manufactured by Tokyo Chemical Industry Co., Ltd.) (350 mg), the atmosphere in the reaction system was replaced with hydrogen atmosphere, and then the resulting mixture was stirred at room temperature for 4 hours. After the reaction was completed, the atmosphere in the reaction system was replaced with nitrogen atmosphere, and the reaction solution was filtered through Celite. The removed solids were washed with a mixed solvent of methanol and acetonitrile (1:1 (v/v)), and the resulting filtrate was concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried to give the title compound (1.65 g) as white solids.

Mass spectrum (ESI, m/z): 537 [M+2H]$^{2+}$.

$^1$H-NMR spectrum (400 MHz, DMSO-d$_6$+D$_2$O) δ: 8.20-8.14 (m, 4H), 7.47-7.38 (m, 8H), 7.26-7.21 (m, 4H), 4.1 (dd, J=5.6, 8.4 Hz, 2H), 4.11 (d, J=15.1 Hz, 2H), 4.06 (d, J=15.1 Hz, 2H), 3.64-3.24 (m, 12H), 2.96 (dd, 3=8.4, 16.6 Hz, 2H), 2.68 (dd, J=5.6, 16.6 Hz, 2H).

Example 2-(c)

Preparation of (2S,13S)-3,12-bis(N-(4-((4-guanidinobenzoyloxy)benzyl)sulfamoyl)-6,9-dioxa-3,12-diazatetradecane-1,2,13,14-tetracarboxylic acid

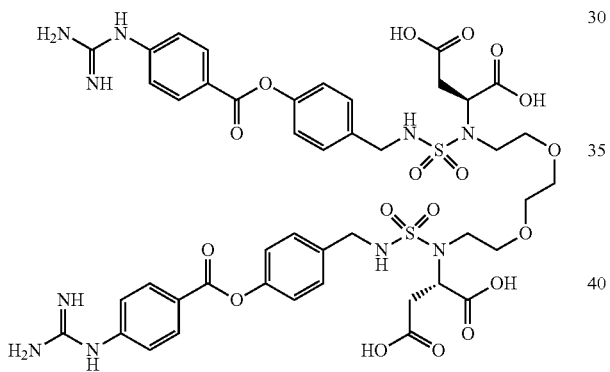

To a solution of (2S,13S)-3,12-bis(N-(4-((4-guanidinobenzoyl)oxy)benzyl)sulfamoyl)-6,9-dioxa-3,12-diazatetradecane-1,2,13,14-tetracarboxylic acid trifluoroacetate (1.00 g) prepared in the Example 2-(b) in water (24.0 mL)/acetonitrile (6.00 mL) in a 100 mL round-bottom flask was added a saturated aqueous ammonium acetate solution with stirring to adjust the pH to 4.0. The resulting mixture was stirred at room temperature for 1 hour, the precipitated solids were collected by filtration, and dried under reduced pressure to give the title compound (756 mg) as white solids.

Mass spectrum (ESI, m/z): 537 [M+2H]$^{2+}$.

$^1$H-NMR spectrum (400 MHz, DMSO-d$_6$+D$_2$O) δ: 7.90-7.79 (m, 4H), 7.34-7.19 (m, 8H), 7.12-7.06 (m, 4H), 4.57-4.47 (m, 2H), 4.26 (d, J=14.9 Hz, 2H), 4.19 (d, J=14.9 Hz, 2H), 3.66-3.12 (m, 12H), 3.00-2.87 (m, 2H), 2.59-2.30 (m, 2H).

Example 3

Example 3-(a)

Preparation of (2S,16S)-tetra-tert-butyl 3,15-bis(N-((benzyloxy)carbonyl)-N-(4-((4-(2,3-bis(tert-butoxycarbonyl)guanidino)benzoyl)oxy)benzyl)sulfamoyl)-6,9,12-trioxa-3,15-diazaheptadecane-1,2,16,17-tetracarboxylate

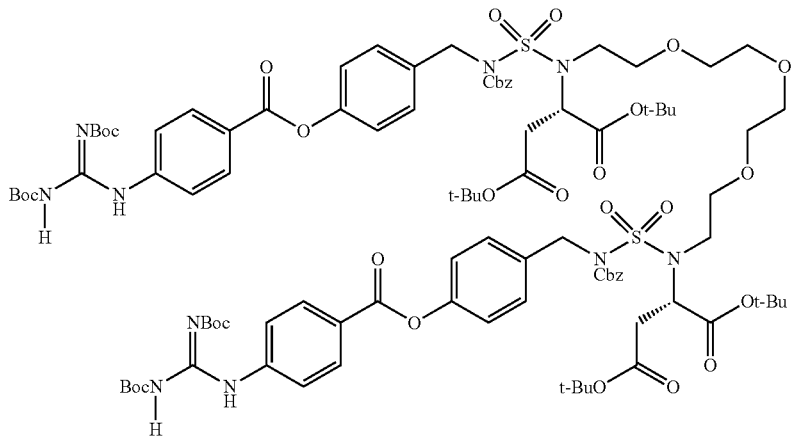

To a solution of 4-(hydroxymethyl)phenyl 4-(2,3-bis(tert-butoxycarbonyl)guanidino)benzoate (1.68 g) prepared according to the same manner as the Reference Example 1-(g), (2S,16S)-tetra-tert-butyl 3,15-bis(N-((benzyloxy)carbonyl)sulfamoyl)-6,9,12-trioxa-3,15-diazaheptadecane-1,2,16,17-tetracarboxylate (1.69 g) prepared according to the same manner as the Reference Example 3-(c), and triphenylphosphine (1.07 g) in tetrahydrofuran (30 mL) in a 200 mL round-bottom flask was added diisopropyl azodicarboxylate (a 1.9 M solution in toluene) (2.15 mL) at room temperature under argon atmosphere with stirring, and the resulting mixture was stirred at room temperature for 2 hours. Additionally, triphenylphosphine (165 mg) and diisopropyl azodicarboxylate (a 1.9 M solution in toluene) (330 μL) were added thereto at room temperature, and the resulting mixture was stirred at room temperature for 1 hour. After the reaction was completed, the reaction solution was concentrated under reduced pressure. The resulting residues were subjected to medium pressure preparative chromatography (silica gel, elution solvent; hexane:ethyl acetate), and the fractions comprising the target compound were concentrated under reduced pressure. The resulting residues were purified by medium pressure preparative chromatography (silica gel, elution solvent; dichloroethane:ethyl acetate) to give the title compound (3.21 g) as a white foam.

Mass spectrum (ESI, m/z): 1006 $[M+2H]^{2+}$.

$^1$H-NMR spectrum (400 MHz, CDCl$_3$) δ: 11.63 (s, 2H), 10.64 (s, 2H), 8.19-8.13 (m, 4H), 7.85-7.77 (m, 4H), 7.43-7.22 (m, 14H), 7.15-7.08 (m, 4H), 5.19 (d, J=12.2 Hz, 2H), 5.15 (d, J=12.2 Hz, 2H), 5.08-4.89 (m, 4H), 4.68 (dd, J=6.1, 8.3 Hz, 2H), 3.80-3.67 (m, 2H), 3.63-3.19 (m, 12H), 3.40-3.25 (m, 2H), 2.91 (dd, J=8.3, 16.8 Hz, 2H), 2.66 (dd, J=6.1, 16.8 Hz, 2H), 1.55 (s, 18H), 1.53 (s, 18H), 1.45 (s, 36H).

Example 3-(b)

Preparation of (2S,163)-3,15-bis(N-(4-((4-guanidinobenzoyl)oxy)benzyl)sulfamoyl)-6,9,12-trioxa-3,15-diazaheptadecane-1,2,16,17-tetracarboxylic acid trifluoroacetate and the resulting mixture was stirred at room temperature for 15 hours. The reaction solution was concentrated under reduced pressure. To a solution of the concentrated residues in dichloromethane (1 mL) was added trifluoroacetic acid (1 mL) at room temperature, and the resulting mixture was stirred at room temperature for 3 hours. The reaction solution was concentrated under reduced pressure. To a solution of the concentrated residues in methanol (3 mL) was added 5% palladium carbon (wetted with 54.28% water, STD-type manufactured by NE CHEMCAT Corporation) (106 mg), the atmosphere in the reaction system was replaced with hydrogen atmosphere, and then the resulting mixture was stirred at room temperature for 30 minutes. After the reaction was completed, the reaction solution was filtered through Celite, and the resulting filtrate was concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried. The resulting residues were subjected to medium pressure preparative chromatography (silica gel, elution solvent; acetonitrile solution with 0.1% trifluoroacetic acid:aqueous solution with 0.1% trifluoroacetic acid), and the fractions comprising the target compound were freeze-dried. To a solution of the resulting residues in acetonitrile solution with 0.1% trifluoroacetic acid (3 mL)/aqueous solution with 0.1% trifluoroacetic acid (3 mL) was 12 added a saturated aqueous ammonium acetate solution to adjust the pH to 4.0, and the resulting mixture was stirred at room temperature for 30 minutes. The reaction solution was concentrated under reduced pressure. The resulting residues were subjected to medium pressure preparative chromatography (silica gel, elution solvent; acetonitrile solution with 0.1% trifluoroacetic acid aqueous solution with 0.1% trifloroacetic acid), and the fractions comprising the target compound were freeze-dried to give the title compound (78 mg) as white solids.

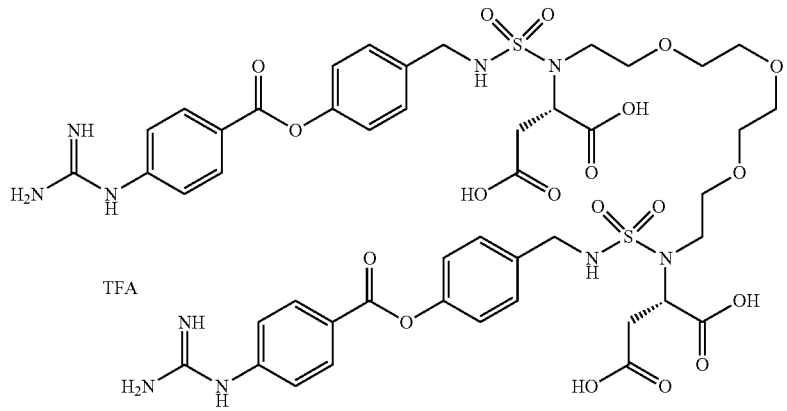 [SMILES: N=C(N)Nc1ccc(C(=O)Oc2ccc(CNS(=O)(=O)N(CCOCCOCCOCCN([C@@H](CC(=O)O)C(=O)O)S(=O)(=O)NCc3ccc(OC(=O)c4ccc(NC(=N)N)cc4)cc3)[C@@H](CC(=O)O)C(=O)O)cc2)cc1]

To a solution of (2S,16S)-tetra-tert-butyl 3,15-bis(N-((benzyloxy)carbonyl)-N-(4-((4-(2,3-bis(tert-butoxycarbonyl)guanidino)benzoyl)oxy)benzyl)sulfamoyl)-6,9,12-trioxa-3,15-diazaheptadecane-1,2,16,17-tetracarboxylate (300 mg) prepared in the Example 3-(a) in dichloromethane (2.5 mL) in a 30 mL cylindrical flask was added trifluoroacetic acid (500 μL) at 0° C. under argon atmosphere with stirring, Mass spectrum (ESI, m/z): 559 $[M+2H]^{2+}$.

$^1$H-NMR spectrum (400 MHz, DMSO-d$_6$+D$_2$O) δ: 8.21-8.13 (m, 4H), 7.47-7.38 (m, 8H), 7.28-7.19 (m, 4H), 4.65-4.54 (m, 2H), 4.11 (d, J=15.2 Hz, 2H), 4.06 (d, J=15.2 Hz, 2H), 3.63-3.19 (m, 16H), 2.95 (dd, J=0.3, 16.6 Hz, 2H), 2.75-2.63 (m, 2H).

Example 3-(c)

Preparation of 2S,16S)-3,15-bis(N-(4-(4-guanidino-benzoyl)oxy)benzyl)sulfamoyl)-6,9,12-trioxa-3,15-diazaheptadecane-1,2,16,17-tetracarboxylic acid hydrochloride

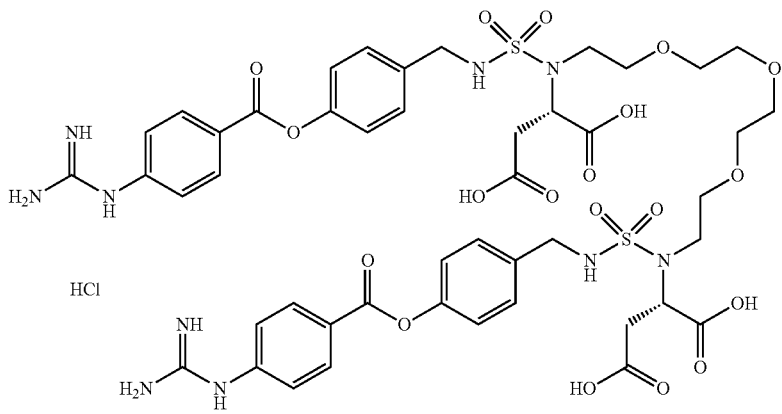 [SMILES: N=C(N)Nc1ccc(C(=O)Oc2ccc(CNS(=O)(=O)N(CCOCCOCCOCCN([C@@H](CC(=O)O)C(=O)O)S(=O)(=O)NCc3ccc(OC(=O)c4ccc(NC(=N)N)cc4)cc3)[C@@H](CC(=O)O)C(=O)O)cc2)cc1 ; Cl]

To a solution of (2S,16S)-tetra-tert-butyl 3,15-bis(N-((benzyloxy)carbonyl)-N-(4-((4-(2,3-bis(tert-butoxycarbonyl)guanidino)benzoyl)oxy)benzyl)sulfamoyl-6,9,12-trioxa-3,15-diazaheptadecane-1,2,16,17-tetracarboxylate (6.77 g) prepared according to the same manner as the Example 3-(a) in dichloromethane (40 mL) in a 300 mL round-bottom flask was added trifluoroacetic acid (20 mL) at 0° C. under argon atmosphere with stirring, and the resulting mixture was stirred at room temperature for 15 hours. The reaction solution was concentrated under reduced pressure. To a solution of the concentrated residues in tetrahydrofuran (45 mL)/water (13 mL) was added 5% palladium carbon (wetted with 54.28% water, STD-type manufactured by NE CHEMCAT Corporation) (1.20 g), the atmosphere in the reaction system was replaced with hydrogen atmosphere, and then the resulting mixture was stirred at room temperature for 2 hours. After the reaction was completed, the reaction solution was filtered through Celite and the resulting filtrate was concentrated under reduced pressure. The resulting residues were subjected to medium pressure preparative chromatography (silica gel, elution solvent; acetonitrile solution with 0.1% trifluoroacetic acid:aqueous solution with 0.1% trifluoroacetic acid), and the fractions comprising the target compound were concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried. A solution of the resulting residues in 0.1N hydrochloric acid (168 mL) was freeze-dried to give the title compound (1.36 g) as white solids.

Mass spectrum (ESI, n/z): 559 [M+2H]$^{2+}$.

$^1$H-NMR spectrum (400 MHz, DMSO-$d_6$+$D_2O$) δ: 8.21-0.13 (m, 4H), 7.48-7.38 (m, 8H), 7.27-7.20 (m, 4H), 4.60 (dd, J=5.5, 8.4 Hz, 2H), 4.11 (d, J=15.4 Hz, 2H), 4.06 (d, J=15.4 Hz, 2H), 3.71-3.21 (m, 16H), 2.96 (dd, J=8.4, 16.6 Hz, 2H), 2.73-2.65 (m, 2H).

Example 4-(a)

Preparation of (2S,19S)-tetra-tert-butyl 3,18-bis(N-((benzyloxy)carbonyl-)-N-(4-((4-(2,3-bis(tert-botoxycarbonyl)guanidino)benzoyl)oxy)benzyl)sulfamoyl)-6,9,12,15-tetraoxa-3,1-diazaicosane-1,2,19,20-tetracarboxylate

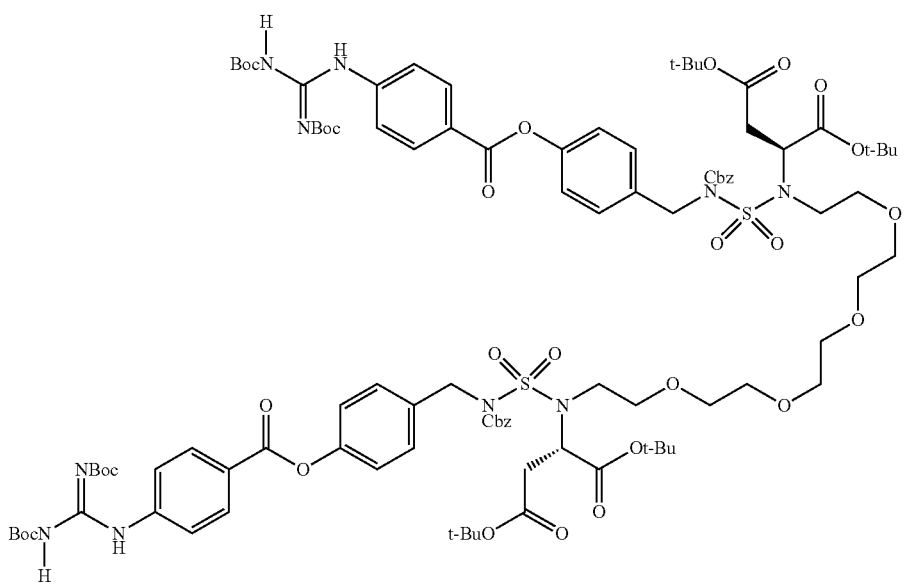

To a solution of (2S,19S)-tetra-tert-butyl 3,18-bis(N-((benzyloxy)carbonyl) sulfamoyl)-6,9,12,15-tetraoxa-3,18-diazaicosane-1,2,19,20-tetracarboxylate (1.30 g) prepared according to the same manner as the Reference Example 4-(c), 4-(hydroxymethyl)phenyl 4-(2,3-bis(tert-butoxycarbonyl)guanidino)benzoate (1.31 g) prepared according to the same manner as the Reference Example 1-(g) and triphenylphosphine (0.88 g) in tetrahydrofuran (20 ml) in a 103 mL round-bottom flask was added diisopropyl azodicarboxylate (a 1.9 M solution in toluene) (1.80 mL) at room temperature under argon gas flow with stirring, and the resulting mixture was stirred at room temperature for 2 hours. After the reaction was completed. The reaction solution was concentrated under reduced pressure. The resulting residues were purified by medium pressure preparative chromatography (silica gel, elution solvent; hexane:ethyl acetate) to give the title compound (2.00 g) as a white foam.

Mass spectrum (S_, m/z) 1028 [M+2H]$^{2+}$.

$^1$H-NMR spectrum (100 MHz, CDCl$_3$) δ: 11.61 (s, 2H), 10.64 (s, 2=), 8.19-8.12 (m, 4H), 7.84-7.77 (m, 4H), 7.43-7.21 (m, 14H), 7.15-7.09 (m, 4H), 5.19 (d, J=12.1 Hz, 2H), 5.15 (d, J=12.1 Hz, 2H), 5.03-4.89 (m, 4H), 4.68 (dd, J=6.0, 8.3 Hz, 2H), 3.78-3.67 (m, 2H), 3.65-3.51 (m, 16H), 3.39-3.27 (m, 2H), 2.91 (dd, 8.3, 16.7 Hz, 2H), 2.66 (dd, J=6.0, 16.7 Hz, 2H), 1.55 (s, 181-), 1.53 (s, 18H), 1.45 (s, 36H).

Example 4-(b)

Preparation of (2S,19S)-3,18-bis(N-(4-((4-guanidinobenzoyl)oxy)benzyl)sulfamoyl)-6,9,12,15-tetraoxa-3,18-diazaicosane-1,2,19,20-tetracarboxylic acid trifluoroacetate

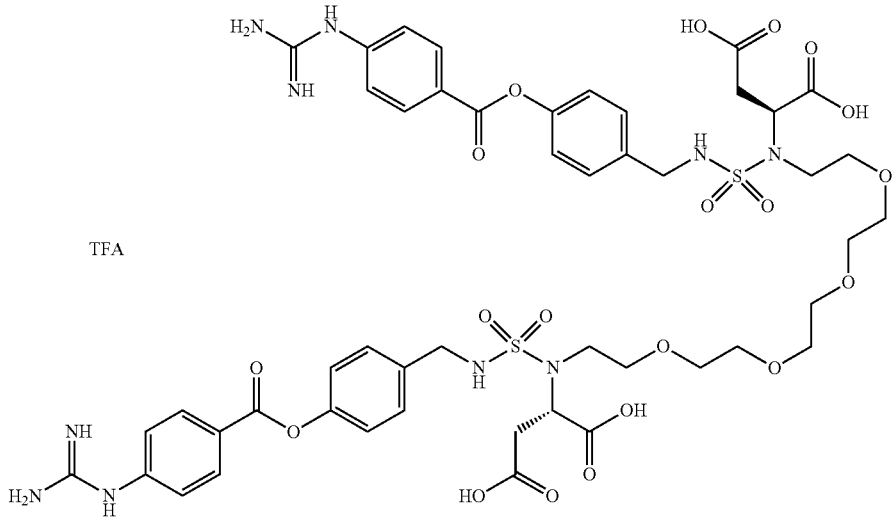 [SMILES: N=C(N)Nc1ccc(C(=O)Oc2ccc(CNS(=O)(=O)N(CCOCCOCCOCCOCCN([C@@H](CC(=O)O)C(=O)O)S(=O)(=O)NCc3ccc(OC(=O)c4ccc(NC(=N)N)cc4)cc3)[C@@H](CC(=O)O)C(=O)O)cc2)cc1]

To a solution of (2S,19S)-tetra-tert-butyl 3,18-bis(N-((benzyloxy)carbonyl)-N-(4-((4-(2,3-bis(tert-butoxycarbonyl)guanidino)benzoyl)oxy)benzyl)sulfamoyl)-6,9,12,15-tetraoxa-3,18-diazaicosane-1,2,19,20-tetracarboxylate (2.00 g) prepared in the Example 4-(a) in dichloromethane (15 mL) in a 50 mL round-bottom flask was added trifluoroacetic acid (15 mL) at room temperature under argon atmosphere with stirring, and the resulting mixture was stirred at room temperature for 90 hours. The reaction solution was concentrated under reduced pressure. The concentrated residues was dissolved into dichloromethane (15 mL), trifluoroacetic acid (15 mL) was added thereto, and the resulting mixture was stirred at room temperature for 4 hours. The reaction solution was concentrated under reduced pressure. To a solution of the concentrated residues in methanol (20 mL) was added 5% palladium carbon (wetted with 54.28% water, STD-type manufactured by NE CHEMCAT Corporation) (1.03 g) at room temperature under argon atmosphere with stirring, and the resulting mixture was stirred at room temperature under hydrogen atmosphere for 2 hours. After the reaction was completed, the reaction solution was filtered through Celite, washed with methanol, and the resulting filtrate was concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried to give the title compound (710 mg) as white solids.

Mass spectrum (ESI, m/z): 1161 [M+H]$^+$.

$^1$H-NMR spectrum (400 MHz, DMSO-$d_6$+$D_2O$) δ: 8.20-8.13 (m, 4H), 7.47-7.38 (m, 8H), 7.27-7.20 (m, 4H), 4.60 (dd, J=5.5, 8.4 Hz, 2H), 4.11 (d, J=15.3 Hz, 2H), 4.06 (d, J=15.3 Hz, 2H), 3.66-3.22 (m, 20H), 2.96 (dd, J=8.4, 16.6 Hz, 2H), 2.74-2.64 (m, 2H).

Example 4-(c)

Preparation of (2S,19S)-3,18-bis(N-(4-((4-guanidinobenzoyl)oxy)benzyl)sulfamoyl)-6,9,12,15-tetraoxa-3,18-diazaicosane-1,2,19,20-tetracarboxylic acid hydrochloride

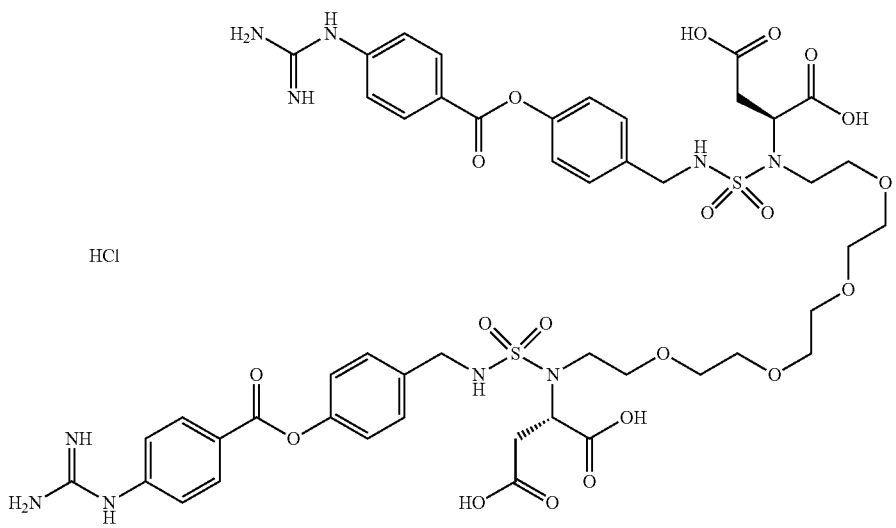 [SMILES: N=C(N)Nc1ccc(C(=O)Oc2ccc(CNS(=O)(=O)N(CCOCCOCCOCCOCCN([C@@H](CC(=O)O)C(=O)O)S(=O)(=O)NCc3ccc(OC(=O)c4ccc(NC(=N)N)cc4)cc3)[C@@H](CC(=O)O)C(=O)O)cc2)cc1 ; Cl]

(2S,19S)-3,18-bis(N-(4-((4-guanidinobenzoyl)oxy)benzyl)sulfamoyl)-6,9,12,15-tetraoxa-3,18-diazaicosane-1,2,19,20-tetracarboxylic acid trifluoroacetate (4.60 g) prepared according to the same manner as the Example 4-(b) in a 1,000 mL round-bottom flask was dissolved into acetonitrile (40 mL) and 0.1 M hydrochloric acid (150 mL), and the resulting solution was freeze-dried to give the title compound (4.02 g) as white solids.

Mass spectrum (ESI, m/z): 1161 [M+H]$^+$.

$^1$H-NMR spectrum (400 MHz, DMSO-$d_6$+$D_2O$) δ: 8.20-8.14 (m, 4H), 7.47-7.39 (m, 8H), 7.26-7.20 (m, 4H), 4.60 (dd, J=5.4, 8.5 Hz, 2H), 4.12 (d, J=15.3 Hz, 2H), 4.06 (d, J=15.3 Hz, 2H), 3.77-3.21 (m, 20H), 2.96 (dd, J=8.5, 16.7 Hz, 2H), 2.69 (dd, J=5.4, 16.7 Hz, 2H).

Example 5

Example 5-(a)

Preparation of (2S,22S)-tetra-tert-butyl 3,21-bis(N-((benzyloxy)carbonyl)-N-(4-((4-(2,3-bis(tert-butoxycarbonyl)guanidino)benzoyl)oxy)benzyl)sulfamoyl)-6,9,12,15,18-pentaoxa-3,21-diazatricosane-1,2,22,23-tetracarboxylate

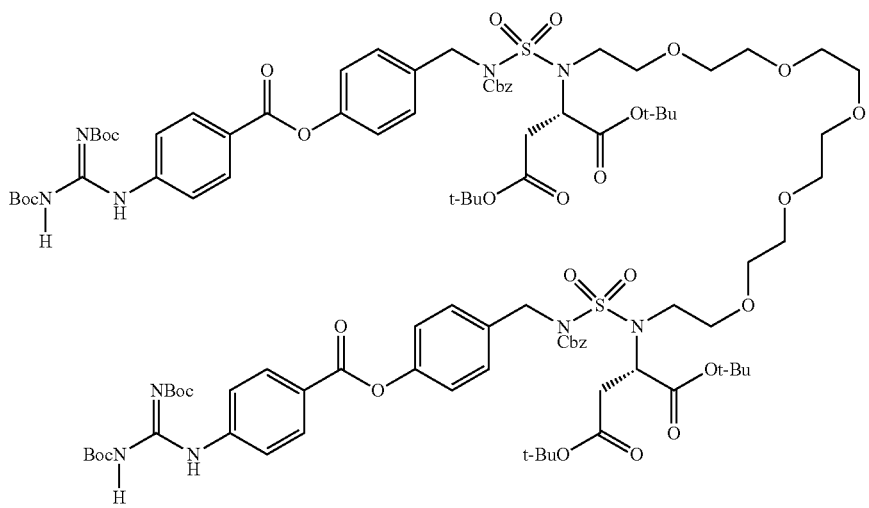

To a solution of (2S,22S)-tetra-tert-butyl 3,21-bis(N-((benzyloxy)carbonyl)sulfamoyl)-6,9,12,15,18-pentaoxa-3,21-diazatricosane-1,2,22,23-tetracarboxylate (443 mg) prepared in the Reference Example 5-(c), 4-(hydroxymethyl)phenyl 4-(2,3-bis(tert-butoxycarbonyl)guanidino)benzoate (390 mg) prepared according to the same manner as the Reference Example 1-(g), and triphenylphosphine (225 mg) in tetrahydrofuran (10 mL) in a 100 mL round-bottom flask was added diisopropyl azodicarboxylate (a 1.9 M solution in toluene) (0.450 mL) at room temperature under argon atmosphere with stirring, and the resulting mixture was stirred at room temperature for 30 minutes. After the reaction was completed, the reaction solution was concentrated under reduced pressure. The resulting residues were purified by medium pressure preparative chromatography (silica gel, elution solvent; hexane:ethyl acetate) to give the title compound (591 mg) as a white foam.

Mass spectrum (ESI, m/z): 2121 [M+Na]$^+$.

$^1$H-NMR spectrum (400 MHz, CDCl$_3$) δ: 11.63 (s, 2H), 10.64 (s, 2H), 8.19-8.12 (m, 4H), 7.85-7.77 (m, 4H), 7.42-7.21 (m, 14H), 7.15-7.09 (m, 4H), 5.19 (d, J=12.0 Hz, 2H), 5.15 (d, J=12.0 Hz, 2H), 4.97 (d, J=16.1 Hz, 2H), 4.94 (d, J=16.1 Hz, 2H), 4.68 (dd, J=6.0, 8.2 Hz, 2H), 3.78-3.47 (m, 22H), 3.38-3.26 (m, 2H), 2.91 (dd, J=8.2, 16.7 Hz, 2H), 2.66 (dd, J=6.0, 16.7 Hz, 2H), 1.55 (s, 18H), 1.53 (s, 18H), 1.45 (s, 36H).

Example 5-(b)

Preparation of (2S,22S)-3,21-bis(N-(4-((4-guanidinobenzoyl)oxy)benzyl)sulfamoyl)-6,9,12,15,18-pentaoxa-3,21-diazatricosane-1,2,22,23-tetracarboxylic acid trifluoroacetate To a solution of (2S,22S)-tetra-tert-butyl 3,21-bis(N-((benzyloxy)carbonyl)-N-(4-((4-(2,3-bis(tert-butoxycarbonyl)guanidino)benzoyl)oxy)benzyl)sulfamoyl)-6,9,12,15,18-pentaoxa-3,21-diazatricosane-1,2,22,23-tetracarboxylate (591 mg) prepared in the Example 5-(a) in dichloromethane (5 mL) in a 50 mL round-bottom flask was added trifluoroacetic acid (5 mL) at room temperature under argon atmosphere with stirring, and the resulting mixture was stirred at room temperature for 4 hours. The reaction solution was concentrated under reduced pressure. To a solution of the concentrated residues in ethanol (10 mL) was added 5% palladium carbon (wetted with 54.28% water, STD-type manufactured by NE CHEMCAT Corporation) (200 mg) at room temperature under argon atmosphere with stirring, and the resulting mixture was stirred at room temperature under hydrogen atmosphere for 40 minutes. After the reaction was completed, the reaction solution was filtered through Celite, and the removed solids were washed with ethanol. The resulting filtrate was concentrated under reduced pressure. The resulting residues were subjected to medium pressure preparative chromatography (ODS silica gel, elution solvent; acetonitrile solution with 0.1% trifluoroacetic acid: aqueous solution with 0.1% trifluoroacetic acid), and the fractions comprising the target compound were freeze-dried to give the title compound (167 mg) as white solids.

Mass spectrum (ESI, m/z): 603 [M+2H]$^{2+}$.

$^1$H-NMR spectrum (400 MHz, DMSO-d$_6$+D$_2$O) δ: 8.20-8.12 (m, 4H), 7.46-7.39 (m, 8H), 7.26-7.20 (m, 4H), 4.64-4.52 (m, 2H), 4.20-4.04 (m, 4H), 3.76-3.23 (m, 24H), 3.02-2.89 (m, 2H), 2.75-2.42 (m, 2H).

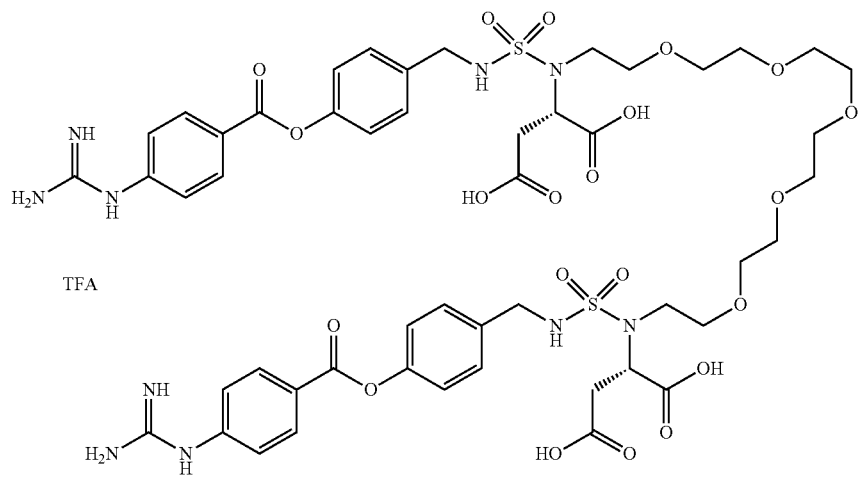 [SMILES: N=C(N)Nc1ccc(C(=O)Oc2ccc(CNS(=O)(=O)N(CCOCCOCCOCCOCCOCCN([C@@H](CC(=O)O)C(=O)O)S(=O)(=O)NCc3ccc(OC(=O)c4ccc(NC(=N)N)cc4)cc3)[C@@H](CC(=O)O)C(=O)O)cc2)cc1]

Example 5-(c)

Preparation of (2S,22S)-3,21-bis(N-(4-((4-guanidinobenzoyl)oxy)benzyl)sulfamoyl)-6,9,12,15,18-pentaoxa-3,21-diazatricosane-1,2,22,23-tetracarboxylic acid hydrochloride

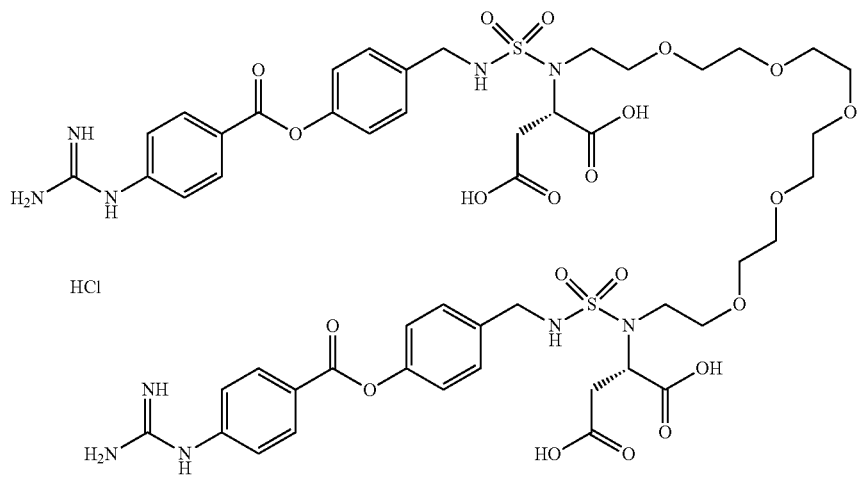 [SMILES: N=C(N)Nc1ccc(C(=O)Oc2ccc(CNS(=O)(=O)N(CCOCCOCCOCCOCCOCCN([C@@H](CC(=O)O)C(=O)O)S(=O)(=O)NCc3ccc(OC(=O)c4ccc(NC(=N)N)cc4)cc3)[C@@H](CC(=O)O)C(=O)O)cc2)cc1 ; Cl]

To a solution of (2S,22S)-tetra-tert-butyl 3,21-bis(N-((benzyloxy)carbonyl)-N-(4-((4-(2,3-bis(tert-butoxycarbonyl)guanidino)benzoyl)oxy)benzyl)sulfamoyl)-6,9,12,15,18-pentaoxa-3,21-diazatricosane-1,2,22,23-tetracarboxylate (3.36 g) prepared according to the same manner as the Example 5-(a) in dichloromethane (25 mL) in a 300 mL round-bottom flask was added trifluoroacetic acid (12.5 mL) at 0° C. under argon atmosphere with stirring, and the resulting mixture was stirred at room temperature for 14 hours. The reaction solution was concentrated under reduced pressure. To a solution of the concentrated residues in ethanol (40 mL) was added 5% palladium carbon (wetted with 54.28% water, STD-type manufactured by NE CHEMCAT Corporation) (1.12 g), the atmosphere in the reaction system was replaced with hydrogen atmosphere, and then the resulting mixture was stirred at room temperature for 2 hours. After the reaction was completed, the reaction solution was filtered through Celite, and the resulting filtrate was concentrated under reduced pressure. The resulting residues were subjected to medium pressure preparative chromatography (silica gel, elution solvent; acetonitrile solution with 0.1% trifluoroacetic acid:aqueous solution with 0.1% trifluoroacetic acid), and the fractions comprising the target compound were concentrated under reduced pressure. The resulting residues were subjected to medium pressure preparative chromatography (ODS silica gel, elution solvent; acetonitrile solution with 0.1% trifluoroacetic acid:aqueous solution with 0.1% trifluoroacetic acid), and the fractions comprising the target compound were freeze-dried. A solution of the resulting residues in 0.1N hydrochloric acid (160 mL) was freeze-dried to give the title compound (1.29 g) as white solids.

Mass spectrum (ESI, m/z): 603 $[M+2H]^{2+}$.

$^1$H-NMR spectrum (400 MHz, DMSO-$d_6$+$D_2O$) δ: 8.20-8.13 (m, 4H), 7.47-7.39 (m, 8H), 7.27-7.20 (m, 4H), 4.61 (dd, J=5.3, 8.5 Hz, 2H), 4.12 (d, J=15. Hz, 2H), 4.06 (d, J=15.3 Hz, 2H), 3.71-3.21 (m, 24H), 2.96 (dd, J=8.5, 16.7 Hz, 2H), 2.69 (dd, J=0.3, 16.7 Hz, 2H).

Example 6

Example 6-(a)

Preparation of (2S,25S)-tetra-tert-butyl 3,24-bis(N-((benzyloxy)carbonyl)-N-(4-((4-(2,3-bis(tert-butoxycarbonyl)guanidino)benzoyl)oxy)benzyl)sulfamoyl)-6,9,12,15,18,21-hexaoxa-3,24-diazahexacosane-1,2,25,26-tetracarboxylate

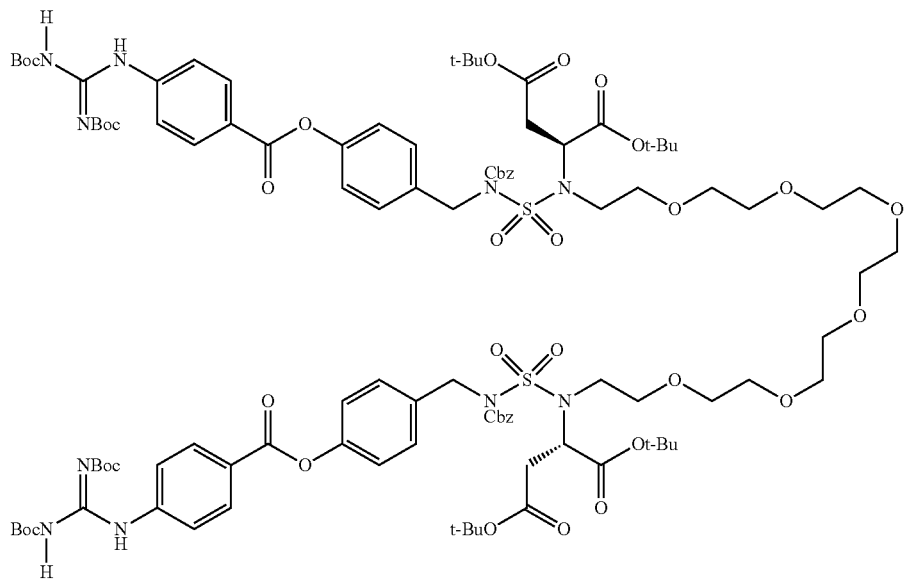

To a solution of (2S,25S)-tetra-ter-butyl 3,24-bis(N-((benzyloxy)carbonyl)sulfamoyl)-6,9,12,15,18,21-hexaoxa-3,24-diazahexacosane-1,2,25,26-tetracarboxylate (2.50 g) prepared in the Reference Example 6(c), 4-(hydroxymethyl)phenyl 4-(2,3-bis(tert-butoxycarbonyl)guanidino)benzoate (2.21 g) prepared according to the same manner as the Reference Example 1-(g), and triphenylphosphine (1.41 g) in tetrahydrofuran (30 mL) in a 200 mL round-bottom flask was added diisopropyl azodicarboxylate (a 1.9 M solution in toluene) (2.83 mL) at room temperature under argon atmosphere with stirring, and the resulting mixture was stirred at room temperature for 2 hours. After the reaction was completed, the reaction solution was concentrated under reduced pressure. The resulting residues were purified by medium pressure preparative chromatography (silica gel, elution solvent; hexane:ethyl acetate) to give the title compound (3.84 g) as a colorless oil.

Mass spectrum (ESI, m/z): 1072 $[M+2H]^{2+}$.

$^1$H-NMR spectrum (400 MHz, CDCl$_3$) δ: 11.63 (s, 2H), 10.64 (s, 2H), 8.19-8.13 (m, 4H), 7.85-7.78 (m, 4H), 7.43-7.23 (m, 14H), 7.16-7.10 (m, 4H), 5.19 (d, J=12.0 Hz, 2H), 5.15 (d, J=12.0 Hz, 2H), 4.97 (d, J=16.1 Hz, 2H), 4.94 (d, J=16.1 Hz, 2H), 4.68 (dd, J=6.0, 8.3 Hz, 2H), 3.79-3.47 (m, 26H), 3.39-3.25 (m, 2H), 2.91 (dd, J=8.3, 16.7 Hz, 2H), 2.66 (dd, J=6.0, 16.7 Hz, 2H), 1.55 (s, 18H), 1.53 (s, 18H), 1.45 (s, 36H).

Example 6-(b)

Preparation of (2S,25S)-3,24-bis(N-(4-((4-guanidinobenzoyl)oxy)benzyl)sulfamoyl)-6,9,12,15,18,21-hexaoxa-3,24-diazahexacosane-1,2,25,26-tetracarboxylic acid trifluoroacetate

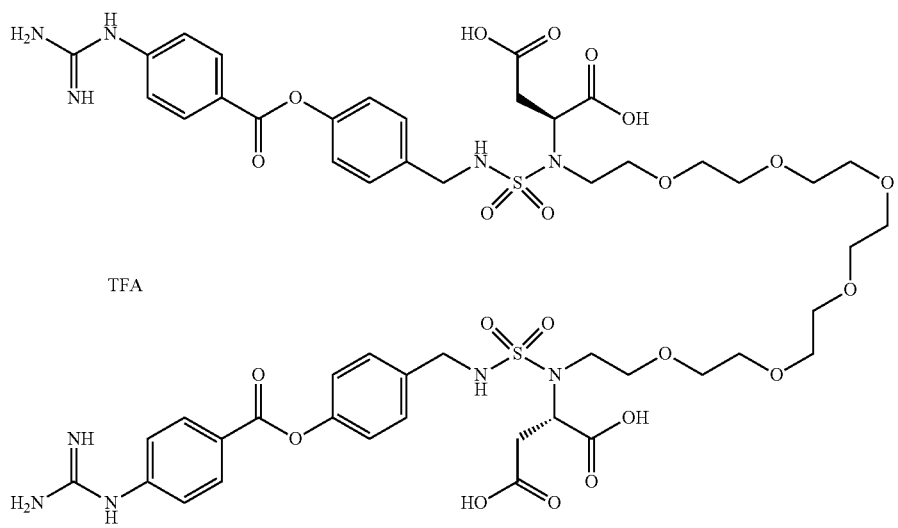 [SMILES: N=C(N)Nc1ccc(C(=O)Oc2ccc(CNS(=O)(=O)N(CCOCCOCCOCCOCCOCCOCCN([C@@H](CC(=O)O)C(=O)O)S(=O)(=O)NCc3ccc(OC(=O)c4ccc(NC(=N)N)cc4)cc3)[C@@H](CC(=O)O)C(=O)O)cc2)cc1]

To a solution of (2S,25S)-tetra-tert-butyl 3,24-bis(N-((benzyloxy)carbonyl)-N-(4-((4-(2,3-bis(tert-butoxycarbonyl)guanidino)benzoyl)oxy)benzyl)sulfamoyl)-6,9,12,15,18,21-hexaoxa-3,24-diazahexacosane-1,2,25,26-tetracarboxylate (300 mg) prepared in the Example 6-(a) in dichloromethane (2.5 mL) in a 30 mL cylindrical flask was added trifluoroacetic acid (0.43 mL) at 0° C. under argon atmosphere with stirring, and the resulting mixture was stirred at room temperature for 14 hours. The reaction solution was concentrated under reduced pressure. To a solution of the concentrated residues in dichloromethane (1 mL) was added trifluoroacetic acid (1 mL) at room temperature, and the resulting mixture was stirred at room temperature for 3 hours. The reaction solution was concentrated under reduced pressure. To a solution of the concentrated residues in methanol (3 mL) was added 51 palladium carbon (wetted with 54.28% water, STD-type manufactured by NE CHEMCAT Corporation (100 mg), the atmosphere in the reaction system was replaced with hydrogen atmosphere, and then the resulting mixture was stirred at room temperature for 2 hours. After the reaction was completed, the reaction solution was filtered through Celite and the resulting filtrate was concentrated under reduced pressure. The resulting residues were subjected to medium pressure preparative chromatography (CBS silica gel, elution solvent; aqueous solution with 0.1% trifluoroacetic acid acetonitrile solution with 0.1% trifluoroacetic acid), and the fractions comprising the target compound were freeze-dried to give the title compound (115.3 mg) as white solids.

Mass spectrum (ESI, m/z): 625 $[M+2H]^{20+}$.

$^1$H-NMR spectrum (400 MHz, DMSO-$d_6$+$D_2O$) δ: 8.20-8.14 (m, 4H), 7.47-7.39 (m, 8H), 7.27-7.20 (m, 4H), 4.60 (dd, J=5.4, 8.5 Hz, 23), 4.11 (d, J=13.2 Hz, 2H), 4.06 (d, J=15.2 Hz, 2H), 3.67-3.21 (m, 28H), 2.96 (dd, J=8.3, 16.6 Hz, 2H), 2.74-2.64 (m, 2).

Example 6-(c)

Preparation of (2S,25S)-3,24-bis(N-(4-((4-guanidinobenzoyl)oxy)benzyl)sulfamoyl)-6,9,12,15,18,21-hexaoxa-3,24-diazahexacosane-1,2,25,26-tetracarboxylic acid hydrochloride

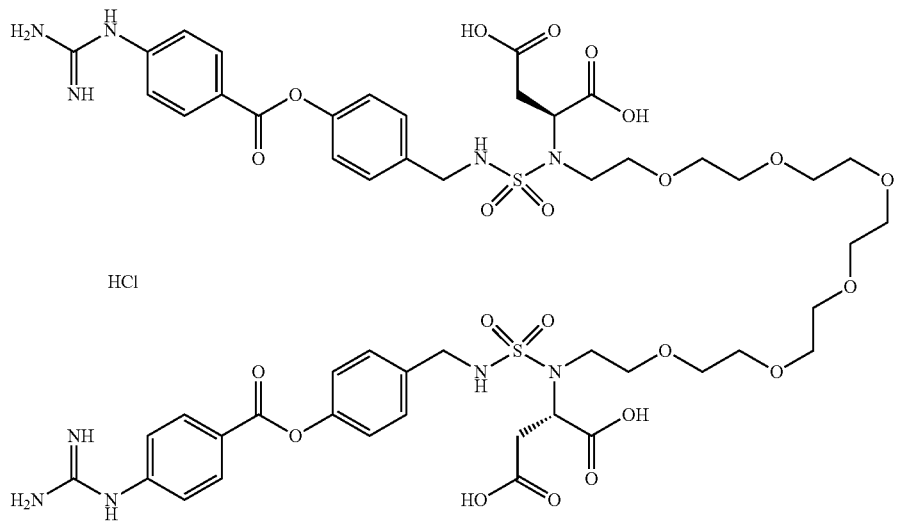 [SMILES: N=C(N)Nc1ccc(C(=O)Oc2ccc(CNS(=O)(=O)N(CCOCCOCCOCCOCCOCCOCCN([C@@H](CC(=O)O)C(=O)O)S(=O)(=O)NCc3ccc(OC(=O)c4ccc(NC(=N)N)cc4)cc3)[C@@H](CC(=O)O)C(=O)O)cc2)cc1 ; Cl]

To a solution of (2S,25S)-tetra-tert-butyl 3,24-bis(N-((benzyloxy)carbonyl)-N-(4-((4-(2,3-bis(tert-butoxycarbonyl)guanidino)benzoyl)oxy)benzyl)sulfamoyl)-6,9,12,15,18,21-hexaoxa-3,24-diazahexacosane-1,2,25,26-tetracarboxylate (3.23 g) prepared in the Example 6-(a) in dichloromethane (24 mL) in a 100 mL round-bottom flask was added trifluoroacetic acid (12 mL) at 0° C. under argon atmosphere with stirring, and the resulting mixture was stirred at room temperature for 8 hours. The reaction solution was concentrated under reduced pressure. To a solution of the concentrated residues in tetrahydrofuran (20 mL)/water (20 mL) was added 5% palladium carbon (wetted with 54.28% water, STD-type manufactured by NE CHEMCAT Corporation) (1.00 g), the atmosphere in the reaction system was replaced with hydrogen atmosphere, and then the resulting mixture was stirred at room temperature for 30 minutes. After the reaction was completed, the reaction solution was filtered through Celite, and the resulting filtrate was concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried. The resulting residues were subjected to medium pressure preparative chromatography (silica gel, acetonitrile solution with 0.1% trifluoroacetic acid aqueous solution with 0.1% trifluoroacetic acid), and the fractions comprising the target compound were concentrated under reduced pressure. A solution of the resulting residues in 0.1N hydrochloric acid (100 mL)/acetonitrile (20 mL) was freeze-dried. A solution of the resulting residues in acetonitrile (20 mL) was freeze-dried to give the title compound (1.23 g) as white solids.

Mass spectrum (ESI, m/z): 625 [M+2H]$^{2+}$.

$^1$H-NMR spectrum (400 MHz, DMSO-d$_6$+D$_2$O) δ: 8.21-8.13 (m, 4H), 7.47-7.38 (m, 8H), 7.27-7.20 (m, 4H), 4.60 (dd, J=5.6, 8.5 Hz, 2H), 4.12 (d, J=15.2 Hz, 2H), 4.06 (d, J=15.2 Hz, 2H), 3.80-3.19 (m, 28H), 2.96 (dd, J=8.5, 16.6 Hz, 2H), 2.69 (dd, J=5.6, 16.6 Hz, 2H).

Example 7

Example 7-(a)

Preparation of (2S,2'S)-tetra-tert-butyl 2,2'-(propane-1,3-diylbis((N-((benzyloxy)carbonyl)-N-(4-((4-(2,3-bis(tert-butoxycarbonyl)guanidino)benzoyl)oxy)benzyl)sulfamoyl)azanediyl))disuccinate

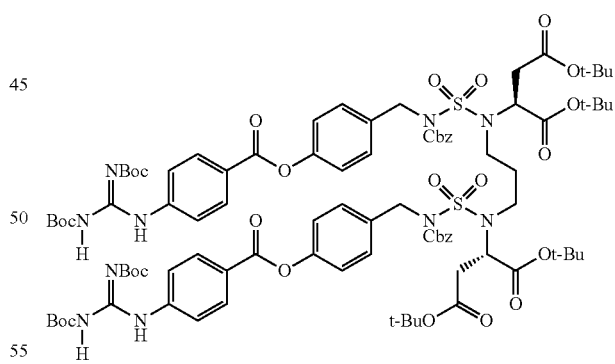

To a solution of 4-(hydroxymethyl)phenyl 4-(2,3-bis(tert-butoxycarbonyl)guanidino)benzoate (2.24 g) prepared according to the same manner as the Reference Example 1-(g), (2,2'S)-tetra-tert-butyl 2,2'-(propane-1,3-diylbis((N-((benzyloxy)carbonyl) sulfamoyl) azanediyl))disuccinate (2.10 g) prepared in the Reference Example 7-(c), and triphenylphosphine (1.40 g) in dehydrated tetrahydrofuran (12 mL) in a 100 mL round-bottom flask was added diisopropyl azodicarboxylate (a 1.9 M solution in toluene) (2.80 mL) under ice-cooling under argon atmosphere with stirring, and the resulting mixture was stirred at room temperature for 16 hours. After the reaction was completed, the reaction solution was concentrated under reduced pressure. The resulting residues were purified by medium pressure preparative chromatography (silica gel, elution solvent; hexane: ethyl acetate) to give the title compound (3.13 g) as a white foam.

Mass spectrum (EST, n/z): 947 [M+2H]$^{2+}$.

$^1$H-NMR spectrum (400 MHz, CDCl$_3$) δ: 11.62 (s, 2H), 10.63 (s, 2H), 8.19-8.12 (m, 4H), 7.85-7.77 (m, 4H), 7.43-7.23 (m, 14H), 7.15-7.10 (m, 4H), 5.19 (d, J=12.0 Hz, 2H), 5.15 (d, J=12.0 Hz, 2H), 5.04-4.89 (m, 4H), 4.61 (dd, J=5.8, 8.6 Hz, 2H), 3.43-3.28 (m, 2H), 3.10-2.97 (m, 2H), 2.87 (d, 7-8.6, 16.4 Hz, 2H), 2.58 (dd, J=5.8, 16.4 Hz, 2H), 1.99-1.85 (m, 2), 1.55 (s, 18H), 1.53 (s, 18H), 1.45 (s, 18), 1.45 (s, 18H).

Example 2-(b)

Preparation of (2S,2')-2,2'-propane-1,3-diylbis((N-(4-((4-guanidinobenzoyl)oxy)benzyl)sulfamoyl)azanediyl)disuccinic acid

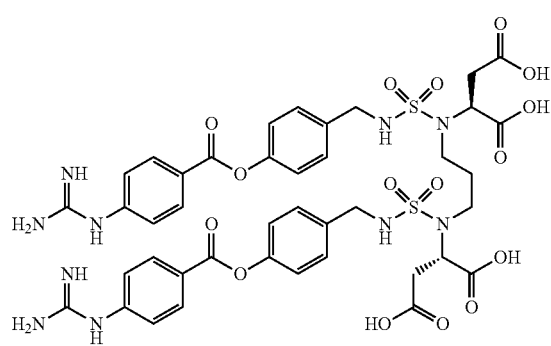 [SMILES: N=C(N)Nc1ccc(C(=O)Oc2ccc(CNS(=O)(=O)N(CCCN([C@@H](CC(=O)O)C(=O)O)S(=O)(=O)NCc3ccc(OC(=O)c4ccc(NC(=N)N)cc4)cc3)[C@@H](CC(=O)O)C(=O)O)cc2)cc1]

To a solution of (2S,2'S)-tetra-tert-butyl 2,2'-(propane-1,3-diylbis((N-((benzyloxy)carbonyl)-N-(4-((4-(2,3-bis(tert-butoxycarbonyl)guanidino)benzoyl)oxy)benzyl)sulfamoyl)azanediyl))disuccinate (3.13 g) prepared in the Example 7-(a) in dehydrated dichloromethane (15 mL) in a 200 mL round-bottom flask was added trifluoroacetic acid (5.00 mL) under ice-cooling under argon atmosphere with stirring, and the resulting mixture was stirred at room temperature for 16 hours. The reaction solution was concentrated under reduced pressure. To a solution of the concentrated residues in ethanol (10 mL) was added 10% palladium carbon (wetted with ca. 55% water, manufactured by Tokyo Chemical Industry Co., Ltd.) (200 mg), the atmosphere in the reaction system was replaced with hydrogen atmosphere, and then the resulting mixture was stirred at room temperature for 5 hours. After the reaction was completed, the atmosphere in the reaction system was replaced with nitrogen atmosphere, and the reaction solution was filtered through Celite. The removed solids were washed with a mixed solvent of ethanol and acetonitrile (1:1 (v/v)), and the resulting filtrate was concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), the fractions comprising the target compound were combined, and a saturated aqueous ammonium acetate solution was added thereto to adjust the pH to 4.0. The resulting mixture was stirred at room temperature for 1 hour, the precipitated solids were collected by filtration, and dried under reduced pressure to give the title compound (925 mg) as white solids.

Mass spectrum (ESI, m/z): 999 [M+H]$^+$.

$^1$H-NMR spectrum (400 MHz, DMSO-d$_6$+D$_2$O) δ: 7.72-7.52 (m, 4H), 7.25-7.16 (m, 4H), 7.02-6.90 (m, 8H), 4.50-4.31 (m, 4H), 3.97-3.74 (m, 2H), 3.70-2.78 (m, 6H), 2.59-2.29 (m, 2H), 2.15-1.99 (m, 2H).

Example 8

Example 8-(a)

Preparation of (2S,2'S)-tetra-tert-butyl 2,2'-(butane-1,4-diylbis((N-((benzyloxy)carbonyl)-N-(4-((4-(2,3-bis(tert-butoxycarbonyl)guanidino)benzoyl)oxy)benzyl)sulfamoyl)azanediyl))disuccinate

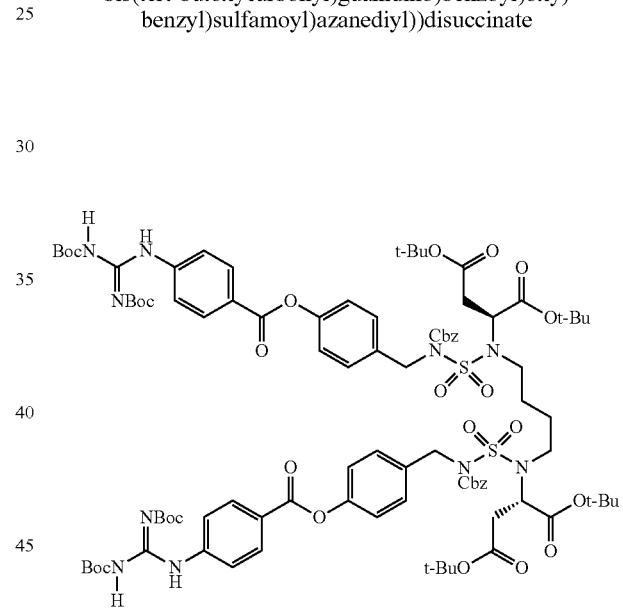

To a solution of 4-(hydroxymethyl)phenyl 4-(2,3-bis(tert-butoxycarbonyl)guanidino)benzoate (2.90 g) prepared according to the same manner as the Reference Example 1-(g), (2S,2'S)-tetra-tert-butyl 2,2'-(butane-1,4-diylbis((N-((benzyloxy)carbonyl)sulfamoyl)azanediyl))disuccinate (2.72 g) prepared in the Reference Example 8-(c), and triphenylphosphine (1.80 g) in dehydrated tetrahydrofuran (15 mL) in a 100 mL round-bottom flask was added diisopropyl azodicarboxylate (a 1.9 M solution in toluene) (3.60 mL) under ice-cooling under argon atmosphere with stirring, and the resulting mixture was stirred at room temperature for 2 hours. After the reaction was completed, the reaction solution was concentrated under reduced pressure. The resulting residues were purified by medium pressure preparative chromatography (silica gel, elution solvent; hexane: ethyl acetate) to give the title compound (3.23 g) as a white foam.

Mass spectrum (DUIS, m/z): 954 [M+2H]$^{2+}$.

$^1$H-NMR spectrum (400 MHz, CDCl$_3$) δ: 11.62 (s, 2H), 10.63 (s, 2H), 8.20-8.12 (m, 4H), 7.85-7.77 (m, 4H), 7.45-7.23 (m, 14H), 7.15-7.10 (m, 4H), 5.19 (d, J=12.0 Hz, 2H), 5.15 (d, J=12.0 Hz, 2H), 5.03-4.89 (m, 4H), 4.60 (dd, J=5.6, 8.8 Hz, 2H), 3.43-3.28 (m, 2H), 3.11-2.96 (m, 2H), 2.83 (dd, J=8.8, 16.4 Hz, 2H), 2.56 (dd, J=5.6, 16.4 Hz, 2H), 1.55 (s, 18H), 1.53 (s, 18H), 1.45 (s, 18H), 1.45 (s, 18H), 1.73-1.19 (m, 4H).

Example 8-(b)

Preparation of (2S,2'S)-2,2'-(butane-1,4-diylbis((N-(4-((4-guanidinobenzoyl)oxy)benzyl)sulfamoyl)azanediyl))disuccinic acid trifluoroacetate

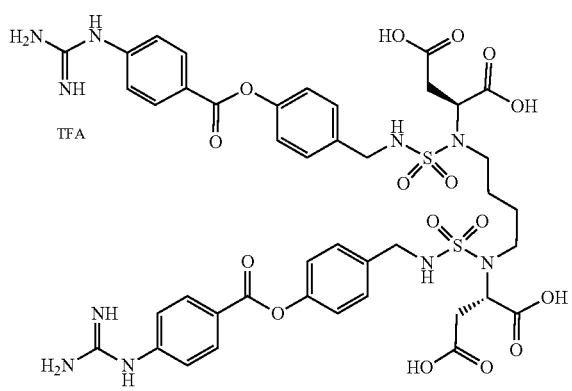 [SMILES: N=C(N)Nc1ccc(C(=O)Oc2ccc(CNS(=O)(=O)N(CCCCN([C@@H](CC(=O)O)C(=O)O)S(=O)(=O)NCc3ccc(OC(=O)c4ccc(NC(=N)N)cc4)cc3)[C@@H](CC(=O)O)C(=O)O)cc2)cc1 ; Cl]

To a solution of (2S,2'S)-tetra-tert-butyl 2,2'-(butane-1,4-diylbis((N-((benzyloxy)carbonyl)-N-(4-((4-(2,3-bis(tert-butoxycarbonyl)guanidino)benzoyl)oxy)benzyl)sulfamoyl)azanediyl))disuccinate (3.23 g) prepared in the Example 8-(a) in dehydrated dichloromethane (15 mL) in a 200 mL round-bottom flask was added trifluoroacetic acid (5.00 mL) under ice-cooling under argon atmosphere with stirring, and the resulting mixture was stirred at room temperature for 16 hours. The reaction solution was concentrated under reduced pressure. To a solution of the concentrated residues in ethanol (10 mL) was added 10% palladium carbon (wetted with ca. 55% water, manufactured by Tokyo Chemical Industry Co., Ltd.) (210 mg), the atmosphere in the reaction system was replaced with hydrogen atmosphere, and then the resulting mixture was stirred at room temperature for 4 hours. After the reaction was completed, the atmosphere in the reaction system was replaced with nitrogen atmosphere, and the reaction solution was filtered through Celite. The removed solids were washed with a mixed solvent of ethanol and acetonitrile (1:1 (v/v)), and the resulting filtrate was concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), the fractions comprising the target compound were combined, and a saturated aqueous ammonium acetate solution was added thereto to adjust the pH to 4.0.

The resulting mixture was stirred at room temperature for 1 hour, the precipitated solids were collected by filtration, and dried under reduced pressure to give the title compound 1.25 g) as white solids.

Mass spectrum (ESI, m/z): 1011 [M–H]$^-$.

$^1$H-NMR spectrum (400 MHz, DMSO-d$_6$+D$_2$O) δ: 7.86-7.74 (m, 4H), 7.30-7.15 (m, 8H), 7.06-6.97 (m, 4H), 4.58-4.42 (m, 2H), 4.30-4.10 (m, 4H), 3.94-2.79 (m, 6H), 2.63-2.29 (m, 2H), 1.68-1.44 (m, 4H).

Example 8-(c)

Preparation of (2S,2'S)-2,2'-(butane-1,4-diylbis((N-(4-((4-guanidinobenzoyl)oxy)benzyl)sulfamoyl)azanediyl))disuccinic acid hydrochloride

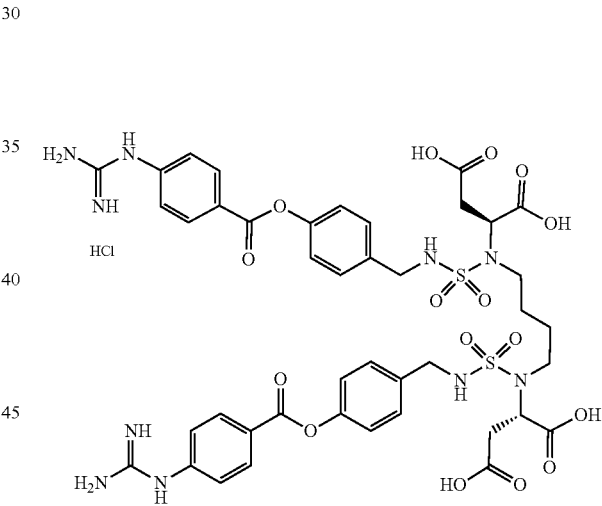

(2S,2'S)-2,2'-butane-1,4-diylbis((N-(4-((4-guanidinobenzoyl)oxy)benzyl)sulfamoyl)azanediyl))disuccinic acid trifluoroacetate (730 mg) prepared in the Example 8-(b) in a 300 mL round-bottom flask was dissolved into acetonitrile (10 mL) and 0.1 M hydrochloric acid (31 mL), and the resulting solution was freeze-dried to give the title compound (731 mg) as white solids.

Mass spectrum (ESI, M/z): 1011 [M–H]$^-$.

$^1$H-NMR spectrum (400 MHz, DMSO-d$_6$+D$_2$O) δ: 8.20-8.13 (m, 4H), 7.47-7.39 (m, 8H), 1.26-7.20 (m, 4H), 4.56-4.46 (m, 2H), 4.14 (d, J=15.2 Hz, 2H), 4.09 (d, J=15.2 Hz, 2H), 3.30-3.03 (m, 4H), 2.97 (dd, J=9.2, 16.5 Hz, 2H), 2.62 (br dd, J=4.8, 16.5 Hz, 2H), 1.65-1.46 (m, 4H).

Example 9

Example 9-(a)

Preparation of (2S,2'S)-tetra-tert-butyl 2,2'-(pentane-1,5-diylbis((N-((benzyloxy)carbonyl)-N-(4-((4-(2,3-bis(tert-butoxycarbonyl)guanidino)benzoyl)oxy)benzyl)sulfamoyl)azanediyl))disuccinate

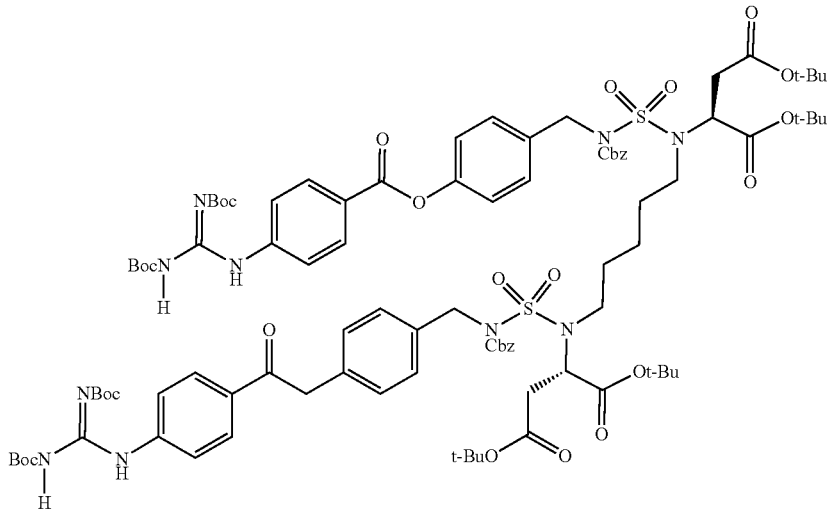

To a solution of (2S,2'S)-tetra-tert-butyl 2,2'-(pentane-1,5-diylbis((N-((benzyloxy)carbonyl)sulfamoyl)azanediyl)) disuccinate (505 mg) prepared in the Reference Example 9-(c) in tetrahydrofuran (10 mL) in a 100 mL round-bottom flask were added 4-(hydroxymethyl)phenyl 4-(2,3-bis(tert-butoxycarbonyl)guanidino)benzoate (524 mg) prepared according to the same manner as the Reference Example 1-(g), triphenylphosphine (308 mg), and diisopropyl azodicarboxylate (a 1.9 M solution in toluene) (0.595 mL) at room temperature under argon atmosphere with stirring, and the resulting mixture was stirred at room temperature overnight. After the reaction was completed, to the reaction solution was added water, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (333.1 mg) as a white foam.

Mass spectrum (ESI, m/z): 961 $[M+2H]^{2+}$.

$^1$H-NMR spectrum (400 MHz, CDCl$_3$) δ: 11.62 (s, 2H), 10.63 (s, 2H), 3.19-8.13 (m, 4H), 7.84-7.77 (m, 4H), 7.45-7.22 (m, 14H), 7.16-7.10 (m, 4H), 5.19 (d, J=12.2 Hz, 2H), 5.15 (d, J=12.2 Hz, 2H), 4.97 (d, J=16.0 Hz, 2H), 4.92 (d, J=16.0 Hz, 2H), 4.61 (dd, J=5.7, 8.8 Hz, 2H), 3.42-3.31 (m, 2H), 3.09-2.96 (m, 2H), 2.33 (dd, J=8.3, 16.4 Hz, 2H), 2.55 (dd, J=5.7, 16.4 Hz, 2H), 1.53 (s, 18H), 1.45 (s, 18H), 1.45 (s, 18H), 1.74-1.19 (m, 22H), 1.00-0.82 (m, 2H).

Example 9-(b)

Preparation of (2S,2'S)-2,2'-(pentane-1,5-diylbis((N-(4-((4-guanidinobenzoyl oxy)benzyl)sulfamoyl)azanediyl))disuccinic acid

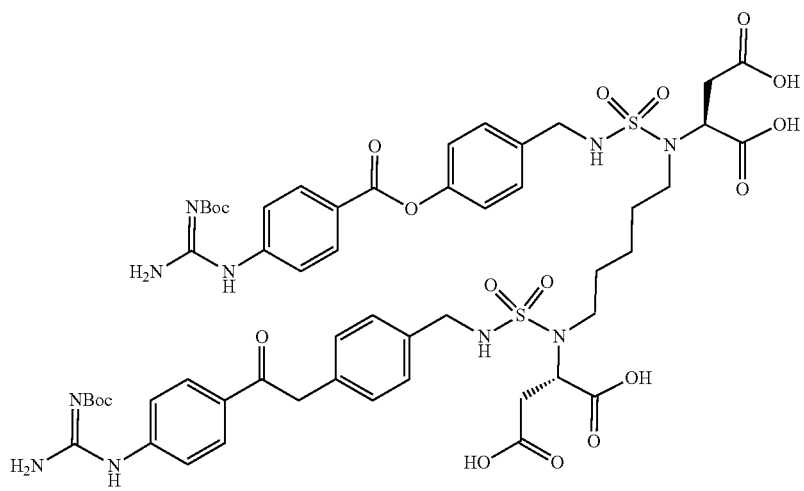

To a solution of (2S,2'S)-tetra-tert-butyl 2,2'-(pentane-1,5-diylbis(N-((benzyloxy)carbonyl)-N-(4-((4-(2,3-bis(tert-butoxycarbonyl)guanidino)benzoyl)oxy)benzyl)sulfamoyl)azanediyl))disuccinate (388 mg) prepared in the Example 9-(a) in dichloromethane (10 mL) in a 100 mL round-bottom flask was added trifluoroacetic acid (3.56 mL) at 0° C. under air atmosphere with stirring, and the resulting mixture was stirred at room temperature overnight. The reaction solution was concentrated under reduced pressure. To a solution of the concentrated residues in ethanol (10 mL) was added 5% palladium carbon (wetted with 55.32% water, STD-type manufactured by NE CHEMCAT Corporation) (181 mg) at room temperature under air atmosphere with stirring, and the resulting mixture was stirred at room temperature under hydrogen atmosphere for 3 hours. After the reaction was completed, the reaction solution was filtered through Celite, washed with a mixed solvent of ethanol and acetonitrile (1:1 (v/v)), and the resulting filtrate was concentrated under reduced pressure. The concentrated residues were subjected to medium pressure preparative chromatography (ODS silica gel, elution solvent; aqueous solution with 0.1% trifloroacetic acid:acetonitrile solution with 0.1% trifluoroacetic acid), and the fractions comprising the target compound were freeze-dried. The resulting solids were dissolved into water (4 mL) and acetonitrile (1 mL), and to the resulting solution was added a saturated aqueous ammonium acetate solution to adjust the pH to 4.0. The resulting mixture was stirred at room temperature for 1 hour, the resulting precipitates were collected by filtration, and dried to give the title compound (50.7 mg) as white solids.

Mass spectrum (ESI, m/z): 1025 [M−H]⁻.

$^1$H-NMR spectrum (400 MHz, DMSO-$d_6$+$D_2O$) δ: 7.94-7.77 (m, 4H), 7.41-6.93 (m, 12H), 4.60-4.39 (m, 2H), 4.35-4.00 (m, 4H), 3.74-2.77 (m, 6H), 2.62-2.26 (m, 2H), 1.79-1.43 (m, 4H), 1.32-1.09 (m, 2H).

Example 10

Example 10-(a)

Preparation of tetra-tert-butyl 3,18-bis(((4-((4-(2,3-bis(tert-butoxycarbonyl)guanidino)benzoyl)oxy)benzyl)oxy)carbonyl)-6,9,12,15-tetraoxa-3,18-diaza-icosane-1,2,19,20-tetracarboxylate

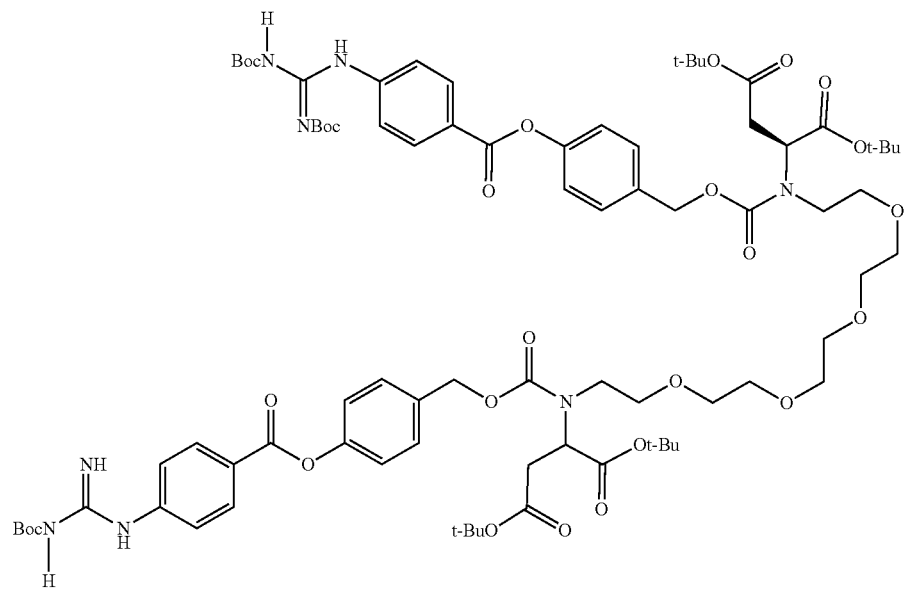

To a solution of tetra-tert-butyl 6,9,12,15-tetraoxa-3,18-diazaicosane-1,2,19,20-tetracarboxylate (403 mg) prepared in the Reference Example 10-(c) in dichloromethane (15 mL) in a 100 mL round-bottom flask was added 1-(((4-((4-(2,3-bis(tert-butoxycarbonyl)guanidino)benzoyl)oxy)benzyl)oxy)carbonyl)-3-methyl-1H-imidazol-3-ium trifluoromethanesulfonate (1.03 g) prepared according to the same manner as the Reference Example 10-(b) at room temperature under argon atmosphere with stirring, the resulting mixture was stirred at room temperature for 24 hours, and left to stand for 15 hours. After the reaction was completed, the reaction solution was concentrated under reduced pressure. The resulting residues were purified by medium pressure preparative chromatography (silica gel, elution solvent; hexane:ethyl acetate) to give the title compound (235.1 mg) as a colorless oil.

Mass spectrum (ESI, m/z): 1738 [M+N]$^+$.

$^1$H-NMR spectrum (400 MHz, CDCl$_3$) δ: 11.62 (s, 2H), 10.64 (s, 2H), 8.19-8.12 (m, 4H), 7.84-7.78 (m, 4H), 7.44-7.38 (m, 4H), 7.22-7.16 (m, 4H), 5.27-5.02 (m, 4H), 4.62-4.41 (m, 2H), 3.76-3.52 (m, 18H), 3.50-3.35 (m, 2H), 3.15-2.95 (m, 2H), 2.79-2.64 (m, 2H), 1.61-1.49 (m, 36H), 1.46-1.33 (m, 36H).

Example 10-(b)

Preparation of 3,18-bis(((4-((4-guanidinobenzoyl)oxy)benzyl)oxy)carbonyl)-6,9,12,15-tetraoxa-3,18-diazaicosane-1,2,19,20-tetracarboxylic acid trifluoroacetate To a solution of tetra-tert-butyl 3,18-bis' (4-(4-(2,3-bis(tert-butoxycarbonyl)guanidino)benzoyl)oxy)benzyl)oxy)carbonyl)-6,9,12,15-tetraoxa-3,1-diazaicosane-1,2,19,20-tetracarboxylate (1.50 g) prepared according to the same manner as the Example 10-(a) in dichloromethane (21.4 mL) in a 100 mL round-bottom flask was added trifluoroacetic acid (5.35 mL) at 0° C. under argon atmosphere with stirring, and the resulting mixture was stirred at room temperature for 15 hours. After the reaction was completed, the reaction solution was concentrated under reduced pressure. The resulting residues were subjected to medium pressure preparative chromatography (silica gel, elution solvent; acetonitrile solution with 0.1% trifluoroacetic acid: aqueous solution with 0.1% trifluoroacetic acid), and the fractions comprising the target compound were concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried to give the title compound (790 mg) as white solids.

Mass spectrum (ESI, m/z): 1091 [M+H]$^+$.

$^1$H-NMR spectrum (400 MHz, CD$_3$CN/D$_2$O=1/1) δ: 8.26-8.17 (m, 4H), 7.52-7.41 (m, 8I), 7.30-7.22 (m, 4H), 5.18-5.08 (m, 4H), 4.62-4.48 (m, 2H), 3.66-3.48 (m, 20H), 3.19-3.00 (m, 2H), 2.89-2.76 (m, 2H).

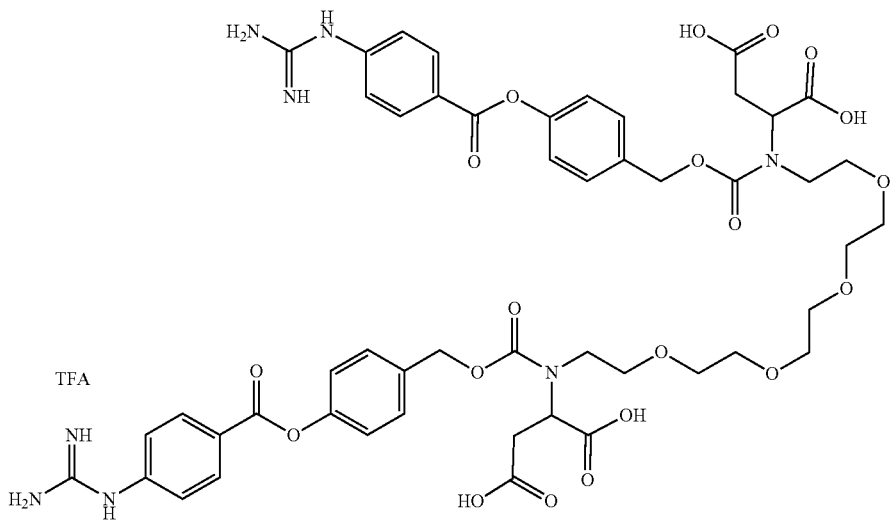 [SMILES: N=C(N)Nc1ccc(C(=O)Oc2ccc(COC(=O)N(CCOCCOCCOCCOCCN(C(=O)OCc3ccc(OC(=O)c4ccc(NC(=N)N)cc4)cc3)C(CC(=O)O)C(=O)O)C(CC(=O)O)C(=O)O)cc2)cc1]

Example 11

Example 11-(a)

Preparation of tetra-tert-butyl 2,2'-(1,20-bis(4-((4-(2,3-bis(tert-butoxycarbonyl)guanidino)benzoyl)oxy)phenyl)-3,18-dioxo-2,19-dioxa-4,17-diazaicosane-4,17-diyl)disuccinate

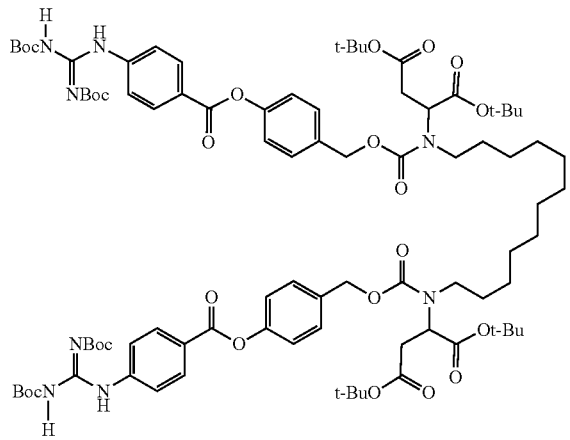

To a solution of tetra-tert-butyl 2,2'-(dodecane-1,12-diyl-bis(azanediyl))disuccinate (0.920 g) prepared in the Reference Example 11-(a) in acetonitrile (30 mL) in a 200 mL round-bottom flask was added 1-(((4-((4-(2,3-bis(tert-butoxycarbonyl)guanidino)benzoyl)oxy)benzyl)oxy)carbonyl)-3-methyl-1H-imidazol-3-ium trifluoromethanesulfonate (2.5 g) prepared according to the same manner as the Reference Example 10-(b) at room temperature under argon atmosphere with stirring, and the resulting mixture was stirred at room temperature for 71 hours. After the reaction was completed, the reaction solution was concentrated under reduced pressure. The resulting residues were purified by medium pressure preparative chromatography (silica gel, elution solvent; hexane:ethyl acetate) to give the title compound (1.64 g) as a colorless oil.

Mass spectrum (ESI, m/z): 1702 [M+Na]$^+$.

$^1$H-NMR spectrum (400 MHz, CDCl$_3$) δ: 11.62 (s, 2H), 10.64 (s, 2H), 3.18-8.14 (m, 4H), 7.85-7.77 (m, 4H), 7.48-7.37 (m, 4H), 7.29-7.16 (m, 4H), 5.28-5.00 (m, 42), 4.47-4.31 (m, 2H), 3.56-3.36 (m, 2H), 3.16-2.98 (m, 4H), 2.73-2.43 (m, 2H), 1.72-1.18 (m, 92H).

Example 11-(b)

Preparation of 2,2'-(1,20-bis(4-((4-guanidinobenzoyl)oxy)phenyl 3,18-dioxo-2,19-dioxa-4,17-diazaicosane-4,17-diyl)disuccinic acid trifluoroacetate

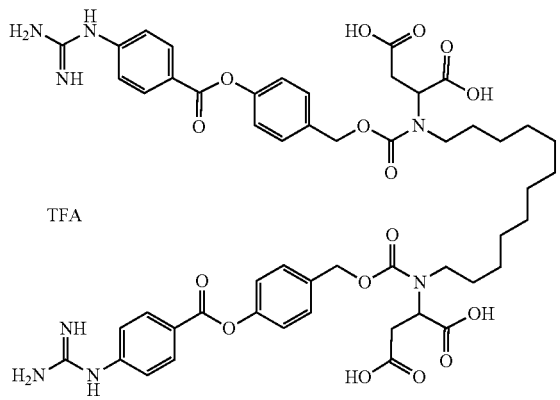 [SMILES: N=C(N)Nc1ccc(C(=O)Oc2ccc(COC(=O)N(CCCCCCCCCCCCN(C(=O)OCc3ccc(OC(=O)c4ccc(NC(=N)N)cc4)cc3)C(CC(=O)O)C(=O)O)C(CC(=O)O)C(=O)O)cc2)cc1]

To a solution of tetra-tert-butyl 2,2'-(1,20-bis(4-((4-(2,3-bis(tert-butoxycarbonyl)guanidino)benzoyl)oxy)phenyl)-3,18-dioxo-2,19-dioxa-4,17-diazaicosane-4,17-diyl)disuccinate (260 ng) prepared according to the same manner as the Example 11-(a) in dichloromethane (4 mL) in a 10 mL round-bottom flask was added trifluoroacetic acid (3.947 mL) at 0° C. under argon atmosphere with stirring, and the resulting mixture was stirred at room temperature for 14 hours. Alter the reaction was completed, the reaction solution was concentrated under reduced pressure. The resulting residues were subjected to medium pressure preparative chromatography (ODS silica gel, elution solvent; aqueous solution with 0.1% trifluoroacetic acid aceronitrile solution with 0.1% trifluoroacetic acid), and the fractions comprising the target compound were freeze-dried. The resulting residues were subjected to medium pressure preparative chromatography (silica gel, elution solvent; acetonitrile solution with 0.1% trifluoroacetic acid:aqueous solution with 0.1% trifluoroacetic acid), and the fact ions comprising the target compound were freeze-dried to give the title compound (117.6 mg) as white solids.

Mass spectrum (ESI, m/z): 1055 [M+H]$^+$.

$^1$H-NMR spectrum (400 MHz, CD$_3$CN/D$_2$O=1/1) δ: 8.28-8.12 (m, 4H), 7.51-7.39 (m, 8H), 7.29-7.19 (m, 4H), 5.17-5.02 (m, 4H), 4.51-4.42 (m, 2H), 3.46-3.29 (m, 2H), 3.27-2.99 (m, 4H), 2.77-2.60 (m, 2H), 1.61-1.40 (m, 4H), 1.32-1.09 (m, 16H).

Example 11-(c)

Preparation of 2,2'-(1,20-bis(4-((4-guanidinobenzoyl)oxy)phenyl)-3,18-dioxo-2,19-dioxa-4,17-diazaicosane-4,17-diyl)disuccinic acid

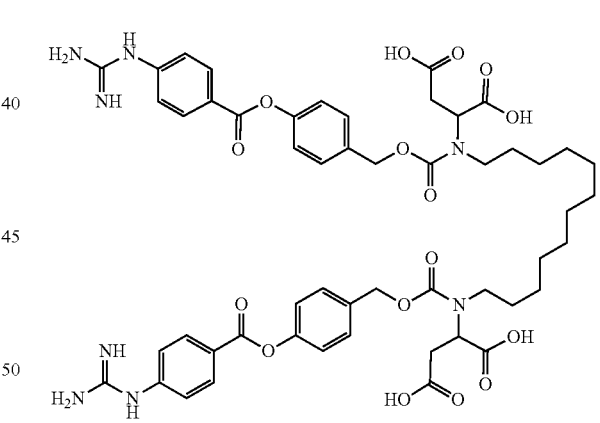

To a solution of tetra-tert-butyl 2,2'-(1,20-bis(4-((4-(2,3-bis(tert-butoxycarbonyl)guanidino)benzoyl)oxy)phenyl)-3,18-dioxo-2,19-dioxa-4,17-diazaicosane-4,17-diyl)disuccinate (1.64 g) prepared in the Example 11-(a) in dichloromethane (24 mL) in a 200 mL round-bottom flask was added trifluoroacetic acid (6.00 mL) at 0° C. under argon atmosphere with stirring, and the resulting mixture was stirred at room temperature for 19 hours. After the reaction was completed, the reaction solution was concentrated under reduced pressure. The resulting residues were subjected to medium pressure preparative chromatography (silica gel, elution solvent; acetonitrile solution with 0.1% trifluoroacetic acid:aqueous solution with 0.1% trifluoroacetic acid), and the fractions comprising the target compound were concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were concentrated under reduced pressure. The concentrated suspension was stirred at room temperature for 30 minutes, the precipitated solids were collected by filtration, and dried under reduced pressure to give the title compound (497 mg) as white solids.

Mass spectrum (ESI, m/z): 1055 [M+H]$^+$.

$^1$H-NMR spectrum. (40 MHz, DMSO-d$_6$+D$_2$O) δ: 8.13-8.00 (m, 4H), 77.51-7.32 (m, 8H), 7.23-6.86 (m, 4H), 5.21-4.77 (m, 4H), 4.39-3.94 (m, 2H), 3.79-2.78 (m, 6H), 2.60-2.38 (m, 2H), 1.52-0.69 (m, 20).

Example 12

Example 12-(a)

Preparation of (3S,6S,25S,28S)-di-tert-butyl 3,28-bis(((4-((4-(2,3-bis(tert-butoxycarbonyl)guanidino)benzoyl)oxy)benzyl)oxy)carbonyl)amino)-6,25-bis(2-(tert-butoxy)-2-oxoethyl)-4,7,24,27-tetraoxo-11,14,17,20-tetraoxa-5,8,23,26-tetraazatriacontane-1,30-dioate To a solution of (3S,6S,25S,28S)-di-tert-butyl 3,28-diamino-6,25-bis(2-(tert-butoxy)-2-oxoethyl)-4,7,24,27-tetraoxo-11,14,17,20-tetraoxa-5,8,23,26-tetraazatriacontane-1,30-dioate (1.50 g) prepared according to the same manner as the Reference Example 12-(d) in dichloromethane (30 mL) in a 200 mL round-bottom flask was added 1-(((4-(4-(2,3-bis(tert-butoxycarbonyl)guanidino)benzoyl)oxy)benzyl)oxy)carbonyl)-3-methyl-1H-imidazo-3-ium trifluoromethanesulfonate (2.91 g) prepared according to the same manner as the Reference Example 10-(b) at room temperature under argon atmosphere with stirring, and the resulting mixture was stirred at room temperature for 20 hours. After the reaction was completed, the reaction solution was concentrated under reduced pressure. The resulting residues were purified by medium pressure preparative chromatography (DIOL silica gel, elution solvent; hexane:ethyl acetate) to give the title compound (1.79 g) as a white foam.

Mass spectrum (ESI, m/z): 973 [M+2H]$^{2+}$.

$^1$H-NMR spectrum (400 MHz, CDCl$_3$) δ: 11.62 (s, 2H), 10.64 (s, 2H), 8.19-8.13 (m, 4H), 7.85-7.78 (m, 4H), 7.55 (d, J=8.5 Hz, 2H), 7.46-7.38 (m, 4H), 7.23-7.18 (m, 4H), 7.15-7.06 (m, 2H), 5.93 (d, J=8.3 Hz, 2H), 5.17 (d, J=12.4 Hz, 2H)), 5.11 (d, J=12.4 Hz, 2H), 4.80-4.66 (m, 2H), 4.58-4.42 (m, 2H), 3.70-3.33 (m, 20H), 2.95-2.81 (m, 4H), 2.72 (dd, J=6.4, 16.8 Hz, 2H), 2.61 (dd, J=6.0, 16.8 Hz, 2H), 1.55 (s, 18H), 1.53 (s, 18H), 1.44 (s, 18H), 1.43 (s, 18H).

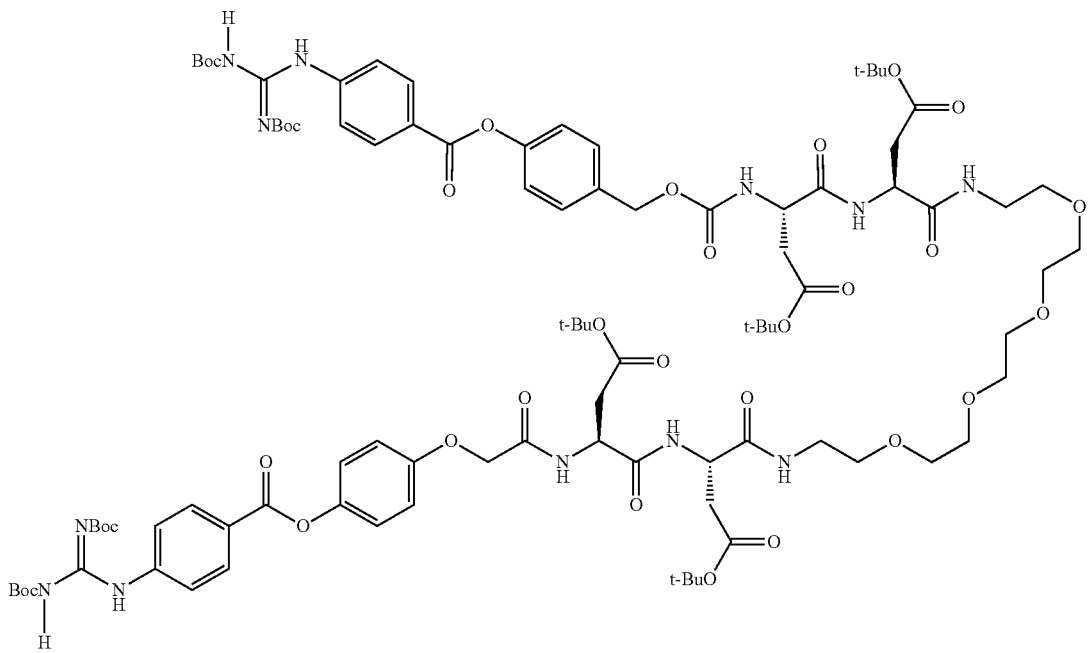

Example 12-(b)

Preparation of (3S,6S,25S,28S)-6,25-bis(carboxymethyl)-3,28-bis((((4-((4-guanidinobenzoyl)oxy)benzyl)oxy)carbonyl)amino)-4,7,24,27-tetraoxo-11,14,17,20-tetraoxa-5,8,23,26-tetraazatriacontane-1,30-dioic acid trifluoroacetate

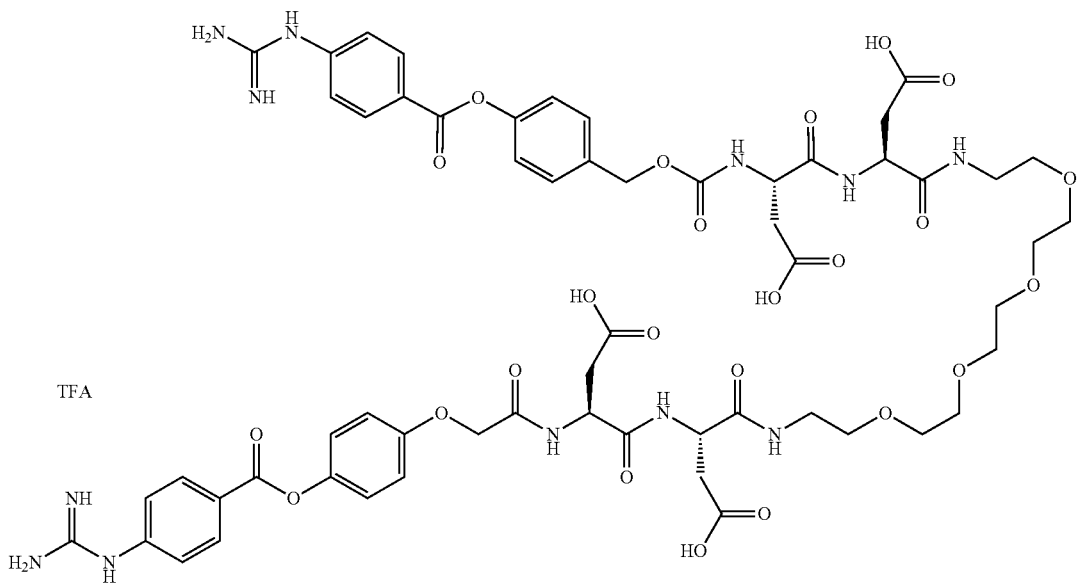 [SMILES: N=C(N)Nc1ccc(C(=O)Oc2ccc(COC(=O)N[C@@H](CC(=O)O)C(=O)N[C@@H](CC(=O)O)C(=O)NCCOCCOCCOCCOCCNC(=O)[C@H](CC(=O)O)NC(=O)[C@H](CC(=O)O)NC(=O)COc3ccc(OC(=O)c4ccc(NC(=N)N)cc4)cc3)cc2)cc1]

To a solution of (3S,6S,25S,28S)-di-tert-butyl 3,28-bis ((((4-((4-(2,3-bis(tert-butoxycarbonyl)guanidino)benzoyl)oxy)benzyl)oxy)carbonyl)amino)-6,25-bis(2-(tert-butoxy)-2-oxoethyl)-4,7,24,27-tetraoxo-11,14,17,20-tetraoxa-5,8,23,26-tetraazatriacontane-1,30-dioate (1.79 g) prepared in the Example 12-(a) in dichloromethane (12 mL) in a 200 mL round-bottom flask was added trifluoroacetic acid (3 mL) at 0° C. under argon atmosphere with stirring, and the resulting mixture was stirred at room temperature for 15 hours. The reaction solution was concentrated under reduced pressure. To the concentrated residues were added dichloromethane (5 ml) and trifluoroacetic acid (10 mL) at room temperature, and the resulting mixture was stirred at room temperature for 3 hours. After the reaction was completed, the reaction solution was concentrated under reduced pressure. To a solution of the resulting residues in water (15 mL)/acetonitrile (10 mL) was added a saturated aqueous ammonium acetate solution to adjust the pH to 4.0. The reaction solution was concentrated under reduced pressure, and the concentrated solution was stirred at room temperature for 1 hour. To the reaction solution was added methanol, and the resulting mixture was left no stand at room temperature for 2 days. To the reaction solution was added trifluoroacetic acid (80 μL) to adjust the pH to 4.0. The reaction solution was concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried to give the title compound (900 mg) as white solids.

Mass spectrum (ESI, m/z): 660 $[M+2H]^{2+}$.

$^1$H-NMR spectrum (400 Mhz, $CD_3CN/D_2O$=1/1) δ: 8.26-8.17 (m, 4H), 7.52-7.41 (m, 8H), 7.30-7.22 (m, 4H), 5.20-5.07 (m, 4), 4.70-4.59 (m, 2H), 4.52-4.45 (m, 2H), 3.65-3.45 (m, 16H), 3.37-3.25 (m, 4H), 2.92-2.65 (m, 8H).

Example 12-(c)

Preparation of (3S,6S,25S,28S)-6,25-bis(carboxymethyl)-3,28-bis((((4-((4-guanidinobenzoyl)oxybenzyl)oxy)carbonyl)amino)-4,7,24,27-tetraoxo-11,14,17,20-tetraoxa-5,8,23,26-tetraazatriacontane-1,30-dioic acid

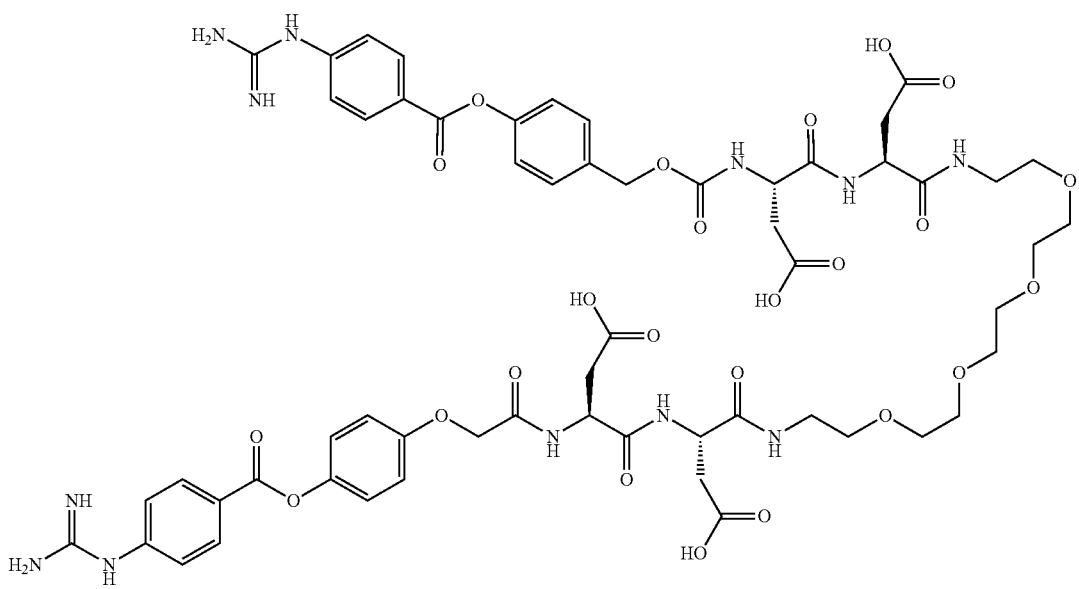 [SMILES: N=C(N)Nc1ccc(C(=O)Oc2ccc(COC(=O)N[C@@H](CC(=O)O)C(=O)N[C@@H](CC(=O)O)C(=O)NCCOCCOCCOCCOCCNC(=O)[C@H](CC(=O)O)NC(=O)[C@H](CC(=O)O)NC(=O)COc3ccc(OC(=O)c4ccc(NC(=N)N)cc4)cc3)cc2)cc1]

To a solution of (3S,6S,25S,28S)-di-tert-butyl 3,28-bis(((4-(4-((4-(2,3-bis(tert-butoxycarbonyl)guanidino)benzoyl)oxy)benzyl)oxy)carbonyl)amino)-6,25-bis(2-(tert-butoxy)-2-oxoethyl)-4,7,24,27-tetraoxo-11,14,17,20-tetraoxa-5,8,23,26-tetraazatriacontane-1,30-dioate (180 mg) prepared according to the same manner as the Example 12-(a) in dichloromethane (1.132 mL) in a 30 mL cylindrical flask was added trifluoroacetic acid (283 μL) at 0° C. under argon atmosphere with stirring, and the resulting mixture was stirred at room temperature for 14 hours. After the reaction was completed, the reaction solution was concentrated under reduced pressure. To a solution of the resulting residues in water (1.5 mL)/acetonitrile (0.75 mL) was added a saturated aqueous ammonium acetate solution to adjust the pH to 4.0. The resulting mixture was stirred at room temperature for 1 hour, the precipitated solids were collected by filtration, and dried under reduced pressure to give the title compound (72 mg) as white solids.

Mass spectrum (ESI, m/z): 660 $[M+2H]^{2+}$.

$^1$H-NMR spectrum (400 MHz, DMSO-$d_6$+$D_2O$) δ: 8.12-7.94 (m, 4H), 7.47-7.26 (m, 8H), 7.21-7.11 (m, 4H), 5.18-4.90 (m, 4H), 4.45-4.17 (m, 4H), 3.71-3.25 (m, 16H), 3.23-3.02 (m, 4H), 2.65-2.32 (m, 8H).

Example 13

Example 13-(a)

Preparation of (3S,6S,23S,26S)-di-tert-butyl 3,26-bis(((((4-((4-(2,3-bis(tert-butoxycarbonyl)guanidino)benzoyl)oxy)benzyl)oxy)carbonyl)amino)-6,23-bis(2-(tert-butoxy)-2-oxoethyl)-4,7,22,25-tetraoxo-5,8,21,24-tetraazaoctacosane-1,28-dioate

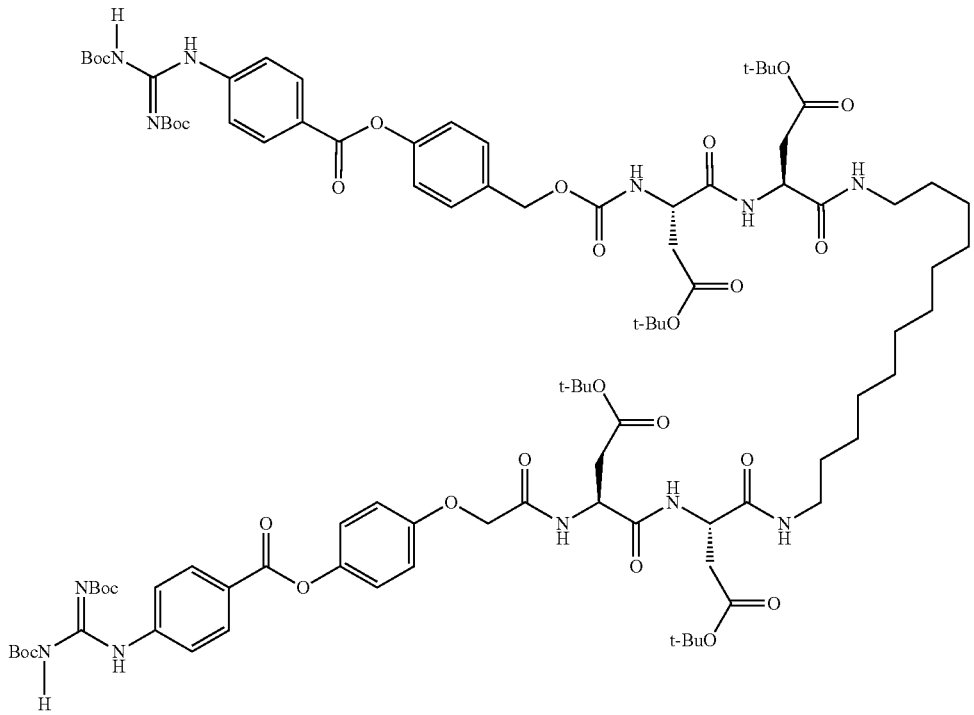

To a solution of (3S,6S,23S,26S)-di-tert-butyl 3,26-diamino-6,23-bis(2-(tert-butoxy)-2-oxoethyl)-4,7,22,25-tetraoxo-5,8,21,24-tetraazaoctacosane-1,28-dioate (950 mg) prepared in the Reference Example 13-(d) in dichloromethane 130 mL) in a 200 mL round-bottom flask was added 1-(((4-((4-(2,3-bis(tert-butoxycarbonyl)guanidino)benzoyl)oxy)benzyl)oxy)carbonyl)-3-methyl-1H-imidazol-3-ium trifluoromethanesulfonate (1.80 g) prepared according to the same manner as the Reference Example 10-(b) at room temperature under argon atmosphere with stirring, and the resulting mixture was stirred at room temperature for 1 hour. After the reaction was completed, the reaction solution was concentrated under reduced pressure. To the concentrated solution was added hexane (12; mL), the resulting mixture was stirred at room temperature for 10 minutes, the precipitated solids were collected by filtration, and dried under reduced pressure to give the title compound (1.60 g) as white solids.

Mass spectrum (ESI, m/z): 955 [M+2H]$^+$.

$^1$H-NMR spectrum (400 MHz, CDCl$_3$) δ: 11.62 (s, 2H), 10.64 (s, 2H), 8.19-8.13 (m, 4H), 1.85-7.78 (m, 4H), 7.50 (br d, J=8.7 Hz, 2H), 7.46-7.39 (m, 1H), 7.24-7.18 (m, 4H), 6.89-677 (m, 2H), 5.77 (br d, J=8.2 Hz, 2H), 5.17 (d, J=12.2 Hz, 2H), 0.12 (d, J=12.2 Hz, 2H), 4.76-4.65 (n, 2H), 4.55-4.38 (m, 2H), 3.27-3.13 (m, 4H), 3.00 (br dd, J=4.0, 17.2 Hz, 2H), 2.86 (dd, J=5.0, 17.2 Hz, 2H), 2.16 (dd, J=6.8, 17.0 Hz, 2H), 2.54 (dd, J=6.0, 17.0 Hz, 2H), 1.55 (s, 18H), 1.57 (s, 18H), 1.44 (s, 18H), 1.43 (a, 16H), 1.72-1.35 (m, 4H), 1.33-1.18 (m, 16H).

Example 13-(b)

Preparation of (3S,6S,23S,26S)-6,23-bis(carboxymethyl)-3,26-bis((((4-((4-guanidinobenzoyl)oxy)benzyl)oxy)carbonyl)amino)-4,7,22,25-tetraoxo-5,8,21,24-tetraazaoctacosane-1,28-dioic acid trifluoroacetate

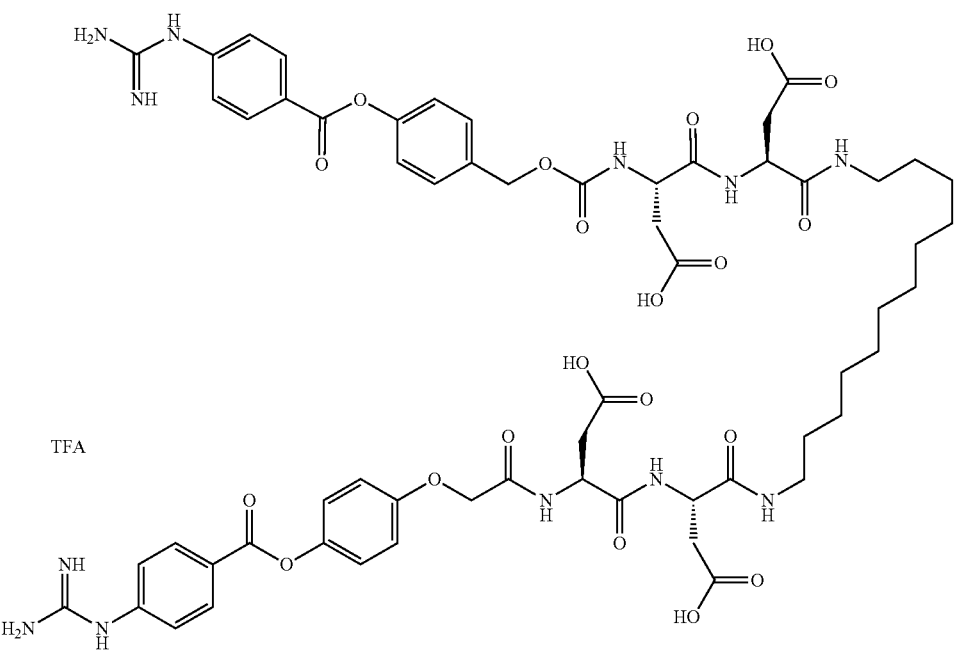 [SMILES: N=C(N)Nc1ccc(C(=O)Oc2ccc(COC(=O)N[C@@H](CC(=O)O)C(=O)N[C@@H](CC(=O)O)C(=O)NCCCCCCCCCCCCNC(=O)[C@H](CC(=O)O)NC(=O)[C@H](CC(=O)O)NC(=O)COc3ccc(OC(=O)c4ccc(NC(=N)N)cc4)cc3)cc2)cc1]

To a solution of (3S,6S,23S,26S)-di-tert-butyl 3,26-bis(((((4-((4-(2,3-bis(tert-butoxycarbonyl)guanidino)benzoyl)oxy)benzyl)oxy)carbonyl)amino)-6,23-bis(2-(tert-butoxy)-2-oxoethyl)-4,7,22,25-tetraoxo-5,8,21,24-tetraazaoctacosane-1,28-dioate (228.4 mg) prepared according to the same manner as the Example 13-(a) in dichloromethane (3 mL) in a 30 mL round-bottom flask was added trifluoroacetic acid (733 µL) at 0° C. under argon atmosphere with stirring, and the resulting mixture was stirred at room temperature for 17 hours. After the reaction was completed, the reaction solution was concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried to give the title compound (137.7 mg) as white solids.

Mass spectrum (ESI, m/z): 640 [M-2H]$^{2-}$.

$^1$H-NMR, spectrum (400 MHz, DMSO-d$_6$+D$_2$O) δ: 8.24-8.13 (m, 4H), 7.50-7.41 (m, 8H), 7.30-7.21 (m, 4H), 5.14-5.00 (m, 4H), 4.55-4.43 (m, 2H), 4.42-4.27 (m, 2H), 3.10-2.93 (m, 4H), 2.77-2.43 (m, 8H), 1.42-1.29 (m, 4H), 1.27-1.14 (m, 16H).

Example 13-(c)

Preparation of (3S,6S,23S,26S)-6,23-bis(carboxymethyl)-3,26-bis((((4-((4-guanidinobenzoyl)oxy)benzyl)oxy)carbonyl)amino)-4,7,22,25-tetraoxo-5,8,21,24-tetraazaoctacosane-1,28-dioic acid

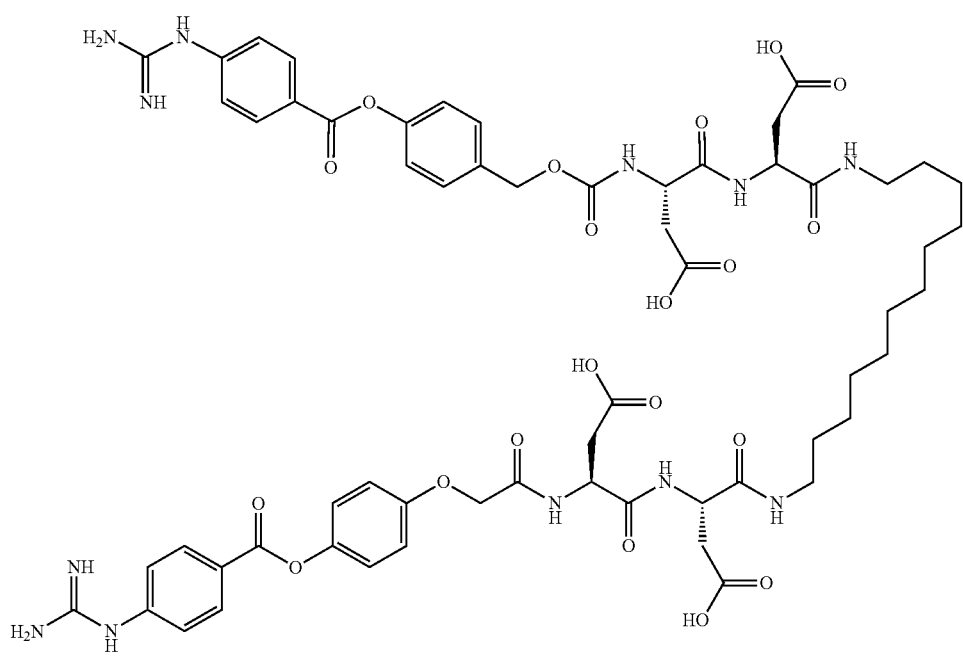 [SMILES: N=C(N)Nc1ccc(C(=O)Oc2ccc(COC(=O)N[C@@H](CC(=O)O)C(=O)N[C@@H](CC(=O)O)C(=O)NCCCCCCCCCCCCNC(=O)[C@H](CC(=O)O)NC(=O)[C@H](CC(=O)O)NC(=O)COc3ccc(OC(=O)c4ccc(NC(=N)N)cc4)cc3)cc2)cc1]

To a solution of (3S,6S,23S,26S)-di-tert-butyl 3,26-bis (((((4-((4-(2,3-bis(tert-butoxycarbonyl)guanidino)benzoyl) oxy)benzyl)oxy)carbonyl)amino)-6,23-bis(2-(tert-butoxy)-2-oxoethyl)-4,7,22,25-tetraoxo-5,8,21,24-tetraazaoctacosane-1,28-dioate (1.60 g) prepared in the Example 13-(a) in dichloromethane (20 mL) in a 100 mL round-bottom flask was added trifluoroacetic acid (10 mL) at 0° C. under argon atmosphere with stirring, and the resulting mixture was stirred at room temperature for 15 hours. After the reaction was completed, the reaction solution was concentrated under reduced pressure. The resulting residues were subjected to medium pressure preparative chromatography (silica gel, elution solvent; acetonitrile solution with 0.1% trifluoroacetic acid:aqueous solution with 0.1% trifluoroacetic acid), and the fractions comprising the target compound were concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were concentrated under reduced pressure. The concentrated suspension was stirred at room temperature for 30 minutes, the precipitated solids were collected by filtration, and dried under reduced pressure to give the title compound (583 mg) as white solids.

Mass spectrum (ESI, m/z): 640 $[M-2H]^{2-}$.

$^1$H-NMR spectrum (400 MHz, DMSO-$d_6$+$D_2O$) δ: 8.12-7.97 (m, 4H), 7.48-7.29 (m, 8H), 7.21-7.10 (m, 4H), 5.23-4.91 (m, 4H), 4.46-4.30 (m, 2H), 4.26-4.14 (m, 2H), 3.08-2.82 (m, 4H), 2.71-2.30 (m, 8H), 1.33-0.89 (m, 20H).

Example 14

Example 14-(a)

Preparation of (3S,22S)-di-tert-butyl 3,22-bis(2-((((4-((4-(2,3-bis(tert-butoxycarbonyl)guanidino)benzoyl)oxy)benzyl)oxy)carbonyl)(3-(tert-butoxycarbonyl)benzyl)amino)acetamido)-4,21-dioxo-8,11,14,17-tetraoxa-5,20-diazatetracosane-1,24-dioate

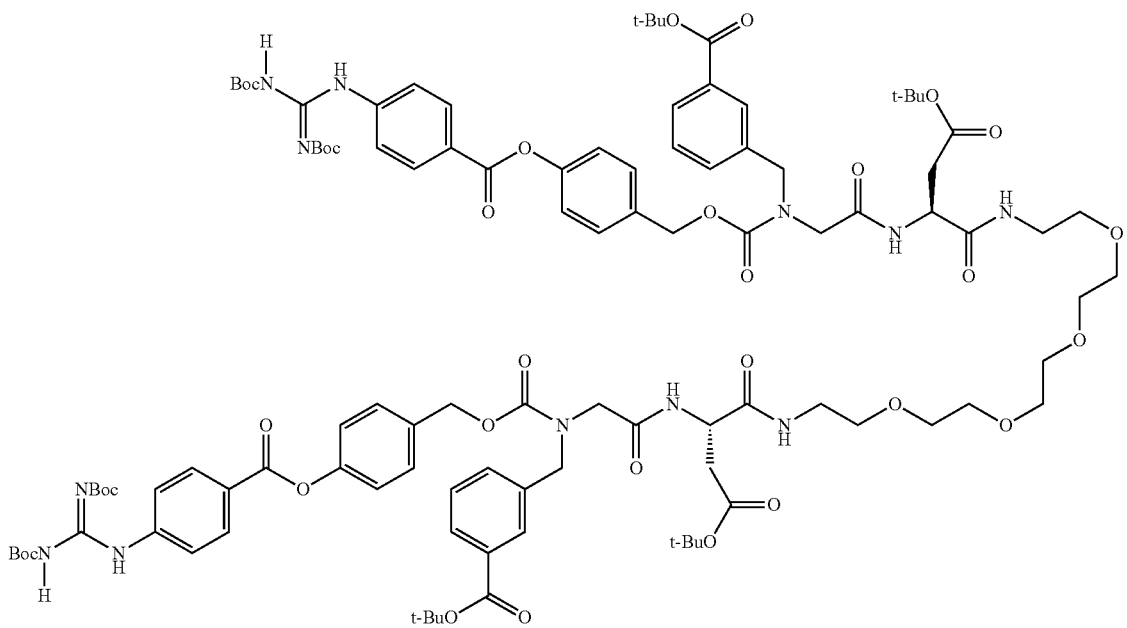

To a solution of 2-((((4-((4-(2,3-bis(tert-butoxycarbonyl)guanidino)benzoyl)oxy)benzyl)oxy)carbonyl)(3-(tert-butoxycarbonyl)benzyl)amino)acetic acid (3.83 g) prepared in the Reference Example 14-(e) in dehydrated dichloromethane (10 mL) in a 200 mL round-bottom flask were added 1-hydroxybenzotriazol (0.700 g), 1-(3-dimethylaminopropyl)-3-ethylcarbodiimide hydrochloride (1.00 g), and N,N-diisopropylethylamine (1.70 mL) under ice-cooling under argon atmosphere with stirring, then a solution of (3S,22S)-di-tert-butyl 3,22-diamino-4,21-dioxo-8,11,14,17-tetraoxa-5,20-diazatetracosane-1,24-dioate (1.36 g) prepared in the Reference Example 12-(b) in dehydrated dichloromethane (5 mL) was added thereto with stirring under ice-cooling, and the resulting mixture was stirred at room temperature for 16 hours. After the reaction was completed, to the reaction solution was added a saturated aqueous ammonium chloride solution, and the resulting mixed solution was extracted with dichloromethane. The resulting organic layer was washed with saturated aqueous sodium hydrogen carbonate solution and water, dried over anhydrous sodium sulfate, filtered, and concentrated under reduced pressure. The resulting residues were purified by medium pressure preparative chromatography (DIOL silica gel, elation solvent; hexane:ethyl acetate; to give the title compound (3.17 g) as a white foam.

Mass spectrum (ESI, m/z): 1049 [M+2H]$^{2+}$.

$^{1}$H-NMR spectrum (400 MHz, CDCl$_3$) δ: 11.62 (s, 2H), 10.64 (s, 2H), 1.19-8.12 (m, 4H), 1.4-78 (m, 8H), 7.53-6.95 (m, 16H), 5.27-5.13 (m, 4H), 4.80-4.54 (m, 6H), 3.97-3.81 (m, 4H), 3.67-3.32 (m, 20H), 2.97-2.38 (m, 4H), 1.76-1.30 (m, 72H).

Example 14-(b)

Preparation of (3S,22S)-3,22-bis(2-((3-carboxybenzyl) (((4-((4-guanidinobenzoyl)oxy)benzyl)oxy) carbonyl)amino)acetamido)-4,21-dioxo-8,1,14,17-tetraoxa-5,20-diazatetracosane-1,24-dioic acid trifluoroacetate

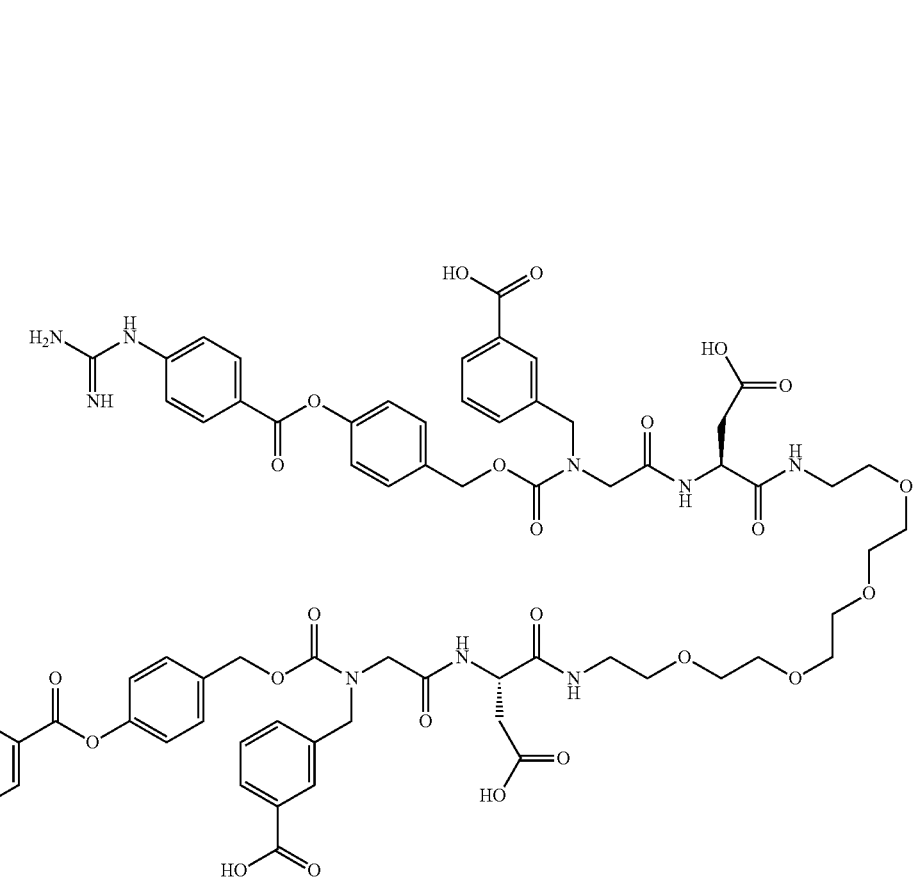

To a solution of (3S,22S)-di-tert-butyl 3,22-bis 2-(((4-(4-((2,3-bis(tert-butoxycarbonyl)guanidino)benzoyl)oxy)benzyl)oxy)carbonyl) (3-(tert-butoxycarbonyl)benzyl)amino)acetamido)-4,21-dioxo-8,11,14,17-tetraoxa-5,20-diazatetracosane-1,24-dioate (3.17 g) prepared in the Example 14-(a) in dehydrated dichloromethane (8 mL) in a 200 mL round-bottom flask was added trifluoroacetic acid (2.00 mL) under ice-cooling under argon atmosphere with stirring, and the resulting mixture was stirred at room temperature for 16 hours. The reaction solution was concentrated under reduced pressure. To a solution of the concentrated residues in dehydrated dichloromethane (8 mL) was added trifluoroacetic acid (2.00 mL) at room temperature under argon atmosphere with stirring, and the resulting mixture was stirred at room temperature for 5 hours. The reaction solution was concentrated under reduced pressure. To a solution of the concentrated residues in dehydrated dichloromethane (8 mL) was added trifluoroacetic acid (2.00 mL) at room temperature under argon atmosphere with stirring, and the resulting mixture was stirred at room temperature for 30 minutes. After the reaction was completed, the reaction solution was concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried to give the title compound (1.23 g) as white solids.

Mass spectrum (ESI, m/z): 736 [M+2H]$^{2+}$.

$^{1}$H-NMR spectrum (400 MHz, CD$_3$CN+D$_2$O) δ: 8.24-8.18 (m, 4H), 7.95-7.87 (m, 4H), 7.71-7.34 (m, 12H), 7.28-7.11 (m, 4H), 5.18 (s, 4H), 4.71-4.53 (m, 6H), 4.03-3.89 (m, 4H), 3.62-2.90 (m, 20H), 2.83-2.57 (m, 4H).

Example 15

Example 15-(a)

Preparation of (4S,7S,26S,29S)-di-tert-butyl 3,30-bis(((4-((4-(2,3-bis(tert-butoxycarbonyl)guanidino)benzoyl)oxy)benzyl)oxy)carbonyl)-4,7,26,29-tetrakis(2-(tert-butoxy)-2-oxoethyl)-5,8,25,28-tetraoxo-12,15,18,21-tetraoxa-3,6,9,24,27,30-hexaazadotriacontane-1,32-dioate

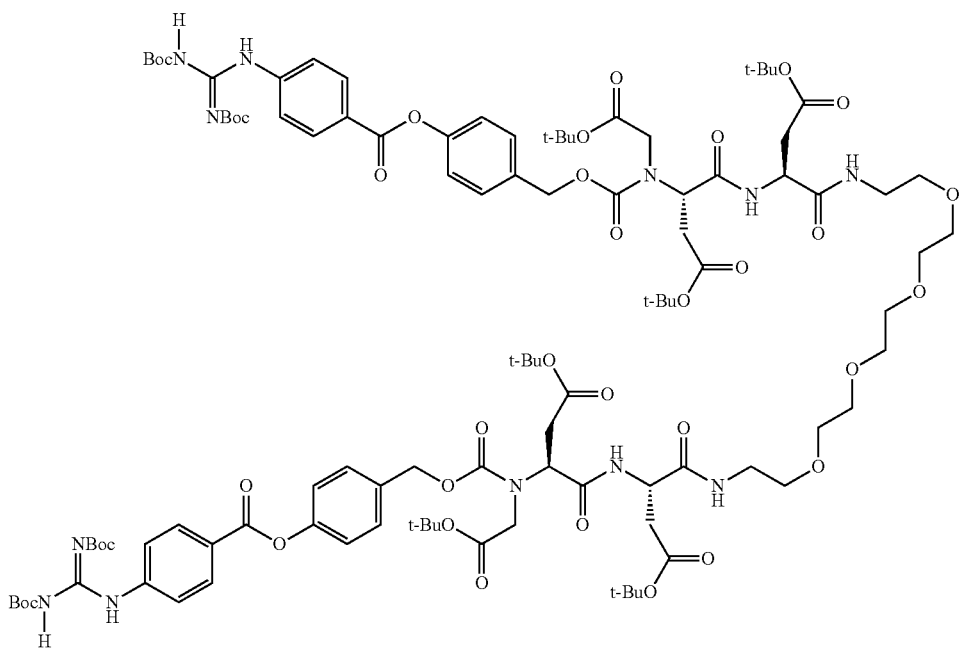

To a solution of (S)-2-(((((4-((4-(2,3-bis(tert-butoxycarbonyl)guanidino)benzoyl)oxy)benzyl)oxy)carbonyl) (2-(tert-butoxy)-2-oxoethyl)amino)-4-(tert-butoxy)-oxobutanoic acid (108 mg) prepared in the Reference Example 15-(e) in dichloromethane (5 mL) in a 100 mL round-bottom flask were added COMU (62 mg and N,N-diisopropylethylamine (27 µL) at room temperature under argon atmosphere with stirring, and the resulting mix are was stirred at room temperature for 30 minutes. Then, a solution of (3S,22S)-di-tert-butyl 3,22-diamino-4,21-dioxo-8,11,14,17-tetraoxa-5,20-diazatetracosane-1,24-dioate 135 mg) prepared in the Reference Example 12-(b) in dichloromethane (2 mL) was added thereto with stirring at room temperature, and the resulting mixture was stirred at room temperature for 20 minutes. After the reaction was completed, the reaction solution was concentrated under reduced pressure. The resulting residues were purified by medium pressure preparative chromatography (DIOL silica gel, elution solvent; hexane:ethyl acetate) to give the title compound (10.9 mg) as a colorless oil.

Mass spectrum (ESI, m/z): 17 $[M+2H]^{2-}$.

$^{1}$H-NMR spectrum (400 MHz, CDCl$_3$) δ: 11.62 (br s, 2H), 10.64 (s, 2H), 8.73-8.24 (m, 2H), 5.19-8.13 (m, 4H), 7.85-7.78 (m, 48), 7.44-7.33 (m, 4H), 7.24-7.15 (m, 4H), 7.12-6.92 (m, 2H), 5.26-5.06 (m, 4H), 4.69-4.59 (m, 2H), 4.58-4.25 (m, 2H), 4.17-3.86 (m, 4H), 3.69-3.29 (m, 20H), 3.24-3>01 (m, 2H), 2.88-2.57 (m, 6H), 1.91-1.33 (m, 90H).

Example 15-(b)

Preparation of (4S,7S,26S,29)-4,7,26,29-tetrakis(carboxymethyl)-3,30-bis((4-((4-guanidinobenzoyl)oxy)benzyl)oxy)carbonyl)-5,8,25,28-tetraoxo-12,15,18,21-tetraoxa-3,6,9,24,27,30-hexaazadotriacontane-1,32-dioic acid trifluoroacetate

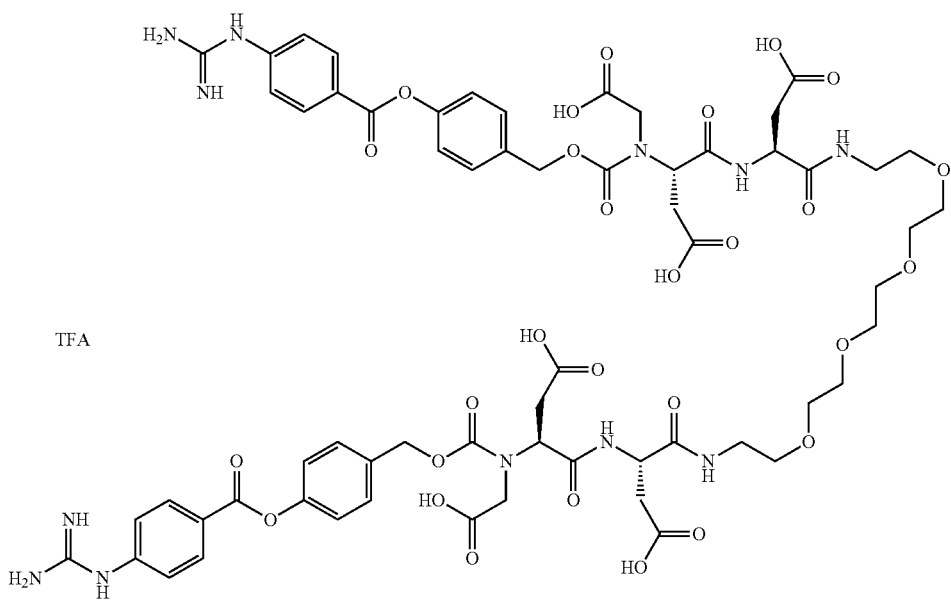 [SMILES: N=C(N)Nc1ccc(C(=O)Oc2ccc(COC(=O)N(CC(=O)O)[C@@H](CC(=O)O)C(=O)N[C@@H](CC(=O)O)C(=O)NCCOCCOCCOCCOCCNC(=O)[C@H](CC(=O)O)NC(=O)[C@H](CC(=O)O)N(CC(=O)O)C(=O)OCc3ccc(OC(=O)c4ccc(NC(=N)N)cc4)cc3)cc2)cc1]

To a solution of (4S,7S,26S,29S)-di-tert-butyl 3,30-bis((4-((4-(2,3-bis(tert-butoxycarbonyl)guanidino)benzoyl)oxy)benzyl)oxy)carbonyl)-4,7,26,29-tetrakis(2-(tert-butoxy) 2-oxoethyl)-5,8,25,28-tetraoxo-12,15,18,21-tetraoxa-3,6,9,24,27,30-hexaazadotriacontane-1,32-dioate (115 mg) prepared in the Example 15-(a) in dichloromethane (1.2 mL) in a 30 mL cylindrical flask was added trifluoroacetic acid (310 μL) at 0° C. under argon atmosphere with stirring, and the resulting mixture was stirred at room temperature for 21 hours. After the reaction was completed, the reaction solution was concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried to give the title compound (31 mg) as white solids.

Mass spectrum (ESI, m/z) 716 $[M-2H]^{2-}$.

$^1$H-NMR spectrum (400 MHz, $CD_3CN/D_2O=1/1$) δ: 6.22-8.17 (m, 42), 7.52-7.40 (m, 8H), 730-7.21 (m, 4H), 5.22-5.05 (m, 4H), 4.65-3.93 (m, 8H), 3.64-3.47 (m, 16H), 3.36-3.28 (m, 4H), 3.19-3.0n (m, 2H), 2.86-2.51 (m, 6H).

Example 16

Example 16-(a)

Preparation of (3S,22S)-di-tert-butyl 3,22-bis(4-((4-(2,3-bis(tert-butoxycarbonyl)guanidino)benzoyl)oxy)benzyl)oxy)carbonyl) (3-(tert-butoxycarbonyl)benzyl)amino)-4,21-dioxa-8,11,14,17-tetraoxa-5,20-diazatetracosane-1,24-dioate

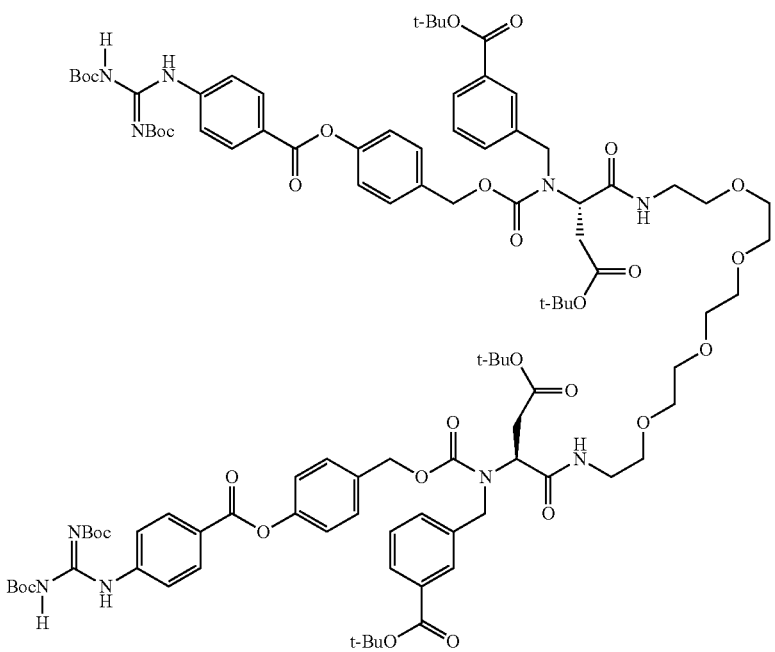

To a solution of (S)-2-(((((4-((4-(2,3-bis(tert-butoxycarbonyl)guanidino)benzoyl)oxy)benzyl)oxy)carbonyl) (3-(tert-butoxycarbonyl)benzyl)amino)-4-(tert-butoxy)-4-oxobutanoic acid (230 mg) prepared in the Reference Example 16-(c) in dehydrated dichloromethane 12 mL) in a 30 mL cylindrical flask were added COMU (120 mg) and N,N-diisopropylethylamine (0.100 mL) under ice-cooling under argon atmosphere with stirring, and the resulting mixture was stirred under ice-cooling for 30 minutes. Then, a solution of 3,6,9,12-tetraoxatetradecane-, 14-diamine (30 mg in dehydrated dichlormethane (2 ml) was added thereto with stirring under ice-cooling, and the resulting mixture was stirred at room temperature for 3 days. After toe reaction was completed, the reaction solution was concentrated under reduced pressure. The resulting residues were purified by medium pressure preparative chromatography (silica gel, elution solvent; hexane:ethyl acetate) to give the title compound (671 mg) as a colorless oil.

Mass spectrum (ESI, m/z): 992 $[M+2H]^{2+}$.

$^1$H-NMR spectrum (400 MHz, CDCl$_3$) δ: 11.62 (s, 2H), 10.64 (s, 2H), 0.1-8.11 (m, 4H), 7.97-7.77 (m, 8H), 7.61-7.04 (m, 12H), 6.68-6.57 & 6.18-5.99 (m, total 2H), 5.32-4.26 (W, 10H), 3.71-2.84 (m, 22H), 2.60-2.42 (m, 2H), 1.64-1.50 (m, 54H), 1.43-1.33 (m, 18H).

Example 16-(b)

Preparation of (3S,22S)-3,22-bis((3-carboxybenzyl)(((4-(14-guanidinobenzoyl)oxy)benzyl)oxy)carbonyl)amino)-4,21-dioxo-8,11,14,17-tetraoxa-5,20-diazatetracosane-1,24-dioic acid trifluoroacetate

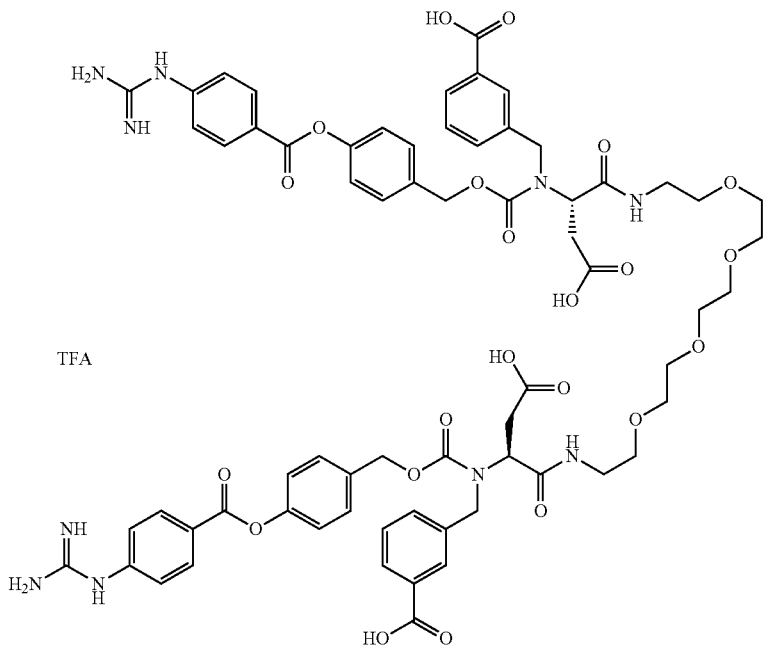 [SMILES: N=C(N)Nc1ccc(C(=O)Oc2ccc(COC(=O)N(Cc3cccc(C(=O)O)c3)[C@@H](CC(=O)O)C(=O)NCCOCCOCCOCCOCCNC(=O)[C@H](CC(=O)O)N(Cc3cccc(C(=O)O)c3)C(=O)OCc3ccc(OC(=O)c4ccc(NC(=N)N)cc4)cc3)cc2)cc1]

To a solution of (3S,22S)-di-tert-butyl 3,22-bis((((4-(4-(2,3-bis(tert-butoxycarbonyl)guanidino)benzoyl)oxy)benzyl)oxy)carbonyl) (3-(tert-butoxycarbonyl)benzyl amino)-4,21-dioxo-8,11,14,17-tetraoxa-5,20-diazatetracosane-1,24-dioate (67 mg) prepared in the Example 16-(a) in dehydrated dichloromethane (1 mL) in a 50 mL round-bottom flask was added trifluoroacetic acid (0.250 mL) under ice-cooling under argon atmosphere with stirring, and the resulting mixture was stirred at room temperature for 16 hours. The reaction solution was concentrated under reduced pressure. To a solution of the concentrated residues in dehydrated dichloromethane (2 mL) was added trifluoroacetic acid (0.250 mL) at room temperature under argon atmosphere with stirring, and the resulting mixture was stirred at room temperature for 5 hours. After the reaction was completed, the reaction solution was concentrated under reduced pressure. The resulting residues were subjected no medium pressure preparative chromatography (ODS silica gel, elation solvent; aqueous solution with 0.1% trifluoroacetic acid acetonitrile solution with 0.1% trifluoroacetic acid), and the fractions comprising the target compound were freeze-dried to give the title compound (15 mg) as white solids.

Mass spectrum (ESI, m/z): 679 $[M+2H]^{2-}$.

$^1$H-NMR spectrum (400 MHz, DMSO-$d_6$+$D_2O$) δ: 8.21-8.01 (m, 6H), 7.89-7.79 (m, 4H), 7.55-7.37 (m, 10H), 7.32-7.15 (m, 6H), 5.26-5.07 (m, 4H), 4.98-4.76 (m, 2H), 4.62-4.41 (m, 4H), 3.52-3.21 (m, 16H), 3.15-3.03 (m, 4H), 2.87-2.77 (m, 2H), 2.57-2.44 (m, 2H).

Example 17

Example 17-(a)

Preparation of (2S,2'S)-tetra-tert-butyl 2,2'-(5,8,11,14-tetraoxa-2,17-diazaoctadecane-1,18-dioyl; bis(3,1-phenylene))bis(methylene))bis(((4-((4-(2,3-bis(tert-butoxycarbonyl)guanidino)benzyl)oxy)benzyl)oxy)carbonyl)azanediyl)disuccinate

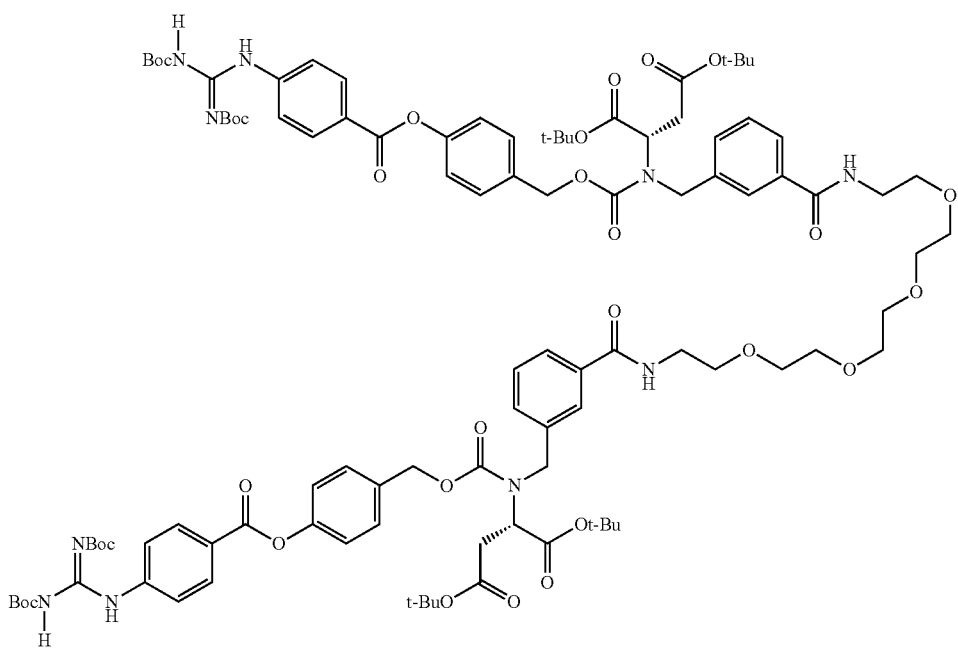

To a solution of (S)-3-(((((4-((4-(2,3-bis(tert-butoxycarbonyl)guanidino)benzoyl)oxy)benzyl)oxy)carbonyl) (1,4-di-tert-butoxy-1,4-dioxobutan-2-yl)amino)methyl)benzoic acid (401 mg) prepared in the Reference Example 17-(d) in dehydrated dichloromethane (2 mL) in a 50 mL round-bottom flask were added COMU 202 mg) and N,N-diisopropylethylamine (0.160 mL) under ice-cooling under argon atmosphere with stirring, and the resulting mixture was stirred under ice-cooling for 30 minutes. Then, a solution of 3,6,9,12-tetraoxatetradecane-1,14-diamine (50 mg) in dehydrated dichloromethane (2 mL) was added thereto with stirring under ice-cooling, and the resulting mixture was stirred at room temperature for 16 hours. After the reaction was completed, the reaction solution was concentrated under reduced pressure. The resulting residues were purified by medium pressure preparative chromatography (silica gel, elution solvent; hexane:ethyl acetate) to give the title compound (16 mg) as a colorless oil.

Mass spectrum (ESI, m/z); 992 $[M+2H]^{2+}$.

$^1$H-NMR spectrum (400 MHz, $CDCl_3$) δ: 11.62 (br s, 2H), 10.64 (s, 2H), 8.21-8.9 (m, 4H), 7.86-7.76 (m, 6H), 7.74-7.69 (m, 21), 7.56-6.98 (m, 14H), 5.37-5.04 (m, 4H), 4.91-4.71 (m, 2H), 4.60-4.27 (m, 4H), 3.78-3.50 (m, 20H), 3.18-2.95 (m, 21), 2.69-2.52 (m, 2H), 1.69-1.16 (m, 72H).

Example 17-(b)

Preparation of (2S,2'S)-2,2'-(((5,8,11,14-tetraoxa-2,17-diazaoctadecane-1,18-dioyl)bis(3,1-phenylene))bis(methylene))bis((((4-((4-guanidinobenzoyloxy)benzyloxycarbonyl)azanediyl))disuccinic acid trifluoroacetate

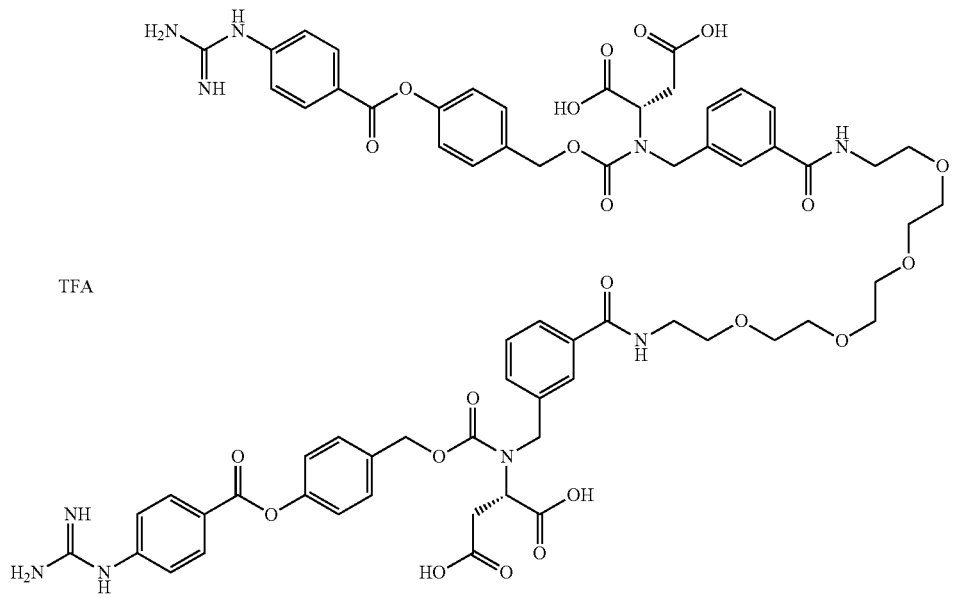 [SMILES: N=C(N)Nc1ccc(C(=O)Oc2ccc(COC(=O)N(Cc3cccc(C(=O)NCCOCCOCCOCCOCCNC(=O)c4cccc(CN(C(=O)OCc5ccc(OC(=O)c6ccc(NC(=N)N)cc6)cc5)[C@@H](CC(=O)O)C(=O)O)c4)c3)[C@@H](CC(=O)O)C(=O)O)cc2)cc1]

To a solution of (2S,2'S)-tetra-tert-butyl 2,2'-(((5,8,11,14-tetraoxa-2,17-diazaoctadecane-1,18-dioyl)bis(3,1-phenylene))bis(ethylene))bis(4-((4-(2,3-bis(tert-butoxycarbonyl)guanidino)benzoyl)oxy)benzyl)oxy)carbonyl)azanediyl))disuccinate (160 mg) prepared in the Example 17-(a) in dehydrated dichloromethane (4 mL) in a 50 mL round-bottom flask was added trifluoroacetic acid (1.00 mL) under ice-cooling under argon atmosphere with stirring, and the resulting mixture was stirred at room temperature for 16 hours. The reaction solution was concentrated under reduced pressure. To a solution of the concentrated residues in dehydrated dichloromethane (2 mL) was additionally added trifluoroacetic acid (1.00 mL) at room temperature under argon atmosphere with stirring, and the resulting mixture was stirred at room temperature for 3 hours. After the reaction was completed, the reaction solution was concentrated under reduced pressure. The resulting residues were subjected to medium pressure preparative chromatography (ODS silica gel, elation solvent; aqueous solution with 0.1% trifluoroacetic acid:acetonitrile solution with 0.1% trifluoroacetic acid), and the fractions comprising the target compound were freeze-dried to give the title compound (65 mg) as white solids.

Mass spectrum (ESI, m/z): 679 $[M+2H]^{2+}$.

$^1$H-NMR spectrum (400 MHz, $CD_3CN+D_2O$) δ: 8.25-8.16 (m, 4H), 7.77-7.73 (m, 2H), 7.70-7.64 (m, 2H), 7.51-7.07 (m, 16H), 5.22-5.07 (m, 4H), 4.73-4.45 (m, 6H), 3.62-3.43 (m, 20H), 3.12-2.52 (m, 4H).

Example 18

Example 18-(a)

Preparation of (2S,2'S)-tetra-tert-butyl 2,2'-((5,8,11,14-tetraoxa-2,17-diazaoctadecane-1,18-dioyl)bis(3,1-phenylene))bis(methylene))bis((N-(benzyloxy)carbonyl)-N-(4-((4-(2,3-bis(tert-butoxycarbonyl)guanidinobenzoyl)oxy)benzyl)sulfamoyl)azanediyl))disuccinate

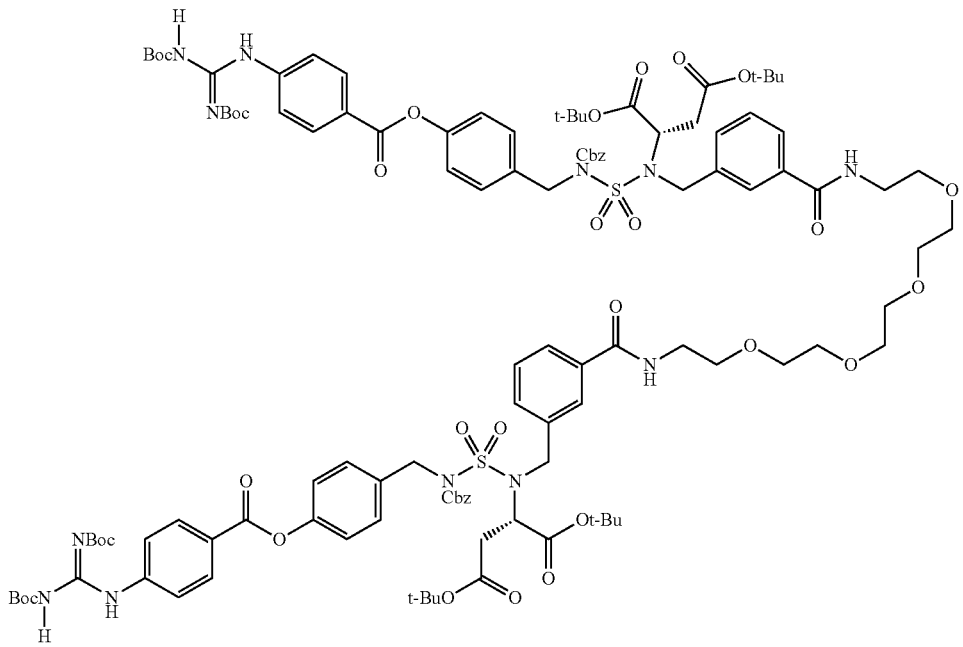

To a solution of (S)-3-(((N-((benzyloxy)carbonyl)-N-(4-((4-(2,3-bis(tert-butoxycarbonyl)guanidino)benzoyl)oxy)benzyl)sulfamoyl) (1,4-di-1-tert-butoxy-1,4-dioxobutan-2-yl)amino)methyl)benzoic acid (205 mg) prepared in the Reference Example 18-(c), 3,6,9,12-tetraoxatetradecane-1,14-diamine (22.1 mg), 1-(3-dimethylaminopropyl)-3-ethylcarbodiimide hydrochloride (39.0 mg), and trimethylamine (40 μL) in dichloromethane (5 mL) in a 50 mL round-bottom flask was added 1-hydroxybenzotriazol (28.5 mg) at room temperature under argon gas flow with stirring, and the resulting mixture was stirred at room temperature for 18 hours. After the reaction was completed, to the reaction solution was added 1N hydrochloric acid, and the resulting mixed solution was extracted with dichloromethane. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (190 mg) as a white foam.

Mass spectrum (ESI, m/z): 1161 $[M+2H]^{2+}$.

$^1$H-NMR spectrum (400 MHz, CDCl$_3$) δ: 11.62 (s, 2H), 10.64 (s, 2H), 8.19-8.11 (m, 4H), 7.84-7.77 (m, 4H), 7.74-7.65 (m, 4H), 7.45-7.23 (m, 18H), 7.14-7.09 (m, 4H), 7.07-6.99 (m, 2H), 5.21 (s, 4H), 4.91-4.69 (m, 8H), 4.29 (d, J=16.8 Hz, 2H), 3.67-3.56 (m, 20H), 2.58 (dd, J=8.8, 16.7 Hz, 2H), 2.43 (dd, J=5.2, 16.7 Hz, 2H), 1.55 (s, 18H), 1.53 (s, 18H), 1.44 (s, 18H), 1.36 (s, 18H).

Example 18-(b)

Preparation of (2S,2'S)-2,2'-((((5,8,11,14-tetraoxa-2,17-diazaoctadecane-1,18-dioyl)bis(3,1-phenylene))bis(methylene))bis(N-(4-((4-guanidinobenzoyl)oxy)benzyl)sulfamoyl)azanediyl))disuccinic acid trifluoroacetate

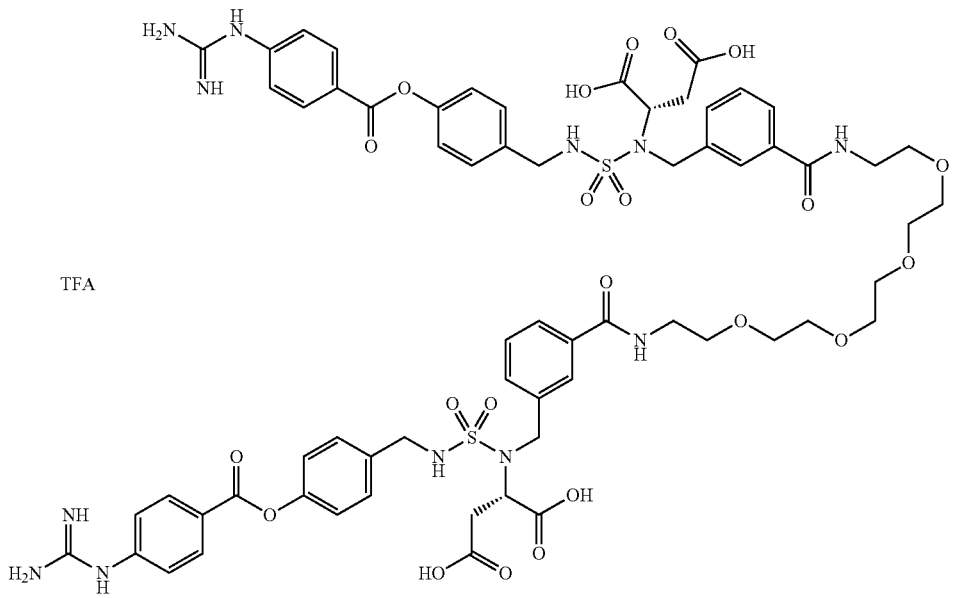 [SMILES: N=C(N)Nc1ccc(C(=O)Oc2ccc(CNS(=O)(=O)N(Cc3cccc(C(=O)NCCOCCOCCOCCOCCNC(=O)c4cccc(CN([C@@H](CC(=O)O)C(=O)O)S(=O)(=O)NCc5ccc(OC(=O)c6ccc(NC(=N)N)cc6)cc5)c4)c3)[C@@H](CC(=O)O)C(=O)O)cc2)cc1]

To a solution of (2S,2'S)-tetra-tert-butyl 2,2'-((((5,8,11,14-tetraoxa-2,17-diazaoctadecane-1,18-dioyl)bis(3,1-phenylene))bis(methylene))bis((N-((benzyloxy)carbonyl)-N-(4-((4-(2,3-bis(tert-butoxycarbonyl)guanidino)benzoyl)oxy)benzyl)sulfamoyl)azanediyl)disuccinate (190 mg) prepared according to the same manner as the Example 18-(a) in dichloromethane (3 mL) in a 50 mL round-bottom flask was added trifluoroacetic acid (3 mL) at room temperature under argon atmosphere with stirring, and the resulting mixture was stirred at room temperature for 18 hours. The reaction solution was concentrated under reduced pressure. To a solution of the concentrated residues in methanol (5 mL) was added 5% palladium carbon (wetted with 54.28% water, STD-type manufactured by NE CHEMCAT Corporation) (51 mg) at room temperature under argon atmosphere with stirring, and the resulting mixture was stirred at room temperature under hydrogen atmosphere for 2 ours. After the reaction was completed, the reaction solution was filtered through Celite. The removed solids were washed with methanol, and the resulting filtrate was concentrated under reduced pressure. The resulting residues were subjected to medium pressure preparative chromatography (ODS silica gel, elution solvent; acetonitrile solution with 0.1% trifluoroacetic acid:aqueous solution with 0.1% trifluoroacetic acid), and the fractions comprising the target compound were freeze-dried to give the title compound (80 mg) as white solids.

Mass spectrum (ESI, m/z): 714 $[M+2H]^{2+}$.

$^1$H-NMR spectrum (400 MHz, DMSO-$d_6$+$D_2O$) δ: 8.20-8.13 (m, 4H), 7.90-7.85 (m, 2H), 7.79-7.73 (m, 2H), 7.64-7.57 (m, 2H), 7.49-7.39 (m, 10H), 7.26-7.20 (m, 4H), 4.57 (d, J=15.9 Hz, 2H), 4.40-4.09 (m, 8H), 3.66-3.29 (m, 20H), 2.83 (dd, J=9.8, 16.5 Hz, 2H), 2.61 (dd, J=3.6, 16.5 Hz, 2H).

Example 19

Example 19-(a)

Preparation of tetra-tert-butyl 3,12-bis(10-(2,3-bis(tert-butoxycarbonyl)guanidino)-13-oxo-6,7,8,13-tetrahydrodibenzo[b,f][1,4]dioxecin-4-carbonyl)-6,9-dioxa-3,12-diazatetradecane-1,2,13,14-tetracarboxylate

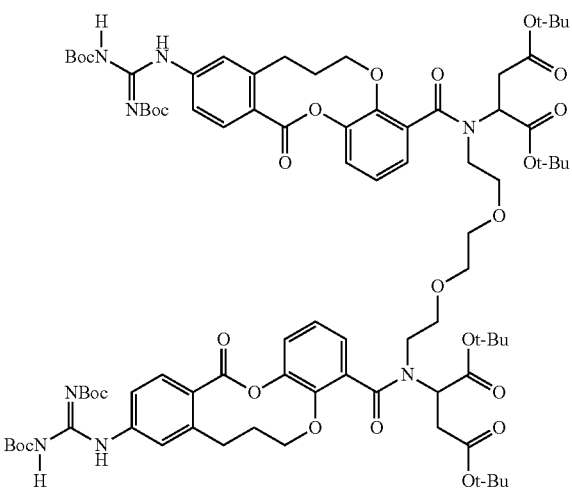

To a solution of tetra-tert-butyl 6,9-dioxa-3,12-diazatetradecane-1,2,13,14-tetracarboxylate (1.44 g) prepared in the Reference Example 19-(q) and 10-(2,3-bis(tert-butoxycarbonyl)guanidino)-13-oxo-6,7,8,13-tetrahydrodibenzo[b,f][1,4]dioxecin-4-carboxylic acid (3.00 g) prepared in the Reference Example 19-(n) in dimethylformamide (20 mL) in a 100 mL round-bottom flask were added N,N-diisopropylethylamine (1.15 mL) and COMU (2.53 g) at room temperature under air atmosphere with stirring, and the resulting mixture was stirred at room temperature overnight. After the reaction was completed, to the reaction solution was added saturated aqueous sodium hydrogen carbonate solution, and the resulting mixed solution was extracted with ethyl acetate. The resulting organic layer was washed sequentially with 0.02 M hydrochloric acid and saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (2.13 g) as a pale yellow foam.

Mass spectrum (ESI, m/z; 1660 [M+H]$^+$.

$^1$H-NM spectrum (530 MHz, CDCl$_1$) δ: 11.62-11.51 (m, 2H), 10.58-10.36 (m, 2H), 8.12-7.70 (m, 4H), 7.65-7.51 (m, 2), 7.49-7.40 (m, 2H), 7.35-6.91 (m, 4H), 4.70-2.53 (m, 26H), 2.39-0.78 (m, 76H).

Example 19-(b)

Preparation of 3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid trifluoroacetate

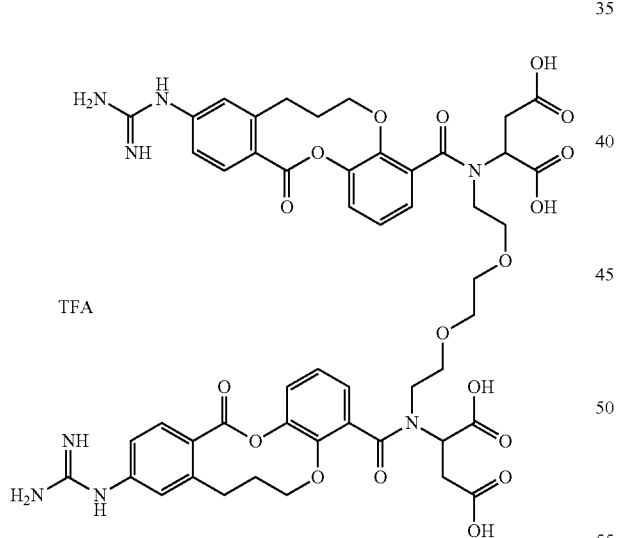

TFA

To a solution of tetra-tert-butyl 3,12-bis(10-(2,3-his (tert-butoxycarbonyl)guanidino)-13-oxo-6,7,8,13-tetrahydrodibenzo[b,f][1,2,13,14]dioxecin-4-carbonyl)-6,9-dioxa-3,12-diazatetradecane-1,2,13,14-tetracarboxylate (2.10 g) prepared in the Example 19-(a) in dichloromethane (8 mL) in a 100 mL round-bottom flask was added trifluoroacetic acid (2.0 mL) at 0° C. under air atmosphere with stirring, and the resulting mixture was stirred at room temperature for 16 hours. Additionally, trifluoroacetic acid (2.0 mL) was added thereto with stirring at room temperature, and the resulting mixture was stirred at room temperature for 4 hours. After the reaction was completed, the reaction solution was concentrated under reduced pressure. The resulting residues were subjected to medium pressure preparative chromatography (silica gel, elution solvent; aqueous solution with 0.1% trifluoroacetic acid:acetonitrile solution with 0.1% trifluoroacetic acid), and the fractions comprising the target compound were freeze-dried. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried. The resulting solids were dissolved into water/acetonitrile, and the resulting solution was freeze-dried to give the title compound (377 mg) as white solids.

Mass spectrum (ESI, m/z): 1055 [M+H]$^+$.

$^1$H-NMR spectrum (500 MHz, DMSO-d$_6$+D$_2$O) δ: 7.92-7.81 (m, 2R), 7.58-7.47 (m, 2H), 7.36-7.0 (m, 8H), 4.61-2.36 (m, 26H), 2.12-1.65 (m, 4H).

Example 19-(c)

Preparation of 3,12-bis(10-guanidine-13-oxo-6,7,8,13-tetrahydrodibenzo[b,f][1,4]dioxecin-4-carbonyl)-6,9-dioxa-3,12-diazatetradecane-1,2,13,14-tetracarboxylic acid hydrochloride

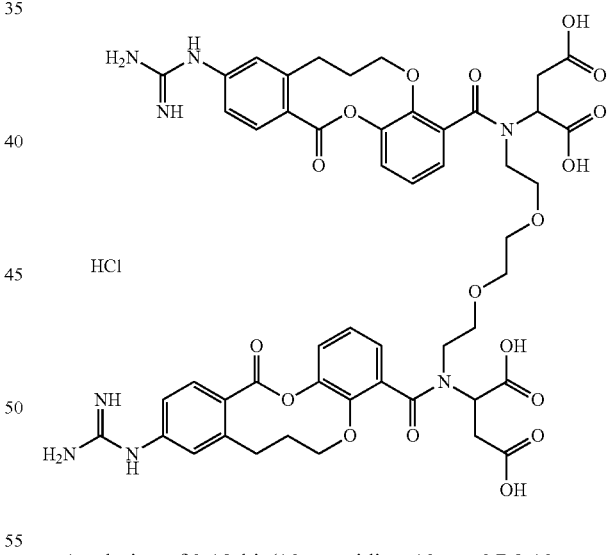

HCl

A solution of 3,12-bis(10-guanidino-13-ox-6,7,8,13-tetrahydrodibenzo[b,f][1,4]dioxecin-4-carbonyl)-6,9-dioxa-3,12-diazatetradecane-1,2,13,14-tetracarboxylic acid trifluoroacetate (344 mg) prepared in the Example 19-(b) in 0.1 M hydrochloric acid (30 mL)/acetonitrile (8 mL) in a 300 mL round-bottom flask was freeze-dried to give the title compound (288.5 mg) as white solids.

Mass spectrum (ESI, M/z) 1055 [M+H]$^+$.

$^1$H-NMR spectrum (400 MHz, DMSO-d$_6$+D$_2$O) δ: 7.94-7.81 (m, 2H), 7.61-7.47 (a, 2H), 7.36-7.05 (m, 8H), 4.58-4.41 (m, 2H), 4.04-2.43 (m, 24H), 2.13-1.71 (m, 4K).

Example 20

Example 20-(a)

Preparation of (2S,13S)-tetra-tert-butyl 3,12-bis(10-(2,3-bis(tert-butoxycarbonyl)guanidino)-13-oxo-6,7,8,13-tetrahydrodibenzo[b,f][1,4]dioxecin-4-carbonyl)-6,9-dioxa-3,12-diazatetradecane-1,2,13,14-tetracarboxylate

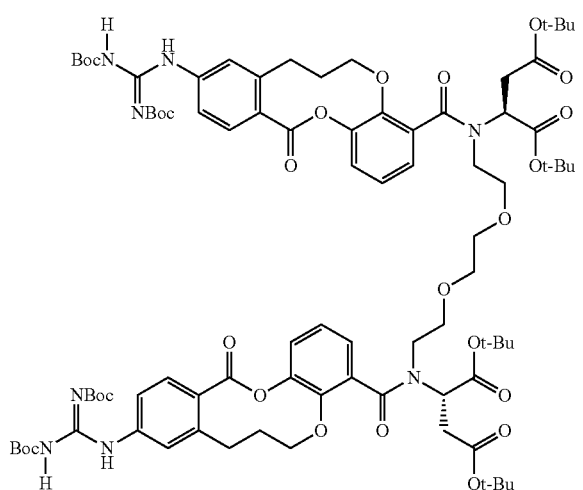

To a suspension of 10-(2,3-bis(tert-butoxycarbonyl)guanidino)-13-oxo-6,7,8,13-tetrahydrodibenzo[b,f][1,4]dioxecin-4-carboxylic acid (2.20 g) prepared according to the same manner as the Reference Example 19-(n) in dehydrated dimethylformamide (10 mL) in a 200 mL round-bottom flask were added N,N-diisopropylethylamine (1.00 mL) and COMU (1.85 g) under ice-cooling under argon atmosphere with stirring, and the resulting mixture was stirred under ice-cooling for 30 minutes. Then, a solution of (2S,13S)-tetra-tert-butyl 6,9-dioxa-3,12-diazatetradecane-1,2,13,14-tetracarboxylate (1.10 g) prepared according to the same manner as the Reference Example 2-(b) in dehydrated dimethylformamide (5 mL) was added thereto with stirring under ice-cooling, and the resulting mixture was stirred at room temperature for 16 hours. After the reaction was completed, to the reaction solution was added saturated aqueous sodium hydrogen carbonate solution, and the resulting mixed solution was extracted with ethyl acetate. The resulting organic layer was washed sequentially with 0.1 M hydrochloric acid and saturated brine, dried over anhydrous sodium sulfate, filtered, and concentrated under reduced pressure. The resulting residues were subjected to medium pressure preparative chromatography (DIOL silica gel, elution solvent; hexane:ethyl acetate), and the fractions comprising the target compound were concentrated under reduced pressure. The resulting residues were purified by medium pressure preparative chromatography (silica gel, elution solvent; hexane:ethyl acetate) to give the title compound (2.09 g) as a yellow oil.

Mass spectrum (ESI, m/z): 1678 [M−H]−.

$^1$H-NMR spectrum (400 MHz, CDCl$_3$) δ: 11.62 (s, 2H), 10.54 (s, 2H), 8.01-7.91 (m, 2H), 7.86-7.77 (m, 2H), 7.65-7.50 (m, 2H), 7.49-7.40 (m, 2H), 7.29-6.98 (m, 4H), 4.66-4.34 (m, 2H), 4.22-2.57 (m, 24H), 2.21-1.29 (m, 76H).

Example 20-(b)

Preparation of (2S,13S)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid trifluoroacetate

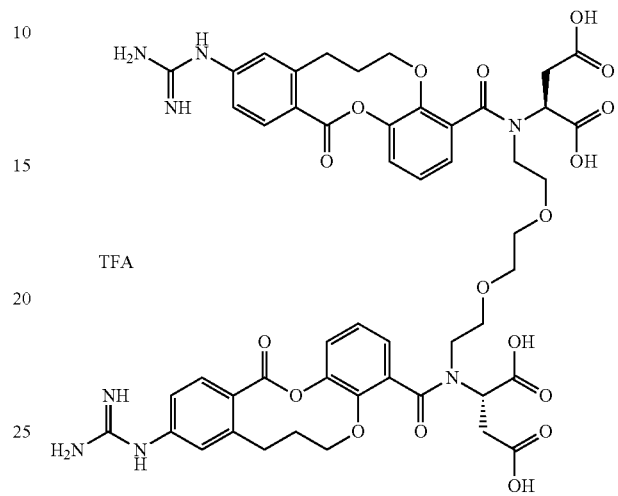

To a solution of (2S,13S)-tetra-tert-butyl 3,12-bis(10-(2,3-bis(tert-butoxycarbonyl)guanidino)-13-oxo-6,7,8,13-tetrahydrodibenzo[b,f][1,4]dioxecin-4-carbonyl)-6,9-dioxa-3,12-diazatetradecane-1,2,13,14-tetracarboxylate (2.09 g) prepared in the Example 20-(a) in dehydrated dichloromethane (9 mL) in a 200 mL round-bottom flask was added trifluoroacetic acid (3.00 mL) under ice-cooling under argon atmosphere with stirring, and the resulting mixture was stirred at room temperature for 2 hours. The reaction solution was concentrated under reduced pressure. To a solution of the concentrated residues in dehydrated dichloromethane (9 mL) was added trifluoroacetic acid (3.00 mL) at room temperature under argon atmosphere with stirring, and the resulting mixture was stirred at room temperature for 16 hours. The reaction solution was concentrated under reduced pressure. The resulting residues were subjected to medium pressure preparative chromatography (silica gel, elution solvent; acetonitrile solution with 0.1% trifluoroacetic acid: aqueous solution with 0.1% trifluoroacetic acid), and the fractions comprising the target compound were freeze-dried. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried. The resulting residues were subjected to medium pressure preparative chromatography (silica gel, elution solvent; acetonitrile solution with 0.1% trifluoroacetic acid:aqueous solution with 0.1% trifluoroacetic acid), and the fractions comprising the target compound were freeze-dried. The resulting solids were dissolved into a mixed solvent of aqueous solution with 0.1% trifluoroacetic acid and acetonitrile solution with 0.1% trifluoroacetic acid (4:1 (v/v)), and the resulting solution was freeze-dried. The resulting solids were dissolved into a mixed solvent of water and acetonitrile (4:1 (v/v)), and the resulting solution was freeze-dried to give the title compound (589 mg) as white solids.

Mass spectrum (ESI, m/z): 1055 [M+H]+

$^1$H-NMR spectrum (400 MHz, DMSO-d$_6$+D$_2$O) δ: 7.94-7.81 (m, 2H), 7.60-7.46 (m, 2H), 7.36-7.03 (m, 8H), 4.56-4.34 (m, 2H), 4.22-2.40 (m, 24H), 2.10-1.71 (m, 4H). .

Example 20-(c)

Preparation of (2S,13S)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid hydrochloride

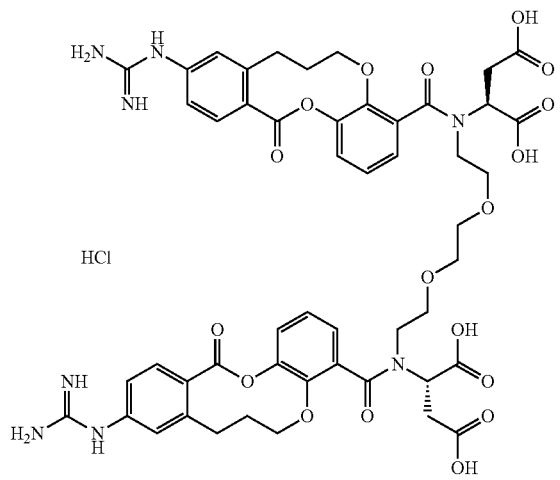 [SMILES: N=C(N)Nc1ccc2c(c1)CCCOc1c(cccc1C(=O)N(CCOCCOCCN(C(=O)c1cccc3c1OCCCc1cc(NC(=N)N)ccc1C(=O)O3)[C@@H](CC(=O)O)C(=O)O)[C@@H](CC(=O)O)C(=O)O)OC2=O ; Cl]

A solution of (2S,13S)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid trifluoroacetate (533 mg) prepared in the Example 20-(b) in acetonitrile (11.5 mL)/0.1 M hydrochloric acid (46.0 mL) in a 300 mL round-bottom flask was freeze-dried to give the title compound (421 mg) as white solids.

Mass spectrum (ESI, m/z): 1055 [M+H]$^+$.

$^1$H-NMR spectrum (400 MHz, DMSO-d$_6$+D$_2$O) δ: 7.94-7.81 (m, 2H), 7.61-7.46 (m, 2H), 7.36-7.04 (m, 8H), 4.57-4.38 (m, 2H), 4.04-2.45 (m, 24H), 2.12-1.70 (m, 4H).

Example 20-(d)

Preparation of (2S,13S)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid

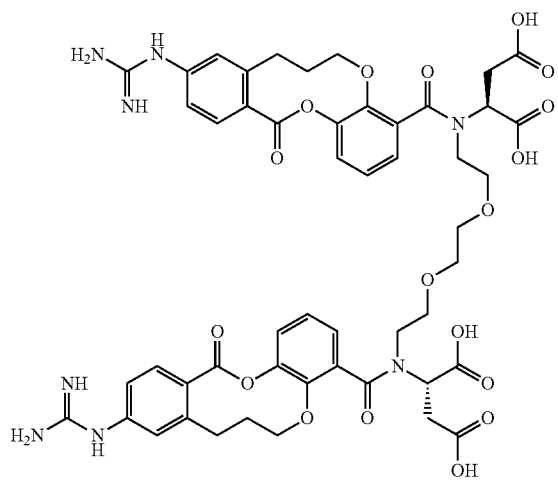 [SMILES: N=C(N)Nc1ccc2c(c1)CCCOc1c(cccc1C(=O)N(CCOCCOCCN(C(=O)c1cccc3c1OCCCc1cc(NC(=N)N)ccc1C(=O)O3)[C@@H](CC(=O)O)C(=O)O)[C@@H](CC(=O)O)C(=O)O)OC2=O]

To (2S,13S)-tetra-tert-butyl 3,12-bis(10-(2,3-bis(tert-butoxycarbonyl)guanidino)-13-oxo-6,7,8,13-tetrahydrodibenzo[b,f][1,4]dioxecin-4-carbonyl)-6,9-dioxa-3,12-diazatetradecane-1,2,13,14-tetracarboxylate (6.98 g) prepared according to the same manner as the Example 20-(a) in a 20 mL round-bottom flask was added 4 M hydrogen chloride/dioxane (40 mL) at room temperature, and the resulting mixture was stirred at room temperature for 15 hours. After the reaction was completed, the reaction solution was concentrated under reduced pressure. To the concentrated residues was added toluene, and the resulting mixture was subjected to azeotropy. Then, to the concentrated residues were aided acetonitrile and the resulting mixture was subjected to azeotropy. A solution of the resulting residues in acetonitrile (10 mL)/water (2D mL)/trifluoroacetic acid (0.5 mL) was subjected to medium pressure preparative chromatography (ODS silica gel, elution solvent; aqueous solution with 0.1% trifluoroacetic acid acetonitrile solution with 0.1% trifluoroacetic acid), and the fractions comprising the target compound were freeze-dried. A solution of the resulting residues in acetonitrile (40 m L)/water (5.5 mL) was subjected to me-ium pressure preparative chromatography (ODS silica gel, elution solvent; aqueous solution with 0.1% trifluoroacetic acid acetonitrile solution with 0.1% trifluoroacetic acid), and the fractions comprising the target compound were freeze-dried. To a solution of the resulting residues in water (75 mL)/acetonitrile (25 mL) as added a saturated aqueous ammonium acetate solution with stirring to adjust the pH to 4.2. The resulting mixture was stirred at room temperature for 7 hours, the precipitated solids were collected by filtration, and dried under reduced pressure to give the title compound (3.16 g) as white solids.

Mass spectrum (ESI, m/z): 1055 [M+H]$^+$.

$^1$H-NMR spectrum (400 MHz, DMSO-d$_6$-D$_2$O) δ: 7.83-7.64 (m, 2H), 7.53-7.36 (m, 2), 7.29-7.00 (m, 8H), 4.62-2.37 (m, 26H), 2.05-1.65 (m, 4H).

Example 21

Example 21-(a)

Preparation of (2R,13R)-tetra-tert-butyl 3,12-bis(10-(2,3-bis(tert-butoxycarbonyl)guanidino)-13-oxo-6,7,8,13-tetrahydrodibenzo[b,f][1,4]dioxecin-4-carbonyl)-6,9-dioxa-3,12-diazatetradecane-1,2,13,14-tetracarboxylate

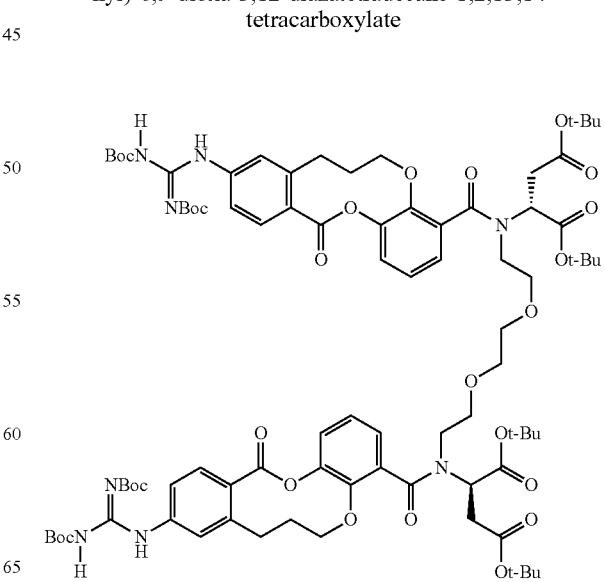

To a suspension of 10-(2,3-bis(tert-butoxycarbonyl)guanidino)-13-oxo-6,7,8,13-tetrahydrodibenzo[b,f][1,4]dioxecin-4-carboxylic acid (2.20 g) prepared according to the same manner as the Reference Example 19-(n) in dehydrated dimethylformamide (10 mL) in a 200 mL round-bottom flask were added N,N-diisopropylethylamine (1.00 mL) and COMU (1.85 g) under ice-cooling under argon atmosphere with stirring, and the resulting mixture was stirred under ice-cooling for 30 minutes. Then, a solution of (2R,13R)-tetra-tert-butyl 6,9-dioxa-3,12-diazatetradecane-1,2,13,14-tetracarboxylate (1.25 g) prepared in the Reference Example 21-(b) in dehydrated dimethylformamide (5 mL) was added thereto with stirring under ice-cooling, and the resulting mixture was stirred at room temperature for 16 hours. After the reaction was completed, to the reaction solution was added saturated aqueous sodium hydrogen carbonate solution, and the resulting mixed solution was extracted with ethyl acetate. The resulting organic layer was washed sequentially with 0.1 M hydrochloric acid and saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (2.16 g) as a yellow foam.

Mass spectrum (ESI, m/z): 1678 [M−H]⁻.

¹H-NMR spectrum (400 MHz, CDCl₃) δ: 11.62 (s, 2H), 10.54 (s, 2H), 8.01-7.92 (m, 2H), 7.86-7.78 (m, 2H), 7.65-7.50 (m, 2H), 7.49-7.40 (m, 2H), 7.31-6.97 (m, 4H), 4.67-4.35 (m, 2H), 4.22-2.56 (m, 24H), 2.22-1.29 (m, 76H).

Example 21-(b)

Preparation of (2R,13R)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid trifluoroacetate To a solution of (2R,13R)-tetra-tert-butyl 3,12-bis(10-(2,3-bis(tert-butoxycarbonyl)guanidino)-13-oxo-6,7,8,13-tetrahydrodibenzo[b,f][1,4]dioxecin-4-carbonyl)-6,9-dioxa-3,12-diazatetradecane-1,2,13,14-tetracarboxylate (2.16 g) prepared in the Example 21-(a) in dichloromethane (9 mL) in a 200 mL round-bottom flask was added trifluoroacetic acid (3 mL) under ice-cooling under argon atmosphere with stirring, and the resulting mixture was stirred at room temperature overnight. The reaction solution was concentrated under reduced pressure. The concentrated residues were dissolved into dichloromethane (9 mL), trifluoroacetic acid (3 mL) was added thereto under ice-cooling under argon atmosphere with stirring, and the resulting mixture was stirred at room temperature for 6 hours. After the reaction was completed, the reaction solution was concentrated under reduced pressure. The resulting residues were subjected to medium pressure preparative chromatography (silica gel, elution solvent; aqueous solution with 0.1% trifluoroacetic acid acetonitrile solution with 0.1% trifluoroacetic acid), and the fractions comprising the target compound were freeze-dried. The resulting residues were subjected to medium pressure preparative chromatography (ODS silica gel, elution solvent; aqueous solution with 0.1% trifluoroacetic acid acetonitrile solution with 0.1% trifluoroacetic acid), and the fractions comprising the target compound were freeze-dried to give the title compound (0.757 g) as white solids.

Mass spectrum (ESI, m/z): 1053 [M−H]⁻.

¹H-NMR spectrum (500 MHz, DMSO-d₆+D₂O) δ: 7.92-7.82 (m, 2H), 7.58-7.44 (m, 2H), 7.33-7.06 (m, 8H), 4.63-4.38 (m, 2H), 4.17-2.43 (m, 24H), 2.17-1.71 (m, 4H).

Example 21-(c)

Preparation of (2R,13R)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid hydrochloride

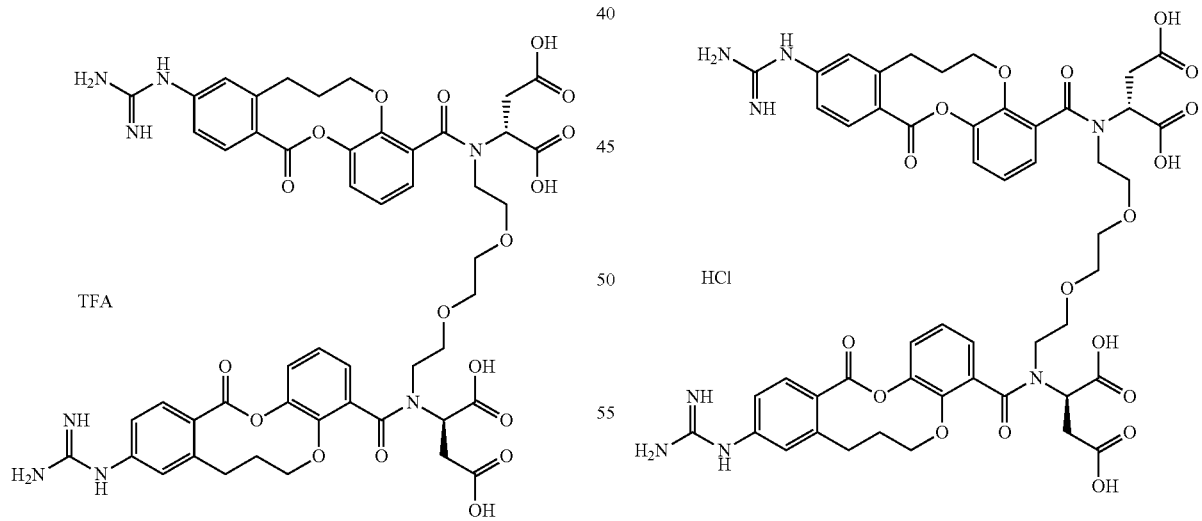

A solution of (2R,13R)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid trifluoroacetate (734 mg) prepared in the Example 21-(b) in 0.1 M hydrochloric acid (63.0 mL)/acetonitrile (16 mL) in a 300 mL round-bottom flask was freeze-dried to give the title compound (640 mg) as white solids.

Mass spectrum (ESI, m/z): 1055 [M+H]+.

¹H-NMR spectrum (400 MHz, DMSO-d₆+D₂O) δ: 7.94-7.81 (m, 2H), 7.60-7.48 (m, 2H), 7.35-7.04 (m, 8H), 4.56-4.40 (m, 2H), 4.04-2.43 (m, 24H), 2.11-1.70 (m, 4H).

Example 22-(a)

Preparation of (2S,13S)-3,12-bis(N-(4-((4-guanidinobenzoyl)oxy)benzyl)-N-methylsulfamoyl)-6,9-dioxa-3,12-diazatetradecane-1,2,13,14-tetracarboxylic acid trifluoroacetate

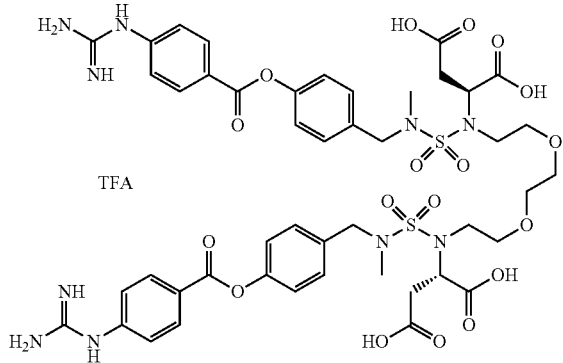 [SMILES: CN(Cc1ccc(OC(=O)c2ccc(NC(=N)N)cc2)cc1)S(=O)(=O)N(CCOCCOCCN([C@@H](CC(=O)O)C(=O)O)S(=O)(=O)N(C)Cc1ccc(OC(=O)c2ccc(NC(=N)N)cc2)cc1)[C@@H](CC(=O)O)C(=O)O]

To a suspension of (2S,13S) 3,2-bis(N-(4-((4-aminobenzoyl)oxy)benzyl)-N-methylsulfamoyl)-6,9-dioxa-3,12-diazatetradecane-1,2,13,14-tetracarboxylic acid hydrochloride (51.6 mg) prepared in the Reference Example 22-(e) in tert-butanol (1.0 mL) in a 30 mL cylindrical flask were added cyanamide (12.6 mL) and a 4 M hydrogen chloride dioxane solution (71 μL) at room temperature under argon gas flow with stirring, and the resulting mixture was stirred at 60° C. for 5 hours. After the reaction was completed, to the reaction solution was added water (5 mL). Then, a 10% aqueous ammonium acetate solution was added thereto to adjust the pH to 4, and the resulting mixture was stirred at room temperature for 1 hour. The precipitated solids were collected by filtration, washed with water, and dried under reduced pressure. The resulting solids were subjected to medium pressure preparative chromatography (ODS silica gel, elution solvent; aqueous solution with 0.1% trifluoroacetic acid:acetonitrile solution with 0.1% trifluoroacetic acid), and the resulting mixture was freeze-dried to give the title compound (13.4 mg) as white solids.

Mass spectrum (ESI, m/z): 1101 [M+H]+.

¹H-NMR spectrum (400 MHz, DMSO-d₆+D₂O) δ: 8.22-8.13 (m, 4H), 7.49-7.38 (m, 8H), 7.32-7.22 (m, 4H), 4.57 (dd, J=5.5, 3.3 Hz, 2H), 4.38 (d, J=15.8 Hz, 2H), 4.34 (d, J=15.8 Hz, 2H), 3.91-3.49 (m, 12H), 2.98 (dd, J=8.3, 16.6 Hz, 2H), 2.77-2.61 (m, 8H).

Example 23-(a)

Preparation of tetrabenzyl 3,3-(((ethane-1,2-diylbis(oxy))bis(ethane-2,1-diyl))bis((N-((benzyloxy)carbonyl)-N-(4-((4-(2,3-bis(tert-butoxycarbonyl)guanidino)benzoyl)oxy)benzyl)sulfamoyl)azanediyl)dipentanedioate

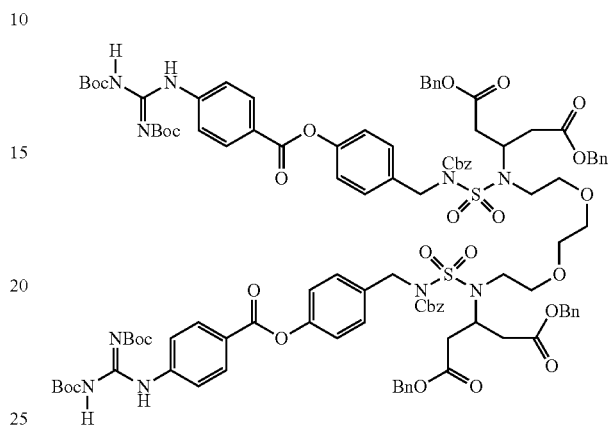

To a solution of tetrabenzyl 3,3'-(((ethane-1,2-diylbis(oxy))bis(ethane-2,1-diyl))bis((N-((benzyloxy)carbonyl)sulfamoyl)azanediyl))dipentanedioate (1.47 g) prepared in the Reference Example 23-(e) and 4-(hydroxymethyl)phenyl 4-(2,3-bis(tert-butoxycarbonyl)guanidino)benzoate (1.26 g) prepared according to the same manner as the Reference Example 1-(g) in dehydrated tetrahydrofuran (30 mL) in a 300 mL round-bottom flask was added triphenylphosphine (0.90 g) at room temperature under argon atmosphere with stirring, and the resulting mixture was stirred at room temperature. Then, diisopropyl azodicarboxylate (a 1.9 M solution in toluene) (1.80 mL) was added thereto at room temperature under water-cooling, and the resulting mixture was stirred at room temperature for 4 hours. After the reaction was completed, the reaction solution was diluted with ethyl acetate (100 mL), 1% aqueous potassium hydrogen sulfate solution (50 mL) and saturated brine (50 mL) were added thereto, and the resulting mixed solution was extracted with ethyl acetate. The resulting organic layer was washed with saturated brine (100 mL), saturated aqueous sodium hydrogen carbonate solution (50 mL), and saturated brine (50 mL), dried over anhydrous magnesium sulfate, filtered, and concentrated under reduced pressure. The resulting residues were subjected to medium pressure preparative chromatography (silica gel, elution solvent; hexane:ethyl acetate), and the fractions comprising the target compound were concentrated under reduced pressure. The resulting residues were subjected to medium pressure preparative chromatography (silica gel, elution solvent; dichloromethane:ethyl acetate), and the fractions comprising the target compound were concentrated under reduced pressure. The resulting residues were purified by medium pressure preparative chromatography (silica gel, elution solvent; toluene:ethyl acetate) to give the title compound (0.68 g) as a white foam.

Mass spectrum (ESI, m/z): 1066 [M+2H]²⁺.

¹H-NMR spectrum (400 MHz, CDCl₃) δ: 11.62 (br s, 2H), 10.63 (s, 2H), 8.18-8.12 (m, 4H), 7.83-7.78 (m, 4H), 7.39-7.06 (m, 383H), 5.15-5.10 (m, 4H), 5.10-5.01 (m, 81H), 4.91

(s, 4H), 4.50-4.39 (m, 2H), 3.56-3.36 (m, 12H), 2.81 (dd, J=6.5, 16.4 Hz, 4H), 2.69 (dd, J=7.3, 16.4 Hz, 4H), 1.60-1.493 (m, 36H).

Example 23-(b)

Preparation of 3,3'-(((ethane-1,2-diylbis(oxy))bis(ethane-2,1-diyl)bis((N-(4-((4-(2,3-bis(tert-butoxycarbonyl)guanidino)benzoyl)oxy)benzyl)sulfamoyl)azanediyl))dipentanedioic acid

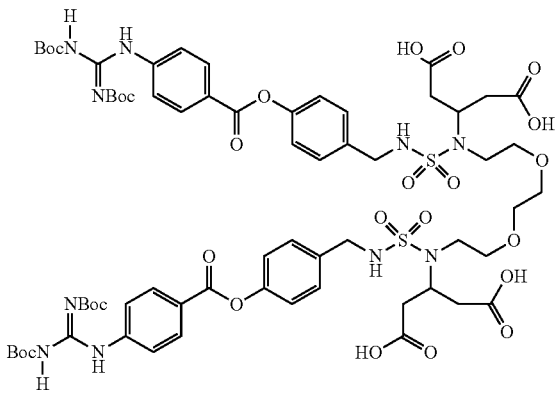

To a solution of tetrabenzyl 3,3'-(((ethane-1,2-di ylbis(oxy))bis(ethane-2,1-diyl))bis((N-((benzyloxy)carbonyl)-N-(4-((4-(2,3-bis(tert-butoxycarbonyl)guanidino)benzoyl)oxy)benzyl)sulfamoyl)azanediyl))dipentanedioate (326.7 mg) prepared in the Example 23-(a) in ethanol (5 mL)/tetrahydrofuran (2 mL) in a 30 mL cylindrical flask was added ASCA-2 (wetted with 52% water, manufactured by NE CHEMCAT Corporation) (213.3 mg) at room temperature user nitrogen atmosphere, and the resulting mixture was stirred at room temperature under hydrogen atmosphere for 2 hours. After the reaction was completed, the reaction solution was filtered, and washed with ethanol. The resulting filtrate and the wash liquid were combined, and concentrated under reduced pressure. The resulting residues were subjected to medium pressure preparative chromatography (DIOL silica gel, elution solvent; ethyl acetate:acetic acid), the fractions comprising the target compound were washed with water (five times) and saturated brine (once), dried over anhydrous magnesium sulfate, filtered, and concentrated under reduced pressure. The resulting residues were subjected to medium pressure preparative chromatography (DIOL silica gel, elution solvent; ethyl acetate:acetic acid), and the fractions comprising the target compound were concentrated under reduced pressure. The resulting residues were subjected to medium pressure preparative chromatography (DIOL silica gel, elution solvent; ethyl acetate:acetic acid), and the fractions comprising the target compound were concentrated under reduced pressure. The resulting residues were subjected to medium pressure preparative chromatography (DIOL silica gel, elution solvent; ethyl acetate:acetic acid), and the fractions comprising the target compound were concentrated under reduced pressure. The concentrated residues were diluted with ethyl acetate, washed with water (three times) and saturated brine (once), dried over anhydrous magnesium sulfate, filtered, concentrated under reduced pressure, hexane was added thereto, and the resulting mixture was concentrated under reduced pressure to give the title compound (85.6 mg) as white solids.

Mass spectrum (ESI, m/z): 752 $[M+2H]^{2+}$.

$^1$H-NMR spectrum (400 MHz, CDCl$_3$) δ: 11.66 (br s, 2H), 10.60 (br s, 2H), 0.14-8.09 (m, 4H), 7.77-7.72 (m, 4H), 7.42-7.34 (m, 4H), 7.19-7.11 (m, 4H), 5.57-5.34 (m, 2H), 4.37-4.06 (m, 6H), 3.50-3.27 (m, 12H), 2.96 (dd, J=7.0, 16.4 Hz, 4H), 2.70 (dd, J=6.4, 16.4 Hz, 4H), 1.53 (s, 36H).

Example 23-(c)

Preparation of 3,3'-(((ethane-1,2-diylbis(oxy))bis(ethane-2,1-diyl))bis((N-(4-((4-guanidinobenzoyl)oxy)benzyl)sulfamoyl)azanediyl))dipentanedioic acid

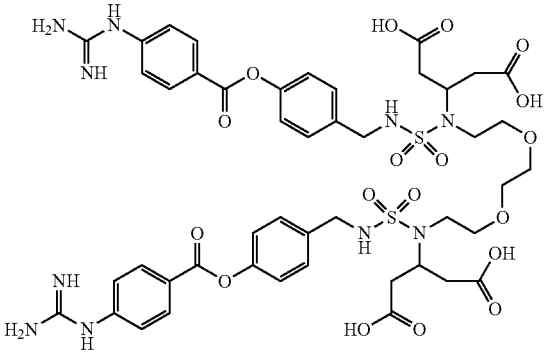 [SMILES: N=C(N)Nc1ccc(C(=O)Oc2ccc(CNS(=O)(=O)N(CCOCCOCCN(C(CC(=O)O)CC(=O)O)S(=O)(=O)NCc3ccc(OC(=O)c4ccc(NC(=N)N)cc4)cc3)C(CC(=O)O)CC(=O)O)cc2)cc1]

To 3,3'-(((ethane-1,2-diylbis(oxy))bis(ethane-2,1-diyl))bis((N-(4-((4-(2,3-bis(tert-butoxycarbonyl)guanidino)benzoyl)oxy)benzyl)sulfamoyl)azanediyl))dipentanedioic acid (85.6 mg) prepared in the Example 23-(b) in a 50 mL round-bottom flask was added a 4 M hydrogen chloride/dioxane solution (5 mL), and the resulting mixture was stirred at room temperature for 19 hours. After the reaction was completed, the reaction solution was concentrated under reduced pressure. To the concentrated residues was added cyclohexane, and the resulting mixture was concentrated under reduced pressure. To the concentrated residues was added dehydrated diethyl ether, the resulting mixture was subjected to sonication, stirred at room temperature for 1 hour, the resulting solids were collected by filtration, and washed with diethyl ether. The resulting solids were preparatively isolated by supercritical fluid chromatography (Column; Torus DEA OBD Prep column (trade name, manufactured by Waters Corporation), elution solvent; carbon dioxide:methanol), and the fractions comprising the target compound were freeze-dried to give the title compound (2.0 mg) as white solids.

Mass spectrum (DUIS, m/z): 551 $[M+2H]^{2+}$.

$^1$H-NMR spectrum (500 MHz, (CF$_3$)$_2$CDOD+D$_2$O) δ: 8.27 (d, J=7.9 Hz, 4H), 7.49 (d, J=7.9 Hz, 4H), 7.38 (d, J=8.0 Hz, 4H), 7.16 (d, J=8.0 Hz, 4H), 4.69-4.56 (m, 2H), 4.35-4.27 (m, 4H), 3.83-3.42 (m, 12H), 2.88-2.59 (m, 8H).

Example 24-(a)

Preparation of (2S,2'S)-2,2'-((1,12-bis(4-((4-guanidinobenzoyl)oxy)phenyl)-5,8-dioxa-2,11-diazadodecanedisulfonyl)bis(azanediyl))disuccinic acid

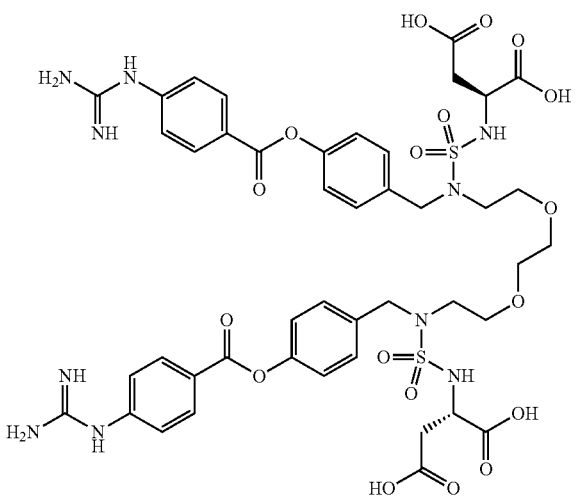 [SMILES: N=C(N)Nc1ccc(C(=O)Oc2ccc(CN(CCOCCOCCN(Cc3ccc(OC(=O)c4ccc(NC(=N)N)cc4)cc3)S(=O)(=O)N[C@@H](CC(=O)O)C(=O)O)S(=O)(=O)N[C@@H](CC(=O)O)C(=O)O)cc2)cc1]

To a suspension of (2S,2'S)-2,2'-((1,12-bis(4-((4-aminobenzoyl)oxy)phenyl)-5,8-dioxa-2,11-diazadodecanedisulfonyl)bis(azanediyl))disuccinic acid hydrochloride (0.83 g) prepared in the Reference Example 24-(g) in tert-butanol (7 mL) in a 100 mL round-bottom flask were added cyanamide (0.20 g) and a 4 M hydrogen chloride/dioxane solution (1.17 mL) at room temperature under argon gas flow with stirring, and the resulting mixture was stirred at 60° C. for 5 hours. After the reaction was completed, the reaction solution was concentrated under reduced pressure. The concentrated residues were subjected to azeotropy with toluene once, and then with acetonitrile once. The resulting residues were dissolved into acetonitrile (2.0 mL)/water (4.0 mL)/trifluoroacetic acid (0.06 mL), the resulting solution was subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried. The resulting residues were dissolved into acetonitrile (8 mL)/water (32 mL), to the resulting solution was added a saturated aqueous ammonium acetate solution with stirring to adjust the pH to 4.17, and the resulting mixture was stirred at room temperature for 17 hours. The precipitated solids were collected by filtration, washed with water, and dried under reduced pressure to give the title compound (0.20 g) as white solids.

Mass spectrum (ESI, m/z): 537 $[M+2H]^{2+}$.

$^1$H-NMR spectrum (400 MHz, DMSO-$d_6$+$D_2O$) δ: 8.09-8.00 (m, 4H), 7.40-7.29 (m, 4H), 7.27-7.17 (m, 4H), 7.13-7.03 (m, 4H), 4.40-4.18 (m, 4H), 3.97-3.84 (m, 2H), 3.40-3.07 (m, 12H), 2.67-2.40 (m, 4H).

Example 25-(a)

Preparation of (2S,13S)-tetra-tert-butyl 3,12-bis(N-((benzyloxy)carbonyl)-N-(3-(((4-(2,3-bis(tert-butoxycarbonyl)guanidino)benzoyl)oxy)benzyl)sulfamoyl)-6,9-dioxa-3,12-diazatetradecane-1,2,13,14-tetracarboxylate

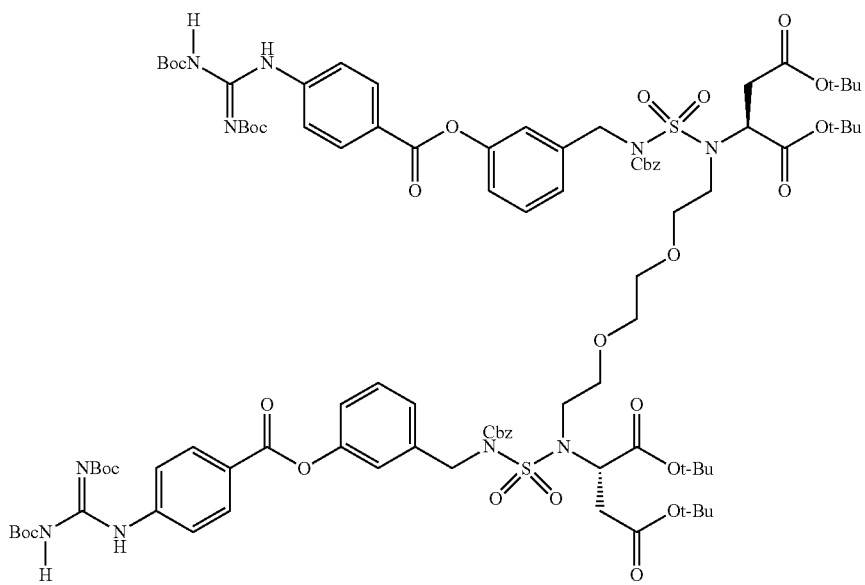

(1) To a solution of (2S,13S)-tetra-tert-butyl 3,2-bis(N-((benzyloxy)carbonyl)sulfamoyl)-6,9-dioxa-3,12-diazatetradecane-1,2,13,14-tetracarboxylate (206.4 mg) prepared according no the same manner as the Reference Example 2-(c) and 3-(hydroxymethyl)phenyl 4-(2,3-bis(tert-butoxycarbonyl)guanidino)benzoate (203.8 mg) prepared according to the same manner as the Reference Example 1-(g)-14 in dehydrated tetrahydrofuran (2 mL) in a 10 mL two-necked flask was added triphenylphosphine (146.9 mg) at room temperature under argon gas flow with stirring. Then, diisopropyl azodicarboxylate (a 1.9 M solution in toluene) (295 μL) was added dropwise thereto a room temperature over 5 minutes, and the resulting mixture was stirred for 5 hours, (2) To a solution of (2S,13S)-tetra-tert-butyl 3,12-bis(N-((benzyloxy)carbonyl) sulfamoyl)-6,9-dioxa-3,12-diazatetradecane-1,2,13,14-tetracarboxylate (2.14 g) prepared according to the same manner as the Reference Example 2-(c) and 3-(hydroxymethyl)phenyl 4-(2,3-bis(tert-butoxycarbonyl)guanidino)benzoate (2.11 g) prepared according to the same manner as the Reference Example 1-(g)-14 in dehydrated tetrahydrofuran (20 mL) in a 100 mL three-necked flask was added triphenylphosphine (1.53 g) at room temperature under argon gas flow with stirring. Then, diisopropyl azodicarboxylate (a 1.9 M solution in toluene) (3.05 mL was added dropwise thereto at room temperature over 10 minutes, and the resulting mixture was stirred for 4 hours.

The reaction solution in (1) and the reaction solution in (2) were combined, water (40 mL) was added Thereto, and the resulting mixed solution was extracted with ethyl acetate (100 mL). The resulting organic layer was washed with a saturated aqueous sodium chloride solution (40 mL), dried over anhydrous magnesium sulfate, and concentrated under reduced pressure. The resulting residues were subjected to medium pressure preparative chromatography (silica gel, elution solvent; hexane:ethyl acetate), and the fractions comprising the target compound were concentrated under reduced pressure. The resulting residues were purified by medium pressure preparative chromatography (silica gel, elution solvent; toluene:ethyl acetate) to give the title compound (3.51 g) as a white foam.

Mass spectrum (ESI, m/z): 984 [M+2H]=+v.

$^1$H-NMR spectrum (400 MHz, CDCl$_3$) δ: 11.61 (s, 2H), 10.62 (s, 2H), 8.15-8.11 (m, 4H), 7.86-7.77 (m, 4H), 7.36-7.10 (m, 18H), 5.18 (d, J=12.1 Hz, 2H), 5.14 (d, J=12.1 Hz, 2H), 5.00-4.90 (m, 4H), 4.69 (dd, J=6.2, 8.1 Hz, 2H), 3.77-3.66 (m, 2H), 3.60-3.44 (m, 8H), 3.40-3.28 (m, 2H), 2.90 (dd, J=8.1, 16.7 Hz, 2H), 2.66 (dd, J=6.2, 16.7 Hz, 2H), 1.56 (s, 18H), 1.53 (s, 18H), 1.44 (s, 18H), 1.44 (s, 18H).

Example 25-(b)

Preparation of (2S,13S)-3,12-bis(N-(3-((4-guanidinobenzoyl)oxy)benzyl)sulfamoyl)-6,9-dioxa-3,12-diazatetradecane-1,2,13,14-tetracarboxylic acid To a solution of (2S,13S)-tetra-tert-butyl 3,12-bis(N-((benzyloxy)carbonyl)-N-(3-(((4-(2,3-bis(tert-butoxycarbonyl)guanidino)benzoyl)oxy)benzyl)sulfamoyl)-6,9-dioxa-3,12-diazatetradecane-1,2,13,14-tetracarboxylate (3.50 g) prepared in the Example 25-(a) in dehydrated toluene (13.5 mL) in a 300 mL round-bottom flask was added trifluoroacetic acid (13.5 mL) at room temperature with stirring, and the resulting mixture was stirred at 50° C. for 15 hours. After the reaction was completed, the reaction solution was concentrated under reduced pressure. The concentrated residues were subjected to azeotropy with toluene (25 mL) twice and then with acetonitrile (25 mL) four times, and dried under reduced pressure to give (2S,13S)-3,12-bis(N-((benzyloxy)carbonyl)-N-(3-((4-guanidinobenzoyl)oxy)benzyl)sulfamoyl)-6,9-dioxa-3,12-diazatetradecane-1,2,13,14-tetracarboxylic acid trifluoroacetate as a white foam. To a solution of the resulting (2S,13S)-3,12-bis(N-((benzyloxy)carbonyl)-N-(3-((4-guanidinobenzoyl)oxy)benzyl)sulfamoyl)-6,9-dioxa-3,12-diazatetradecane-1,2,13,14-tetracarboxylic acid trifluoroacetate (2.39 g) in acetic acid (20 mL)/water (4 mL) in a 500 mL round-bottom flask was added ASCA-2 (wetted with 52% water, manufactured by NE CHEMCAT Corporation) (360.3 mg) at room temperature, the atmosphere in the reaction system was replaced with hydrogen atmosphere, and then the resulting mixture was stirred at room temperature for 5 hours. After the reaction was completed, the reaction solution was filtered through Celite, washed with acetic acid/water solution, and concentrated under reduced pressure. The resulting residues were preparatively isolated by high performance liquid chromatography (Column; XSelect CSH C18 OBD Prep Column (trade name, manufactured by Waters Corporation), elution solvent; aqueous solution with 0.1% formic acid:acetonitrile solution with 0.1% formic acid), and the fractions comprising the target compound were freeze-dried. To the resulting residues was added acetonitrile (50 mL)/water (50 mL), and diluted aqueous ammonium acetate solution and diluted aqueous acetic acid solution were added thereto to adjust the pH to 4.20. The reaction solution was concentrated under reduced pressure until white solids precipitated. The resulting mixture was stirred at room temperature for 14 hours, cooled by

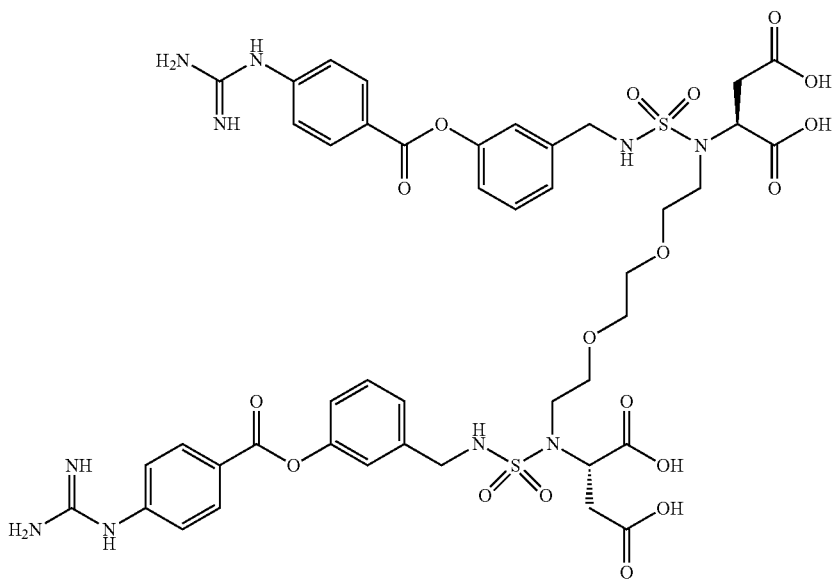 [SMILES: N=C(N)Nc1ccc(C(=O)Oc2cccc(CNS(=O)(=O)N(CCOCCOCCN([C@@H](CC(=O)O)C(=O)O)S(=O)(=O)NCc3cccc(OC(=O)c4ccc(NC(=N)N)cc4)c3)[C@@H](CC(=O)O)C(=O)O)c2)cc1]

ice water, stirred for a while, the precipitated solids were collected by filtration, washed with cold water, and dried under reduced pressure to give the title compound (0.91 g) as white solids.

Mass spectrum (DUIS, m/z): 537 [M+2H]$^{2+}$.

$^1$H-NMR spectrum (400 MHz, (CF$_3$)$_2$CDOD) δ: 8.30 (d, J=8.5 Hz, 4H), 7.50 (dd, J=7.9 Hz, J=7.9 Hz, 2H), 7.43-7.34 (m, 6H), 7.26-7.20 (m, 2H), 7.17-7.10 (m, 2H), 4.66-4.55 (m, 2H), 4.37-4.31 (m, 4H), 3.84-3.41 (m, 12H), 3.33 (dd, J=9.9, 16.2 Hz, 2H), 2.95-2.79 (m, 2H).

Example 26-(a)

Preparation of (2S,2'S)-tetra-tert-butyl 2,2'-((oxybis(ethane-2,1-diyl))bis((10-(2,3-bis(tert-butoxycarbonyl)guanidino)-13-oxo-6,7,8,13-tetrahydrodibenzo[b,f][1,4]dioxecin-4-carbonyl)azanediyl))disuccinate

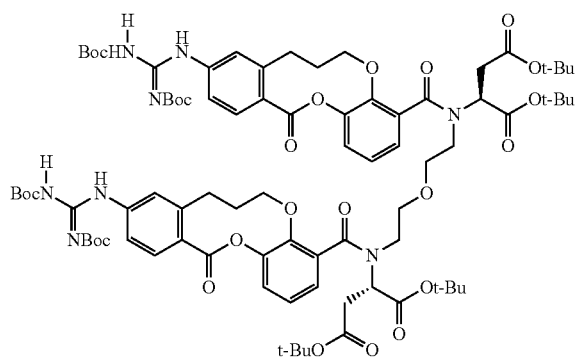

To a suspension of 10-(2,3-bis(tert-butoxycarbonyl)guanidino)-13-oxo-6,7,8,13-tetrahydrodibenzo[b,f][1,4]dioxecin-4-carboxylic acid (6.25 g) prepared according to the same manner as the Reference Example 19-(n) in dimethylformamide (46 mL) in a 200 mL round-bottom flask were added COMU (5.19 g) and N,N-diisopropylethylamine (2.8 mL) at 0° C. under argon gas flow with stirring, and the resulting mixture was stirred at 0° C. for 10 minutes. Then, a solution of (2S,2'S)-tetra-tert-butyl 2,2'-((oxybis(ethane-2,1-diyl))bis(azanediyl))disuccinate (3.01 g) prepared according to the same manner as the Reference Example 1-(c) in dimethylformamide (8 mL) was added dropwise thereto with stirring at 0° C., and the resulting mixture was stirred at room temperature for 19 hours. After the reaction was completed, to the reaction solution was added saturated aqueous sodium hydrogen carbonate solution, and the resulting mixed solution was extracted with toluene. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (5.63 g) as slightly yellow solids.

Mass spectrum (ESI, m/z): 819 [M+2H]$^{2+}$.

$^1$H-NMR spectrum (400 MHz, DMSO-d$_6$) δ: 11.47-11.13 (m, 2H), 10.38-10.03 (m, 2H), 7.94-7.70 (m, 4H), 7.65-7.38 (m, 4H), 7.35-6.92 (m, 4H), 4.59-4.29 (m, 2H), 4.17-2.37 (m, 20H), 2.18-0.99 (m, 76H).

Example 26-(b)

Preparation of (2S,2'S)-2,2'-((oxybis(ethane-2,1-diyl))bis((10-guanidino-13-oxo-6,7,8,13-tetrahydrodibenzo[b,f][1,4]dioxecin-4-carbonyl)azanediyl)) disuccinic acid

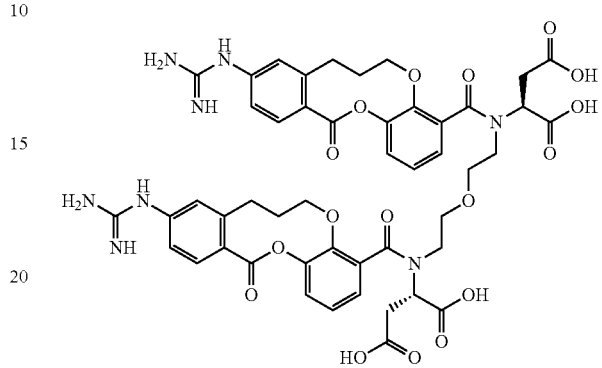

To (2S,2'S)-tetra-tert-butyl 2,2'-((oxybis(ethane-2,1-diyl)) bis((10-(2,3-bis(tert-butoxycarbonyl)guanidino)-13-oxo-6,7,8,13-tetrahydrodibenzo[b,f][1,4]dioxecin-4-carbonyl) azanediyl))disuccinate (6.7 g) prepared in the Example 26-(a) in a 200 mL round-bottom flask was added a 4 M hydrogen chloride/dioxane solution (34 mL) at room temperature under argon gas flow with stirring, and the resulting mixture was stirred at room temperature for 16 hours. After the reaction was completed, the reaction solution was concentrated under reduced pressure. The concentrated residues were subjected to azeotropy with toluene once, and then with acetonitrile once. The resulting residues were dissolved into acetonitrile (17 mL)/water (17 mL)/trifluoroacetic acid (340 μL), the resulting solution was subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried. The resulting residues were dissolved into acetonitrile (37 mL)/water (2 mL)/trifluoroacetic acid (390 μL), the resulting solution was subjected to medium pressure preparative chromatography (silica gel, elution solvent; aqueous solution with 0.1% trifluoroacetic acid:acetonitrile solution with 0.1% trifluoroacetic acid), and the fractions comprising the target compound were freeze-dried. The resulting residues were dissolved into water (70 mL)/acetonitrile (20 mL), and a saturated aqueous ammonium acetate solution was added thereto with stirring to adjust the pH to 4.2. Water (15 mL) was added thereto, and the resulting mixture was stirred at room temperature for 8 hours. The precipitated solids were collected by filtration, washed with water, and dried under reduced pressure to give the title compound (3.25 g) as white solids.

Mass spectrum (ESI, m/z): 1011 [M+H]$^+$.

$^1$H-NMR spectrum (500 MHz, (CF$_3$)$_2$CDOD) δ: 8.02-7.48 (m, 4H), 7.47-6.92 (m, 8H), 5.54-2.50 (m, 22H), 2.44-1.61 (m, 4H).

Example 27-(a)

Preparation of (2S,16S)-tetra-tert-butyl 3,15-bis(10-(2,3-bis(tert-butoxycarbonyl)guanidino)-13-oxo-6,7,8,13-tetrahydrodibenzo[b,f][1,4]dioxecin-4-carbonyl)-6,9,12-trioxa-3,15-diazaheptadecane-1,2,16,17-tetracarboxylate

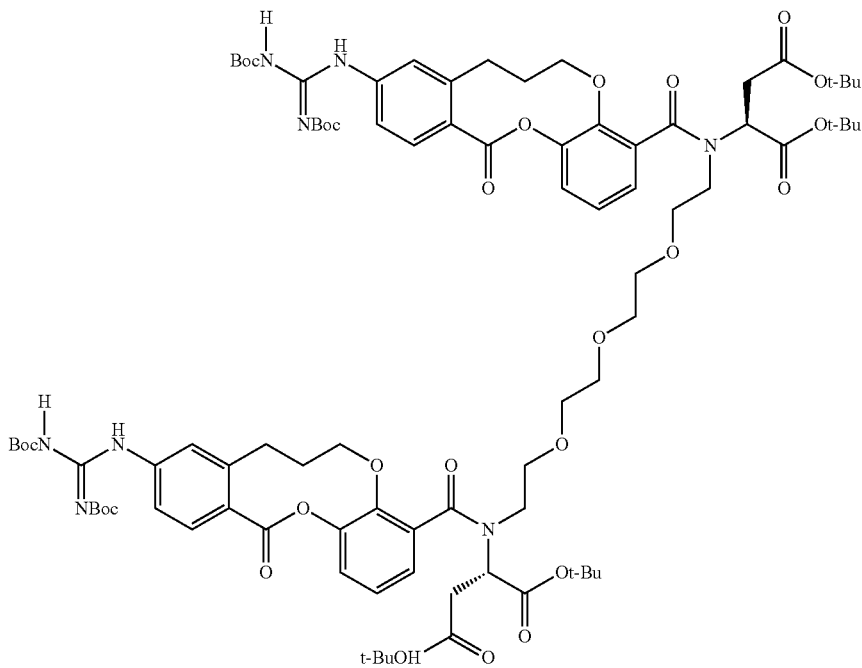

To a solution of 10-(2,3-bis(tert-butoxycarbonyl)guanidino)-13-oxo-6,7,8,13-tetrahydrodibenzo[b,f][1,4]dioxecin-4-carboxylic acid (5.65 g) prepared according to the same manner as the Reference Example 19-(n) in dimethylformamide (30 mL) in a 200 mL round-bottom flask were added N,N-diisopropylethylamine (2.42 mL) and COMU (4.46 g) at 0° C. under argon gas flow with stirring, and the resulting mixture was stirred at C° C. for 30 minutes. Then, a solution of (2S,16S)-tetra-tert-butyl 6,9,12-trioxa-3,45-diazaheptadecane-1,2,16,17-tetracarboxylate (3.01 g) prepared according to the same manner as the Reference Example 3-(b) in dimethylformamide (15 mL) was added thereto with stirring at 0° C., and the resulting mixture was stirred at room temperature for 19 hours. After the reaction was completed, to the reaction solution was added saturated aqueous sodium hydrogen carbonate solution, and the resulting mixed solution was extracted with toluene. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (6.18 g) as a yellow foam.

Mass spectrum (ESI, m/z); 863 [M+2H]$^{2+}$.

$^1$H-NMR spectrum (400 MHz, DMSO-d$_6$) δ: 11.36-11.21 (m, 2H), 10.26-10.14 (m, 2H), 7.91-7.76 (m, 4H), 7.62-7.40 (m, 4H), 7.33-6.99 (m, 4H)), 4.50-4.36 (m, 2H), 3.96-2.42 (m, 28H), 2.11-1.70 (m, 4H), 1.51 (s, 18H), 1.45-1.38 (m, 54H).

Example 27-(b)

Preparation of (2S,16S)-3,15-bis(10-guanidino-13-oxo-6,7,8,13-tetrahydrodibenzo[b,f][1,4]dioxecin-4-carbonyl)-6,9,12-trioxa-3,15-diazaheptadecane-1,2,16,17-tetracarboxylic acid water, and dried under reduced pressure to give the title compound (2.83 g) as white solids.

Mass spectrum (ESI, m/z): 550 $[M+2H]^{2+}$.

$^1$H-NMR spectrum (500 MHz, $(CF_3)_2CDOD$) δ: 7.93-7.69 (m, 2H), 7.65-7.50 (m, 2H), 7.43-7.00 (m, 8H), 5.20-2.65 (m, 30H), 2.34-1.74 (m, 4H).

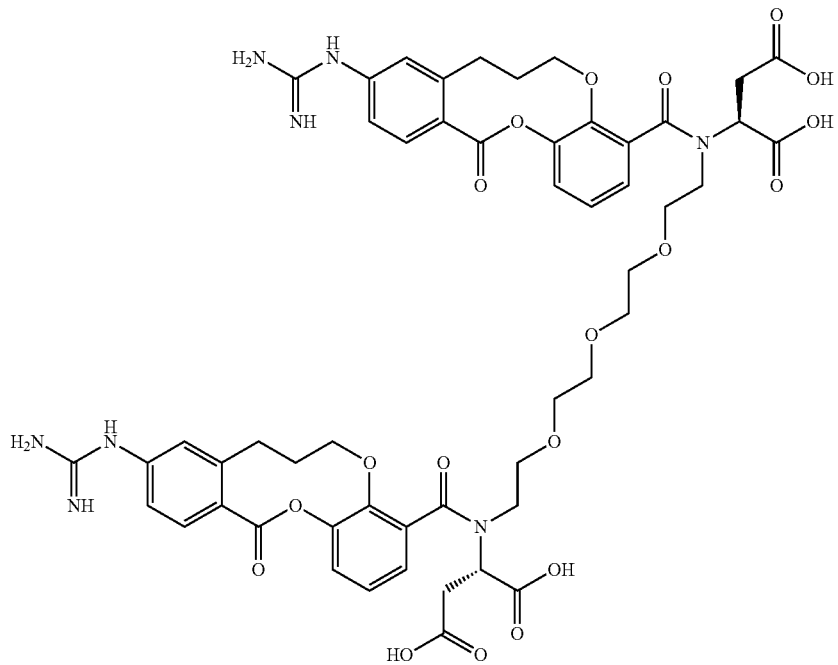 [SMILES: N=C(N)Nc1ccc2c(c1)CCCOc1c(cccc1C(=O)N(CCOCCOCCOCCN(C(=O)c1cccc3c1OCCCc1cc(NC(=N)N)ccc1C(=O)O3)[C@@H](CC(=O)O)C(=O)O)[C@@H](CC(=O)O)C(=O)O)OC2=O]

To (2S,16S)-tetra-tert-butyl 3,15-bis(10-(2,3-bis(tert-butoxycarbonyl)guanidino)-13-oxo-6,7,8,13-tetrahydrodibenzo[b,f][1,4]dioxecin-4-carbonyl)-6,9,12-trioxa-3,15-diazaheptadecane-1,2,16,17-tetracarboxylate (6.9 g) prepared in the Example 27-(a) in a 300 mL round-bottom flask was added a 4 M hydrogen chloride/dioxane solution (35 mL) at room temperature under argon gas flow with stirring, and the resulting mixture was stirred at room temperature for 16 hours. After the reaction was completed, the reaction solution was concentrated under reduced pressure. The concentrated residues were subjected to azeotropy with toluene once, and then with acetonitrile once. The resulting residues were dissolved into acetonitrile (8.0 mL)/water (12.0 mL)/trifluoroacetic acid (0.02 mL), the resulting solution was subjected to medium pressure preparative chromatography (ODS, elution solvent; aqueous solution with 0.1% trifluoroacetic acid:acetonitrile solution with 0.1% trifluoroacetic acid), and the fractions comprising the target compound were freeze-dried. The resulting residues were dissolved into acetonitrile (30 mL)/water (3 mL), the resulting solution was subjected to medium pressure preparative chromatography (silica gel, elution solvent; aqueous solution with 0.1% trifluoroacetic acid:acetonitrile solution with 0.1% trifluoroacetic acid), and the fractions comprising the target compound were freeze-dried. The resulting residues were dissolved into acetonitrile (14 mL)/water (56 mL), a saturated aqueous ammonium acetate solution was added thereto with stirring to adjust the pH to 4.1, and the resulting mixture was stirred at room temperature for 17 hours. The precipitated solids were collected by filtration, washed with

Example 28-(a)

Preparation of (2S,2'S)-tetrabenzyl 2,2'-(([1,1'-biphenyl]-3,3'-diylbis(methylene))bis((10-(2,3-bis(tert-butoxycarbonyl)guanidino)-13-oxo-6,7,8,13-tetrahydrodibenzo[b,f][1,4]dioxecin-4-carbonyl)azanediyl)) disuccinate

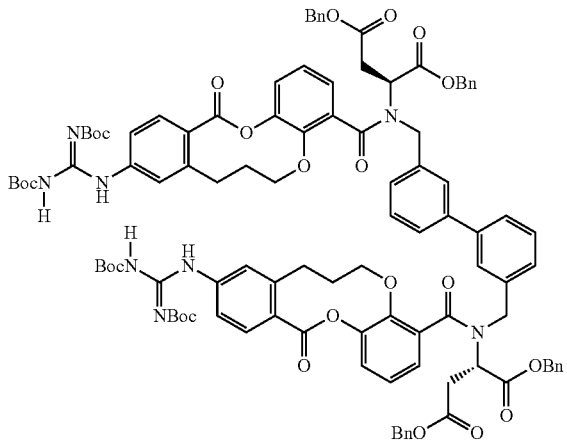

To a suspension of 10-(2,3-bis(tert-butoxycarbonyl)guanidino)-13-oxo-6,7,8,13-tetrahydrodibenzo[b,f][1,4]dioxecin-4-carboxylic acid (234.8 mg) prepared according to the same manner as the Reference Example 19-(n) and (2S,2'S)-tetrabenzyl 2,2'-(([1,1'-biphenyl]-3,3'-diylbis(methylene))bis(azanediyl))disuccinate (153.5 mg) prepared in the Reference Example 28-(c) in dimethylformamide (1.5 mL) in a 20 mL cylindrical flask was added 4-(4,6-dimethoxy-1,3,5-triazin-2-yl)-4-methylmorpholinium chloride n-hydrate (159.1 mg) at room temperature under argon gas flow with stirring, and the resulting mixture was stirred at room temperature for 19 hours. Additionally, 4-(4,6-dimethoxy-1,3,5-triazin-2-yl)-4-methylmorpholinium chloride n-hydrate (177.2 mg) was added thereto at room temperature with stirring, and the resulting mixture was stirred at room temperature for 99.5 hours. After the reaction was completed, to the reaction solution was added saturated aqueous sodium hydrogen carbonate solution, and the resulting mixture was extracted with ethyl acetate. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (221.0 mg) as a white foam.

Mass spectrum (ESI, m/z): 941 [M+2H]$^{2+}$.

$^1$H-NMR spectrum (400 MHz, DMSO-ds) δ: 11.78-10.84 (m, 2H), 10.69-9.93 (m, 2H), 8.15-6.58 (m, 40H), 5.32-0.69 (m, 66H).

Example 28-(b)

Preparation of (2S,2'S)-tetrabenzyl 2,2'-(([1,1'-biphenyl]-3,3'-diylbis(methylene))bis((10-guanidino-13-oxo-6,7,8,13-tetrahydrodibenzo[b,f][1,4]dioxecin-4-carbonyl)azanediyl))disuccinate formate

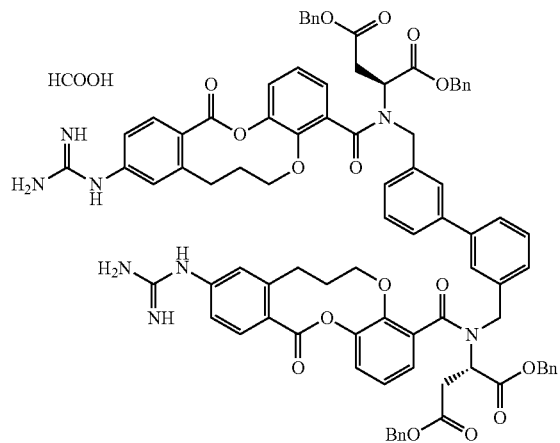 [SMILES: "HCOOH" ; N=C(N)Nc1ccc2c(c1)CCCOc1c(cccc1C(=O)N(Cc1cccc(-c3cccc(CN(C(=O)c4cccc5c4OCCCc4cc(NC(=N)N)ccc4C(=O)O5)[C@@H](CC(=O)OCc4ccccc4)C(=O)OCc4ccccc4)c3)c1)[C@@H](CC(=O)OCc1ccccc1)C(=O)OCc1ccccc1)OC2=O]

To a solution of (2S,2'S)-tetrabenzyl 2,2'-(([1,1'-biphenyl]-3,3'-diylbis(methylene))bis((10-(2,3-bis(tert-butoxycarbonyl)guanidino)-13-oxo-6,7,8,13-tetrahydrodibenzo[b,f][1,4]dioxecin-4-carbonyl)azanediyl))disuccinate (221 mg) prepared in the Example 28-(a) in toluene (0.5 mL) in a 100 mL round-bottom flask was added formic acid (0.5 mL) at room temperature under argon gas flow with stirring, and the resulting mixture was stirred at room temperature for 44 hours. After the reaction was completed, the reaction solution was concentrated under reduced pressure. The concentrated residues were subjected to azeotropy with toluene twice. To the concentrated residues was added tert-butyl methyl ether, the precipitated solids were collected by filtration through a membrane filter, washed with tert-butyl methyl ether, and dried under reduced pressure to give the title compound (127.9 mg) as white solids.

Mass spectrum (DUIS, m/z): 1480 [M+H]$^+$.

$^1$H-NMR spectrum (400 MHz, DMSO-d$_6$+D$_2$O) δ: 8.40 (s, 2H), 8.03-6.82 (m, 40H), 5.31-4.22 (m, 14H), 4.22-0.72 (m, 16H).

Example 28-(c)

Preparation of (2S,2'S)-2,2'-(([1,1'-biphenyl]-3,3'-diylbis(methylene))bis(((10-guanidino-13-oxo-6,7,8,13-tetrahydrodibenzo[b,f][1,4]dioxecin-4-carbonyl)azanediyl))disuccinic acid

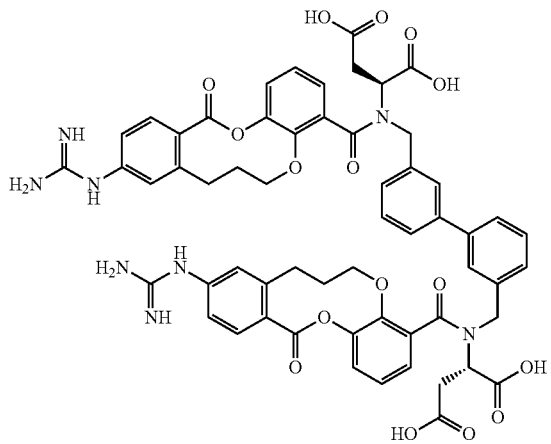 [SMILES: N=C(N)Nc1ccc2c(c1)CCCOc1c(cccc1C(=O)N(Cc1cccc(-c3cccc(CN(C(=O)c4cccc5c4OCCCc4cc(NC(=N)N)ccc4C(=O)O5)[C@@H](CC(=O)O)C(=O)O)c3)c1)[C@@H](CC(=O)O)C(=O)O)OC2=O]

To a solution of (2S,2'S)-tetrabenzyl 2,2'-(([1,1'-biphenyl]-3,3'-diylbis(methylene))bis((10-guanidino-13-oxo-6,7,8,13-tetrahydrodibenzo[b,f][1,4]dioxecin-4-carbonyl)azanediyl))disuccinate formate (127.9 mg) prepared in the Example 28-(b) in acetic acid (0.7 mL)/water (0.14 mL) in a 20 mL cylindrical flask was added ASCA-2 (wetted with 54.29% water, ASCA-2 manufactured by NE CHEMCAT Corporation) (19.6 mg) at room temperature, and the resulting mixture was stirred at room temperature under hydrogen atmosphere for 4.5 hours. Additionally, ASCA-2 (wetted with 54.29% water, manufactured by NE CHEMCAT Corporation) (26.1 mg) was added thereto with stirring at room temperature, and the resulting mixture was stirred at room temperature under hydrogen atmosphere for 3 hours. After the reaction was completed, the reaction solution was filtered through Celite, washed with acetic acid, and the resulting filtrate was concentrated under reduced pressure. The concentrated residues were subjected to azeotropy with toluene once, and then with acetonitrile once. The resulting residues were dissolved into acetonitrile (5.7 mL)/water (0.3 mL)/trifluoroacetic acid (60 μL), the resulting solution was subjected to medium pressure preparative chromatography (silica gel, elution solvent; aqueous solution with 0.1% trifluoroacetic acid:acetonitrile solution with 0.1% trifluoroacetic acid), and the fractions comprising the target compound were freeze-dried. The resulting residues were dissolved into water (5 mL)/acetonitrile (1 mL)/trifluoroacetic acid (50 μL), and a saturated aqueous ammonium acetate solution was added thereto with stirring to adjust the pH to 4.1. Water (3 mL) was added thereto, and the resulting mixture was stirred at room temperature for 6 hours. The precipitated solids were collected by filtration, washed with water, and dried under reduced pressure to give the title compound (27.8 mg) as white solids.

Mass spectrum (ESI, m/z): 1117 [M−H]⁻.

¹H-NMR spectrum (400 MHz, DMSO-d₆+D₂O) δ: 8.10-6.84 (m, 20H), 5.56-1.32 (m, 22H).

Example 29-(a)

Preparation of (2S,2'S)-tetra-tert-butyl 2,2'-(((((oxybis(ethane-2,1-diyl))bis(oxy))bis(3-((2-(trimethylsilyl)ethoxy)carbonyl)-5,1-phenylene))bis(methylene))bis((10-(2,3-bis(tert-butoxycarbonyl)guanidino)-13-oxo-6,7,8,13-tetrahydrodibenzo[b,f][1,4]dioxecin-4-carbonyl)azanediyl))disuccinate

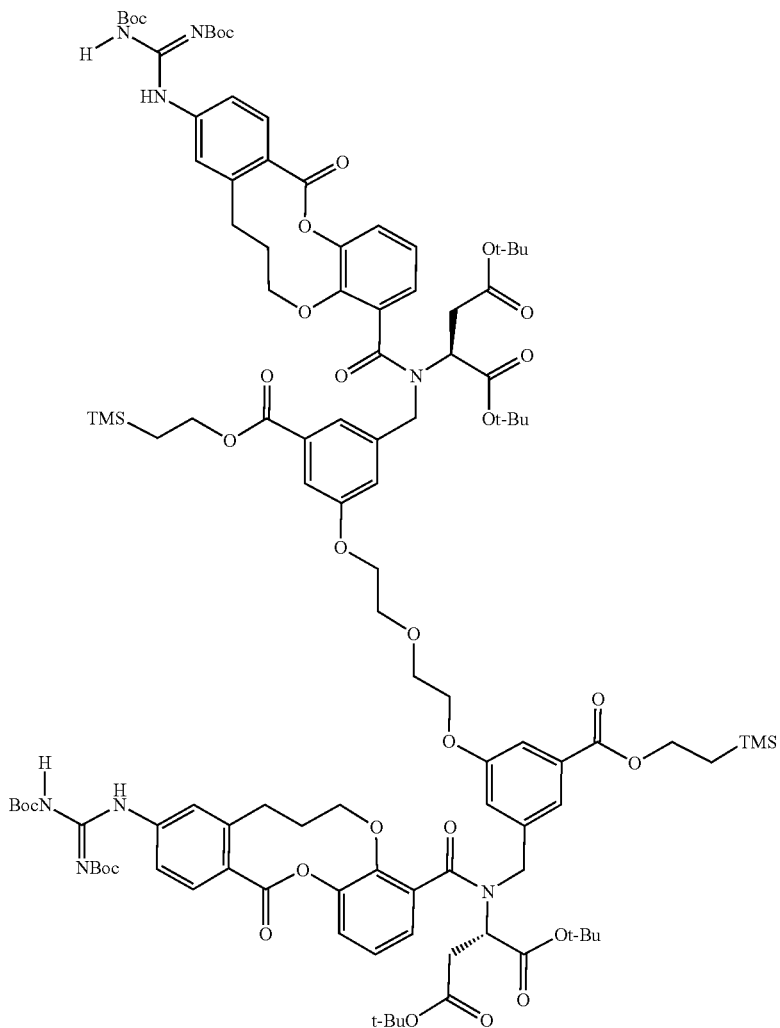

(1) A solution of (S)-di-tert-butyl 2-(10-(2,3-bis(tert-butoxycarbonyl)guanidino)-N-(3-(2-(2-hydroxyethoxy)ethoxy)-5-((2-(trimethylsilyl)ethoxy)carbonyl)benzyl)-13-oxo-6,7,8,13-tetrahydrodibenzo[b,f][1,4]dioxecin-4-carboxamido)succinate (416.2 mg) prepared in the Reference Example 29-(h), (S)-di-tert-butyl 2-(10-(2,3-bis(tert-butoxycarbonyl)guanidino)-N-(3-hydroxy-5-((2-(trimethylsilyl)ethoxy carbonyl)benzyl)-13-oxo-6,7,8,13-tetrahydrodibenzo[b,f][1,4]dioxecin-4-carboxamido)succinate (380.4 g) prepared according to the same manner as the Reference Example 29-(f), and triphenylphosphine (148.8 mg) in dehydrated dichloromethane (2 mL) in a 50 mL round-bottom flask was homogeneously stirred at room temperature under argon atmosphere, and ice-cooled. Then, diisopropyl azodicarboxylate (a 1.9 M solution in toluene) (0.30 mL) was added dropwise thereto, and after the addition was completed, the resulting mixture was stirred under ice-cooling for 0.2 hour, and at room temperature for 3 hours. After the reaction was completed, the reaction solution was subjected to medium pressure preparative chromatography (silica gel, elution solvent; hexane:ethyl acetate), and the fractions comprising the target compound were concentrated under reduced pressure.

(2) A solution of (S)-di-tert-butyl 2-(10-(2,3-bis(tert-butoxycarbonyl)guanidino)-N-(3-(2-(2-hydroxyethoxy)ethoxy) 5-((2-(trimethylsilyl)ethoxycarbonyl)benzyl)-13-oxo-6,7,8,3-tetrahydrodibenzo[b,f][1,4]dioxecin-4-carboxamido)sucinate (375 mg) prepared in the Reference Example 29-(h), (S)-di-tert-butyl 2-(10-(2,3-bis(tert-butoxycarbonyl guanidino)-N-(3-hydroxy-5-((2-(trimethylsilyl)ethoxy)carbonyl)benzyl)-13-oxo-6,7,8,13-tetrahydrodibenzo[b,f][1,4]dioxecin-4-carboxamido)succinate (348 mg) prepared according to the same manner as the Reference Example 29-(f), and triphenylphosphine (145.1 ma) in dehydrated dichloromethane (2 mL) in a 50 mL round-bottom flask was homogeneously stirred at room temperature under argon atmosphere, and ice-cooled. Then, diisopropyl azodicarboxylate (a 1.9 M solution in toluene) (0.30 mL) was added dropwise thereto, and after the addition was completed, the resulting mixture was stirred under ice-cooling for 0.1 hour, and at room temperature for 1.5 hours. Triphenylphosphine (194 mg) and diisopropyl azodicarboxylate (a 1.9 M solution in toluene) (150 μL) were added thereto, and the resulting mixture was stirred at room temperature for 1 hour. After the reaction was completed, the reaction solution was diluted with dichloromethane, subjected to medium pressure preparative chromatography (silica gel, elution solvent; hexane:ethyl acetate), and the fractions comprising the target compound were concentrated under reduced pressure.

The resulting residues in (1) and the resulting residues in (2) were combined, preparatively isolated by high performance liquid chromatography (Column; XSelect CSH Fluoro Phenyl OBD prep Column (trade name, manufactured by Waters Corporation), elution solvent; aqueous solution with 0.1% formic acid:acetonitrile solution with 0.1% formic acid), and the fractions comprising the target compound were concentrated under reduced pressure. To the concentrated residues were added ethyl acetate and saturated aqueous sodium hydrogen carbonate solution, the resulting mixture was stirred at room temperature, and the resulting mixed solution was extracted with ethyl acetate. The resulting organic layer was washed with saturated brine, dried over anhydrous magnesium sulfate, filtered, and concentrated under reduced pressure to give the title compound (0.57 g) as a white foam.

Mass spectrum (DUIS, m/z): 1069 [M+2H]$^{2+}$.
$^1$H-NMR spectrum (400 MHz, CDCl$_3$) δ: 11.61 (s, 2H), 10.55 (s, 2H), 8.05-7.91 (m, 2H), 7.88-7.78 (m, 2H), 7.69-7.38 (m, 8H), 7.34-7.04 (m, 6H), 4.65-2.40 (m, 30H), 2.32-1.71 (m, 4H), 1.65-1.21 (m, 72H), 1.18-1.06 (m, 4H), 0.07 (s, 18H).

Example 29-(b)

Preparation of (S)-5,5'-((oxybis(ethane-2,1-diyl))bis(oxy))bis(3-((10-(2,3-bis(tert-butoxycarbonyl)guanidino)-N—((S)-1,4-di-tert-butoxy-1,4-dioxobutan-2-yl)-13-oxo-6,7,8,13-tetrahydrodibenzo[b,f][1,4]dioxecin-4-carboxamido)methyl)benzoic acid)

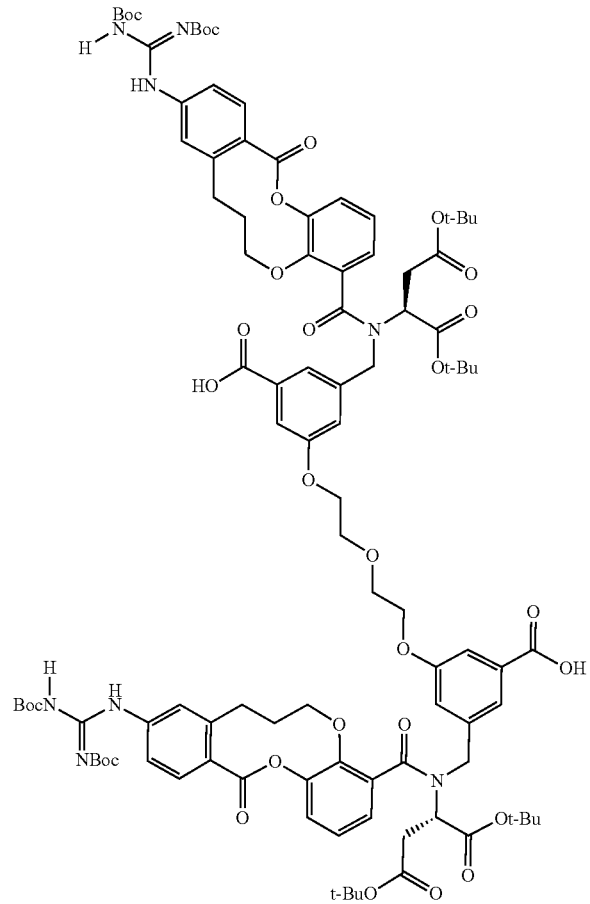

To a solution of (2S,2'S)-tetra-tert-butyl 2,2'-(((((oxybis(ethane-2,1-diyl))bis(oxy)?bis(3-((2-(trimethylsilyl)ethoxy)carbonyl)-5,1-phenylene))bis(methylene))bis((10-(2,3-bis(tert-butoxycarbonyl)guanidino)-13-oxo-6,7,8,13-tetrahydrodibenzo[b,f][1,4]dioxecin-4-carbonyl)azanediyl)) disuccinate 789.8 mg) prepared according t the same manner as the Example 29-(a) in dehydrated tetrahydrofuran (4 mL) in a 100 mL round-bottom flask was added tetrabutylammonium fluoride (a 1.0 M solution in tetrahydrofuran) (4 mL) at room temperature under argon atmosphere with stirring, and the resulting mixture was stirred at room temperature for 3.5 hours. After the reaction was completed, the reaction solution was diluted with toluene (50 mL), then washed with a saturated aqueous ammonium chloride solution (25 mL) twice, with a 5% aqueous potassium hydrogen sulfate solution (25 mL) twice, and with saturated brine (25 mL), dried over anhydrous magnesium sulfate, filtered, and concentrated under reduced pressure to give the title compound (730.5 mg) as a white foam.

Mass spectrum (DUIS, m/z): 968 [M+2H]$^{2+}$.

$^1$H-NMR spectrum (400 MHz, CDCl$_3$) δ: 11.62 (br s, 2H), 10.54 (s, 2H), 8.08-7.90 (m, 2H), 7.89-7.75 (m, 2H), 7.71-7.35 (m, 8H), 7.33-7.01 (m, 6H), 4.68-2.41 (m, H), 2.34-1.68 (m, 4H)), 1.68-1.18 (m, 72H).

Example 29-(c)

Preparation of (2S,2'S)-2,2'-(((((oxybis(ethane-2,1-diyl))bis(oxy))bis(3-carboxy-5,1-phenylene))bis(methylene))bis((10-guanidino-13-oxo-6,7,8,13-tetrahydrodibenzo[b,f][1,4]dioxecin-4-carbonyl)azanediyl))disuccinic acid hydrochloride

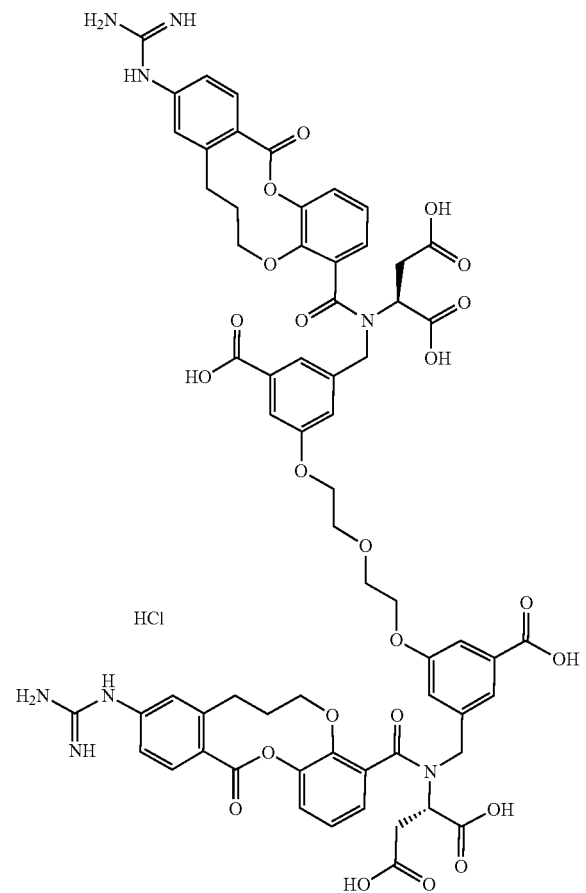 [SMILES: N=C(N)Nc1ccc2c(c1)CCCOc1c(cccc1C(=O)N(Cc1cc(OCCOCCOc3cc(CN(C(=O)c4cccc5c4OCCCc4cc(NC(=N)N)ccc4C(=O)O5)[C@@H](CC(=O)O)C(=O)O)cc(C(=O)O)c3)cc(C(=O)O)c1)[C@@H](CC(=O)O)C(=O)O)OC2=O ; Cl]

To (S)-5,5'-((oxybis(ethane-2,1-diyl))bis(oxy))bis(3-((10-(2,3-bis(tert-butoxycarbonyl)guanidino)-N—((S)-1,4-di-tert-butoxy-1,4-dioxobutan-2-yl)-13-oxo-6,7,8,13-tetrahydrodibenzo[b,f][1,4]dioxecin-4-carboxamido)methyl)benzoic acid) (725 mg) prepared in the Example 29-(b) in a 100 mL round-bottom flask was added a 4 M hydrogen chloride/dioxane solution (15 mL) at room temperature under nitrogen atmosphere, and the resulting mixture was stirred at room temperature for 14 hours. After the reaction was completed, the liquid component was removed from the reaction solution, and the resulting residues were washed with dehydrated diethyl ether. Then, dehydrated diethyl ether was added thereto, and the resulting mixture was subjected to sonication. The resulting mixture was stirred at room temperature for 1 hour, the resulting solids were collected by filtration, washed with dehydrated diethyl ether, and dried under reduced pressure. To the resulting solids was added ethanol (15 ml), and the resulting mixture was concentrated under reduced pressure. To the concentrated residues was added a small amount of ethanol to give a homogeneous solution, ethyl acetate was added thereto, the resulting mixture was subjected to sonication, and the resulting mixture was stirred at room temperature for 1 hour. The resulting solids were collected by filtration, washed with ethyl acetate, and dried under reduced pressure to give the title compound (461.4 mg) as white solids.

Mass spectrum (DUIS, m/z): 656 [M+2H]$^{2+}$.

$^1$H-NMR spectrum (500 MHz, (CF$_3$)$_2$CDOD) δ: 9.02-7.90 (m, 2H), 7.84-7.51 (m, 6H), 7.46-7.11 (m, 10H), 4.77-2.74 (m, 26H), 2.46-2.24 (m, 2H), 2.06-1.85 (m, 2H).

Example 30-(a

Preparation of (2S,2'S)-2,2'-(oxybis(ethane-2,1-diyl))bis((3-((4-guanidinobenzoyl)oxy)benzoyl)azanediyl))disuccinic acid

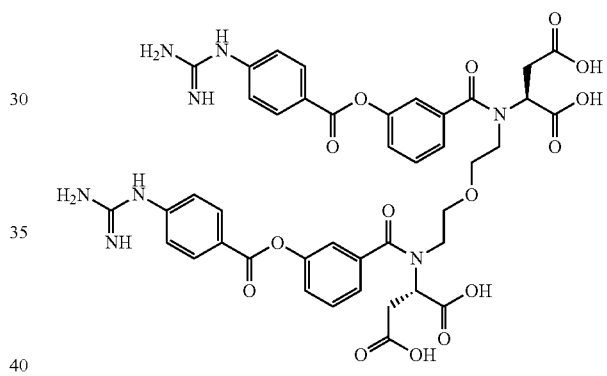

To a solution of (2S,2'S)-2,2'-((oxybis(ethane-2,1-diyl))bis((3-(4-aminobenzoyl)oxy)benzoyl)azanediyl))disuccinic acid hydrochloride (1.35 g) prepared in the Reference Example 30-(c) in tert-butanol (5.5 mL) in a 200 mL round-bottom flask were added a 4 M hydrogen chloride/cyclopentyl methyl ether solution (1.14 mL) and cyanamide (247.5 ng) at room temperature under argon gas flow with stirring, and the resulting mixture was stirred at 60° C. for 3 hours. After the reaction was completed, the reaction solution was concentrated under reduced pressure. The concentrated residues were subjected to azeotropy with toluene once, and then with acetonitrile once. The resulting residues were dissolved into acetonitrile (3.5 mL)/water (3.5 mL)/trifluoroacetic acid (70 µL), the resulting solution was subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried. The resulting residues were dissolved into acetonitrile (5.7 mL)/water (0.3 mL)/trifluoroacetic acid (60 µL), the resulting solution was subjected to medium pressure preparative chromatography (silica gel, elution solvent; aqueous solution with 0.1% trifluoroacetic acid:acetonitrile solution with 0.1% trifluoroacetic acid), and the fractions comprising the target compound were freeze-dried. The resulting residues were dissolved into water (8 mL)/acetonitrile (2 mL), and to the resulting solution was added a saturated aqueous ammonium acetate solution with stirring to adjust the pH to 4.2. Water (10 mL) was added thereto, and the resulting mixture was stirred at room temperature for 6 hours. The precipitated solids were collected by filtration, washed with water, and dried under reduced pressure. The resulting solids were preparatively isolated by high performance liquid chromatography (Column; XSelect CSH C18 OBD Prep Column (trade name, manufactured by Waters Corporation), elution solvent; aqueous solution with 0.1% formic acid acetonitrile solution with 0.1% formic acid), to the fractions comprising the target compound was added dropwise a saturated aqueous ammonium acetate solution to adjust the pH to 4.2, and the resulting mixture was freeze-dried. Then, the resulting residues were dissolved into water (8 mL)/acetonitrile (2 mL)/trifluoroacetic acid (0.1 mL), and to the resulting solution was added a saturated aqueous ammonium acetate solution with stirring to adjust the pH to 4.2. Water (5 mL) was added thereto, the resulting mixture was stirred at room temperature for 6 hours, and the resulting solids were collected by filtration. To the resulting solids were added water (8 mL)/acetonitrile (8 mL), the resulting mixture was stirred at room temperature for 6 hours, and the resulting solids were collected by filtration. To the resulting solids were added water (8 mL)/acetonitrile (8 mL), the resulting mixture was stirred at room temperature for 6 hours, the resulting solids were collected by filtration, and dried under reduced pressure to give the title compound (51.4 mg) as white solids.

Mass spectrum (ESI, m/z): 897 [M−H]⁻.

$^1$H-NMR spectrum (400 MHz, DMSO-$d_6$+$D_2O$) δ: 8.44-6.95 (m, 16H), 4.67-4.22 (m, 2H), 4.21-2.24 (m, 12H).

REFERENCE EXAMPLE

Reference Example 1-(a)

Preparation of (S)-di-tert-butyl 2-(2-nitrophenylsulfonamide)succinate

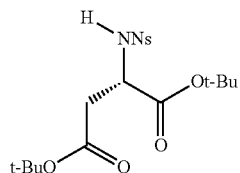

To a solution of L-aspartic acid di-tert-butyl ester hydrochloride (20 g) and N,N-diisopropylethylamine (31 mL) in dichloromethane (200 mL) in a 500 mL three-necked flask was added dividedly 2-nitrobenzenesulfonyl chloride (17.30 g) under argon atmosphere with stirring so that the internal temperature did not exceed 5° C., and the resulting mixture was stirred at room temperature for 2 hours. After the reaction was completed, the reaction solution was washed with a 5% aqueous citric acid solution (200 mL) twice, water (200 mL), and saturated brine (200 mL), dried over anhydrous magnesium sulfate, filtered, and concentrated under reduced pressure. To a solution of the concentrated residues in dichloromethane (70 mL) was added hexane (490 mL), the resulting mixture was stirred at room temperature for 10 minutes, the precipitated solids were collected by filtration, and dried under reduced pressure to give the title compound (18.19 g) as white solids.

Mass spectrum (ESI, m/z): 429 [M−H]⁻.

Reference Example 1-(b)

Preparation of (2S,2'S)-tetra-tert-butyl 2,2'-((oxybis(ethane-2,1-diyl))bis(((2-nitrophenyl)sulfonyl)azanediyl)))disuccinate

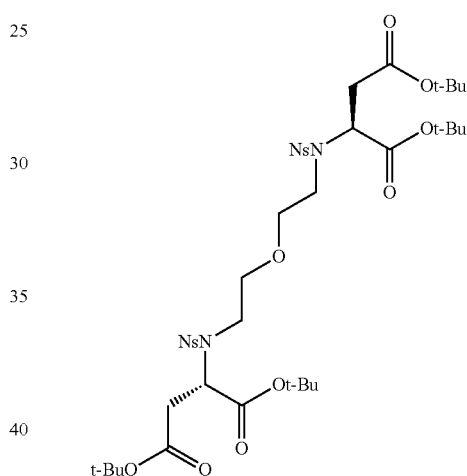

To a solution of (S)-di-tert-butyl 2-(2-nitrophenylsulfonamide)succinate (20.0 g) prepared according to the same manner as the Reference Example 1-(a), 2,2'-oxydiethanol (2.41 g), and 1,1'-azobis(N,N-dimethylformamide) (11.60 g) in tetrahydrofuran (50 mL) in a 200 mL round-bottom flask was added tributylphosphine (16.60 mL) at room temperature under argon atmosphere with stirring, and the resulting mixture was stirred at room temperature for 20 hours. After the reaction was completed, to the reaction solution was added water, and the resulting mixed solution was extracted with ethyl acetate. The resulting organic layer was washed with water, dried over anhydrous magnesium sulfate, filtered, and concentrated under reduced pressure. The resulting residues were purified by medium pressure preparative chromatography (silica gel, elution solvent; hexane:ethyl acetate) to give the title compound (16.80 g) as a pale yellow foam.

$^1$H-NMR spectrum (400 MHz, CDCl$_3$) δ: 8.16-8.05 (m, 2H), 7.75-7.65 (m, 4H), 7.64-7.57 (m, 2H), 4.97-4.90 (m, 2H), 3.73-3.53 (m, 6H), 3.32-3.21 (m, 2H), 2.98 (dd, J=7.3, 16.4 Hz, 2H), 2.71 (dd, J=6.8, 16.4 Hz, 2H), 1.46 (s, 18H), 1.31 (s, 18H).

Reference Example 1-(c)

Preparation of (2S,2'S)-tetra-tert-butyl 2,2'-((oxybis(ethane-2,1-diyl))bis(azanediyl))disuccinate

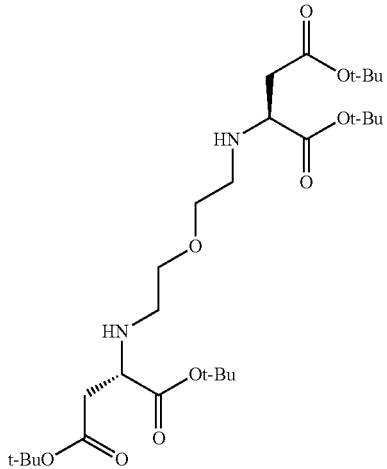 [SMILES: CC(C)(C)OC(=O)C[C@H](NCCOCCN[C@@H](CC(=O)OC(C)(C)C)C(=O)OC(C)(C)C)C(=O)OC(C)(C)C]

To a suspension of (2S,2'S)-tetra-tert-butyl 2,2'-((oxybis(ethane-2,1-diyl))bis(((2-nitrophenyl)sulfonyl)azanediyl))disuccinate (16.80 g) prepared in the Reference Example 1-(b) and potassium carbonate (7.52 g) in dimethylformamide (100 mL) in a 500 mL round-bottom flask was added 4-tert-butylthiophenol (9.10 mL) at room temperature under argon atmosphere with stirring, and the resulting mixture was stirred at room temperature for 16 hours. After the reaction was completed, to the reaction solution was added water, and the resulting mixed solution was extracted with tert-butyl methyl ether. The resulting organic layer was washed with saturated brine, dried over anhydrous magnesium sulfate, filtered, and concentrated under reduced pressure. The resulting residues were purified by medium pressure preparative chromatography (DIOL silica gel, elution solvent; hexane:ethyl acetate) to give the title compound (8.10 g) as a slightly yellow oil.

Mass spectrum (ESI, m/z): 561 [M+H]⁺.

Reference Example 1-(d)

Preparation of (2S,2'S)-tetra-tert-butyl 2,2'-((oxybis(ethane-2,1-diyl))bis((N-((benzyloxy)carbonyl)sulfamoyl)azanediyl))disuccinate

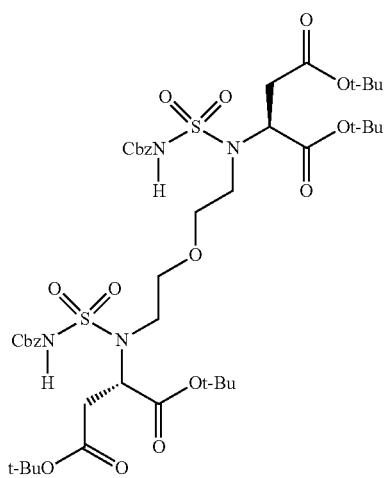 [SMILES: CC(C)(C)OC(=O)C[C@@H](C(=O)OC(C)(C)C)N(CCOCCN([C@@H](CC(=O)OC(C)(C)C)C(=O)OC(C)(C)C)S(=O)(=O)NC(=O)OCc1ccccc1)S(=O)(=O)NC(=O)OCc1ccccc1]

To a solution of chlorosulfonyl isocyanate (0.81 mL) in dichloromethane (20 mL) in a 100 mL round-bottom flask was added benzyl alcohol (0.975 ML) at 0° C. under argon atmosphere with stirring, and the resulting mixture was stirred at 0° C. for 15 minutes. Then, triethylamine (1.55 mL) and (2S,2'S)-tetra-tert-butyl 2,2'-((oxybis(ethane-2,1-diyl))bis(azanediyl))disuccinate (2.5 g) prepared in the Reference Example 1-(c) were added thereto with stirring at 0° C., and the resulting mixture was stirred at room temperature for 2 hours. After the reaction was completed, the reaction solution was concentrated under reduced pressure. To the concentrated residues was added 1N hydrochloric acid, and the resulting mixed solution was extracted with ethyl acetate. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (3.30 g) as a slightly yellow foam.

$^1$H-NMR spectrum (400 MHz, CDCl₃) δ: 8.39 (br s, 2H), 7.40-7.29 (m, 10H), 5.19 (d, J=12.2 Hz, 2H), 5.14 (d, J=12.2 Hz, 2H), 4.91-4.84 (m, 2H), 3.69-3.58 (m, 2H), 3.56-3.46 (m, 4H), 3.45-3.32 (m, 2H), 2.92 (dd, J=6.8, 16.7 Hz, 2H), 2.76 (dd, J=7.3, 16.7 Hz, 2H), 1.45 (s, 18H), 1.45 (s, 18H).

Reference Example 1-(e)

Preparation of 4-(2,3-bis(tert-butoxycarbonyl)guanidino)benzoic acid

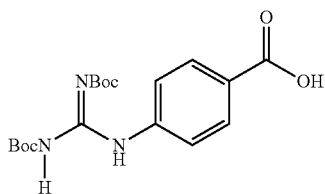

To a solution of 4-aminobenzoic acid (442 mg) and tert-butyl (((tert-butoxycarbonyl)imino) (1H-pyrazol-1-yl)methyl)carbamate (1.00 g) in methanol (10 mL) in a 100 mL round-bottom flask was added triethylamine (988 μL) at room temperature under argon atmosphere with stirring, the resulting mixture was stirred at room temperature for 173 hours, left to stand at room temperature for 38 hours, and stirred at room temperature for 9 hours. After the reaction was completed, to the reaction solution were added a 10% aqueous citric acid solution (10 mL) and methanol (10 mL), and the resulting mixture was stirred at room temperature for 15 hours. The precipitated solids were collected by filtration, and dried under reduced pressure to give the title compound (986.9 mg) as white solids.

Mass spectrum (EST, m/z) 380 [M+H]⁺.

According to the same method as the Reference Example 1-(e), Reference Example 1-(e)-2 to Reference Example 1-(e)-3 were prepared.

TABLE 1

| Reference Example No. | Compound name<br>Structural formula<br>Mass spectrum |
|---|---|
| 1-(e)-2 | 4-(2,3-bis(tert-butoxycarbonyl)guanidino)-2-fluorobenzoic acid<br>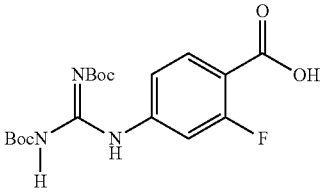<br>(ESI, m/z): 398 [M + H]⁺. |
| 1-(e)-3 | 4-(2,3-bis(tert-butoxycarbonyl)guanidino)-2-methylbenzoic acid<br>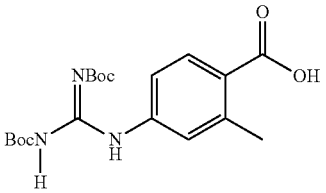<br>(ESI, m/z): 394 [M + H]⁺. |

Reference Example 1-(f)

Preparation of 4-formylphenyl 4-(2,3-bis(tert-butoxycarbonyl)guanidino)benzoate

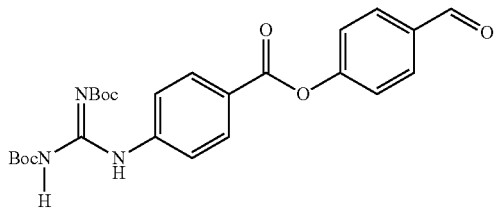

To a suspension of 4-(2,3-bis(tert-butoxycarbonyl)guanidino)benzoic acid (5.00 g) prepared according to the same manner as the Reference Example 1-(e) in dehydrated dichloromethane (50 mL) in a 200 mL round-bottom flask were added 1-(3-dimethylaminopropyl)-3-ethylcarbodiimide hydrochloride (3.80 g) and 4-dimethylaminopyridine (0.500 g) at room temperature under argon atmosphere with stirring, and the resulting mixture was stirred at room temperature for 30 minutes. Then, 4-hydroxybenzaldehyde (1.77 g) was added thereto with stirring at room temperature, and the resulting mixture was stirred at room temperature for 5.5 hours. To the reaction solution was added silica gel (50 g) (DAISOGEL IR-60-40/63-W (trade name) manufactured by Osaka Soda Co., Ltd.), the resulting mixture was stirred, and then filtered. The filtered residues were washed with dichloromethane (50 mL), and a mixed solvent of ethyl acetate (50 mL)/hexane (50 mL). The resulting filtrate was concentrated under reduced pressure to give the title compound (5.90 g) as pink solids.

Mass spectrum (ESI, m/z): 484 [M+H]⁺.

According to the same method as the Reference Example 1-(f), Reference Example 1-(f)-2 to Reference Example 1-(f)-12 were prepared.

TABLE 2

| Reference Example No. | Compound name<br>Structural formula<br>Mass spectrum |
|---|---|
| 1-(f)-2 | 4-formylphenyl 4-(2,3-bis(tert-butoxycarbonyl)guanidino)-2-fluorobenzoate<br>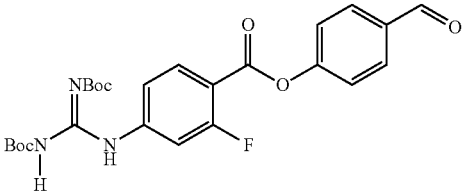<br>(ESI, m/z): 502 [M + H]⁺. |
| 1-(f)-3 | 4-formylphenyl 4-(2,3-bis(tert-butoxycarbonyl)guanidino)-2-methylbenzoate<br>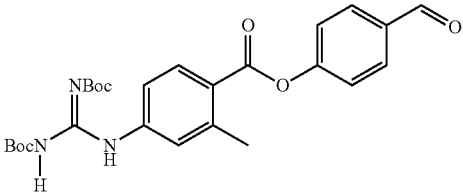<br>(ESI, m/z): 498 [M + H]⁺. |
| 1-(f)-4 | 2-fluoro-4-formylphenyl 4-(2,3-bis(tert-butoxycarbonyl)guanidino)benzoate<br>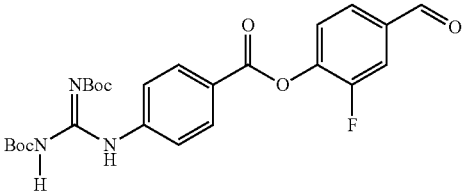<br>(ESI, m/z): 502 [M + H]⁺. |
| 1-(f)-5 | 2-chloro-4-formylphenyl 4-(2,3-bis(tert-butoxycarbonyl)guanidino)benzoate<br>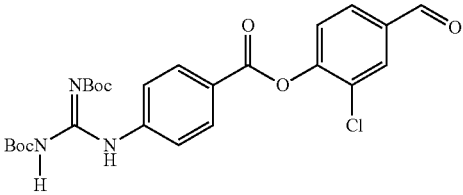<br>(ESI, m/z): 518 [M + H]⁺. |

TABLE 2-continued

| Reference Example No. | Compound name<br>Structural formula<br>Mass spectrum |
|---|---|
| 1-(f)-6 | 4-formyl-2-methoxyphenyl 4-(2,3-bis(tert-butoxycarbonyl)guanidino)benzoate<br>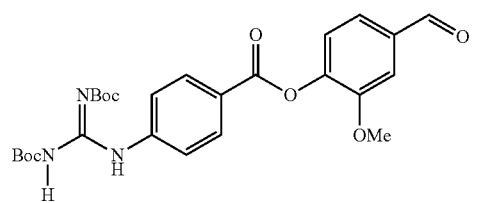<br>(ESI, m/z): 514 [M + H]⁺. |
| 1-(f)-7 | 4-formyl-2-methylphenyl 4-(2,3-bis(tert-butoxycarbonyl)guanidino)benzoate (ESI, m/z): 498 [M + H]⁺.<br>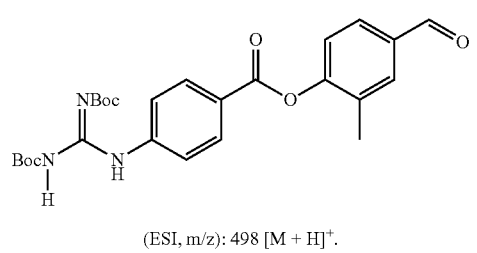<br>(ESI, m/z): 498 [M + H]⁺. |
| 1-(f)-8 | 3-fluoro-4-formylphenyl 4-(2,3-bis(tert-butoxycarbonyl)guanidino)benzoate<br>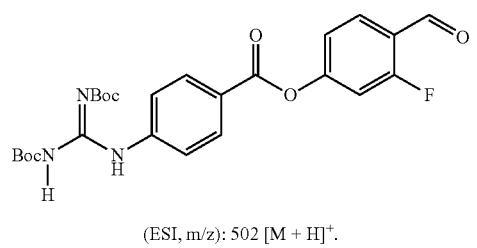<br>(ESI, m/z): 502 [M + H]⁺. |
| 1-(f)-9 | 3-chloro-4-formylphenyl 4-(2,3-bis(tert-butoxycarbonyl)guanidino)benzoate<br>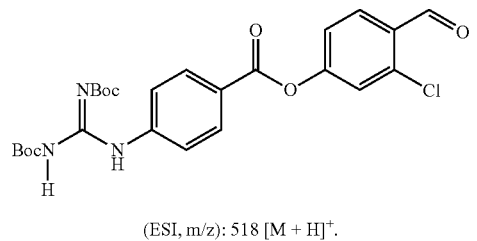<br>(ESI, m/z): 518 [M + H]⁺. |
| 1-(f)-10 | 4-formyl-3-methoxyphenyl 4-(2,3-bis(tert-butoxycarbonyl)guanidino)benzoate<br>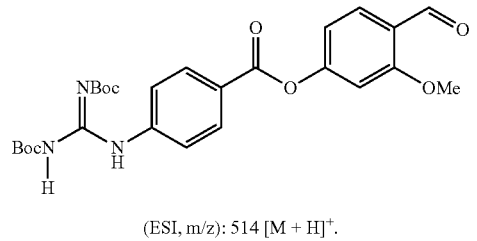<br>(ESI, m/z): 514 [M + H]⁺. |

TABLE 2-continued

| Reference Example No. | Compound name<br>Structural formula<br>Mass spectrum |
|---|---|
| 1-(f)-11 | 4-formyl-3-methylphenyl 4-(2,3-bis(tert-butoxycarbonyl)guanidino)benzoate<br>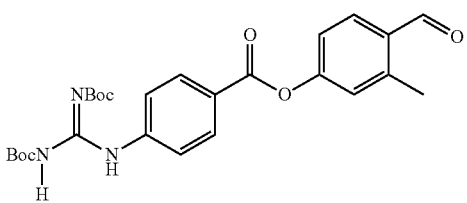<br>(ESI, m/z): 498 [M + H]⁺. |
| 1-(f)-12 | 3-formylphenyl 4-(2,3-bis(tert-butoxycarbonyl)guanidino)benzoate<br>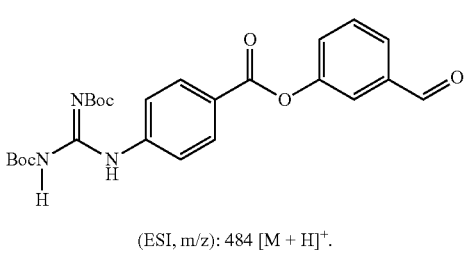<br>(ESI, m/z): 484 [M + H]⁺. |

Reference Example 1-(g)

Preparation of 4-(hydroxymethyl)phenyl 4-(2,3-bis(tert-butoxycarbonyl)guanidino)benzoate

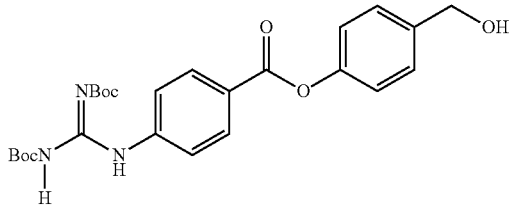

To a solution of 4-formylphenyl 4-(2,3-bis(tert-butoxycarbonyl)guanidino)benzoate (5.90 g) prepared in the Reference Example 1-(f) in dehydrated dichloromethane (60 mL) in a 500 mL round-bottom flask was added acetic acid (0.840 mL) under argon atmosphere with stirring, and then was added dividedly sodium triacetoxyborohydride (3.90 g) under ice-cooling, and the resulting mixture was stirred at room temperature for 16 hours. Then, sodium triacetoxyborohydride (3.90 g) was added dividedly thereto under ice-cooling, and the resulting mixture was stirred at room temperature for 48 hours. Then, sodium triacetoxyborohydride (1.30 g) was added dividedly thereto under ice-cooling, and the resulting mixture was stirred at room temperature for 72 hours. After the reaction was completed, to the reaction solution was added water, and the resulting mixed solution was extracted with dichloromethane. The resulting organic layer was washed with saturated brine, dried over anhydrous sodium sulfate, filtered, and concentrated under reduced pressure to give the title compound (5.36 g) as brown solids.

Mass spectrum (ESI, m/z): 486 [M+H]⁺.

The Reference Example 1-(g) was also prepared as follows.

To a solution of 4-hydroxybenzenemethanol (2.00 g, in dehydrated dimethylformamide (10 mL) in a 100 mL round-bottom flask were added tert-butylchlorodimethylsilane (2.67 g) and imidazole (2.20 g) under ice-cooling under argon atmosphere with stirring, and the resulting mixture was stirred at room temperature for 16 hours. After the reaction was completed, the reaction solution was diluted with ethyl acetate, 0.1 M hydrochloric acid was added thereto, and the resulting mixed solution was extracted with ethyl acetate.

The resulting organic layer was washed with saturated brine, dried over anhydrous sodium Sulfate, filtered, and concentrated under reduced pressure. The resulting residues were purified by medium pressure preparative chromatography (silica gel, elution solvent; hexane:ethyl acetate) to give 4-(((tert-butyldimethylsilyl)oxy)methyl)phenol (3.67 g) as a colorless oil.

To a solution of the resulting 4-(((tert-butyldimethylsilyl)oxy)methyl)phenol (1.00 g) in dehydrated dichloromethane (15 mL) in a 100 mL round-bottom flask was added 4-(2,3-bis(tert-butoxycarbonyl)guanidino)benzoic acid (1.50 g) prepared according to the same manner as the Reference Example 1-(e), 1-(3-dimethylaminopropyl)-3-ethylcarbodiimide hydrochloride (0.910 g), and 4-dimethylaminopyridine (0.145 g) at room temperature under argon atmosphere with stirring, and the resulting mixture was stirred at room temperature for 17 hours. After the reaction was completed, to the reaction solution was added water, and the resulting mixed solution was extracted with dichloromethane and ethyl acetate. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give 4-(((tert-butyldimethylsilyl)oxy)methyl)phenyl 4-(2,3-bis(tert-butoxycarbonyl)guanidino)benzoate (1.34 g) as white solids.

To a solution of the resulting 4-(((tert-butyldimethylsilyl)oxy)methyl)phenyl 4-(2,3-bis(tert-butoxycarbonyl)guanidino)benzoate (1.34 g) in dehydrated tetrahydrofuran (10 mL) in a 100 mL round-bottom flask was added tetrabutylammonium fluoride (a 1.0 M solution in tetrahydrofuran) (3.50 mL) under ice-cooling under argon atmosphere with stirring, and the resulting mixture was stirred at room temperature for 1 hour. After the reaction was completed, to the reaction solution was added water, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (silica gel, elution solvent; dichloroethane:methanol) to give the title compound (968 mg) as white solids.

Mass spectrum (ESI, m/z): 486 [M+H]⁺.

According to the same method as the Reference Example 1-(g), Reference Example 1-(g)-2 to Reference Example 1-(g)-3 were prepared.

TABLE 3

| Reference Example No. | Compound name<br>Structural formula<br>Mass spectrum |
|---|---|
| 1-(g)-2 | tert-butyl 5-((4-(2,3-bis(tert-butoxycarbonyl)guanidino)benzoyl)oxy)-2-(hydroxymethyl)benzoate<br>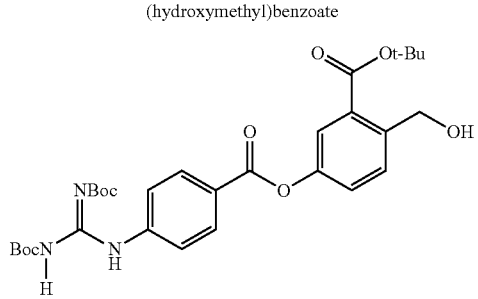<br>(ESI, m/z): 586 [M + H]⁺. |
| 1-(g)-3 | (S)-di-tert-butyl 2-(5-((4-(2,3-bis(tert-butoxycarbonyl)guanidino)benzoyl)oxy)-2-(hydroxymethyl)benzamide)succinate<br>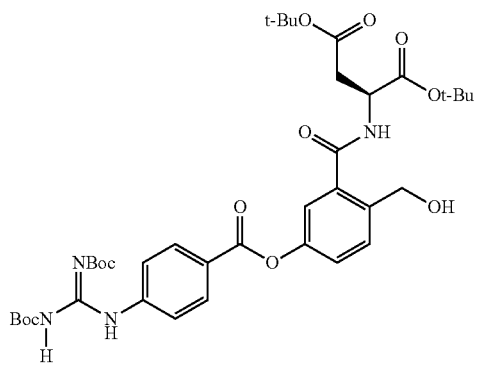<br>(ESI, m/z): 757 [M + H]⁺. |

Reference Example 1-(g)-4

Preparation of 4-(hydroxymethyl)phenyl 4-(2,3-bis(tert-butoxycarbonyl)guanidino)-2-fluorobenzoate

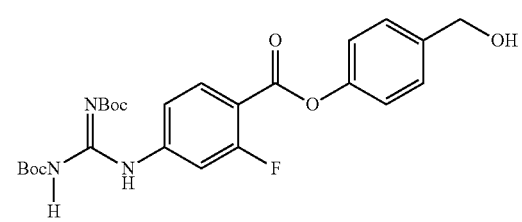

To a solution of 4-formylphenyl 4-(2,3-bis(tert-butoxycarbonyl)guanidino)-2-fluorobenzoate (3.43 g) prepared in the Reference Example 1-(f)-2 in tetrahydrofuran (35 mL) in a 200 mL four-necked flask were added sodium borohydride (385 mg) and acetic acid (468 μL) at 0° C. with stirring, and the resulting mixture was stirred at room temperature for 1 hour. After the reaction was completed, to the reaction solution was added water, and the resulting mixed solution was extracted with dichloromethane. The resulting organic layer was washed with water and saturated brine, dried over anhydrous sodium sulfate, filtered, and concentrated under reduced pressure to give the title compound (3.28 g).

Mass spectrum (ESI, m/z): 504 [M+H]$^+$.

According to the same method as the Reference Example 1-(g)-4, Reference Example 1-(g)-5 to Reference Example 1-(g)-14 were prepared.

TABLE 4

| Reference Example No. | Compound name Structural formula Mass spectrum |
|---|---|
| 1-(g)-5 | 4-(hydroxymethyl)phenyl 4-(2,3-bis(tert-butoxycarbonyl)guanidino)-2-methylbenzoate<br>(ESI, m/z): 500 [M + H]$^+$. |
| 1-(g)-6 | 2-fluoro-4-(hydroxymethyl)phenyl 4-(2,3-bis(tert-butoxycarbonyl)guanidino)benzoate<br>(ESI, m/z): 504 [M + H]$^+$. |
| 1-(g)-7 | 2-chloro-4-(hydroxymethyl)phenyl 4-(2,3-bis(tert-butoxycarbonyl)guanidino)benzoate<br>(ESI, m/z): 520 [M + H]$^+$. |
| 1-(g)-8 | 4-(hydroxymethyl)-2-methoxyphenyl 4-(2,3-bis(tert-butoxycarbonyl)guanidino)benzoate<br>(ESI, m/z): 516 [M + H]$^+$. |

TABLE 4-continued

| Reference Example No. | Compound name Structural formula Mass spectrum |
|---|---|
| 1-(g)-9 | 4-(hydroxymethyl)-2-methylphenyl 4-(2,3-bis(tert-butoxycarbonyl)guanidino)benzoate<br>(ESI, m/z): 500 [M + H]$^+$. |
| 1-(g)-10 | 3-fluoro-4-(hydroxymethyl)phenyl 4-(2,3-bis(tert-butoxycarbonyl)guanidino)benzoate<br>(ESI, m/z): 504 [M + H]$^+$. |
| 1-(g)-11 | 3-chloro-4-(hydroxymethyl)phenyl 4-(2,3-bis(tert-butoxycarbonyl)guanidino)benzoate<br>(ESI, m/z): 520 [M + H]$^+$. |
| 1-(g)-12 | 4-(hydroxymethyl)-3-methoxyphenyl 4-(2,3-bis(tert-butoxycarbonyl)guanidino)benzoate<br>(ESI, m/z): 516 [M + H]$^+$. |
| 1-(g)-13 | 4-(hydroxymethyl)-3-methylphenyl 4-(2,3-bis(tert-butoxycarbonyl)guanidino)benzoate<br>(ESI, m/z): 500 [M + H]$^+$. |

TABLE 4-continued

| Reference Example No. | Compound name Structural formula Mass spectrum |
|---|---|
| 1-(g)-14 | 3-(hydroxymethyl)phenyl 4-(2,3-bis(tert-butoxycarbonyl)guanidino)benzoate<br><br>(ESI, m/z): 486 [M + H]⁺. |

Reference Example 2-(a)

Preparation of (2S,13S)-tetra-tert-butyl 3,12-bis((2-nitrophenyl)sulfonyl)-6,9-dioxa-3,12-diazatetradecane-1,2,13,14-tetracarboxylate

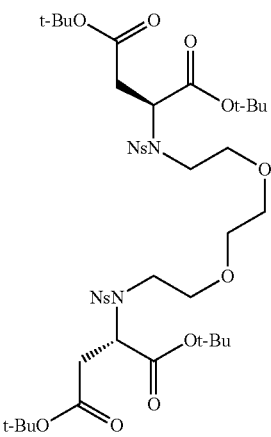

To a solution of (S)-di-tert-butyl 2-(2-nitrophenylsulfonamide)succinate (5.00 g) prepared in the Reference Example 1-(a) in dehydrated tetrahydrofuran (30 mL) in a 200 mL round-bottom flask were added triethyleneglycol (0.740 mL), tributylphosphine (3.30 mL), and 1,1'-azobis(N,N-dimethylformamide) (2.30 g) under ice-cooling under argon atmosphere with stirring, and the resulting mixture was stirred at room temperature for 20 hours. After the reaction was completed, to the reaction solution was added water, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (5.64 g) as a pale yellow oil.

Mass spectrum (ESI, m/z): 997 [M+Na]⁺.

Reference Example 2-(b)

Preparation of (2S,13S)-tetra-tert-butyl 6,9-dioxa-3,12-diazatetradecane-1,2,13,14-tetracarboxylate

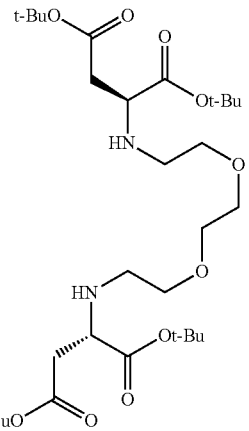

To a solution of (2S,13S)-tetra-tert-butyl 3,12-bis((2-nitrophenyl)sulfonyl)-6,9-dioxa-3,12-diazatetradecane-1,2,13,14-tetracarboxylate (5.64 g) prepared in the Reference Example 2-(a) in dehydrated dimethylformamide (20 mL) in a 300 mL round-bottom flask were added potassium carbonate (2.40 g) and 4-tert-butylthiophenol (2.45 mL) at room temperature under argon atmosphere with stirring, and the resulting mixture was stirred at room temperature for 2 hours. After the reaction was completed, to the reaction solution was added saturated aqueous sodium hydrogen carbonate solution, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (DIOL silica gel, elution solvent; hexane:ethyl acetate) to give the title compound (3.45 g) as a yellow oil.

Mass spectrum (ESI, m/z): 605 [M+H]⁺.

Reference Example 2-(c)

Preparation of (2S,13S)-tetra-tert-butyl 3,12-bis(N-((benzyloxy)carbonyl)sulfamoyl)-6,9-dioxa-3,12-diazatetradecane-1,2,13,14-tetracarboxylate

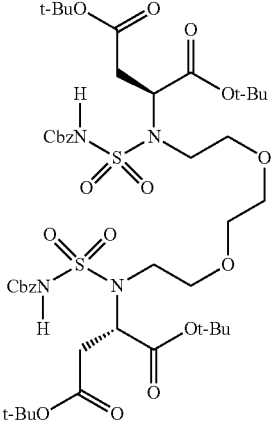 [SMILES: CC(C)(C)OC(=O)C[C@@H](C(=O)OC(C)(C)C)N(CCOCCOCCN([C@@H](CC(=O)OC(C)(C)C)C(=O)OC(C)(C)C)S(=O)(=O)NC(=O)OCc1ccccc1)S(=O)(=O)NC(=O)OCc1ccccc1]

To a solution of chlorosulfonyl isocyanate (1.20 mL) in dehydrated dichloromethane (20 mL) in a 200 mL round-bottom flask was added benzyl alcohol (1.41 mL) under ice-cooling under argon atmosphere with stirring, and the resulting mixture was stirred under ice-cooling for 30 minutes. Then, triethylamine (3.20 mL) and a solution of (2S,13S)-tetra-tert-butyl 6,9-dioxa-3,12-diazatetradecane-1,2,13,14-tetracarboxylate (3.45 g) prepared in the Reference Example 2-(b) in dehydrated dichloromethane (6 mL) were added thereto with stirring under ice-cooling, and the resulting mixture was stirred at room temperature for 1 hour. After the reaction was completed, to the reaction solution was added saturated aqueous sodium hydrogen carbonate solution, and the resulting mixed solution was extracted with dichloromethane. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (3.93 g) as a slightly yellow oil.

Mass spectrum (ESI, m/z): 1053 [M+Na]$^+$.

Reference Example 3-(a)

Preparation of (2S,16S)-tetra-tert-butyl 3,15-bis((2-nitrophenyl)sulfonyl)-6,9,12-trioxa-3,15-diazaheptadecane-1,2,16,17-tetracarboxylate

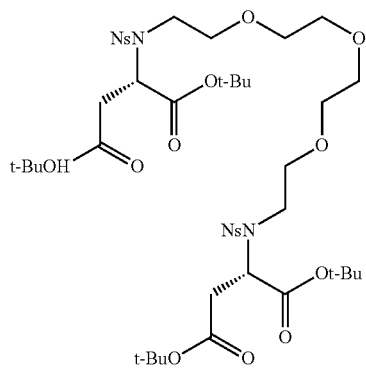

To a solution of 2,2'-((oxybis(ethane-2,1-diyl))bis(oxy)) diethanol (1.24 q), (S)-di-tert-butyl 2-(2-nitrophenylsulfonamide)succinate (5 g) prepared according to the same manner as the Reference Example 1-(a), and 1,1'-azobis(N,N-dimethylformamide) (2.60 g) in tetrahydrofuran (50 mL) in a 300 mL round-bottom flask was added tributylphosphine (3.73 mL) at room temperature under argon atmosphere with stirring, and the resulting mixture was stirred at room temperature for 15 hours. Additionally, 1,1'-azobis(N,N-dimethylformamide) (1.00 g) and tributylphosphine (1.44 mL) were added thereto at room temperature, and the resulting mixture was stirred at room temperature for 23 hours. After the reaction was completed, to the reaction solution was added water, and the resulting mixed solution was extracted with ethyl acetate. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (2.88 g) as a yellow oil.

Mass spectrum (ESI, m/z): 1036 [M+NH$_4$]$^+$.

Reference Example 3-(b)

Preparation of (2S,16S)-tetra-tert-butyl 6,9,12-trioxa-3,15-diazaheptadecane-1,2,16,17-tetracarboxylate

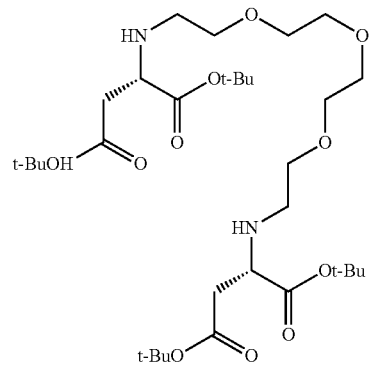

To a suspension of (2S,16S)-tetra-tert-butyl 3,15-bis((2-nitrophenyl) sulfonyl)-6,9,12-trioxa-3,15-diazaheptadecane-1,2,16,17-tetracarboxylate (2.88 g) prepared in the Reference Example 3-(a) and potassium carbonate (1.15 g) in dimethylformamide (30 mL) in a 300 mL round-bottom flask was added 4-tert-butylthiophenol (1.19 mL) at room temperature under argon atmosphere with stirring, and the resulting mixture was stirred at room temperature for 3 hours. After the reaction was completed, to the reaction solution was added water, and the resulting mixed solution was extracted with tert-butyl methyl ether. The resulting organic layer was washed with saturated brine, dried over anhydrous sodium sulfate, filtered, and concentrated under reduced pressure. The resulting residues were purified by medium pressure preparative chromatography (DIOL silica gel, elution solvent; hexane:ethyl acetate, to give the title compound (1.82 g) as a yellow oil.

Mass spectrum (ESI, m/z): 649 [M+H]$^+$.

Reference Example 3-(c)

Preparation of (2S,16S)-tetra-tert-butyl 3,15-bis(N-((benzyloxy)carbonyl)sulfamoyl)-6,9,12-trioxa-3,15-diazaheptadecane-1,2,16,17-tetracarboxylate

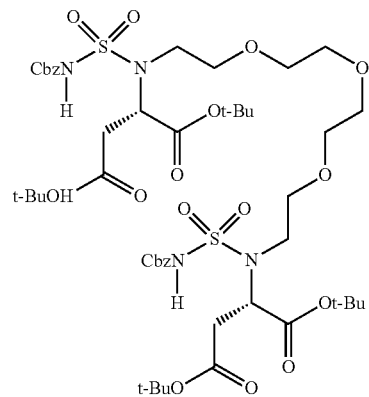

To a solution of chlorosulfonyl isocyanate (605 µL) in dichloromethane (20 mL) in a 100 mL round-bottom flask was added benzyl alcohol (722 µL) at 0° C. under argon atmosphere with stirring, and the resulting mixture was stirred at 0° C. for 30 minutes. Then, triethylamine (1.56 mL) and a solution of (2S,16S)-tetra-tert-butyl 6,9,12-trioxa-3,15-diazaheptadecane-1,2,16,17-tetracarboxylate (1.82 g) prepared in the Reference Example 3-(b) in dichloromethane (20 mL) was added thereto with stirring at 0° C., and the resulting mixture was stirred at room temperature for 1 hour. After the reaction was completed, to the reaction solution was added a saturated aqueous ammonium chloride solution, and the resulting mixed solution was extracted with dichloromethane. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (710 mg) as a slightly yellow oil.

Mass spectrum (ESI, m/z): 1097 [M+Na]+.

Reference Example 4-(a)

Preparation of (2S,19S)-tetra-tert-butyl 3,18-bis((2-nitrophenyl)sulfonyl)-6,9,12,15-tetraoxa-3,18-diazaicosane-1,2,19,20-tetracarboxylate

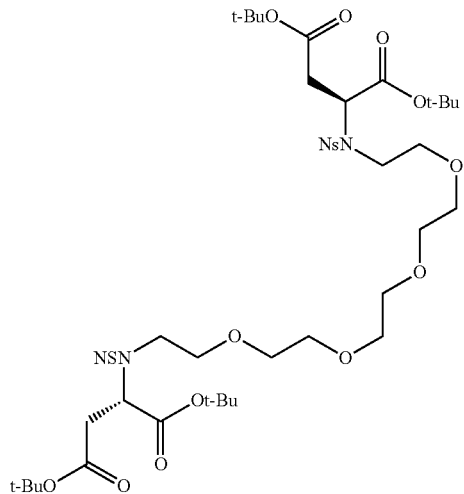

To a solution of 1,1'-azobis(N,N-dimethylformamide) (0.80 g), 3,6,9,12-tetraoxatetradecane-1,14-diol (0.45 mL), and (S)-di-tert-butyl 2-(2-nitrophenylsulfonamide)succinate (2.01 g) prepared according to the same manner as the Reference Example 1-(a) in tetrahydrofuran (20 mL) in a 100 mL round-bottom flask was added tributylphosphine (1.15 mL) at room temperature under argon gas flow with stirring, and the resulting mixture was stirred at room temperature for 16 hours. After the reaction was completed, the reaction solution was concentrated under reduced pressure. The resulting residues were purified by medium pressure preparative chromatography (silica gel, elution solvent; hexane:ethyl acetate) to give the title compound (1.56 g) as a white foam.

Mass spectrum (ESI, m/z): 1085 [M+Na]+.

Reference Example 4-(b)

Preparation of (2S,19S)-tetra-tert-butyl 6,9,12,15-tetraoxa-3,18-diazaicosane-1,2,19,20-tetracarboxylate

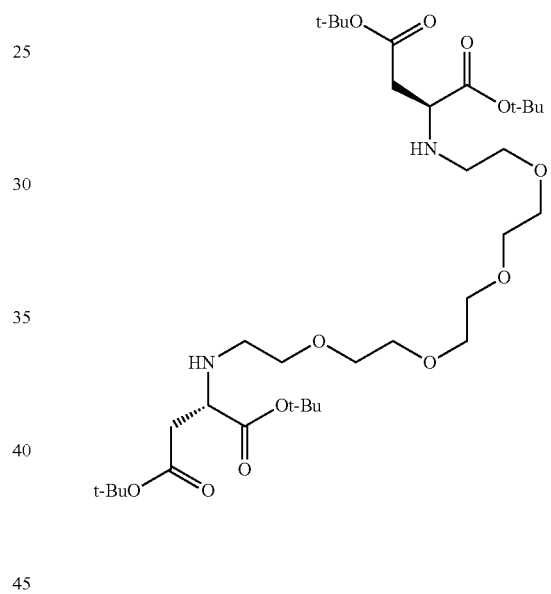

To a solution of (2S,19S)-tetra-tert-butyl 3,18-bis((2-nitrophenyl)sulfonyl)-6,9,12,15-tetraoxa-3,18-diazaicosane-1,2,19,20-tetracarboxylate (1.56 g) prepared in the Reference Example 4-(a) in dimethylformamide (20 mL) in a 102 mL round-bottom flask were added potassium carbonate (0.62 g) and 4-tert-butylthiophenol (0.620 mL) at room temperature under argon atmosphere with stirring, and the resulting mixture was stirred at room temperature for 24 hours. After the reaction was completed, to the reaction solution was added saturated aqueous sodium hydrogen carbonate solution, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (DIOL silica gel, elution solvent; hexane:ethyl acetate) to give the title compound (0.93 g) as a colorless oil.

Mass spectrum (EST, m/z): 693 [M+H]+.

Reference Example 4-(c)

Preparation of (2S,19S)-tetra-tert-butyl 3,18-bis(N-((benzyloxy)carbonyl)sulfamoyl)-6,9,12,15-tetraoxa-3,1-diazaicosane-1,2,19,20-tetracarboxylate

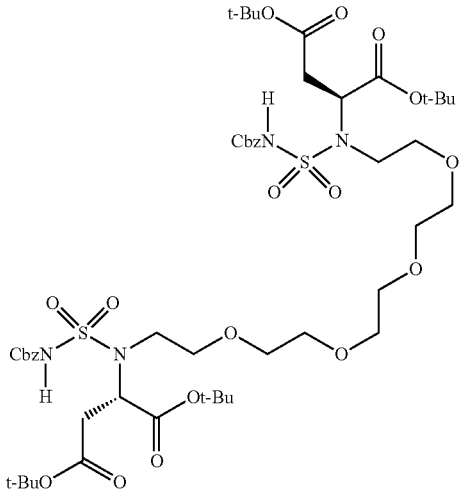 [SMILES: CC(C)(C)OC(=O)C[C@@H](C(=O)OC(C)(C)C)N(CCOCCOCCOCCOCCN([C@@H](CC(=O)OC(C)(C)C)C(=O)OC(C)(C)C)S(=O)(=O)NC(=O)OCc1ccccc1)S(=O)(=O)NC(=O)OCc1ccccc1]

To a solution of chlorosulfonyl isocyanate (0.290 mL) in dichloromethane (10 mL) in a 100 mL round-bottom flask was added benzyl alcohol (0.350 mL) at 0° C. under argon atmosphere with stirring, and the resulting mixture was stirred at 0° C. for 30 minutes. Then, triethylamine (0.560 mL) and a solution of (2S,19S)-tetra-tert-butyl 6,9,12,15-tetraoxa-3,18-diazaicosane-1,2,19,20-tetracarboxylate (0.93 g) prepared in the Reference Example 4-(b) in dichloromethane (10 mL) were added thereto with stirring at 0° C., and the resulting mixture was stirred at room temperature for 4 hours. After the reaction was completed, to the reaction solution was added saturated aqueous sodium hydrogen carbonate solution, and the resulting mixed solution was extracted with ethyl acetate. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (680 mg) as a colorless oil.

Mass spectrum (ESI, m/z): 1141 [M+Na]$^+$.

Reference Example 5-(a)

Preparation of (2S,22S)-tetra-tert-butyl 3,21-bis((2-nitrophenyl)sulfonyl)-6,9,12,15,18-pentaoxa-3,21-diazatricosane-1,2,22,23-tetracarboxylate

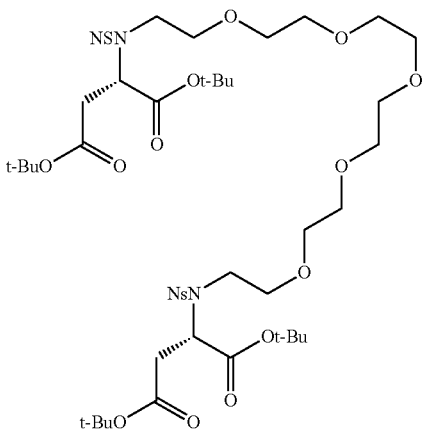

To a solution of (S)-di-tert-butyl 2-(2-nitrophenylsulfonamide)succinate (3.01 g) prepared according to the same manner as the Reference Example 1-(a), 3,6,9,12,15-pentaoxaheptadecane-1,17-diol (0.830 mL), and 1,1'-azobis(N,N-dimethylformamide) (1.44 g) in tetrahydrofuran (30 mL) in a 100 mL round-bottom flask was added tributylphosphine (2.10 mL) at room temperature under argon atmosphere with stirring, and the resulting mixture was stirred at room temperature for 4 hours. Additionally, 1,1'-azobis(N,N-dimethylformamide) (1.44 g) and tributylphosphine (2.10 mL) were aided thereto three times every hour. After the reaction was completed, the precipitated solids were filtered, washed with tert-butyl methyl ether, and the resulting filtrate was concentrated under reduced pressure. The resulting residues were purified by medium pressure preparative chromatography (silica gel, elution solvent; hexane:ethyl acetate) to give the title compound (1.30 g) as orange solids.

$^1$H-NMR spectrum (400 MHz, CDCl$_3$) δ: 8.14-8.07 (m, 2H), 7.72-7.66 (m, 4H), 7.63-7.57 (m, 2H), 4.97-4.39 (m, 2H), 3.77-3.53 (m, 22H), 3.35-3.23 (m, 2H), 3.02 (dd, J=7.7, 16.5 Hz, 2H), 2.74 (dd, J=6.5, 16.5 Hz, 2H), 1.46 (s, 18H), 1.30 (s, 18H).

Reference Example 5-(b)

Preparation of (2S,22S)-tetra-tert-butyl 6,9,12,15,18-pentaoxa-3,21-diazatricosane-1,2,22,23-tetracarboxylate

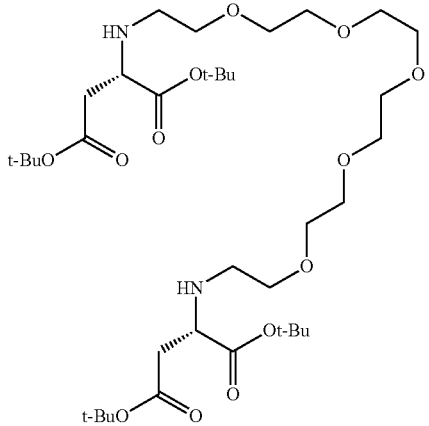 [SMILES: CC(C)(C)OC(=O)C[C@H](NCCOCCOCCOCCOCCOCCN[C@@H](CC(=O)OC(C)(C)C)C(=O)OC(C)(C)C)C(=O)OC(C)(C)C]

To a suspension of (2S,22S)-tetra-tert-butyl 3,21-bis((2-nitrophenyl)sulfonyl)-6,9,12,15,18-pentaoxa-3,21-diazatricosane-1,2,22,23-tetracarboxylate (1.30 g) prepared in the Reference Example 5-(a) and potassium carbonate (492 mg) in dimethylformamide (15 mL) in a 100 mL round-bottom flask was added 4-tert-butylthiophenol (0.500 mL) at room temperature under argon atmosphere with stirring, and the resulting mixture was stirred at room temperature for 3 hours. Additionally, 4-tert-butylthiophenol (0.500 mL) was added thereto, and the resulting mixture was stirred at room temperature for 2 hours. After the reaction was completed, to the reaction solution was added water, and the resulting mixed solution was extracted with tert-butyl methyl ether. The resulting organic layer was washed with saturated brine, dried over anhydrous magnesium sulfate, filtered, and concentrated under reduced pressure. The resulting residues were purified by medium pressure preparative chromatography (DIOL silica gel, elution solvent; dichloroethane:methanol) to give the title compound (310 mg) as a slightly yellow oil.

Mass spectrum (ESI, m/z): 759 [M+Na]$^+$.

Reference Example 5-(c)

Preparation of (2S,22S)-tetra-tert-butyl 3,21-bis(N-((benzyloxy)carbonyl)sulfamoyl)-6,9,12,15,18-pentaoxa-3,21-diazatricosane-1,2,22,23-tetracarboxylate

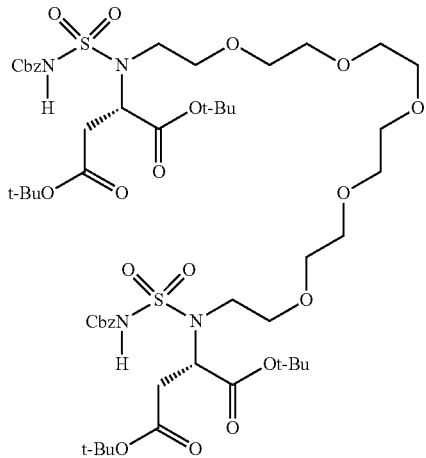 [SMILES: CC(C)(C)OC(=O)C[C@@H](C(=O)OC(C)(C)C)N(CCOCCOCCOCCOCCOCCN([C@@H](CC(=O)OC(C)(C)C)C(=O)OC(C)(C)C)S(=O)(=O)NC(=O)OCc1ccccc1)S(=O)(=O)NC(=O)OCc1ccccc1]

To a solution of chlorosulfonyl isocyanate (0.195 mL) in dichloromethane (10 mL) in a 100 mL round-bottom flask was added benzyl alcohol (0.110 mL) at 0° C. under argon atmosphere with stirring, and the resulting mixture was stirred at 0° C. for 10 minutes. Then, triethylamine (0.10 mL) and (2S,22S)-tetra-tert-butyl 6,9,12,15,18-pentaoxa-3,21-diazatricosane-1,2,22,23-tetracarboxylate (310 mg) prepared in the Reference Example 5-(b) were added thereto with stirring at 0° C., and the resulting mixture was stirred at room temperature for hour. After the reaction was completed, to the reaction solution was added saturated aqueous sodium hydrogen carbonate solution, and the resulting mixed solution was extracted with dichloromethane. The resulting organic layer was washed with saturated brine, dried over anhydrous magnesium sulfate, filtered, and concentrated under reduced pressure. The resulting residues were purified by medium pressure preparation chromatography (silica gel, elution solvent; dichloroethane:methanol) co give the title compound (443 mg) as a slightly yellow foam, Mass spectrum (ESI, m/Z): 1185 [M-Na]$^+$.

Reference Example 6-(a)

Preparation of (2S,25S)-tetra-tert-butyl 3,24-bis((2-nitrophenyl)sulfonyl)-6,9,12,15,18,21-hexaoxa-3,24-diazahexacosane-1,2,25,26-tetracarboxylate

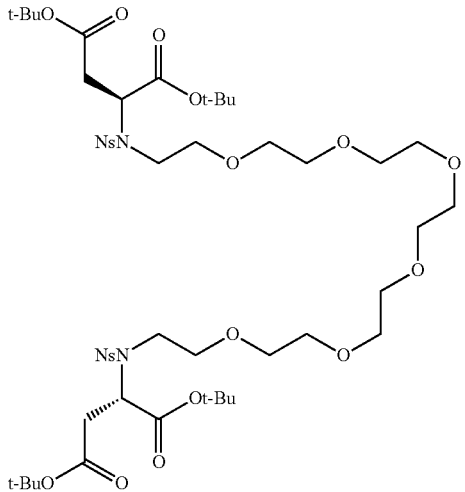

To a solution of 3,6,9,12,15,18-hexaoxaicosane-1,20-diol (1.89 g), (S)-di-tert-butyl 2-(2-nitrophenylsulfonamide)succinate (4.94 g) prepared according to the same manner as the Reference Example 1-(a), and 1,1'-azobis(N,N-dimethylformamide) (2.57 g) in tetrahydrofuran (50 mL) in a 300 mL round-bottom flask was added tributylphosphine (3.70 mL) at room temperature under argon atmosphere with stirring, and the resulting mixture was stirred at room temperature for 30 hours. After the reaction was completed, to the reaction solution was added water, and the resulting mixed solution was extracted with ethyl acetate. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (5.52 g) as a yellow oil.

Mass spectrum (ESI, m/z): 1173 [M+Na]$^+$.

Reference Example 6-(b)

Preparation of (2S,25S)-tetra-tert-butyl 6,9,12,15,18,21-hexaoxa-3,24-diazahexacosane-1,2,25,26-tetracarboxylate

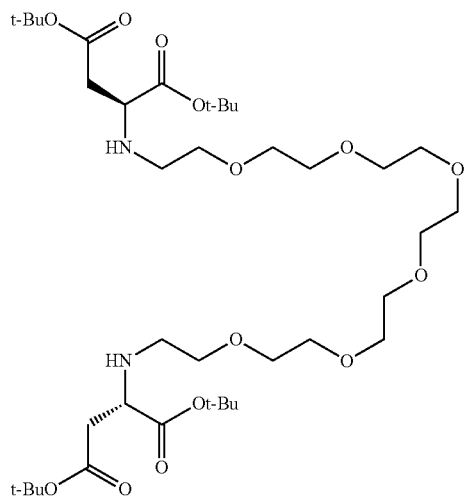 [SMILES: CC(C)(C)OC(=O)C[C@H](NCCOCCOCCOCCOCCOCCOCCN[C@@H](CC(=O)OC(C)(C)C)C(=O)OC(C)(C)C)C(=O)OC(C)(C)C]

To a solution of (2S,25S)-tetra-tert-butyl 3,24-bis((2-nitrophenyl)sulfonyl)-6,9,12,15,18,21-hexaoxa-3,24-diazahexacosane-1,2,25,26-tetracarboxylate (5.52 g) prepared in the Reference Example 6-(a) in dimethylformamide (50 mL) in a 300 mL round-bottom flask were added potassium carbonate (3.98 g) and 4-tert-butylthiophenol (3.22 mL) at room temperature under argon atmosphere with stirring, and the resulting mixture was stirred at room temperature for 2 hours. After the reaction was completed, to the reaction solution was added water, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (DIOL silica gel, elution solvent; hexane:ethyl acetate) to give the title compound (2.98 g) as a slightly yellow oil.

Mass spectrum (ESI, m/z): 782 [M+H]$^+$.

Reference Example 6-(c)

Preparation of (2S,25S)-tetra-tert-butyl 3,24-bis(N-((benzyloxy)carbonyl)sulfamoyl)-6,9,12,15,18,21-hexaoxa-3,24-diazahexacosane-1,2,25,26-tetracarboxylate

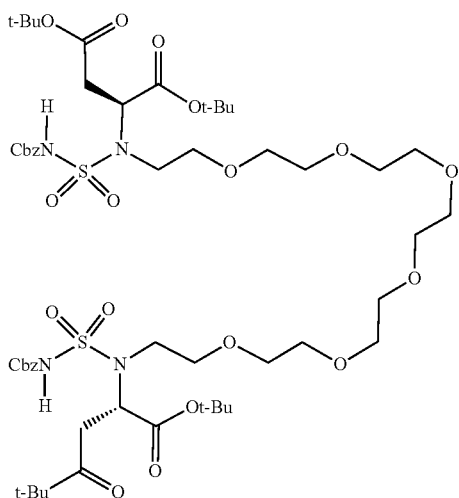 [SMILES: CC(C)(C)OC(=O)C[C@@H](C(=O)OC(C)(C)C)N(CCOCCOCCOCCOCCOCCOCCN([C@@H](CC(=O)C(C)(C)C)C(=O)OC(C)(C)C)S(=O)(=O)NC(=O)OCc1ccccc1)S(=O)(=O)NC(=O)OCc1ccccc1]

To a solution of chlorosulfonyl isocyanate (823 μL) in dichloromethane (30 mL) in a 200 mL round-bottom flask was added benzyl alcohol (982 μL) at 0° C. under argon atmosphere with stirring, and the resulting mixture was stirred at 0° C. for 30 minutes. Then, triethylamine (2.13 mL) and a solution of (2S,25S)-tetra-tert-butyl 6,9,12,15,18,21-hexaoxa-3,24-diazahexacosane-1,2,25,26-tetracarboxylate (2.98 g) prepared in the Reference Example 6-(b) in dichloromethane (30 mL) were added thereto with stirring at 0° C., and the resulting mixture was stirred at room temperature for 2 hours. After the reaction was completed, to the reaction solution was added saturated aqueous sodium hydrogen carbonate solution, and the resulting mixed solution was extracted with dichloromethane. The resulting organic layer was washed with saturated brine, dried over anhydrous magnesium sulfate, filtered, and concentrated under reduced pressure. The resulting residues were subjected to medium pressure preparative chromatography (silica gel, elution solvent; dichloroethane:methanol), and the fractions comprising the target compound were concentrated under reduced pressure. The resulting residues were purified by medium pressure preparative chromatography (silica gel, elution solvent; dichloroethane:ethyl acetate) to give the title compound (3.60 g) as a colorless oil.

Mass spectrum (ESI, m/z): 1230 [M+Na]+.

Reference Example 7-(a)

Preparation of (2S,2'S)-tetra-tert-butyl 2,2'-(propane-1,3-diylbis(((2-nitrophenyl)sulfonyl)azanediyl))disuccinate

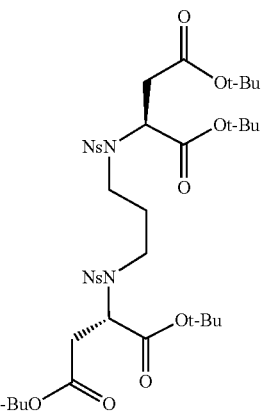

To a solution of (S)-di-tert-butyl 2-(2-nitrophenylsulfonamide)succinate (1.90 g) prepared according to the same manner as the Reference Example 1-(a) in dehydrated tetrahydrofuran (20 m-) in a 200 mL round-bottom flask were added triethyleneglycol (0.15 mL), tributylphosphine (1.25 mL), and 1,1'-azobis(N,N-dimethylformamide) (870 mg) under ice-cooling under argon atmosphere with stirring, and the resulting mixture was stirred at room temperature for 16 hours. After the reaction was completed, to the reaction solution was added water, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (1.86 g) as a white foam.

Mass spectrum (ESI, m/z) 923 [M+Na]+.

Reference Example 7-(b)

Preparation of (2S,2'3)-tetra-tert-butyl 2,2'-(propane-1,3-diylbis(azanediyl)disuccinate

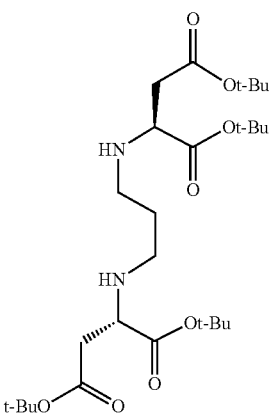 [SMILES: CC(C)(C)OC(=O)C[C@H](NCCCN[C@@H](CC(=O)OC(C)(C)C)C(=O)OC(C)(C)C)C(=O)OC(C)(C)C]

To a solution of (2S,2'S)-tetra-tert-butyl 2,2'-(propane-1,3-diylbis(((2-nitrophenyl)sulfonyl)azanediyl))disuccinate (2.04 g) prepared according to the same manner as the Reference Example 7-(a) in dehydrated dimethylformamide (20 mL) in a 100 mL round-bottom flask were added potassium carbonate (940 mg) and 4-tert-butylthiophenol (0.95 mL) at room temperature under argon atmosphere with stirring, and the resulting mixture was stirred at room temperature for 5 hours. After the reaction was completed, to the reaction solution was added saturated aqueous sodium hydrogen carbonate solution, and the resulting mixed solution was extracted with tert-butyl methyl ether. The resulting organic layer was washed with saturated brine, dried over anhydrous sodium sulfate, filtered, and concentrated under reduced pressure. The resulting residues were purified by medium pressure preparative chromatography (DIOL silica gel, elution solvent; hexane:ethyl acetate) to give the title compound (1.10 g) as a slightly yellow oil.

Mass spectrum (ESI, m/z): 531 [M+H]$^+$.

Reference Example 7-(c)

Preparation of (2S,2'S)-tetra-tert-butyl 2,2'-(propane-1,3-diylbis((N-((benzyloxy)carbonyl)sulfamoyl)azanediyl))disuccinate

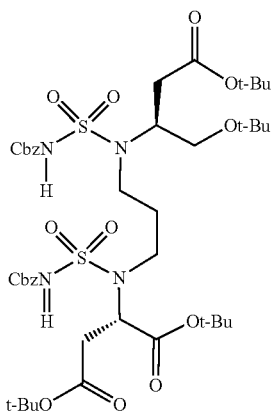

To a solution of chlorosulfonyl isocyanate (0.430 mL) in dehydrated dichloromethane (10 mL) in a 100 mL round-bottom flask was added benzyl alcohol (0.515 mL) under ice-cooling under argon atmosphere with stirring, and the resulting mixture was stirred under ice-cooling for 30 minutes. Then, triethylamine (1.20 mL) and a solution of (2S,2'S)-tetra-tert-butyl 2,2'-(propane-1,3-diylbis(azanediyl))disuccinate (1.10 g) prepared in the Reference Example 7-(b) in dehydrated dichloromethane (10 mL) were added thereto with stirring under ice-cooling, and the resulting mixture was stirred at room temperature for 16 hours. After the reaction was completed, to the reaction solution was added saturated aqueous sodium hydrogen carbonate solution, and the resulting mixed solution was extracted with dichloromethane. The resulting organic layer was washed with saturated brine, dried over anhydrous magnesium sulfate, filtered, and concentrated under reduced pressure. The resulting residues were purified by medium pressure preparative chromatography (silica gel, elution solvent; dichloroethane:ethyl acetate) to give the title compound (2.10 g) as a slightly yellow oil.

Mass spectrum (ESI, m/z): 979 [M+Na]$^+$.

Reference Example 8-(a)

Preparation of (2S,2'S)-tetra-tert-butyl 2,2'-(butane-1,4-diylbis(((2-nitrophenyl)sulfonyl)azanediyl))disuccinate

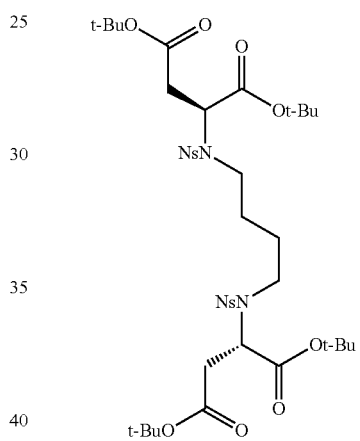

To a solution of (S)-di-tert-butyl 2-(2-nitrophenylsulfonamide)succinate (7.50 g) prepared according to the same manner as the Reference Example 1-(a) in dehydrated tetrahydrofuran (50 ml) in a 200 mL round-bottom flask were added butane-1,4-diol (0.750 mL), tributylphosphine (5.15 mL), and 1,1'-azobis(N, N-dimethylformamide) (3.60 g) under ice-cooling under argon atmosphere with stirring, and the resulting mixture was stirred at room temperature for 16 hours. Additionally, butane-1,4-diol (1.15 mL), tributylphosphine (7.20 mL), and 1,1'-azobis(N,N-dimethylformamide) (5.00 g) were added thereto at room temperature, and the resulting mixture was stirred at room temperature for 16 hours. After the reaction was completed, to the reaction solution was added water, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (2.70 g) as an orange oil.

Mass spectrum (ESI, m/z): 932 [M+NH$_4$]$^+$.

Reference Example 8-(b)

Preparation of (2S,2'S)-tetra-tert-butyl 2,2'-(butane-1,4-diylbis(azanediyl))disuccinate

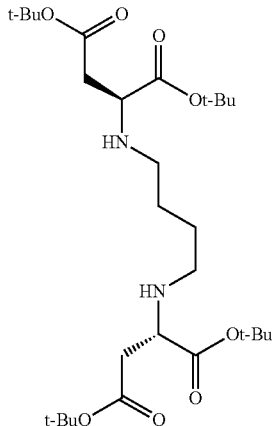 [SMILES: CC(C)(C)OC(=O)C[C@H](NCCCCN[C@@H](CC(=O)OC(C)(C)C)C(=O)OC(C)(C)C)C(=O)OC(C)(C)C]

To a solution of (2S,2'S)-tetra-tert-butyl 2,2'-(butane-1,4-diylbis(((2-nitrophenyl)sulfonyl)azanediyl))disuccinate (3.26 g) prepared according to the same manner as the Reference Example 8-(a) in dehydrated dimethylformamide (20 mL) in a 200 mL round-bottom flask were added potassium carbonate (1.50 g) and 4-tert-butylthiophenol (1.50 mL) at room temperature under argon atmosphere with stirring, and the resulting mixture was stirred at room temperature for 16 hours. After the reaction was completed, to the reaction solution was added saturated aqueous sodium hydrogen carbonate solution, and the resulting mixed solution was extracted with tert-butyl methyl ether. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (1.56 g) as a slightly yellow oil.

Mass spectrum (ESI, m/z): 545 [M+H]$^+$.

Reference Example 8-(c)

Preparation of (2S,2'S)-tetra-tert-butyl 2,2'-(butane-1,4-diylbis((N-((benzyloxy)carbonyl)sulfamoyl)azanediyl))disuccinate

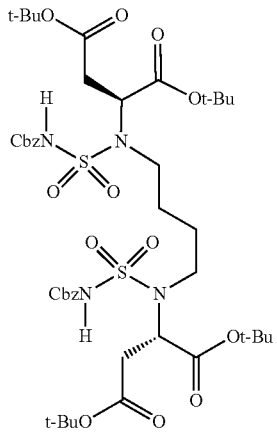 [SMILES: CC(C)(C)OC(=O)C[C@@H](C(=O)OC(C)(C)C)N(CCCCN([C@@H](CC(=O)OC(C)(C)C)C(=O)OC(C)(C)C)S(=O)(=O)NC(=O)OCc1ccccc1)S(=O)(=O)NC(=O)OCc1ccccc1]

To a solution of chlorosulfonyl isocyanate (0.600 mL) in dehydrated dichloromethane (10 mL) in a 100 mL round-bottom flask was added benzyl alcohol (0.710 mL) under ice-cooling under argon atmosphere with stirring, and the resulting mixture was stirred under ice-cooling for 30 minutes. Then, triethylamine (1.60 mL) and a solution of (2S,2'S)-tetra-tert-butyl 2,2'-(butane-1,4-diylbis(azanediyl))disuccinate (1.56 g) prepared in the Reference Example 8-(b) in dehydrated dichloromethane (10 mL) were added thereto with stirring under ice-cooling, and the resulting mixture was stirred at room temperature for 16 hours. After the reaction was completed, to the reaction solution was added saturated aqueous sodium hydrogen carbonate solution, and the resulting mixed solution was extracted with dichloromethane. The resulting organic layer was washed with saturated brine, dried ever anhydrous magnesium sulfate, filtered, and concentrated under reduced pressure. The resulting residues were purified by medium pressure preparative chromatography (silica gel, elution solvent; dichloroethane:ethyl acetate) to give the title compound (2.74 g) as a colorless oil.

Mass spectrum (ESI, m/z): 988 [M+NH$_4$]$^+$.

Reference Example 9-(a)

Preparation of (2S,2'S)-tetra-tert-butyl 2,2'-(pentane-1,5-diylbis(((2-nitrophenyl)sulfonyl)azanediyl))disuccinate

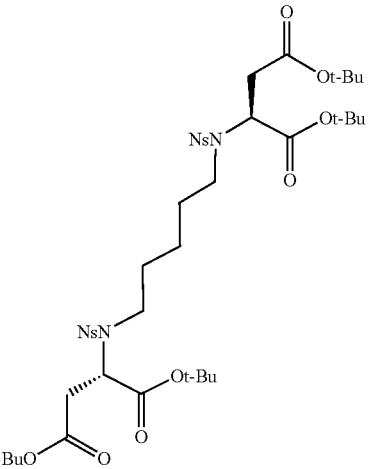

To a solution of (S)-di-tert-butyl 2-(2-nitrophenylsulfonamide)succinate (2.03 g) prepared according to the same manner as the Reference Example 1-(a) in tetrahydrofuran (15 mL) in a 100 mL round-bottom flask were added pentane-1,5-diol (0.235 mL), tributylphosphine (1.32 mL), and 1,1'-azobis(N,N-dimethylformamide) (0.917 g) under ice-cooling under argon atmosphere with stirring, and the resulting mixture was stirred at room temperature for 21.5 hours. Additionally, tributylphosphine (1.32 mL) and 1,1'-azobis(N,N-dimethylformamide) (0.915 g) were added thereto with stirring at room temperature, and the resulting mixture was stirred at room temperature for 6 hours. After the reaction was completed, to the reaction solution was added water, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (881.4 mg) as a pale yellow oil.

Mass spectrum (ESI, m/z): 927 [M−H]$^-$.

Reference Example 9-(b)

Preparation of (2S,2'S)-tetra-tert-butyl 2,2'-(pentane-1,5-diylbis(azanediyl))disuccinate

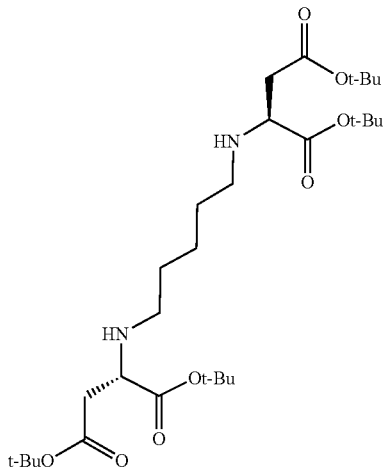 [SMILES: CC(C)(C)OC(=O)C[C@H](NCCCCCN[C@@H](CC(=O)OC(C)(C)C)C(=O)OC(C)(C)C)C(=O)OC(C)(C)C]

To a solution of (2S,2'S)-tetra-tert-butyl 2,2'-(pentane-1,5-diylbis((2-nitrophenyl)sulfonyl)azanediyl))disuccinate (681 mg) prepared in the Reference Example 9-(a) in dimethylformamide (3 mL) in a 30 mL cylindrical flask were added potassium carbonate (393 mg) and 4-tert-butylthiophenol (0.394 mL) at room temperature under argon atmosphere with stirring, and the resulting mixture was stirred at room temperature overnight. After the reaction was completed, to the reaction solution was added water, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (443.0 mg) as a pale yellow oil.

Mass spectrum (ESI, n/z) δ59 [M+H]$^+$.

Reference Example 9-(c)

Preparation of (2S,2'S)-tetra-tert-butyl 2,2'-(pentane-1,5-diylbis((N-((benzyloxy)carbonyl)sulfamoyl)azanediyl))disuccinate

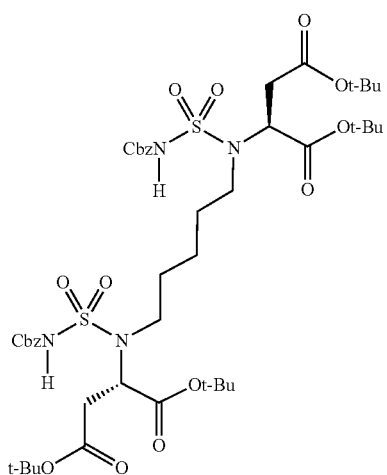 [SMILES: CC(C)(C)OC(=O)C[C@@H](C(=O)OC(C)(C)C)N(CCCCCN([C@@H](CC(=O)OC(C)(C)C)C(=O)OC(C)(C)C)S(=O)(=O)NC(=O)OCc1ccccc1)S(=O)(=O)NC(=O)OCc1ccccc1]

To a solution of chlorosulfonyl isocyanate (0.165 mL) in dichloromethane (10 mL) in a 100 mL round-bottom flask was added benzyl alcohol (0.200 mL) at 0° C. under argon atmosphere with stirring, and the resulting mixture was stirred at 0° C. for 1 hour. Then, triethylamine (0.445 mL) and a solution of (2S,2'S)-tetra-tert-butyl 2,2'-(pentane-1,5-diylbis(azanediyl))disuccinate (443 mg) prepared in the Reference Example 9-(b) in dichloromethane (6 mL) were added thereto with stirring at 0° C., and the resulting mixture was stirred at room temperature for 1 hour. After the reaction was completed, to the reaction solution was added saturated aqueous sodium hydrogen carbonate solution, and the resulting mixed solution was extracted with dichloromethane. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate, and then ethyl acetate:methanol) to give the title compound (505.3 mg) as a pale yellow oil.

Mass spectrum (ESI, m/z): 983 [M−H]$^-$.

Reference Example 10-(a)

Preparation of 4-((4-(2,3-bis(tert-butoxycarbonyl)guanidino)benzoyl)oxy)benzyl 1H-imidazole-1-carboxylate

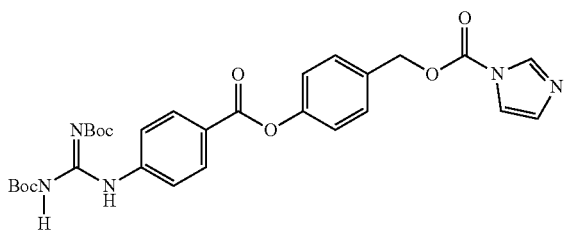

To a solution of 4-(hydroxymethyl)phenyl 4-(2,3-bis(tert-butoxycarbonyl)guanidino)benzoate (904.2 mg) prepared according to the same manner as the Reference Example 1-(g) in dichloromethane (9 mL) in a 100 mL round-bottom flask were added 1,1'-carbonyldiimidazole (3749 mg) and 4-dimethylaminopyridine (51.7 mg) at room temperature under argon atmosphere with stirring, and the resulting mixture was stirred at room temperature for 1 hour. After the reaction was completed, to the reaction solution was added water, and the resulting mixed solution was extracted with dichloromethane. The resulting organic layer was washed with a 5% aqueous sodium hydrogen sulfite solution and saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (1.0039 g) as white solids.

Mass spectrum (ESI, m/): 580 [M+H]$^+$.

Reference Example 10-(b)

Preparation of 1-(((4-((4-(2,3-bis(tert-butoxycarbonyl)guanidino)benzoyl)oxy)benzyl)oxy)carbonyl)-3-methyl-1H-imidazol-3-ium trifluoromethanesulfonate

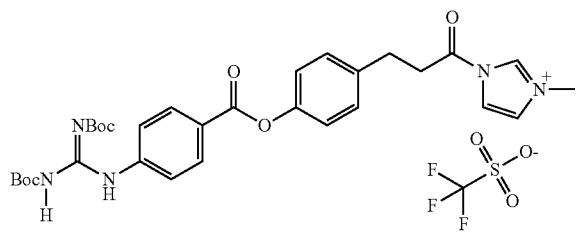

To a solution of 4-((4-(2,3-bis(tert-butoxycarbonyl)guanidino)benzoyl)oxy)benzyl 1H-imidazole-1-carboxylate (1.00 g) prepared in the Reference Example 16-(a) in dichloromethane (10 mL) in a 100 mL round-bottom flask was added methyl trifluoromethanesulfonate (208 µL) at 0° C. under argon atmosphere with stirring, and the resulting mixture was stirred at 0° C. for hours. After the reaction was completed, to the reaction solution was added diethyl ether (20 mL), the resulting mixture was stirred at room temperature for 1 hour, the precipitated solids were collected by filtration, and dried under reduced pressure to give the title compound (1.09 g) as white solids.

Mass spectrum (ESI, m/z): 594 $[M-CF_3SO_3]^+$.

Reference Example 10-(c)

Preparation of tetra-tert-butyl 6,9,12,15-tetraoxa-3,18-diazaicosane-1,2,19,20-tetracarboxylate

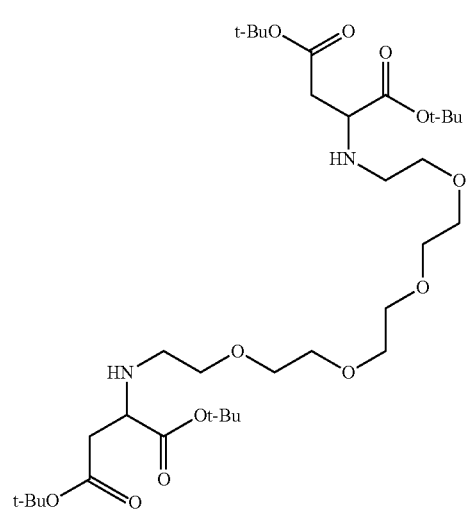

To a solution of 3,6,9,12-tetraoxatetradecane-1,14-diamine (508.4 mg) and di-tert-butyl maleate (1.16 g) in acetonitrile (10 mL) in a 100 mL round-bottom flask was added 1,8-diazabicyclo[5.4.0]-7-undecene (319 µL) at room temperature under argon atmosphere with stirring, and the resulting mixture was stirred at room temperature for 22 hours. After the reaction was completed, the reaction solution was concentrated under reduced pressure. The resulting residues were purified by medium pressure preparative chromatography (DIOL silica gel, elution solvent; hexane: ethyl acetate) to give the title compound (993.2 mg) as a colorless oil.

Mass spectrum (ESI, m/z): 693 $[M+H]^+$.

According to the same method as the Reference Example 10-(c), Reference Example 10-(c)-2 to Reference Example 10-(c)-7 were prepared.

TABLE 5

| Reference Example No. | Compound name<br>Structural formula<br>Mass spectrum |
|---|---|
| 10-(c)-2 | tri-tert-butyl 6,9,12,15,18,21-hexaoxa-3-azatricosane-1,2,23-tricarboxylate<br>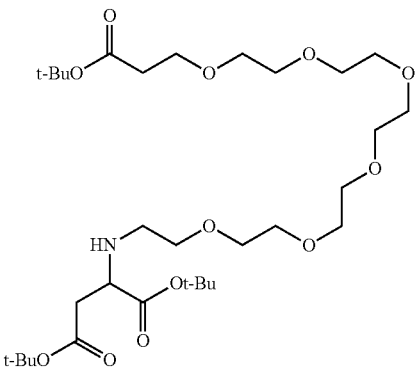<br>(ESI, m/z): 638 $[M + H]^+$. |
| 10-(c)-3 | tri-tert-butyl 6,9,12,15,18-pentaoxa-3-azaicosane-1,2,20-tricarboxylate<br>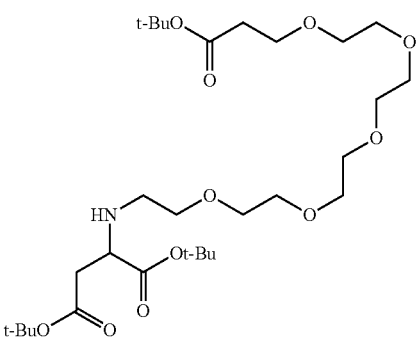<br>(ESI, m/z): 594 $[M + H]^+$. |

TABLE 5-continued

| Reference Example No. | Compound name<br>Structural formula<br>Mass spectrum |
|---|---|
| 10-(c)-4 | tri-tert-butyl 6,9,12,15-tetraoxa-3-azaheptadecane-1,2,17-tricarboxylate<br>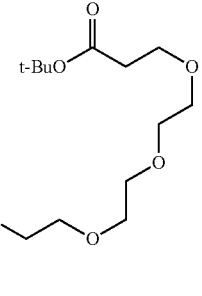<br>(ESI, m/z): 550 [M + H]+. |
| 10-(c)-5 | tri-tert-butyl 6,9,12-trioxa-3-azatetradecane-1,2,14-tricarboxylate<br>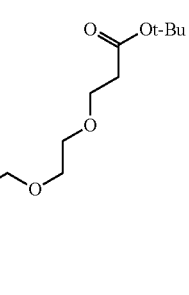<br>(ESI, m/z): 506 [M + H]+. |
| 10-(c)-6 | di-tert-butyl 2-((2-(2-(3-(tert-butoxy)-3-oxopropoxy)ethoxy)ethyl)amino)succinate<br>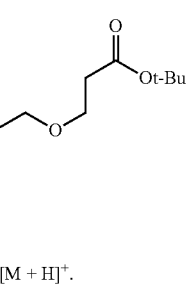<br>(CI, m/z): 462 [M + H]+. |
| 10-(c)-7 | di-tert-butyl 2-((2-(3-(tert-butoxy)-3-oxopropoxy)ethyl)amino)succinate<br>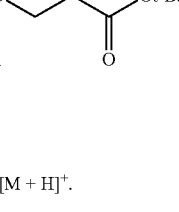<br>(CI, m/z): 418 [M + H]+. |

Reference Example 11-(a)

Preparation of tetra-tert-butyl 2,2'-(dodecane-1,12-diylbis(azanediyl))disuccinate

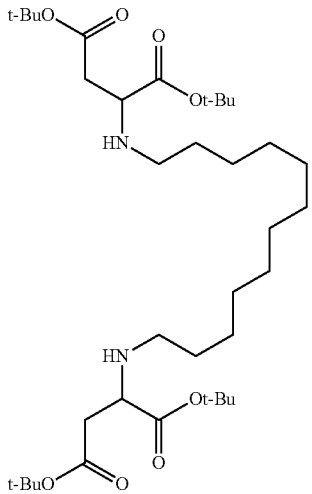 [SMILES: CC(C)(C)OC(=O)CC(NCCCCCCCCCCCCNC(CC(=O)OC(C)(C)C)C(=O)OC(C)(C)C)C(=O)OC(C)(C)C]

To a solution of dodecane-1,12-diamine (1.50 g) and di-tert-butyl maleate (4.08 g) in acetonitrile (30 mL) in a 100 mL round-bottom flask was added 1,8-diazabicyclo[5.4.0]-7-undecene (1.13 mL) at room temperature under argon atmosphere with stirring, and the resulting mixture was stirred at room temperature for 22 hours. After the reaction was completed, the reaction solution was concentrated under reduced pressure. The resulting residues were purified by medium pressure preparative chromatography (silica gel, elution solvent; hexane:ethyl acetate) to give the title compound (4.1 g) as a colorless oil.

$^1$H-NMR spectrum (400 MHz, CDCl$_3$) δ: 3.48-3.42 (m, 2H), 2.68-2.55 (m, 4H), 2.53-2.44 (m, 4H), 1.53-1.37 (m, 40H), 1.34-1.20 (m, 16H).

Reference Example 12-(a)

Preparation of (3S,22S)-di-tert-butyl 3,22-bis(((benzyloxy)carbonyl)amino)-4,21-dioxo-8,11,14,17-tetraoxa-5,20-diazatetracosane-1,24-dioate

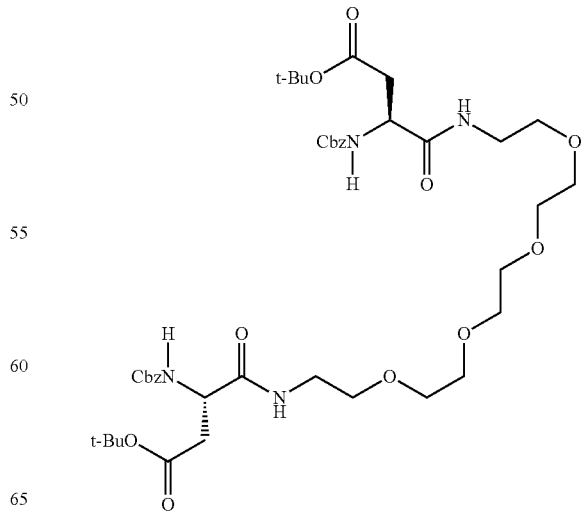

To a solution of (S)-2-((benzyloxy)carbonyl)amino)-4-(tert-butoxy)-4-oxobutanoic acid (13.56 g) in dichlormethane (225 mL) in a 1000 mL round-bottom flask were added COMU (19.6 g) and N,N-diisopropylethylamine (8.62 mL) at room temperature under argon atmosphere with stirring, and the resulting mixture was stirred at room temperature for 1 hour. Then, a solution of 3,6,9,12-tetraoxatetradecane-1,14-diamine (3 g) in dichloromethane (30 mL) was added thereto with stirring at room temperature, and the resulting mixture was stirred at room temperature for 22 hours. After the reaction was completed, the reaction solution was concentrated under reduced pressure. To the concentrated residues was added ethyl acetate, the resulting solution was washed with saturated aqueous sodium hydrogen carbonate solution, dried over anhydrous sodium sulfate, filtered, and concentrated under reduced pressure. The resulting residues were purified by medium pressure preparative chromatography (DIOL silica gel, elution solvent; hexane:ethyl acetate) to give the title compound (8.54 g) as a slightly yellow oil.

Mass spectrum (ESI, Y/z): 869 [M+Na]$^+$.

According to the same method as the Reference Example 12-(a), Reference Example 12-(a)-2 to Reference Example 12-(a)-6 were prepared.

TABLE 6

| Reference Example No. | Compound name<br>Structural formula<br>Mass spectrum |
|---|---|
| 12-(a)-2 | (2S)-di-tert-butyl 2-(2-(((benzyloxy)carbonyl)amino-4-(tert-butoxy)-4-oxobutaneamide)succinate<br><br>(ESI, m/z): 551 [M + H]$^+$. |
| 12-(a)-3 | (S)-di-tert-butyl 2-((S)-2-(((benzyloxy)carbonyl)amino)-4-(tert-butoxy)-4-oxobutaneamide)succinate<br><br>(ESI, m/z): 551 [M + H]$^+$. |

TABLE 6-continued

| Reference Example No. | Compound name<br>Structural formula<br>Mass spectrum |
|---|---|
| 12-(a)-4 | (S)-di-tert-butyl 2-((S)-2-((S)-2-(((benzyloxy)carbonyl)amino)-4-(tert-butoxy)-4-oxobutaneamide)-4-(tert-butoxy)-4-oxobutaneamide)succinate<br><br>(ESI, m/z): 722 [M + H]$^+$. |
| 12-(a)-5 | (S)-di-tert-butyl 2-(2-(((benzyloxy)carbonyl)amino)acetamido)succinate<br><br>(ESI, m/z): 437 [M + H]$^+$. |
| 12-(a)-6 | (S)-di-tert-butyl 2-(2-bromoacetamido)succinate<br><br>(ESI, m/z): 336 [M + H]$^+$. |

Reference Example 12-(b)

Preparation of (3S,22S)-di-tert-buty 3,22-diamino-4, 21-dioxo-8,11,14,17-tetraoxa-5,20-diazatetracosane-1,24-dioate

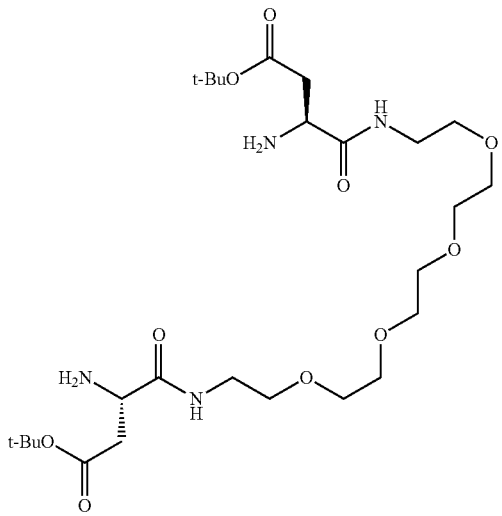 [SMILES: CC(C)(C)OC(=O)C[C@H](N)C(=O)NCCOCCOCCOCCOCCNC(=O)[C@@H](N)CC(=O)OC(C)(C)C]

To a solution of (3S,22S)-di-tert-butyl 3,22-bis(((benzyloxy)carbonyl)amino)-4,21-dioxo-8,11,14,17-tetraoxa-5,20-diazatetracosane-1,24-dioate (6.52 g) prepared according to the same manner as the Reference Example 12-(a) in ethanol (40 mL) in a 300 mL round-bottom flask was added 10% palladium carbon (wetted with 54.51% water, PE-type manufactured by NE CHEMCAT Corporation) (652 mg) at room temperature under argon atmosphere with stirring, the atmosphere in the reaction system was replaced with hydrogen atmosphere, and then the resulting mixture was stirred at room temperature for 2 hours. After the reaction was completed, in the reaction solution was added ethyl acetate and Celite, the resulting mixture was filtered, and the resulting filtrate was concentrated under reduced pressure to give the title compound (4.63 g) as a slightly yellow oil.

Mass spectrum (ESI, m/z): 579 [M+H]$^+$.

According to the same method as the Reference Example 12-(b), Reference Example 12-(b)-2 to Reference Example 12-(b)-5 were prepared.

TABLE 7

| Reference Example No. | Compound name<br>Structural formula<br>Mass spectrum |
|---|---|
| 12-(b)-2 | (2S)-di-tert-butyl 2-(2-amino-4-(tert-butoxy)-4-oxobutaneamide)succinate<br>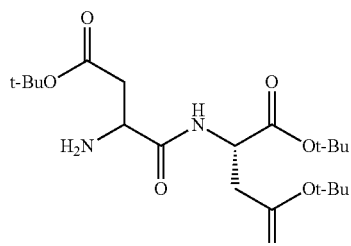<br>(ESI, m/z): 417 [M + H]$^+$. |

TABLE 7-continued

| Reference Example No. | Compound name<br>Structural formula<br>Mass spectrum |
|---|---|
| 12-(b)-3 | (S)-di-tert-butyl 2-((S)-2-amino-4-(tert-butoxy)-4-oxobutaneamide)succinate<br>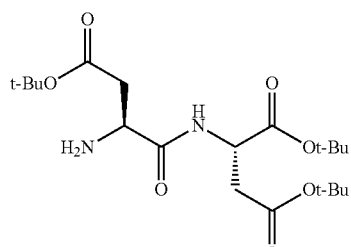<br>(ESI, m/z): 417 [M + H]$^+$. |
| 12-(b)-4 | (S)-di-tert-butyl 2-((S)-2-((S)-2-amino-4-(tert-butoxy)-4-oxobutaneamide)-4-(tert-butoxy)-4-oxobutaneamide)succinate<br>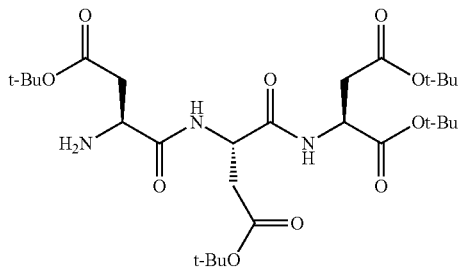<br>(ESI, m/z): 588 [M + H]$^+$. |
| 12-(b)-5 | (S)-di-tert-butyl 2-(2-aminoacetamido)succinate<br>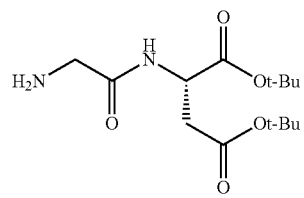<br>(ESI, m/z): 303 [M + H]$^+$. |

Reference Example 12-(c)

Preparation of (3S,6S,25S,28S)-di-tert-butyl 3,28-bis(((benzyloxy)carbonyl)amino)-6,25-bis(2-(tert-butoxy)-2-oxoethyl)-4,7,24,27-tetraoxo-11,14,17,20-tetraoxa-5,8,23,26-tetraazatriacontane-1,30-dioate

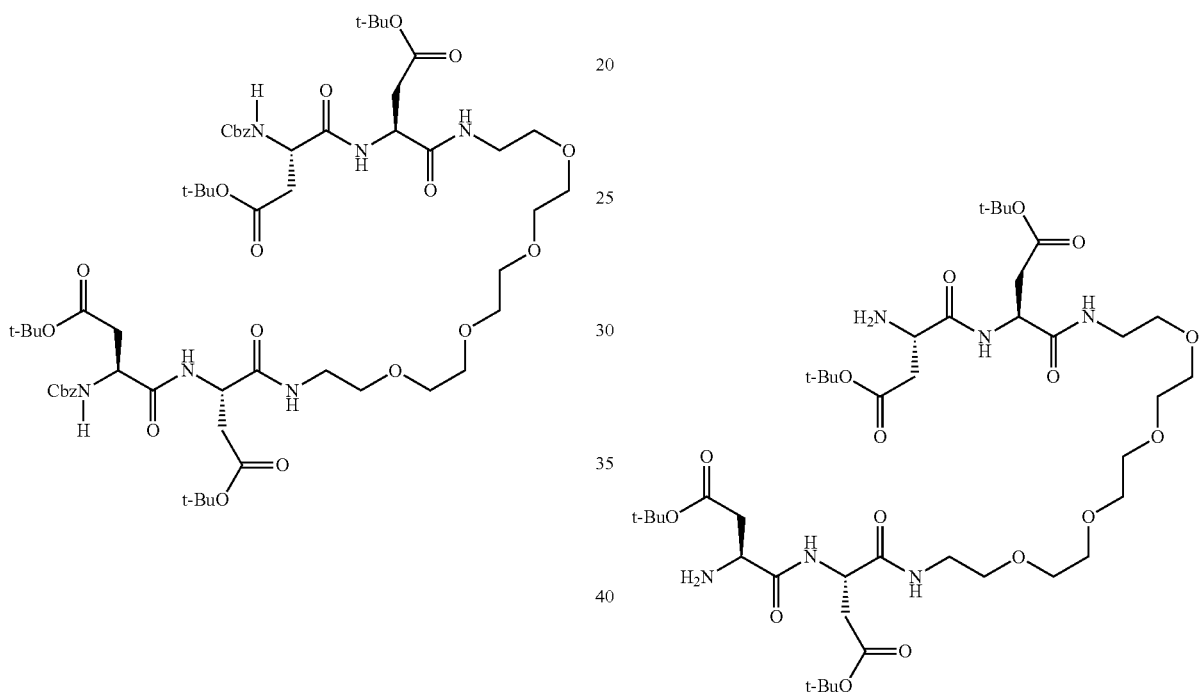

To a solution of (S)-2-((benzyloxy)carbonyl)amino)-4-(tert-butoxy)-4-oxobutanoic acid (5.85 g) in dichloromethane (100 mL) in a 200 mL round-bottom flask were added COMU (8.45 g) and N,N-diisopropylethylamine (3.71 mL) at room temperature under argon gas flow with stirring, and the resulting mixture was stirred at room temperature for 1 hour. Then, a solution of (3S,22S)-di-tert-butyl 3,22-diamino-4,21-dioxo-8,11,14,17-tetraoxa-5,20-diazatetracosane-1,24-dioate (3.16 g) prepared according to the same manner as the Reference Example 12-(b) in dichloromethane (20 mL) was added thereto with stirring at room temperature, and the resulting mixture was stirred at room temperature for 15 hours. After the reaction was completed, the reaction solution was concentrated under reduced pressure. To the concentrated residues was added ethyl acetate, the resulting solution was washed with saturated aqueous sodium hydrogen carbonate solution three times, dried over anhydrous sodium sulfate, filtered, and concentrated under reduced pressure. The resulting residues were purified by medium pressure preparative chromatography (DNH silica gel, elution solvent; hexane:ethyl acetate) to give the title compound (5.18 g) as a white foam.

Mass spectrum (ESI, m/z): 1212 [M+Na]$^+$.

Reference Example 12-(d)

Preparation of (3S,6S,25S,28S)-di-tert-butyl 3,28-diamino-6,25-bis(2-(tert-butoxy)-2-oxoethyl)-4,2,24,27-tetraoxo-11,14,17,20-tetraoxa-5,8,23,26-tetraazatriacontane-1,30-dioate To a solution of (3S,6S,25S,28S)-di-tert-butyl 3,28-bis(((benzyloxy)carbonyl)amino)-6,25-bis(2-(tert-butoxy)-2-oxoethyl)-4,7,24,27-tetraoxo-11,14,17,20-tetraoxa-5,8,23,26-tetraazatriacontane-1,30-dioate (400 mg) prepared in the Reference Example 12-(c) in ethanol (8 mL)/tetrahydrofuran (4 mL) in a 100 mL round-bottom flask was added 10% palladium carbon (wetted with 54.51% water, PE-type manufactured by NE CHEMCAT Corporation) (40.5 mg) at room temperature under argon atmosphere with stirring, the atmosphere in the reaction system was replaced with hydrogen atmosphere, and then the resulting mixture was stirred at room temperature for 2 hours. After the reaction was completed, to the reaction solution was added ethyl acetate and Celite, the resulting mixture was filtered, and the resulting filtrate was concentrated under reduced pressure to give the title compound (329.2 mg) as a colorless oil.

Mass spectrum (ESI, m/z): 922 [M+H]$^+$.

Reference Example 13-(a)

Preparation of (5S,22S)-tert-butyl 22-(((benzyloxy)carbonyl)amino)-5-(2-(tert-butoxy)-2-oxoethyl)-3,6,21-trioxo-1-phenyl-2-oxa-4,7,20-triazatetracosane-24-oate

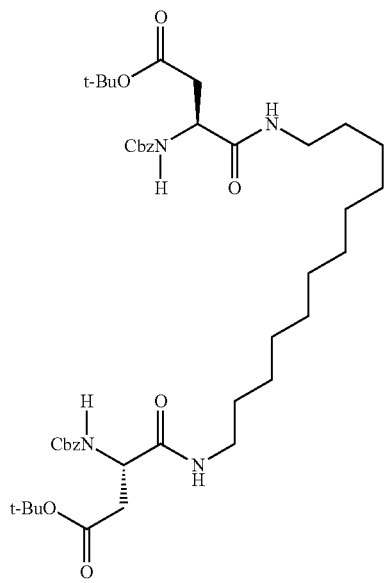 [SMILES: CC(C)(C)OC(=O)C[C@H](NC(=O)OCc1ccccc1)C(=O)NCCCCCCCCCCCCNC(=O)[C@H](CC(=O)OC(C)(C)C)NC(=O)OCc1ccccc1]

To a solution of (S)-2-(((benzyloxy)carbonyl)amino)-4-(tert-butoxy)-4-oxobutanoic acid (3.55 g) in dichloromethane (50 mL) in a 200 mL round-bottom flask were added COMU (5.13 g) and N,N-diisopropylethylamine (2.26 mL) at room temperature under argon atmosphere with stirring, and the resulting mixture was stirred at room temperature for 1 hour. Then, a solution of dodecane-1,12-diamine (1.00 g) in dichloromethane (10 mL) was added thereto with stirring at room temperature, and the resulting mixture was stirred at room temperature for 3.5 hours. Additionally, (S)-2-(((benzyloxy)carbonyl)amino)-4-(tert-butoxy)-4-oxobutanoic acid (1.29 g), COMU (1.92 g), and N,N-diisopropylethylamine (869 µL) were added thereto at room temperature, and the resulting mixture was stirred at room temperature for 1 hour. After the reaction was completed, the reaction solution was concentrated under reduced pressure. To the concentrated residues was added ethyl acetate, the resulting solution was washed with saturated aqueous sodium hydrogen carbonate solution three times, dried over anhydrous sodium sulfate, filtered, and concentrated under reduced pressure. The resulting residues were subjected to medium pressure preparative chromatography (silica gel, elution solvent; hexane:ethyl acetate), and the fractions comprising the target compound were concentrated under reduced pressure. To the concentrated residues were added tert-butyl methyl ether and dichloromethane, and the resulting solution was concentrated under reduced pressure to give the title compound (4.09 g) as a slightly yellow semisolids.

Mass spectrum (ESI, m/z): 811 [M+H]$^+$.

Reference Example 13-(b)

Preparation of (3S,3's)-di-tert-butyl 4,4'-(dodecane-1,12-diylbis(azanediyl))bis(3-amino-4-oxobutanoate)

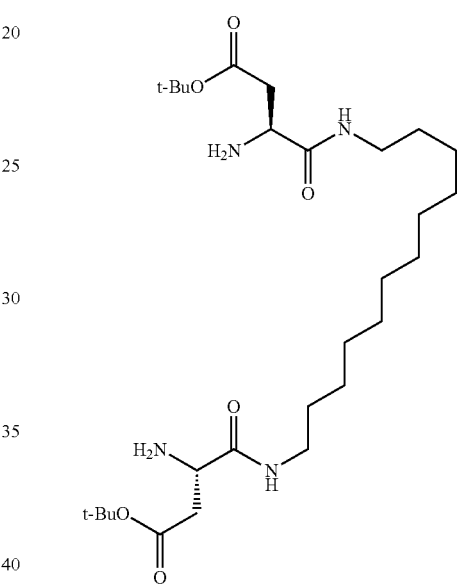

To a solution of (5S,22S)-tert-butyl 22-(((benzyloxy)carbonyl)amino)-5-(2-(tert-butoxy)-2-oxoethyl)-3,6,21-trioxo-1-phenyl-oxa-4,7,20-triazatetracosane-24-oate (4.09 g) prepared in the Reference Example 13-(a) in ethanol (20 mL)/tetrahydrofuran 20 mL) in a 200 mL round-bottom flask was added 10% palladium carbon (wetted with 54.51% water, PE-type manufactured by NE CHEMCAT Corporation) (400 mg) at room temperature under argon atmosphere with stirring, the atmosphere in the reaction system was replaced with hydrogen atmosphere, and then the resulting mixture was stirred at room temperature for 3 hours. After the reaction was completed, to the reaction solution was added ethyl acetate and Celite, the resulting mixture was filtered, and the resulting filtrate was concentrated under reduced pressure to give the title compound (2.35 g) as white solids.

$^1$H-NMR spectrum (400 MHz, CDCl$_3$) δ: 7.41-7.28 (m, 2H), 3.64 (dd, J=3.8, 8.5 Hz, 2H), 3.31-3.16 (m, 4H), 2.86 (dd, J=3.8, 16.6 Hz, 2H), 2.49 (dd, J=8.5, 16.7 Hz, 2H), 1.45 (s, 18H), 1.55-1.39 (m, 4H), 1.36-1.22 (m, 16H).

Reference Example 13-(c)

Preparation of (3S,6S,23S,26S)-di-tert-butyl 3,26-bis(((benzyloxy)carbonyl)amino)-6,23-bis(2-(tert-butoxy)-2-oxoethyl)-4,7,22,25-tetraoxo-5,8,21,24-tetraazaoctacosane-1,28-dioate

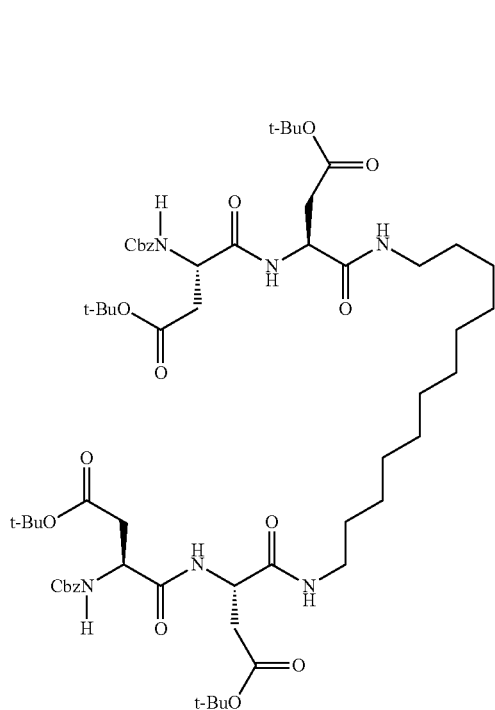 [SMILES: CC(C)(C)OC(=O)C[C@H](NC(=O)OCc1ccccc1)C(=O)N[C@@H](CC(=O)OC(C)(C)C)C(=O)NCCCCCCCCCCCCNC(=O)[C@H](CC(=O)OC(C)(C)C)NC(=O)[C@H](CC(=O)OC(C)(C)C)NC(=O)OCc1ccccc1]

To a solution of (S)-2-(((benzyloxy)carbonyl)amino)-4-(tert-butoxy)-4-oxobutanoic acid (1.97 g) in dichloromethane (20 mL) in a 100 mL round-bottom flask were added COMU (2.85 g) and N,N-diisopropylethylamine (1.25 mL) at room temperature under argon atmosphere with stirring, and the resulting mixture was stirred at room temperature for 1 hour. Then, a solution of (3S,3'S)-di-tert-butyl 4,4'-(dodecane-1,12-diylbis(azanediyl))bis(3-amino-4-oxobutanoate) (1.00 g) prepared in the Reference Example 13-(b) in dichloromethane (10 mL) was added thereto with stirring at room temperature, and the resulting mixture was stirred at room temperature for 3.5 hours. After the reaction was completed, the reaction solution was concentrated under reduced pressure. To the concentrated residues was added ethyl acetate, the resulting solution was washed with saturated aqueous sodium hydrogen carbonate solution three times, dried over anhydrous sodium sulfate, filtered, and concentrated under reduced pressure. The resulting residues were subjected to medium pressure preparative chromatography (silica gel, elution solvent; hexane:ethyl acetate), and the fractions comprising the target compound were concentrated under reduced pressure. The resulting residues were purified by medium pressure preparative chromatography (DNH silica gel, hexane:ethyl acetate) to give the title compound (1.93 g) as white solids.

Mass spectrum (ESI, m/z): 1176 (M+Na)$^+$.

Reference Example 13-(d)

Preparation of (3S,6S,23S,26S)-di-tert-butyl 3,26-diamino-6,23-bis(2-(tert-butoxy)-2-oxoethyl)-4,7,22,25-tetraoxo-5,8,21,24-tetraazaoctacosane-1,28-dioate

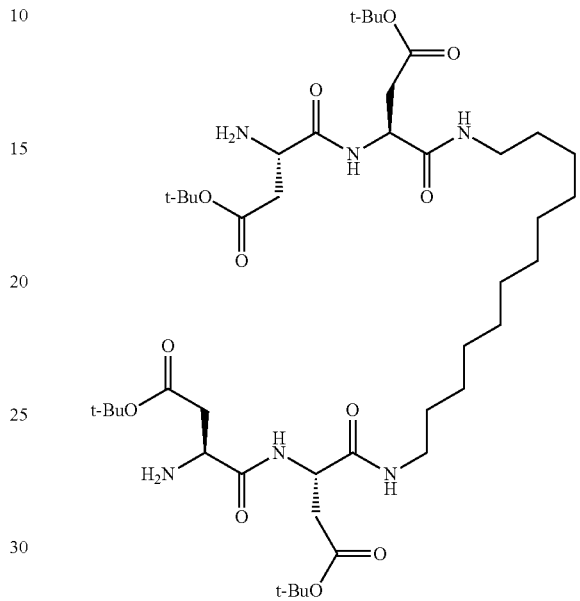

To a solution of (3S,6S,23S,26S)-di-tert-butyl 3,26-bis(((benzyloxy)carbonyl)amino)-6,23-bis(2-(tert-butoxy)-2-oxoethyl)-4,7,22,25-tetraoxo-5,8,21,24-tetraazaoctacosane-1,28-dioate (1.93 g) prepared in the Reference Example 13-(c) in ethanol (20 mL)/tetrahydrofuran (20 mL) in a 200 mL round-bottom flask was added 10% palladium carbon (wetted with 54.51% water, PE-type manufactured by NE CHEMCAT Corporation) (193 mg) at room temperature under argon atmosphere with stirring, the atmosphere in the reaction system was replaced with hydrogen atmosphere, and then the resulting mixture was stirred at room temperature for 1 hour. After the reaction was completed, to the reaction solution was added ethyl acetate and Celite, the resulting mixture was filtered, and the resulting filtrate was concentrated under reduced pressure to give the title compound (1.48 g) as white solids.

$^1$H-NMR spectrum (400 MHz, CDCl$_3$) δ: 8.17 (d, J=8.4 Hz, 2H), 6.80-6.62 (m, 2H), 4.71-4.63 (m, 2H), 3.66-3.59 (m, 2H), 3.29-3.10 (m, 4H), 2.90 (dd, J=4.6, 16.8 Hz, 2H), 2.82 (dd, J=4.9, 16.8 Hz, 2H), 2.67-2.52 (m, 4H), 1.45 (s, 18H), 1.45 (s, 18H), 1.53-1.39 (m, 4H), 1.32-1.20 (m, 16H).

Reference Example 14-(a)

Preparation of 2-(trimethylsilyl)ethyl 2-(((benzyloxy)carbonyl)amino)acetate

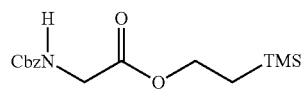

To a suspension of N-carbobenzyloxyglycine (5.00 g) in dehydrated dichloromethane (100 mL) in a 300 mL round-bottom flask were added 1-(3-dimethylaminopropyl)-3-ethylcarbodiimide hydrochloride (5.05 g), 4-dimethylaminopyridine (0.900 g), and 2-(trimethylsilyl)ethanol (3.75 mL) under ice-cooling under argon atmosphere with stirring, and the resulting mixture was stirred at room temperature for 5 days. After the reaction was completed, to the reaction solution was added saturated aqueous sodium hydrogen carbonate solution, and the resulting mixed solution was extracted with dichloromethane. The resulting organic layer was washed with water, dried over anhydrous sodium sulfate, filtered, and concentrated under reduced pressure. The resulting residues were purified by medium pressure preparative chromatography (silica gel, elution solvent; hexane:ethyl acetate) to give the title compound (6.42 g) as a colorless oil.

Mass spectrum (ESI, m/z): 332 [M+Na]$^+$.

Reference Example 14-(b)

Preparation of 2-(trimethylsilyl)ethyl 2-aminoacetate

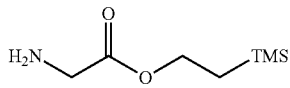

To a solution of 2-(trimethylsilyl)ethyl 2-(((benzyloxy)carbonyl)amino)acetate (6.42 g) prepared in the Reference Example 14-(a) in ethanol (40 mL) in a 200 mL round-bottom flask was added 10% palladium carbon (wetted with ca. 55% water, manufactured by Tokyo Chemical Industry Co., Ltd.) (600 mg), the atmosphere in the reaction system was replaced with hydrogen atmosphere, and then the resulting mixture was stirred at room temperature for 2 hours. After the reaction was completed, the atmosphere in the reaction system was replaced with nitrogen atmosphere, and the reaction solution was filtered through Celite. The removed solids were washed with ethyl acetate, and then the resulting filtrate was concentrated under reduced pressure to give the title compound (3.57 g) as a brown oil.

$^1$H-NMR spectrum (400 MHz, CDCl$_3$) δ: 4.26-4.19 (m, 21), 3.40 (s, 2H), 1.07-0.93 (m, 2H), 0.03 (s, 9H).

Reference Example 14-(c)

Preparation of tert-butyl 3-(((2-oxo-2-(2-(trimethylsilyl)ethoxy)ethyl)amino)methyl)benzoate

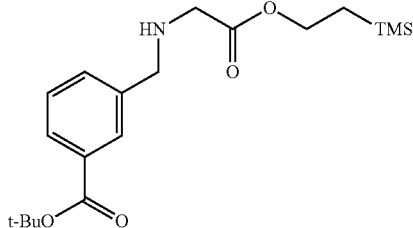 [SMILES: CC(C)(C)OC(=O)c1cccc(CNCC(=O)OCC[Si](C)(C)C)c1]

To a solution of tert-butyl 3-formylbenzoate (2.00 g) in dehydrated dichloromethane (20 mL) in a 100 mL round-bottom flask were added magnesium sulfate (1.52 g), sodium acetate (1.20 g), and 2-(trimethylsilyl)ethyl 2-aminoacetate (1.87 g) prepared in the Reference Example 14-(b) under ice-cooling under argon atmosphere with stirring, and the resulting mixture was stirred at room temperature for 16 hours. Then, acetic acid (0.850 mL) was added thereto, sodium triacetoxyborohydride (3.10 g) was added dividedly thereto with stirring under ice-cooling, and the resulting mixture was stirred at room temperature for 4 hours. After the reaction was completed, the reaction solution was filtered, to the resulting filtrate was added saturated aqueous sodium hydrogen carbonate solution, and the resulting mixed solution was extracted with dichloromethane. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (2.37 g) as a colorless oil.

Mass spectrum (ESI, m/s): 366 [M–H]$^+$.

According to the same method as the Reference Example 14-(c), Reference Example 14-(c)-2 was prepared.

TABLE 8

| Reference Example No. | Compound name<br>Structural formula<br>Mass spectrum |
|---|---|
| 14-(c)-2 | (S)-di-tert-butyl 2-(2-((3-(tert-butoxycarbonyl)benzyl)amino)acetamido)succinate |

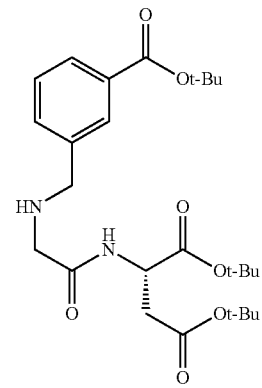

(ESI, m/z): 493 [M + H]$^+$.

Reference Example 14-(d)

Preparation of tert-butyl 3-(((((4-((4-(2,3-bis(tert-butoxycarbonyl)guanidino)benzoyl)oxy)benzyl)oxy)carbonyl)(2-oxo-2-(2-(trimethylsilyl)ethoxy)ethyl)amino)methyl)benzoate

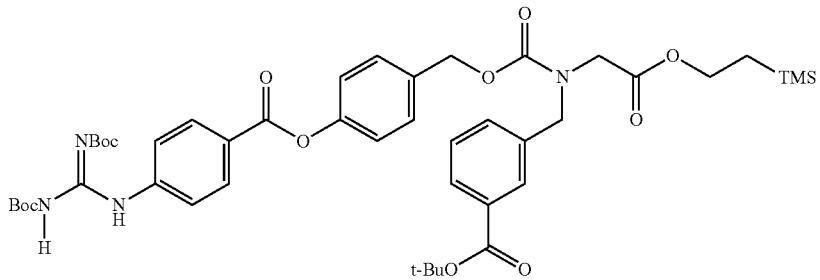

To a suspension of 1-(((4-((4-(2,3-bis(tert-butoxycarbonyl)guanidino)benzoyl)oxy)benzyl)oxy)carbonyl)-3-methyl-1H-imidazol-3-ium trifluoromethanesulfonate (3.70 g) prepared according to the same manner as the Reference Example 10-(b) in dehydrated acetonitrile (10 mL) in a 100 mL round-bottom flask was added a solution of tert-butyl 3-(((2-oxo-2-(2-(trimethylsilyl)ethoxy)ethyl)amino)methyl)benzoate (2.37 g) prepared in the Reference Example 14-(c) in dehydrated acetonitrile (5 mL) at room temperature under argon atmosphere with stirring, and the resulting mixture was stirred at room temperature for 16 hours. After the reaction was completed, the reaction solution was concentrated under reduced pressure. The resulting residues were purified by medium pressure preparative chromatography (silica gel, elution solvent; hexane:ethyl acetate) to give the title compound (4.71 g) as a colorless oil.

Mass spectrum (ESI, m/z): 877 [M+H]$^+$.

Reference Example 14-(e)

Preparation of 2-(((((4-((4-(2,3-bis(tert-butoxycarbonyl)guanidino)benzoyl)oxy)benzyl)oxy)carbonyl)(3-(tert-butoxycarbonyl)benzyl)amino)acetic acid

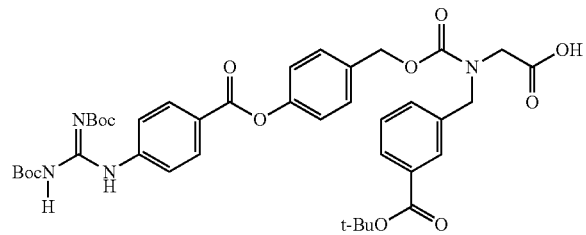

To a solution of tert-butyl 3-(((((4-((2,3-bis(tert-butoxycarbonyl)guanidino)benzoyl)oxy)benzyl)oxy)carbonyl)(2-oxo-2-(2-(trimethylsilyl)ethoxy)ethyl)amino)methyl)benzoate (4.71 g) prepared in the Reference Example 14-(d) in dehydrated tetrahydrofuran (20 mL) in a 100 mL round-bottom flask was added tetrabutylammonium fluoride (a 1.0 MA solution in tetrahydrofuran) (7.00 mL) under ice-cooling under argon atmosphere with stirring, and the resulting mixture was stirred at room temperature for 21 hours. After the reaction was completed, to the reaction solution was added a saturated aqueous ammonium chloride solution, and the resulting mixed solution was extracted with ethyl acetate. The resulting organic layer was washed with saturated brine, dried over anhydrous sodium sulfate, filtered, and concentrated under reduced pressure to give the title compound (3.98 g) as a white foam.

Mass spectrum (EST, m/z): 777 [M+H]$^+$.

Reference Example 15-(a)

Preparation of (S)-4-tert-butyl 1-(2-(trimethylsilyl)ethyl) 2-(((benzyloxy)carbonyl)amino)succinate

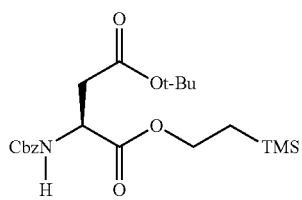 [SMILES: CC(C)(C)OC(=O)C[C@H](NC(=O)OCc1ccccc1)C(=O)OCC[Si](C)(C)C]

To a solution of (S)-2-(((benzyloxy)carbonyl)amino)-4-(tert-butoxy)-4-oxobutanoic acid (5 g) in dichloromethane (75 mL) in a 200 mL round-bottom flask were added 1-(3-dimethylaminopropyl)-3-ethylcarbodiimide hydrochloride (3.26 g) and 4-dimethylaminopyridine (573 mg) at room temperature under argon atmosphere with stirring, and the resulting mixture was stirred at room temperature for 20 minutes. Then, 2-(trimethylsilyl)ethanol (2.42 mL) were added thereto with stirring at room temperature, and the resulting mixture was stirred at room temperature for 15 hours. Additionally, 1-(3-dimethylaminopropyl)-3-ethylcarbodiimide hydrochloride (3.29 g) and 4-dimethylaminopyridine (561.5 mg) were added thereto at room temperature, and the resulting mixture was stirred at room temperature for 23 hours. After the reaction was completed, to the reaction solution was added a saturated aqueous ammonium chloride solution, and the resulting mixed solution was extracted with dichloromethane. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane: ethyl acetate) to give the title compound (5.32 g) as a colorless oil.

Mass spectrum (ESI, m/z): 424 [M+H]$^+$.

Reference Example 15-(b)

Preparation of (S)-4-tert-butyl 1-(2-(trimethylsilyl)ethyl) 2-aminosuccinate

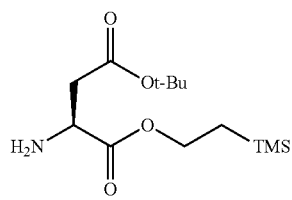 [SMILES: CC(C)(C)OC(=O)C[C@H](N)C(=O)OCC[Si](C)(C)C]

To a solution of (S)-4-tert-butyl 1-(2-(trimethylsilyl)ethyl) 2-(((benzyloxy)carbonyl)amino)succinate (5.32 g) prepared in the Reference Example 15-(a) in ethanol (25 mL)/tetrahydrofuran (25 mL) in a 300 mL round-bottom flask was added 10% palladium carbon (wetted with 54.51% water, PE-type manufactured by NE CHEMCAT Corporation) (558.5 mg) at room temperature under argon atmosphere with stirring, the atmosphere in the reaction system was replaced with hydrogen atmosphere, and then the resulting mixture was stirred at room temperature for 1 hour. After the reaction was completed, to the reaction solution was added ethyl acetate and Celite, the resulting mixture was filtered, and the resulting filtrate was concentrated under reduced pressure to give the title compound (3.49 as a colorless oil.

Mass spectrum (CI, m/z) 20 [M+H]$^+$.

Reference Example 15-(c)

Preparation of (S)-4-tert-butyl 1-(2-trimethylsilyl)ethyl) 2-((2-(tert-butoxy)-2-oxoethyl)amino)succinate

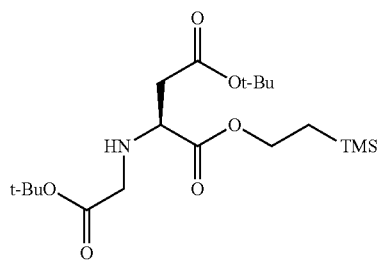 [SMILES: CC(C)(C)OC(=O)CN[C@@H](CC(=O)OC(C)(C)C)C(=O)OCC[Si](C)(C)C]

To a solution of (S-4-tert-butyl 1-(2-(trimethylsilyl)ethyl) 2-aminosuccinate (2.0 g) prepared according to the same manner as the Reference Example 15-(b) and potassium carbonate (1.99 g) in acetonitrile (50 mL) in a 200 mL round-bottom flask was added tert-butyl bromoacetate (1.15 mL) at room temperature under argon atmosphere with stirring, and the resulting mixture was 13 stirred at 70° C. for 2 hours. After the reaction was completed, the reaction solution was filtered, then the removed solids were washed with ethyl acetate, and the resulting filtrate was concentrated under reduced pressure. The resulting residues were purified by medium pressure preparative chromatography (silica gel, elution solvent; hexane:ethyl acetate) to give the title compound (2.12 g) as a colorless oil.

Mass spectrum (ESI, m/z): 404 [M+H]$^+$.

According to the same method as the Reference Example 15-(c), Reference Example 15-(c)-2 to Reference Example 15-(c)-9 were prepared.

TABLE 9

| Reference Example No. | Compound name<br>Structural formula<br>Mass spectrum |
|---|---|
| 15-(c)-2 | (2S)-di-tert-butyl 2-(4-(tert-butoxy)-2-((2-(tert-butoxy)-2-oxoethyl)amino)-4-oxobutaneamide)succinate<br><br>(ESI, m/z): 531 [M + H]$^+$. |
| 15-(c)-3 | tert-butyl 3-(((2-(tert-butoxy)-2-oxoethyl)amino)methyl)benzoate<br><br>(ESI, m/z): 322 [M + H]$^+$. |
| 15-(c)-4 | di-tert-butyl 6,9,12,15-tetraoxa-3-azaoctadecane-1,18-dioate<br><br>(ESI, m/z): 436 [M + H]$^+$. |

TABLE 9-continued

| Reference Example No. | Compound name<br>Structural formula<br>Mass spectrum |
|---|---|
| 15-(c)-5 | tert-butyl 1-(3-(tert-butoxycarbonyl)phenyl)-5,8,11,14-tetraoxa-2-azaheptadecane-17-oate<br>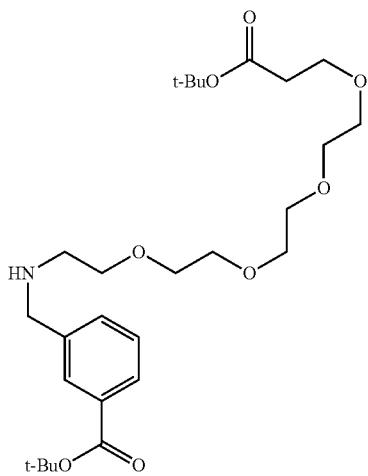<br>(DUIS, m/z): 512 [M + H]⁺. |
| 15-(c)-6 | (S)-di-tert-butyl 2-((2-(tert-butoxy)-2-oxoethyl)amino)succinate<br>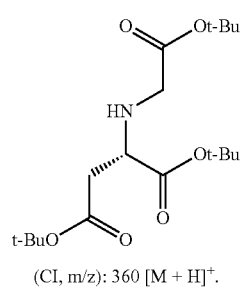 [SMILES: CC(C)(C)OC(=O)CN[C@@H](CC(=O)OC(C)(C)C)C(=O)OC(C)(C)C]<br>(CI, m/z): 360 [M + H]⁺. |
| 15-(c)-7 | (S)-di-tert-butyl 2-((3-(tert-butoxycarbonyl)benzyl)amino)succinate<br>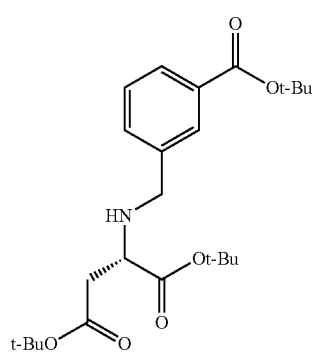<br>(ESI, m/z): 436 [M + H]⁺. |
| 15-(c)-8 | (2S,2'S)-tetra-tert-butyl 2,2'-((1-oxoethane-1,2-diyl)bis(azanediyl))disuccinate<br>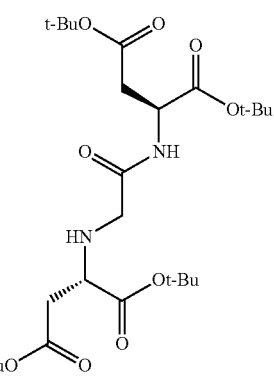<br>(ESI, m/z): 531 [M + H]⁺. |
| 15-(c)-9 | (E)-di-tert-butyl 2-((6-(tert-butoxy)-6-oxohexyl)amino)succinate<br>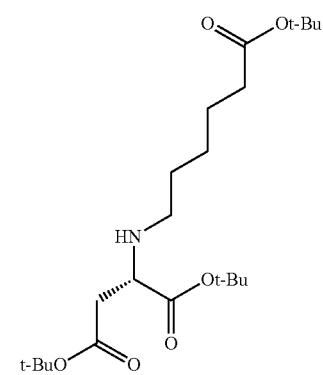<br>m/z): 416 [M + H]⁺. |

Reference Example 15-(d)

Preparation of (S)-4-tert-butyl 1-(2-(trimethylsilyl)ethyl) 2-((((4-((4-(2,3-bis(tert-butoxycarbonyl)guanidino)benzoyl)oxy)benzoyl)oxy)carbonyl) (2-(tert-butoxy)-2-oxoethyl)amino)succinate

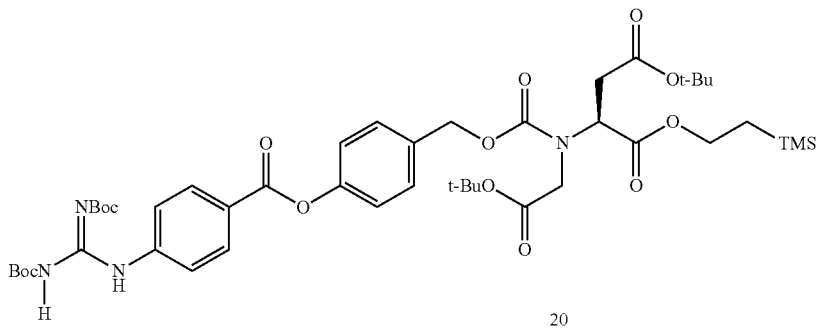

To a solution of 1-(((4-((4-(2,3-bis(tert-butoxycarbonyl)guanidino)benzoyl)oxy)benzyl)oxy)carbonyl)-3-methyl-1H-imidazol-3-ium trifluoromethanesulfonate (462.5 mg) prepared according to the same manner as the Reference Example 10-(b) in acetonitrile (6 mL) in a 100 mL round-bottom flask was added (S)-4-tert-butyl 1-(2-(trimethylsilyl)ethyl) 2-((2-(tert-butoxy)-2-oxoethyl)amino)succinate (309.5 mg) prepared according to the same manner as the Reference Example 15-(c) at room temperature under argon atmosphere with stirring, the resulting mixture was stirred at room temperature for 4 hours, left to stand at room temperature for 12 days, and stirred at room temperature for 57 hours. After the reaction was completed, the reaction solution was concentrated under reduced pressure. The resulting residues were purified by medium pressure preparative chromatography (silica gel, elution solvent; hexane:ethyl acetate) to give the title compound (268.3 mg) as a colorless oil.

Mass spectrum (ESI, m/z): 915 [M+H]$^+$.

Reference Example 15-(e)

Preparation of (S)-2-((((4-((4-(2,3-bis(tert-butoxycarbonyl)guanidino)benzoyl)oxy)benzyl)oxy)carbonyl)(2-(tert-butoxy)-2-oxoethyl)amino)-4-(tert-butoxy)-4-oxobutanoic acid

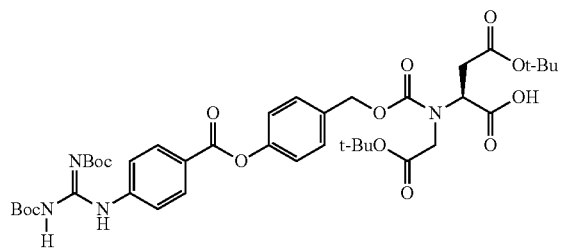

To a solution of (S) 4-tert-butyl 1-(2-(trimethylsilyl)ethyl) 2-((((4-((4-(2,3-bis(tert-butoxycarbonyl)guanidino)benzoyl)oxy)benzyl)oxy)carbonyl)(2-(tert-butoxy)-2-oxoethyl)amino)succinate (268 mg) prepared in the Reference Example 15-(d) in dehydrated tetrahydrofuran (5 mL) in a 100 mL round-bottom flask was added tetrabutylammonium fluoride (a 1.0 M solution in tetrahydrofuran) (288 μL) at 0° C. under argon atmosphere with stirring, and the resulting mixture was stirred at room temperature for 16 hours. After the reaction was completed, to the reaction solution was added a saturated aqueous ammonium chloride solution, and the resulting mixed solution was extracted with dichloromethane. The resulting organic layer was washed with saturated brine, dried over anhydrous sodium sulfate, filtered, and concentrated under reduced pressure. The resulting residues were subjected to medium pressure preparative chromatography (silica gel, elution solvent; dichloroethane:methanol), and the fractions comprising the target compound were concentrated under reduced pressure. The resulting residues were purified by medium pressure preparative chromatography (silica gel, elution solvent; ethyl acetate:methanol) to give the title compound (110 mg) as a colorless oil.

Mass spectrum (ESI, m/z): 815 [M+H]$^+$.

Reference Example 16-(a)

Preparation of (S)-4-tert-butyl 1-(2-(trimethylsilyl)ethyl)2-((3-(tert-butoxycarbonyl)benzyl)amino)succinate

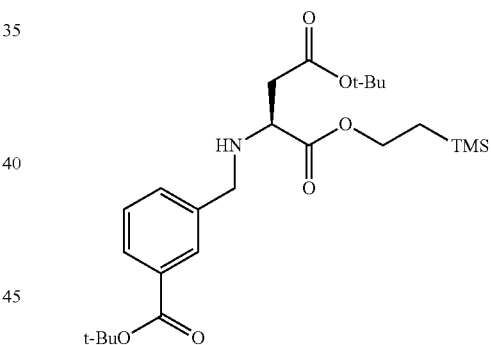

To a solution of (S)-4-tert-butyl 1-(2-(trimethylsilyl)ethyl) 2-aminosuccinate (500 mg) prepared according to the same manner as the Reference Example 15-(b) in dehydrated acetonitrile (10 μL) in a 100 mL round-bottom flask were added anhydrous potassium carbonate (500 mg) and tert-butyl 3-(chloromethyl)benzoate (430 mg) at room temperature under argon atmosphere with stirring, and the resulting mixture was stirred at 60° C. for hours. Additionally, tert-butyl 3-(chloromethyl)benzoate (315 mg) and anhydrous potassium carbonate (360 mg) were added thereto with stirring at room temperature, and the resulting mixture was stirred at 60° C. for 3 hours. After the reaction was completed, the reaction solution was allowed to cool to room temperature, and filtered. The removed solids were washed with ethyl acetate, and the resulting filtrate was concentrated under reduced pressure. The resulting residues were purified by medium pressure preparative chromatography (silica gel, elution solvent; hexane:ethyl acetate) to give the title compound (332 mg) as a colorless oil.

Mass spectrum (ESI, m/z): 480 [M+H]$^+$.

Reference Example 16-(b)

Preparation of (S)-4-tert-butyl 1-(2-(trimethylsilyl)ethyl)2-((((4-((4-(2,3-bis(tert-butoxycarbonyl)guanidino)benzoyl)oxy)benzyl)oxy)carbonyl)(3-(tert-butoxycarbonyl)benzyl)amino)succinate

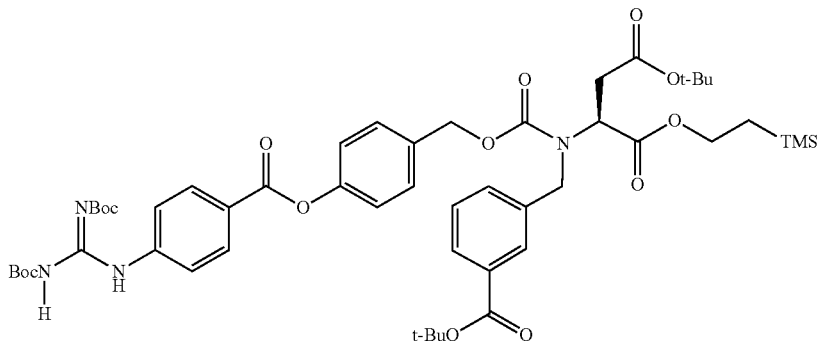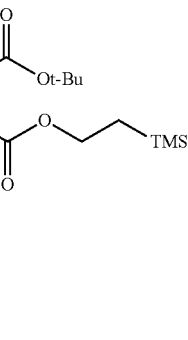

To a suspension of 1-(((4-((4-(2,3-bis(tert-butoxycarbonyl)guanidino)benzoyl)oxy)benzyl)oxy)carbonyl)-3-methyl-1H-imidazol-3-ium trifluoromethanesulfonate (430 mg) prepared according to the same manner as the Reference Example 10-(b) in dehydrated acetonitrile (4 mL) in a 50 mL round-bottom flask was added a solution of (S)-4-tert-butyl 1-(2-(trimethylsilyl)ethyl)2-((3-(tert-butoxycarbonyl)benzyl)amino)succinate (332 mg) prepared in the Reference Example 16-(a) in dehydrated acetonitrile (2 mL) at room temperature under argon atmosphere with stirring, and the resulting mixture was stirred at room temperature for 6 days. After the reaction was completed, the reaction solution was concentrated under reduced pressure. The resulting residues were purified by medium pressure preparative chromatography (silica gel, elution solvent; hexane:ethyl acetate) to give the title compound (223 mg) as a white foam.

Mass spectrum (ESI, m/z): 991 [M+H]$^+$.

Reference Example 16-(c)

Preparation of (S)-2-(((((4-((4-(2,3-bis(tert-butoxycarbonyl)guanidino)benzoyl)oxy)benzyl)oxy)carbonyl)(3-(tert-butoxycarbonyl)benzyl)amino)-4-(tert-butoxy)-4-oxobutanoic acid

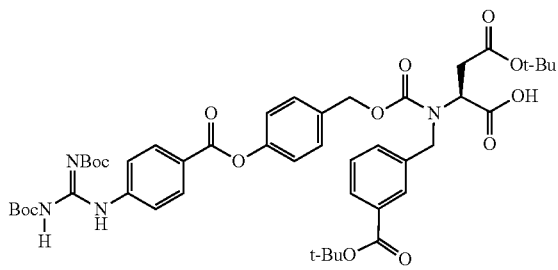

To a solution of (S)-9-tert-butyl 1-(2-(trimethylsilyl)ethyl) 2-((((4-((4-(2,3-bis(tert-butoxycarbonyl)guanidino)benzoyl)oxy)benzyl)oxy)carbonyl) (3-(tert-butoxycarbonyl)benzyl)amino)succinate (223 mg) prepared in the Reference Example 16-(b) in dehydrated tetrahydrofuran (2 mL) in a 50 mL round-bottom flask was added tetrabutylammonium fluoride (a 1.0 M solution in tetrahydrofuran) (0.270 mL) under ice-cooling under argon atmosphere with stirring, and the resulting mixture was stirred at room temperature for 16 hours. After the reaction was completed, to the reaction solution was added a saturated aqueous ammonium chloride solution, and the resulting mixed solution was extracted with ethyl acetate. The resulting organic layer was washed with saturated brine, dried over anhydrous sodium sulfate, filtered, and concentrated under reduced pressure to give the title compound (230 mg), as a white foam.

Mass spectrum (ESI, m/z): 891 [M+H]$^+$.

Reference Example 17-(a)

Preparation of 2-(trimethylsilyl)ethyl 3-formylbenzoate

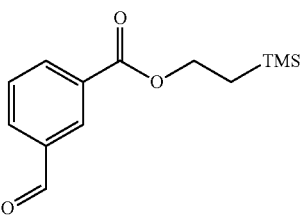 [SMILES: C[Si](C)(C)CCOC(=O)c1cccc(C=O)c1]

(1) To a suspension of m-formylbenzoic acid (2.00 g) in dehydrated dichloromethane (30 mL) in a 200 mL round-bottom flask were added oxalyl chloride (1.20 mL) and dimethylformamide (50 μL) under ice-cooling under argon atmosphere with stirring, and the resulting mixture was stirred at room temperature for 3 hours. After the reaction was completed, the reaction solution was concentrated under reduced pressure.

(2) To a solution of 2-(trimethylsilyl)ethanol (2.10 mL) and pyridine (1.10 mL) in dehydrated dichloromethane (30 mL) in a 200 mL round-bottom flask was added dropwise a solution of the concentrated residues in (1) in dichloromethane (30 mL) under ice-cooling under argon atmosphere with stirring, and the resulting mixture was stirred at room temperature for 16 hours. After the reaction was completed, the reaction solution was concentrated under reduced pressure. To the concentrated residues was added water, and the resulting mixture was extracted with ethyl acetate. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (3.00 g) as a colorless oil.

Mass spectrum (CI, m/z): 251 [M+H]$^+$.

Reference Example 17-(b)

Preparation of (S)-di-tert-butyl 2-((3-((2-(trimethylsilyl)ethoxy)carbonyl)benzyl)amino)succinate

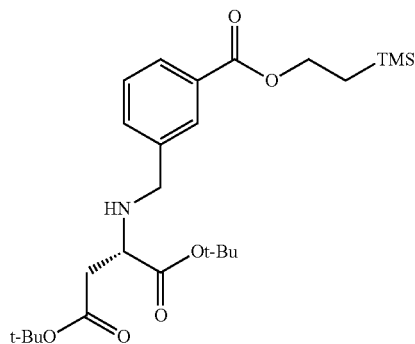 [SMILES: CC(C)(C)OC(=O)C[C@H](NCc1cccc(C(=O)OCC[Si](C)(C)C)c1)C(=O)OC(C)(C)C]

To a solution of 2-(trimethylsilyl)ethyl 3-formylbenzoate (1.50 g) prepared in the Reference Example 17-(a) in dehydrated dichloromethane (20 mL) in a 100 mL round-bottom flask were added magnesium sulfate (1.00 g), sodium acetate (0.740 g), and L-aspartic acid di-tert-butyl ester hydrochloride (2.03 g) under ice-cooling under argon atmosphere with stirring, and the resulting mixture was stirred at room temperature for 16 hours. Then, acetic acid (0.520 mL) was added thereto, sodium triacetoxyborohydride (1.90 g) was added dividedly thereto with stirring under ice-cooling, and the resulting mixture was stirred at room temperature for 2 hours. After the reaction was completed, to the reaction solution was added saturated aqueous sodium hydrogen carbonate solution, and the resulting mixed solution was extracted with dichloromethane. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (2.68 g) as a colorless oil.

Mass spectrum (ESI, m/z): 480 [M+H]$^+$.

Reference Example 17-(c)

Preparation of (S)-di-tert-butyl 2-((((4-((4-(2,3-bis(tert-butoxycarbonyl)guanidino)benzoyl)oxy)benzyl)oxy)carbonyl) (3-((2-(trimethylsilyl)ethoxy)carbonyl)benzyl)amino)succinate

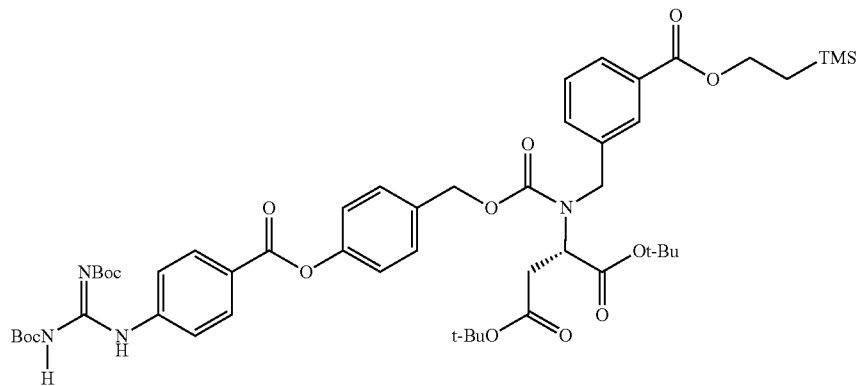

To a suspension of 1-(((4-((4-(2,3-bis(tert-butoxycarbonyl)guanidino)benzoyl)oxy)benzyl)oxy)carbonyl)-3-methyl-1H-imidazol-3-ium trifluoromethanesulfonate (570 mg) prepared according to the same manner as the Reference Example 10-(b) in dehydrated acetonitrile (4 mL) in a 100 mL round-bottom flask was added a solution of (S)-di-tert-butyl 2-((3-((2-(trimethylsilyl)ethoxy)carbonyl)benzyl)amino)succinate (880 mg) prepared in the Reference Example 17-(b) in dehydrated acetonitrile (2 mL) at room temperature under argon atmosphere with stirring, and the resulting mixture was stirred at room temperature for 3 days. After the reaction was completed, the reaction solution was concentrated under reduced pressure. The resulting residues were purified by medium pressure preparative chromatography (silica gel, elution solvent; hexane:ethyl acetate) to give the title compound (391 mg) as a colorless oil.

Mass spectrum (ESI, m/z): 991 [M+H]⁺.

Reference Example 17-(d)

Preparation of (S)-3-(((((4-((4-(2,3-bis(tert-butoxycarbonyl)guanidino)benzoyl)oxy)benzyl)oxy)carbonyl) (1,4-di-tert-butoxy-1,4-dioxobutan-2-yl)amino) methyl)benzoic acid

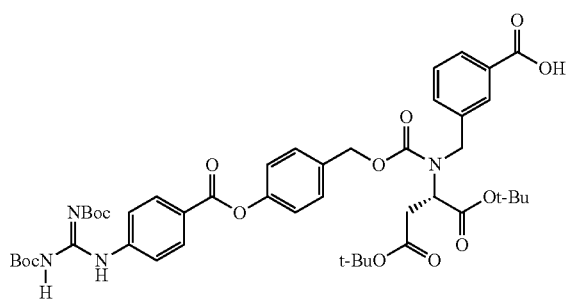

To a solution of (S)-di-tert-butyl 2-(((((4-((4-(2,3-bis(tert-butoxycarbonyl)guanidino)benzoyl)oxy)benzyl)oxy)carbonyl)(3-((2-(trimethylsilyl)ethoxy)carbonyl)benzyl)amino)succinate (391 mg) prepared in the Reference Example 17-(c) in dehydrated tetrahydrofuran (4 mL) in a 100 mL round-bottom flask was added tetrabutylammonium fluoride (a 1.0 M solution in tetrahydrofuran) (0.480 mL) under ice-cooling under argon atmosphere with stirring, and the resulting mixture was stirred at room temperature for 25 hours. Additionally, tetrabutylammonium fluoride (a 1.0 M solution in tetrahydrofuran) (0.160 mL) was added thereto with stirring at room temperature, and the resulting mixture was stirred at room temperature for 4 hours. After the reaction was completed, to the reaction solution was added a saturated aqueous ammonium chloride solution, and the resulting mixed solution was extracted with ethyl acetate. The resulting organic layer was washed with saturated brine, dried over anhydrous sodium sulfate, and filtered. The resulting filtrate was concentrated under reduced pressure to give the title compound (401 mg) as a white foam.

Mass spectrum (ESI, m/z): 891 [M+H]⁺.

Reference Example 18-(a)

Preparation of (S)-di-tert-butyl 2-((N-((benzyloxy)carbonyl)sulfamoyl) (3-((2-(trimethylsilyl)ethoxy)carbonyl)benzyl)amino)succinate

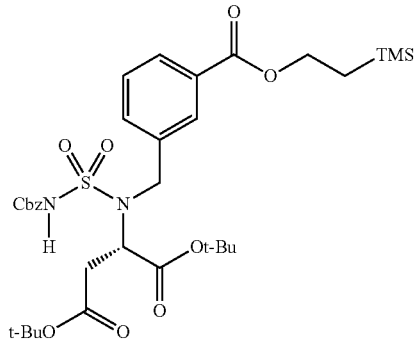 [SMILES: CC(C)(C)OC(=O)C[C@@H](C(=O)OC(C)(C)C)N(Cc1cccc(C(=O)OCC[Si](C)(C)C)c1)S(=O)(=O)NC(=O)OCc1ccccc1]

To a solution of chlorosulfonyl isocyanate (60 μL) in dichloromethane (10 mL) in a 50 mL round-bottom flask was added benzyl alcohol (70 μL) at 0° C. under argon atmosphere with stirring, and the resulting mixture was stirred at 0° C. for 15 minutes. Then, triethylamine (180 μL) and (S)-di-tert-butyl 2-((3-((2-(trimethylsilyl)ethoxy)carbonyl)benzyl)amino)succinate (290 mg) prepared in the Reference Example 17-(b) were added thereto with stirring at 0° C., and the resulting mixture was stirred at room temperature for 18 hours. After the reaction was completed, to the reaction solution was added saturated aqueous sodium hydrogen carbonate solution, and the resulting mixed solution was extracted with ethyl acetate. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) so give the title compound (240.5 mg) as a slightly yellow foam.

Mass spectrum (ESI, m/): 691 [M−H]⁻.

According to the same method as the Reference Example 18-(a), Reference Example 18-(a)-2 to Reference Example 18-(a)-4 wore prepared.

TABLE 10

| Reference Example No. | Compound name<br>Structural formula<br>Mass spectrum |
|---|---|
| 18-(a)-2 | (S)-di-tert-butyl 2-((N-((benzyloxy)carbonyl)sulfamoyl)(3-(tert-butoxycarbonyl)benzyl)amino)succinate<br>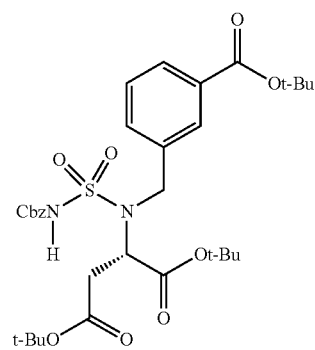<br>(ESI, m/z): 647 [M − H]⁻. |

TABLE 10-continued

| Reference Example No. | Compound name<br>Structural formula<br>Mass spectrum |
|---|---|
| 18-(a)-3 | (S)-di-tert-butyl 2-((N-((benzyloxy)carbonyl)sulfamoyl)(6-(tert-butoxy)-6-oxohexyl)amino)succinate<br>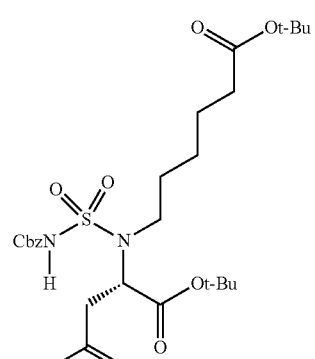<br>(ESI, m/z): 627 [M - H]⁻. |
| 18-(a)-4 | (S)-di-tert-butyl 2-((N-((benzyloxy)carbonyl)sulfamoyl)(methyl)amino)succinate<br>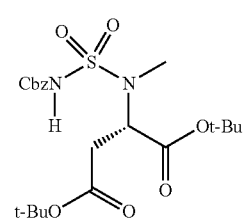<br>(ESI, m/z): 471 [M - H]⁻. |

According to the same method as the Reference Example 18-(a) except for using tert-butanol instead of benzyl alcohol, Reference Example 18(a)-5 to Reference Example 18-(a)-14 were prepared.

TABLE 11

| Reference Example No. | Compound name<br>Structural formula<br>Mass spectrum |
|---|---|
| 18-(a)-5 | (S)-di-tert-butyl 2-((N-(tert-butoxycarbonyl)sulfamoyl)amino)succinate<br>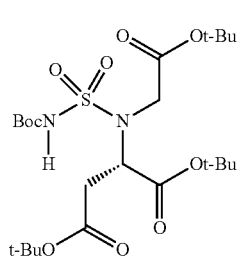<br>(ESI, m/z): 423 [M - H]⁻. |

TABLE 11-continued

| Reference Example No. | Compound name<br>Structural formula<br>Mass spectrum |
|---|---|
| 18-(a)-6 | (S)-di-tert-butyl 2-((2-(tert-butoxy)-2-oxoethyl)(N-(tert-butoxycarbonyl)sulfamoyl)amino)succinate<br>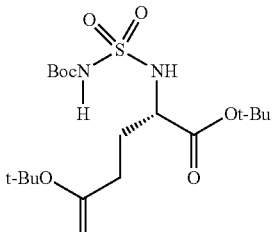<br>(ESI, m/z): 537 [M - H]⁻. |
| 18-(a)-7 | (S)-di-tert-butyl 2-((N-(tert-butoxycarbonyl)sulfamoyl)amino)pentanedioate<br>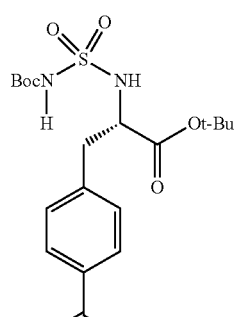<br>(ESI, m/z): 437 [M - H]⁻. |
| 18-(a)-8 | (S)-tert-butyl 4-(3-(tert-butoxy)-2-((N-(tert-butoxycarbonyl)sulfamoyl)amino)-3-oxopropyl)benzoate<br>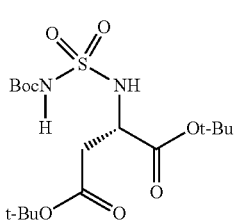<br>(ESI, m/z): 499 [M - H]⁻. |

TABLE 11-continued

| Reference Example No. | Compound name<br>Structural formula<br>Mass spectrum |
|---|---|
| 18-(a)-9 | (S)-tert-butyl 2-((N-(tert-butoxycarbonyl)sulfamoyl)amino)-3-(4-((tert-butyldimethylsilyl)oxy)phenyl)propanoate<br>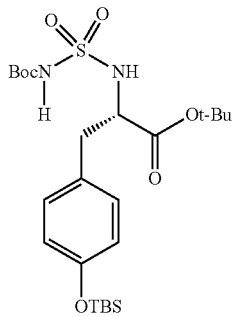<br>(ESI, m/z): 529 [M − H]⁻. |
| 18-(a)-10 | (S)-tert-butyl 2-((N-(tert-butoxycarbonyl)sulfamoyl)amino)-3-phenylpropanoate<br>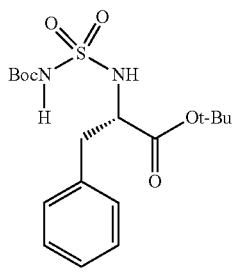<br>(DUIS, m/z): 399 [M − H]⁻. |
| 18-(a)-11 | tert-butyl 6-((N-(tert-butoxycarbonyl)sulfamoyl)amino)hexanoate<br>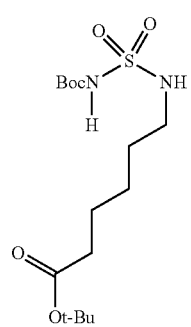<br>(ESI, m/z): 365 [M − H]⁻. |
| 18-(a)-12 | tert-butyl 2-((N-(tert-butoxycarbonyl)sulfamoyl)amino)acetate<br>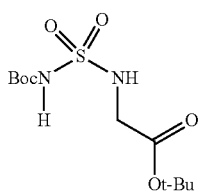<br>(ESI, m/z): 309 [M − H]⁻. |
| 18-(a)-13 | (S)-tert-butyl 2-((N-(tert-butoxycarbonyl)sulfamoyl)amino)propanoate<br>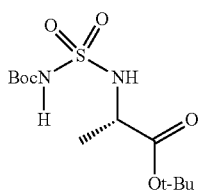<br>(ESI, m/z): 323 [M − H]⁻. |
| 18-(a)-14 | tert-butyl N-methylsulfamoylcarbamate<br>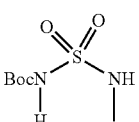<br>(ESI, m/z): 209 [M − H]⁻. |

Reference Example 18-(b)

Preparation of (S)-di-tert-butyl 2-((N-((benzyloxy)carbonyl)-N-(4-((4-(2,3-bis(tert-butoxycarbonyl)guanidino)benzoyl)oxy)benzyl)sulfamoyl)(3-((2-(trimethylsilyl)ethoxy)carbonyl)benzyl)amino)succinate

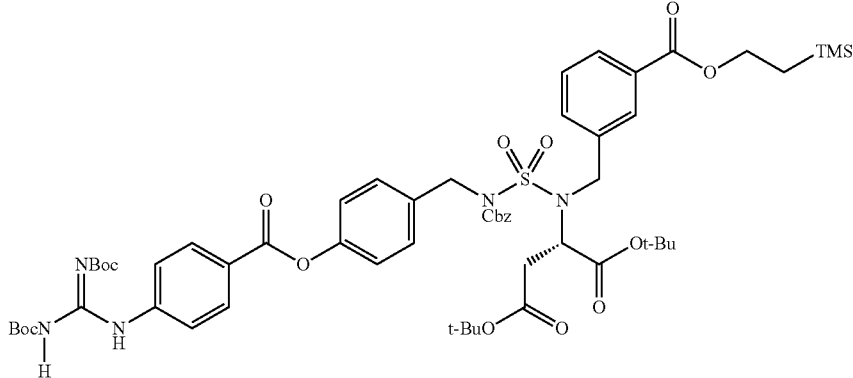

To a solution of (S)-di-tert-butyl 2-((N-((benzyloxy)carbonyl)sulfamoyl)(3-((2-(trimethylsilyl)ethoxy)carbonyl)benzyl)amino)succinate (240 mg) prepared according to the same manner as the Reference Example 18-(a), 4-(hydroxymethyl)phenyl 4-(2,3-bis(tert-butoxycarbonyl)guanidino)benzoate (188 mg) prepared according to the same manner as the Reference Example 1-(g), and triphenylphosphine (111 mg) in tetrahydrofuran (10 mL) in a 50 mL round-bottom flask was added diisopropyl azodicarboxylate (81 μL) at room temperature under argon atmosphere with stirring, and the resulting mixture was stirred at room temperature for 30 minutes. After the reaction was completed, the reaction solution was concentrated under reduced pressure. The resulting residues were purified by medium pressure preparative chromatography (silica gel, elution solvent; hexane:ethyl acetate) to give the title compound (352.3 mg) as a white foam.

Mass spectrum (ESI, m/z): 1161 [M+H]+.

Reference Example 18-(c)

Preparation of (S)-3-(((N-((benzyloxy)carbonyl)-N-(4-((4-(2,3-bis(tert-butoxycarbonyl)guanidino)benzoyl)oxy)benzyl)sulfamoyl)(1,4-di-tert-butoxy-1,4-dioxobutan-2-yl)amino)methyl)benzoic acid

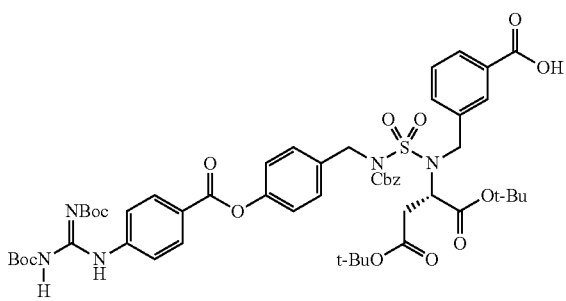

To a solution of (S)-di-tert-butyl 2-((N-((benzyloxy)carbonyl)-N-(4-((4-(2,3-bis(tert-butoxycarbonyl)guanidino)benzoyl)oxy)benzyl)sulfamoyl)(3-((2-(trimethylsilyl)ethoxy)carbonyl)benzyl)amino)succinate (350 mg) prepared in the Reference Example 18-(b) in tetrahydrofuran (10 mL) in a 50 mL round-bottom flask was added tetrabutylammonium fluoride (a 1.0 M solution in tetrahydrofuran) (0.450 mL) at room temperature under argon atmosphere with stirring, and the resulting mixture was stirred at room temperature for 2 hours. Additionally, tetrabutylammonium fluoride (a 1.0 M solution in tetrahydrofuran) (0.450 mL) was added thereto, and the resulting mixture was stirred at room temperature for 18 hours. After the reaction was completed, to the reaction solution was added a saturated aqueous ammonium chloride solution, and the resulting mixed solution was extracted with ethyl acetate. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (205 mg) as a white foam.

Mass spectrum (ESI, m/z): 1060 [M+H]+.

Reference Example 19-(a)

Preparation of methyl 2,3-bis(benzyloxy)benzoate

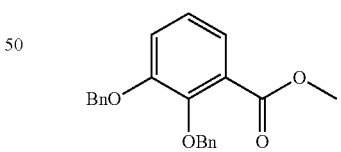

To a suspension of methyl 2,3-dihydroxybenzoate (15.4 g), potassium carbonate (41.2 g), and tetrabutylammonium bromide (1.53 g) in acetone (150 mL) in a 500 mL round-bottom flask was added benzyl bromide (24.3 mL) at 0° C. under argon gas flow with stirring, and the resulting mixture was stirred at room temperature for 5 hours. After the reaction was completed, the reaction solution was concentrated under reduced pressure. To the concentrated residues was added water (40 mL) at 0° C., the resulting mixture was stirred, and the resulting mixed solution was extracted with ethyl acetate. The resulting organic layer was washed with saturated brine, dried over anhydrous magnesium sulfate, filtered, and concentrated under reduced pressure to give the title compound (38.9 g) as a colorless oil.

Mass spectrum (ESI, m/z): 371 [M+Na]⁺.

Reference Example 19-(b)

Preparation of 2,3-bis(benzyloxy)benzoic acid

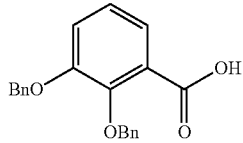 [SMILES: O=C(O)c1cccc(OCc2ccccc2)c1OCc1ccccc1]

To a solution of methyl 2,3-bis(benzyloxy)benzoate (36.9 g) prepared in the Reference Example 19-(a) in tetrahydrofuran (70 mL)/methanol (70 mL) in a 500 mL round-bottom flask was added a 5 M aqueous sodium hydroxide solution (45.0 mL) at room temperature under air atmosphere with stirring, and the resulting mixture was stirred at 50° C. for 2 hours. After the reaction was completed, to the ice-cooled reaction solution were added 6 M hydrochloric acid (52.0 mL) and water (100 mL). The resulting mixture was stirred at room temperature for 1 hour, the precipitated solids were collected by filtration, and dried under reduced pressure to give the title compound (31.0 g) as white solids.

Mass spectrum (ESI, m/z): 333 [M–H]⁻.

Reference Example 19-(c)

Preparation of 3-(benzyloxy)-2-hydroxybenzoic acid

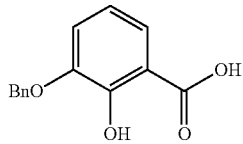 [SMILES: O=C(O)c1cccc(OCc2ccccc2)c1O]

To a solution of 2,3-bis(benzyloxy)benzoic acid (15 g) prepared in the Reference Example 19-(b) in N,N-dimethylacetamide (24 mL) in a 200 mL round-bottom flask was added piperidine (18.0 mL) at room temperature under argon gas flow with stirring, and the resulting mixture was stirred at 150° C. for 7.25 hours. After the reaction was completed, the reaction solution was poured into hydrochloric acid to adjust the pH to 2 to 3, and the precipitated solids were collected by filtration. The resulting solids were dissolved into ethyl acetate, the resulting solution was washed sequentially with water, 1 M hydrochloric acid, and saturated brine, dried over magnesium sulfate, filtered, and concentrated under reduced pressure to give the title compound (9.483 q) as white solids.

Mass spectrum EST, m/z) 267 [M+Na].

Reference Example 19-(d)

Preparation of 2-(trimethylsilyl)ethyl 3-(benzyloxy)-2-hydroxybenzoate

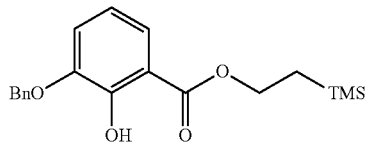 [SMILES: C[Si](C)(C)CCOC(=O)c1cccc(OCc2ccccc2)c1O]

To a solution of 3-(benzyloxy)-2-hydroxybenzoic acid (5.05 g) prepared in the Reference Example 19-(c), 2-(trimethylsilyl)ethanol (3.21 mL), and triphenylphosphine (6.43 g) in tetrahydrofuran (30 mL) in a 200 mL round-bottom flask was added diisopropyl azodicarboxylate (a 1.9 M solution in toluene) (12.9 mL) at room temperature under argon atmosphere with stirring, and the resulting mixture was stirred at room temperature for 16.5 hours. Additionally, 2-(trimethylsilyl)ethanol (3.21 mL), triphenylphosphine (6.51 g), and diisopropyl azodicarboxylate (a 1.9 M solution in toluene) (13.0 mL) were added thereto with stirring at room temperature, and the resulting mixture was stirred at room temperature for 2.5 hours. After the reaction was completed, to the reaction solution was added water, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (2.980 g) as a yellow oil.

Mass spectrum (ESI, m/z): 343 [M–H]⁻.

Reference Example 19-(e)

Preparation of methyl 2-(3-hydroxyprop-1-yn-1-yl)-4-nitrobenzoate

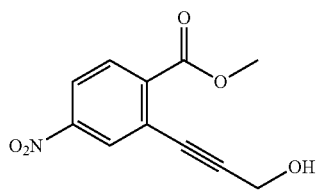 [SMILES: COC(=O)c1ccc([N+](=O)[O-])cc1C#CCO]

To a solution of methyl 2-bromo-4-nitrobenzoate (5.30 g) in tetrahydrofuran (30 mL) in a 100 mL round-bottom flask were added propargyl alcohol (2.90 mL), triethylamine (5.60 mL), copper(I) iodide (40 mg), and dichloro[1,1'-bis(diphenylphosphino)ferrocene]palladium dichloromethane adduct (165 mg) at room temperature under argon atmosphere with stirring, the resulting mixture was stirred at 45° C. for 8 hours, stirred at room temperature for 14 hours, stirred at 45° C. for 10 hours, stirred at room temperature for 13 hours, and stirred at 45° C. for 7 hours. After the reaction was completed, to the reaction solution was added ethyl acetate and Celite, the resulting mixture was filtered, and the resulting filtrate was concentrated under reduced pressure. The resulting residues were purified by medium pressure preparative chromatography (silica gel, elution solvent; hexane:ethyl acetate) to give the title compound (4.35 g) as orange solids.

Mass spectrum (CI, m/z): 236 [M+H]⁺.

Reference Example 19-(f)

Preparation of methyl 4-amino-2-(3-hydroxypropyl)benzoate

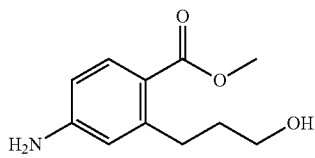

To a solution of methyl 2-(3-hydroxyprop-1-yn-1-yl)-4-nitrobenzoate (1.50 g) prepared in the Reference Example 19-(e) in ethanol (15 mL)/tetrahydrofuran (15 mL) in a 300 mL round-bottom flask was added 10% palladium carbon (wetted with 54.51% water, PE-type manufactured by NE CHEMCAT Corporation) (161.3 mg) at room temperature under argon atmosphere with stirring, the atmosphere in the reaction system was replaced with hydrogen atmosphere, and then the resulting mixture was stirred at room temperature for 8 hours. To the reaction solution was added ethyl acetate and Celite, the resulting mixture was filtered, the resulting filtrate was concentrated under reduced pressure, and left to stand at room temperature for 2 days. To a solution of the concentrated residues in ethanol (15 mL)/3 tetrahydrofuran (15 mL) was added 10% palladium carbon (wetted with 54.51% water, PR-type manufactured by NE CHEMCAT Corporation) (480 mg) under argon atmosphere with stirring, the atmosphere in the reaction system was replaced with hydrogen atmosphere, and then the resulting mixture was stirred at room temperature for 8 hours. After the reaction was completed, to the reaction solution was added ethyl acetate and Celite, the resulting mixture was filtered, and the resulting filtrate was concentrated under reduced Pressure. The resulting residues were purified by medium pressure preparative chromatography (silica gel, elution solvent; hexane:ethyl acetate to give the title compound (902.6 mg) as a colorless oil.

Mass spectrum (ESI, m/z): 210 [M+H]⁺.

Reference Example 19-(g)

Preparation of 4-((tert-butoxycarbonyl)amino)-2-(3-hydroxypropyl)benzoic acid

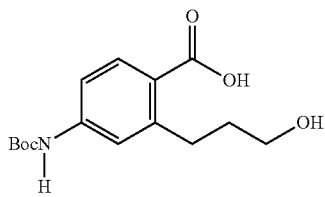 [SMILES: CC(C)(C)OC(=O)Nc1ccc(C(=O)O)c(CCCO)c1]

To a solution of methyl 4-amino-2-(3-hydroxypropyl) benzoate (900 mg) prepared in the Reference Example 19-(f) in methanol (9 mL) in a 100 mL round-bottom flask was added a 1N aqueous sodium hydroxide solution (9 mL) at room temperature under argon atmosphere with stirring, and the resulting mixture was stirred at 50° C. for 5 hours. Then, di-tert-butyl dicarbonate (1.92 g) was added thereto with stirring at 0° C., and the resulting mixture was stirred at room temperature for 16 hours. After the reaction was completed, to the reaction solution were added water (9 mL) and 1N hydrochloric acid (18 mL), and the resulting mixed solution was extracted with ethyl acetate. The resulting organic layer was washed with saturated brine, dried over anhydrous magnesium sulfate, filtered, and concentrated under reduced pressure to give the title compound (1.33 g) as a brown foam.

Mass spectrum (ESI, m/z): 294 [M−H]⁻.

Reference Example 19-(h)

Preparation of benzyl 4-((tert-butoxycarbonyl) amino)-2-(3-hydroxypropyl)benzoate

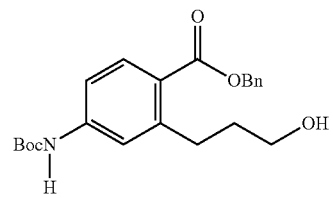 [SMILES: CC(C)(C)OC(=O)Nc1ccc(C(=O)OCc2ccccc2)c(CCCO)c1]

To a solution of 4-((tert-butoxycarbonyl)amino)-2-(3-hydroxypropyl)benzoic acid (1.33 g) prepared in the Reference Example 19-(g) in dimethylformamide (13 mL) in a 200 mL round-bottom flask were added benzyl bromide (642 μL) and N,N-diisopropylethylamine (1.57 mL) at room temperature under argon atmosphere with stirring, and the resulting mixture was stirred at room temperature for 18 hours. After the reaction was completed, to the reaction solution was added water, and the resulting mixed solution was extracted with tert-butyl methyl ether. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the target compound (1.32 g) as a colorless oil.

Mass spectrum (ESI, m/z): 386 [M+H]⁻.

Reference Example 19-(i)

Preparation of 2-(trimethylsilyl)ethyl 3-(benzyloxy)-2-(3-(2-((benzyloxy)carbonyl)-5-((tert-butoxycarbonyl)amino)phenyl)propoxy)benzoate

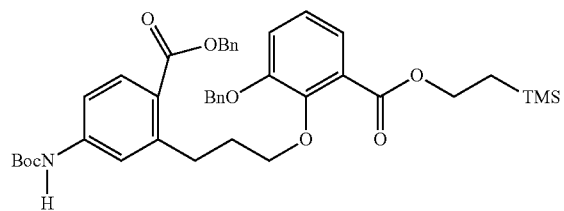 [SMILES: CC(C)(C)OC(=O)Nc1ccc(C(=O)OCc2ccccc2)c(CCCOc2c(OCc3ccccc3)cccc2C(=O)OCC[Si](C)(C)C)c1]

To a solution of 2-(trimethylsilyl)ethyl 3-(benzyloxy)-2-hydroxybenzoate (2.98 g) prepared in the Reference Example 19-(d) in tetrahydrofuran (20 mL) in a 200 mL round-bottom flask were added benzyl 4-((tert-butoxycarbonyl)amino)-2-(3-hydroxypropyl)benzoate (2.32 g) prepared according to the same manner as the Reference Example 19-(h), tributylphosphine (3.40 mL), and 1,1'-azobis(N,N-dimethylformamide) (2.40 g) under ice-cooling under argon atmosphere with stirring, and the resulting mixture was stirred at room temperature overnight. After the reaction was completed, to the reaction solution was added water, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (3.131 g) as a yellow oil.

Mass spectrum (ESI, m/z): 734 [M+Na].

According to the same method as the Reference Example 19-(1), Reference Example 19-(i)-2 to Reference Example 19-(i)-4 were prepared.

TABLE 12

| Reference Example No. | Compound name Structural formula Mass spectrum |
|---|---|
| 19-(i)-2 | benzyl 2-(3-(2-(benzyloxy)-6-(((tert-butyldimethylsilyl)oxy)methyl)phenoxy)propyl)-4-((tert-butoxycarbonyl)amino)benzoate<br>(ESI, m/z): 734 [M + Na]⁺. |
| 19-(i)-3 | benzyl 2-(3-(2-(benzyloxy)-5-(((tert-butyldimethylsilyl)oxy)methyl)phenoxy)propyl)-4-((tert-butoxycarbonyl)amino)benzoate<br>(ESI, m/z): 734 [M + Na]⁺. |
| 19-(i)-4 | benzyl 2-(3-(2-(benzyloxy)-4-(((tert-butyldimethylsilyl)oxy)methyl)phenoxy)propyl)-4-((tert-butoxycarbonyl)amino)benzoate<br>(ESI, m/z): 734 [M + Na]⁺. |

Reference Example 19-(j)

Preparation of 4-((tert-butoxycarbonyl)amino)-2-(3-(2-hydroxy-6-((2-(trimethylsilyl)ethoxy)carbonyl)phenoxy)propyl)benzoic acid To a solution of 2-(trimethylsilyl)ethyl 3-(benzyloxy)-2-(3-(2-((benzyloxy)carbonyl)-5-(tert-butoxycarbonyl)amino)phenyl)propoxy)benzoate (3.13 g) prepared in the Reference Example 19-(i) in tetrahydrofuran (10 mL)/ethanol (10 mL) in a 200 mL round-bottom flask was added 10% palladium carbon (wetted with ca. 55% water, manufactured by Tokyo Chemical industry Co., Ltd.) (0.938 g) at room temperature under air atmosphere with stirring, and the resulting mixture was stirred at room temperature under hydrogen atmosphere for 2.5 hours. After the reaction was completed, the reaction solution was filtered throngs Celite, and concentrated under reduced pressure to give the title compound (2.166 g) as a colorless oil.

Mass spectrum (ESI, m/z): 530 [M–H]⁻.

Reference Example 19-(j)-2

Preparation of 4-((tert-butoxycarbonyl)amino)-2-(3-(2-(((tert-butyldimethylsilyl)oxy)methyl)-6-hydroxyphenoxy)propyl)benzoic acid To a solution of benzyl 2-(3-(2-(benzyloxy)-6-(((tert-butyldimethylsilyl)oxy)methyl)phenoxy)propyl)-4-((tert-butoxycarbonyl)amino)benzoate (100 mg) prepared in the Reference Example 19-(i)-2 in ethyl acetate (4.00 mL) in a 50 mL round-bottom flask was added BNA-5D (wetted with 52.97% water, manufactured by NE CHEMCAT Corporation) (20 mg) at room temperature, the atmosphere in the reaction system was replaced with hydrogen atmosphere, and then the resulting mixture was stirred at room temperature for 4 hours. After the reaction was completed, the reaction solution was filtered through Celite, washed with ethyl acetate, and the resulting filtrate was concentrated under reduced pressure to give the title compound (84 mg) as a brown oil.

Mass spectrum (ESI, m/z): 530 [M−H]⁻.

According to the same method as the Reference Example 19-(j)-2, Reference Example 19-(j)-3 to Reference Example 19-(j)-4 were prepared.

TABLE 13

| Reference Example No. | Compound name Structural formula Mass spectrum |
|---|---|
| 19-(j)-3 | 4-((tert-butoxycarbonyl)amino)-2-(3-(5-(((tert-butyldimethylsilyl)oxy)methyl)-2-hydroxyphenoxy)propyl)benzoic acid 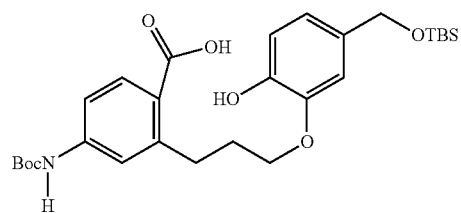 (ESI, m/z): 554 [M + Na]⁺. |
| 19-(j)-4 | 4-((tert-butoxycarbonyl)amino)-2-(3-(4-(((tert-butyldimethylsilyl)oxy)methyl)-2-hydroxyphenoxy)propyl)benzoic acid 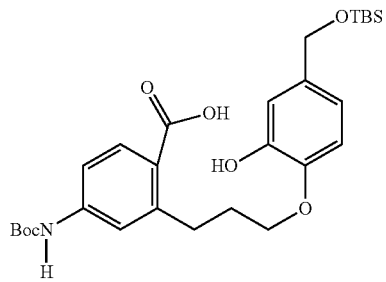 (ESI, m/z): 530 [M − H]⁻. |

Reference Example 19-(k)

Preparation of 2-(trimethylsilyl)ethyl 10-((tert-butoxycarbonyl)amino)-13-oxo-6,7,8,13-tetrahydrodibenzo[b,f][1,4]dioxecin-4-carboxylate

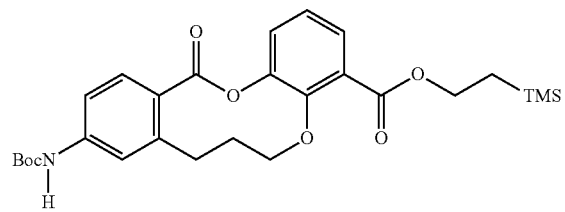 [SMILES: CC(C)(C)OC(=O)Nc1ccc2c(c1)CCCOc1c(cccc1C(=O)OCC[Si](C)(C)C)OC2=O]

To a solution of 4-((tert-butoxycarbonyl)amino)-2-(3-(2-hydroxy-6-((2-(trimethylsilyl)ethoxy)carbonyl)phenoxy)propyl)benzoic acid (1.18 g) prepared in the Reference Example 19-(j) and 4-dimethylaminopyridine (0.015 g) in pyridine (10 mL) in a 100 mL round-bottom flask was added 1-(3-dimethylaminopropyl)-3-ethylcarbodiimide hydrochloride (0.641 g) at room temperature under argon gas flow with stirring, and the resulting mixture was stirred at room temperature overnight. After the reaction was completed, to the reaction solution was added water, and the resulting mixed solution was extracted with ethyl acetate. The resulting organic layer was washed sequentially with 0.5 M hydrochloric acid and saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (0.722) as a colorless oil.

Mass spectrum (ESI, m/z): 512 [M−H]⁻.

According to the same method as the Reference Example 19-(k), Reference Example 19-(k)-2 to Reference Example 19-(k)-4 were prepared.

TABLE 14

| Reference Example No. | Compound name Structural formula Mass spectrum |
|---|---|
| 19-(k)-2 | tert-butyl (4-(((tert-butyldimethylsilyl)oxy)methyl)-13-oxo-6,7,8,13-tetrahydrodibenzo[b,f][1,4]dioxecin-10-yl)carbamate 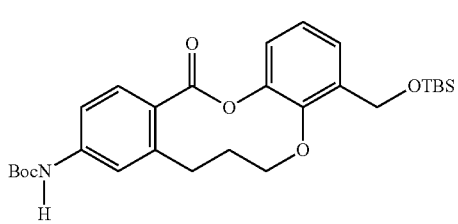 (ESI, m/z): 512 [M − H]⁻. |

TABLE 14-continued

| Reference Example No. | Compound name<br>Structural formula<br>Mass spectrum |
|---|---|
| 19-(k)-3 | tert-butyl (3-(((tert-butyldimethylsilyl)oxy)methyl)-13-oxo-6,7,8,13-tetrahydrodibenzo[b,f][1,4]dioxecin-10-yl)carbamate<br>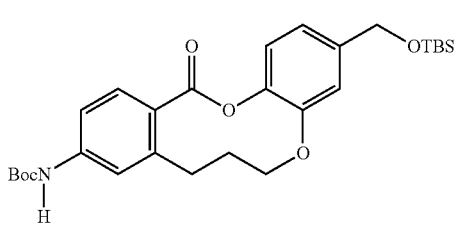<br>(ESI, m/z): 512 [M − H]⁻. |
| 19-(k)-4 | tert-butyl (2-(((tert-butyldimethylsilyl)oxy)methyl)-13-oxo-6,7,8,13-tetrahydrodibenzo[b,f][1,4]dioxecin-10-yl)carbamate<br>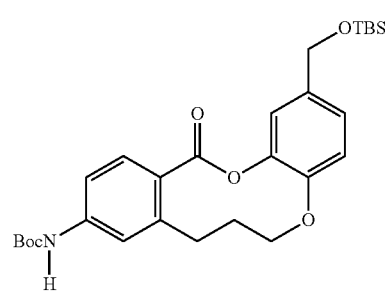<br>(ESI, m/z): 512 [M − H]⁻. |

Reference Example 19-(l)

Preparation of 10-((tert-butoxycarbonyl)amino)-1-oxo-6,7,8,13-tetrahydrodibenzo[b,f][1,4]dioxecin-4-carboxylic acid

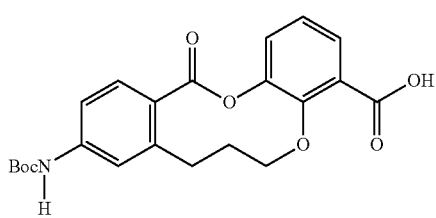

To a solution of 2-(trimethylsilyl)ethyl 10-((tert-butoxycarbonyl)amino)-13-oxo-6,7,8,13-tetrahydrodibenzo[b,f][1,4]dioxecin-4-carboxylate (0.500 g) prepared according to the same manner as the Reference Example 19-(k) in tetrahydrofuran (3 mL) in a 30 mL cylindrical flask was added tetrabutylammonium fluoride (1.95 mL) (a 1.0 M solution in tetrahydrofuran) at room temperature under air atmosphere with stirring, and the resulting mixture was stirred at room temperature overnight. After the reaction was completed, to the reaction solution was added water, and the resulting mixed solution was extracted with ethyl acetate. The resulting organic layer was washed sequentially with 0.1N hydrochloric acid and saturated brine, dried over anhydrous magnesium sulfate, filtered, and concentrated under reduced pressure to give the title compound (0.455 g) as a pale yellow foam.

Mass spectrum (ESI, m/z): 412 [M−H]⁻.

According to the same method as the Reference Example 19-(l), Reference Example 19-(l)-2 to Reference Example 19-(l)-4 were prepared.

TABLE 15

| Reference Example No. | Compound name<br>Structural formula<br>Mass spectrum |
|---|---|
| 19-(l)-2 | tert-butyl (4-(hydroxymethyl)-13-oxo-6,7,8,13-tetrahydrodibenzo[b,f][1,4]dioxecin-10-yl)carbamate<br>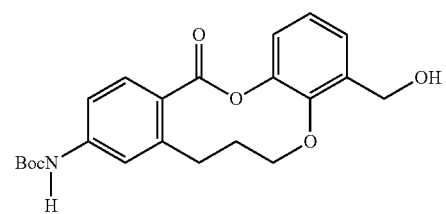 [SMILES: CC(C)(C)OC(=O)Nc1ccc2c(c1)CCCOc1c(cccc1C(=O)O)OC2=O]<br>(ESI, m/z): 398 [M − H]⁻. |
| 19-(l)-3 | tert-butyl (3-(hydroxymethyl)-13-oxo-6,7,8,13-tetrahydrodibenzo[b,f][1,4]dioxecin-10-yl)carbamate<br>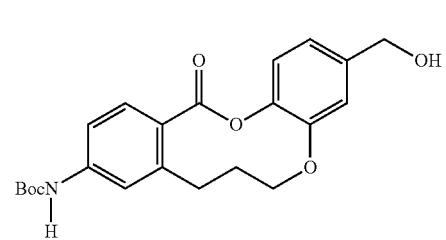<br>(ESI, m/z): 398 [M − H]⁻. |
| 19-(l)-4 | tert-butyl (2-(hydroxymethyl)-13-oxo-6,7,8,13-tetrahydrodibenzo[b,f][1,4]dioxecin-10-yl)carbamate<br>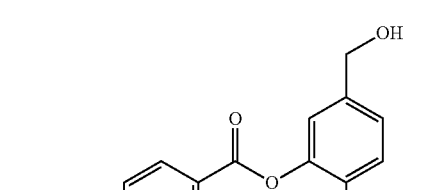<br>(ESI, m/z): 398 [M − H]⁻. |

Reference Example 19-(m)

Preparation of 10-amino-13-oxo-6,7,8,13-tetrahydrodibenzo[b,f][1,4]dioxecin-4-carboxylic acid hydrochloride

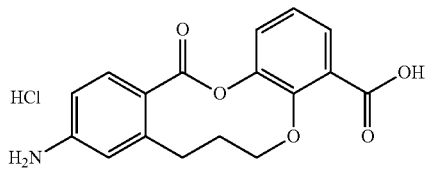 [SMILES: Cl ; Nc1ccc2c(c1)CCCOc1c(cccc1C(=O)O)OC2=O]

To a solution of 10-((tert-butoxycarbonyl)amino)-13-oxo-6,7,8,13-tetrahydrodibenzo[b,f][1,4]dioxecin-4-carboxylic acid (2.52 g) prepared according to the same manner as the Reference Example 19-(l) in tetrahydrofuran (5 mL) in a 30 m cylindrical flask was added a 4 M hydrogen chloride/cyclopentyl methyl ether solution (14.93 mL) at room temperature under argon gas flow with stirring, and the resulting mixture was stirred at 53° C. for 5 hours. After the reaction was completed, the reaction solution was allowed to cool to room temperature, and hexane and diisopropylether were added thereto. The resulting precipitates were collected by filtration, washed with hexane and diisopropylether, and air-dried overnight to give the title compound (2.073 g) as white solids.

Mass spectrum (ESI, m/z) 314 [M+H]$^+$.

According to the same method as the Reference Example 19-(m), Reference Example 19-(m)-2 to Reference Example 19-(m)-4 were prepared.

TABLE 16

| Reference Example No. | Compound name<br>Structural formula<br>Mass spectrum |
|---|---|
| 19-(m)-2 | (S)-2-((N-((10-amino-13-oxo-6,7,8,13-tetrahydrodibenzo[b,f][1,4]dioxecin-4-yl)methyl)sulfamoyl)amino)succinic acid hydrochloride<br>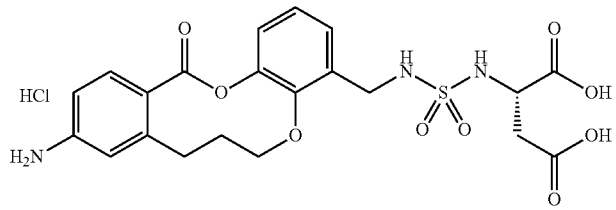 [SMILES: Cl ; Nc1ccc2c(c1)CCCOc1c(CNS(=O)(=O)N[C@@H](CC(=O)O)C(=O)O)cccc1OC2=O]<br>(ESI, m/z): 494 [M + H]$^-$. |
| 19-(m)-3 | (S)-2-((N-((10-amino-13-oxo-6,7,8,13-tetrahydrodibenzo[b,f][1,4]dioxecin-3-yl)methyl)sulfamoyl)amino)succinic acid hydrochloride<br>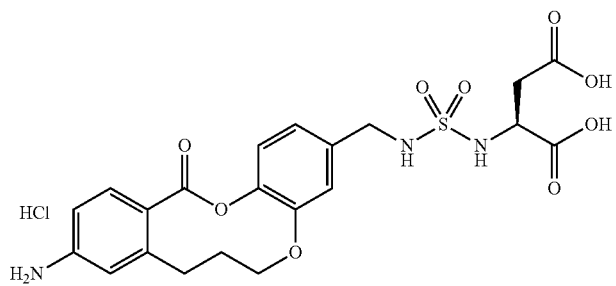 [SMILES: Cl ; Nc1ccc2c(c1)CCCOc1cc(CNS(=O)(=O)N[C@@H](CC(=O)O)C(=O)O)ccc1OC2=O]<br>(ESI, m/z): 494 [M + H]$^-$. |

TABLE 16-continued

| Reference Example No. | Compound name<br>Structural formula<br>Mass spectrum |
|---|---|
| 19-(m)-4 | (S)-2-((N-((10-amino-13-oxo-6,7,8,13-tetrahydrodibenzo[b,f][1,4]dioxecin-2-yl)methyl)sulfamoyl)amino)succinic acid hydrochloride<br>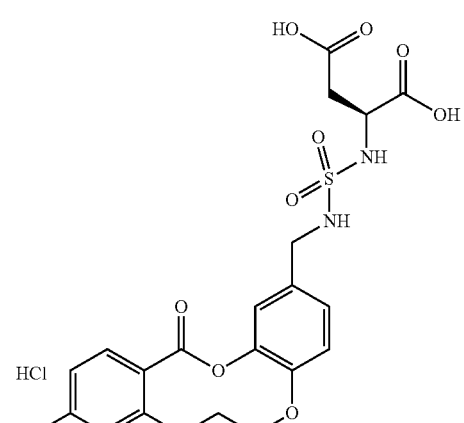<br>(ESI, m/z): 494 [M + H]⁻. |

Reference Example 19-(n)

Preparation of 10-(2,3-bis(tert-butoxycarbonyl)guanidino)-13-oxo-6,7,8,13-tetrahydrodibenzo[b,f][1,4]dioxecin-4-carboxylic acid

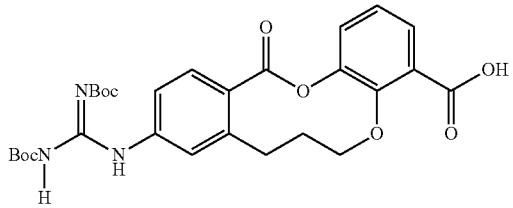

To a solution of 10-amino-13-oxo-6,7,8,13-tetrahydrodibenzo[b,f][1,4]dioxecin-4-carboxylic acid hydrochloride (2.07 g) prepared according to the same manner as the Reference Example 19-(m) and triethylamine (4.10 mL) in tert-butanol (10 ml) in a 100 mL round-bottom flask was added tert-butyl (((tert-butoxycarbonyl)imino) (1H-pyrazol-1-yl)methyl)carbamate (5.53 g) at room temperature under argon gas flow with stirring, and the resulting mixture was stirred at room temperature for 5 days. After the reaction was completed, the reaction solution was concentrated under reduced pressure, methanol (300 mL) and a 10% aqueous citric acid solution (175 mL) were added thereto, and the resulting mixture was stirred at room temperature for 1 hour. The precipitated solids were collected by filtration, washed with a mixed solvent of methanol and water 11:2 (v/v)) (200 mL), air-dried overnight, dried under reduced pressure at 50° C. for 6 hours, and additionally air-dried overnight to give the title compound (3.243 g) as white solids.

Mass spectrum (ESI, m/z): 556 [M+H]⁺.

Reference Example 19-(o)

Preparation of (R)-di-tert-butyl 2-(2-nitrophenylsulfonamide)succinate

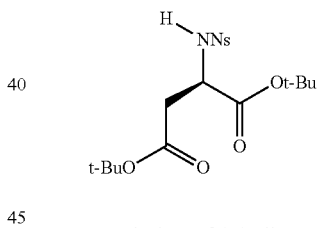

To a solution of (R)-di-tert-butyl 2-aminosuccinate hydrochloride (14.0 g) and N,N-diisopropylethylamine (21.7 mL) in dichloromethane (60 mL) in a 360 mL round-bottom flask was added dividedly 2-nitrobenzenesulfonyl chloride (11.5 g) at 0° C. under argon atmosphere with stirring, and the resulting mixture was stirred at room temperature for 1.5 hours. After the reaction was completed, to the reaction solution was added water, and the resulting mixed solution was extracted with dichloromethane. The resulting organic layer was washed with saturated brine, dried over anhydrous magnesium sulfate, filtered, and concentrated under reduced pressure. The concentrated residues were dissolved into dichloromethane, filtered through Celite, and the resulting filtrate was concentrated under reduced pressure. To the resulting residues were added acetone (30 mL), water (60 mL), and ethanol (6 mL), and the resulting mixture was stirred at room temperature for 1 hour. The resulting precipitates were collected by filtration, and air-dried to give the title compound (19.74 g) as white solids.

Mass spectrum (ESI, m/z): 429 [M−H]⁻.

Reference Example 19-(p)

Preparation of tetra-tert-butyl 3,12-bis((2-nitrophenyl)sulfonyl)-6,9-dioxa-3,12-diazatetradecane-1,2,13,14-tetracarboxylate

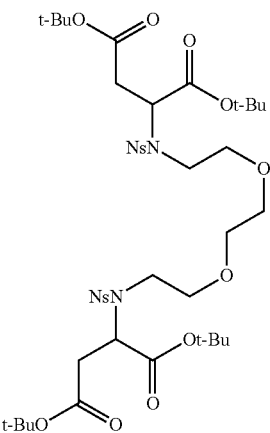

To a solution of (S)-di-tert-butyl 2-(2-nitrophenylsulfonamide)succinate (4.53 g) prepared according to the same manner as the Reference Example 1-(a) and (R)-di-tert-butyl 2-(2-nitrophenylsulfonamide)succinate (4.51 g) prepared in the Reference Example 19-(o) in tetrahydrofuran (40 mL) in a 300 mL round-bottom flask were added triethyleneglycol (1.45 mL), tributylphosphine (5.90 mL), and 1,1'-azobis(N,N-dimethylformamide) (4.11 g) under ice-cooling under argon atmosphere with stirring, and the resulting mixture was stirred at room temperature overnight. Additionally, tributylphosphine (5.92 mL) and 1,1'-azobis(N,N-dimethylformamide) (4.10 g) were added thereto with stirring under ice-cooling, and the resulting mixture was stirred at room temperature overnight. After the reaction was completed, to the reaction solution was added water, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (4.66 g) as a pale yellow oil.

Mass spectrum (ESI, m/z): 997 [M-Na].

Reference Example 19-(q)

Preparation of tetra-tert-butyl 6,9-dioxa-3,12-diazatetradecane-1,2,13,14-tetracarboxylate

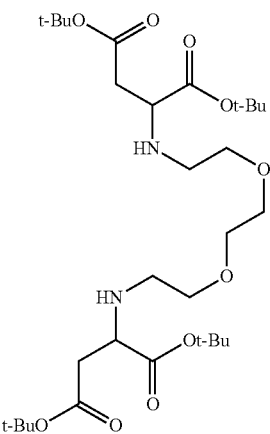 [SMILES: CC(C)(C)OC(=O)CC(NCCOCCOCCNC(CC(=O)OC(C)(C)C)C(=O)OC(C)(C)C)C(=O)OC(C)(C)C]

To a solution of tetra-tert-butyl 3,12-bis((2-nitrophenyl)sulfonyl)-6,9-dioxa-3,12-diazatetradecane-1,2,13,14-tetracarboxylate (4.66 g) prepared in the Reference Example 19-(p) in dimethylformamide (30 mL) in a 300 mL round-bottom flask were added potassium carbonate (2.00 g) and 4-tert-butylthiophenol (2.01 mL) at room temperature under argon atmosphere with stirring, and the resulting mixture was stirred at room temperature overnight. After the reaction was completed, to the reaction solution was added 1N hydrochloric acid, and the resulting mixture was washed with ethyl acetate. To the resulting aqueous layer was added a 1N aqueous sodium hydroxide solution, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate, and then ethyl acetate:methanol) to give the title compound (2.442 g) as a pale yellow oil.

Mass spectrum (ESI, m/z) 605 [M+H]$^+$.

Reference Example 21-(a)

Preparation of (2R,13R)-tetra-tert-butyl 3,12-bis(2-nitrophenyl)sulfonyl)-6,9-dioxa-3,12-diazatetradecane-1,2,13,14-tetracarboxylate

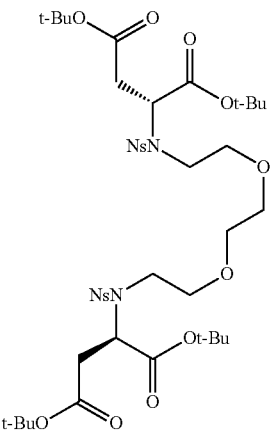

To a solution of (R)-di-tert-butyl 2-(2-nitrophenylsulfonamide)succinate (8.28 g) prepared in the Reference Example 19-(o) in tetrahydrofuran (40 mL) in a 300 mL round-bottom flask were added triethyleneglycol (1.33 mL), tributylphosphine (5.42 mL), and 1,1'-azobis(N,N-dimethylformamide) (3.78 g) under ice-cooling under argon atmosphere with stirring, and the resulting mixture was stirred for 30 minutes, then stirred at room temperature overnight. After the reaction was completed, to the reaction solution was added water, and the resulting mixed solution was extracted with ethyl acetate. The resulting organic layer was washed with saturated brine, dried over anhydrous sodium sulfate, filtered, and concentrated under reduced pressure. The resulting residues were purified by medium pressure preparative chromatography (silica gel, elution solvent; hexane:ethyl acetate) to give the title compound (6.47 g) as a pale yellow oil.

Mass spectrum (ESI, m/z): 992 [M+NH$_4$]$^+$.

Reference Example 21-(b)

Preparation of (2R,13R)-tetra-tert-butyl 6,9-dioxa-3,12-diazatetradecane-1,2,13,14-tetracarboxylate

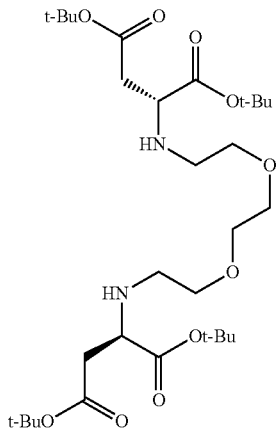 [SMILES: CC(C)(C)OC(=O)C[C@@H](NCCOCCOCCN[C@H](CC(=O)OC(C)(C)C)C(=O)OC(C)(C)C)C(=O)OC(C)(C)C]

To a solution of (2R,13R)-tetra-tert-butyl 3,12-bis((2-nitrophenyl)sulfonyl)-6,9-dioxa-3,12-diazatetradecane-1,2,13,14-tetracarboxylate (6.47 g) prepared in the Reference Example 21-(a) in dimethylformamide (50 mL) in a 200 mL round-bottom flask were added potassium carbonate (2.78 g) and 4-tert-butylthiophenol (2.80 mL) at room temperature under argon atmosphere with stirring, and the resulting mixture was stirred at room temperature overnight, After the reaction was completed, to the reaction Solution was added 1N hydrochloric acid, and the resulting mixture was washed with ethyl acetate. To the resulting aqueous layer was added a 1N aqueous sodium hydroxide solution, and the resulting mixed solution was extracted with tert-butyl methyl ether. The resulting organic layer was washed with saturated brine, dried over anhydrous sodium sulfate, filtered, and concentrated under reduced pressure to give the title compound (3.297 g) as a slightly yellow oil.

Mass spectrum (ESI, r/z): 605 [M+H]$^+$.

Reference Example 22-(a)

Preparation of (2S,13S)-tetra-tert-butyl 3,12-bis(N-((benzyloxy)carbonyl)-N-methylsulfamoyl)-6,9-dioxa-3,12-diazatetradecane-1,2,13,14-tetracarboxylate

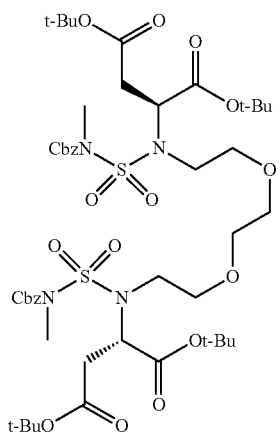 [SMILES: CN(C(=O)OCc1ccccc1)S(=O)(=O)N(CCOCCOCCN([C@@H](CC(=O)OC(C)(C)C)C(=O)OC(C)(C)C)S(=O)(=O)N(C)C(=O)OCc1ccccc1)[C@@H](CC(=O)OC(C)(C)C)C(=O)OC(C)(C)C]

To a solution of (2S,13S)-tetra-tert-butyl 3,12-bis(N-((benzyloxy)carbonyl)sulfamoyl)-6,9-dioxa-3,12-diazatetradecane-1,2,13,14-tetracarboxylate (1.96 g) prepared according to the same manner as the Reference Example 2-(c) in dehydrated tetrahydrofuran (15 mL) in a 50 mL three-necked flask was added methanol (170 µL) at room temperature under argon atmosphere with stirring. Then, tributylphosphine (1.40 mL) and 1,1'-azobis(N,N-dimethylformamide) (982.3 mg) were sequentially added thereto, and the resulting mixture was stirred at room temperature for 25 hours. After the reaction was completed, the reaction solution was poured into water (20 mL), and the resulting mixed solution was extracted with ethyl acetate (60 mL). The resulting organic layer was washed with a saturated aqueous sodium chloride solution (20 mL), dried over anhydrous magnesium sulfate, filtered, and concentrated under reduced pressure. The resulting residues were purified by medium press re preparative chromatography (silica gel, elution solvent; hexane:ethyl acetate) to give the title compound (1.71 g) as a colorless oil.

Mass spectrum (EST, m/z) 108 [M+Na]$^+$.

Reference Example 22-(b)

Preparation of (2S,13S)-tetra-tert-buty 3,12-bis N-methylsulfamoyl)-6,9-dioxa-3,2-diazatetradecane-1,2,13,14-tetracarboxylate

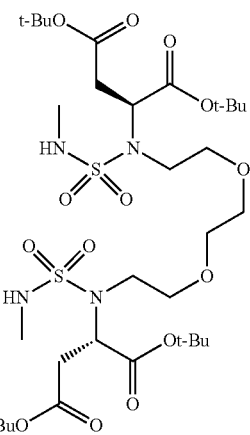

To a solution of (2S,13S)-tetra-tert-butyl 3,12-bis(N-((benzyloxy)carbonyl)-N-methy sulfamoyl)-6,9-dioxa-3,12-diazatetradecane-1,2,13,14-tetracarboxylate (1.71 g) prepared in the Reference Example 22-(a) in ethanol (20 mL) in a 200 mL round-bottom flask was added 5% palladium carbon (wetted with 54.28% water, STD-type manufactured by NE CHEMCAT Corporation) (345.1 mg) at room temperature, and the resulting mixture was degassed under reduced pressure. Then, after the atmosphere was replaced with hydrogen atmosphere, the mixture was stirred at room temperature for 7 hours. After the reaction was completed, the reaction solution was filtered through Celite, washed with ethyl acetate, and concentrated under reduced pressure to give the title compound (1.25 g) as a colorless oil.

Mass spectrum (ESI, m/z) 789 [M-]

Reference Example 22-(c)

Preparation of (2S,13S)-tetra-tert-butyl 3,12-bis(N-methyl-N-(4-((4-nitrobenzoyl)oxy)benzyl)sulfamoyl)-6,9-dioxa-3,12-diazatetradecane-1,2,13,14-tetracarboxylate

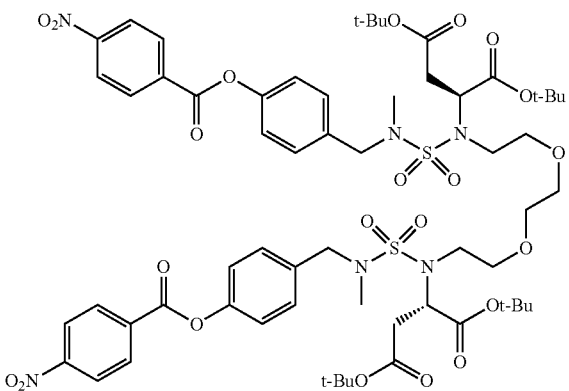 [SMILES: CN(Cc1ccc(OC(=O)c2ccc(N)cc2)cc1)S(=O)(=O)N(CCOCCOCCN([C@@H](CC(=O)OC(C)(C)C)C(=O)OC(C)(C)C)S(=O)(=O)N(C)Cc1ccc(OC(=O)c2ccc(N)cc2)cc1)[C@@H](CC(=O)OC(C)(C)C)C(=O)OC(C)(C)C]

To a solution of (2S,13S)-tetra-tert-butyl 3,12-bis(N-methylsulfamoyl)-6,9-dioxa-3,12-diazatetradecane-1,2,13,14-tetracarboxylate (79.0 mg) prepared in the Reference Example 22-(b) in dehydrated tetrahydrofuran (1.5 mL) in a 10 m two-necked flask was added 4-(hydroxymethyl)phenyl 4-nitrobenzoate (60.1 mg) at room temperature under argon atmosphere with stirring. Then, tributylphosphane (61.5 mg) and 1,1'-azobis(N,N-dimethylformamide) (52.3 mg) were sequentially added thereto, and the resulting mixture was stirred at room temperature for 17 hours. After the reaction was completed, the reaction solution was poured into water (15 mL), and extracted with ethyl acetate (40 mL). The resulting organic layer was washed with a saturated aqueous sodium chloride solution (15 mL), dried over anhydrous magnesium sulfate, filtered, and concentrated under reduced pressure. The resulting residues were purified by medium pressure preparative chromatography (silica gel, elution solvent; hexane:ethyl acetate) to give the title compound (94.8 mg) as a whine foam.

Mass spectrum (ESI, m/z): 1324 [M+Na]$^+$.

Reference Example 22-(d)

Preparation of (2S,13S)-terra-tert-butyl 3,12-bis(N-(4-((4-aminobenzoyl)oxy)benzyl)-N-methylsulfamoyl)-6,9-dioxa-3,12-diazatetradecane-1,2,13,14-tetracarboxylate

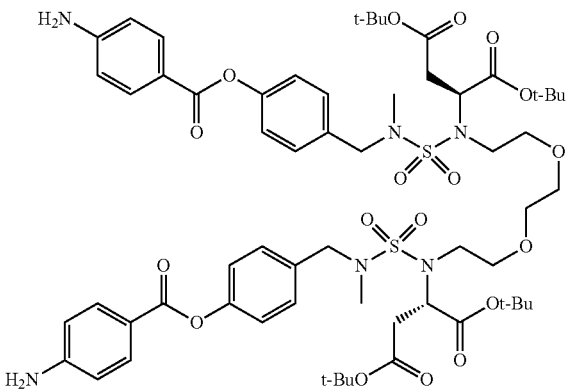

To a solution of (2S,13S)-tetra-tert-butyl 3,12-bis(N-methyl-N-(4-((4-nitrobenzoyl)oxy)benzyl)sulfamoyl)-6,9-dioxa-3,12-diazatetradecane-1,2,13,14-tetracarboxylate (91.3 mg) prepared in the Reference Example 22-(c) in ethanol (1 ml)/tetrahydrofuran (1 mL) in a 30 mL cylindrical flask was added 5% palladium carbon (wetted with 48.57% water, AER-type manufactured by NE CHEMCAT Corporation) (9.8 mg) at room temperature, and the resulting mixture was degassed under reduced pressure. Then, after the atmosphere was replaced with hydrogen atmosphere, the mixture was stirred at room temperature for 11 hours. After the reaction was completed, the reaction solution was filtered through Celite, washed with ethyl acetate, and then concentrated under reduced pressure. The resulting residues were purified by medium pressure preparative chromatography (silica gel, elution solvent; hexane:ethyl acetate) to give the title compound (64.7 mg) as a white foam.

Mass spectrum (ESI, m/z): 1264 [M+Na]$^+$.

Reference Example 22-(e)

Preparation of (2S,13S)-3,12-bis(N-(4-((4-aminobenzoyl)oxy)benzyl)-N-methylsulfamoyl)-6,9-dioxa-3,12-diazatetradecane-1,2,13,14-tetracarboxylic acid hydrochloride

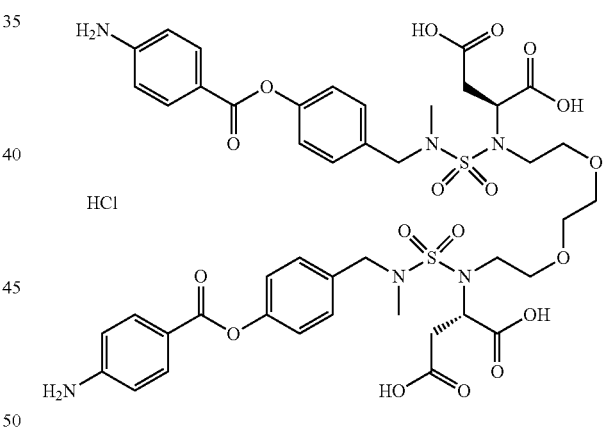

To (2S,13S)-tetra-tert-butyl 3,12-bis(N-4-((4-aminobenzoyl)oxy)benzyl)-N-methylsulfamoyl)-6,9-dioxa-3,12-diazatetradecane-1,2,13,14-tetracarboxylate (59.6 mg) prepared in the Reference Example 22-(d) in a 30 mL cylindrical flask was added a 4 M hydrogen chloride/cyclopentyl methyl ether solution (1.0 mL), and the resulting mixture was stirred at room temperature for 23 hours. After the reaction was completed, the reaction solution was concentrated under reduced pressure. To the concentrated residues was added dichloromethane (3 mL), and the resulting mixture was concentrated under reduced pressure. Said procedure was repeated three times to give the title compound (53.7 mg) as white solids.

Mass spectrum (ESI, m/z) 1017 [M+H]$^+$.

Reference Example 23-(a)

Preparation of dibenzyl 3-oxopentanedioate

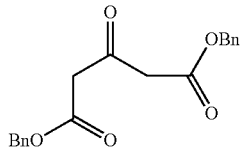 [SMILES: O=C(CC(=O)OCc1ccccc1)CC(=O)OCc1ccccc1]

To a 100 mL round-bottom flask with a Dean-Stark dehydrating tube were added dimethyl 3-oxopentanedioate (24.82 g) and phenylmethanal (30.0 mL), and the resulting mixture was stirred at 180° C. under argon atmosphere for 0.75 hours. After the reaction was completed, the reaction solution was purified by column chromatography (silica gel, elution solvent; hexane:ethyl acetate) to give the title compound (9-32 g) as a colorless oil.

Mass spectrum (231, m/z): 327 [M+H]$^+$.

Reference Example 23-(b)

Preparation of dibenzyl 3,14-bis(2-(benzyloxy)-2-oxoethyl)-7,10-dioxa-4,13-diazahexadecanedioate

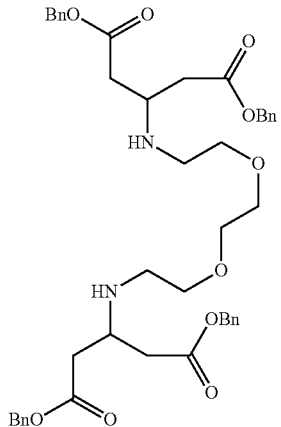 [SMILES: O=C(CC(CC(=O)OCc1ccccc1)NCCOCCOCCNC(CC(=O)OCc1ccccc1)CC(=O)OCc1ccccc1)OCc1ccccc1]

A solution of dibenzyl 3-oxopentanedioate (7.18 g) prepared in the Reference Example 23-(a) in dichloromethane (35 mL) in a 500 mL round-bottom flask was ice-cooled, and acetic acid (3.36 g) was added thereto under argon atmosphere. Then, a solution of 2,2'-(ethane-1,2-diylbis(oxy)) diethanamine (1.63 g) in dichloromethane (35 mL) was added thereto with stirring, and the resulting mixture was stirred at room temperature for 1 hour. Then, sodium triacetoxyborohydride (11.96 g) was added thereto, and the resulting mixture was stirred at room temperature for 65 hours. After the reaction was completed, the reaction solution was diluted with ethyl acetate, poured into saturated aqueous sodium hydrogen carbonate solution (300 mL), the resulting mixture was stirred, and the resulting mixed solution was extracted with ethyl acetate. The resulting organic layer was washed with saturated brine, dried over anhydrous sodium sulfate, filtered, and concentrated under reduced pressure to give the title compound (8.56 g) as a pale yellow liquid.

Mass spectrum (ESI, m/z): 769 [M+H]$^+$.

Reference Example 23-(c)

Preparation of tetrabenzyl 3,3'-(2,2,17,17-tetramethyl-4,15-dioxo-3,8,11,16-tetraoxa-5,14-diazaoctadecane-5,14-diyl)dipentanedioate

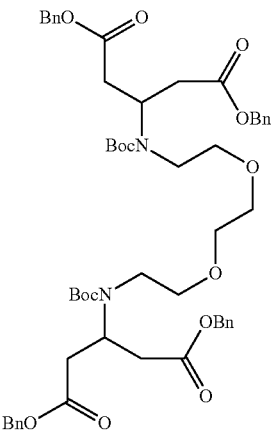 [SMILES: CC(C)(C)OC(=O)N(CCOCCOCCN(C(=O)OC(C)(C)C)C(CC(=O)OCc1ccccc1)CC(=O)OCc1ccccc1)C(CC(=O)OCc1ccccc1)CC(=O)OCc1ccccc1]

To a solution of dibenzyl 3,14-bis(2-(benzyloxy)-2-oxoethyl)-7,10-dioxa-4,13-diazahexadecanedioate (8.56 g) prepared in the Reference Example 23-(b) in dehydrated dichloromethane (70 mL) in a 500 mL round-bottom flask was added di-tert-butyl dicarbonate (6.10 mL) at room temperature under argon atmosphere with stirring, the resulting mixture was stirred at room temperature for 25 hours, and left to stand at room temperature for 72 hours. After the reaction was completed, the reaction solution was concentrated under reduced pressure. The resulting residues were purified by medium pressure preparative chromatography (silica gel, elution solvent; hexane:ethyl acetate) to give the title compound (3.42 g) as a colorless oil.

Mass spectrum (ESI, m/z): 991 [M+Na]$^+$.

Reference Example 23-(d)

Preparation of dibenzyl 3,14-bis(2-(benzyloxy)-2-oxoethyl)-7,10-dioxa-4,13-diazahexadecane-1,16-dioate

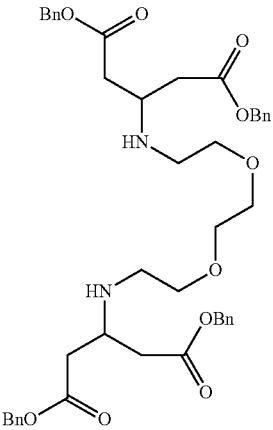 [SMILES: O=C(CC(CC(=O)OCc1ccccc1)NCCOCCOCCNC(CC(=O)OCc1ccccc1)CC(=O)OCc1ccccc1)OCc1ccccc1]

(1) To a solution of tetrabenzyl 3,3'-(2,2,17,17-tetramethyl-4,15-dioxo-3,8,1,16-tetraoxa-5,14-diazaoctadecane-5,14-diyl)dipentanedioate (0.49 g) prepared according to the same manner as the Reference Example 23-(c) in dehydrated ethyl acetate (30 mL) in a 100 mL round-bottom flask was added a 4 M hydrogen chloride/cyclopentyl methyl ether solution (0.5 mL) at room temperature under nitrogen atmosphere with stirring, and the resulting mixture was stirred at room temperature for 2 hours. Additionally, a 4 M hydrogen chloride/cyclopentyl methyl ether solution (1.0 mL) was added thereto at room temperature, the resulting mixture was stirred at room temperature for 3.8 hours, stirred at 60° C. for 3.3 hours, and left to stand at room temperature overnight. Additionally, a 4 M hydrogen chloride/cyclopentyl methyl ether solution (1.0 mL) was added thereto, and the resulting mixture was stirred at 60° C. for 6 hours. After the reaction was completed, the reaction solution was concentrated under reduced pressure, dehydrated diethyl ether was added thereto, and the resulting mixture was subjected to sonication. The resulting supernatant was removed under ice-cooling, to the resulting residues was added dehydrated diethyl ether, and the resulting mixture was subjected to sonication. The resulting residues were dried under reduced pressure.

(2) To a solution of tetrabenzyl 3,3'-(2,2,17,17-tetramethyl-4,15-dioxo-3,8,11,16-tetraoxa-5,14-diazaoctadecane-5,14-diyl)dipentanedioate (3.42 g) prepared in the Reference Example 23-(c) in dehydrated ethyl acetate (30 mL) in a 500 mL round-bottom flask was added a 4 M hydrogen chloride/cyclopentyl methyl ether solution (15 mL) at room temperature under nitrogen atmosphere with stirring, and the resulting mixture was stirred at 60° C. for 5 hours. After the reaction was completed, the reaction solution was concentrated under reduced pressure, dehydrated diethyl ether was added thereto, and the resulting mixture was subjected to sonication. The resulting supernatant was removed under ice-cooling, to the resulting residues was added dehydrated diethyl ether, and the resulting mixture was subjected to sonication. The resulting residues were dried under reduced pressure.

The resulting residues in (1) and the resulting residues in (2) were combined, ethyl acetate (100 mL) was added thereto, the resulting mixture was washed sequentially with saturated aqueous sodium hydrogen carbonate solution (100 mL) and saturated brine (50 mL), dried over anhydrous sodium sulfate, filtered, and the resulting filtrate was concentrated under reduced pressure to give the title compound (1.40 g) as a slightly yellow oil.

Mass spectrum (ESI, m/z): 769 [M+H]$^+$.

Reference Example 23-(e)

Preparation of tetrabenzyl 3,3'-(((ethane-1,2-diylbis(oxy))bis(ethane-2,1-diyl))bis((N-((benzyloxy)carbonyl)sulfamoyl)azanediyl))dipentanedioate

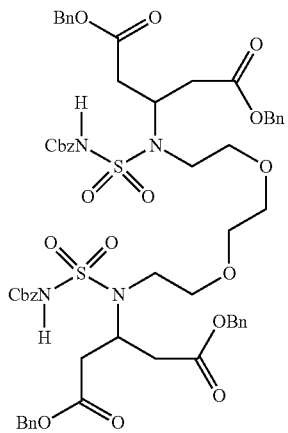 [SMILES: O=C(CC(CC(=O)OCc1ccccc1)N(CCOCCOCCN(C(CC(=O)OCc1ccccc1)CC(=O)OCc1ccccc1)S(=O)(=O)NC(=O)OCc1ccccc1)S(=O)(=O)NC(=O)OCc1ccccc1)OCc1ccccc1]

To a solution of dibenzyl 3,14-bis(2-(benzyloxy)-2-oxoethyl)-7,10-dioxa-4,13-diazahexadecane-1,16-dioate (1.40 g) prepared in the Reference Example 23-(d)-2 in dehydrated dichloromethane (10 mL) in a 300 mL round-bottom flask was added dropwise a solution of benzyl chlorosulfonylcarbamate (1.00 g) in dichloromethane (5 ml) at 0° C. under argon atmosphere with stirring, the resulting mixture was washed with dehydrated dichloromethane (5 mL), and stirred at 0° C. for 2.5 hours. After the reaction was completed, the reaction solution was concentrated under reduced pressure.

The concentrated residues were diluted with ethyl acetate, and washed sequentially with a 5% aqueous potassium hydrogen sulfate solution (50 mL) and saturated brine (50 mL x twice) The resulting organic layer was dried over anhydrous magnesium sulfate, filtered, and concentrated under reduced pressure. The resulting residues were purified by medium pressure preparative chromatography (silica gel, elution solvent; hexane:ethyl acetate) to give the title compound (1.47 q) as a colorless viscous oil.

Mass spectrum (ESI, m/z): 1217 [M+Na]$^+$.

Reference Example 24-(a)

Preparation of (S)-di-tert-butyl 2-((N-((benzyloxy)carbonyl)sulfamoyl)amino)succinate

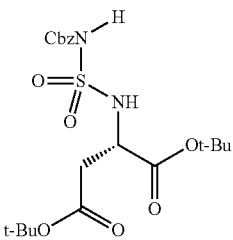 [SMILES: CC(C)(C)OC(=O)C[C@H](NS(=O)(=O)NC(=O)OCc1ccccc1)C(=O)OC(C)(C)C]

To a solution of chlorosulfonyl isocyanate (5.53 g) in dichloromethane (100 mL) in a 300 mL three-necked flask was added dropwise benzyl alcohol (4.06 mL) at 0° C. under argon gas flow with stirring, and the resulting mixture was stirred at 0° C. for 1 hour. Then, L-aspartic acid di-t-butyl ester hydrochloride (10.00 g) and a solution of triethylamine (10.88 mL) in dichloromethane (50.0 mL) were added thereto with stirring at 0° C., and the resulting mixture was stirred at resulting room temperature for 16 hours. After the reaction was completed, to the reaction solution was added saturated aqueous sodium hydrogen carbonate solution, and the resulting mixed solution was extracted with dichloromethane. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (7.516 g) as white solids.

Mass spectrum (ESI, m/z): 457 [M−H]$^-$.

Reference Example 24-(b)

Preparation of (2S,2'S)-tetra-tert-butyl 2,2'-((3,14-dioxo-1,16-diphenyl-2,7,10,15-tetraoxa-4,13-diaza-hexadecanedisulfonyl)bis(azanediyl))disuccinate

Reference Example 24-(c)

Preparation of (2S,2'S)-tetra-tert-butyl 2,2'-(3,14-dioxo-1,16-diphenyl-2,7,10,15-tetraoxa-4,13-diaza-hexadecanedisulfonyl)bis((tert-butoxycarbonyl)azanediyl))disuccinate

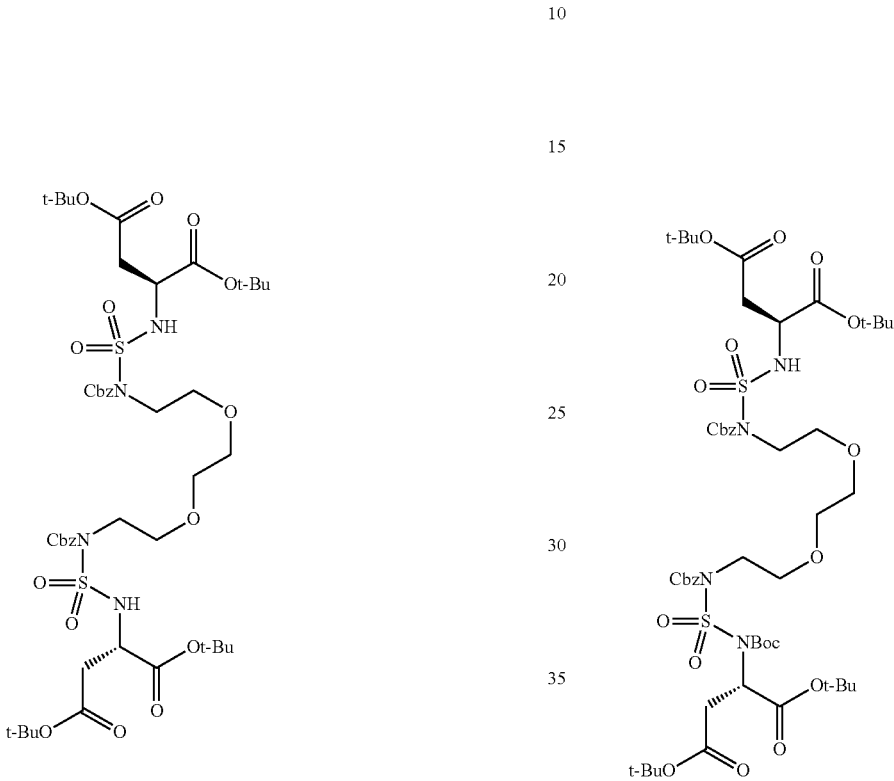

To a solution of (S)-di-tert-butyl 2-((N-((benzyloxy)carbonyl)sulfamoyl)amino)succinate (3.21 g) prepared in the Reference Example 24-(a) in tetrahydrofuran (15 mL) in a 100 mL round-bottom flask were added sequentially triethyleneglycol (0.44 mL), diisopropyl azodicarboxylate (a 1.9 M solution in toluene) (4.21 mL), and triphenylphosphine (2.10 g) at room temperature under argon gas flow with stirring, and the resulting mixture was stirred at room temperature for 4 hours. (S)-di-tert-butyl 2-((N-((benzyloxy)carbonyl)sulfamoyl)amino)succinate (0.80 g), triphenylphosphine (1.05 g), and diisopropyl azodicarboxylate (a 1.9 M solution in toluene) (4.21 mL) were added thereto at room temperature, and the resulting mixture was stirred at room temperature for 1 hour. After the reaction was completed, to the reaction solution was added water, and the resulting mixed solution was extracted with ethyl acetate. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (2.78 g) as a colorless oil.

Mass spectrum (ESI, m/z): 1029 [M−H]⁻.

To a solution of (2S,2'S)-tetra-tert-butyl 2,2'-((3,14-dioxo-1,16-diphenyl-2,7,10,15-tetraoxa-4,13-diazahexadecanedisulfonyl)bis(azanediyl))disuccinate (1.65 g) prepared in the Reference Example 24-(b) in dichloromethane (10 mL) in a 100 mL round-bottom flask were added di-tert-butyl dicarbonate (0.81 mL) and 4-dimethylaminopyridine (0.10 g) at room temperature under argon gas flow with stirring, and the resulting mixture was stirred at room temperature for 2.5 hours. Then, triethylamine (0.45 mL) and 4-dimethylaminopyridine (0.10 g) were added thereto, and the resulting mixture was stirred at room temperature for 16 hours. After the reaction was completed, the reaction solution was concentrated under reduced pressure. The resulting residues were purified by medium pressure preparative chromatography (silica gel, elution solvent; hexane:ethyl acetate) to give the title compound (1.05 g) as a white foam.

Mass spectrum (ST, m/z): 1253 [M+Na]⁺.

Referee Example 24-(d)

Preparation of (2S,2'S)-tetra-tert-butyl 2,2'-((((2-(2-(2-(hydrosulfonylamino)ethoxy)ethoxy)ethyl)amino)sulfonyl)bis(tert-butoxycarbonyl)azanediyl))disuccinate

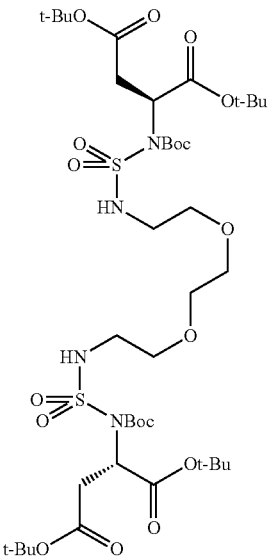 [SMILES: CC(C)(C)OC(=O)C[C@@H](C(=O)OC(C)(C)C)N(C(=O)OC(C)(C)C)S(=O)(=O)NCCOCCOCCNS(=O)(=O)N(C(=O)OC(C)(C)C)[C@@H](CC(=O)OC(C)(C)C)C(=O)OC(C)(C)C]

To a solution of (2S,2'S)-tetra-tert-butyl 2,2'-((3,14-dioxo-1,16-diphenyl-2,7,10,15-tetraoxa-4,13-diazahexadecanedisulfonyl)bis((tert-butoxycarbonyl)azanediyl))disuccinate (0.62 g) prepared in the Reference Example 24-(c) in ethanol (6 mL)/tetrahydrofuran (2 mL) in a 100 mL round-bottom flask was added 5% palladium carbon (wetted with 51.65% water, AER-type manufactured by NE CHEMCAT Corporation) (0.11 g) at room temperature, the atmosphere in the reaction system was replaced with hydrogen atmosphere, and then the resulting mixture was stirred at room temperature for 2.5 hours. After the reaction was completed, the reaction solution was filtered through Celite, and the resulting filtrate was concentrated under reduced pressure to give the title compound (0.48 g) as a white foam.

Mass spectrum (ESI, m/z): 985 [M+Na]$^+$.

Reference Example 24-(e)

Preparation of (2S,2'S)-tetra-tert-butyl 2,2'-((1,12-bis(4-((4-nitrobenzoyl)oxy)phenyl)-5,8-dioxa-2,11-diazadodecanedisulfonyl)bis((tert-butoxycarbonyl)azanediyl))disuccinate

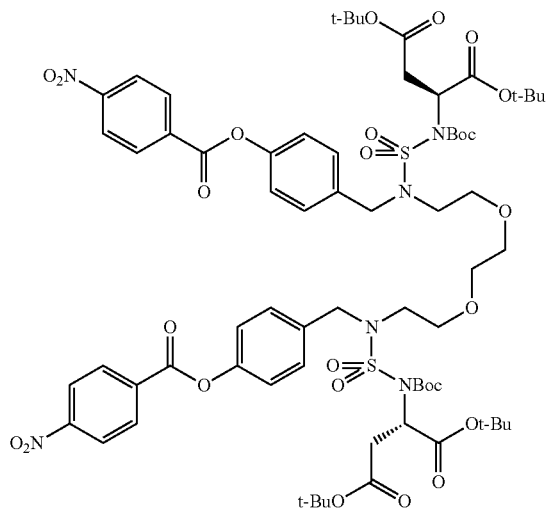 [SMILES: CC(C)(C)OC(=O)C[C@@H](C(=O)OC(C)(C)C)N(C(=O)OC(C)(C)C)S(=O)(=O)N(CCOCCOCCN(Cc1ccc(OC(=O)c2ccc([N+](=O)[O-])cc2)cc1)S(=O)(=O)N(C(=O)OC(C)(C)C)[C@@H](CC(=O)OC(C)(C)C)C(=O)OC(C)(C)C)Cc1ccc(OC(=O)c2ccc([N+](=O)[O-])cc2)cc1]

(1) To a solution of (2S,2'S)-tetra-tert-butyl 2,2'-(((2-(2-(2-(hydrosulfonylamino)ethoxy)ethoxy)ethyl)amino)sulfonyl)bis(tert-butoxycarbonyl)azanediyl))disuccinate (0.47 g) prepared in the Reference Example 24-(d) in tetrahydrofuran (5 mL) in a 100 ml round-bottom flask were added 4-(hydroxymethyl)phenyl 4-nitrobenzoate 0.30 g), tributylphosphine (0.30 mL), and 1,1'-azobis(N,N-dimethylformamide) (0.21 g) at room temperature under argon gas flow with stirring, and the resulting mixture was stirred at room temperature for 7.5 hours. Tributylphosphine (0.150 mL) and 1,1'-azobis(N,N-dimethylformamide) (0.10 g) were added thereto at room temperature, and the resulting mixture was stirred at room temperature for 16 hours. After the reaction was completed, to the reaction solution was added water, and the resulting mixed solution was extracted with ethyl acetate. The resulting organic layer was washed with saturated brine, dried over anhydrous magnesium sulfate, filtered, and concentrated under reduced pressure.

(2) To a solution of (2S,2'S)-tetra-tert-butyl 2,2'-((((2-(2-(hydrosulfonylamino)ethoxy)ethyl)amino)sulfonyl)bis((tert-butoxycarbonyl)azanediyl))disuccinate (0.81 g) prepared in the Reference Example 24-(d) in tetrahydrofuran (8.5 mL) in a 100 mL round-bottom flask were added 4-(hydroxymethyl)phenyl 4-nitrobenzoate (0.51 g), tributylphosphine (0.50 mL), and 1,1'-azobis(N,N-dimethylformamide) (0.35 g) at room temperature under argon gas flow with stirring, and the resulting mixture was stirred at room temperature for 2 hours. Tributylphosphine (0.25 mL) and 1,1'-azobis(N,N-dimethylformamide) (0.17 g) were added thereto at room temperature, and the resulting mixture was stirred at room temperature for 16 hours. After the reaction was completed, to the reaction solution was added water, and the resulting mixed solution was extracted with ethyl acetate. The resulting organic layer was washed with saturated brine, dried over anhydrous magnesium sulfate, filtered, and concentrated under reduced pressure.

The resulting residues in (1) and the resulting residues in (2) were combined, and purified by medium pressure preparative chromatography (silica gel, elution solvent; hexane:ethyl acetate) to give the title compound (1.49 g) as a white foam.

Mass spectrum (ESI, m/z): 1495 [M+Na]$^+$.

Reference Example 24-(f)

Preparation of (2S,2'S)-tetra-tert-butyl 2,2'-((1,12-bis(4-((4-aminobenzoyl)oxy)phenyl)-5,8-dioxa-2,11-diazadodecanedisulfonyl)bis((tert-butoxycarbonyl)azanediyl))disuccinate

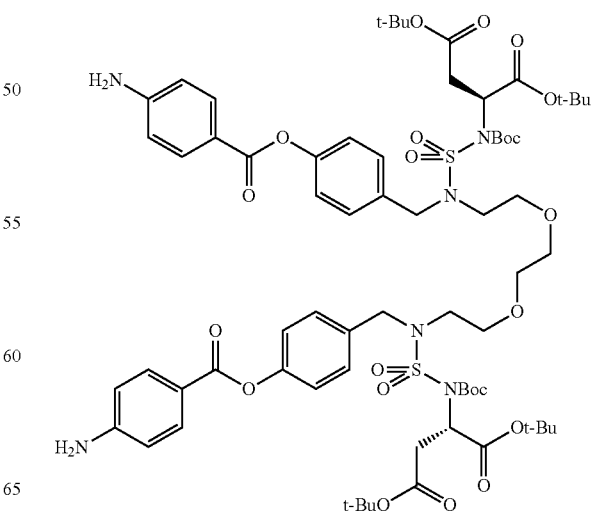

To a solution of (2S,2'S)-tetra-tert-butyl 2,2'-((1,12-bis(4-((4-nitrobenzoyl)oxy)phenyl)-5,8-dioxa-2,11-diazadodecanedisulfonyl)bis((tert-butoxycarbonyl)azanediyl))disuccinate (1.46 g) prepared in the Reference Example 24-(e) in ethanol (10 mL) in a 100 mL round-bottom flask was added 5% palladium carbon (wetted with 51.65% water, AER-type manufactured by NE CHEMCAT Corporation) (0.22 g) at room temperature under argon atmosphere, the atmosphere in the reaction system was replaced with hydrogen atmosphere, and then the resulting mixture was stirred at room temperature for 4 hours. After the reaction was completed, the reaction solution was filtered through Celite, and the resulting filtrate was concentrated under reduced pressure. The resulting residues were subjected to medium pressure preparative chromatography (silica gel, elution solvent; hexane:ethyl acetate), and the fractions comprising the target compound were concentrated under reduced pressure to give the title compound (1.12 g) as a white foam.

Mass spectrum (ESI, m/z): 1435 [M+Na]$^+$.

Reference Example 24-(g)

Preparation of (2S,2'S)-2,2'-((1,12-bis(4-((4-aminobenzoyl)oxy)phenyl)-5,8-dioxa-2,1-diazadodecanedisulfonyl)bis(azanediyl))disuccinic acid hydrochloride

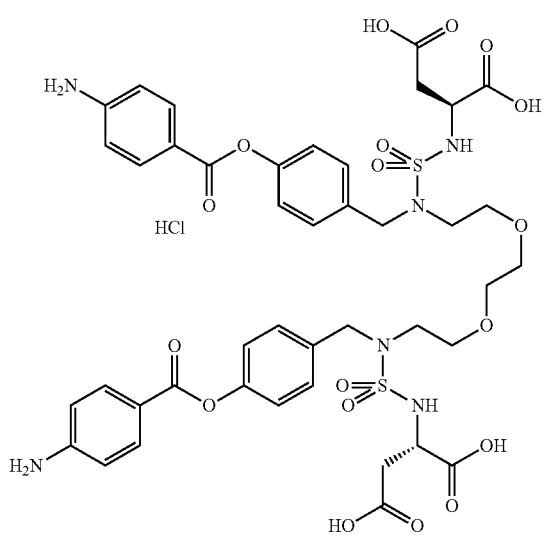 [SMILES: Nc1ccc(C(=O)Oc2ccc(CN(CCOCCOCCN(Cc3ccc(OC(=O)c4ccc(N)cc4)cc3)S(=O)(=O)N[C@@H](CC(=O)O)C(=O)O)S(=O)(=O)N[C@@H](CC(=O)O)C(=O)O)cc2)cc1 ; Cl]

To (2S,2'S)-tetra-tert-butyl 2,2'-((1,12-bis(4-((4-aminobenzoyl)oxy)phenyl)-5,8-dioxa-2,1-diazadodecanedisulfonyl)bis(tert-butoxycarbonyl)azanediyl))disuccinate (1.11 g) prepared in the Reference Example 24-(f) in a 100 mL round-bottom flask was added a 4 M hydrogen chloride/cyclopentyl methyl ether solution (5.0 mL) at room temperature, and the resulting mixture was stirred at room temperature for 28.5 hours. After the reaction was completed, the reaction solution was concentrated under reduced pressure. To the concentrated residues was added dichloromethane, and the resulting mixture was concentrated under reduced pressure. The resulting residues were dried under reduced pressure to give the title compound (0.84 g) as white solids.

Mass spectrum (ESI, m/z) 989 [M+H]$^+$.

Reference Example 28-(a)

Preparation of (S)-dibenzyl 2-(2-nitrophenylsulfonamide)succinate

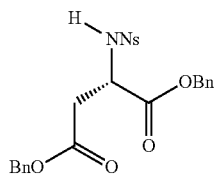

To a solution of L-aspartic acid dibenzyl ester hydrochloride (5.06 g) in dichloromethane (30 mL) in a 200 mL round-bottom flask were added N,N-diisopropylethylamine (6.0 mL) and 2-nitrobenzenesulfonyl chloride (3.55 g) at 0° C. under argon atmosphere with stirring, the resulting mixture was stirred at 0° C. for 10 minutes, and stirred at room temperature for 2 hours. After the reaction was completed, to the reaction solution was added dichloromethane (50 mL), the resulting mixture was washed with a 5% aqueous citric acid solution (80 mL) and saturated brine, dried over anhydrous magnesium sulfate, filtered, and concentrated under reduced pressure. The resulting residues were subjected to medium pressure preparative chromatography (silica gel, elution solvent; hexane:ethyl acetate), and the fractions comprising the target compound were concentrated under reduced pressure. To a solution of the resulting residues in ethyl acetate was added hexane, the resulting mixture was stirred at room temperature for 10 minutes, the precipitated solids were collected by filtration, and dried under reduced pressure to give the title compound (5.92 g) as slightly yellow solids.

Mass spectrum (ESI, m/z): 521 [M+Na]$^+$.

Reference Example 28-(b)

Preparation of (2S,2'S)-tetrabenzyl 2,2'-(([1,1'-biphenyl]-3,3'-diylbis(methylene))bis(((2-nitrophenyl)sulfonyl)azanediyl))disuccinate

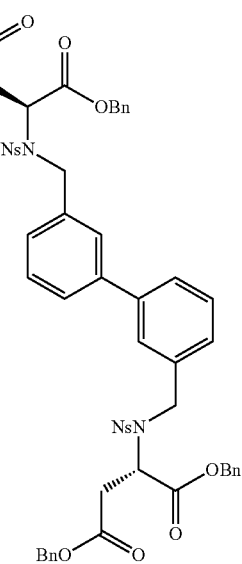

To a 200 mL four-necked flask were added (S)-dibenzyl 2-(2-nitrophenylsulfonamide)succinate (8.9 g) prepared according to the same manner as the Reference Example 28-(a), [1,1'-biphenyl]-, 3'-diyldimethanol (1.82 g), and dichloromethane (40 mL), and triphenylphosphine (5.35 g) was added thereto at 7° C. under nitrogen atmosphere with stirring. Then, diisopropyl azodicarboxylate (a 1.9 M solution in toluene) (10.7 mL) was added dropwise thereto at 4 to 11° C. over 15 minutes, and then the resulting mixture was stirred at room temperature for 4 hours. After the reaction was completed, to the reaction solution was added water (40 mL), and the resulting mixed solution was extracted with dichloromethane (40 mL). The resulting organic layer was washed with saturated brine (40 mL), dried over anhydrous magnesium sulfate, filtered, and concentrated under reduced pressure. The resulting residues were purified by column chromatography (silica gel, elution solvent; hexane:ethyl acetate) to give the title compound (7.1 g) as a yellow foam.

Mass spectrum (ESI, m/z): 1197 [M+Na]$^+$.

Reference Example 28-(c)

Preparation of (2S,2'S)-tetrabenzyl 2,2'-(([1,1'-biphenyl]-3,3'-diylbis((methylene))bis(azanediyl)) disuccinate

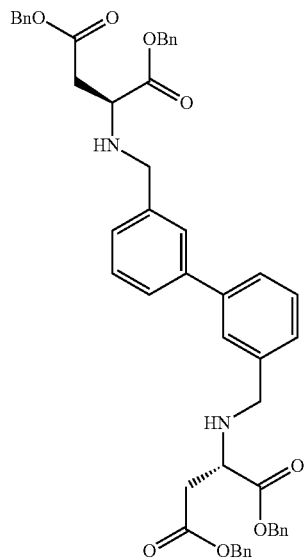 [SMILES: O=C(C[C@H](NCc1cccc(-c2cccc(CN[C@@H](CC(=O)OCc3ccccc3)C(=O)OCc3ccccc3)c2)c1)C(=O)OCc1ccccc1)OCc1ccccc1]

To a 500 mL four-necked flask were added (2S,2'S)-tetrabenzyl 2,2'-(([1,1'-biphenyl]-3,3'-diylbis(methylene)) bis(((2-nitrophenyl)sulfonyl)azanediyl))disuccinate (7.1 g) prepared in the Reference Example 28-(b), potassium carbonate (4.17 g), thiosalicylic acid (3.73 g), and acetonitrile (90 mL) under nitrogen atmosphere, and the resulting mixture was stirred at 80° C. under nitrogen atmosphere for 7 hours. Potassium carbonate (0.74 g), thiosalicylic acid (0.66 g), and acetonitrile (20 mL) were added thereto, and the resulting mixture was stirred for 3 hours. After the reaction was completed, to the reaction solution was added water (50 mL), and the resulting mixed solution was extracted with ethyl acetate (100 mL) twice. The resulting organic layer was washed with saturated aqueous sodium hydrogen carbonate solution (150 mL) twice and with saturated brine (200 mL), dried over anhydrous sodium sulfate, filtered, and concentrated under reduced pressure.

The resulting residues were purified by column chromatography (NH silica gel, elution solvent; hexane ethyl acetate) to give the title compound (4.18 g) as a yellow oil.

Mass spectrum (ESI, m/z): 805 [M+H]$^+$.

Reference Example 29-(a)

Preparation of (S)-di-tert-butyl 2-((3-(benzyloxy)-5-(methoxycarbonyl)benzyl) (tert-butoxycarbonyl) amino)succinate

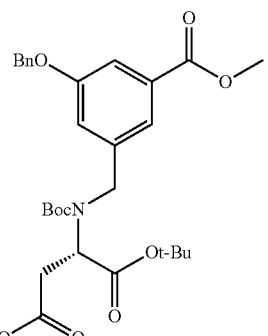

To a solution of methyl 3 (benzyloxy)-5-formylbenzoate (2.08 g) and L-aspartic acid di-tert-butyl hydrochloride (2.18 g) in dichloromethane (40 mL) in a 500 mL round-bottom flask were added N,N-diisopropylethylamine (4.00 TL) and then acetic acid (1.20 mL) at room temperature under argon atmosphere, and the resulting mixture was stirred at room temperature for 16.5 hours. Then, sodium triacetoxyborohydride (4.10 g) was added thereto at room temperature, the resulting mixture was stirred at room temperature under argon atmosphere for 34 hours, and left to stand at room temperature for 72 hours. After the reaction was competed, the reaction solution was diluted with ethyl acetate, saturated aqueous sodium hydrogen carbonate solution (100 mL) was added thereto, the resulting mixture was stirred at room temperature for 1 hour, and the resulting mixed solution was extracted with ethyl acetate. The resulting organic layer was washed with saturated brine, dried over anhydrous sodium sulfate, filtered, and concentrated under reduced pressure to give (S)-di-tert-butyl 2-((3-(benzyloxy)-5-(methoxycarbonyl)benzylamino)succinate. To a solution of the resulting (S)-di-tert-butyl 2-(3-(benzyloxy)-5-(methoxycarbonyl)benzyl)succinate (3.84 g) in dehydrated dichloromethane (40 mL) was added di-tert-butyl dicarbonate (2.00 mL) at room temperature under argon atmosphere with stirring, and the resulting mixture was stirred at room temperature for 66.5 hours. After the reaction was completed, the reaction solution was concentrated under reduced pressure. The resulting residues were purified by medium pressure preparative chromatography (silica gel, elution solvent; hexane:ethyl acetate) to give the title compound (4.02 g as a colorless viscous oil.

Mass spectrum (ESI, m/z); 622 [M-Na]$^+$.

Reference Example 29-(b)

Preparation of (S)-3-(benzyloxy)-5-(((tert-butoxycarbonyl)(1,4-di-tert-butoxy-1,4-dioxobutan-2-yl)amino)methyl)benzoic acid

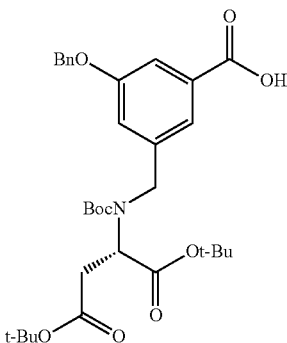 [SMILES: CC(C)(C)OC(=O)C[C@@H](C(=O)OC(C)(C)C)N(Cc1cc(OCc2ccccc2)cc(C(=O)O)c1)C(=O)OC(C)(C)C]

To a solution of (S)-di-tert-butyl 2-((3-(benzyloxy)-5-(methoxycarbonyl)benzyl)(tert-butoxycarbonyl)amino)succinate (9.54 g) prepared in the Reference Example 29-(a) in tetrahydrofuran (90 mL)/methanol (45 mL) in a 500 mL round-bottom flask was added a 1 M aqueous sodium hydroxide solution (50 mL) at 0° C. under argon atmosphere with stirring, and the resulting mixture was stirred at room temperature for 6 hours. 1 M hydrochloric acid (50 mL) was added thereto at room temperature, the resulting mixture was stirred for a while, ethyl acetate (200 mL), a 5% aqueous potassium hydrogen sulfate solution (10 mL), and saturated brine (75 mL) were added thereto, and the resulting mixed solution was extracted with ethyl acetate. The resulting organic layer was washed with saturated brine (100 mL), dried over anhydrous magnesium sulfate, filtered, and concentrated under reduced pressure to give the title compound (8.95 g) as a white foam.

Mass spectrum (ESI, m/z): 600 [M+Na]+.

Reference Example 29-(c)

Preparation of (S)-di-tert-butyl 2-((3-(benzyloxy)-5-((2-(trimethylsilyl)ethoxy)carbonyl)benzyl)(tert-butoxycarbonyl)amino)succinate

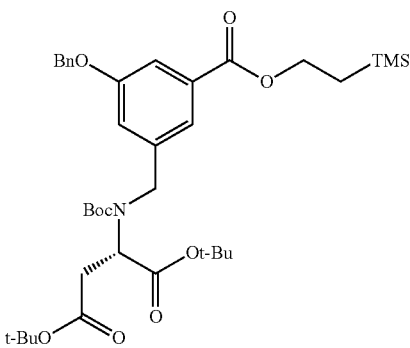 [SMILES: CC(C)(C)OC(=O)C[C@@H](C(=O)OC(C)(C)C)N(Cc1cc(OCc2ccccc2)cc(C(=O)OCC[Si](C)(C)C)c1)C(=O)OC(C)(C)C]

To a solution of (S)-3-(benzyloxy)-5-(((tert-butoxycarbonyl)(1,4-di-tert-butoxy-1,4-dioxobutan-2-yl)amino)methyl)benzoic acid (8.95 g) prepared in the Reference Example 29-(b), 2-(trimethylsilyl)ethanol (2.21 g), and 4-dimethylaminopyridine (0.19 g) in dehydrated dichloromethane (270 mL) in a 500 mL round-bottom flask was added 1-(3-dimethylaminopropyl)-3-ethylcarbodiimide hydrochloride (3.55 g) at room temperature under argon atmosphere under water-cooling with stirring, and the resulting mixture was stirred at room temperature for 3.5 hours. Additionally, 4-dimethylaminopyridine (0.30 g) was added thereto with stirring at room temperature, and the resulting mixture was stirred at room temperature for 15 hours. After the reaction was completed, the reaction solution was concentrated under reduced pressure. To the concentrated residues was added ethyl acetate (250 mL), the resulting mixture was washed sequentially with a mixed solution of a 5% aqueous potassium hydrogen sulfate solution (200 mL) and saturated brine (50 mL), saturated brine (100 mL), saturated aqueous sodium hydrogen carbonate solution (50 mL), and saturated brine (50 mL), dried over anhydrous magnesium sulfate, filtered, and concentrated under reduced pressure. The resulting residues were subjected to medium pressure preparative chromatography (silica gel, elution solvent; hexane:ethyl acetate), and the fractions comprising the target compound were concentrated under reduced pressure to give the title compound (9.09 g) as a colorless oil.

Mass spectrum (ESI, m/z): 708 [M+Na]+.

Reference Example 29-(d)

Preparation of (S)-di-tert-butyl 2-((3-(benzyloxy)-5-((2-(trimethylsilyl)ethoxy)carbonyl)benzyl)amino)succinate

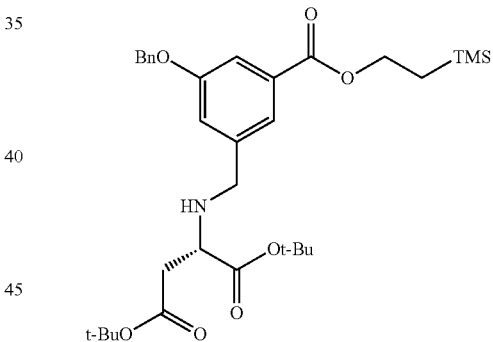

To (S)-di-tert-butyl 2-((3-(benzyloxy)-5-((2-(trimethylsilyl)ethoxy)carbonyl)benzyl)(tert-butoxycarbonyl, amino succinate (8.91 g) prepared in the Reference Example 29-(c) in a 500 mL round-bottom flask was added a 1 M hydrogen chloride/ethyl acetate solution (200 mL) at room temperature under nitrogen atmosphere, and the resulting mixture was stirred at room temperature for 6 hours. After the reaction was completed, the reaction solution was poured into saturated aqueous sodium hydrogen carbonate solution (300 ml), the resulting mixture was stirred for 1 hour, saturated brine (300 mL) was added thereto, and the resulting mixed solution was extracted with ethyl acetate. The resulting organic layer was dried over anhydrous sodium sulfate, filtered, and concentrated under reduced pressure. To the concentrated residues was added diethyl ether, the resulting insoluble matters were removed by filtration, washed with diethyl ether, the resulting filtrate and the wash liquid were combined, and concentrated under reduced pressure. The resulting residues were purified by medium pressure preparative chromatography (DIOL silica gel, elution solvent; hexane:ethyl acetate) to give the title compound (3.72 g) as a colorless viscous oil. Another traction was concentrated under reduced pressure. The resulting residues were purified by medium pressure preparative chromatography (DIOL silica gel, elution solvent; hexane:ethyl acetate) to give the title compound (1.02 g) as a colorless viscous oil.

Mass spectrum (ESI, m/z); 608 [M+Na]⁺.

Reference Example 29-(e)

Preparation of (S)-di-tert-butyl 2-(N-(3-(benzyloxy)-5-((2-(trimethylsilyl)ethoxy)carbonyl)benzyl)-10-(2,3-bis(tert-butoxycarbonyl) guanidino)-13-oxo-6,7,8,13-tetrahydrodibenzo[b,f][1,4]dioxecin-4-carboxamido)succinate

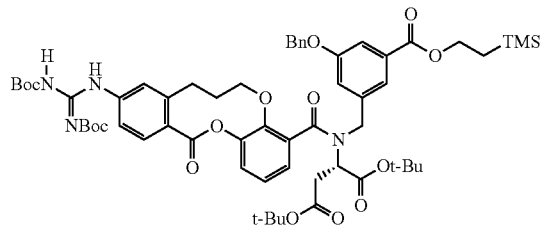

To a solution of 10-(2,3-bis(tert-butoxycarbonyl)guanidino)-13-oxo-6,7,8,13-tetrahydrodibenzo[b,f][1,4]dioxecin-4-carboxylic acid (0.97 g) prepared according to the same manner as the Reference Example 19-(n) in dehydrated dimethylformamide (10 mL) in a 100 mL round-bottom flask was added COMU (0.91 g) at room temperature under argon atmosphere with stirring, and the resulting mixture was stirred at room temperature for 1 hour. Then, N,N-diisopropylethylamine (0.46 mL) was added thereto at room temperature, the resulting mixture was cooled by ice water, and stirred for 0.5 hour. Then, a solution of (S)-di-tert-butyl 2-((3-(benzyloxy)-5-((2-(trimethylsilyl)ethoxy)carbonyl) benzyl)amino)succinate (1.02 g) prepared in the Reference Example 29-(d) in dehydrated dimethylformamide (10 mL) was added thereto with stirring with cooling by ice water, and the resulting mixture was stirred at room temperature for 1 hour. Additionally, N,N-diisopropylethylamine (0.16 mL) was added thereto, and the resulting mixture was stirred for 45.5 hours. Additionally, COMU (0.31 g) and N,N-diisopropylethylamine (0.20 mL) were added thereto at room temperature, and the resulting mixture was stirred at room temperature for 7 hours. After the reaction was completed, the reaction solution was diluted with toluene (100 mL), poured into saturated aqueous sodium hydrogen carbonate solution (100 mL), the resulting mixture was thoroughly stirred, left to stand, and the resulting mixed solution was extracted with toluene. The resulting organic layer was washed with water (100 mL). To the organic layer were added saturated brine (100 mL) and ethyl acetate, the resulting mixture was shaken, left to stand, and the resulting mixed solution was extracted with ethyl acetate. The resulting organic layer was dried over anhydrous magnesium sulfate, filtered, and concentrated under reduced pressure. The resulting residues were purified by medium pressure preparative chromatography (silica gel, elution solvent; hexane:ethyl acetate) to give the title compound (1.05 g) as a slightly yellow foam.

Mass spectrum (DUIS, m/z): 1123 [M+H]⁺.

Reference Example 29-(f)

Preparation of (S)-di-tert-butyl 2-(10-(2,3-bis(tert-butoxycarbonyl)guanidino)-N-(3-hydroxy-5-((2-(trimethylsilyl)ethoxy)carbonyl)benzyl)-13-oxo-6,7,8,13-tetrahydrodibenzo[b,f][1,4]dioxecin-4-carboxamido)succinate

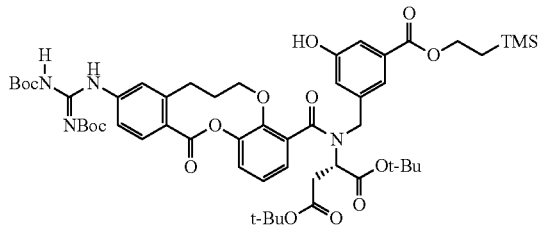

To a solution of (S)-di-tert-butyl 2-N-(3-(benzyloxy)-5-((2-(trimethylsilyl)ethoxy)carbonyl)benzyl)-10-(2,3-bis(tert-butoxycarbonyl)guanidino)-13-oxo-6,7,3,18-tetrahydrodibenzo[b,f][1,4]dioxecin-4-carboxamido)succinate (3.23 g) prepared in the Reference Example 29-(e) in ethanol (40 mL)/tetrahydrofuran (20 ml) in a 500 mL round-bottom flask was added ASCA-2 (wetted with 52% water, manufactured by NE CHEMCAT Corporation) (0.60 g at room temperature under nitrogen atmosphere, and the resulting mixture was stirred at room temperature under hydrogen atmosphere for 3 hours. After the reaction was completed, the reaction solution was filtered through Celite, washed with ethanol, the resulting filtrate and the wash liquid were combined, and concentrated under reduced pressure. The concentrated residues were diluted with ethyl acetate, and the resulting mixture was concentrated under reduced pressure. The resulting residues were purified by medium pressure preparative chromatography (silica gel, elution solvent; hexane:ethyl acetate) to give the title compound (0.40 g) as slightly yellow solids.

Mass spectrum (DUIS, m/z): 1033 [M+H]⁺.

Reference Example 29-(g)

Preparation of (S)-di-tert-butyl 2-N-(3-(2-(2-(benzyloxy)ethoxy)ethoxy)-5-((2-(trimethylsilyl)ethoxy) carbonyl)benzyl)-10-(2,3-bis(tert-butoxycarbonyl) guanidino)-13-oxo-6,7,8,13-tetrahydrodibenzo[b,f] [1,4]dioxecin-4-carboxamido)succinate

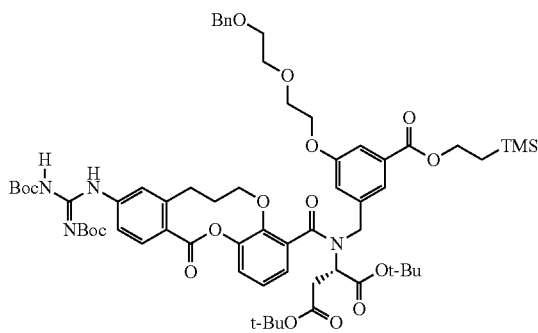

A solution of 2-(2-(benzyloxy)ethoxy)ethan-1-ol (0.1 mL), (S)-di-tert-butyl 2-(10-(2,3-bis(tert-butoxycarbonyl)guanidino)-N-(3-hydroxy-5-((2-(trimethylsilyl)ethoxy)carbonyl)benzyl)-13-oxo-6,7,8,13-tetrahydrodibenzo[b,f][1,4]dioxecin-4-carboxamido)succinate (504.8 mg) prepared in the Reference Example 29-(f), and triphenylphosphine (161.6 mg) in dehydrated dichloromethane (2 mL) in a 20 mL cylindrical flask was homogeneously stirred at room temperature under argon atmosphere, and ice-cooled. Then, diisopropyl azodicarboxylate (a 1.9 M solution in toluene) (0.32 mL) was added dropwise thereto, and after the addition was completed, the resulting mixture was stirred under ice-cooling for 0.2 hour, and stirred at room temperature for 2.5 hours. Additionally, triphenylphosphine (27.8 mg) was added thereto at room temperature, additionally diisopropyl azodicarboxylate (a 1.9 M solution in toluene) (0.07 mL) was added thereto under ice-cooling, and the resulting mixture was stirred at room temperature for 15 hours. After the reaction was completed, the reaction solution was purified by medium pressure preparative chromatography (silica gel, elution solvent; hexane:ethyl acetate) to give the title compound (452.8 mg) as a white foam.

Mass spectrum (DUIS, m/z): 1211 [M+H]$^+$.

Reference Example 29-(h)

Preparation of (S)-di-tert-butyl 2-(10-(2,3-bis(tert-butoxycarbonyl)guanidino)-N-(3-(2-(2-hydroxyethoxy)ethoxy)-5-((2-(trimethylsilyl)ethoxy)carbonyl)benzyl)-13-oxo-6,7,8,13-tetrahydrodibenzo[b,f][1,4]dioxecin-4-carboxamido)succinate

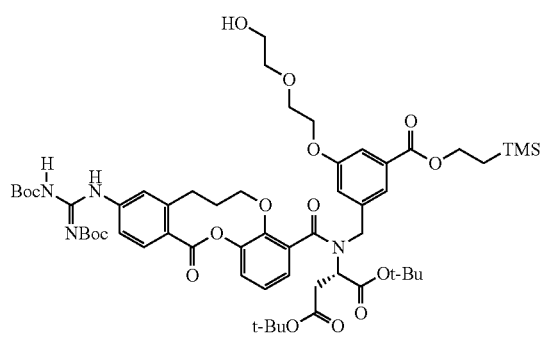

To a solution of (S)-di-tert-butyl 2-(N-(3-(2-(2-(benzyloxy)ethoxy)ethoxy)-5-((2-(trimethylsilyl)ethoxy)carbonyl)benzyl)-10-(2,3-bis(tert-butoxycarbonyl)guanidino)-13-oxo-6,7,8,13-tetrahydrodibenzo[b,f][1,4]dioxecin-4-carboxamido)succinate (448.7 mg) prepared in the Reference Example 29-(g) in ethanol (5 mL)/tetrahydrofuran (2.5 mL) in a 100 mL round-bottom flask was added ASCA-2 (wetted with 52% water, manufactured by NE CHEMCAT Corporation) (83.4 mg) at room temperature under nitrogen atmosphere, and the resulting mixture was stirred at room temperature under hydrogen atmosphere for 2 hours. After the reaction was completed, the reaction solution was filtered through Celite, washed with ethanol, the resulting filtrate and the wash liquid were combined, and concentrated under reduced pressure. The concentrated residues were diluted with ethyl acetate, and concentrated under reduced pressure to give the title compound (420.2 mg) as a white foam.

Mass spectrum (DUIS, m/z): 1121 [M+H]$^+$.

Reference Example 30-(a)

Preparation of (2S,2'S)-tetra-tert-butyl 2,2'-((oxybis(ethane-2,1-diyl))bis((3-((4-nitrobenzoyl)oxy)benzoyl)azanediyl))disuccinate

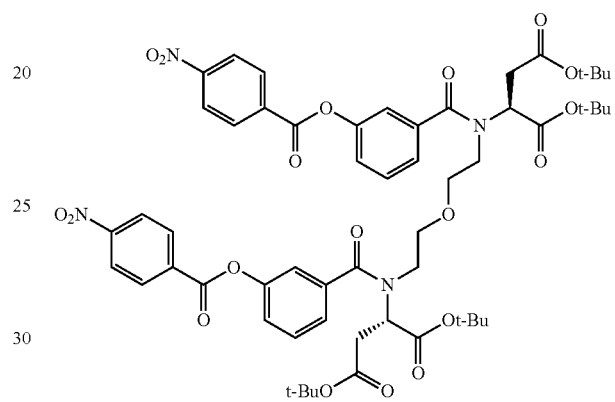

To a solution of 3-((4-nitrobenzoyl)oxy)benzoic acid (1.50 g) in dimethylformamide (18 mL) in a 100 mL round-bottom flask were added COMU (2.52 g) and N,N-diisopropylethylamine (1.32 mL) at 0° C. under argon gas flow with stirring, and the resulting mixture was stirred at 0° C. for 10 minutes. Then, a solution of (2S,2'S)-tetra-tert-butyl 2,2'-((oxybis(ethane-2,1-diyl))bis(azanediyl))disuccinate (1.41 g) prepared according to the same manner as the Reference Example 1-(c) in dimethylformamide (6.00 mL) was added dropwise thereto with stirring at 0° C., and the resulting mixture was stirred at room temperature for 5 hours. Additionally, 3-((4-nitrobenzoyl)oxy)benzoic acid (0.76 g), COMU (2.52 g), and COMU (2.52 g) were added thereto with stirring at room temperature, and the resulting mixture was stirred at room temperature for 24 hours. After the reaction was completed, to the reaction solution was added saturated aqueous sodium hydrogen carbonate solution, and the resulting mixed solution was extracted with toluene. The resulting organic layer was washed with saturated brine, dried over anhydrous magnesium sulfate, filtered, and concentrated under reduced pressure. The resulting residues were subjected to medium pressure preparative chromatography (silica gel, elution solvent; hexane:ethyl acetate), and the fractions comprising the target compound were concentrated under reduced pressure. The resulting residues were purified by medium pressure preparative chromatography (silica gel, elution solvent; hexane:ethyl acetate) to give the title compound (1.40 g) as a slightly yellow foam.

Mass spectrum (ESI, m/z): 1121 [M+Na]$^+$.

Reference Example 30-(b)

Preparation of (2S,2'S)-tetra-tert-butyl 2,2'-((oxybis(ethane-2,1-diyl))bis((3-((4-aminobenzoyl)oxy)benzoyl)azanediyl))disuccinate

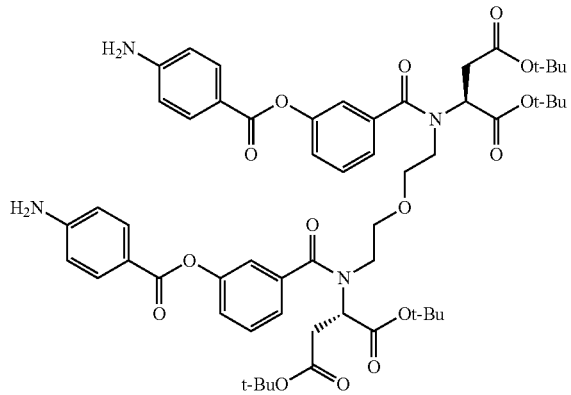 [SMILES: CC(C)(C)OC(=O)C[C@@H](C(=O)OC(C)(C)C)N(CCOCCN(C(=O)c1cccc(OC(=O)c2ccc([N+](=O)[O-])cc2)c1)[C@@H](CC(=O)OC(C)(C)C)C(=O)OC(C)(C)C)C(=O)c1cccc(OC(=O)c2ccc([N+](=O)[O-])cc2)c1]

To a solution of (2S,2'S)-tetra-tert-butyl 2,2'-((oxybis(ethane-2,1-diyl))bis((3-((4-nitrobenzoyl)oxy)benzoyl)azanediyl))disuccinate (1.4 g) prepared in the Reference Example 30-(a) in ethanol (10 mL) in a 200 mL round-bottom flask was added 5% palladium carbon (wetted with 48.57% water, AER-type manufactured by NE CHEMCAT Corporation) (147.1 mg) at room temperature, and the resulting mixture was stirred at room temperature under hydrogen atmosphere for 4 hours. The reaction mixture was filtered through Celite, washed with ethyl acetate, and the resulting filtrate was concentrated under reduced pressure to give (2S,2'S)-tetra-tert-butyl 2,2'-((oxybis(ethane-2,1-diyl)))bis((3-((4-(hydroxyamino)benzoyl)oxy)benzoyl)azanediyl))disuccinate (1.45 g). To a solution of the resulting tetra-tert-butyl 2,2'-((oxybis(ethane-2,1-diyl))bis((3-((4-(hydroxyamino)benzoyl)oxy)benzoyl)azanediyl))(2S,2'S)-disuccinate (1.45 g) in ethanol (10 mL) was added 5% palladium carbon (wetted with 48.57% water, AER-type manufactured by NE CHEMCAT Corporation) (0.73 g) at room temperature, and the resulting mixture was stirred at room temperature under hydrogen atmosphere for 2 hours. After the reaction was completed, the reaction mixture was filtered through Celite, washed with ethyl acetate, and the resulting filtrate was concentrated under reduced pressure to give the title compound (1.27 g) as a slightly yellow foam.

Mass spectrum (DUIS, m/z): 1039 $[M+H]^+$.

Reference Example 30-(c)

Preparation of (2S,2'S)-2,2'-((oxybis(ethane-2,1-diyl))bis((3-((4-aminobenzoyl)oxy)benzoyl)azanediyl))disuccinic acid hydrochloride

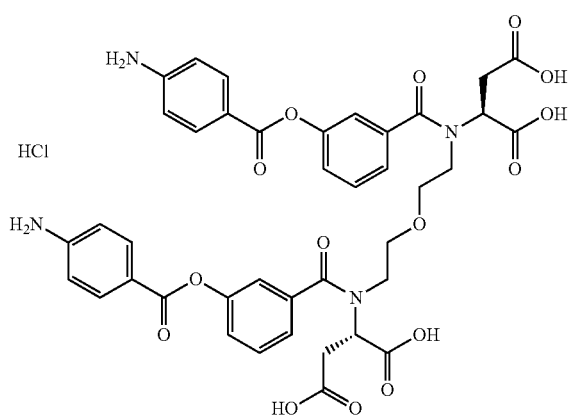 [SMILES: Cl ; Nc1ccc(C(=O)Oc2cccc(C(=O)N(CCOCCN(C(=O)c3cccc(OC(=O)c4ccc(N)cc4)c3)[C@@H](CC(=O)O)C(=O)O)[C@@H](CC(=O)O)C(=O)O)c2)cc1]

To a solution of (2S,2'S)-tetra-tert-butyl 2,2'-((oxybis(ethane-2,1-diyl))bis((3-((4-aminobenzoyl)oxy)benzoyl)azanediyl))disuccinate (1.27 g) prepared in the Reference Example 30-(b) in dioxane (20 mL) in a 200 mL round-bottom flask was added dropwise a 4 M hydrogen chloride/dioxane solution (10 mL) at room temperature under argon gas flow with stirring, and the resulting mixture was stirred at room temperature for 0.5 hour. Additionally, a 4 M hydrogen chloride/dioxane solution (10 mL) and dioxane (20 mL) were added thereto with stirring at room temperature, and the resulting mixture was stirred at room temperature for 18 hours. Additionally, a 4 M hydrogen chloride/dioxane solution (10 mL) and dioxane (20 mL) were added thereto. After the reaction was completed, the reaction solution was concentrated under reduced pressure. The resulting concentrated residues were subjected to azeotropy with toluene once to give the title compound (1.35 g) as slightly yellow solids.

Mass spectrum (ESI, m/z): 813 $[M-H]^+$.

Reference Example 31-(a)

Preparation of (S)-di-tert-butyl 2-((((4-((4-(2,3-bis(tert-butoxycarbonyl)guanidino)benzoyl)oxy)benzyl)oxy)carbonyl)amino)succinate

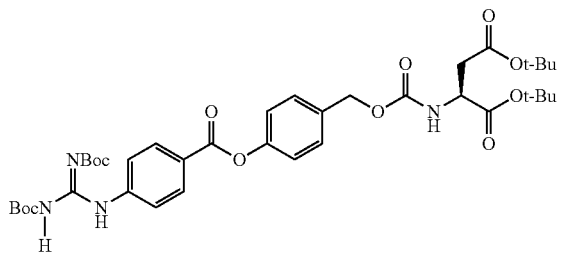

(1) To a solution of L-aspartic acid di-tert-butyl ester hydrochloride (3.40 g) and pyridine (4.20 mL) in dehydrated dichloromethane (20 mL) in a 200 mL three-necked flask was added dropwise a solution of bis(trichloromethyl) carbonate (1.16 g) in dehydrated dichloromethane (10 mL) at −20° C. under argon gas flow with stirring, and the resulting mixture was stirred at −20° C. for 2 hours.

(2) To a suspension of 4-(hydroxymethyl)phenyl 4-(2,3-bis(tert-butoxycarbonyl)guanidino)benzoate (3.14 g) prepared according to the same manner as the Reference Example 1-(g) and N,N-diisopropylethylamine (5.00 mL) in dehydrated dichloromethane (20 mL) in a 300 mL round-bottom flask was added the reaction solution prepared in (1) under ice-cooling under argon atmosphere with stirring, and the resulting mixture was stirred at room temperature for 16 hours. The reaction solution was concentrated under reduced pressure. A solution of the concentrated residues in dehydrated dimethylformamide (50 mL) was stirred at 65° C. for 1 hour, at 75° C. for 2 hours, and at 65° C. for 2 hours. After the reaction was completed, to the reaction solution was added saturated aqueous sodium hydrogen carbonate solution, and the resulting mixed solution was extracted with dichloromethane. The resulting organic layer was washed with saturated brine, dried over anhydrous sodium sulfate, filtered, and concentrated under reduced pressure. The resulting residues were purified by medium pressure preparative chromatography (silica gel, elution solvent; hexane: ethyl acetate) to give the title compound (1.46 g) as white solids.

Mass spectrum (ESI, m/z): 757 [M+H]+.

Reference Example 31-(b)

Preparation of (5)-2-((((4-((4-guanidinobenzoyl)oxy)benzyl)oxy)carbonyl)amino)succinic acid trifluoroacetate

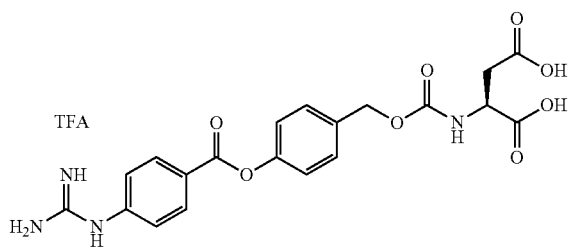 [SMILES: N=C(N)Nc1ccc(C(=O)Oc2ccc(COC(=O)N[C@@H](CC(=O)O)C(=O)O)cc2)cc1]

To a solution of (S)-di-tert-butyl 2-((((4-((4-(2,3-bis(tert-butoxycarbonyl)guanidino)benzoyl)oxy)benzyl)oxy)carbonyl)amino)succinate (1.46 g) prepared in the Reference Example 31-(a) in dehydrated dichloromethane (15 mL) in a 500 mL round-bottom flask was added trifluoroacetic acid (3.00 mL) under ice-cooling under argon atmosphere with stirring, and the resulting mixture was stirred under ice-cooling for 3 hours. The reaction solution was concentrated under reduced pressure. To a solution of the concentrated residues in dehydrated dichloromethane (15 mL) was added trifluoroacetic acid (3.00 mL) under ice-cooling under argon atmosphere with stirring, and the resulting mixture was stirred at room temperature for 3 hours. Additionally, trifluoroacetic acid (3.00 mL) was added thereto with stirring at room temperature, and the resulting mixture was stirred at room temperature for 1 hour. After the reaction was completed, the reaction solution was concentrated under reduced pressure. The concentrated residues were dissolved into a mixed solvent of water and acetonitrile (1:1 (v/v)), and the resulting solution was freeze-dried. The resulting residues were subjected to medium pressure preparative chromatography (silica gel, elution solvent; acetonitrile solution with 0.1% trifluoroacetic acid:aqueous solution with 0.1% trifluoroacetic acid), and the fractions comprising the target compound were concentrated under reduced pressure. The concentrated residues were dissolved into a mixed solvent of water and acetonitrile (1:1 (v/v)), and the resulting solution was freeze-dried to give the title compound (1.17 g) as white solids.

Mass spectrum (ESI, m/z): 445 [M+H]+.

Reference Example 31-(c)

Preparation of (S)-2-((((4-((4-guanidinobenzoyl)oxy)benzyl)oxy)carbonyl)amino)succinic acid hydrochloride

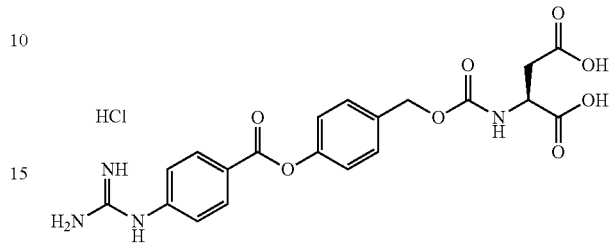

To a solution of (S)-2-((((4-((4-guanidinobenzoyl)oxy)benzyl)oxy)carbonyl)amino)succinic acid trifluoroacetate (220 mg) prepared in the Reference Example 31-(b) in acetonitrile (1.5 mL)/water (1 ml) in a 50 mL round-bottom flask was added 1N hydrochloric acid (0.430 mL) at room temperature with stirring, and the resulting mixture was freeze-dried to give the title compound (180 mg) as white solids.

Mass spectrum (ESI, m/z): 445 [M−H]−.

Reference Example 32-(a)

Preparation of (S)-di-tert-butyl 2-(((4-(benzyloxy)phenoxy)carbonyl)amino)succinate

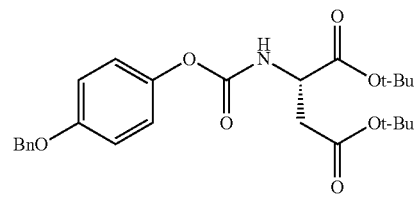 [SMILES: CC(C)(C)OC(=O)C[C@H](NC(=O)Oc1ccc(OCc2ccccc2)cc1)C(=O)OC(C)(C)C]

To a solution of 4-(benzyloxy)phenol (0.99 g) in ethyl acetate (25 mL) in a 100 mL was added 1,1'-carbonyldiimidazole (2.05 g) at room temperature under argon atmosphere with stirring, and the resulting mixture was stirred a room temperature for 1 hour. Then, acetic acid (1.70 mL) and L-aspartic acid di-tert-butyl ester hydrochloride (2.03 g) were added thereto with stirring at room temperature, and the resulting mixture was stirred at room temperature for 120 hours. After the reaction was completed, to the reaction solution was added 1N hydrochloric acid, and the resulting mixed solution was extracted with ethyl acetate. The resulting organic layer was washed sequentially with saturated aqueous sodium hydrogen carbonate solution and saturated brine, dried over anhydrous magnesium sulfate, filtered, and concentrated under reduced pressure. The resulting residues were purified by column chromatography (silica gel, elution solvent; hexane:ethyl acetate) to give the title compound (0.43 g) as white solids.

Mass spectrum (EST, m/Z): 470 [M−H]−.

According to the same method as the Reference Example 32-(a), Reference Example 33-(a) to Reference Example 34-(a) were prepared.

TABLE 17

| Reference Example No. | Compound name<br>Structural formula<br>Mass spectrum |
|---|---|
| 33-(a) | (S)-di-tert-butyl 2-(((4-(benzyloxy)phenethoxy)carbonyl)amino)succinate<br><br>(DUIS, m/z): 500 [M + H]⁺. |
| 34-(a) | (S)-di-tert-butyl 2-(((3-(4-(benzyloxy)phenyl)propoxy)carbonyl)amino)succinate<br><br>(DUIS, m/z): 514 [M + H]⁺. |

Reference Example 32-(b)

Preparation of (S)-di-tert-butyl 2-(((4-hydroxyphenoxy)carbonyl)amino)succinate

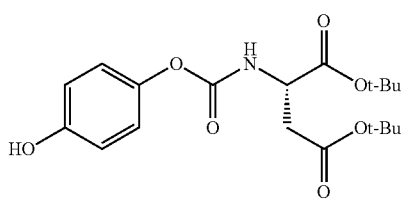 [SMILES: CC(C)(C)OC(=O)C[C@H](NC(=O)Oc1ccc(O)cc1)C(=O)OC(C)(C)C]

To a solution of (S)-di-tert-butyl 2-(((4-(benzyloxy)phenoxy)carbonyl)amino)succinate (0.43 g) prepared according to the same manner as the Reference Example 32-(a) in ethanol (20 mL) in a 100 mL round-bottom flask was added 10% palladium carbon (wetted with 54.51% water, PE-type manufactured by NE CHEMCAT Corporation) (42 mg) at room temperature under argon atmosphere with stirring, the atmosphere in the reaction system was replaced with hydrogen atmosphere, and then the resulting mixture was stirred at room temperature for 3 hours. After the reaction was completed, the atmosphere in the reaction system was replaced with argon atmosphere, the reaction solution was filtered through Celite, washed with ethanol, and the resulting filtrate was concentrated under reduced pressure. The resulting residues were purified by column chromatography (silica gel, elution solvent; hexane:ethyl acetate) to give the title compound (350.5 mg) as white solids.

Mass spectrum (ESI, m/z): 380 [M−H]⁻.

According to the same method as the Reference Example 32-(b), Reference Example 33-(b) to Reference Example 34-(b) were prepared.

TABLE 18

| Reference Example No. | Compound name<br>Structural formula<br>Mass spectrum |
|---|---|
| 33-(b) | (S)-di-tert-butyl 2-(((4-hydroxyphenethoxy)carbonyl)amino)succinate<br><br>(CI, m/z): 410 [M + H]⁺. |
| 34-(b) | (S)-di-tert-butyl 2-(((3-(4-hydroxyphenyl)propoxy)carbonyl)amino)succinate<br><br>(CI, m/z): 424 [M + H]⁺. |

Reference Example 32-(c)

Preparation of (S)-di-tert-butyl 2-(((4-((4-(2,3-bis(tert-butoxycarbonyl)guanidino)benzoyl)oxy)phenoxy)carbonyl)amino) succinate

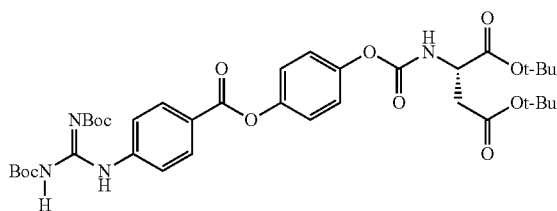

To a suspension of (S)-di-tert-butyl 2-(((4-hydroxyphenoxy)carbonyl)amino)succinate (350 mg) prepared in the Reference Example 32-(b), 4-(2,3-bis(tert-butoxycarbonyl)guanidino)benzoic acid (458 mg) prepared according to the same manner as the Reference Example 1-(e), and 1-(3-dimethylaminopropyl)-3-ethylcarbodiimide hydrochloride (262 mg) in dichloromethane (10 mL) in a 50 mL round-bottom flask was added 4-dimethylaminopyridine (57 mg) at room temperature under argon atmosphere with stirring, and the resulting mixture was stirred at room temperature for 1 hour. After the reaction was completed, to the reaction solution was added silica gel, the resulting mixture was eluted with a mixed solvent of ethyl acetate/hexane, and the resulting eluate was concentrated under reduced pressure. The resulting residues were purified by column chromatography (silica gel, elution solvent; hexane ethyl acetate) to give the title compound (447.1 mg) as white solids.

Mass spectrum (ESI, m/z): 743 [M+H]$^+$.

According to the same method as the Reference Example 32-(c), Reference Example 33-(c) to Reference Example 34-(c) were prepared.

TABLE 19

| Reference Example No. | Compound name<br>Structural formula<br>Mass spectrum |
|---|---|
| 33-(c) | (S)-di-tert-butyl 2-(((4-((4-(2,3-bis(tert-butoxycarbonyl)guanidino)benzoyl)oxy)phenethoxy)carbonyl)amino)succinate<br>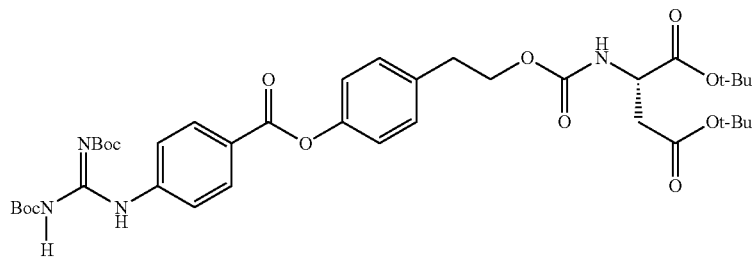<br>(ESI, m/z): 771 [M + H]$^+$. |
| 34-(c) | (S)-di-tert-butyl 2-(((3-(4-((4-(2,3-bis(tert-butoxycarbonyl)guanidino)benzoyl)oxy)phenyl)propoxy)carbonyl)amino)succinate<br>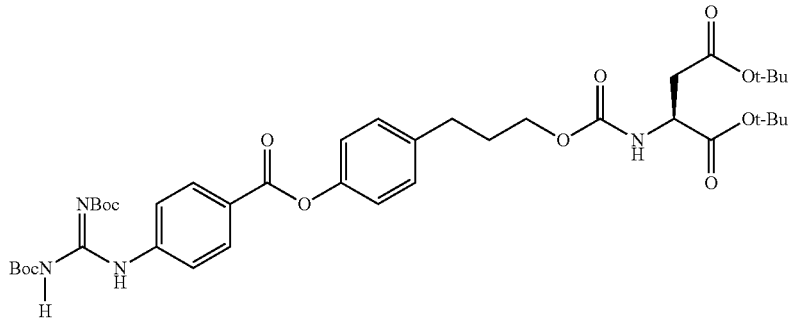<br>(DUIS, m/z): 785 [M + H]$^+$. |

Reference Example 32-(d)

Preparation of (S)-2-(((4-((4-guanidinobenzoyl)oxy)phenoxy)carbonyl)amino)succinic acid trifluoroacetate

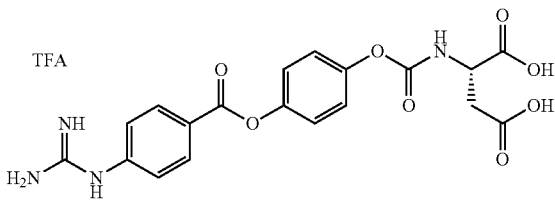 [SMILES: N=C(N)Nc1ccc(C(=O)Oc2ccc(OC(=O)N[C@@H](CC(=O)O)C(=O)O)cc2)cc1]

To a solution of (S)-di-tert-butyl 2-(((4-((4-(2,3-bis(tert-butoxycarbonyl)guanidino)benzoyl)oxy)phenoxy)carbonyl)amino) succinate (440 mg) prepared in the Reference Example 32-(c) in dichloromethane (6 mL) in a 50 mL round-bottom flask was added trifluoroacetic acid (3 mL) at room temperature under argon atmosphere with stirring, and the resulting mixture was stirred at room temperature for 5 hours. After the reaction was completed, the reaction solution was concentrated under reduced pressure. To the concentrated residues was added dichloromethane, and the resulting mixture was subjected to azeotropy three times. Then, to the concentrated residues was added acetonitrile, and the resulting mixture was subjected to azeotropy three times. The concentrated residues were dissolved into a mixed solvent of water/acetonitrile, and the resulting solution was freeze-dried to give the title compound (295 mg) as white solids.

Mass spectrum (ESI, m/z): 431 [M+H]$^+$.

Reference Example 33-(d)

Preparation of (S)-2-(((4-((4-guanidinobenzoyl)oxy)phenethoxy)carbonyl)amino)succinic acid trifluoroacetate

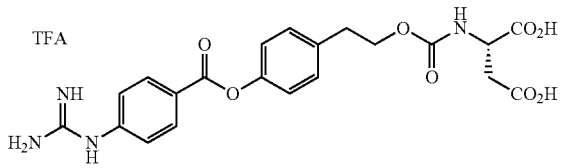 [SMILES: N=C(N)Nc1ccc(C(=O)Oc2ccc(CCOC(=O)N[C@@H](CC(=O)O)C(=O)O)cc2)cc1]

The title compound was prepared by using the Reference Example 33-(c) according to the same method as the Reference Example 32-(d).

Mass spectrum (ESI, m/z): 459 [M+H]$^+$.

Reference Example 34-(d)

Preparation of (S)-2-(((3-(4-((4-guanidinobenzoyl)oxy)phenyl)propoxy)carbonyl)amino)succinic acid

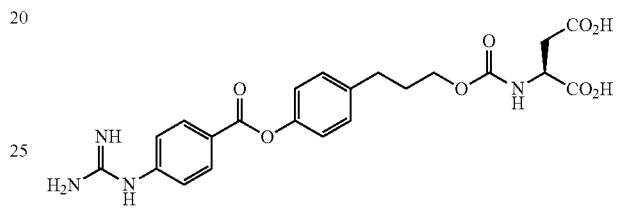

To a solution of (S)-di-tert-butyl 2-(((3-(4-((4-(2,3-bis(tert-butoxycarbonyl)guanidino)benzoyl)oxy)phenyl)propoxy)carbonyl)amino)succinate (340 mg) prepared in the Reference Example 34-(c) in dichloromethane (6 mL) in a 50 mL round-bottom flask was added trifluoroacetic acid (3 mL) at room temperature under argon atmosphere with stirring, and the resulting mixture was stirred at room temperature for 18 hours. The reaction solution was concentrated under reduced pressure. To the concentrated residues was added dichloromethane, and the resulting mixture was subjected to azeotropy three times. The concentrated residues were dissolved into a mixed solvent of water and acetonitrile (1:1 (v/v)), and the resulting solution was freeze-dried. To the concentrated residues were added dichloromethane (5 mL) and trifluoroacetic acid (5 mL), and the resulting mixture was stirred overnight. After the reaction was completed, the reaction solution was concentrated under reduced pressure. The concentrated residues were dissolved into a mixed solvent of water and acetonitrile (1:1 (v/v)), and the resulting solution was freeze-dried. The resulting residues were preparatively isolated by high performance liquid chromatography (Column; XBridge BEH C18 OBD Prep Column, elution solvent; aqueous solution with 0.1% trifluoroacetic acid:acetonitrile solution with 0.1% trifluoroacetic acid), and the fractions comprising the target compound were concentrated under reduced pressure. The precipitated solids were collected by filtration, and dried under reduced pressure to give the title compound (145.2 mg) as white solids.

Mass spectrum (ESI, m/z): 473 [M+H]$^+$.

Reference Example 35-(a)

Preparation of tri-tert-butyl 3-(((4-((4-(2,3-bis(tert-butoxycarbonyl)guanidino)benzoyl)oxy)benzyl)oxy)carbonyl)-6,9,12,15,18,21-hexaoxa-3-azatricosane-1,2,23-tricarboxylate

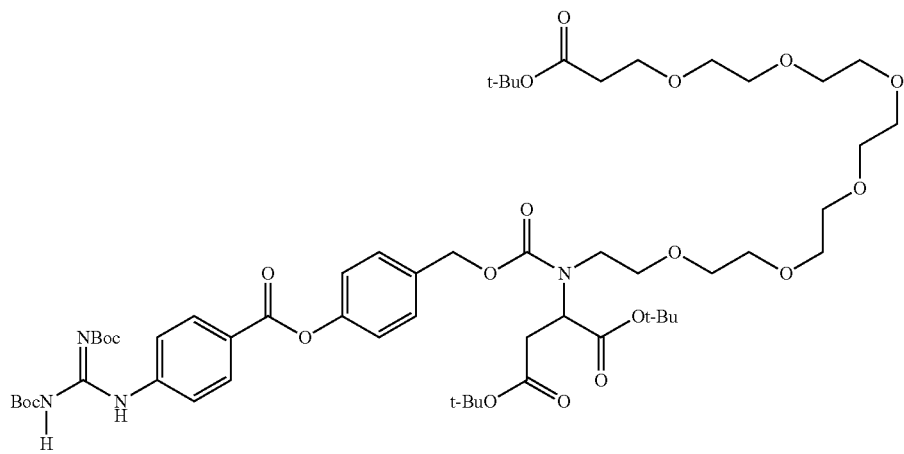

To a suspension of 1-(((4-((4-(2,3-bis(tert-butoxycarbonyl)guanidino)benzoyl)oxy)benzyl)oxy)carbonyl)-3-methyl-1H-imidazol-3-ium trifluoromethanesulfonate (400 mg) prepared according to the same manner as the Reference Example 10-(b) in dehydrated dichloromethane (4 mL) in a 50 mL round-bottom flask was added tri-tert-butyl 6,9,12,15,18,21-hexaoxa-3-azatricosane-1,2,23-tricarboxylate (415 mg) prepared in the Reference Example 10-(c)-2 at room temperature under argon atmosphere with stirring, and the resulting mixture was stirred at room temperature for 6 days. After the reaction was completed, the reaction solution was concentrated under reduced pressure. The resulting residues were purified by medium pressure preparative chromatography (silica gel, elution solvent; hexane:ethyl acetate) to give the title compound (264 mg) as a colorless oil.

Mass spectrum (ESI, m/z): 1150 [M+H]⁻.

According to the same method as the Reference Example 35-(a), Reference Example 36-(a) to Reference Example 51-(a) were prepared.

TABLE 20

| Reference Example No. | Compound name<br>Structural formula<br>Mass spectrum |
|---|---|
| 36-(a) | tri-tert-butyl 3-(((4-((4-(2,3-bis(tert-butoxycarbonyl)guanidino)benzoyl)oxy)benzyl)oxy)carbonyl)-6,9,12,15,18-pentaoxa-3-azaicosane-1,2,20-tricarboxylate<br>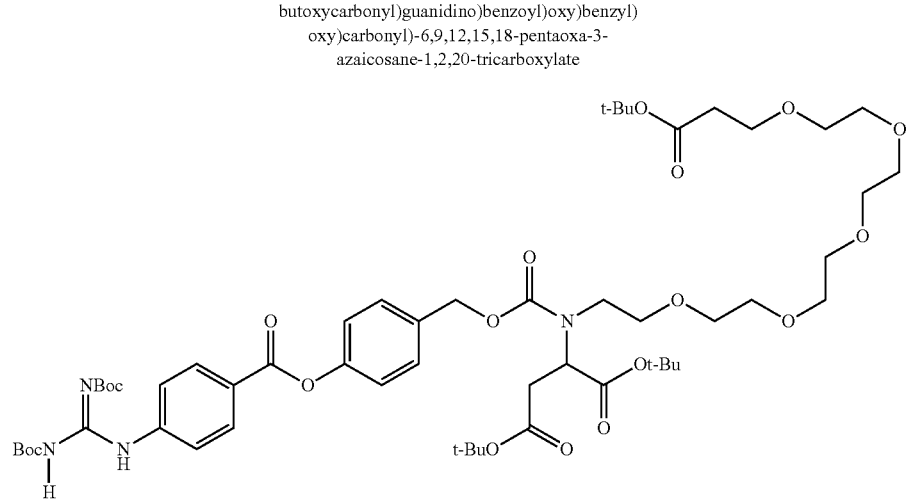<br>(ESI, m/z): 1106 [M + H]⁺. |

TABLE 20-continued

| Reference Example No. | Compound name<br>Structural formula<br>Mass spectrum |
|---|---|
| 37-(a) | tri-tert-butyl 3-(((4-((4-(2,3-bis(tert-butoxycarbonyl)guanidino)benzoyl)oxy)benzyl)oxy)carbonyl)-6,9,12,15-tetraoxa-3-azaheptadecane-1,2,17-tricarboxylate |

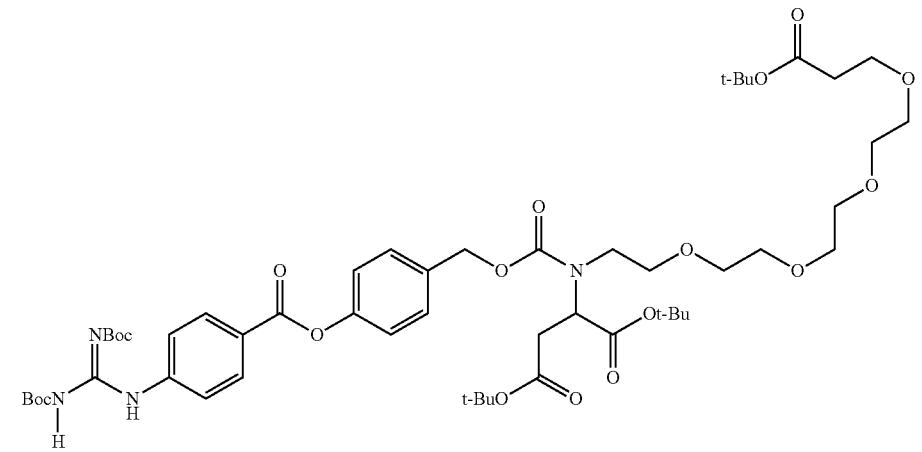

(ESI, m/z): 1062 [M + H]+.

| 38-(a) | tri-tert-butyl 3-(((4-((4-(2,3-bis(tert-butoxycarbonyl)guanidino)benzoyl)oxy)benzyl)oxy)carbonyl)-6,9,12-trioxa-3-azatetradecane-1,2,14-tricarboxylate |

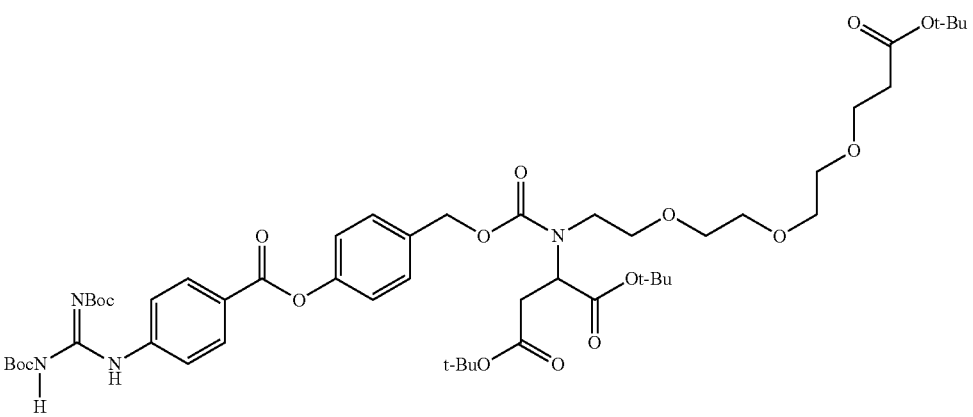

(DUIS, m/z): 1018 [M + H]+.

TABLE 20-continued

| Reference Example No. | Compound name Structural formula Mass spectrum |
|---|---|

39-(a)　di-tert-butyl 2-(((4-((4-(2,3-bis(tert-butoxycarbonyl)guanidino)benzoyl)oxy)benzyl)oxy)carbonyl)(2-(2-(3-(tert-butoxy)-3-oxopropoxy)ethoxy)ethyl)amino)succinate (ESI, m/z): 974 [M + H]⁺.

40-(a)　di-tert-butyl 2-(((4-((4-(2,3-bis(tert-butoxycarbonyl)guanidino)benzoyl)oxy)benzyl)oxy)carbonyl)(2-(3-(tert-butoxy)-3-oxopropoxy)ethoxy)ethyl)amino)succinate (ESI, m/z): 930 [M + H]⁺.

41-(a)　(2S)-di-tert-butyl 2-(2-((((4-((4-(2,3-bis(tert-butoxycarbonyl)guanidino)benzoyl)oxy)benzyl)oxy)carbonyl)amino)-4-(tert-butoxy)-4-oxobutaneamide)succinate (ESI, m/z): 928 [M + H]⁺.

TABLE 20-continued

| Reference Example No. | Compound name Structural formula Mass spectrum |
|---|---|
| 42-(a) | (S)-di-tert-butyl 2-((S)-2-((S)-2-((((4-((4-(2,3-bis(tert-butoxycarbonyl)guanidino)benzoyl)oxy)benzyl)oxy)carbonyl)amino)-4-(tert-butoxy)-4-oxobutaneamida)-4-(tert-butoxy)-4-oxobutaneamide)succinate |

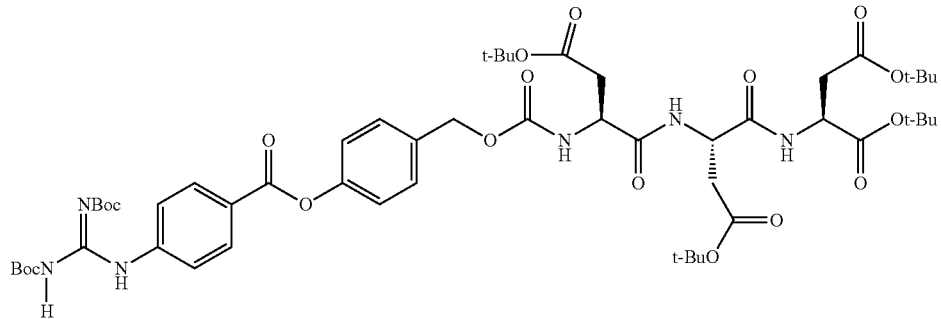

(ESI, m/z): 1100 [M + H]⁺.

| 43-(a) | (S)-di-tert-butyl 2-(2-((((4-((4-(2,3-bis(tert-butoxycarbonyl)guanidino)benzoyl)oxy)benzyl)oxy)carbonyl)(3-(tert-butoxycarbonyl)benzyl)amino)acezamido)succinate |

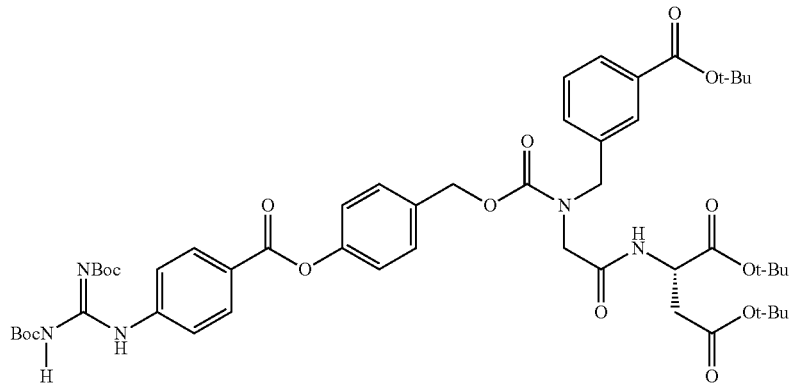

(ESI, m/z): 1004 [M + H]⁺.

TABLE 20-continued

| Reference Example No. | Compound name Structural formula Mass spectrum |
|---|---|
| 44-(a) | (2S)-di-tert-butyl 2-(2-((((4-((4-(2,3-bis(tert-butoxycarbonyl)guanidino)benzoyl)oxy)benzyl)oxy)carbonyl)(2-(tert-butoxy)-2-oxoethyl)amino)-4-(tert-butoxy)-4-oxobutaneamide)succinate<br>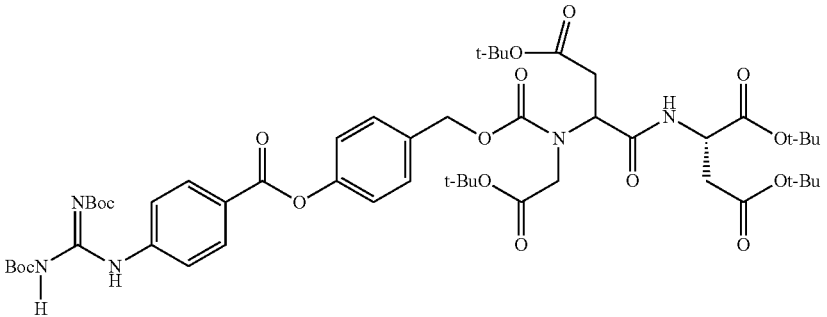<br>(ESI, m/z): 1043 [M + H]⁺. |
| 45-(a) | tert-butyl 3-((((4-((4-(2,3-bis(tert-butoxycarbonyl)guanidino)benzoyl)oxy)benzyl)oxy)carbonyl)(2-(tert-butoxy)-2-oxoethyl)amino)methyl)benzoate<br>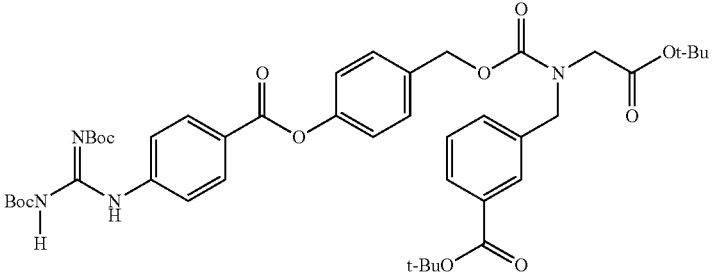<br>(DUIS, m/z): 833 [M + H]⁺. |
| 46-(a) | di-tert-butyl 3-(((4-((4-(2,3-bis(tert-butoxycarbonyl)guanidino)benzoyl)oxy)benzyl)oxy)carbonyl)-6,9,12,15-tetraoxa-3-azaoctadecane-1,18-dioate<br>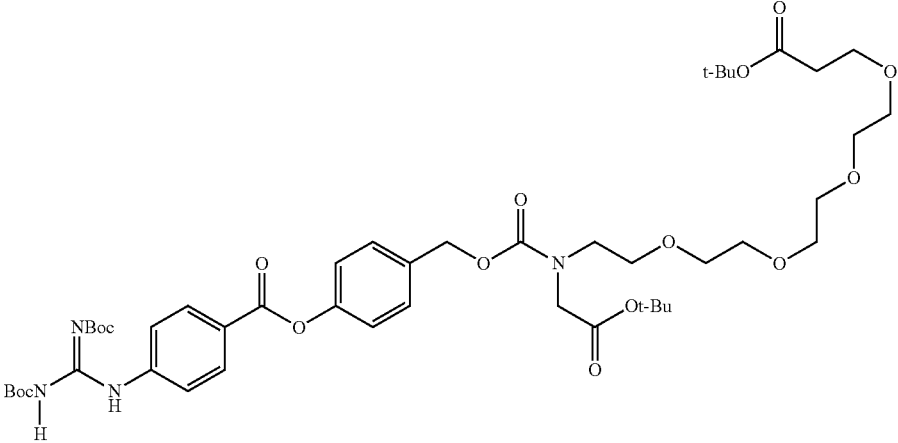 |

TABLE 20-continued

| Reference Example No. | Compound name Structural formula Mass spectrum |
|---|---|

(ESI, m/z): 948 [M + H]⁺.

47-(a)     tert-butyl 3-(2-(((4-((4-(2,3-bis(tert-butoxycarbonyl)guanidino)benzoyl)oxy)benzyl)oxy)carbonyl)-19,19-dimethyl-17-oxo-5,8,11,14,18-pentaoxa-2-azaicosyl)benzoate

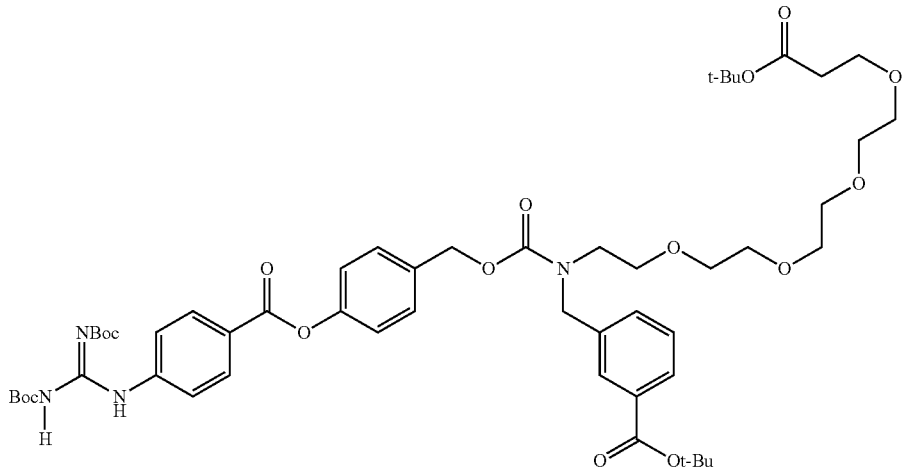

(DUIS, m/z): 948 [M + H]⁺.

48-(a)     (S)-di-tert-butyl 2-((((4-((4-(2,3-bis(tert-butoxycarbonyl)guanidino)benzoyl)oxy)benzyl)oxy)carbonyl)(2-(tert-butoxy)-2-oxoethyl)amino)succinate

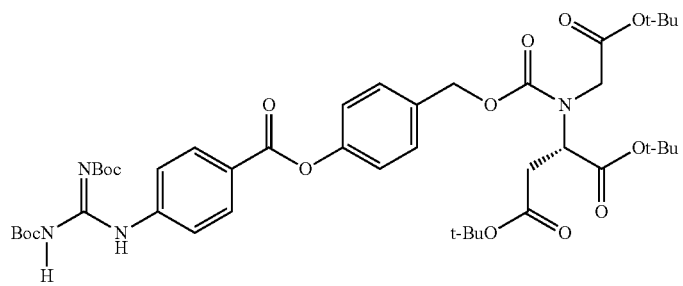

(ESI, m/z): 872 [M + H]⁺.

TABLE 20-continued

| Reference Example No. | Compound name Structural formula Mass spectrum |
|---|---|
| 49-(a) | (S)-di-tert-butyl 2-((((4-((4-(2,3-bis(tert-butoxycarbonyl)guanidino)benzoyl)oxy)benzyl)oxy)carbonyl)(3-(tert-butoxycarbonyl)benzyl)amino)succinate |

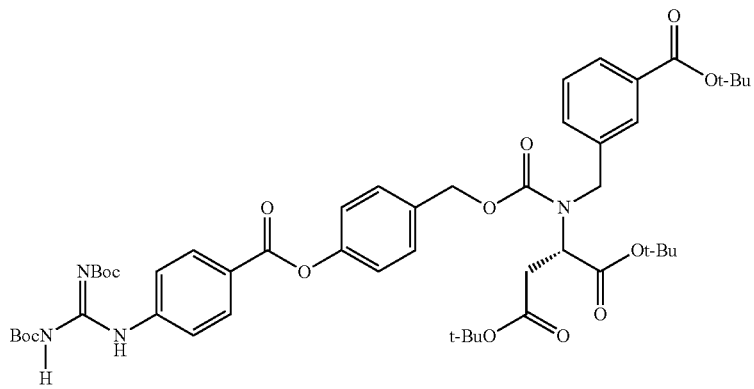

(ESI, m/z): 947 [M + H]⁺.

| 50-(a) | (S)-di-tert-butyl 2-(2-((((4-((4-(2,3-bis(tert-butoxycarbonyl)guanidino)benzoyl)oxy)benzyl)oxy)carbonyl)((S)-1,4-di-tert-butoxy-1,4-dioxobutan-2-yl)amino)acetamido)succinate |

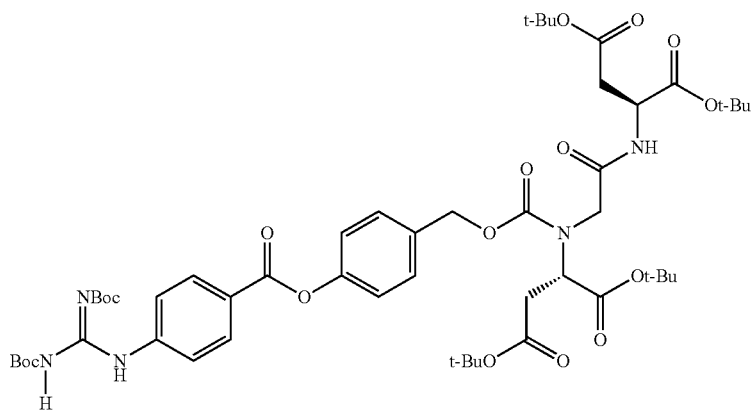

(ESI, m/z): 1042 [M + H]⁺.

TABLE 20-continued

| Reference Example No. | Compound name<br>Structural formula<br>Mass spectrum |
|---|---|
| 51-(a) | (S)-di-tert-butyl 2-((((4-((4-(2,3-bis(tert-butoxycarbonyl)guanidino)benzoyl)oxy)benzyl)oxy)carbonyl)(6-(tert-butoxy)-6-oxohexyl)amino)succinate<br>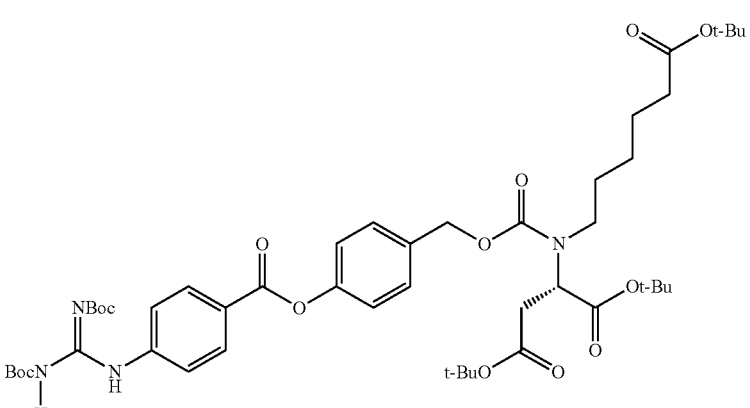<br>(ESI, m/z): 927 [M + H]⁺. |

Reference Example 35-(b)

Preparation of 3-(((4-((4-guanidinobenzoyl)oxy)benzyl)oxy)carbonyl)-6,9,12,15,18,21-hexaoxa-3-azatricosane-1,2,23-tricarboxylic acid

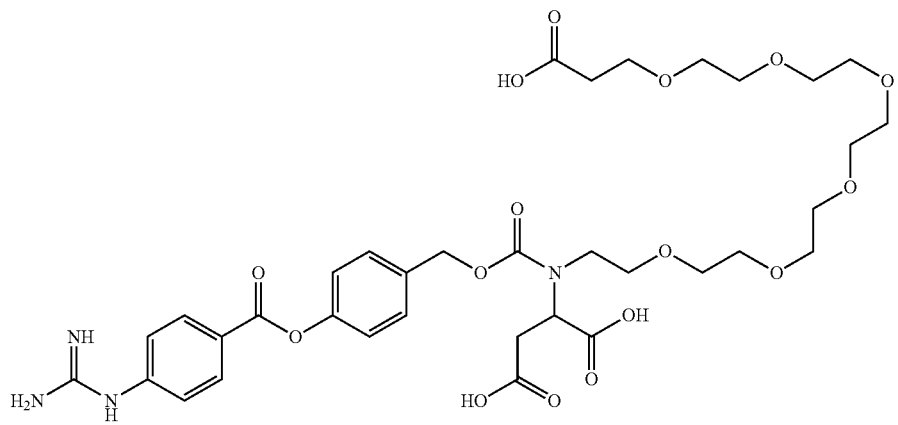 [SMILES: N=C(N)Nc1ccc(C(=O)Oc2ccc(COC(=O)N(CCOCCOCCOCCOCCOCCOCCC(=O)O)C(CC(=O)O)C(=O)O)cc2)cc1]

To a solution of tri-tert-butyl 3-(((4-((4-(2,3-bis(tert-butoxycarbonyl)guanidino)benzoyl)oxy)benzyl)oxy)carbonyl)-6,9,12,15,18,21-hexaoxa-3-azatricosane-1,2,23-tricarboxylate (264 mg) prepared in the Reference Example 35-(a) in dehydrated dichloromethane (4 mL) in a 50 mL round-bottom flask was added trifluoroacetic acid (1.00 mL) under ice-cooling under argon atmosphere with stirring, and the resulting mixture was stirred at room temperature for 6 hours. The reaction solution was concentrated under reduced pressure. To a solution of the concentrated residues in dehydrated dichloromethane (2 mL) was added trifluoroacetic acid (1.00 mL) at room temperature under argon atmosphere with stirring, and the resulting mixture was stirred at room temperature for 18 hours. After the reaction was completed, the reaction solution was concentrated under reduced pressure. To a solution of the resulting residues in water (8 mL)/acetonitrile (2 mL)/trifluoroacetic acid was added a saturated aqueous ammonium acetate solution to adjust the pH to 4.0. The resulting solution was subjected to medium pressure preparative chromatography (ODS silica gel, elution solvent; water:acetonitrile:methanol), and the fractions comprising the target compound were concentrated under reduced pressure. The concentrated residues were freeze-dried to give the title compound (144 mg) as white solids.

Mass spectrum (ESI, m/z): 781 [M+H]⁺.

Reference Example 36-(b)

Preparation of 3-(((4-((4-guanidinobenzoyl)oxy)benzyl)oxy)carbonyl)-6,9,12,15,18-pentaoxa-3-azaicosane-1,2,20-tricarboxylic acid

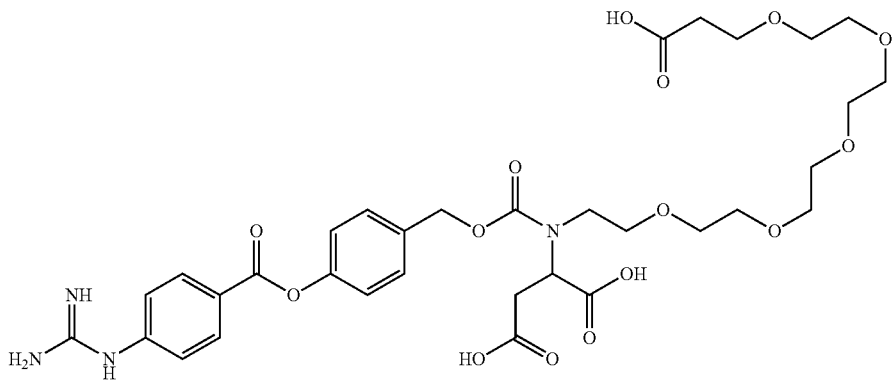 [SMILES: N=C(N)Nc1ccc(C(=O)Oc2ccc(COC(=O)N(CCOCCOCCOCCOCCOCCC(=O)O)C(CC(=O)O)C(=O)O)cc2)cc1]

The title compound was prepared by using the Reference Example 36-(a) according to the same method as the Reference Example 35-(b).
Mass spectrum (ESI, m/z): 737 [M+H]$^+$.

Reference Example 37-(b)

Preparation of 3-(((4-((4-guanidinobenzoyl)oxy)benzyl)oxy)carbonyl)-6,9,12,15-tetraoxa-3-azaheptadecane-1,2,17-tricarboxylic acid To a solution of tri-tert-butyl 3-(((4-((4-(2,3-bis(tert-butoxycarbonyl)guanidino)benzoyl)oxy)benzyl)oxy)carbonyl)-6,9,12,15-tetraoxa-3-azaheptadecane-1,2,17-tricarboxylate (264 mg) prepared in the Reference Example 37-(a) in dichloromethane (3.2 mL) in a 50 mL round-bottom flask was added trifluoroacetic acid (800 μL) at room temperature under argon gas flow with stirring, and the resulting mixture was stirred at room temperature for 15 hours. The reaction solution was concentrated under reduced pressure. To the concentrated residues were added dichloromethane (800 μL) and trifluoroacetic acid (800 μL) at room temperature, and the resulting mixture was stirred at room temperature for 3 hours. After the reaction was completed, the reaction solution was concentrated under reduced pressure. The resulting residues were subjected to medium pressure preparative chromatography (silica gel, elution solvent; acetonitrile solution with 0.1% trifluoroacetic acid: aqueous solution with 0.1% trifluoroacetic acid), and the fractions comprising the target compound were concentrated under reduced pressure to give a white foam (330 mg). To a part of the resulting white foam (114 mg) were added water (2 mL)/acetonitrile (200 μL), and the resulting solution was concentrated under reduced pressure. To the resulting residues was added a saturated aqueous ammonium acetate solution to adjust the pH to 4.0. The resulting solution was

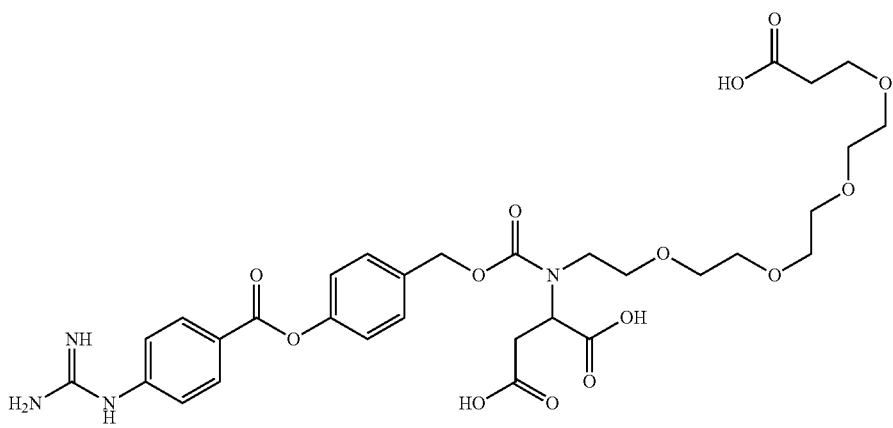 [SMILES: N=C(N)Nc1ccc(C(=O)Oc2ccc(COC(=O)N(CCOCCOCCOCCOCCC(=O)O)C(CC(=O)O)C(=O)O)cc2)cc1]

subjected to Bond Elut C18 (elution solvent; water:acetonitrile:methanol), and the fractions comprising the target compound were concentrated under reduced pressure. The concentrated residues were dissolved into a mixed solvent of water/acetonitrile, and the resulting solution was freeze-dried to give the title compound (57 mg) as white solids.
Mass spectrum (ESI, m/z): 693 [M+H]$^+$.

Reference Example 38-(b)

Preparation of 3-((4-(4-guanidinobenzoyl)oxy)benzyl)oxy)carbonyl)-6,9,12-trioxa-3-azatetradecane-1,2,14-tricarboxylic acid

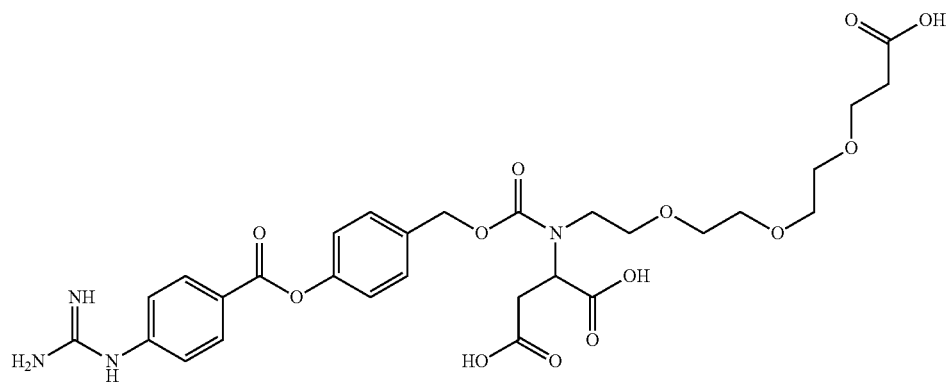 [SMILES: N=C(N)Nc1ccc(C(=O)Oc2ccc(COC(=O)N(CCOCCOCCOCCC(=O)O)C(CC(=O)O)C(=O)O)cc2)cc1]

The title compound was prepared by using the Reference Example 38-(a) according to the same method as the Reference Example 37-(b).

Mass spectrum (ESI, m/z): 649 [M+H]$^+$.

Reference Example 39-(b)

Preparation of 2-((2-(2-(2-carboxyethoxy)ethoxy)ethyl) (((4-((4-guanidinobenzoyl)oxy)benzyl)oxy)carbonyl)amino)succinic acid

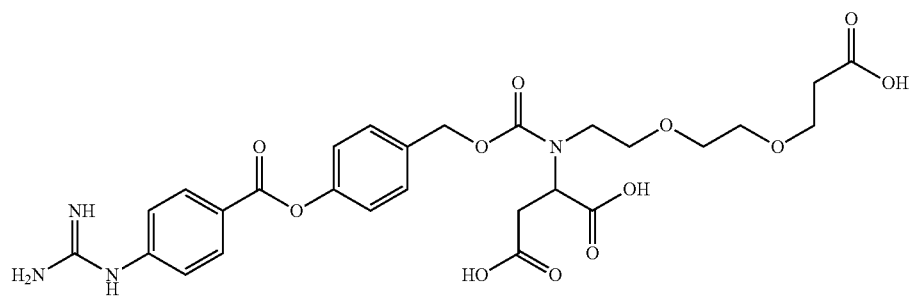 [SMILES: N=C(N)Nc1ccc(C(=O)Oc2ccc(COC(=O)N(CCOCCOCCC(=O)O)C(CC(=O)O)C(=O)O)cc2)cc1]

The title compound was prepared by using the Reference Example 39-(a) according to the same method as the Reference Example 37-(b).

Mass spectrum (ESI, m/z): 605 [M+H]$^+$.

Reference Example 40-(b)

Preparation of 2-((2-(2-carboxyethoxy)ethyl)<(4-((4-guanidinobenzoyl)oxy)benzyl)oxy)carbonyl)amino)succinic acid

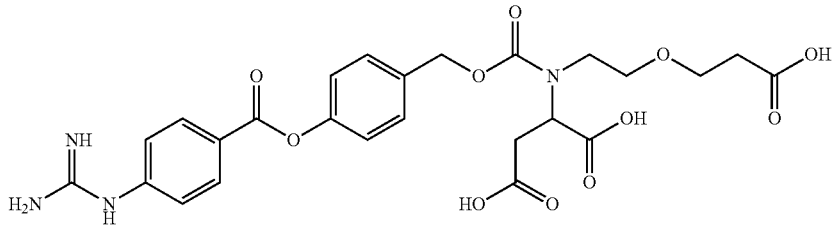 [SMILES: N=C(N)Nc1ccc(C(=O)Oc2ccc(COC(=O)N(CCOCCC(=O)O)C(CC(=O)O)C(=O)O)cc2)cc1]

The title compound was prepared by using the Reference Example 40-(a) according to the same method as the Reference Example 37-(b).

Mass spectrum (ESI, m/z): 561 [M+H]$^+$.

Reference Example 41-(b)

Preparation of (2S)-2-(3-carboxy-2-((((4-((4-guanidinobenzoyl)oxy)benzyl)oxy)carbonyl)amino)propaneamine)succinic acid trifluoroacetate

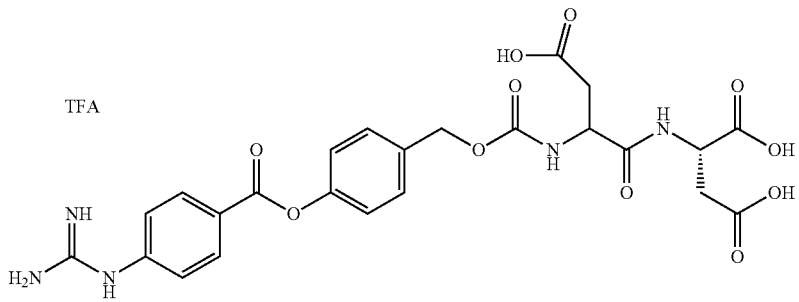 [SMILES: N=C(N)Nc1ccc(C(=O)Oc2ccc(COC(=O)NC(CC(=O)O)C(=O)N[C@@H](CC(=O)O)C(=O)O)cc2)cc1]

To a solution of (2S)-di-tert-butyl 2-(2-(((4-((4-(2,3-bis(tert-butoxycarbonyl)guanidino)benzoyl)oxy)benzyl)oxy)carbonyl)amino)-4-(tert-butoxy)-4-oxobutanamide)succinate (395 mg) prepared according to the same manner as the Reference Example 41-(a) in dehydrated dichloromethane (2 mL) in a 100 mL round-bottom flask was added trifluoroacetic acid (0.500 mL) under ice-cooling under argon atmosphere with stirring, and the resulting mixture was stirred at room temperature for 16 hours. The reaction solution was concentrated under reduced pressure. To a solution of the concentrated residues in dehydrated dichloromethane (2 mL) was added trifluoroacetic acid (3.500 mL) at room temperature under argon atmosphere with stirring, and the resulting mixture was stirred at room temperature for 5 hours. After the reaction was completed, the reaction solution was concentrated under reduced pressure. The resulting residues were dissolved into a mixed solvent of water and acetonitrile (1:1 (v/v)), and the resulting solution was freeze-dried. The resulting residues were subjected to medium pressure preparative chromatography (silica gel, elution solvent; acetonitrile solution with 0.1% trifluoroacetic acid:aqueous solution with 0.1% trifluoroacetic acid), and the fractions comprising the target compound were concentrated under reduced pressure. The concentrated residues were dissolved into a mixed solvent of water and acetonitrile (1:1 (v/v)), and the resulting solution was freeze-dried to give the title compound (292 mg) as white solids.

Mass spectrum (ESI, m/z): 560 [M−H]$^+$.

Reference Example 41-(c)

Preparation of (2S)-2-(3-carboxy-2-(((4-((4-guanidinobenzoyl)oxy)benzyl)oxy)carbonyl)amino)propaneamine)succinic acid

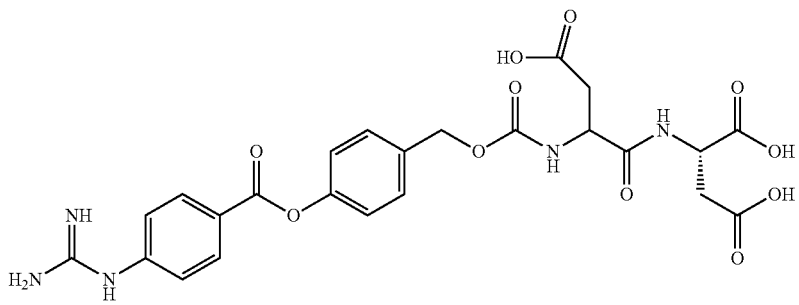 [SMILES: N=C(N)Nc1ccc(C(=O)Oc2ccc(COC(=O)NC(CC(=O)O)C(=O)N[C@@H](CC(=O)O)C(=O)O)cc2)cc1]

To a solution of (22)-di-tert-butyl 2-(2-((((4-((4-(2,3-bis(tert-butoxycarbonyl)guanidino)benzoyl)oxy)benzyl)oxy)carbonyl)amino)-4-(tert-butoxy)-4-oxobutaneamide)succinate (1.79 g) prepared according to the same manner as the Reference Example 41-(a) in dehydrated dichloromethane (10 mL) in a 200 ml, round-bottom flask was added trifluoroacetic acid (2.50 mL) under ice-cooling under argon atmosphere with stirring, and the resulting mixture was stirred at room temperature for 16 hours. After the reaction was completed, the reaction solution was concentrated under reduced pressure. To a solution of the concentrated residues in dehydrated dichloromethane (10 mL) was added trifluoroacetic acid (2.50 mL at room temperature under argon atmosphere with stirring, and the resulting mixture was stirred at room temperature for 6 hours. The reaction solution was concentrated under reduced pressure. To a solution of the resulting residues in water (20 mL)/acetonitrile (5 mL)/trifluoroacetic acid (1 mL) was added a saturated aqueous ammonium acetate solution to adjust the pH to 4.0, and the resulting mixture was stirred at room temperature for 16 hours. The reaction solution was subjected to medium pressure preparative chromatography (ODS silica gel, elution solvent; water:(acetonitrile:methanol=1:1 (v/v) mixed solvent)), and the fractions comprising the target compound were concentrated under reduced pressure. The concentrated residues were dissolved into a mixed solvent of water and acetonitrile (1:1 (v/v)), and the resulting solution was freeze-dried to give the title compound (855 mg) as white solids.

Mass spectrum (ESI, m/z): 560 [M+H]$^+$.

Reference Example 42-(b)

Preparation of (S)-2-((S)-3-carboxy-2-((S)-3-carboxy-2-(((((4-((4-guanidinobenzoyl)oxy)benzyl)oxy)carbonyl)amino)propaneamine) propaneamine)succinic acid trifluoroacetate

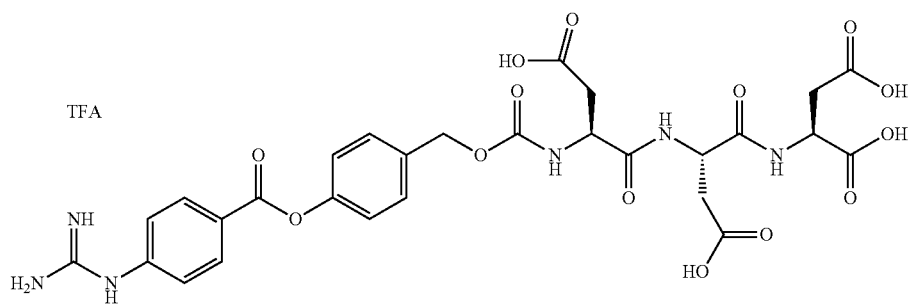 [SMILES: N=C(N)Nc1ccc(C(=O)Oc2ccc(COC(=O)N[C@@H](CC(=O)O)C(=O)N[C@@H](CC(=O)O)C(=O)N[C@@H](CC(=O)O)C(=O)O)cc2)cc1]

To a solution of (S)-di-tert-butyl 2-((S)-2-((S)-2-(((((4-((4-(2,3-bis(tert-butoxycarbonyl)guanidino)benzoyl)oxy)benzyl)oxy)carbonyl)amino)-4-(tert-butoxy)-4-oxobutaneamide)-4-(tert-butoxy)-4-oxobutaneamide)succinate (570 mg) prepared in the Reference Example 42-(a) in dichloromethane (5 mL) in a 50 mL round-bottom flask was added trifluoroacetic acid (5 mL) at room temperature under argon atmosphere with stirring, and the resulting mixture was stirred at room temperature for 40 hours. After the reaction was completed, the reaction solution was concentrated under reduced pressure. To a mixed solution of the resulting residues in acetonitrile/water was added a saturated aqueous ammonium acetate solution to adjust the pH to 4.0. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried to give the title compound (304.2 mg) as white solids.

Mass spectrum (ESI, m/z): 675 [M+H]$^+$.

Reference Example 43-(b)

Preparation of (S)-2-(2-((3-carboxybenzyl) (((4-((4-guanidinobenzoyl)oxy)benzyl)oxy)carbonyl)amino)acetamido)succinic acid

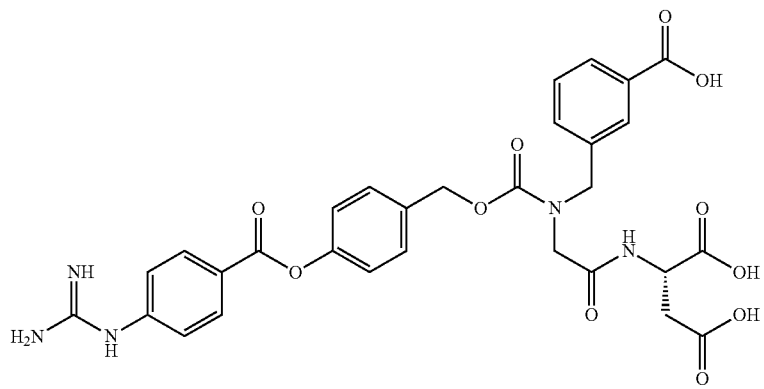 [SMILES: N=C(N)Nc1ccc(C(=O)Oc2ccc(COC(=O)N(CC(=O)N[C@@H](CC(=O)O)C(=O)O)Cc3cccc(C(=O)O)c3)cc2)cc1]

To a solution of (S)-di-tert-butyl 2-(2-(((((4-((4-(2,3-bis(tert-butoxycarbonyl)guanidino)benzoyl)oxy)benzyl)oxy)carbonyl) (3-(tert-butoxycarbonyl)benzyl)amino)acetamido)succinate (2.34 g) prepared in the Reference Example 43-(a) in dehydrated dichloromethane (8 ml) in a 200 mL round-bottom flask was added trifluoroacetic acid (2.00 mL) under ice-cooling under argon atmosphere with stirring, and the resulting mixture was stirred at room temperature for 16 hours. The reaction solution was concentrated under reduced pressure. To a solution of the concentrated residues in dehydrated dichloromethane (8 mL) was added trifluoroacetic acid (2.00 mL) at room temperature under argon atmosphere with stirring, and the resulting mixture was stirred at room temperature for 5 hours. After the reaction was completed, the reaction solution was concentrated under reduced pressure. To the resulting residues were added water (36 mL)/acetonitrile (12 mL), and then a saturated aqueous ammonium acetate solution was added thereto to adjust the pH to 4.0. The resulting mixture was stirred at room temperature for 1 hour, the precipitated solids were collected by filtration, and dried under reduced pressure to give the title compound (1.36 g) as white solids.

Mass spectrum (ESI, m/z): 636 [M+H]$^+$.

Reference Example 44-(b)

Preparation of (2S)-2-(3-carboxy-2-((carboxymethyl) (((4-((4-guanidinobenzoyl)oxy)benzyl)oxy)carbonyl)amino)propaneamine)succinic acid

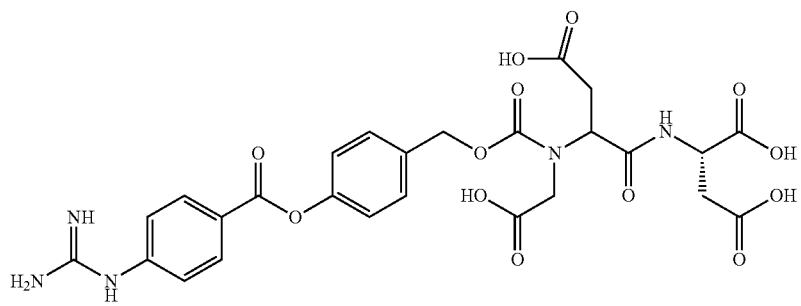 [SMILES: N=C(N)Nc1ccc(C(=O)Oc2ccc(COC(=O)N(CC(=O)O)C(CC(=O)O)C(=O)N[C@@H](CC(=O)O)C(=O)O)cc2)cc1]

433

To a solution of (2S)-di-tert-butyl 2-(2-((((4-((4-(2,3-bis(tert-butoxycarbonyl)guanidino)benzoyl)oxy)benzyl)oxy)carbonyl)(2-(tert-butoxy)-2-oxoethyl)amino)-4-(tert-butoxy)-4-oxobutaneamide)succinate (189 mg) prepared in the Reference Example 44-(a) in dehydrated dichloromethane (4 mL) in a 50 mL round-bottom flask was added trifluoroacetic acid (1.00 mL) under ice-cooling under argon atmosphere with stirring, and the resulting mixture was stirred at room temperature for 6 hours. The reaction solution was concentrated under reduced pressure. To a solution of the concentrated residues in dehydrated dichloromethane (2 mL) was added trifluoroacetic acid (1.00 mL) at room temperature under argon atmosphere with stirring, and the resulting mixture was stirred at room temperature for 18 hours. After the reaction was completed, the reaction solution was concentrated under reduced pressure. To a solution of the resulting residues in water (10 mL)/acetonitrile (3 mL)/trifluoroacetic acid (1 mL) was added a saturated aqueous ammonium acetate solution to adjust the pH to 4.0. The reaction solution was subjected to medium pressure preparative chromatography (ODS silica gel, elution solvent; water:(acetonitrile:methanol=1:1 (v/v) mixed solvent)), and the fractions comprising the target compound were freeze-dried to give the title compound (92 mg) as white solids.

Mass spectrum (ESI, m/z): 618 [M+H]$^+$.

Reference Example 45-(b)

Preparation of 3-(((carboxymethyl)(((4-((4-guanidinobenzoyl)oxy)benzyl)oxy)carbonyl)amino)methyl)benzoic acid trifluoroacetate

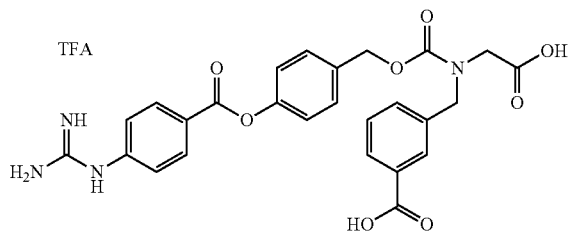 [SMILES: N=C(N)Nc1ccc(C(=O)Oc2ccc(COC(=O)N(CC(=O)O)Cc3cccc(C(=O)O)c3)cc2)cc1]

The title compound was prepared by using the Reference Example 45-(a) according to the same method as the Reference Example 32-(d).

Mass spectrum (ESI, m/z): 521 [M+H]$^+$.

Reference Example 46-(b)

Preparation of 3-(((4-((4-guanidinobenzoyl)oxy)benzyl)oxy)carbonyl)-6,9,12,15-tetraoxa-3-azaoctadecane-1,18-dioic acid trifluoroacetate

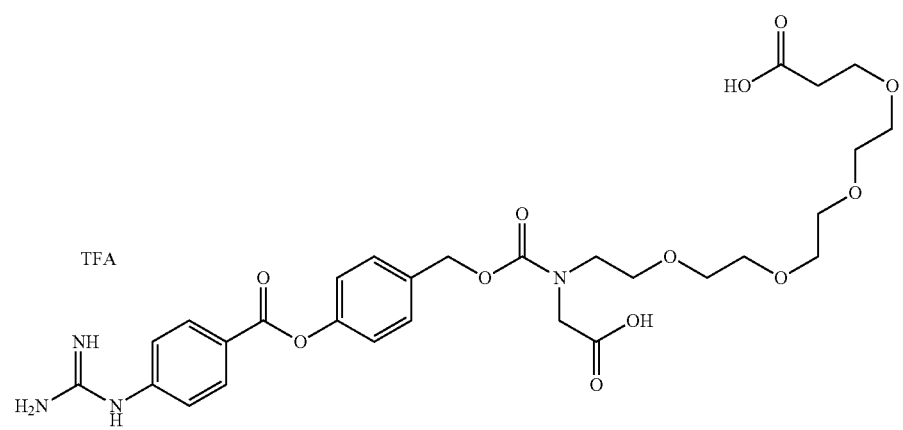 [SMILES: N=C(N)Nc1ccc(C(=O)Oc2ccc(COC(=O)N(CCOCCOCCOCCOCCC(=O)O)CC(=O)O)cc2)cc1]

The title compound was prepared by using the Reference Example 46-(a) according to the same method as the Reference Example 31-(b).

Mass spectrum (ESI, m/z): 635 [M+H]$^+$.

Reference Example 46-(c)

Preparation of 3-(((4-((4-guanidinobenzoyl)oxy)benzyl)oxy)carbonyl)-6,9,12,15-tetraoxa-3-azaoctadecane-1,18-dioic acid hydrochloride

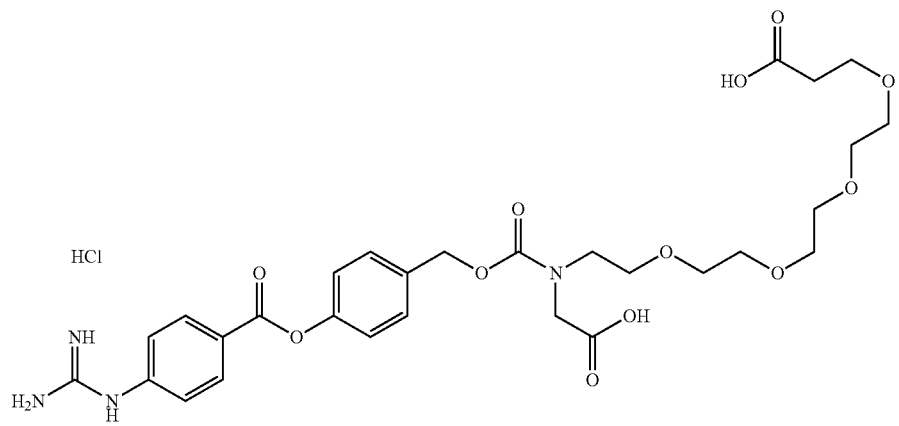 [SMILES: N=C(N)Nc1ccc(C(=O)Oc2ccc(COC(=O)N(CCOCCOCCOCCOCCC(=O)O)CC(=O)O)cc2)cc1 ; Cl]

The title compound was prepared by using the Reference Example 46-(b) according to the same method as the Reference Example 31-(c).

Mass spectrum (ESI, m/z): 635 [M+H]$^+$.

Reference Example 46-(c)

Preparation of 3-(((4-((4-guanidinobenzoyl)oxy)benzyl)oxy)carbonyl)-6,9,12,15-tetraoxa-3-azaoctadecane-1,18-dioic acid hydrochloride

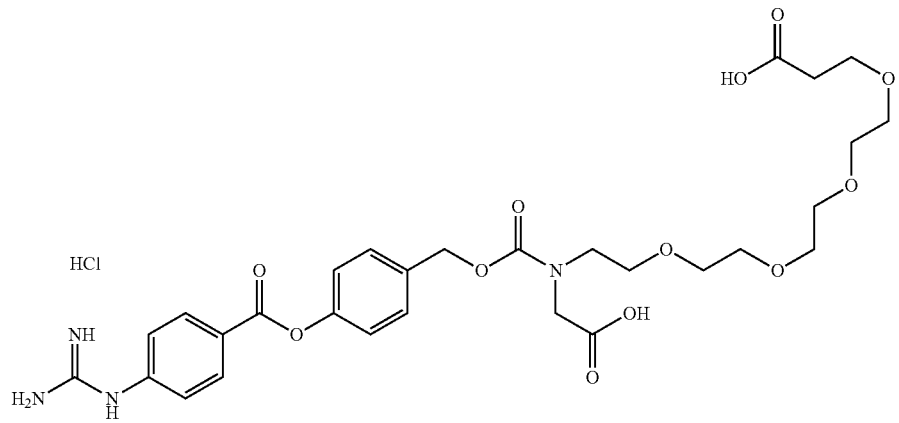 [SMILES: N=C(N)Nc1ccc(C(=O)Oc2ccc(COC(=O)N(CCOCCOCCOCCOCCC(=O)O)CC(=O)O)cc2)cc1 ; Cl]

The title compound was prepared by using the Reference Example 46-(b) according to the same method as the Reference Example 31-(c).

Mass spectrum (ESI, m/z): 635 [M+H]$^+$.

Reference Example 46-(d)

Preparation of 3-(((4-((4-guanidinobenzoyl)oxy)benzyl)oxy)carbonyl)-6,9,12,15-tetraoxa-3-azaoctadecane-1,18-dioic acid

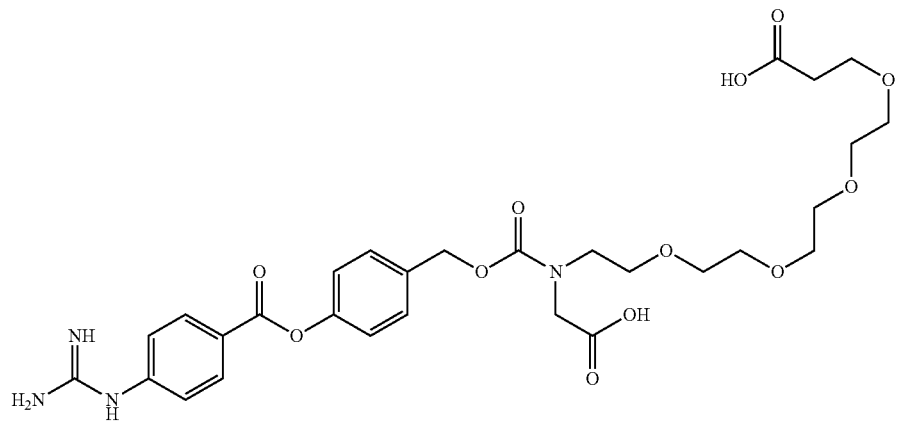 [SMILES: N=C(N)Nc1ccc(C(=O)Oc2ccc(COC(=O)N(CCOCCOCCOCCOCCC(=O)O)CC(=O)O)cc2)cc1]

The title compound was prepared by using the Reference Example 46-(a) according to the same method as the Reference Example 35-(b).

Mass spectrum (ESI, m/z): 635 [M+H]$^+$.

Reference Example 47-(b)

Preparation of 4-(3-carboxybenzyl)-1-(4-((4-guanidinobenzoyl)oxy)phenyl)-3-oxo-2,7,10,13,16-pentaoxa-4-azanonadecane-19-acid trifluoroacetate

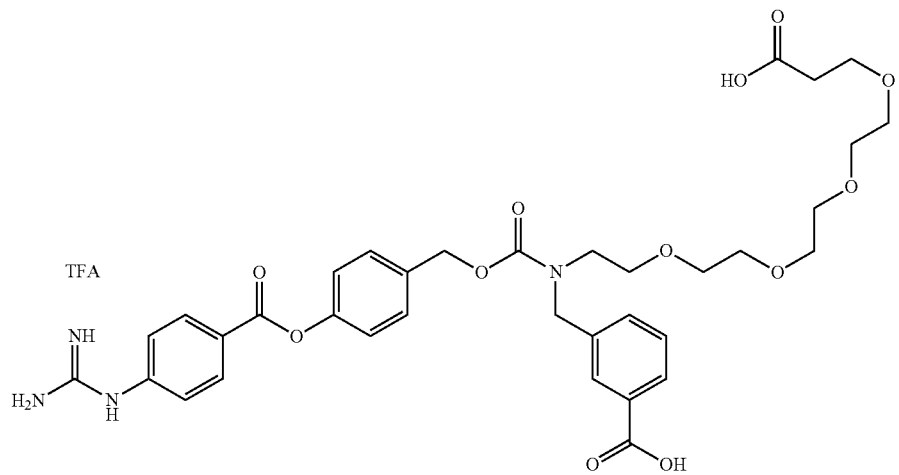 [SMILES: N=C(N)Nc1ccc(C(=O)Oc2ccc(COC(=O)N(CCOCCOCCOCCOCCC(=O)O)Cc3cccc(C(=O)O)c3)cc2)cc1]

The title compound was prepared by using the Reference Example 47-(a) according to the same method as the Reference Example 31-(b).

Reference Example 48-(b)

Preparation of (S)-2-((carboxymethyl) (((4-((4-guanidinobenzoyl)oxy)benzyl)oxy)carbonyl)amino) succinic acid trifluoroacetate

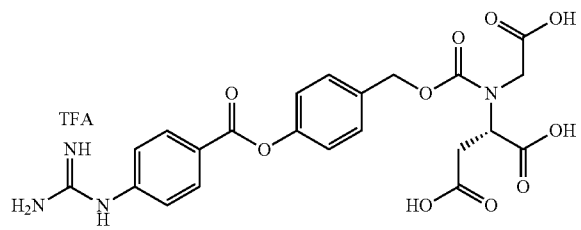 [SMILES: N=C(N)Nc1ccc(C(=O)Oc2ccc(COC(=O)N(CC(=O)O)[C@@H](CC(=O)O)C(=O)O)cc2)cc1]

To a solution of (S)-di-tert-butyl 2-((((4-((4-(2,3-bis(tert-butoxycarbonyl)guanidino)benzoyl)oxy)benzyl)oxy)carbonyl) (2-(tert-butoxy)-2-oxoethyl)amino)succinate (270 mg) prepared in the Reference Example 48-(a) in dichloromethane (2.85 mL) in a 100 mL round-bottom flask was added trifluoroacetic acid (712 µL) at room temperature under argon gas flow with stirring, and the resulting mixture was stirred at room temperature for 15 hours. The reaction solution was concentrated under reduced pressure. To the concentrated residues were added trifluoroacetic acid (1424 µL) and dichloromethane (1424 µL), and the resulting mixture was stirred at room temperature for 2.5 hours. After the reaction was completed, the reaction solution was concentrated under reduced re-sure. The resulting residues were subjected to medium pressure preparative chromatography (silica gel, elution solvent; acetonitrile solution with 0.1% trifluoroacetic acid:aqueous solution with 0.1% trifluoroacetic acid), and the fractions comprising the target compound were concentrated under reduced pressure. The precipitated solids were collected by filtration, and dried under reduced pressure to give the title compound (124.3 mg) as white solids.

Mass spectrum (ESI, m/z): 503 [M+H]$^+$.

Reference Example 48-(c)

Preparation of (S)-2-((carboxymethyl)(((4-((4-guanidinobenzoyl)oxy)benzyl)oxy)carbonyl)amino) succinic acid

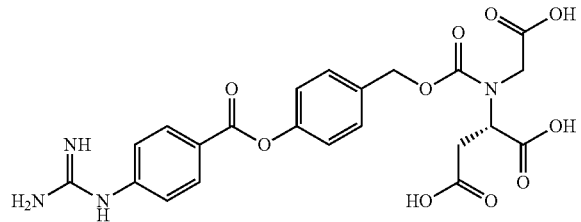 [SMILES: N=C(N)Nc1ccc(C(=O)Oc2ccc(COC(=O)N(CC(=O)O)[C@@H](CC(=O)O)C(=O)O)cc2)cc1]

To a solution of (S)-di-tert-butyl 2-((((4-((4-(2,3-bis(tert-butoxycarbonyl)guanidino)benzoyl)oxy)benzyl)oxy)carbonyl)(2-(tert-butoxy)-2-oxoethyl)amino)succinate (1.566 g) prepared in the Reference Example 48-(a) in dichloromethane (10 mL) in a 100 mL round-bottom flask was added trifluoroacetic acid (2.5 mL) at 0° C. under argon gas flow with stirring, and the resulting mixture was stirred at room temperature for 15 hours. The reaction solution was concentrated under reduced pressure. To the concentrated residues were added dichloromethane (2.50 mL) and trifluoroacetic acid (2.50 mL) at room temperature, and the resulting mixture was stirred at room temperature for 3 hours. After the reaction was completed, the reaction solution was concentrated under reduced pressure. Dichloromethane (2 mL) was added thereto at room temperature, and the resulting mixture was stirred at room temperature for 1 hour. The reaction solution was concentrated under reduced pressure. To a solution of the resulting residues in water (10 mL)/acetonitrile (2 mL) was added a saturated aqueous ammonium acetate solution to adjust the pH to 3.9. The resulting mixture was stirred in an ice bath for 30 minutes, the precipitated solids were collected by filtration, and dried under reduced pressure. The resulting solids were subjected to medium pressure preparative chromatography (silica gel, elution solvent; acetonitrile solution with 0.1% trifluoroacetic acid aqueous solution with 0.1% trifluoroacetic acid), and the fractions comprising the target compound were concentrated under reduced pressure. The precipitated solids were collected by filtration, and dried under reduced pressure to give solids. To a solution of the resulting solids in water (3 mL/trifluoroacetic acid (1 mL) was added a saturated aqueous ammonium acetate solution to adjust the pH to 4.0. The resulting mixture was stirred at room temperature for 30 minutes, the precipitated solids were collected by filtration, and dried under reduced pressure to give the title compound (503 mg) as white solids.

Mass spectrum (ESI, m/z): 503 [M+H]$^+$.

Reference Example 49-(b)

Preparation of (S)-2-(3-carboxybenzyl) (((4-((4-guanidinobenzoyl)oxy)benzyl)oxy)carbonyl)amino) succinic acid trifluoroacetate

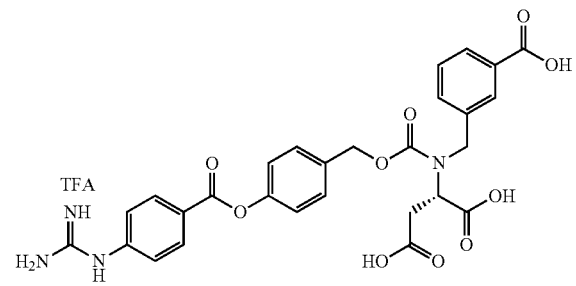 [SMILES: N=C(N)Nc1ccc(C(=O)Oc2ccc(COC(=O)N(Cc3cccc(C(=O)O)c3)[C@@H](CC(=O)O)C(=O)O)cc2)cc1]

To a solution of (S)-di-tert-butyl 2-((((4-((4-(2,3-bis(tert-butoxycarbonyl)guanidino)benzoyl)oxy)benzyl)oxy)carbonyl) (3-(tert-butoxycarbonyl)benzyl)amino)succinate (167 mg) prepared according to the same manner as the Reference Example 49-(a) in dehydrated dichloromethane (2 mL) in a 100 mL round-bottom flask was added trifluoroacetic acid (0.500 mL) under ice-cooling under argon atmosphere with stirring, and the resulting mixture was stirred at room temperature for 16 hours. The reaction solution was concentrated under reduced pressure. To a solution of the concentrated residues in dehydrated dichloromethane (2 mL) was added trifluoroacetic acid (0.500 mL) at room temperature under argon atmosphere with stirring, and the resulting mixture was stirred at room temperature for 5 hours. After the reaction was completed, the reaction solution was concentrated under reduced pressure. The concentrated residues were dissolved into a mixed solvent of water and acetonitrile (1:1 (v/v)), and the resulting solution was freeze-dried to give the title compound (125 mg) as white solids.

Mass spectrum (ESI, m/z): 579 [M+H]$^+$.

Reference Example 49-(c)

Preparation of (S)-2-((3-carboxybenzyl)(((4-((4-guanidinobenzoyl)oxy)benzyl)oxy)carbonyl)amino)succinic acid

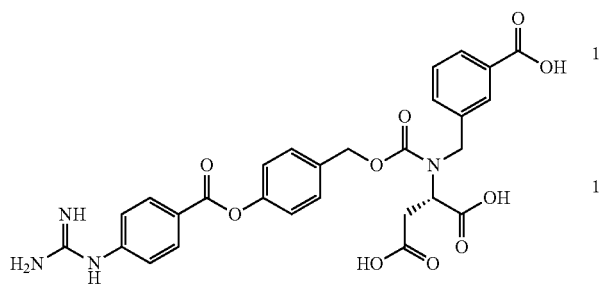

To a solution of (S)-di-tert-butyl 2-((((4-((4-(2,3-bis(tert-butoxycarbonyl)guanidino)benzoyl)oxy)benzyl)oxy)carbonyl)(3-(tert-butoxycarbonyl)benzyl)amino)succinate (1.76 g) prepared according to the same manner as the Reference Example 49-(a) in dehydrated dichloromethane (20 mL) in a 100 mL round-bottom flask was added trifluoroacetic acid (5.00 mL) under ice-cooling under argon atmosphere with stirring, and the resulting mixture was stirred at room temperature for 15 hours. After the reaction was completed, the reaction solution was concentrated under reduced pressure. To a solution of the resulting residues in dehydrated dichloromethane (20 mL) was added trifluoroacetic acid (5.00 mL) at room temperature under argon atmosphere with stirring, and the resulting mixture was stirred at room temperature for 5 hours. The reaction solution was concentrated under reduced pressure. To the concentrated residues were added water (25 mL)/acetonitrile (5 mL), then a saturated aqueous ammonium acetate solution was added thereto to adjust the pH to 4.0, and the resulting mixture was stirred at room temperature for 30 minutes. A part of the reaction solution (29 mL) was stirred at room temperature for 24 hours, the precipitated solids were collected by filtration, and dried under reduced pressure to give the title compound (1.07 g) as white solids.

Mass spectrum (ESI, m/z): 579 [M+H]$^+$.

Reference Example 50-(b)

Preparation of (S)-2-(2-(((S)-1,2-dicarboxyethyl)(((4-((4-guanidinobenzoyl)oxy)benzyl)oxy)carbonyl)amino)acetamido)succinic acid

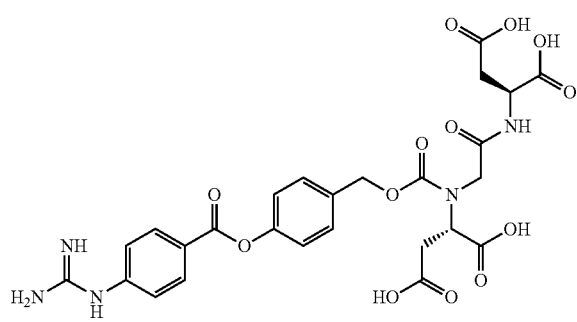 [SMILES: N=C(N)Nc1ccc(C(=O)Oc2ccc(COC(=O)N(CC(=O)N[C@@H](CC(=O)O)C(=O)O)[C@@H](CC(=O)O)C(=O)O)cc2)cc1]

The title compound was prepared by using the Reference Example 50-(a) according to the same method as the Reference Example 43-(b).

Mass spectrum (ESI, m/z): 618 [M+H]$^+$.

Reference Example 51-(b

Preparation of (S)-2-((5-carboxypentyl) (((4-((4-guanidinobenzoyl)oxy)benzyl)oxy)carbonyl)amino)succinic acid

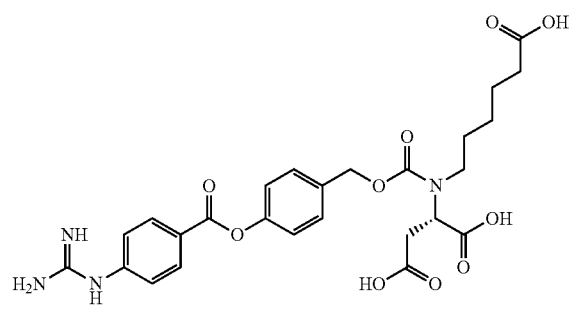 [SMILES: N=C(N)Nc1ccc(C(=O)Oc2ccc(COC(=O)N(CCCCCC(=O)O)[C@@H](CC(=O)O)C(=O)O)cc2)cc1]

The title compound was prepared by using she Reference Example 51-(a) according to the same method as the Reference Example 48-(c).

Mass spectrum (ESI, T/z) δ59 [M+H]$^+$.

Reference Example 52-(a)

Preparation of (S)-di-tert-butyl 2-((N-((benzyloxy)carbonyl)-N-(4-((4-(2,3-bis(tert-butoxycarbonyl)guanidino)benzoyl)oxy)benzyl)sulfamoyl) (3-(tert-butoxycarbonyl)benzyl)amino)succinate

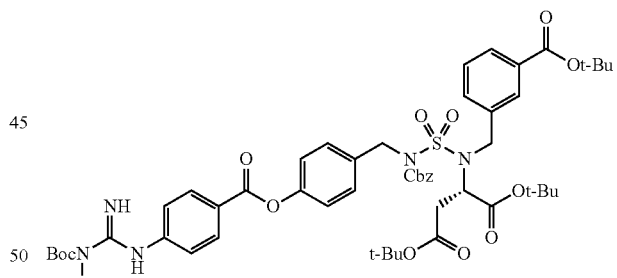

To a solution of 4-(hydroxymethyl)phenyl 4-(2,3-bis(tert-butoxycarbonyl)guanidino)benzoate (2.56 g) prepared according to the same manner as the Reference Example 1-(g) and (S)-di-tert-butyl 2-((N-((benzyloxy)carbonyl)sulfamoyl)(3-(tert-butoxycarbonyl)benzyl)amino)succinate (3.07 g) prepared in the Reference Example 18-(a)-2 in tetrahydrofuran (10 mL) in a 100 mL round-bottom flask were added triphenylphosphine (1.51 g) and diisopropyl azodicarboxylate (a 1.9 M solution in toluene) (3.00 mL) at 0° C. under argon gas flow with stirring, and the resulting mixture was stirred at room temperature for 1 hour. After the reaction was completed, the reaction solution was concentrated under reduced pressure. The resulting residues were purified by medium pressure preparative chromatography (silica gel, elution solvent; hexane:ethyl acetate) to give the title compound (1.52 g) as a white foam.
Mass spectrum (ESI, m/z): 1116 [M+H]$^+$.

According to the same method as the Reference Example 52-(a), Reference Example 53-(a) to Reference Example 83-(a) were prepared.

TABLE 21

| Reference Example No. | Compound name<br>Structural formula<br>Mass spectrum |
|---|---|
| 53-(a) | (S)-di-tert-butyl 2-((N-((benzyloxy)carbonyl)-N-(4-((4-(2,3-bis(tert-butoxycarbonyl)guanidino)benzoyl)oxy)benzyl)sulfamoyl)(6-(tert-butoxy)-6-oxohexyl)amino)succinate<br>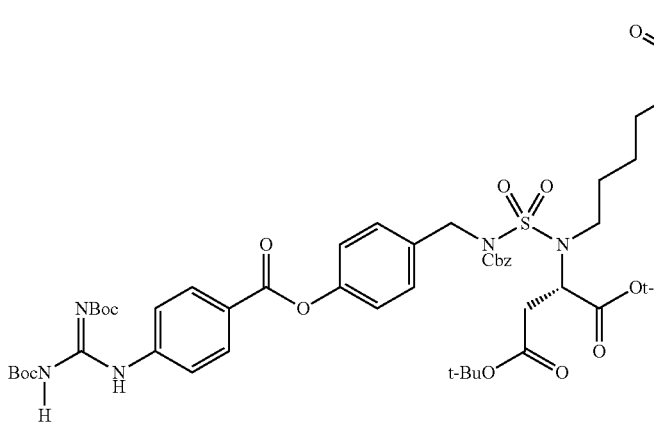<br>(ESI, m/z): 1096 [M + H]$^+$. |
| 54-(a) | (S)-di-tert-butyl 2-((N-((benzyloxy)carbonyl)-N-(4-((4-(2,3-bis(tert-butoxycarbonyl)guanidino)benzoyl)oxy)benzyl)sulfamoyl)(methyl)amino)succinate<br>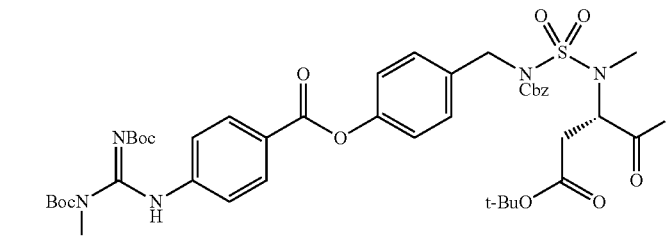<br>(ESI, m/z): 940 [M + H]$^+$. |
| 55-(a) | (S)-di-tert-butyl 2-((N-(4-((4-(2,3-bis(tert-butoxycarbonyl)guanidino)benzoyl)oxy)benzyl)-N-(tert-butoxycarbonyl)sulfamoyl)amino)succinate<br>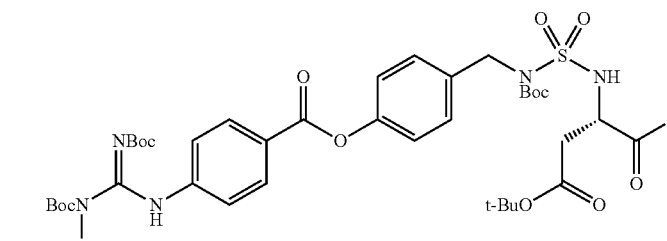<br>(ESI, m/z): 892 [M + H]$^+$. |

TABLE 21-continued

| Reference Example No. | Compound name Structural formula Mass spectrum |
|---|---|

56-(a)

(S)-di-tert-butyl 2-((N-(4-((4-(2,3-bis(tert-butoxycarbonyl)guanidino)benzoyl)oxy)benzyl)-N-(tert-butoxycarbonyl)sulfamoyl)(2-(tert-butoxy)-2-oxoethyl)amino)succinate

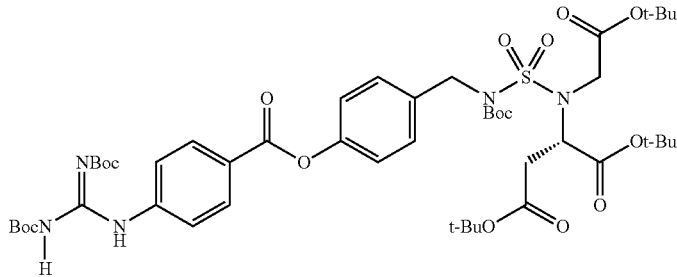

(ESI, m/z): 1006 [M + H]⁺.

57-(a)

(S)-di-tert-butyl 2-((N-(4-((4-[2,3-bis(tert-butoxycarbonyl)guanidino)benzoyl)oxy)benzyl)-N-(tert-butoxycarbonyl)sulfamoyl)amino)pentanedioate

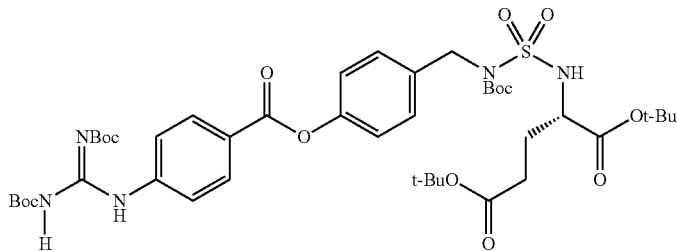

(ESI, m/z): 906 [M + H]⁺.

58-(a)

(S)-4-(((N-(1-(tert-butoxy)-3-(4-(tert-butoxycarbonyl)phenyl)-1-oxopropan-2-yl)sulfamoyl)(tert-butoxycarbonyl)amino)methyl)phenyl 4-(2,3-bis(tert-butoxycarbonyl)guanidino)benzoate

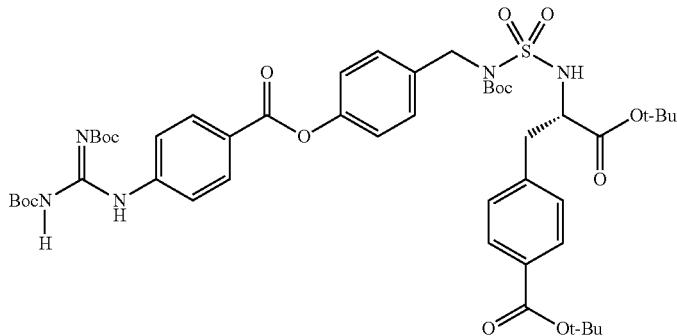

(ESI, m/z): 968 [M + H]⁺.

TABLE 21-continued

| Reference Example No. | Compound name Structural formula Mass spectrum |
|---|---|
| 59-(a) | (S)-4-(((N-(1-(tert-butoxy)-3-(4-((tert-butyldimethylsilyl)oxy)phenyl)-1-oxopropan-2-yl)sulfamoyl)(tert-butoxycarbonyl)amino)methyl)phenyl 4-(2,3-bis(tert-butoxycarbonyl)guanidino)benzoate |

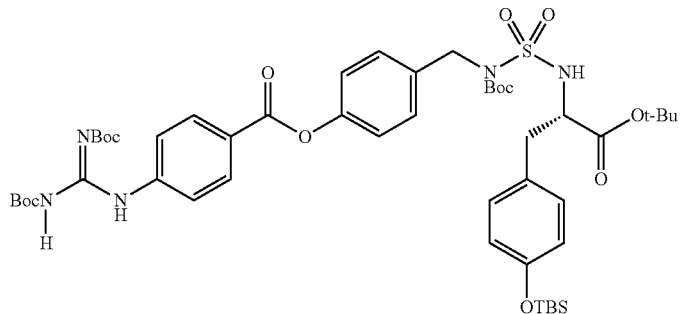

(ESI, m/z): 998 [M + H]⁺.

| 60-(a) | (S)-4-(((N-(1-(tert-butoxy)-1-oxo-3-phenylpropan-2-yl)sulfamoyl)(tert-butoxycarbonyl)amino)methyl)phenyl 4-(2,3-bis(tert-butoxycarbonyl)guanidino)benzoate |
|---|---|

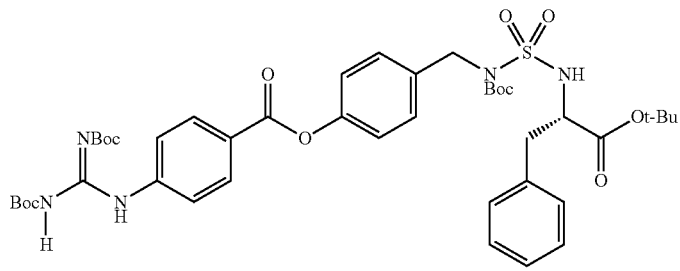

(ESI, m/z): 868 [M + H]⁺.

| 61-(a) | 4-(((N-(6-(tert-butoxy)-6-oxohexyl)sulfamoyl)(tert-butoxycarbonyl)amino)methyl)phenyl 4-(2,3-bis(tert-butoxycarbonyl)guanidino)benzoate |
|---|---|

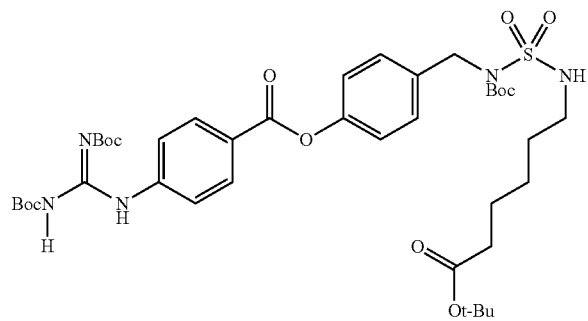

(ESI, m/z): 834 [M + H]⁺.

TABLE 21-continued

| Reference Example No. | Compound name<br>Structural formula<br>Mass spectrum |
|---|---|
| 62-(a) | 4-(((N-(2-(tert-butoxy)-6-oxohexyl)sulfamoyl)(tert-butoxycarbonyl)amino)methyl)phenyl 4-(2,3-bis(tert-butoxycarbonyl)guanidino)benzoate<br>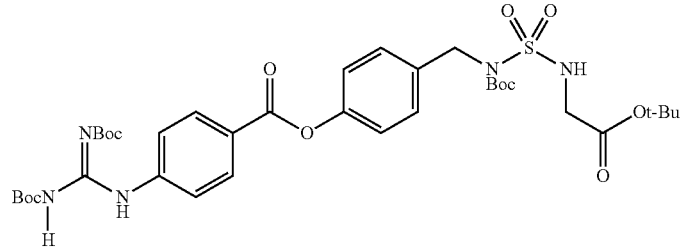<br>(ESI, m/z): 778 [M + H]⁺. |
| 63-(a) | (S)-4-(((N-(1-(tert-butoxy)-1-oxopropan-2-yl)sulfamoyl)(tert-butoxycarbonyl)amino)methyl)phenyl 4-(2,3-bis(tert-butoxycarbonyl)guanidino)benzoate<br>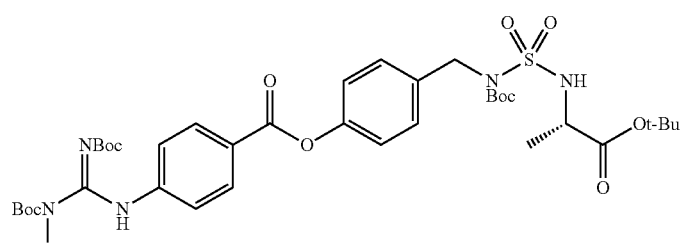<br>(ESI, m/z): 792 [M + H]⁺. |
| 64-(a) | 4-(((tert-butoxycarbonyl)(N-methylsulfamoyl)amino)methyl)phenyl 4-(2,3-bis(tert-butoxycarbonyl)guanidino)benzoate<br>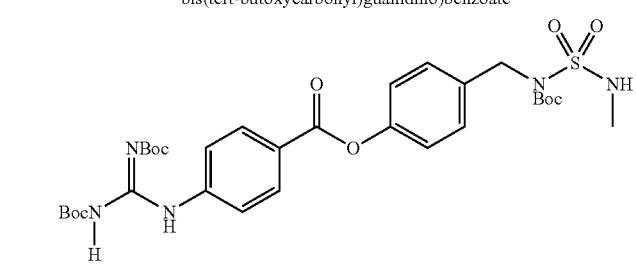<br>(ESI, m/z): 678 [M + H]⁺. |
| 65-(a) | (S)-di-tert-butyl 2-((N-(4-((4-(2,3-bis(tert-butoxycarbonyl)guanidino)benzoyl)oxy)-3-fluorobenzyl)-N-(tert-butoxycarbonyl)sulfamoyl)amino)succinate<br>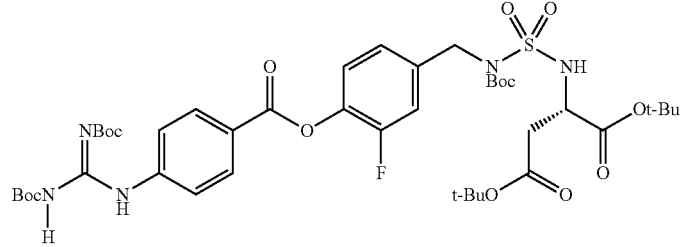<br>(ESI, m/z): 910 [M + H]⁺. |

TABLE 21-continued

| Reference Example No. | Compound name Structural formula Mass spectrum |
|---|---|
| 66-(a) | (S)-di-tert-butyl 2-((N-(4-((4-(2,3-bis(tert-butoxycarbonyl)guanidino)benzoyl)oxy)-3-chlorobenzyl)-N-(tert-butoxycarbonyl)sulfamoyl)amino)succinate<br><br>(ESI, m/z): 926 [M + H]+. |
| 67-(a) | (S)-di-tert-butyl 2-((N-)4-((4-(2,3-bis(tert-butoxycarbonyl)guanidino)benzoyl)oxy)-3-methoxybenzyl)-N-(tert-butoxycarbonyl)sulfamoyl)amino)succinate<br><br>(ESI, m/z): 922 [M + H]+. |
| 68-(a) | (S)-di-tert-butyl 2-((N-(4-((4-(2,3-bis(tert-butoxycarbonyl)guanidino)benzoyl)oxy)-3-methylbenzyl)-N-(tert-butoxycarbonyl)sulfamoyl)amino)succinate<br><br>(ESI, m/z): 906 [M + H]+. |
| 69-(a) | (S)-di-tert-butyl 2-((N-(4-((4-(2,3-bis(tert-butoxycarbonyl)guanidino)benzoyl)oxy)-2-fluorobenzyl)-N-(tert-butoxycarbonyl)sulfamoyl)amino)succinate<br><br>(ESI, m/z): 910 [M + H]+. |

TABLE 21-continued

| Reference Example No. | Compound name<br>Structural formula<br>Mass spectrum |
|---|---|
| 70-(a) | (S)-di-tert-butyl 2-((N-(4-((4-(2,3-bis(tert-butoxycarbonyl)guanidino)benzoyl)oxy)-2-chlorobenzyl)-N-(tert-butoxycarbonyl)sulfamoyl)amino)succinate<br><br>(ESI, m/z): 926 [M + H]$^+$. |
| 71-(a) | (S)-di-tert-butyl 2-((N-(4-((4-(2,3-bis(tert-butoxycarbonyl)guanidino)benzoyl)oxy)-2-methoxybenzyl)-N-(tert-butoxycarbonyl)sulfamoyl)amino)succinate<br><br>(ESI, m/z): 922 [M + H]$^+$. |
| 72-(a) | (S)-di-tert-butyl 2-((N-(4-((4-(2,3-bis(tert-butoxycarbonyl)guanidino)benzoyl)oxy)-2-methylbenzyl)-N-(tert-butoxycarbonyl)sulfamoyl)amino)succinate<br><br>(ESI, m/z): 906 [M + H]$^+$. |

TABLE 21-continued

| Reference Example No. | Compound name Structural formula Mass spectrum |
|---|---|

73-(a)     (S)-di-tert-butyl 2-((N-(3-((4-(2,3-bis(tert-butoxycarbonyl)guanidino)benzoyl)oxy)benzyl)-N-(tert-butoxycarbonyl)sulfamoyl)amino)succinate

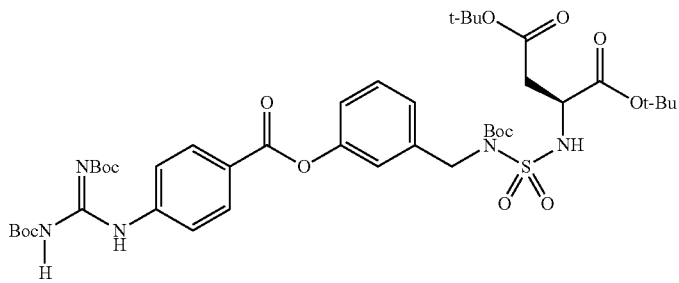

(ESI, m/z): 892 [M + H]⁺.

74-(a)     (S)-di-tert-butyl 2-((N-(4-((4-(2,3-bis(tert-butoxycarbonyl)guanidino)-2-fluorobenzoyl)oxy)benzyl)-N-(tert-butoxycarbonyl)sulfamoyl)amino)succinate

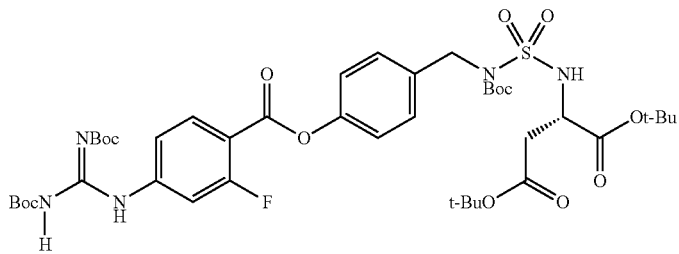

(ESI, m/z): 910 [M + H]⁺.

75-(a)     (S)-di-tert-butyl 2-((N-(4-((4-(2,3-bis(tert-butoxycarbonyl)guanidino)-2-methylbenzoyl)oxy)benzyl)-N-(tert-butoxycarbonyl)sulfamoyl)amino)succinate

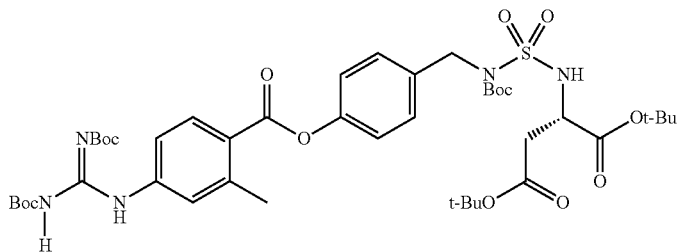

(ESI, m/z): 906 [M + H]⁺.

TABLE 21-continued

| Reference Example No. | Compound name Structural formula Mass spectrum |
|---|---|
| 76-(a) | (S)-di-tert-butyl 2-((N-(4-((4-(2,3-bis(tert-butoxycarbonyl)guanidino)benzoyl)oxy)-2-(tert-butoxycarbonyl)benzyl)-N-(tert-butoxycarbonyl)sulfamoyl)amino)succinate 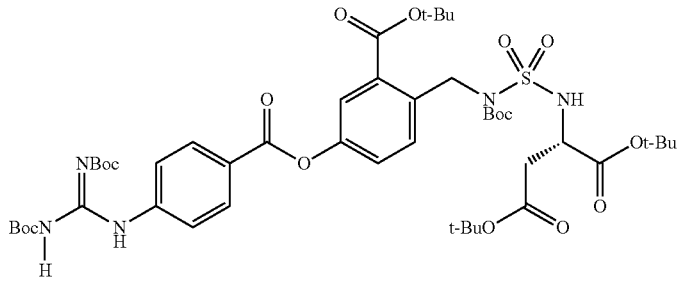 (ESI, m/z): 992 [M + H]⁺. |
| 77-(a) | (S)-di-tert-butyl 2-((N-(4-((4-(2,3-bis(tert-butoxycarbonyl)guanidino)benzoyl)oxy)-2-(((S)-1,4-di-tert-butoxy-1,4-dioxobutan-2-yl)carbamoyl)benzyl)-N-(tert-butoxycarbonyl)sulfamoyl)amino)succinate 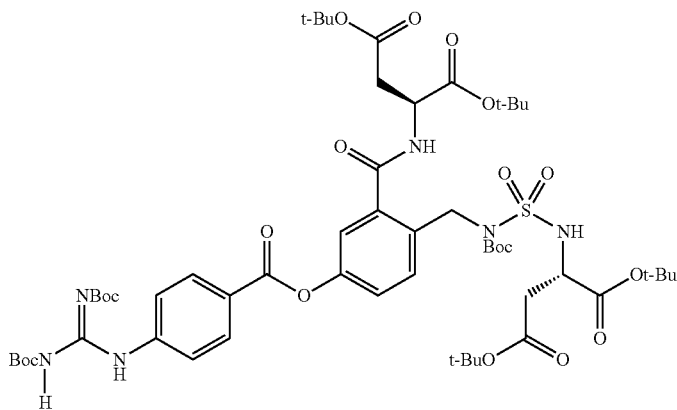 (ESI, m/z): 1164 [M + H]⁺. |
| 78-(a) | 4-(((N-(2-(tert-butoxy)-2-oxoethyl)sulfamoyl)(tert-butoxycarbonyl)amino)methyl)-3-chlorophenyl 4-(2,3-bis(tert-butoxycarbonyl)guanidino)benzoate 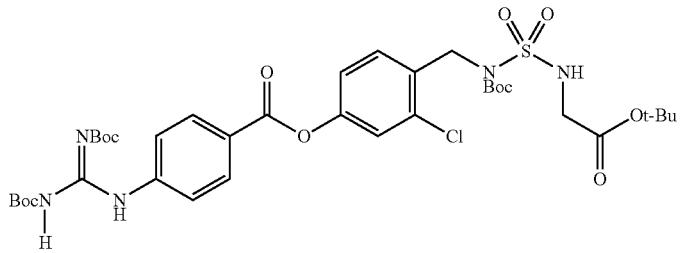 (ESI, m/z): 812 [M + H]⁺. |

TABLE 21-continued

| Reference Example No. | Compound name<br>Structural formula<br>Mass spectrum |
|---|---|
| 79-(a) | tert-butyl 5-((4-(2,3-bis(tert-butoxycarbonyl)guanidino)benzoyl)oxy)-2-(((N-(2-(tert-butoxy)-2-oxoethyl)sulfamoyl)(tert-butoxycarbonyl)amino)methyl)benzoate<br>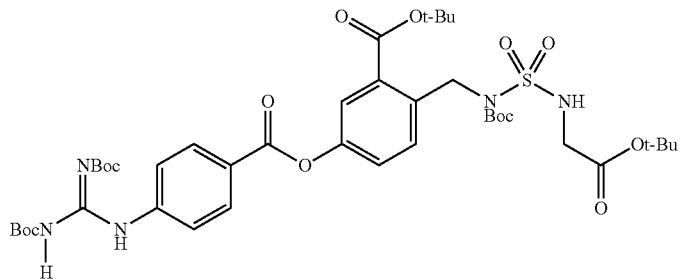<br>(ESI, m/z): 878 [M + H]$^+$. |
| 80-(a) | (S)-di-tert-butyl 2-(5-((4-(2,3-bis(tert-butoxycarbonyl)guanidino)benzoyl)oxy)-2-(((N-(2-(tert-butoxy)-2-oxoethyl)sulfamoyl)(tert-butoxycarbonyl)amino)methyl)benzamide)succinate<br>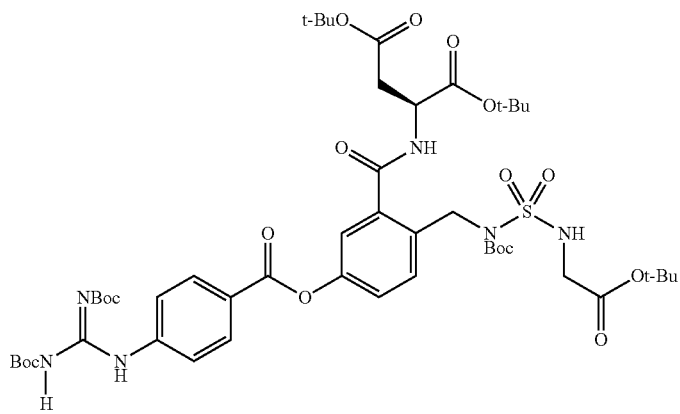<br>(ESI, m/z): 1050 [M + H]$^+$. |
| 81-(a) | (S)-di-tert-butyl 2-((N-(tert-butoxycarbonyl)-N-((10-((tert-butoxycarbonyl)amino)-13-oxo-6,7,8,13-tetrahydrodibenzo[b,f][1,4]dioxecin-4-yl)methyl)sulfamoyl)amino)succinate<br>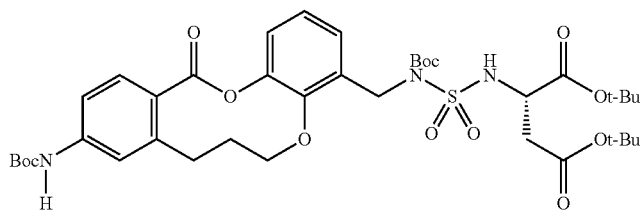 [SMILES: CC(C)(C)OC(=O)C[C@H](NS(=O)(=O)N(Cc1cccc2c1OCCCc1cc(NC(=O)OC(C)(C)C)ccc1C(=O)O2)C(=O)OC(C)(C)C)C(=O)OC(C)(C)C]<br>(ESI, m/z): 804 [M − H]$^+$. |

| Reference Example No. | Compound name Structural formula Mass spectrum |
|---|---|
| 82-(a) | (S)-di-tert-butyl 2-((N-(tert-butoxycarbonyl)-N-((10-((tert-butoxycarbonyl)amino)-13-oxo-6,7,8,13-tetrahydrodibenzo[b,f][1,4]dioxecin-3-yl)methyl)sulfamoyl)amino)succinate 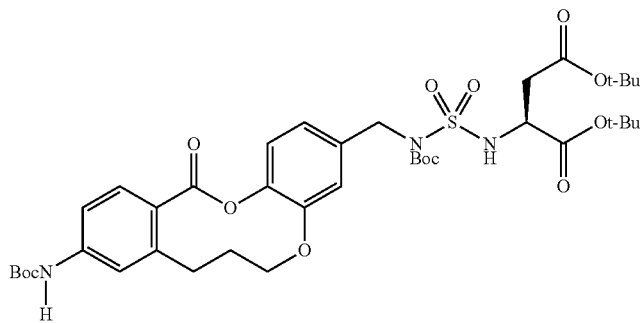 [SMILES: CC(C)(C)OC(=O)C[C@H](NS(=O)(=O)N(Cc1ccc2c(c1)OCCCc1cc(NC(=O)OC(C)(C)C)ccc1C(=O)O2)C(=O)OC(C)(C)C)C(=O)OC(C)(C)C] (ESI, m/z): 804 [M − H]+. |
| 83-(a) | (S)-di-tert-butyl 2-((N-(tert-butoxycarbonyl)-N-((10-((tert-butoxycarbonyl)amino)-13-oxo-6,7,8,13-tetrahydrodibenzo[b,f][1,4]dioxecin-2-yl)methyl)sulfamoyl)amino)succinate 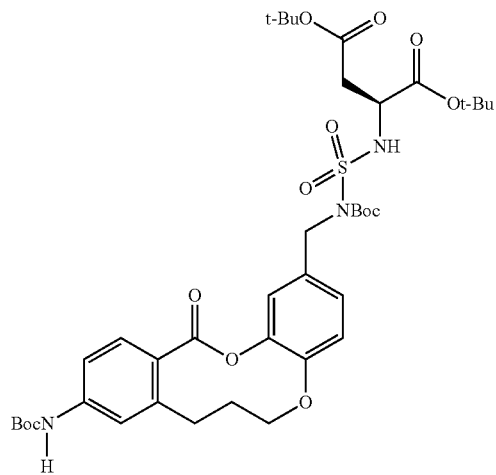 [SMILES: CC(C)(C)OC(=O)C[C@H](NS(=O)(=O)N(Cc1ccc2c(c1)OC(=O)c1ccc(NC(=O)OC(C)(C)C)cc1CCCO2)C(=O)OC(C)(C)C)C(=O)OC(C)(C)C] (ESI, m/z): 804 [M − H]+. |

Reference Example 52-(b)

Preparation of (S)-2-((3-carboxybenzyl)(N-(4-((4-guanidinobenzoyl)oxy)benzyl)sulfamoyl)amino) succinic acid trifluoroacetate

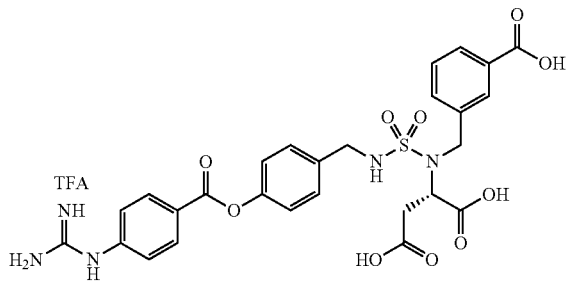 [SMILES: N=C(N)Nc1ccc(C(=O)Oc2ccc(CNS(=O)(=O)N(Cc3cccc(C(=O)O)c3)[C@@H](CC(=O)O)C(=O)O)cc2)cc1]

To a solution of (S)-di-tert-butyl 2-((N-((benzyloxy)carbonyl)-N-(4-((4-(2,3-bis(tert-butoxycarbonyl)guanidino)benzoyl)oxy)benzyl)sulfamoyl) (3-(tert-butoxycarbonyl)benzyl)amino)succinate (2.42 g) prepared according to the same manner as the Reference Example 52-(a) in dichloromethane (20 ml) in a 10 mL round-bottom flask was added trifluoroacetic acid (20 mL) at room temperature under argon atmosphere with stirring, and the resulting mixture was stirred at room temperature for 4 hours. The reaction solution was concentrated under reduced pressure. To a solution of the concentrated residues in methanol (20 mL) was added 10% palladium carbon (wetted with ca. 55% water, manufactured by Tokyo Chemical Industry Co., Ltd.) (484 mg) at room temperature under argon atmosphere with stirring, the atmosphere in the reaction system was replaced with hydrogen atmosphere, and then the resulting mixture was stirred at room temperature for 2 hours. After the reaction was completed, the reaction solution was filtered through Celite, washed with methanol, and the resulting filtrate was concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried to give the title compound (1.10 g) as white solids.

Mass spectrum (ESI, m/z): 614 $[M+H]^+$.

Reference Example 52-(c)

Preparation of (S)-2-((3-carboxybenzyl)(N-(4-((4-guanidinobenzoyl)oxy)benzyl)sulfamoyl)amino) succinic acid

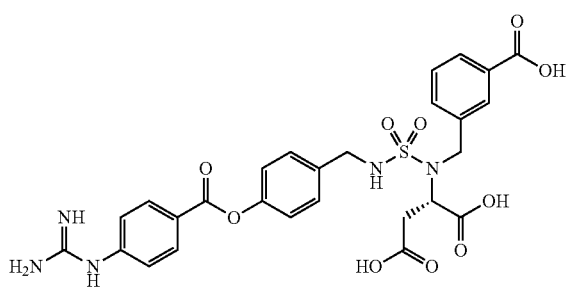 [SMILES: N=C(N)Nc1ccc(C(=O)Oc2ccc(CNS(=O)(=O)N(Cc3cccc(C(=O)O)c3)[C@@H](CC(=O)O)C(=O)O)cc2)cc1]

To a solution of (S)-di-tert-butyl 2-((N-((benzyloxy)carbonyl)-N-(4-(14-(2,3-bis(tert-butoxycarbonyl)guanidino)benzoyl)oxy)benzyl)sulfamoyl)(3-(tert-butoxycarbonyl)benzyl)amino)succinate (106 mg) prepared according to the same manner as the Reference Example 52-(a) in dichloromethane (1.5 mL) in a 20 mL cylindrical flask was added trifluoroacetic acid (1.5 mL) at room temperature under argon atmosphere with stirring, and the resulting mixture was stirred at room temperature for 2 hours. The reaction solution was concentrated under reduced pressure. To a solution of the concentrated residues in methanol (2 mL) was added 5% palladium carbon (wetted with 54.28% water, STD-type manufactured by NE CHEMCAT Corporation) (80 mg) at room temperature under argon atmosphere with stirring, the atmosphere in the reaction system was replaced with hydrogen atmosphere, and then the resulting mixture was stirred at room temperature for 1 hour. After the reaction was completed, the reaction solution was filtered through Celite, and the resulting filtrate was concentrated under reduced pressure. To a solution of the resulting residues in water/acetonitrile was added a saturated aqueous ammonium acetate solution to adjust the pH to 4.0. The resulting mixture was stirred at room temperature for 1 hour, the precipitated solids were collected by filtration, and dried under reduced pressure to give the title compound (34 mg) as white solids.

Mass spectrum (ESI, m/z): 614 $[M+H]^+$.

Reference Example 53-(b)

Preparation of (S)-2-((5-carboxypentyl) (N-(4-((4-guanidinobenzoyl)oxy)benzyl)sulfamoyl)amino) succinic acid trifluoroacetate

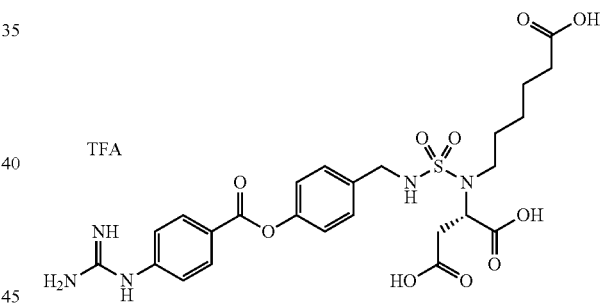

The title compound was prepared by using the Reference Example 43-(a) according to the same method as the Reference Example 52-(b).

Mass spectrum (ESI, m/z): 594 $[M+H]^+$.

Reference Example 54-(b)

Preparation of (S)-2-((N-(4-((4-guanidinobenzoyl)oxy)benzyl)sulfamoyl)(methyl)amino)succinic acid

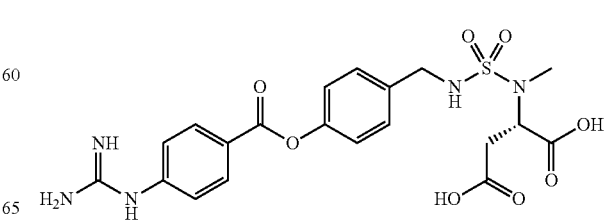

To a solution of (3)-di-tert-butyl 2-(N-((benzyloxy)carbonyl)-N-(4-((4-(2,3-bis(tert-butoxycarbonyl)guanidino)benzyl)oxy)benzyl)sulfamoyl)(methyl(amino)succinate (614 mg) prepared according to the same manner as the Reference Example 54-(a in dehydrated dichloromethane (6 mL) in a 100 mL round-bottom flask was added trifluoroacetic acid (2.00 mL) under ice-cooling under argon atmosphere with stirring, and the resulting mixture was stirred at room temperature for 16 hours. The reaction solution was concentrated under reduced pressure. To a solution of the concentrated residues in methanol (6 mL) was added 10% palladium carbon (wetted with ca. 55% water, manufactured by Tokyo Chemical Industry Co., Ltd.) (50 mg) at room temperature under argon atmosphere with stirring, the atmosphere in the reaction system was replaced with hydrogen atmosphere, and then the resulting mixture was stirred at room temperature for 2 hours. After the reaction was completed, the reaction solution was filtered through Celite, washed with a mixed solvent of methanol and acetonitrile (1:1 (v/v)), and the resulting filtrate was concentrated under reduced pressure. To a mixed solution of the resulting residues in water (10 mL)/acetonitrile (4 mL)/trifluoroacetic acid was added a saturated aqueous ammonium acetate solution to adjust the pH to 4.0. The resulting mixture was stirred at room temperature for 1 hour, and filtered to give the filtered residues. The resulting filtered residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were concentrated under reduced pressure. To the resulting residues was added a saturated aqueous ammonium acetate solution to adjust the pH to 4.0. The resulting mixture was stirred at room temperature for 1 hour, the precipitated solids were collected by filtration, and dried under reduced pressure to give the title compound (198 mg) as white solids.

Mass spectrum (ESI, m/z): 494 [M+H]$^+$.

Reference Example 55-(b)

Preparation of (S)-2-((N-(4-((4-guanidinobenzoyl)oxy)benzyl)sulfamoyl)amino)succinic acid

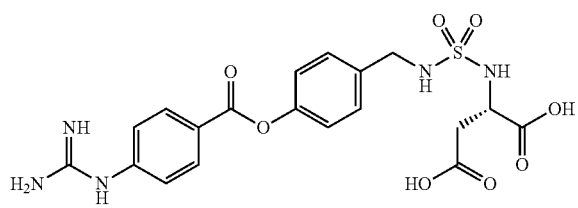 [SMILES: N=C(N)Nc1ccc(C(=O)Oc2ccc(CNS(=O)(=O)N[C@@H](CC(=O)O)C(=O)O)cc2)cc1]

To a solution of (S)-di-tert-butyl 2-((N-(4-((4-(2,3-bis(tert-butoxycarbonyl)guanidino)benzoyl)oxy)benzyl)-N-(tert-butoxycarbonyl)sulfamoyl)amino)succinate (370 mg) prepared according to the same manner as the Reference Example 55-(a) in dichloromethane (1.5 ml) in a 30 mL cylindrical flask was added trifluoroacetic acid (1.500 mL) at room temperature under argon gas flow with stirring, and the resulting mixture was stirred at room temperature for 14 hours. The reaction solution was concentrated under reduced pressure. To the concentrated residues was added trifluoroacetic acid (1.5 mL), and the resulting mixture was stirred at room temperature for 4 hours. After the reaction was completed, the reaction solution was concentrated under reduced pressure. To a solution of the resulting residues in water (4 mL) was added a saturated aqueous ammonium acetate solution at room temperature to adjust the pH to 3.97. The resulting mixture was stirred at room temperature for 2 hours, the precipitated solids were collected by filtration, and dried under reduced pressure to give the title compound (177.3 mg) as white solids.

Mass spectrum (ESI, m/z): 480 [M+H]$^+$.

Reference Example 56-(b)

Preparation of (S)-2-((carboxymethyl) (N-(4-((4-guanidinobenzoyl)oxy)benzyl)sulfamoyl)amino) succinic acid

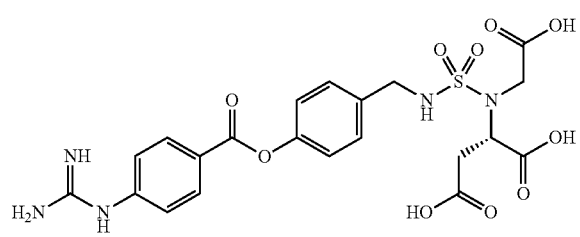 [SMILES: N=C(N)Nc1ccc(C(=O)Oc2ccc(CNS(=O)(=O)N(CC(=O)O)[C@@H](CC(=O)O)C(=O)O)cc2)cc1]

To a solution of (S)-di-tert-butyl 2-((N-(4-((4-(2,3-bis(tert-butoxycarbonyl)guanidino)benzoyl)oxy)benzyl)-N-(tert-butoxycarbonyl)sulfamoyl) (2-(tert-butoxy)-2-oxoethyl)amino)succinate (450 mg) prepared in the Reference Example 56-(a) in dichloromethane (5 mL) in a 50 mL round-bottom flask was added trifluoroacetic acid (5.00 mL) at room temperature under argon atmosphere with stirring, and the resulting mixture was stirred at room temperature for 18 hours. The reaction solution was concentrated under reduced pressure. To the concentrated residues were added dichloromethane (3 mL) and trifluoroacetic acid (5.00 mL), and the resulting mixture was stirred at room temperature for 24 hours, After the reaction was completed, the reaction solution was concentrated under reduced pressure. The resulting residues were subjected to medium pressure preparative chromatography (ODS silica gel, elution solvent; aqueous solution with 0.1% trifluoroacetic acid acetonitrile solution with 0.1% trifluoroacetic acid), and the fractions comprising the target compound were concentrated under reduced pressure. The resulting residues were subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were concentrated under reduced pressure. The precipitated solids were collected by filtration, and dried under reduced pressure to give the title compound (36 mg) as white solids.

Mass spectrum (ESI, m/z): 538 [M+H]$^+$.

Reference Example 57-(b)

Preparation of (S)-2-((N-(4-((4-guanidinobenzoyl) oxy)benzyl)sulfamoyl)amino)pentanedioic acid

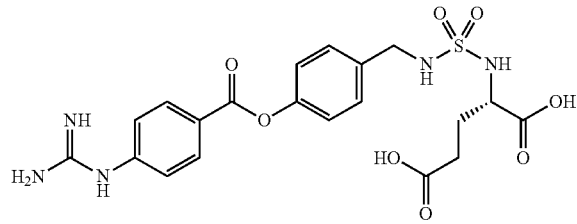 [SMILES: N=C(N)Nc1ccc(C(=O)Oc2ccc(CNS(=O)(=O)N[C@@H](CCC(=O)O)C(=O)O)cc2)cc1]

To a solution of (S)-di-tert-butyl 2-((N-(4-((4-(2,3-bis (tert-butoxycarbonyl)guanidino)benzoyl)oxy)benzyl)-N-(tert-butoxycarbonyl)sulfamoyl)amino)pentanedioate (550 mg) prepared in the Reference Example 57-(a) in dehydrated dichloromethane (6 mL) in a 50 mL round-bottom flask was added trifluoroacetic acid (2.00 mL) under ice-cooling under argon atmosphere with stirring, and the resulting mixture was stirred at room temperature for 16 hours. The reaction solution was concentrated under reduced pressure. To a solution of the concentrated residues in dehydrated dichloromethane (6 mL) was added trifluoroacetic acid (2.00 mL) at room temperature under argon atmosphere with stirring, and the resulting mixture was stirred at room temperature for 1 hour. After the reaction was completed, the reaction solution was concentrated under reduced pressure. To a solution of the concentrated residues in water (8 mL)/acetonitrile (2 mL) was added a saturated aqueous ammonium acetate solution to adjust the pH to 4.0. The resulting mixture was stirred at room temperature for 1 hour, and filtered. The filtered residues were subjected to medium pressure preparative chromatography (ODS silica gel, elution solvent; aqueous solution with 0.1% trifluoroacetic acid:acetonitrile solution with 0.1% trifluoroacetic acid), the fractions comprising the target compound were combined, and acetonitrile was distilled away under reduced pressure. To the concentrated residues was added a saturated aqueous ammonium acetate solution to adjust the pH to 4.0. The resulting mixture was stirred at room temperature for 1 hour, the precipitated solids were collected by filtration, and dried under reduced pressure to give the title compound (227 mg) as white solids.

Mass spectrum (ESI, m/z): 494 [M+H]$^+$.

Reference Example 58-(b)

Preparation of (S)-4-(2-carboxy-2-((N-(4-((4-(guanidinobenzoyl)oxy)benzyl)sulfamoyl)amino)ethyl) benzoic acid

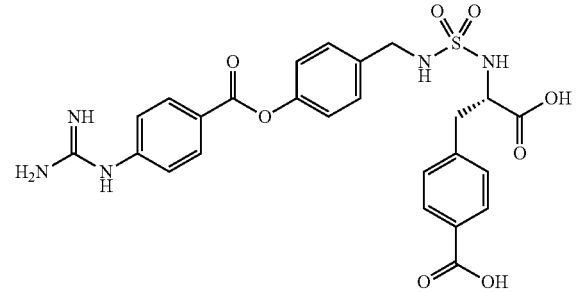 [SMILES: N=C(N)Nc1ccc(C(=O)Oc2ccc(CNS(=O)(=O)N[C@@H](Cc3ccc(C(=O)O)cc3)C(=O)O)cc2)cc1]

The title compound was prepared by using the Reference Example 58-(a) according to the same method as the Reference Example 43-(b).

Mass Spectrum (ESI, M/z): 556 [M+H]$^+$.

Reference Example 59-(b)

Preparation of (S)-4-(((N-(1-(tert-butoxy)-3-(4-hydroxyphenyl)-1-oxopropan-2-yl)sulfamoyl)(tert-butoxycarbonyl)amino)methyl)phenyl 4-(2,3-bis (tert-butoxycarbonyl)guanidino)benzoate

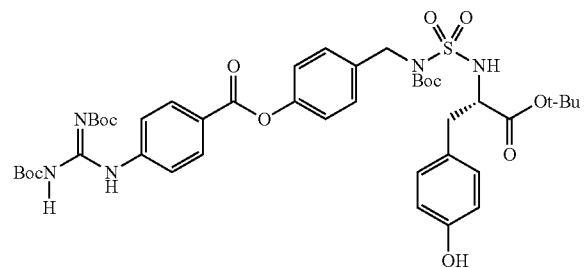

To a solution of (S)-4-(((N-1-(tert-butoxy)-3-(4-(tert-butyldimethylsilyl)oxy)phenyl)-1-oxopropan-2-yl)sulfamoyl) (tert-butoxycarbonyl)amino)methyl)phenyl 4-(2,3-bis (tert-butoxycarbonyl)guanidino)benzoate (359 mg prepared in the Reference Example 59-(a) in dehydrated tetrahydrofuran (4.00 mL) in a 100 mL round-bottom flask was added tetrabutylammonium fluoride (a 1.0 M solution in tetrahydrofuran (10.500 mL) under ice-cooling under argon atmosphere with stirring, and the resulting mixture was stirred at room temperature for 1 hour. After the reaction was completed, to the reaction solution was added a saturated aqueous ammonium chloride solution, and the resulting mixed solution was extracted with ethyl acetate. The resulting organic layer was washed with water, dried over anhydrous sodium sulfate, filtered, and concentrated under reduced pressure. The resulting residues were purified by medium pressure preparative chromatography (silica gel, elution solvent; hexane:ethyl acetate) to give the title compound (296 mg) as a white foam.

Mass spectrum (ESI, m/z): 884 [M+H]$^+$.

Reference Example 59-(c)

Preparation of (S)-2-((N-(4-((4-guanidinobenzoyl) oxy)benzyl)sulfamoyl)amino)-3-(4-hydroxyphenyl) propanoic acid trifluoroacetate

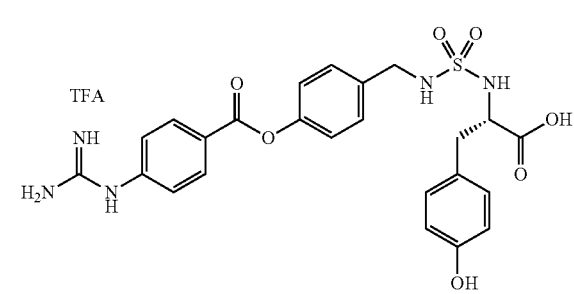 [SMILES: N=C(N)Nc1ccc(C(=O)Oc2ccc(CNS(=O)(=O)N[C@@H](Cc3ccc(O)cc3)C(=O)O)cc2)cc1]

The title compound was prepared by using the Reference Example 59-(b) according to the same method as the Reference Example 42-(b).
Mass spectrum (ESI, m/z): 528 [M+H]$^+$.

Reference Example 60-(b)

Preparation of (S)-2-((N-(4-((4-guanidinobenzoyl)oxy)benzyl)sulfamoyl)amino)-3-phenylpropanoic acid

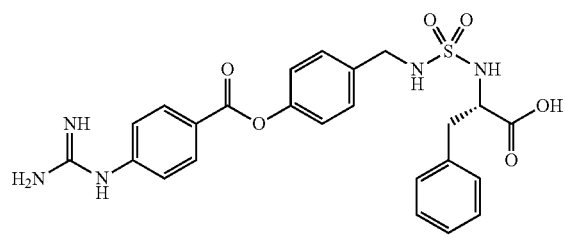 [SMILES: N=C(N)Nc1ccc(C(=O)Oc2ccc(CNS(=O)(=O)N[C@@H](Cc3ccccc3)C(=O)O)cc2)cc1]

The title compound was prepared by using the Reference Example 60-(a) according to the same method as the Reference Example 43-(b).
Mass spectrum (ESI, m/z): 512 [M+H]$^+$.

Reference Example 61-(b)

Preparation of 6-((N-(4-((4-guanidinobenzoyl)oxy)benzyl)sulfamoyl)amino)hexanoic acid

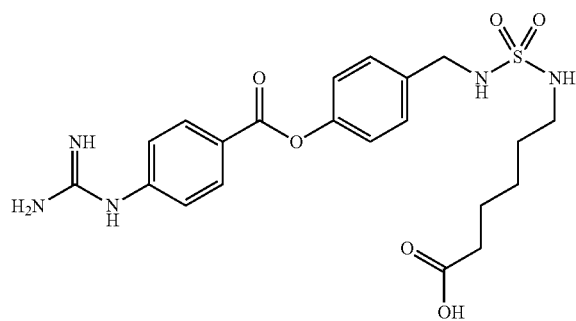 [SMILES: N=C(N)Nc1ccc(C(=O)Oc2ccc(CNS(=O)(=O)NCCCCCC(=O)O)cc2)cc1]

The title compound was prepared by using the Reference Example 61-(a) according to the same method as the Reference Example 57-(b).
Mass spectrum (ESI, m/z): 478 [M+H]$^+$.

Reference Example 62-(b)

Preparation of 2-((N-(4-((4-guanidinobenzoyl)oxy)benzyl)sulfamoyl)amino)acetic acid

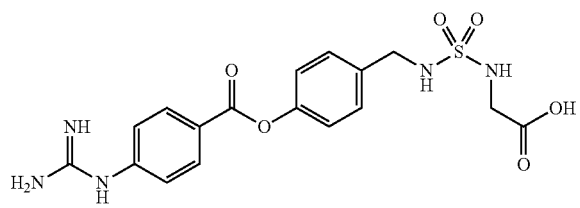 [SMILES: N=C(N)Nc1ccc(C(=O)Oc2ccc(CNS(=O)(=O)NCC(=O)O)cc2)cc1]

The title compound was prepared by using the Reference Example 62-(a) according to the same method as the Reference Example 57-(b).
Mass spectrum (ESI, m/z): 422 [M+H]$^+$.

Reference Example 63-(b)

Preparation of (S)-2-((N-(4-((4-guanidinobenzoyl)oxy)benzyl)sulfamoyl)amino)propanoic acid

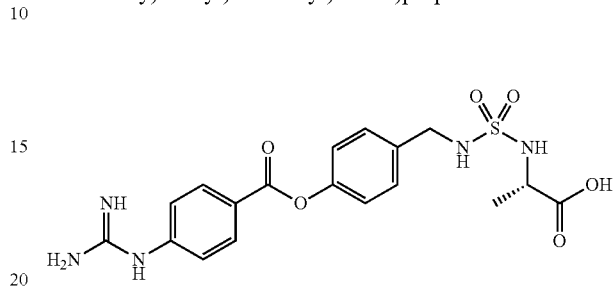

The title compound was prepared by using the Reference Example 63-(a) according to the same method as the Reference Example 43-(b).
Mass spectrum (EST, m/z): 436 [M+H]$^+$.

Reference Example 64-(b)

Preparation of 4-(((N-methylsulfamoyl)amino)methyl)phenyl 4-guanidinobenzoate trifluoroacetate

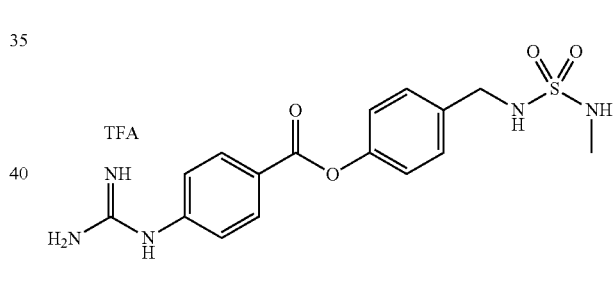

The title compound was prepared by using the Reference Example 64-(a) according to the same method as the Reference Example 32-(d).
Mass spectrum (ESI, m/z): 378 [M+H]$^+$.

Reference Example 65-(b)

Preparation of (S)-2-((N-(3-fluoro-4-((4-guanidinobenzoyl)oxy)benzyl)sulfamoyl)amino)succinic acid trifluoroacetate

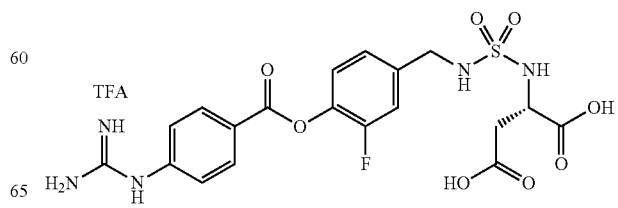

The title compound was prepared by using the Reference Example 65-(a) according to the same method as the Reference Example 43-(b).
Mass spectrum (ESI, m/z): 498 [M+H]⁺.

Reference Example 66-(b)

Preparation of (S)-2-((N-(3-chloro-4-((4-guanidinobenzoyl)oxy)benzyl)sulfamoyl)amino)succinic acid trifluoroacetate

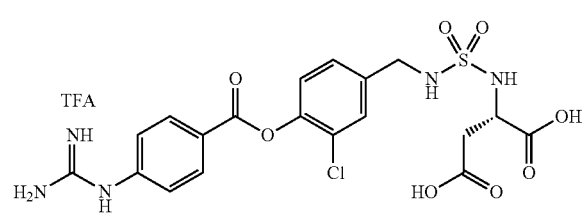 [SMILES: N=C(N)Nc1ccc(C(=O)Oc2ccc(CNS(=O)(=O)N[C@@H](CC(=O)O)C(=O)O)cc2F)cc1]

The title compound was prepared by using the Reference Example 66-(a) according to the same method as the Reference Example 42-(b).
Mass spectrum (ESI, m/z): 514 [M+H]⁺.

Reference Example 67-(b)

Preparation of (S)-2-((N-(4-((4-guanidinobenzoyl)oxy)-3-methoxybenzyl)sulfamoyl)amino)succinic acid trifluoroacetate

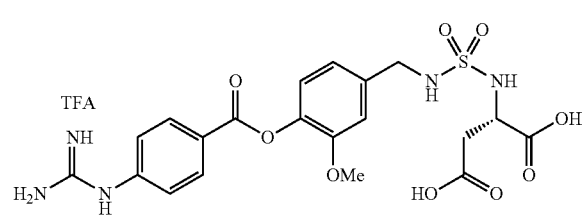 [SMILES: COc1cc(CNS(=O)(=O)N[C@@H](CC(=O)O)C(=O)O)ccc1OC(=O)c1ccc(NC(=N)N)cc1]

The title compound was prepared by using the Reference Example 67-(a) according to the same method as the Reference Example 42-(b).
Mass spectrum (ESI, m/z): 510 [M+H]⁺.

Reference Example 68-(b)

Preparation of (S)-2-<(N-(4-((4-guanidinobenzoyloxy)-3-methylbenzyl)sulfamoyl)amino)succinic acid

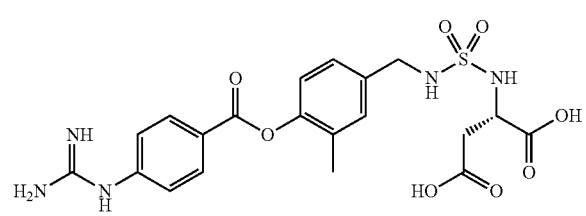 [SMILES: Cc1cc(CNS(=O)(=O)N[C@@H](CC(=O)O)C(=O)O)ccc1OC(=O)c1ccc(NC(=N)N)cc1]

The title compound was prepared by using the Reference Example 66-(a) according to the same method as the Reference Example 43-(b).
Mass spectrum (ESI, m/z): 494 [M+H]⁺.

Reference Example 69-(b)

Preparation of (S)-2-((N-(2-fluoro-4-((4-guanidinobenzoyl)oxy)benzyl)sulfamoyl)amino)succinic acid

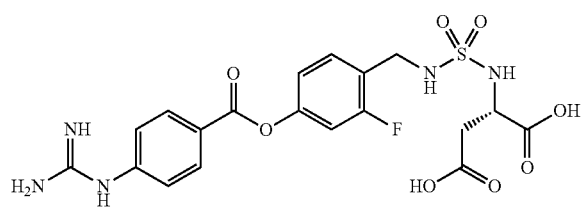 [SMILES: N=C(N)Nc1ccc(C(=O)Oc2ccc(CNS(=O)(=O)N[C@@H](CC(=O)O)C(=O)O)c(F)c2)cc1]

The title compound was prepared by using the Reference Example 69-(a) according to the same method as the Reference Example 43-(b).

Reference Example 70-(b)

Preparation of (S)-2-((N-(2-chloro-4-((4-guanidinobenzoyl)oxy)benzyl)sulfamoyl)amino)succinic acid

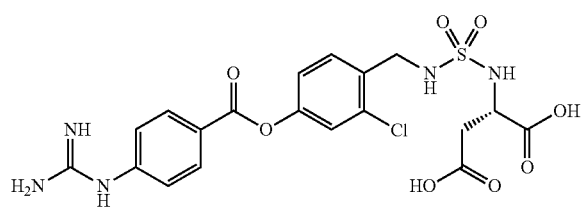 [SMILES: N=C(N)Nc1ccc(C(=O)Oc2ccc(CNS(=O)(=O)N[C@@H](CC(=O)O)C(=O)O)c(Cl)c2)cc1]

The title compound was prepared by using the Reference Example 70-(a) according to the same method as the Reference Example 56-(b).
Mass spectrum (ESI, m/z): 514 [M+H]⁺.

Reference Example 71-(b)

Preparation of (S)-2-((N-(4-((4-guanidinobenzoyl)oxy)-2-methoxybenzyl)sulfamoyl)amino)succinic acid trifluoroacetate

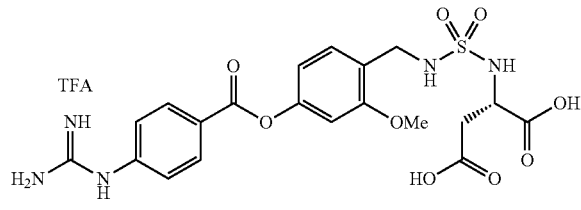 [SMILES: COc1cc(OC(=O)c2ccc(NC(=N)N)cc2)ccc1CNS(=O)(=O)N[C@@H](CC(=O)O)C(=O)O]

The title compound was prepared by using the Reference Example 71-(a) according to the same method as the Reference Example 42-(b).
Mass spectrum (ESI, m/z): 510 [M+H]⁺.

Reference Example 72-(b)

Preparation of (S)-2-((N-(4-((4-guanidinobenzoyl)oxy)-2-methylbenzyl)sulfamoyl)amino)succinic acid

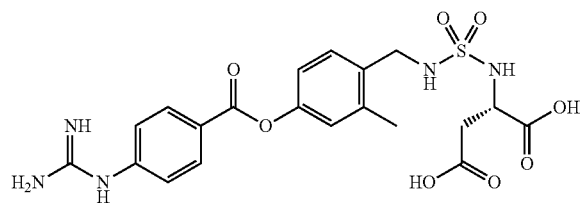 [SMILES: Cc1cc(OC(=O)c2ccc(NC(=N)N)cc2)ccc1CNS(=O)(=O)N[C@@H](CC(=O)O)C(=O)O]

The title compound was prepared by using the Reference Example 72-(a) according to the same method as the Reference Example 43-(b).
Mass spectrum (ESI, m/z): 494 [M+H]$^+$.

Reference Example 73-(b)

Preparation of (S)-2-((N-(3-((4-guanidinobenzoyl)oxy)benzyl)sulfamoyl)amino)succinic acid trifluoroacetate

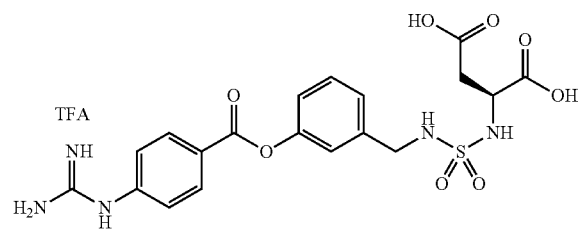 [SMILES: N=C(N)Nc1ccc(C(=O)Oc2cccc(CNS(=O)(=O)N[C@@H](CC(=O)O)C(=O)O)c2)cc1]

To a solution of (S)-di-tert-butyl 2-((N-(3-((4-(2,3-bis(tert-butoxycarbonyl)guanidino)benzoyl)oxy)benzyl)-N-(tert-butoxycarbonyl)sulfamoyl)amino)succinate (351 mg) prepared according to the sane manner as the Reference Example 73-(a) in dehydrated dichloromethane (6 ML) in a 50 mL round-bottom flask was added trifluoroacetic acid (2.00 mL) under ice-cooling under argon atmosphere with stirring, and the resulting mixture was stirred at room temperature for 16 hours. The reaction solution was concentrated under reduced pressure. To a solution of the concentrated residues in dehydrated dichloromethane (6 mL was added trifluoroacetic acid (2.00 mL) at room temperature under argon atmosphere with stirring, and the resulting mixture was stirred at room temperature for 1 hour. After the reaction was completed, the reaction solution was concentrated under reduced pressure. To a solution of the resulting residues in water (8 mL)/acetonitrile (2 mL) was added a saturated aqueous ammonium acetate solution to adjust the pH to 4.0, to the resulting suspension was added trifluoroacetic acid to give a solution. The resulting solution was subjected to medium pressure preparative chromatography (ODS silica gel, elution solvent; aqueous solution with 0.1% trifluoroacetic acid:acetonitrile solution with 0.1% trifluoroacetic acid), and the fractions comprising the target compound were freeze-dried to give the title compound (210 mg) as white solids.
Mass spectrum (ESI, m/z): 480 [M+H]$^+$.

Reference Example 74-(b)

Preparation of (S)-2-((N-(4-((2-fluoro-4-guanidinobenzoyl)oxy)benzyl)sulfamoyl)amino)succinic acid

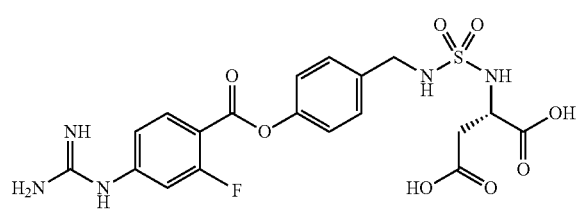 [SMILES: N=C(N)Nc1ccc(C(=O)Oc2ccc(CNS(=O)(=O)N[C@@H](CC(=O)O)C(=O)O)cc2)c(F)c1]

The title compound was prepared by using the Reference Example 74-(a) according to the same method as the Reference Example 43-(b).
Mass spectrum (ESI, m/z): 498 [M+H]$^+$.

Reference Example 75-(b)

Preparation of (S)-2-((N-(4-((4-guanidino-2-methylbenzoyl)oxy)benzyl)sulfamoyl)amino)succinic acid

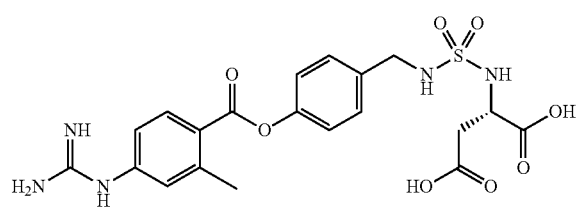 [SMILES: Cc1cc(NC(=N)N)ccc1C(=O)Oc1ccc(CNS(=O)(=O)N[C@@H](CC(=O)O)C(=O)O)cc1]

The title compound was prepared by using the Reference Example 75-(a) according to the same method as the Reference Example 43-(b).
Mass spectrum (ESI, m/z): 494 [M+H]$^+$.

Reference Example 76-(b)

Preparation of (S)-2-((N-(2-carboxy-4-((4-guanidinobenzoyl)oxy)benzyl)sulfamoyl)amino)succinic acid

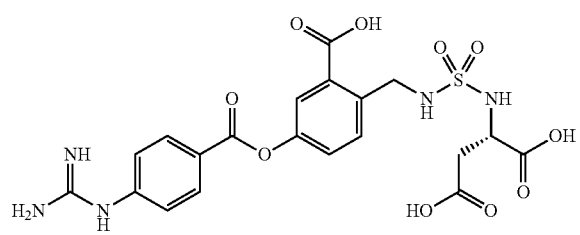 [SMILES: N=C(N)Nc1ccc(C(=O)Oc2ccc(CNS(=O)(=O)N[C@@H](CC(=O)O)C(=O)O)c(C(=O)O)c2)cc1]

The title compound was prepared by using the Reference Example 76-(a) according to the same method as the Reference Example 57-(b).
Mass spectrum (ESI, m/z): 524 [M+H]$^+$.

Reference Example 77-(b)

Preparation of (S)-2-((N-(2-(((S)-1,2-dicarboxyethyl)carbamoyl)-4-((4-guanidinobenzoyl)oxy)benzyl)sulfamoyl)amino)succinic acid trifluoroacetate

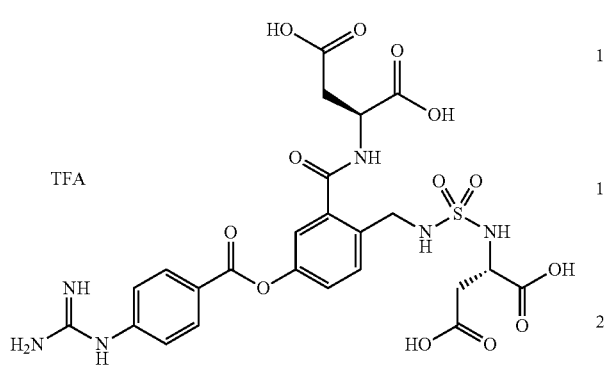

The title compound was prepared by using the Reference Example 77-(a) according to the same method as the Reference Example 42-(b).
Mass spectrum (EST, n/z): 639 [M+H]⁺.

Reference Example 78-(b)

Preparation of 2-((N-(2-chloro-4-((4-guanidinobenzoyl)oxy)benzyl)sulfamoyl)amino)acetic acid

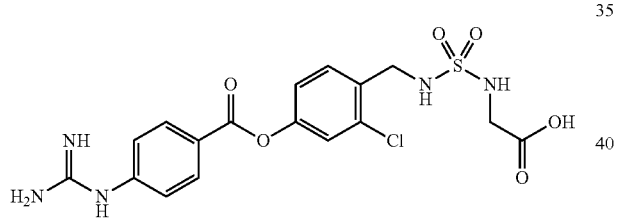

The title compound was prepared by using the Reference Example 78-(a) according to the same method as the Reference Example 57-(b).
Mass spectrum (ESI, m/z): 456 [M+H]⁺.

Reference Example 79-(b)

Preparation of 2-(((N-(carboxymethyl)sulfamoyl)amino)methyl)-5-((4-guanidinobenzoyl)oxy)benzoic acid

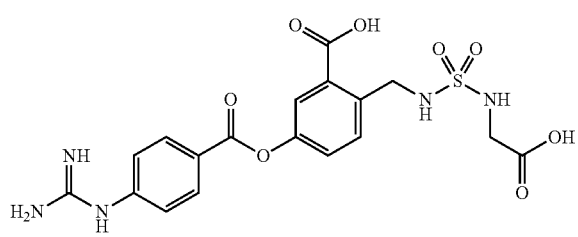 [SMILES: N=C(N)Nc1ccc(C(=O)Oc2ccc(CNS(=O)(=O)NCC(=O)O)c(C(=O)O)c2)cc1]

The title compound was prepared by using the Reference Example 79-(a) according to the same method as the Reference Example 57-(b).
Mass spectrum (ESI, m/z): 466 [M+H]⁺.

Reference Example 80-(b)

Preparation of (S)-2-(2-(((N-(carboxymethyl)sulfamoyl)amino)methyl)-5-((4-guanidinobenzoyl)oxy)benzamide)succinic acid trifluoroacetate

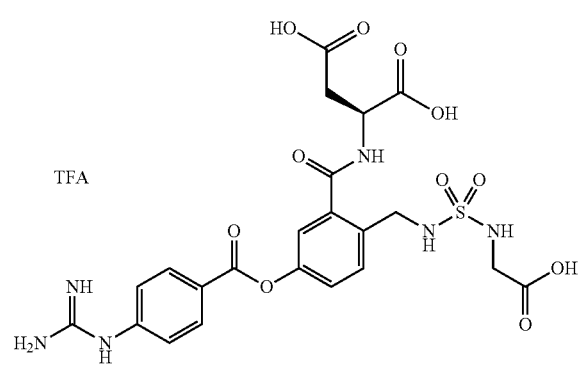 [SMILES: N=C(N)Nc1ccc(C(=O)Oc2ccc(CNS(=O)(=O)NCC(=O)O)c(C(=O)N[C@@H](CC(=O)O)C(=O)O)c2)cc1]

The title compound was prepared by using the Reference Example 80-(a) according to the same method as the Reference Example 42-(b).
Mass spectrum (ESI, m/z): 581 [M+H]⁺.

Reference Example 81-(b)

Preparation of (S)-2-((N-((10-guanidino-13-oxo-6,7,8,13-tetrahydrodibenzo[b,f][1,4]dioxecin-4-yl)methyl)sulfamoyl)amino)succinic acid trifluoroacetate

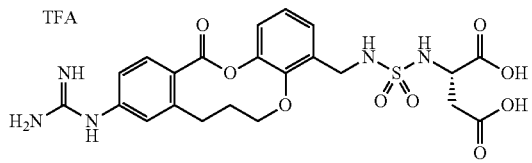 [SMILES: N=C(N)Nc1ccc2c(c1)CCCOc1c(CNS(=O)(=O)N[C@@H](CC(=O)O)C(=O)O)cccc1OC2=O]

To a suspension of (S)-2-((N-((10-amino-13-oxo-6,7,8,13-tetrahydrodibenzo[b,f][1,4]dioxecin-4-yl)methyl)sulfamoyl)amino)succinic acid hydrochloride (1.46 g) prepared in the Reference Example 19-(m)-2 in tert-butanol (1 mL) in a 30 mL round-bottom flask were added a 4 M hydrogen chloride/cyclopentyl methyl ether solution (85 µL) and cyanamide (17.5 mg) at room temperature under argon gas flow with stirring, and the resulting mixture was stirred at 50° C. for 30 hours. After the reaction was completed, the reaction solution was concentrated under reduced pressure. The resulting residues were subjected to medium pressure preparative chromatography (silica gel, elution solvent; acetonitrile solution with 0.1% trifluoroacetic acid:aqueous solution with 0.1% trifluoroacetic acid), and the fractions comprising the target compound were freeze-dried to give the title compound (43.5 mg) as white solids.
Mass spectrum (ESI, m/z): 536 [M+H]⁺.

Reference Example 82-(b)

Preparation of (S)-2-(N-((10-guanidino-13-oxo-6,7,6,13-tetrahydrodibenzo[b,f][1,4]dioxecin-3-yl)methyl)sulfamoyl)amino)succinic acid trifluoroacetate

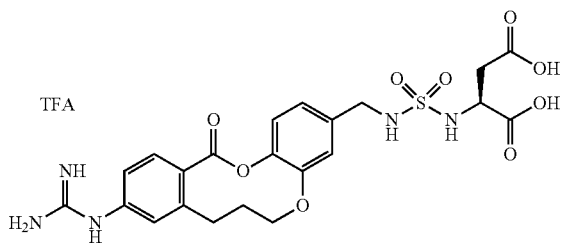 [SMILES: N=C(N)Nc1ccc2c(c1)CCCOc1cc(CNS(=O)(=O)N[C@@H](CC(=O)O)C(=O)O)ccc1OC2=O]

The title compound was prepared by using the Reference Example 19-(m)-3 according to the same method as the Reference Example 81-(b).

Mass spectrum (ESI, m/z): 536 [M+H]$^+$.

Reference Example 83-(b)

Preparation of (S)-2-((N-((10-guanidino-13-oxo-6,7,8,13-tetrahydrodibenzo[b,f][1,4]dioxecin-2-yl)methyl)sulfamoyl)amino)succinic acid trifluoroacetate

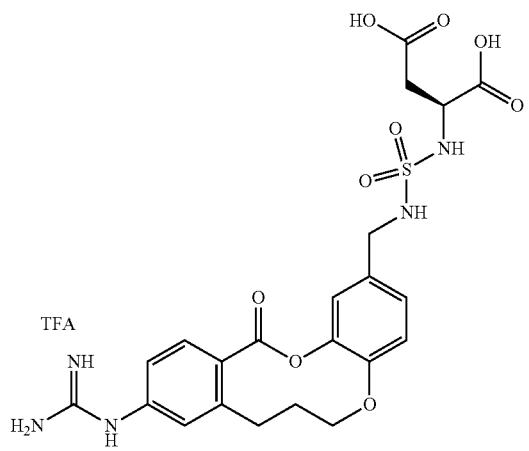 [SMILES: N=C(N)Nc1ccc2c(c1)CCCOc1ccc(CNS(=O)(=O)N[C@@H](CC(=O)O)C(=O)O)cc1OC2=O]

The title compound was prepared by using the Reference Example 19-(m)-4 according to the same method as the Reference Example 81-(b).

Mass spectrum (ESI, m/z): 536 [M+H]$^+$.

Reference Example 84-(a)

Preparation of (4-(benzyloxy)-2-bromophenyl)methanol

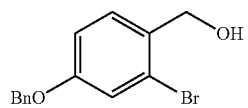

To a mixed solution of 4-(benzyloxy)-2-bromobenzaldehyde (7.17 g) in ethanol (35 mL)/tetrahydrofuran (35 mL) in a 300 mL round-bottom flask was added sodium borohydride (1.03 g) at 0° C. under argon atmosphere with stirring, and the resulting mixture was stirred at 0° C. for 15 minutes. After the reaction was completed, to the reaction solution was added water, and the resulting mixed solution was extracted with ethyl acetate. The resulting organic layer was washed with saturated brine, dried over anhydrous magnesium sulfate, filtered, and concentrated under reduced pressure to give the title compound (7.06 g) as white solids.

Mass spectrum (ESI, m/z): 291 [M−H]$^+$.

According to the same method as the Reference Example 84-(a), Reference Example 84-(a)-2 was prepared.

TABLE 22

| Reference Example No. | Compound name<br>Structural formula<br>Mass spectrum |
|---|---|
| 84-(a)-2 | 2-(benzyloxy)-4-(hydroxymethyl)phenol<br><br>(ESI, m/z): 229 [M − H]$^+$. |

Reference Example 84-(b)

Preparation of ((4-(benzyloxy)-2-bromobenzyl)oxy)(tert-butyl)dimethylsilane

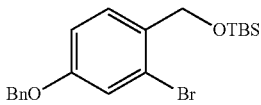 [SMILES: CC(C)(C)[Si](C)(C)OCc1ccc(OCc2ccccc2)cc1Br]

To a solution of (4-(benzyloxy)-2-bromophenyl)methanol (7.06 g) prepared in the Reference Example 84-(a) in dimethylformamide (70 mL) in a 300 mL round-bottom flask were added imidazole (1.97 g) and tert-butyldimethylchlorosilane (4.00 g) at room temperature under argon gas flow with stirring, and the resulting mixture was stirred at room temperature for 30 minutes. After the reaction was completed, to the reaction solution was added water (70 mL), and the resulting mixed solution was extracted with tert-butyl methyl ether (70 mL). The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (9.0 g) as a colorless foam.

Mass spectrum (ESI, m/z) 405 [M−H]$^+$.

According to the same method as the Reference Example 84-(b), Reference Example 84-(b)-2 to 84-(b)-4 were prepared.

TABLE 23

| Reference Example No. | Compound name Structural formula |
|---|---|
| 84-(b)-2 | 2-(benzyloxy)-6-(((tert-butyldimethylsilyl)oxy)methyl)phenol 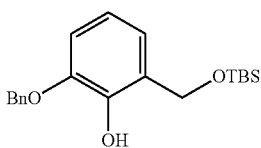 (ESI, m/z): 343[M − H]⁺. |
| 84-(b)-3 | 2-(benzyloxy)-5-(((tert-butyldimethylsilyl)oxy)methyl)phenol 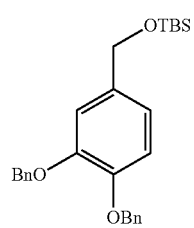 (ESI, m/z): 343[M − H]⁺. |
| 84-(b)-4 | 2-(benzyloxy)-4-(((tert-butyldimethylsilyl)oxy)methyl)phenol 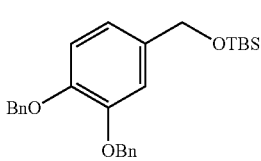 (ESI, m/z): 343[M − H]⁺. |

Reference Example 84-(c)

Preparation of tert-butyl 5-(benzyloxy)-2-(((tert-butyldimethylsilyl)oxy)methyl)benzoate

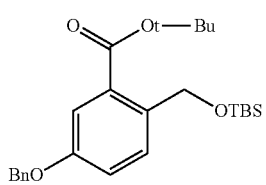

To a solution of ((4-(benzyloxy)-2-bromobenzyl)oxy)(tert-butyl)dimethylsilane (2.87 g) prepared in the Reference Example 84-(b) in tetrahydrofuran (30 mL) in a 300 mL three-necked flask was added dropwise n-butyllithium (a 1.6 M solution in hexane) (5.28 mL) under argon gas flow with stirring so that the temperature did not exceed −60° C., and the resulting mixture was stirred at −70° C. for 50 minutes. Then, a solution of di-tert-butyl dicarbonate (1.86 g) in tetrahydrofuran (10 mL) was added dropwise thereto with stirring so that the temperature did not exceed −60° C., the resulting mixture was stirred at −70° C. for 1 hour, and stirred at room temperature for 40 minutes. After the reaction was completed, to the reaction solution was added a saturated aqueous ammonium chloride solution, and the resulting mixed solution was extracted with ethyl acetate. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (1.13 g) as a colorless oil.

Mass spectrum (ESI, m/z): 451 [M+Na]⁺.

Reference Example 84-(d)

Preparation of tert-butyl 2-(((tert-butyldimethylsilyl)oxy)methyl)-5-hydroxybenzoate

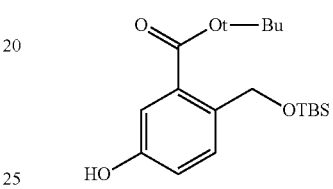

To a solution of tert-butyl 5-(benzyloxy)-2-(((tert-butyldimethylsilyl)oxy)methyl)benzoate (1.126 g) prepared in the Reference Example 84-(c) in ethyl acetate (12 mL) in a 100 mL round-bottom flask was added BNA-5D (wetted with 52.97% water, manufactured by NE CHEMCAT Corporation) (225 mg) at room temperature under argon gas flow with stirring, the atmosphere in the reaction system was replaced with hydrogen atmosphere, and then the resulting mixture was stirred at room temperature for 30 minutes. After the reaction was completed, the reaction solution was filtered through Celite, washed with ethyl acetate, and the resulting filtrate was concentrated under reduced pressure. The resulting residues were purified by medium pressure preparative chromatography (silica gel, elution solvent; hexane:ethyl acetate) to give the title compound (500 mg) as a colorless oil.

Mass spectrum (CI, m/z): 339 [M+H]⁺.

Reference Example 85-(a)

Preparation of 5-(benzyloxy)-2-(((tert-butyldimethylsilyl)oxy)methyl)benzoic acid

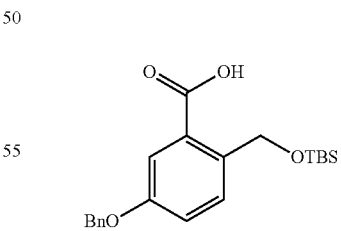

To a solution of ((4 (benzyloxy)-2-bromobenzyl)oxy)(tert-buty)dimethylsilane (3.00 g) prepared in the Reference Example 84-(b) in tetrahydrofuran (30 mL) in a 300 mL three-necked flask was added dropwise n-butyllithium (a 1.6 M solution in hexane) (5.06 ml) under argon gas flow with stirring so that the temperature did not exceed −60° C., and the resulting mixture was stirred at −70° C. for 30 minutes. Then, dry ice (32.4 g) was added thereto with stirring at −70°

C., the resulting mixture was stirred at −70° C. for 1 hour, and stirred at room temperature for 30 minutes. After the reaction was completed, to the reaction solution was added water, then added 1N hydrochloric acid to adjust the pH to 2, and the resulting mixed solution was extracted with ethyl acetate. The resulting organic layer was washed with saturated brine, dried over anhydrous magnesium sulfate, filtered, and concentrated under reduced pressure. The resulting residues were purified by medium pressure preparative chromatography (DIOL silica gel, elution solvent; hexane: ethyl acetate). To the concentrated residues was added hexane (30 mL), the resulting mixture was stirred at room temperature, the precipitated solids were collected by filtration, and dried under reduced pressure to give the title compound (750 mg) as white solids.

Mass spectrum (ESI, m/z): 371 [M−H]+.

Reference Example 85-(b)

Preparation of (S)-di-tert-butyl 2-(5-(benzyloxy)-2-(((tert-butyldimethylsilyl)oxy)methyl)benzamide)succinate

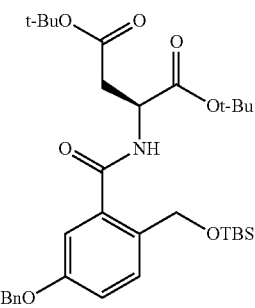 [SMILES: CC(C)(C)OC(=O)C[C@H](NC(=O)c1cc(OCc2ccccc2)ccc1CO[Si](C)(C)C(C)(C)C)C(=O)OC(C)(C)C]

(1) To a solution of ((4-(benzyloxy)-2-bromobenzyl)oxy) tert-butyl)dimethylsilane (48 mg) prepared in the Reference Example 85-(a) in dimethylformamide (500 μL) in a 300 mL round-bottom flask were added L-aspartic acid di-tert-butyl ester hydrochloride (43.3 mg), 1-(3-dimethylaminopropyl)-3-ethylcarbodiimide hydrochloride (30.8 mg), 1-hydroxybenzotriazol (20.1 mg), and N,N-diisopropylethylamine (26 μL) at room temperature under argon gas flow with stirring, and the resulting mixture was stirred at room temperature for 2 hours.

(2) To a solution of ((4-(benzyloxy)-2-bromobenzyl)oxy) (tert-butyl)dimethylsilane (500 mg) prepared in the Reference Example 85-(a) in dimethylformamide (5 mL) in a 50 mL round-bottom flask were added L-aspartic acid di-tert-butyl ester hydrochloride (418 mg), 1-(3-dimethylaminopropyl)-3-ethylcarbodiimide hydrochloride (271.5 mg), 1-hydroxybenzotriazol (191 mg), and N,N-diisopropylethylamine (257 μL) at room temperature under argon gas flow with stirring, and the resulting mixture was stirred at room temperature for 3 hours.

The reaction solution in (1) and the reaction solution in (2) were combined, water was added thereto, and the resulting mixed solution was extracted with ethyl acetate. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (618.9 mg) as a colorless oil.

Mass spectrum (CI, m/z): 600 [M+H]+.

Reference Example 85-(c)

Preparation of (S)-di-tert-butyl 2-(2-(((tert-butyldimethylsilyl)oxy)methyl)-5-hydroxybenzamide)succinate

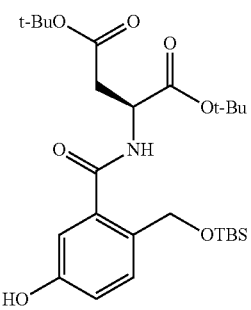 [SMILES: CC(C)(C)OC(=O)C[C@H](NC(=O)c1cc(O)ccc1CO[Si](C)(C)C(C)(C)C)C(=O)OC(C)(C)C]

The title compound was prepared by using the Reference Example 85-(b) according to the same method as the Reference Example 84-(d).

Mass spectrum (CI, m/z): 510 [M+H]+.

Reference Example 86-(a)

Preparation of (S)-di-tert-butyl 2-(N-methyl-2-nitrophenylsulfonamide)succinate

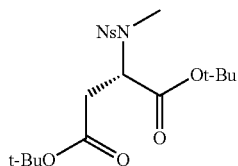

To a solution of (S)-di-tert-butyl 2-(2-nitrophenylsulfonamide)succinate (503.1 mg) prepared according to the same manner as the Reference Example 1-(a) in dimethylformamide (2.5 mL) in a 30 mL cylindrical flask were added potassium carbonate (324 mg) and iodomethane (291 μL) at room temperature under argon atmosphere with stirring, and the resulting mixture was stirred at room temperature for 1.5 hours. After the reaction was completed, to the reaction solution was added water, and the resulting mixed solution was extracted with ethyl acetate. The resulting organic layer was washed with saturated brine, dried over anhydrous magnesium sulfate, filtered, and concentrated under reduced pressure. The resulting residues were purified by medium pressure preparative chromatography (silica gel, elution solvent; hexane:ethyl acetate) to give the title compound (522.4 mg) as a colorless foam.

Mass spectrum (ESI, m/z): 467 [M+Na]+.

Reference Example 86-(b)

Preparation of (S)-di-tert-butyl 2-(methylamino)succinate

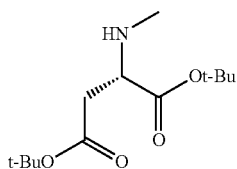 [SMILES: CN[C@@H](CC(=O)OC(C)(C)C)C(=O)OC(C)(C)C]

The title compound was prepared by using the Reference Example 86-(a) according to the same method as the Reference Example 1-(c).

Mass spectrum (ESI, m/z): 260 [M+H]⁻.

Reference Example 87-(a)

Preparation of (S)-dibenzyl 2-(3-hydroxybenzamide)succinate

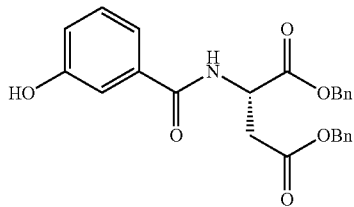 [SMILES: O=C(C[C@H](NC(=O)c1cccc(O)c1)C(=O)OCc1ccccc1)OCc1ccccc1]

(1) To a solution of 3-((tert-butyldimethylsilyl)oxy)benzoic acid in dehydrated dimethylformamide (5 mL) in a 20 mL two-necked flask were added N,N-diisopropylethylamine (390 µL) and COMU (467.2 mg) at 0° C. under argon gas flow with stirring, and the resulting mixture was stirred at 0° C. for 40 minutes. Then, (S)-dibenzyl 2-aminosuccinate hydrochloride (350.1 mg) was added thereto at 0° C., and the resulting mixture was stirred at room temperature for 6 hours. After the reaction was completed, the reaction solution was poured into cold water (20 mL), and the resulting mixed solution was extracted with toluene (50 mL). The resulting organic layer was washed with water (20 mL) and saturated brine (20 mL), dried over anhydrous magnesium sulfate, filtered, and concentrated under reduced pressure. The resulting residues were purified by medium pressure preparative chromatography (silica gel, elution solvent; hexane:ethyl acetate) to give (S)-dibenzyl 2-(3-((tert-butyldimethylsilyl)oxy)benzamide)succinate (302.9 mg) as a slightly pink oil.

To a solution of the resulting (S)-dibenzyl 2-(3-((tert-butyldimethylsilyl)oxy)benzamide)succinate (298.0 mg) in dehydrated tetrahydrofuran (2.5 mL) in a 30 mL cylindrical flask was added tetrabutylammonium fluoride (a 1.0 M solution in tetrahydrofuran) (235 µL) at 0° C. under argon gas flow with stirring, and the resulting mixture was stirred at room temperature for 16 hours.

(2) To a solution of 3-((tert-butyldimethylsilyl)oxy)benzoic acid (252.2 mg) in dehydrated dimethylformamide (5 mL) in a 20 mL two-necked flask were added (S)-dibenzyl 2-aminosuccinate hydrochloride (367.4 mg) and N,N-diisopropylethylamine (345 µL) at 0° C. under argon gas flow with stirring. Then, 1-hydroxybenzotriazol (148.3 mg) and 1-(3-dimethylaminopropyl)-3-ethylcarbodiimide hydrochloride (211.2 mg) were added thereto at 0° C., and the resulting mixture was stirred at room temperature for 18 hours. After the reaction was completed, the reaction solution was poured into water (20 mL), and the resulting mixed solution was extracted with toluene (50 mL). The resulting organic layer was washed with water (20 mL) and saturated brine (20 mL), dried over anhydrous magnesium sulfate, filtered, and concentrated under reduced pressure.

To a solution of the concentrated residues in dehydrated tetrahydrofuran (10 mL) in a 100 mL round-bottom flask was added tetrabutylammonium fluoride (a 1.0 M solution in tetrahydrofuran) (1.5 mL) at 0° C. under argon gas flow with stirring, the resulting mixture was stirred at 0° C. for 30 minutes, and stirred at room temperature for 1 hour.

The reaction solution in (1) and the reaction solution in (2) were combined, poured into a saturated aqueous ammonium chloride solution (20 mL), and the resulting mixed solution was extracted with ethyl acetate (50 mL). The resulting organic layer was washed with saturated brine (20 mL), dried over anhydrous magnesium sulfate, filtered, and concentrated under reduced pressure. The resulting residues were purified by medium pressure preparative chromatography (silica gel, elution solvent; hexane:ethyl acetate) to give the title compound (580.5 mg) as a colorless oil.

Mass spectrum (ESI, m/z): 434 [M+H].

Reference Example 87-(b)

Preparation of (S)-dibenzyl 2-(3-((4-nitrobenzoyl)oxy)benzamide)succinate

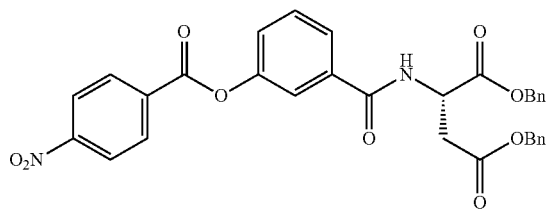 [SMILES: O=C(C[C@H](NC(=O)c1cccc(OC(=O)c2ccc([N+](=O)[O-])cc2)c1)C(=O)OCc1ccccc1)OCc1ccccc1]

To a solution of (S)-dibenzyl 2-(3-hydroxybenzamide)succinate (441.5 mg) prepared in the Reference Example 87-(a) in dehydrated dichloromethane (15 mL) in a 50 mL round-bottom flask were added N,N-diisopropylethylamine (350 µL) and 4-nitrobenzoyl chloride (227.2 mg) at 0° C. under argon gas flow with stirring, the resulting mixture was stirred at 0° C. for 30 minutes, and stirred at room temperature for 30 minutes. After the reaction was completed, the reaction solution was poured into water (20 mL), and the resulting mixed solution was extracted with dichloromethane (50 mL). The resulting organic layer was washed with a saturated aqueous sodium chloride solution (20 mL), dried over anhydrous magnesium sulfate, filtered, and concentrated under reduced pressure. The resulting residues were purified by medium pressure preparative chromatography (silica gel, elution solvent; hexane:ethyl acetate) to give the title compound (561.7 mg) as a slightly yellow oil.

Mass spectrum (ESI, m/z): 583 [M+H]⁺.

Reference Example 87-(a)

Preparation of (S)-2-(3-((4-aminobenzoyl)oxy)benzamide)succinic acid

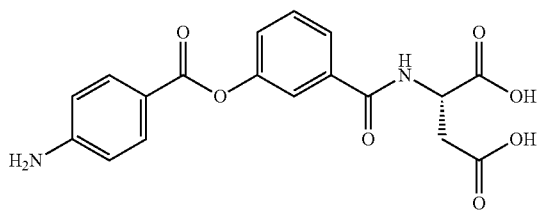 [SMILES: Nc1ccc(C(=O)Oc2cccc(C(=O)N[C@@H](CC(=O)O)C(=O)O)c2)cc1]

To a solution of (S)-dibenzyl 2-(3-((4-nitrobenzoyl)oxy) benzamide)succinate (557.8 mg) prepared in the Reference Example 87-(b) in ethanol (7.5 mL)/tetrahydrofuran (7.5 mL) in a 200 mL round-bottom flask was added 5% palladium carbon (wetted with 48.57% water, AER-type manufactured by NE CHEMCAT Corporation) (56.2 mg) at room temperature, the atmosphere in the reaction system was replaced with hydrogen atmosphere, and then the resulting mixture was stirred at room temperature for 8 hours. After the reaction was completed, the reaction solution was filtered through Celite, washed with tetrahydrofuran, and the resulting filtrate was concentrated under reduced pressure to give the title compound (369.3 mg) as slightly yellow solids.
Mass spectrum (ESI, m/z): 373 [M+H]$^+$.

Reference Example 87-(d)

Preparation of (S)-2-(3-((4-guanidinobenzoyl)oxy) benzamide)succinic acid

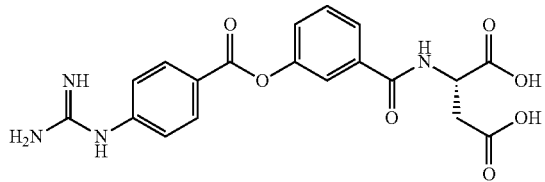 [SMILES: N=C(N)Nc1ccc(C(=O)Oc2cccc(C(=O)N[C@@H](CC(=O)O)C(=O)O)c2)cc1]

(1) To a suspension of (S)-2-(3-((4-aminobenzoyl)oxy) benzamide)succinic acid (63.5 mg) prepared according to the same manner as the Reference Example 87-(c) in tert-butanol (1.0 mL) in a 30 mL cylindrical flask were added cyanamide (21.9 mg) and a 4 M hydrogen chloride/dioxane solution (130 µL) at room temperature under argon gas flow with stirring, and the resulting mixture was stirred at 60° C. for 4 hours.

(2) To a suspension of (S)-2-(3-((4-aminobenzoyl)oxy) benzamide)succinic acid (365.4 mg) prepared in the Reference Example 87-(c) in tert-butanol (5.0 mL) in a 50 mL round-bottom flask were added cyanamide (124.3 mg) and a 4 M hydrogen chloride/dioxane solution (735 µL) at room temperature under argon gas flow with stirring, the resulting mixture was stirred at 60° C. for 4 hours, and stirred at room temperature for 16 tours.

The reaction solution in (1) and the reaction solution in (2) were combined, toluene (30 mL) was added thereto, and the resulting mixed solution was extracted with water 20 mL). The resulting organic layer was extracted with water (10 mL). The resulting aqueous layers were combined, and filtered. To the resulting filtrate was added a 10% aqueous ammonium acetate solution to adjust the pH to 4.0. The resulting mixture was stirred at room temperature for 2 hours, the precipitated solids were collected by filtration, and dried under reduced pressure to give the title compound (457.1 mg) as slightly yellowish-white solids, Mass spectrum (ESI, m/z): 415 [M+H]$^+$.

Reference Example 88-(a)

Preparation of (S)-3-(benzyloxy)-5-((10-(2,3-bis (tert-butoxycarbonyl)guanidino)-N-(1,4-di-tert-butoxy-1,4-dioxobutan-2-yl)-13-oxo-6,7,8,13-tetrahydrodibenzo[b,f][1,4]dioxecin-4-carboxamido) methyl)benzoic acid

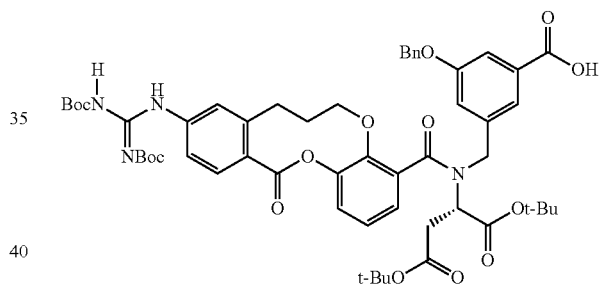

To a solution of (S)-di-tert-butyl 2-(N-(3-(benzyloxy)-5-((2-(trimethylsilyl)ethoxy)carbonyl)benzyl)-10-(2,3-bis (tert-butoxycarbonyl)guanidino)-13-oxo-6,7,8,13-tetrahydrodibenzo[b,f][1,4]dioxecin-4-carboxamido)succinate (200.0 mg) prepared according to the same manner as the Reference Example 29-(e) in dehydrated tetrahydrofuran (5 mL) in a 25 mL cylindrical flask was added tetrabutylammonium fluoride (a 1.0 M solution in tetrahydrofuran) (0.55 mL) at room temperature under argon atmosphere with stirring, and the resulting mixture was stirred at room temperature for 20 hours. After the reaction was completed, to the reaction solution was added toluene (5 mL), the resulting mixture was washed with a saturated aqueous ammonium chloride solution (5 mL) twice, with water (5 mL), and with saturated brine (5 mL), dried over anhydrous magnesium sulfate, filtered, and concentrated under reduced pressure. The resulting residues were purified by medium pressure preparative chromatography (DIOL silica gel, elution solvent; hexane:ethyl acetate) to give the title compound (110.2 mg) as a light brown foam.

Mass spectrum (ESI, m/z): 1023 [M+H]$^+$.

Reference Example 88-(b)

Preparation of (S)-2-(N-(3-(benzyloxy)-5-carboxybenzyl) 10-guanidino-13-oxo-6,7,8,13-tetrahydrodibenzo[b,f][1,4]dioxecin-4-carboxamido)succinic acid hydrochloride

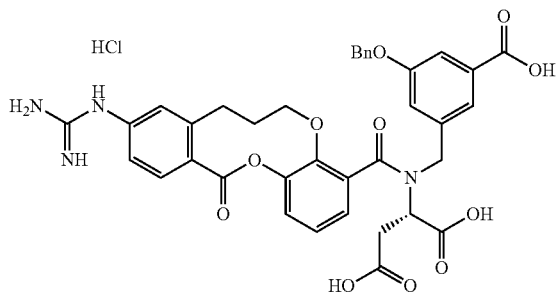 [SMILES: N=C(N)Nc1ccc2c(c1)CCCOc1c(cccc1C(=O)N(Cc1cc(OCc3ccccc3)cc(C(=O)O)c1)[C@@H](CC(=O)O)C(=O)O)OC2=O ; Cl]

To (S)-3-(benzyloxy)-5-((10-(2,3-bis(tert-butoxycarbonyl)guanidino)-N-(1,4-di-tert-butoxy-1,4-dioxobutan-2-yl)-13-oxo-6,7,8,13-tetrahydrodibenzo[b,f][1,4]dioxecin-4-carboxamido)methyl)benzoic acid (104.4 mg) prepared in the Reference Example 88-(a) in a 30 mL near shaped flask was added a 4 M hydrogen chloride/dioxane solution (2 mL) at room temperature under nitrogen atmosphere with stirring, and the resulting mixture was stirred at room temperature for 23 Hours. After the reaction was completed, to the reaction solution was added diethyl ether, and the resulting mixture was concentrated under reduced pressure. The same concentration under reduced pressure was carried out twice. To the concentrated residues was added diethyl ether, and the resulting mixture was subjected to sonication. The resulting solids were filtered, and dried under reduced pressure to give the title compound (72.3 mg) as beige solids.

Mass spectrum (DUIS, m/z): 711 [M+H]$^+$.

Reference Example 88-(c)

Preparation of (S)-2-(N-(3-carboxy-5-hydroxybenzyl)-10-guanidino-13-oxo-6,7,8,13-tetrahydrodibenzo[b,f][1,4]dioxecin-4-carboxamido)succinic acid hydrochloride

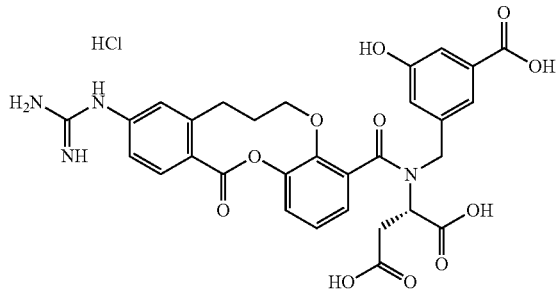 [SMILES: N=C(N)Nc1ccc2c(c1)CCCOc1c(cccc1C(=O)N(Cc1cc(O)cc(C(=O)O)c1)[C@@H](CC(=O)O)C(=O)O)OC2=O ; Cl]

To a solution of (S)-2-(N-(3-(benzyloxy)-5-carboxybenzyl)-1-guanidino-13-ox-6,7,8,13-tetrahydrodibenzo[b,f][1,4]dioxecin-4-carboxamido) succinic acid hydrochloride (69 mg) prepared in the Reference Example 88-(b) in ethanol (2 ml)/tetrahydrofuran (1 mL) in a 30 ml cylindrical flask was added ASCA-2 (wetted with 52% water, manufactured by NE CHEMCAT Corporation) (77.6 mg) at room temperature under nitrogen atmosphere, the atmosphere in the reaction system was replaced with hydrogen atmosphere, and then the resulting mixture was stirred at room temperature for 2 hours. After the reaction was completed, the reaction solution was filtered through Celite, washed with ethanol, and the resulting filtrate was concentrated under reduced pressure. To the concentrated residues was added diethyl ether, the resulting mixture was subjected to sonication, and the resulting mixture was stirred at room temperature for 1 hour. The resulting solids were filtered, and dried under reduced pressure to give the title compound (51.1 mg) as white solids.

Mass spectrum (DUIS, T/z): 621 [M+H]$^+$.

PHARMACOLOGICAL TEST EXAMPLES (Test Example 1): Human Enteropeptidase Inhibition Test Human recombinant enteropeptidase (manufactured by BIO Vision Inc., catalog no.: 7529-50) was diluted with an assay buffer (50 mM tricine (pH8.0), 0.01 W/V % Tween 20, 10 mM CaCl$_2$) to prepare an ng/mL enzyme solution. Then, 5FAM-Abu-Gly-Asp-Asp-Lys-Ile-Val-Gly-Gly-Lys (CPQ2)-Lys-Lys-NH$_2$ (manufactured by CHINESE PEPTIDE COMPANY, purity: 94.5) was diluted with the assay buffer to prepare a 1.5 μM substrate solution. Each test compound was dissolved into DMSO, then diluted with the assay buffer 100 times, and further appropriately diluted with an assay buffer comprising 1% DMSO to prepare each compound solution. 10 μL of the compound solution, 15 μL of the assay buffer, and 50 μL of the substrate solution were added to a 96 well black plate (manufactured by Thermo Fisher Scientific Inc., code no.: 9502867), mixed, then 25 μL of the enzyme solution was added thereto, and mixed to start the reaction. Fluorescence intensities at excitation wavelength 485 nm and fluorescence wavelength 535 nm were measured by using a fluorescence plate reader (Flex station 3) (Test compound addition group). Also, the same reaction as described above except for not adding each test compound was carried out (Test compound non-addition group). Additionally, the same reaction as described above except for not adding each test compound and the enzyme was carried out (Control group). Inhibition rate was calculated by the following equation using fluorescence intensity after 20 minutes of reaction start.

> Inhibition rate (%)=(1−(fluorescence intensity of Test compound addition group−fluorescence intensity of Control group)÷(fluorescence intensity of Test compound non-addition group−fluorescence intensity of Control group))×100

In the present test, each compound of the present invention showed an excellent enteropeptidase inhibitory activity. For example, each compound of Example 1-(b), 2-(b), 3-(b), 4-(b), 5-(b), 6-(b), 7-(b), 8-(b), 9-(b), 10-(b), 11-(b), 12-(c), 13-(b), 14-(b), 15-(b), 16-(b), 17-(b), 18-(b), 19-(b), 20-(b), 21-(b), 23-(c), 24-(a), 25-(b), 27-(b), 28-(c), 29-(c), and 30-(a) showed an inhibition rate of 50% or more at a compound concentration of 100 nM, each compound of Example 1-(b), 2-(b), 3-(b), 4-(b), 5-(b), 6-(b), 7-(b), 8-(b), 9-(b), 10-(b), 11-(b), 12-(c), 13-(b), 14-(b), 15-(b), 16-(b), 17-(b), 18-(b), 19-(b), 20-(b), 21-(b), 22-(a), 23-(c), 24-(a), 25-(b), 26-(b), 27-(b), 28-(c), 29-(c), and 30-(a) also showed an inhibition rate of 50% or more at a compound concentration of 10 nM, and each compound of Example 1-(b), 2-(b), 3-(b), 7-(b), 8-(b), 9-(b), 15-(b), 19-(b), 20-(b), 21-(b), 22-(a), 25-(b), 26-(b), 27-(b), 28-(c), 29-(c), and 30-(a) also showed an inhibition rate of 50% or more at a compound concentration of 1 nM.

Further, each monomer compound constituting each double-headed compound of the present invention, namely each compound corresponding to $A^1$ or $A^2$ of the Compound (I) also showed an enteropeptidase inhibitory activity. For example, each compound of Reference Example 31-(b), 41-(b), 49-(b), 52-(b), 55-(b), 73-(b), and 87-(d) showed an inhibition rate of 50% or more at a compound concentration of 100 nM.

(Test Example 2): Human Trypsin Inhibition Test

Human recombinant trypsin (manufactured by Wako Pure Chemical Industries, Ltd., code no.: 206-17171) was diluted with an assay buffer (0.1 M Tris-HCl (pH8.0), 0.15 M NaCl, 10 mM $CaCl_2$, 0.05% Brij35) to prepare a 10 ng/mL enzyme solution. Then, Boc-Phe-Ser-Arg-MCA (manufactured by PEPTIDE INSTITUTE, INC., code no.: 3107-v) was diluted with the assay buffer to prepare a 40 μM substrate solution. Each test compound was dissolved into DMSO, then diluted with the assay buffer 100 times, and further appropriately diluted with an assay buffer comprising 1% DMSO to prepare each compound solution. 10 μL of the compound solution, 15 μL of the assay buffer, and 50 μL of the substrate solution were added to a 96 well black plate (manufactured by Thermo Fisher Scientific Inc., code no.: 9502867), mixed, and then 25 μL of the enzyme solution was added thereto, and mixed to start the reaction. Fluorescence intensities at excitation wavelength 355 nm and fluorescence wavelength of 460 nm were measured by using a fluorescence plate reader (Flex station 3) (Test compound addition group). Also, the same reaction as described above except for not adding each test compound was carried out (Test compound non-addition group). Additionally, the same reaction as described above except for not adding each test compound and the enzyme was carried out (Control group). Inhibition rate was calculated by the following equation using fluorescence intensity after 20 minutes of reaction start.

Inhibition rate (%)=(1−(fluorescence intensity of Test compound addition group−fluorescence intensity of Control group)÷(fluorescence intensity of Test compound non-addition group−fluorescence intensity of Control group))×100

In the present test, each compound of the present invention showed an excellent trypsin inhibitory activity. For example, each compound of Example 1-(b), 2-(b), 3-(b), 4-(b), 5-(b), 6-(b), 7-(b), 8-(b), 9-(b), 10-(b), 11-(b), 12-(c), 13-(b), 14-(b), 15-(b), 16-(b), 17-(b), 18-(b), 19-(b), 20-(b), 21-(b), 22-(a), 23-(c), 24-(a), 25-(b), 27-(b), 28-(c), 29-(c), and 30-(a) showed an inhibition rate of 50% or more at a compound concentration of 100 nM, each compound of Example 1-(b), 2-(b), 3-(b), 4-(b), 5-(b), 6-(b), 7-(b), 8-(b), 9-(b), 10-(b), 11-(b), 12-(c), 13-(b), 14-(b), 15-(b), 16-(b), 17-(b), 18-(b), 19-(b), 20-(b), 21-(b), 22-(a), 23-(c), 24-(a), 25-(b), 26-(b), 27-(b), 28-(c), and 30-(a) also showed an inhibition rate of 50% or more at a compound concentration of 10 nM, and each compound of Example 1-(b), 2-(b), 3-(b), 5-(b), 7-(b), 8-(b), 9-(b), 12-(c), 14-(b), 17-(b), 18-(b), 19-(b), 20-(b), 22-(a), 23-(c), 24-(a), 26-(b), and 30-(a) also showed an inhibition rate of 50% or more at a compound concentration of 1 nM.

Further, each monomer compound constituting each double-headed compound of the present invention, namely each compound corresponding to $A^1$ or $A^2$ of the Compound (I) also showed an excellent trypsin inhibitory activity. For example, each compound of Reference Example 31-(b), 41-(b), 49-(b), 52-(b), 55-(b), 73-(b), and 87-(d) showed an inhibition rate of 50% or more at a compound concentration of 100 nM.

(Test Example 3): Fecal Protein Concentration-Increasing Test by Single Administration Using HFD-Fed Mouse High fat diet-fed (HFD-fed) mice (D-12492 diet, male, ICR, 6 week old) were orally administered with a 0.5 W/V % methylcellulose suspension comprising each test compound (Compound administration group, 4 or 5 mice/group) or a 0.5 W/V % methylcellulose suspension (Compound non-administration group (Vehicle group), 5, 6, or 7 mice/group), and whole feces of the day were collected. Dried feces were dissolved into a 0.5N aqueous sodium hydroxide solution, followed by centrifugation at 3500 rpm. Then each protein concentration in the resulting supernatant was determined (Lowry method), and the ratio for an increase of protein concentration in feces was calculated by the following equation using the protein concentration in feces contained in 1 g of feces (mg/g feces).

Ratio for an increase of protein concentration in feces=(average protein concentration in feces of Compound administration group)÷(average protein concentration in feces of Compound non-administration group)

In the present test, each compound of the present invention showed an excellent increasing effect on protein concentration in feces. For example, a 1.3 or more fold increase of protein concentration in feces was shown by the compound of Example 4-(b) at a dose of 100 mg/kg, by the compound of Example 17-(b) at a dose of 91 mg/kg, by the compound of Example 14-(b) at a dose of 89 mg/kg, by the compound of Example 1-(b) at a dose of 87 mg/kg, by the compound of Example 2-(b) at a dose of 86 mg/kg, by the compound of Example 10-(b) at a dose of 79 mg/kg, by each compound of Example 26-(b), 27-(b), 28-(C), and 29-(c) at a dose of 50 mg/kg, and by each compound of Example 1-(h), 2-(1c), 3-(b), 5-(b), 6-b), 7-(b), 8-(c), 9-1b, 12-(c), 13-(b), 20-(b), and 21-(b) at a dose of 30 mg/kg.

(Test Example 4): Anti-Obesity Effect Test Using DIO Mouse

Diet-induced obesity (DIO) mice (D-12492 diet, male, C57BL-DIO, 26 to 28-week old) were orally administered with a 0.5 W/V % methylcellulose suspension comprising each test compound (Compound administration group, 5 or 6 mice/group) or a 0.5 W/V % methylcellulose suspension (Compound non-administration group (Vehicle group), 6 mice/group) once daily for 2 weeks. Weight loss rate was calculated by the following equation.

Weight loss rate (%) of each Compound administration group=(1−average weight at the last day of the test of each Compound administration group/average weight at the last day of the test of Vehicle group)×100

In the present test, each compound of the present invention showed an excellent anti-obesity effect. For example, a 4% or more weight loss rate was shown by each compound of Example 3-(c), 5-(c), 6-(c), 7-(b), 8-(b), and 9-(b) at a dose of 100 mg/kg, by each compound of Example 12-(b), 14-(b), and 18-(b) at a dose of 90 mg/kg, by the compound of Example 17-Kb) at a dose of 88 mg/kg, by the compound of Example 10-b) at a dose of 87 mg/kg, by the compound of Example 4-(b) at a dose of 86 mg/kg, each compound of Example 20-(d), 24-(a), 25-(b), 26-(b), 27-(b), 28-(c), and 29-(c) at a dose of 50 mg/kg, each compound of Example 1-(b), 2-(c), and 19-(b) at a dose of 30 mg/kg, and each compound of Example 20-b) and 21-(b) at a dose of 25 mg/kg.

(Test Example 5): Rat Pharmacokinetic (PK) Test (Plasma Concentration after Oral Administration of Compound)

Each test compound was suspended in a 0.5 W/V % methylcellulose 400 solution to prepare a suspension, and the resulting suspension was orally administered to a male SD rat of 7 to 8-week old (weight: 180 to 250 g). After 0.25, 0.5, 1, 2, 4, 8, and 24 hour(s) of the administration of each test compound, blood (EDTA-added blood) was collected from jugular vein under isoflurane inhalation anesthesia. The resulting blood was subjected to centrifugal treatment at 4° C. at 6000 g for 10 minutes to give each blood plasma. To the resulting blood plasma was added acetonitrile, a mixed solvent of acetonitrile and water (1:1 (V/V)), or a mixed solvent of acetonitrile and 0.1 M hydrochloric acid (1:1 (V/V)), then the resulting mixture was mixed at 750 rpm for 3 minutes in a shaker, and subjected to centrifugal separation at 3700 rpm for 2 minutes in a centrifuge to remove proteins. The resulting sample was subjected to LC (liquid chromatography)/MS (mass spectrometry) measurement under the following measurement conditions.

Each compound concentration in blood plasma at each time of blood collection was calculated according to the internal standard method, and, area under the plasma concentration vs. time curve (AUCall (Area Under Curve)) was calculated according to the trapezoidal method.

The LC and MS systems used in the present test are as follows.
LC: LC20 or LC30 HPLC system manufactured by Shimadzu Corporation
  Column: Phenomenex Kinetex C18 (50×2.1 mm, 2.6 µm)
  Column temperature: 40° C.
  Flow rate: 0.3 mL/min
  Mobile phase A: aqueous solution with 0.1% formic acid, Mobile phase B: 50% acetonitrile/methanol solution with 0.1% formic acid
  Gradient: 0 to 2 minute(s); A/B=90/10-10/90, 2 to 3 minutes; A/B=10/90, 3 to 3.01 minutes; A/B=10/90→90/10
MS: Q-Trap3200 manufactured by SCIEX
  Ionization: EST
  Mode: Positive In the present test, each compound of the present invention showed very low exposure amount to blood. For example, an AUCall of 100 ng·h/mL or less was shown by the compound of Example 10-(b) at a dose of 8 mg/kg, by each compound of Example 11-(b), 12-(c), 15-(b), 16-(b), 17-(b), and 18-(b) at a dose of 9 mg/kg, by each compound of Example 2-(c), 3-(c), 4-(b), 5-(c), 6-(c), 7-(b), 8-(b), 9-(b), 13-(b), 19-(b), 20-(c), 21-(c), 26-(b), 28-(c), 29-(c), and 30-(a) at a dose of 10 mg/kg, and by the compound of Example 1-(b) at a dose of 100 mg/kg.

(Test Example 6): Stability Test in Disintegration Test Solution 1 (pH1.2) and Disintegration Rest Solution 2 (pH6.8)

A 1 mM solution of each test compound in DMSO was added to a disintegration test solution 1 (pH1.21 or a disintegration test solution 2 (pH6.8) so that the final concentration became 10 µM, and the stability test was started. A part of the solution was sampled immediately after the start of the test and 20 minutes or 1 hour after the start of the test, 3 times volume of acetonitrile was added thereto, and the resulting solution was mixed. The resulting sample was subjected to LC (liquid chromatography)/UV (ultraviolet absorption) measurement under the following measurement conditions.

The peak area of test compound immediately after the start of the test was set to be a residual rate of 100%, and each residual rate (%) was calculated from the ratio of the peak area of test compound 20 minutes or 1 hour after the start of the test to the peak area of test compound immediately after the start of the test.

LC and UV systems used in the present test are as follows.
LC: LC20 r LC30 HPLC system manufactured by Shimadzu Corporation
  Column: Phenomenex Kinetex C18 (100×2.1 mm, 2.6 µm)
  Column temperature: 40° C.
  Flow rate: 0.25 mL/min
  Mobile phase A: aqueous solution with 0.1% formic acid, Mobile phase B: 50% acetonitrile/methanol solution with 0.1% formic acid
  Gradient: 0 to 3 minutes); A/B=90/10, 3 to 11 minutes; A/B=90/10→5/95, 11 to 15 minutes; A/B=5/95, 15 to 15.1 minutes; A/B=5/95→90/10
  Measured wavelength: 200 to 350 nm
  Analyzed UV wavelength: 265 nm In the present test, each compound of the present invention showed excellent stability in the disintegration test solution 1 (pH1.2) and the disintegration test solution 2 (pH6.8). For example, a residual rate of 95% or more after 20 minutes was shown by each compound of Example 5-(b) and 9-(b), and a residual rate of 95% or more after 1 hour was shown by each compound of Example 22-(a) and 27-(b).

(Test Example 7): Stability Test in the Contents Collected from Small Intestine of DIO Mouse Mice (D-12492 diet, male, $C_{57}$BL-DIO, 28 to 30-week old) fed similarly to the anti-obesity effect test using a DIO mouse in the Test Example 4 are subjected to laparotomy under isoflurane inhalation anesthesia, and the small intestine is collected. A liquid squeezed from the contents of the collected small intestine is used as an enzyme source (undiluted solution of small intestine contents) to evaluate the stability of each test compound.

To the resulting undiluted solution of small intestine contents is added 10 times volume of distilled water, the resulting mixture is placed into a tube (MatrixD) for a disruption instrument FastPrep-24 (MP Biomedicals), and subjected to the disruption instrument FastPrep-24 (rotating speed: 6.5, 30 seconds) to prepare a suspension of small intestine contents. A 1 mM solution of each test compound in DMSO is added to the suspension of small intestine contents preincubated at 37° C. so that the final concentration becomes 10 µM, and the stability test is started. The culture is carried out at 37° C. A part of the solution is sampled immediately and 20 minutes after the start of test, 3 times volume of acetonitrile, acetonitrile/methanol (1/1), or acetonitrile/distilled water (1/1) is added thereto, the resulting mixture is mixed, subjected to centrifugal separation at 13,300 rpm for 3 minutes (a benchtop centrifuge manufactured by Labnet International, Inc.), and then filtered by using a syringe filter (GL Chromatodisc 0.2 μm 13P, GL Sciences Inc.). The resulting filtered sample is subjected to LC (liquid chromatography)/UV (ultraviolet absorption) measurement under the following measurement conditions.

The peak area of test compound immediately after the start of the test is set to be a residual rate of 100%, and each residual rate (%) is calculated from the ratio of the peak area of test compound 20 minutes after the start of the test to the peak area of test compound immediately after the start of the test.

LC/UV systems to be used in the present test are as follows.

LC: LC20 or LC30 HPLC system manufactured by Shimadzu Corporation

Column: Phenomenex Kinetex C18 (100×2.1 mm, 2.6 μm)

Column temperature: 40° C.

Flow race: 0.25 mL/min

Mobile phase A: aqueous solution with 0.1% formic acid, Mobile phase B: 50% acetonitrile/methanol solution with 0.1% formic acid Gradient: 0 to 3 minute(s); A/B=90/10, 3 to 11 minutes; A/B=90/10-5/95, 11 to 15 minutes; A/B=5/95, 15 to 15.1 minutes; A/B=5/95-90/10

Measured wavelength: 200 to 350 nm

Analyzed UV wavelength: 265 nm

In the present test, each compound of the present invention can be confirmed to have excellent metabolic stability.

INDUSTRIAL APPLICABILITY

Compound represented by general formula (I) or pharmaceutically acceptable salts thereof of the present invention have excellent enteropeptidase inhibitory activities and/or excellent trypsin inhibitory activities, and have pharmacokinetic properties that they potently inhibit enteropeptidase and/or trypsin in the intestine after orally administered and show very low exposure amount to blood. According to the present invention, drugs having high safety with reduced side effects caused by exposure of the compounds to blood and useful as agents for the prevention, alleviation, and/or treatment of various diseases involving enteropeptidase inhibition and/or trypsin inhibition such as obesity can be provided.

The invention claimed is:

1. A compound represented by the following formula (I) or a pharmaceutically acceptable salt thereof:

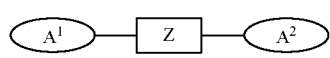
(I)

wherein:

$A^1$ has a structure represented by:

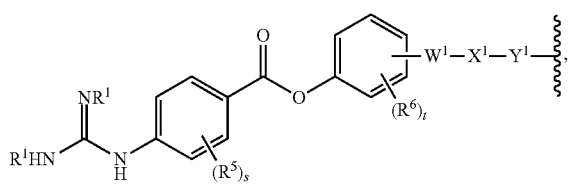

$A^2$ has a structure represented by:

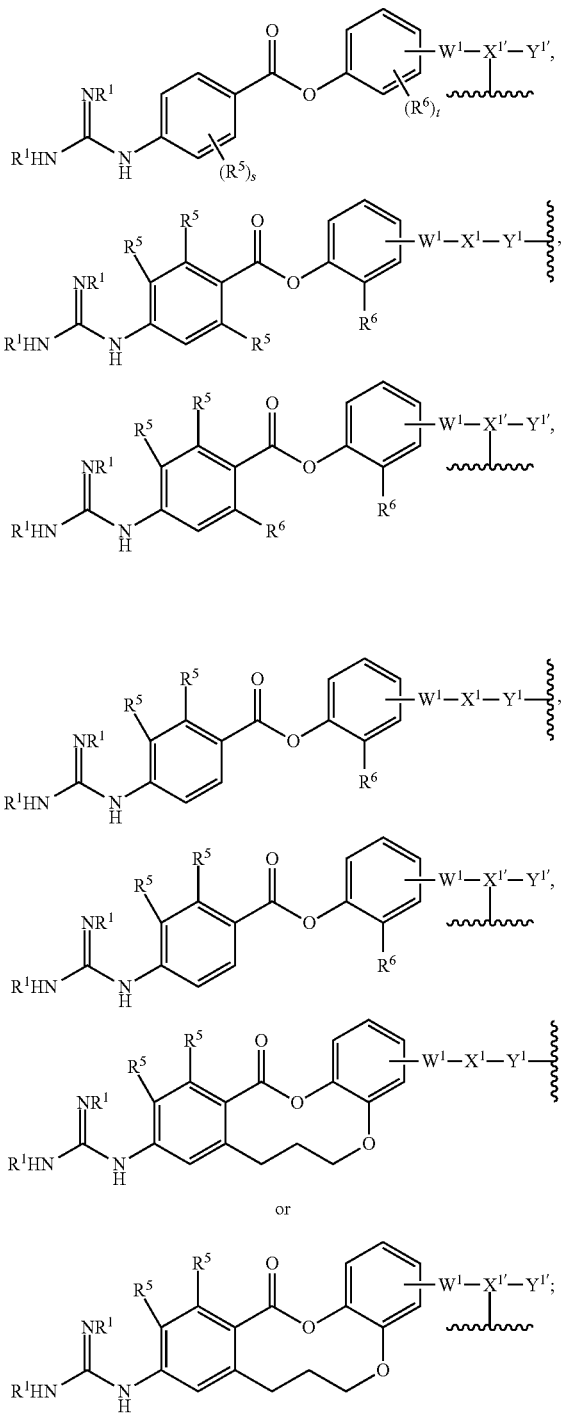

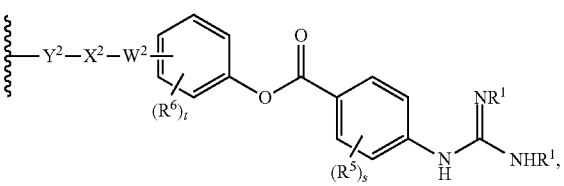

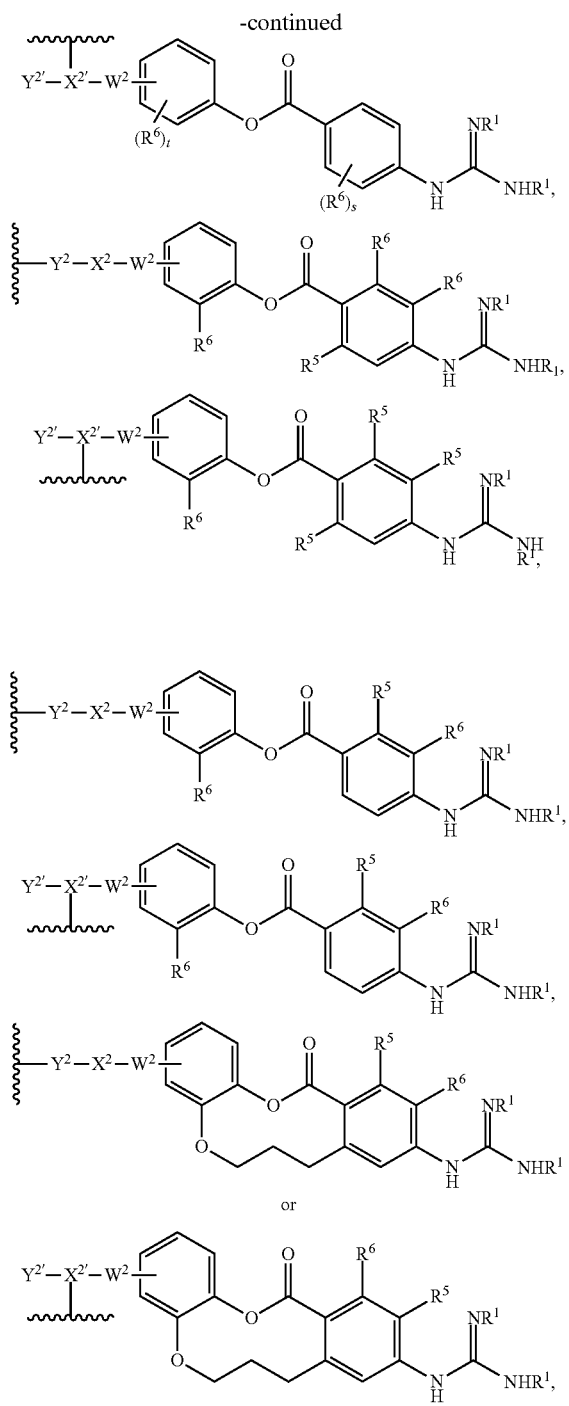

wherein:
R$^1$ each independently represents a hydrogen atom or a —COO—(C$_1$-C$_4$ alkyl group);
W$^1$ and W$^2$ each independently represent a single bond or a C$_1$-C$_4$ alkylene group;
X$^1$ represents —C(=O)—, —O—C(=O)—, or —NG$^{11}$-SO$_2$—;
X$^{1'}$ represents —NG$^Z$-SO$_2$—;
X$^2$ represents —C(=O)—, —C(=O)—O—, or —SO$_2$—NG$^{12}$-;
X$^{2'}$ represents —SO$_2$—NG$^Z$-;
G$^{11}$ and G$^{12}$ each independently represent a hydrogen atom, a C$_1$-C$_4$ alkyl group, or —COOR$^2$;
G$^Z$ represents a single bond that links X$^{1'}$ or X$^{2'}$ to Z;
R$^2$ represents a C$_1$-C$_4$ alkyl group optionally substituted with 1 to 5 aryl group(s);
Y$^1$ represents —NG$^{21}$-, —NG$^{21}$-L$^{11}$-C(=O)—, —NG$^{21}$-L$^{11}$-C(=O)—NH—, —NG$^{21}$-L$^{11}$-C(=O)—NG$^{31}$-L$^{21}$-C(=O)—, —NG$^{21}$-L$^{11}$-C(=O)—NG$^{31}$-L$^{21}$-C(=O)—NH—, —NG$^{21}$-L$^3$-O—, or —NG$^{21}$-G$^{4'}$-;
Y$^{1'}$ represents —NG$^{21}$H, —NG$^{21}$-L$^{11}$-COOH, or —NG$^{21}$-L$^{11}$-C(=O)—NG$^{31}$-L$^{21}$-COOH;
Y$^2$ represents —NG$^{22}$-, —C(=O)-L$^{12}$-NG$^{22}$-, —NH—C(=O)-L$^{12}$-NG$^{22}$-, —C(=O)-L$^{22}$-NG$^{32}$-C(=O)-L$^{12}$-NG$^{22}$-, —NH—C(=O)-L$^{22}$-NG$^{32}$-C(=O)-L$^{12}$-NG$^{22}$-, —O-L$^3$-NG$^{22}$-, or -G$^{4'}$-NG$^{22}$-;
Y$^{2'}$ represents HNG$^{22}$-, HOOC-L$^{12}$-NG$^{22}$-, or HOOC-L$^{22}$-NG$^{32}$-C(=O)-L$^{12}$-NG$^{22}$-;
G$^{21}$, G$^{31}$, G$^{22}$, and G$^{32}$ each independently represent a hydrogen atom, or a C$_1$-C$_6$ alkyl group optionally substituted with 1 to 5 substituent(s) independently selected from the group consisting of a phenyl group optionally substituted with 1 to 5 —COOR$^3$ group(s) and a —COOR$^3$ group;
G$^{4'}$ represents a C$_1$-C$_4$ alkylene group or a C$_1$-C$_4$ alkyleneoxy-C$_1$-C$_4$ alkylene group;
R$^3$ each independently represents a hydrogen atom or a C$_1$-C$_4$ alkyl group optionally substituted with 1 to 5 aryl group(s);
L$^{11}$, L$^{21}$, L$^{12}$, and L$^{22}$ each independently represent a C$_1$-C$_6$ alkylene group optionally substituted with 1 to 5 C$_1$-C$_6$ alkyl group(s) optionally substituted with 1 to 5 —COOR$^4$ group(s), a C$_1$-C$_4$ alkylene-phenylene group, or a phenylene-C$_1$-C$_4$ alkylene group;
L$^3$ represents a C$_1$-C$_4$ alkylene-phenylene group wherein the phenylene moiety is optionally substituted with 1 to 3 —COOR$^4$ group(s);
R$^4$ each independently represents a hydrogen atom or a C$_1$-C$_4$ alkyl group optionally substituted with 1 to 5 substituent(s) independently selected from the group consisting of an aryl group and a trimethylsilyl group;
R$^5$ and R$^6$ each independently represent a hydrogen atom, a halogen atom, a C$_1$-C$_4$ alkyl group, or a C$_1$-C$_4$ alkoxy group;
s and t each independently represent an integer of 1 to 4;
two or more R$^5$ and/or two or more R$^6$ may be the same or different with each other;
or any one of R$^5$ and any one of R$^6$ may be combined with each other to form a C$_1$-C$_4$ alkyleneoxy group;
the symbol

~~~~~~~ represents the point of attachment to Z; and
Z represents a single bond that links X$^{1'}$ or X$^{2'}$ to Z and is a single bond, an arylene group, a heteroarylene group, or a C$_2$-C$_{30}$ alkylene group, provided that one or more methylene group(s) in the chain of said alkylene group may be replaced with group(s) independently selected from the group consisting of —C(=O)—, —NR$^7$—, —O—, an arylene group, and a heteroarylene group, and R$^7$ represents a hydrogen atom or a C$_1$-C$_4$ alkyl group.

2. The compound according to claim 1 or a pharmaceutically acceptable salt thereof, wherein
A¹ has a structure represented by:

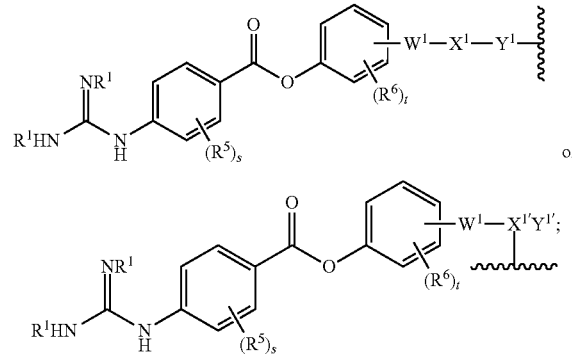

A² has a structure represented by:

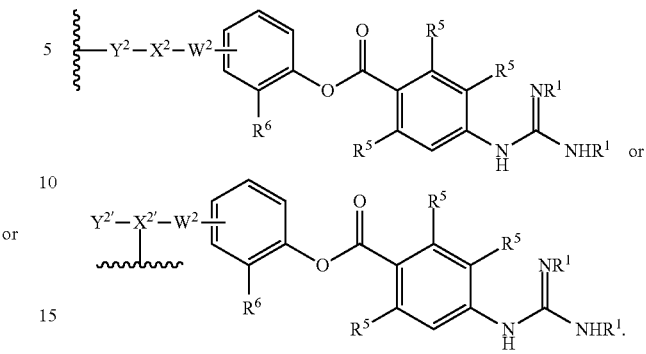

Z represents a single bond, a $C_6$-$C_{12}$ arylene group, —($CH_2$—$CH_2$—O)$_m$—$CH_2$—$CH_2$—, —($CH_2$—O—$CH_2$)$_m$—, —($CH_2$)$_m$—($C_6$-$C_{12}$ arylene)-($CH_2$)$_m$—, or —($CH_2$)$_n$—;

m represents an integer of 1 to 6; and n represents an integer of 2 to 12.

3. The compound according to claim 1 or a pharmaceutically acceptable salt thereof, wherein
A¹ has a structure represented by:

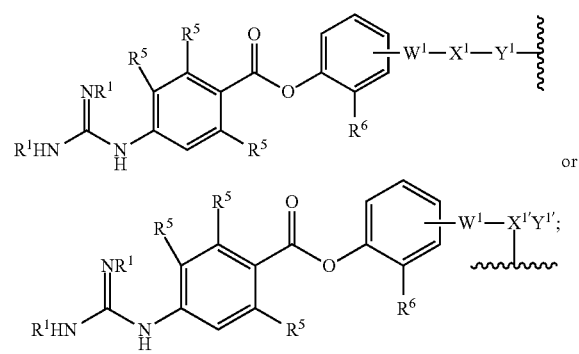

A² has a structure represented by:

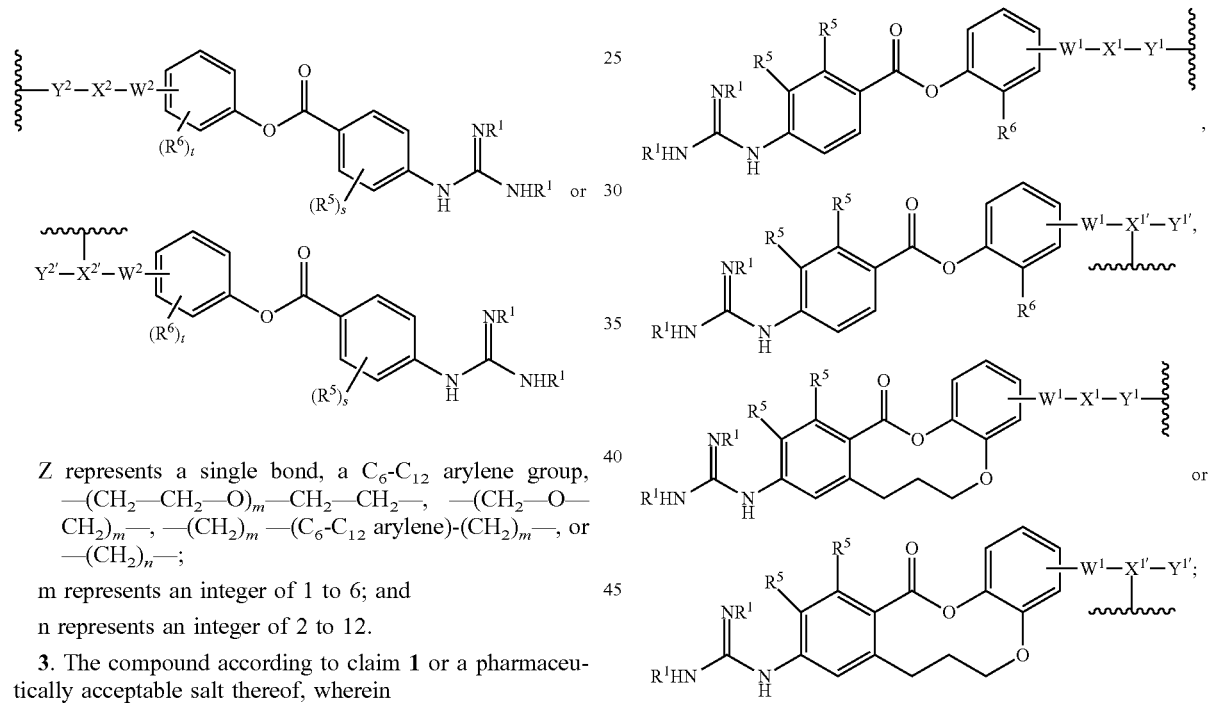

4. The compound according to claim 1 or a pharmaceutically acceptable salt thereof, wherein
A¹ has a structure represented by:

and
A² has a structure represented by:

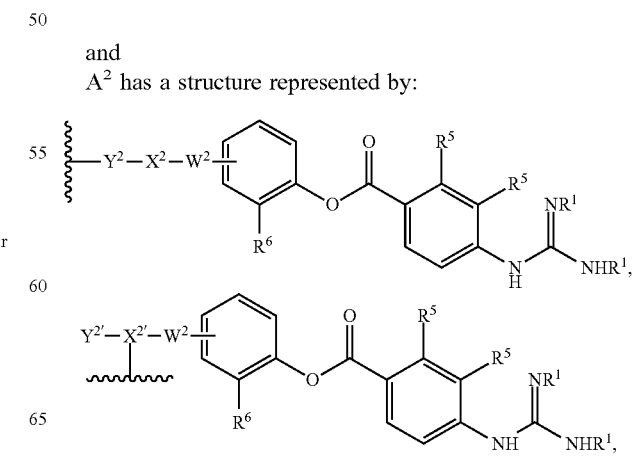

-continued

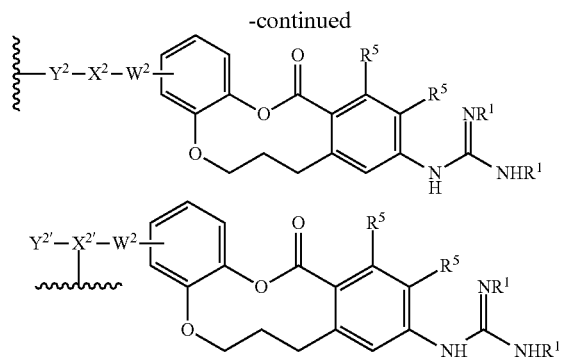

5. The compound according to claim 1, represented by the following formula (V):

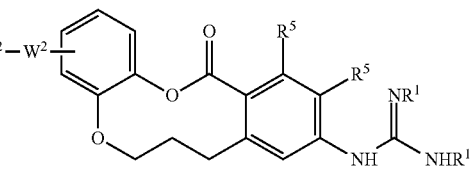

wherein:
R¹ each independently represents a hydrogen atom or a —COO—(C₁-C₄ alkyl group);
W¹ and W² each independently represent a single bond or a C₁-C₄ alkylene group;
X¹ represents —C(=O)— or —NG¹¹-SO₂—;
X² represents —C(=O)— or —SO₂—NG¹²-;
G¹¹ and G¹² each independently represent a hydrogen atom, a C₁-C₄ alkyl group, or —COOR²;
R² represents a C₁-C₄ alkyl group optionally substituted with 1 to 5 aryl group(s);
Y¹ represents —NG²¹-, —NG-L¹¹-C(=O)—, —NG²¹-L¹¹-C(=O)—NH—, —NG²¹-L¹¹-C(=O)—NG³¹-L²¹-C(=O)—, —NG²¹-L¹¹-C(=O)—NG³¹-L²¹-C(=O)—NH—, —NG²¹-L³-O—, or —NG²¹-G⁴'-;
Y² represents —NG²²-, —C(=O)-L¹²-NG²²-, —NH—C(=O)-L¹²-NG²²-, —C(=O)-L²²-NG³²-C(=O)-L¹²-NG²²-, —NH—C(=O)-L²²-NG³²-C(=O)-L¹²-NG²²-, —O-L³-NG²²-, or -G⁴'-NG²²-;
G²¹, G³¹, G²², and G³² each independently represent a hydrogen atom, or a C₁-C₆ alkyl group optionally substituted with 1 to 5 substituent(s) independently selected from the group consisting of a phenyl group optionally substituted with 1 to 5 —COOR³ group(s) and a —COOR³ group;

G⁴' represents a C₁-C₄ alkylene group or a C₁-C₄ alkyleneoxy-C₁-C₄ alkylene group;
R³ each independently represents a hydrogen atom or a C₁-C₄ alkyl group optionally substituted with 1 to 5 aryl groups);
L¹¹, L²¹, L¹², and L²² each independently represent a C₁-C₄ alkylene group optionally substituted with 1 to 5 C₁-C₆ alkyl group(s) optionally substituted with 1 to 5 —COOR⁴ group(s), a C₁-C₄ alkylene-phenylene group, or a phenylene-C₁-C₄ alkylene group;
L³ represents a C₁-C₄ alkylene-phenylene group wherein the phenylene moiety is optionally substituted with 1 to 3 —COOR⁴ group(s);
R⁴ each independently represents a hydrogen atom or a C₁-C₄ alkyl group optionally substituted with 1 to 5 substituent(s) independently selected from the group consisting of an aryl group and a trimethylsilyl group;

(V)

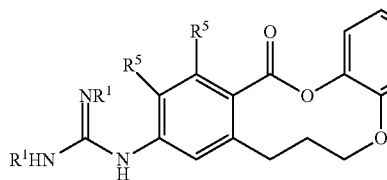

R⁵ each independently represents a hydrogen atom, a halogen atom, a C₁-C₄ alkyl group, or a C₁-C₄ alkoxy group;
Z represents a single bond, a C₆-C₁₂ arylene group, —(CH₂—CH₂—O)ₘ—CH₂—CH₂—, —(CH₂—O—CH₂)ₘ—, —(CH₂)ₘ—(C₆-C₁₂ arylene)-(CH₂)ₘ—, or —(CH₂)ₙ—;
m represents an integer of 1 to 6; and
n represents an integer of 2 to 12,
or a pharmaceutically acceptable salt thereof.

6. The compound according to claim 5 represented by the following formula (VI):

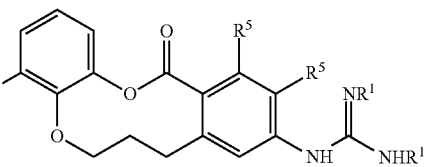

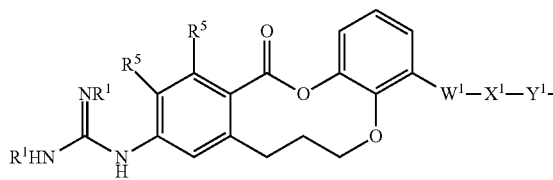

or a pharmaceutically acceptable salt thereof.
7. The compound according to claim 6 or a pharmaceutically acceptable salt thereof, wherein
R¹ each independently represents a hydrogen atom or a tert-butoxycarbonyl group;
W¹ and W² each independently represent a single bond or a C₁-C₂ alkylene group;
X¹ represents —C(=O)— or —NG¹¹-SO₂—;
X² represents —C(=O)— or —SO₂-NG¹²-;
G¹¹ and G¹² each represent a hydrogen atom;
Y¹ represents —NG²¹-, —NG²¹-L¹¹-C(=O)—, —NG²¹-L¹¹-C(=O)—NH—, —NG²¹-L¹¹-C(=O)—NG²¹-

$L^{21}$-C(=O)—, —NG$^{21}$-L$^{11}$-C(=O)-NG$^{21}$-L$^{21}$-C(=O)—NH—, —NG$^{21}$-L$^3$-O—, or —NG$^{21}$-G$^{4'}$-;

$Y^2$ represents —NG$^{22}$-, —C(=O)-L$^{12}$-NG$^{22}$-, —NH—C(=O)-L$^{12}$-NG$^{22}$-, —C(=O)-L$^{22}$-NG$^{32}$-C(=O)-L$^{12}$-NG$^{22}$-, —NH—C(=O)-L$^{22}$-NG$^{32}$-C(=O)-L$^{12}$-NG$^{22}$-, —O-L$^3$-NG$^{22}$-, or -G$^{4'}$-NG$^{22}$-;

$G^{21}$, $G^{31}$, $G^{22}$, and $G^{32}$ each independently represent a hydrogen atom, or a $C_1$-$C_3$ alkyl group optionally substituted with 1 to 3 —COOR$^3$ group(s);

$G^{4'}$ represents a $C_1$-$C_2$ alkylene group or a $C_1$-$C_2$ alkyleneoxy-$C_1$-$C_2$ alkylene group;

$R^3$ each independently represents a hydrogen atom or a tert-butyl group;

$L^{11}$, $L^{21}$, $L^{12}$, and $L^{22}$ each independently represent a $C_1$-$C_2$ alkylene group;

$L^3$ represents a $C_1$-$C_4$ alkylene-phenylene group wherein the phenylene moiety is optionally substituted with 1 to 3 —COOR$^4$ group(s);

$R^4$ each independently represents a hydrogen atom or a $C_1$-$C_4$ alkyl group optionally substituted with 1 to 5 substituent(s) independently selected from the group consisting of an aryl group and a trimethylsilyl group;

$R^5$ each independently represents a hydrogen atom, a halogen atom, a $C_1$-$C_4$ alkyl group, or a $C_1$-$C_4$ alkoxy group;

Z represents a single bond, a biphenylene group, —(CH$_2$—CH$_2$—O)$_m$—CH$_2$—CH$_2$—, —(CH$_2$—O—CH$_2$)$_m$—, —(CH$_2$)$_m$-biphenylene-(CH$_2$)$_m$—, or —(CH$_2$)$_n$—;

m represents an integer of 1 to 6; and n represents an integer of 2 to 12.

8. The compound according to claim 7 or a pharmaceutically acceptable salt thereof, wherein $R^1$ each represents a hydrogen atom;

$W^1$ and $W^2$ each represent a single bond;

$X^1$ represents —C(=O)—;

$X^2$ represents —C(=O)—;

$Y^1$ represents —NG$^{21}$-, —NG$^{21}$-L$^3$-O—, or —NG$^{21}$-G$^{4'}$-;

$Y^2$ represents —NG$^{22}$-, —O-L$^3$-NG$^{22}$-, or -G$^{4'}$-NG$^{22}$-;

$G^{21}$ and $G^{22}$ each independently represent a $C_1$-$C_3$ alkyl group substituted with 1 to 3 carboxy group(s);

$G^{4'}$ represents a $C_1$-$C_2$ alkylene group or a $C_1$-$C_2$ alkyleneoxy-$C_1$-$C_2$ alkylene group;

$L^3$ represents a $C_1$-$C_2$ alkylene-phenylene group wherein the phenylene moiety is optionally substituted with 1 to 2 —COOR$^4$ group(s);

$R^4$ each independently represents a hydrogen atom or a $C_1$-$C_4$ alkyl group optionally substituted with 1 to 5 substituent(s) Independently selected from the group consisting of an aryl group and a trimethylsilyl group;

$R^5$ each independently represents a hydrogen atom, a fluorine atom, a methyl group, or a methoxy group;

Z represents a single bond, [1,1'-biphenyl]-3,3'-diyl, —(CH$_2$—CH$_2$—O)$_m$—CH$_2$—CH$_2$—, —(CH$_2$—O—CH$_2$)$_m$—, —(CH$_2$)$_m$([1,1'-biphenyl]-3,3'-diyl)-(CH$_2$)$_m$—, or —(CH$_2$)$_n$—;

m represents an integer of 1 to 6; and n represents an integer of 2 to 12.

9. The compound according to claim 1 or a pharmaceutically acceptable salt thereof, wherein $A^1$ has a structure represented by:

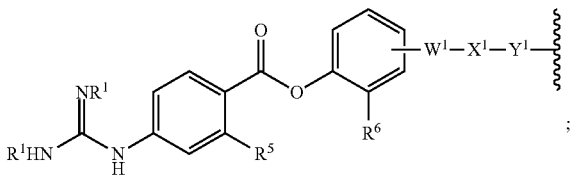

and $A^2$ has a structure represented by:

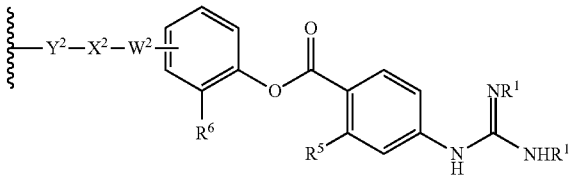

wherein $R^1$ each independently represents a hydrogen atom or a —COO—($C_1$-$C_4$ alkyl group);

$W^1$ and $W^2$ each independently represent a single bond or a $C_1$-$C_4$ alkylene group;

$X^1$ represents —C(=O)—, —O—C(=O)—, or —NG$^{11}$-SO$_2$—;

$X^2$ represents —C(=O)—, —C(=O)—O—, or —SO$_2$-NG$^{12}$-;

$G^{11}$ and $G^{12}$ each independently represent a hydrogen atom or —COOR$^2$;

$R^2$ represents a $C_1$-$C_4$ alkyl group optionally substituted with 1 to 5 aryl group(s);

$Y^1$ represents —NG$^{21}$-, —NG$^{21}$-L$^{11}$-C(=O)—NH—, or —NG$^{21}$-L$^{11}$-C(=O)—NG$^{31}$-L$^{21}$-C(=O)—NH—;

$Y^2$ represents —NG$^{22}$-, —NH—C(=O)-L$^{12}$-NG$^{22}$-, or —NH—C(=O)-L$^{22}$-NG$^{32}$-C(=O)-L$^{12}$-NG$^{22}$-;

$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —COOR$^3$ group(s) and a —COOR$^3$ group;

$R^3$ each independently represents a hydrogen atom or a $C_1$-$C_4$ alkyl group optionally substituted with 1 to 5 aryl group(s);

$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —COOR$^4$ group(s), a $C_1$-$C_4$ alkylene-phenylene group, or a phenylene-$C_1$-$C_4$ alkylene group;

$R^4$ each independently represents a hydrogen atom or a $C_1$-$C_4$ alkyl group optionally substituted with 1 to 5 aryl group(s);

$R^5$ and $R^6$ each independently represent a hydrogen atom, a $C_1$-$C_4$ alkyl group, or a $C_1$-$C_4$ alkoxy group, or $R^5$ and $R^6$ may be combined with each other to form a $C_1$-$C_4$ alkyleneoxy group; and the symbol

∿∿∿ represents the point of attachment to Z;

Z represents —(CH$_2$—CH$_2$—O)$_m$—CH$_2$—CH$_2$— or —(CH$_2$)$_n$—;

m represents an integer of 1 to 6; and n represents an integer of 2 to 12.

10. The compound according to claim 9 or a pharmaceutically acceptable salt thereof, wherein
$A^1$ has a structure represented by:

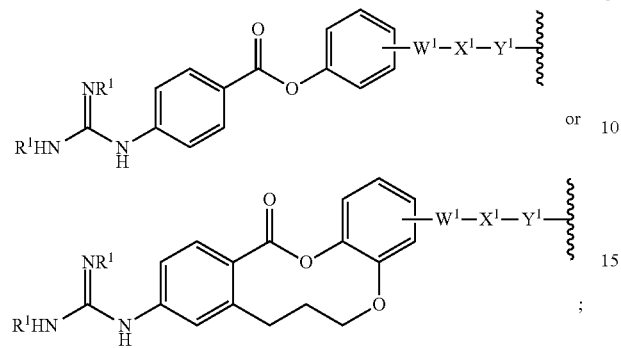

and
$A^2$ has a structure represented by:

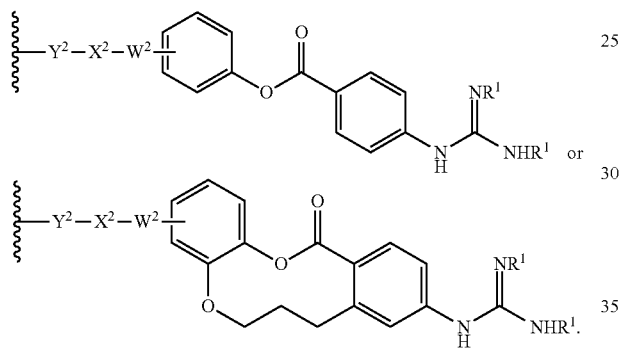

11. The compound according to claim 1 represented by the following formula (VIII):

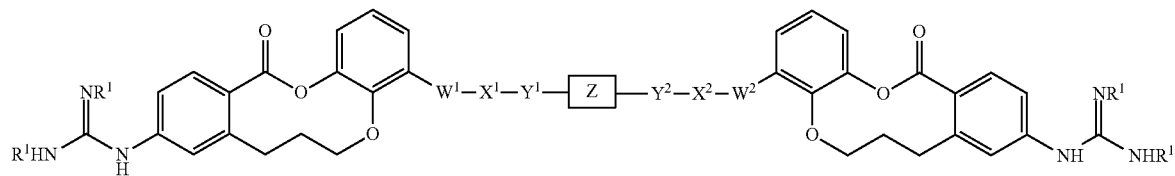

(VIII)

wherein:
$R^1$ each independently represents a hydrogen atom or a —COO—($C_1$-$C_4$ alkyl group);
$W^1$ and $W^2$ each independently represent a single bond or a $C_1$-$C_4$ alkylene group;
$X^1$ represents —C(=O)— or —$NG^{11}$-$SO_2$—;
$X^2$ represents —C(=O)— or —$SO_2$—$NG^{12}$-;
$G^{11}$ and $G^{12}$ each independently represent a hydrogen atom or —$COOR^2$;
$R^2$ represents a $C_1$-$C_4$ alkyl group optionally substituted with 1 to 5 aryl group(s);
$Y^1$ represents —$NG^{21}$-, —$NG^{21}$-$L^{11}$-C(=O)—NH—, or —$NG^{21}$-$L^{11}$-C(=O)—$NG^{31}$-$L^{21}$-C(=O)—NH—;
$Y^2$ represents —$NG^{22}$-, —NH—C(=O)-$L^{12}$-$NG^{22}$-, or —NH—C(=O)-$L^{22}$-$NG^{32}$-C(=O)-$L^{12}$-$NG^{22}$-;

$G^{21}$, $G^{31}$, $G^{22}$, and $G^{32}$ each independently represent a hydrogen atom, or a $C_1$-$C_6$ alkyl group optionally substituted with 1 to 5 substituent(s) independently selected from the group consisting of a phenyl group optionally substituted with 1 to 5 —$COOR^3$ group(s) and a —$COOR^3$ group;
$R^3$ each independently represents a hydrogen atom or a $C_1$-$C_4$ alkyl group optionally substituted with 1 to 5 aryl group(s);
$L^{11}$, $L^{21}$, $L^{12}$, and $L^{22}$ each independently represent a $C_1$-$C_6$ alkylene group optionally substituted with 1 to 5 $C_1$-$C_6$ alkyl group(s) optionally substituted with 1 to 5 —$COOR^4$ group(s), a $C_1$-$C_4$ alkylene-phenylene group, or a phenylene-$C_1$-$C_4$ alkylene group;
$R^4$ each independently represents a hydrogen atom or a $C_1$-$C_4$ alkyl group optionally substituted with 1 to 5 aryl group(s);
Z represents —($CH_2$—$CH_2$—O)$_m$—$CH_2$—$CH_2$— or —($CH_2$)$_n$—;
m represents an integer of 1 to 6; and
n represents an integer of 2 to 12,
or a pharmaceutically acceptable salt thereof.

12. The compound according to claim 11 or a pharmaceutically acceptable salt thereof, wherein
$R^1$ each independently represents a hydrogen atom or a tert-butoxycarbonyl group,
$W^1$ and $W^2$ each independently represent a single bond or a $C_1$-$C_2$ alkylene group;
$X^1$ represents —C(=O)— or —$NG^{11}$-$SO_2$—;
$X^2$ represents —C(=O)— or —$SO_2$-$NG^{12}$-;
$G^{11}$ and $G^{12}$ each represent a hydrogen atom;
$Y^1$ represents —$NG^{21}$-, —$NG^{21}$-$L^{11}$-C(=O)—NH—, or —$NG^{21}$-$L^{11}$-C(=O)-$NG^{31}$-$L^{21}$-C(=O)—NH—;
$Y^2$ represents —$NG^{22}$-, —NH—C(=O)-$L^{12}$-$NG^{22}$-, or —NH—C(=O)-$L^{22}$-$NG^{32}$-C(=O)-$L^{12}$-$NG^{22}$-;
$G^{21}$, $G^{31}$, $G^{22}$, and $G^{32}$ each independently represent a hydrogen atom, or a $C_1$-$C_3$ alkyl group optionally substituted with 1 to 3 —$COOR^3$ group(s);
$R^3$ each independently represents a hydrogen atom or a tert-butyl group;
$L^{11}$, $L^{21}$, $L^{12}$, and $L^{22}$ each independently represent a $C_1$-$C_2$ alkylene group;
Z represents —($CH_2$—$CH_2$—O)$_m$—$CH_2$—$CH_2$— or —($CH_2$)$_n$—;
m represents an integer of 1 to 6; and
n represents an integer of 2 to 12.

13. The compound according to claim 12 or a pharmaceutically acceptable salt thereof, wherein
$R^1$ each represents a hydrogen atom;
$W^1$ and $W^2$ each represent a single bond;
$X^1$ represents —C(=O)—;
$X^2$ represents —C(=O)—;

$Y^1$ represents —$NG^{21}$-;
$Y^2$ represents —$NG^{22}$-;
$G^{21}$ and $G^{22}$ each independently represent a $C_1$-$C^3$ alkyl group substituted with 1 to 3 carboxy group(s);
Z represents —(CH$_2$—CH$_2$—O)$_m$—CH$_2$—CH$_2$—; and
m represents an integer of 1 to 6.

14. The compound according to claim 1, selected from the group consisting of:
- (2S,2'S)-2,2'-((oxybis(ethane-2,1-diyl))bis(N-(4-((4-guanidinobenzoyl)oxy)benzyl)sulfamoyl)azanediyl))disuccinic acid;
- (2S,13S)-3,12-bis(N-(4-((4-guanidinobenzoyl)oxy)benzyl)sulfamoyl)-6,9-dioxa-3,12-diazatetradecane-1,2,13,14-tetracarboxylic acid;
- (2S,16S)-3,15-bis(N-(4-((4-guanidinobenzoyl)oxy)benzyl)sulfamoyl)-6,9,12-trioxa-3,15-diazaheptadecane-1,2,16,17-tetracarboxylic acid;
- (2S,19S)-3,18-bis(N-(4-((4-guanidinobenzoyl)oxy)benzyl)sulfamoyl)-6,9,12,15-tetraoxa-3,18-diazaicosane-1,2,19,20-tetracarboxylic acid;
- (2S,22S)-3,21-bis(N-(4-((4-guanidinobenzoyl)oxy)benzyl)sulfamoyl)-6,9,12,15,18-pentaoxa-3,21-diazatricosane-1,2,22,23-tetracarboxylic acid;
- (2S,25S)-3,24-bis(N-(4-((4-guanidinobenzoyl)oxy)benzyl)sulfamoyl)-6,9,12,15,18,21-hexaoxa-3,24-diazahexacosane-1,2,25,26-tetracarboxylic acid;
- (2S,2'S)-2,2'-(propane-1,3-diylbis((N-(4-((4-guanidinobenzoyl)oxy)benzyl)sulfamoyl)azanediyl))disuccinic acid;
- (2S,2'S)-2,2'-(butane-1,4-diylbis((N-(4-((4-guanidinobenzoyl)oxy)benzyl)sulfamoyl)azanediyl))disuccinic acid;
- (2S,2'S)-2,2'-(pentane-1,5-diylbis((N-(4-((4-guanidinobenzoyl)oxy)benzyl)sulfamoyl)azanediyl))disuccinic acid;
- 3,18-bis(((4-((4-guanidinobenzoyl)oxy)benzyl)oxy)carbonyl)-6,9,12,15-tetraoxa-3,18-diazaicosane-1,2,19,20-tetracarboxylic acid;
- 2,2'-(1,20-bis(4-((4-guanidinobenzoyl)oxy)phenyl)-3,18-dioxo-2,19-dioxa-4,17-diazaicosane-4,17-diyl)disuccinic acid;
- (3S,6S,25S,28S)-6,25-bis(carboxymethyl)-3,28-bis((((4-((4-guanidinobenzoyl)oxy)benzyl)oxy)carbonyl)amino)-4,7,24,27-tetraoxo-11,14,17,20-tetraoxa-5,8,23,26-tetraazatriacontane-1,30-dioic acid;
- (3S,6S,23S,26S)-6,23-bis(carboxymethyl)-3,26-bis((((4-((4-guanidinobenzoyl)oxy)benzyl)oxy)carbonyl)amino)-4,7,22,25-tetraoxo-5,8,21,24-tetraazaoctacosane-1,28-dioic acid;
- (3S,22S)-3,22-bis(2-((3-carboxybenzyl)(((4-((4-guanidinobenzoyl)oxy)benzyl)oxy)carbonyl)amino)acetamido)-4,21-dioxo-8,11,14,17-tetraoxa-5,20-diazatetracosane-1,24-dioic acid;
- (4S,7S,26S,29S)-4,7,26,29-tetrakis(carboxymethyl)-3,30-bis(((4-(4-guanidinobenzoyl)oxy)benzyl)oxy)carbonyl-5,8,25,28-tetraoxo-12,15,18,21-tetraoxa-3,6,9,24,27,30-hexaazadotriacontane-1,32-dioic acid;
- (3S,22S)-3,22-bis((3-carboxybenzyl) (((4-((4-guanidinobenzoyl)oxy)benzyl)oxy)carbonyl)amino)-4,21-dioxo-8,11,14,17-tetraoxa-5,20-diazatetracosane-1,24-dioic acid;
- (2S,2'S)-2,2'-(((5,8,11,14-tetraoxa-2,17-diazaoctadecane-1,18-dioyl)bis(3,1-phenylene))bis(methylene))bis((((4-((4-guanidinobenzoyl)oxy)benzyl)oxy)carbonyl)azanediyl))disuccinic acid;
- (2S,2'S)-2,2'-(((((5,8,11,14-tetraoxa-2,17-diazaoctadecane-1,18-dioyl)bis(3,1-phenylene))bis(methylene))bis(N-(4-((4-guanidinobenzoyl)oxy)benzyl)sulfamoyl)azanediyl))disuccinic acid;
- 3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid;
- (2S,13S)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid;
- (2R,13R)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid;
- (2S,13S)-3,12-bis(N-(4-((4-guanidinobenzoyl)oxy)benzyl)-N-methylsulfamoyl)-6,9-dioxa-3,12-diazatetradecane-1,2,13,14-tetracarboxylic acid;
- 3,3'-(((ethane-1,2-diylbis(oxy))bis(ethane-2,1-diyl))bis((N-(4-((4-guanidinobenzoyl)oxy)benzyl)sulfamoyl)azanediyl))dipentanedioic acid;
- (2S,2'S)-2,2'-((1,12-bis(4-((4-guanidinobenzoyl)oxy)phenyl)-5,8-dioxa-2,11-diazadodecanedisulfonyl)bis(azanediyl))disuccinic acid;
- (2S,13S)-3,12-bis(N-(3-((4-guanidinobenzoyl)oxy)benzyl)sulfamoyl)-6,9-dioxa-3,12-diazatetradecane-1,2,13,14-tetracarboxylic acid;
- (2S,2'S)-2,2'-((oxybis(ethane-2,1-diyl))bis((10-guanidino-13-oxo-6,7,8,13-tetrahydrodibenzo[b,f][1,4]dioxecin-4-carbonyl)azanediyl))disuccinic acid;
- (2S,16S)-3,15-bis(10-guanidino-13-oxo-6,7,8,13-tetrahydrodibenzo[b,f][1,4]dioxecin-4-carbonyl)-6,9,12-trioxa-3,15-diazaheptadecane-1,2,16,17-tetracarboxylic acid;
- (2S,2'S)-2,2'-(([1,1'-biphenyl]-3,3'-diylbis(methylene))bis((10-guanidino-13-oxo-6,7,8,13-tetrahydrodibenzo[b,f][1,4]dioxecin-4-carbonyl)azanediyl))disuccinic acid;
- (2S,2'S)-2,2'-(((((oxybis(ethane-2,1-diyl))bis(oxy))bis(3-carboxy-5,1-phenylene))bis(methylene))bis((10-guanidino-13-oxo-6,7,8,13-tetrahydrodibenzo[b,f][1,4]dioxecin-4-carbonyl)azanediyl))disuccinic acid; and
- (2S,2'S)-2,2'-((oxybis(ethane-2,1-diyl))bis((3-((4-guanidinobenzoyl)oxy)benzyl)azanediyl))disuccinic acid, or a pharmaceutically acceptable salt thereof.

15. The compound according to claim 1, selected from the group consisting of:
- (2S,2'S)-2,2'-(oxybis(ethane-2,1-diyl))bis((N-(4-((4-guanidinobenzoyl)oxy)benzyl)sulfamoyl)azanediyl)disuccinic acid;
- (2S,13S)-3,12-bis(N-(4-((4-guanidinobenzoyl)oxy)benzyl)sulfamoyl)-6,9-dioxa-3,12-diazatetradecane-1,2,13,14-tetracarboxylic acid;
- (2S,2'S)~2,2'-(butane-1,4-diylbis((N-(4-((4-guanidinobenzoyl)oxy)benzyl)sulfamoyl)azanediyl))disuccinic acid;
- (2S,13S)-3,12-bis(10-guanidino-3-oxo-6,7,8,13-tetrahydrodibenzo[b,f][1,4]dioxecin-4-carbonyl)-6,9-dioxa-3,12-diazatetradecane-1,2,13,14-tetracarboxylic acid;
- (2S,2'S)-2,2'-((oxybis(ethane-2,1-diyl))bis((10-guanidino-13-oxo-6,7,8,13-tetrahydrodibenzo[b,f][1,4]dioxecin-4-carbonyl)azanediyl))disuccinic acid;
- (2S,16S)-3,15-bis(10-guanidino-13-oxo-6,7,8,13-tetrahydrodibenzo[b,f][1,4]dioxecin-4-carbonyl)-6,9,12-trioxa-3,15-diazaheptadecane-1,2,16,17-tetracarboxylic acid;

(2S,2'S)-2,2'-(([1,1'-biphenyl]-3,3'-diylbis(methylene))bis((10-guanidino-13-oxo-6,7,8,13-tetrahydrodibenzo[b,f][1,4]dioxecin-4-carbonyl)azanediyl))disuccinic acid; and (2,2'S)-2,2'-(((((oxybis(ethane-2,1-diyl))bis(oxy))bis(3-carboxy-5,1-phenylene))bis(methylene))bis(10-guanidino-13-oxo-6,7,8,13-tetrahydrodibenzo[b,f][1,4]dioxecin-4-carbonyl)azanediyl))disuccinic acid, or a pharmaceutically acceptable salt thereof.

16. The compound according to claim 1, or a pharmaceutically acceptable salt thereof having a molecular weight of 1000 or more.

17. A pharmaceutical composition comprising the compound according to claim 1 or a pharmaceutically acceptable salt thereof.

18. The compound according to claim 13 or a pharmaceutically acceptable salt thereof, wherein in represents 1.

19. The compound according to claim 13 or a pharmaceutically acceptable salt thereof, wherein $G^{21}$ and $G^{22}$ each independently represent an ethyl group substituted with 1 to 3 carboxy group(s).

20. The compound according to claim 13 or a pharmaceutically acceptable salt thereof, wherein m represents 1, and $G^{21}$ and $G^{22}$ each independently represent an ethyl group substituted with 1 to 3 carboxy group(s).

21. A compound, which is (2S,13S)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid, or a pharmaceutically acceptable salt thereof.

22. A compound, which is (2S,2'S)-2,2'-((oxybis(ethane-2,1-diyl))bis((10-guanidino-13-oxo-6,7,8,13-tetrahydrodibenzo[b,f][1,4]dioxecin-4-carbonyl)azanediyl))disuccinic acid, or a pharmaceutically acceptable salt thereof.

23. A compound, which is (2S,16S)-3,15-bis(10-guanidino-13-oxo-6,7,13-tetrahydrodibenzo[b,f][1,4]dioxecin-4-carbonyl)-6,9,12-trioxa-3,15-diazaheptadecane-1,2,16,17-tetracarboxylic acid, or a pharmaceutically acceptable salt thereof.

24. A compound, which is (2S,2'S)-2,2'-(([1,1'-biphenyl]-3,3'-diylbis(methylene))bis((10-guanidino-13-oxo-6,7,8,13-tetrahydrodibenzo[b,f][1,4]dioxecin-4-carbonyl)azanediyl))disuccinic acid, or a pharmaceutically acceptable salt thereof.

25. A compound, which is (2S,2'S)-2,2'-(((((oxybis(ethane-2,1-diyl))bis(oxy))bis(3-carboxy-5,1-phenylene))bis(methylene))bis((10-guanidino-13-oxo-6,7,8,13-tetrahydrodibenzo[b,f][1,4]dioxecin-4-carbonyl)azanediyl))disuccinic acid, or a pharmaceutically acceptable salt thereof.

26. The compound according to claim 21, which is (2S,13S)-3,12-bis(10-guanidino-13-oxo-6,7,8,13-tetrahydrodibenzo[b,f][1,4]dioxecin-4-carbonyl)-6,9-dioxa-3,12-diazatetradecane-1,2,13,14-tetracarboxylic acid.

27. The compound according to claim 22, which is (2S,2'S)-2,2'-((oxybis(ethane-2,1-diyl))bis((10-guanidino-13-oxo-6,7,7,13-tetrahydrodibenzo[b,f][1,4]dioxecin-4-carbonyl)azanediyl))disuccinic acid.

28. The compound according to claim 23, which is (2S,16S)-3,15-bis(10-guanidino-13-oxo-(6,7,8,13-tetrahydrodibenzo[b,f][1,4]dioxecin-4-carbonyl)-6,9,12-trioxa-3,15-diazaheptadecane-1,2,16,17-tetracarboxylic acid.

29. The compound according to claim 24, which is (2S,2'S)-2,2'-(([1,1'-biphenyl]-3,3'-diylbis(methylene))bis((10-guanidino-13-oxo-6,7,8,13-tetrahydrodibenzo[b,f][1,4]dioxecin-4-carbonyl)azanediyl)disuccinic acid.

30. The compound according to claim 25, which is (2S,2'S)-2,2'-(((((oxybis(ethane-2,1-diyl))bis(oxy))bis(3-carboxy-5,1-phenylene))bis(methylene))bis((10-guanidino-13-oxo-6,7,8,13-tetrahydrodibenzo[b,f][1,4]dioxecin-4-carbonyl)azanediyl))disuccinic acid.

31. A pharmaceutical composition comprising the compound according to claim 21, and a pharmaceutically acceptable carrier.

32. A pharmaceutical composition comprising the compound according to claim 22, and a pharmaceutically acceptable carrier.

33. A pharmaceutical composition comprising the compound according to claim 23, and a pharmaceutically acceptable carrier.

34. A pharmaceutical composition comprising the compound according to claim 24, and a pharmaceutically acceptable carrier.

35. A pharmaceutical composition comprising the compound according to claim 25, and a pharmaceutically acceptable carrier.

36. A pharmaceutical composition comprising the compound according to claim 26, and a pharmaceutically acceptable carrier.

37. A pharmaceutical composition comprising the compound according to claim 27, and a pharmaceutically acceptable carrier.

38. A pharmaceutical composition comprising the compound according to claim 28, and a pharmaceutically acceptable carrier.

39. A pharmaceutical composition comprising the compound according to claim 29, and a pharmaceutically acceptable carrier.

40. A pharmaceutical composition comprising the compound according to claim 30, and a pharmaceutically acceptable carrier.

* * * * *